United States Patent
Gege et al.

(10) Patent No.: US 9,751,874 B2
(45) Date of Patent: Sep. 5, 2017

(54) HYDROXY CONTAINING FXR (NR1H4) MODULATING COMPOUNDS

(71) Applicant: Gilead Sciences, Inc., Foster City, CA (US)

(72) Inventors: Christian Gege, Ehingen (DE); Olaf Kinzel, Heidelberg (DE); Claus Kremoser, Heidelberg (DE); Aaron C. Schmitt, Hamden, CT (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 14/971,875

(22) Filed: Dec. 16, 2015

(65) Prior Publication Data

US 2016/0176861 A1    Jun. 23, 2016

(30) Foreign Application Priority Data

Dec. 17, 2014 (EP) .................................. 14004259

(51) Int. Cl.
| | |
|---|---|
| *C07D 417/12* | (2006.01) |
| *C07D 417/14* | (2006.01) |
| *C07D 413/12* | (2006.01) |
| *C07D 261/08* | (2006.01) |
| *C07D 471/04* | (2006.01) |

(52) U.S. Cl.
CPC ......... *C07D 417/12* (2013.01); *C07D 261/08* (2013.01); *C07D 413/12* (2013.01); *C07D 417/14* (2013.01); *C07D 471/04* (2013.01)

(58) Field of Classification Search
CPC .. C07D 417/12; C07D 417/14; C07D 413/12; C07D 261/08
See application file for complete search history.

(56) References Cited

FOREIGN PATENT DOCUMENTS

| WO | WO 2009-012125 A1 | 1/2009 |
|---|---|---|
| WO | WO 2012-087520 A1 | 6/2012 |
| WO | WO 2012-087521 A1 | 6/2012 |
| WO | WO 2013-007387 A1 | 1/2013 |

OTHER PUBLICATIONS

Written Opinion and Search Report dated Mar. 23, 2016 for PCT/EP2015/002511.

*Primary Examiner* — Laura L. Stockton

(57) ABSTRACT

The present invention relates to compounds which bind to the NR1H4 receptor (FXR) and act as agonists of FXR. The invention further relates to the use of the compounds for the preparation of a medicament for the treatment of diseases and/or conditions through binding of said nuclear receptor by said compounds and to a process for the synthesis of said compounds.

12 Claims, 1 Drawing Sheet

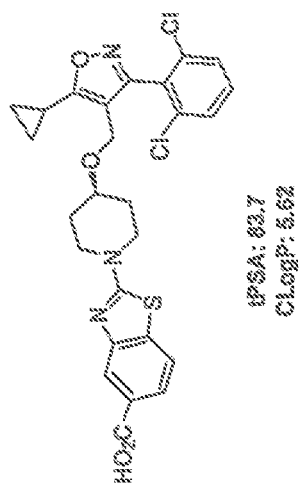
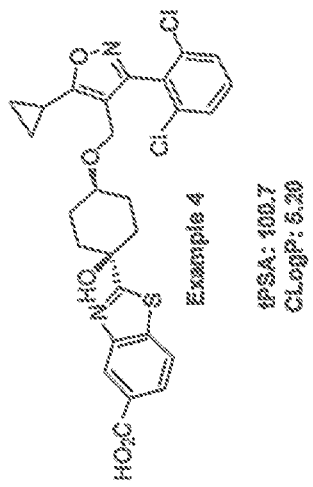

HYDROXY CONTAINING FXR (NR1H4) MODULATING COMPOUNDS

SEQUENCE LISTING

The Sequence Listing associated with this application is provided in text format in lieu of a paper copy, and is hereby incorporated by reference into the specification. The name of the text file containing the Sequence Listing is PX98209US_2017-07-06_SequenceListing.txt. The text file created on Jul. 6, 2017, is about 689 bytes and submitted electronically via EFS-Web.

The present invention relates to compounds which bind to the NR1H4 receptor (FXR) and act as agonists or modulators of FXR. The invention further relates to the use of the compounds for the treatment and/or prophylaxis of diseases and/or conditions through binding of said nuclear receptor by said compounds.

Multicellular organisms are dependent on advanced mechanisms of information transfer between cells and body compartments. The information that is transmitted can be highly complex and can result in the alteration of genetic programs involved in cellular differentiation, proliferation, or reproduction. The signals, or hormones, are often low molecular weight molecules, such as peptides, fatty acid, or cholesterol derivatives.

Many of these signals produce their effects by ultimately changing the transcription of specific genes. One well-studied group of proteins that mediate a cell's response to a variety of signals is the family of transcription factors known as nuclear receptors, hereinafter referred to often as "NR". Members of this group include receptors for steroid hormones, vitamin D, ecdysone, cis and trans retinoic acid, thyroid hormone, bile acids, cholesterol-derivatives, fatty acids (and other peroxisomal proliferators), as well as so-called orphan receptors, proteins that are structurally similar to other members of this group, but for which no ligands are known. Orphan receptors may be indicative of unknown signalling pathways in the cell or may be nuclear receptors that function without ligand activation. The activation of transcription by some of these orphan receptors may occur in the absence of an exogenous ligand and/or through signal transduction pathways originating from the cell surface (D. J. Mangelsdorf et al., Cell 1995, 83, 835; R. M. Evans, Mol. Endocrinol. 2005, 19, 1429).

In general, three functional domains have been defined in NRs. An amino terminal domain is believed to have some regulatory function. It is followed by a DNA-binding domain hereinafter referred to as "DBD" which usually comprises two zinc finger elements and recognizes a specific Hormone Responsive Element hereinafter referred to as "HRE" within the promoters of responsive genes. Specific amino acid residues in the "DBD" have been shown to confer DNA sequence binding specificity (M. Schena and K. R. Yamamoto, Science 1988, 241, 965). A ligand-binding-domain hereinafter referred to as "LBD" is at the carboxy-terminal region of known NRs.

In the absence of hormone, the LBD appears to interfere with the interaction of the DBD with its HRE. Hormone binding seems to result in a conformational change in the NR and thus opens this interference (A. M. Brzozowski et al., Nature 1997, 389, 753). A NR without the LBD constitutively activates transcription but at a low level.

Coactivators or transcriptional activators are proposed to bridge between sequence specific transcription factors, the basal transcription machinery and in addition to influence the chromatin structure of a target cell. Several proteins like SRC-1, ACTR, and Grip1 interact with NRs in a ligand enhanced manner (D. M. Heery et al., Nature 1997, 387, 733; T. Heinzel et al., Nature 1997, 387, 43; K. W. Nettles and G. L. Greene, Annu. Rev. Physiol. 2005, 67, 309).

Nuclear receptor modulators like steroid hormones affect the growth and function of specific cells by binding to intracellular receptors and forming nuclear receptor-ligand complexes. Nuclear receptor-hormone complexes then interact with a HRE in the control region of specific genes and alter specific gene expression (A. Aranda and A. Pascual, Physiol. Rev. 2001, 81, 1269).

The Farnesoid X Receptor alpha (hereinafter also often referred to as NR1H4 when referring to the human receptor) is a prototypical type 2 nuclear receptor which activates genes upon binding to promoter region of target genes in a heterodimeric fashion with Retinoid X Receptor (B. M. Forman et al., Cell 1995, 81, 687). The relevant physiological ligands of NR1H4 are bile acids (D. J. Parks et al., Science 1999, 284, 1365; M. Makishima et al., Science 1999, 284, 1362). The most potent one is chenodeoxycholic acid (CDCA), which regulates the expression of several genes that participate in bile acid homeostasis. Farnesol and derivatives, together called farnesoids, are originally described to activate the rat orthologue at high concentration but they do not activate the human or mouse receptor. FXR is expressed in the liver, throughout the entire gastrointestinal tract including the esophagus, stomach, duodenum, small intestine, colon, ovary, adrenal gland and kidney. Beyond controlling intracellular gene expression, FXR seems to be also involved in paracrine and endocrine signalling by upregulating the expression of the cytokine Fibroblast Growth Factor 15 (rodents) or 19 (monkeys, humans, J. A. Holt et al., Genes Dev. 2003, 17, 1581; T. Inagaki et al., Cell Metab. 2005, 2, 217).

Small molecule compounds which act as FXR modulators have been disclosed in the following publications: WO 2000/037077, WO 2003/015771, WO 2004/048349, WO 2007/076260, WO 2007/092751, WO 2007/140174, WO 2007/140183, WO 2008/051942, WO 2008/157270, WO 2009/005998, WO 2009/012125, WO 2008/025539, WO 2008/025540, WO 2008/157270, WO 2009/005998, WO 2009/149795, WO 2011/020615, WO 2012/087519 and WO 2013/007387. Further small molecule FXR modulators have been recently reviewed (M. L. Crawley, Expert Opin Ther. Pat. 2010, 20, 1047; D. Merk et al., Future Med. Chem. 2012, 4, 1015 and C. Gege et al., Curr. Top. Med. Chem. 2014, 14, 2143).

In WO 2009/012125 isoxazol derivatives of general structure (A) are described as FXR agonists. The compounds contains a central cyclohexane, cycloheptane, piperidine or azepane ring system (X is a carbon or nitrogen atom), for which no substitution is disclosed nor claimed.

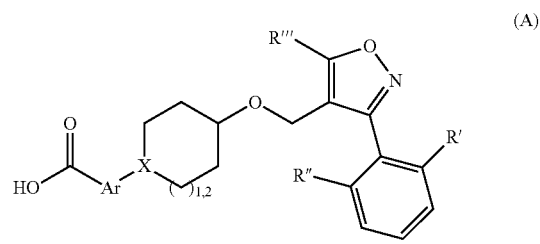

(A)

WO 2012/087520 discloses FXR agonists of general formula (B) where a benzo[d]thiazol-2-yl is linked to the nitrogen of a central pyrrolidine or piperidine ring. Again, no substitution of the central pyrrolidine or piperidine is disclosed.

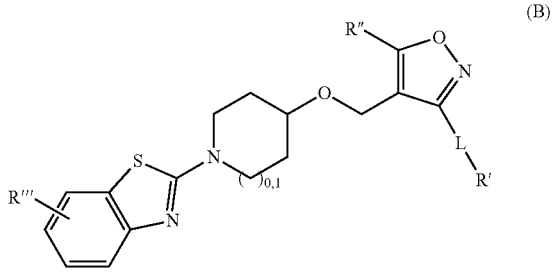

(B)

Similar, WO 2012/087521 discloses FXR agonists of general formula (C) where a 1,2,4-oxadiazol-3-yl is linked to the nitrogen of a central piperidine ring. Again, no substitution of the central piperidine is disclosed.

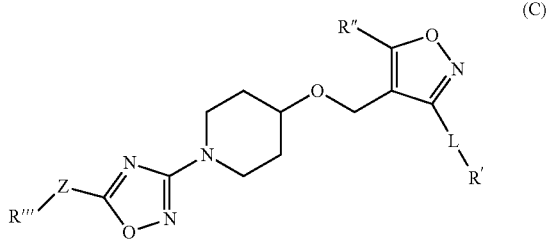

(C)

However, there is still a need for improved FXR-agonists. Thus, the problem underlying the present invention is the generation of novel FXR-agonists with improved physicochemical properties in general and reduced hydrophobicity and improved aqueous solubility in particular compared to compounds known in the art.

Said problem is solved by FXR-agonists according to Formula (1) with improved physicochemical properties as compared to known FXR-agonists. In particular, the introduction of a hydroxyl group at the carbon atom of moiety Q which is linked to moiety A results in a reduction of c log P, increase in topological polar surface area and thus an improvement in aqueous solubility compared to related structures as disclosed in WO2012/087520 as can be taken from FIG. 1 which shows a comparison of calculated c log P and tPSA of Example 4 of the present invention to calculated values of a known FXR-agonist with related structure. At the same time, the compounds of the present invention maintain a high activity on the FXR-receptor, both in a biochemical assay and in a cellular assay. More specifically, compounds of the present invention with a cis conformation of the two oxygen substituents on the central cyclic alkyl moiety Q have a higher activity on the FXR receptor than the ones which have a trans conformation.

Thus, the present invention provides a compound according to the following Formula (1), an enantiomer, diastereomer, tautomer, solvate, prodrug or pharmaceutical acceptable salt thereof

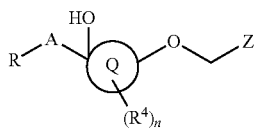

(1)

wherein

R is selected from the group consisting of hydrogen, halogen, $C_{1-6}$-alkyl, $C_{2-6}$-alkenyl, $C_{2-6}$-alkynyl, halo-$C_{1-6}$-alkyl, $C_{0-6}$-alkylene-$R^7$, $C_{0-6}$-alkylene-O—$R^7$, $C_{0-6}$-alkylene-CN, $C_{0-6}$-alkylene-$NR^7R^8$, O—$C_{3-10}$-cycloalkyl, O—$C_{1-6}$-alkylene-O—$R^7$, O—$C_{3-10}$-heterocycloalkyl, $C_{0-6}$-alkylene-$CO_2R^7$, $C_{0-6}$-alkylene-C(O)$R^7$, $C_{0-6}$-alkylene-C(O)$NR^7R^8$, $C_{0-6}$-alkylene-C(O)$NR^7SO_2R^7$, $C_{0-6}$-alkylene-N($R^7$)C(O)$R^7$, $C_{0-6}$-alkylene-SO$_x$—$R^7$, $C_{0-6}$-alkylene-$SO_2R^8$, $C_{0-6}$-alkylene-$SO_3H$, $C_{0-6}$-alkylene-$SO_2$—$NR^7R^8$, $C_{0-6}$-alkylene-$SO_2$—$NR^8COR^7$, $C_{0-6}$-alkylene-N($R^7$)$SO_2$—$R^8$, and $C_{0-6}$-alkylene-$SO_2$—$C_{3-10}$-heterocycloalkyl, wherein alkylene, cycloalkyl, heterocycloalkyl and the 5- or 6-membered heteroaryl are unsubstituted or substituted by 1 to 4 substituents independently selected from the group consisting of halogen, CN, $C_{1-3}$-alkyl, halo-$C_{1-3}$-alkyl, OH, oxo, $CO_2H$, $SO_3H$, O—$C_{1-3}$-alkyl and O-halo-$C_{1-3}$-alkyl;

$R^7$ is independently selected from the group consisting of hydrogen, $C_{1-6}$-alkyl, halo-$C_{1-6}$-alkyl, $C_{0-6}$-alkylene-$C_{3-8}$-cycloalkyl, $C_{0-6}$-alkylene-$C_{3-8}$-heterocycloalkyl, 5- or 6-membered heteroaryl and phenyl, wherein alkyl, alkylene, cyclolalkyl, heterocycloalkyl, phenyl and heteroaryl are unsubstituted or substituted with 1 to 6 substituents independently selected from the group consisting of halogen, CN, OH, oxo, $CO_2H$, $C_{1-3}$-alkyl, halo-$C_{1-3}$-alkyl, O—$C_{1-3}$-alkyl, O-halo-$C_{1-3}$-alkyl, $SO_3H$ and $SO_2$—$C_{1-3}$-alkyl;

$R^8$ is independently selected from the group consisting of hydrogen, $C_{1-6}$-alkyl, halo-$C_{1-6}$-alkyl and $C_{3-6}$-cycloalkyl;

or $R^7$ and $R^8$ when taken together with the nitrogen to which they are attached may complete a 3- to 8-membered ring containing carbon atoms and optionally containing 1 or 2 heteroatoms selected from O, S or N, wherein the ring is unsubstituted or substituted with 1 to 4 substituents independently selected from the group consisting of fluoro, OH, oxo, $C_{1-4}$-alkyl and halo-$C_{1-4}$-alkyl;

A is a 6-10 membered mono- or bicyclic aryl or a 5-10 membered mono- or bicyclic heteroaryl containing 1 to 5 heteroatoms independently selected from the group consisting of N, O and S, wherein aryl and heteroaryl are unsubstituted or substituted with one or two groups independently selected from the group consisting of OH, halogen, CN, O—$C_{1-6}$-alkyl, O-halo-$C_{1-6}$-alkyl, $C_{1-6}$-alkyl, halo-$C_{1-6}$-alkyl, $C_{3-6}$-cycloalkyl, $C_{5-6}$-heterocycloalkyl and halo-$C_{3-6}$-cycloalkyl;

Q is a $C_{3-10}$-cycloalkyl ring, or $C_{5-10}$-bridged cycloalkyl ring wherein the —O—$CH_2$—Z-substituent is not directly adjacent to substituent A, wherein when Q is a bi- or multicyclic ring system, a carbon atom may optionally be replaced by a oxygen, $SO_x$ or $NR^7$;

Z is selected from

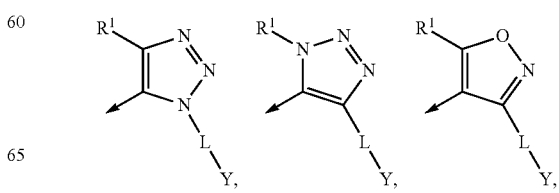

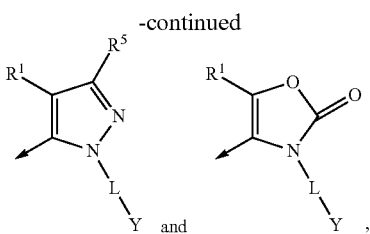

wherein

L is selected from the group consisting of a bond, $C_{1-3}$-alkylene and $C_{1-3}$-alkylene-O—;

Y is selected from the group consisting of phenyl, pyridyl, pyridyl-N-oxide, pyrimidyl, pyridinonyl, pyrimidinonyl, $C_{4-8}$-cycloalkyl, or $C_{4-8}$-heterocycloalkyl, wherein phenyl, pyridyl, pyridyl-N-oxide, pyrimidyl, pyridinonyl, pyrimidinonyl, $C_{4-8}$-cycloalkyl and $C_{4-8}$-heterocycloalkyl are substituted with $R^2$ and $R^3$ and optionally substituted one or two times with a group selected from fluoro, chloro, CN, $NH_2$, $NH(C_{1-3}$-alkyl), $N(C_{1-3}$-alkyl$)_2$, $C_{1-3}$-alkyl, fluoro-$C_{1-3}$-alkyl, OH, $C_{1-3}$-alkoxy, fluoro-$C_{1-3}$-alkoxy, $C_{3-6}$-cycloalkyl and fluoro-$C_{3-6}$-cycloalkyl;

$R^1$ is selected from the group consisting of $C_{1-4}$-alkyl and $C_{3-6}$-cycloalkyl, wherein $C_{1-4}$-alkyl is unsubstituted or substituted with 1 to 3 substituents independently selected from the group consisting of fluoro, hydroxy, $C_{1-3}$-alkoxy and fluoro-$C_{1-3}$-alkoxy, and $C_{3-6}$-cycloalkyl is unsubstituted or substituted with 1 to 3 substituents independently selected from the group consisting of fluoro, hydroxy, $C_{1-3}$-alkyl, fluoro-$C_{1-3}$-alkyl, $C_{1-3}$-alkoxy and fluoro-$C_{1-3}$-alkoxy;

$R^2$ and $R^3$ are independently selected from the group consisting of hydrogen, halogen, $C_{1-3}$-alkyl, halo-$C_{1-3}$-alkyl, $C_{1-3}$-alkoxy, halo-$C_{1-3}$-alkoxy, cyclopropyl and fluoro-cyclopropyl;

$R^4$ is independently selected from the group consisting of halogen, $C_{1-3}$-alkyl, halo-$C_{1-3}$-alkyl, $C_{1-3}$-alkoxy, halo-$C_{1-3}$-alkoxy, $C_m$-cycloalkyl, $C_{1-3}$-alkylene-O—$C_{1-3}$-alkyl and fluoro-$C_{3-6}$-cycloalkyl;

$R^5$ is selected from the group consisting of hydrogen, fluoro, $CH_3$, $CHF_2$ and $CF_3$;

n is selected from 0, 1, 2, 3 and 4;

x is independently selected from 0, 1 and 2.

In another embodiment, the present invention is directed to a compound according to Formula (1) as a medicament.

In a further embodiment, the present invention relates to a compound according to Formula (1) for use in the prophylaxis and/or treatment of diseases mediated by FXR.

In yet a further embodiment, the present invention is directed to the use of a compound according to Formula (1) for the preparation of a medicament for the prophylaxis and/or treatment of diseases mediated by FXR.

In another embodiment, the present invention relates to a method for treating or preventing a disease mediated by FXR in a subject in need thereof, the method comprising administering an effective amount of a compound of Formula (1) to the subject.

In a preferred embodiment in combination with any of the above or below embodiments, the disease mediated by FXR is selected from chronic intrahepatic or some forms of extrahepatic cholestatic conditions; liver fibrosis; obstructive or chronic inflammatory disorders of the liver; liver cirrhosis; liver steatosis and associated syndromes, cholestatic or fibrotic effects that are associated with alcohol-induced cirrhosis or with viral-borne forms of hepatitis; liver failure or liver ischemia after major liver resection; chemotherapy associated steatohepatitis (CASH); acute liver failure; and/or Inflammatory Bowel Diseases.

In an equally preferred embodiment in combination with any of the above or below embodiments, the disease is selected from lipid and lipoprotein disorders; Type II Diabetes and clinical complications of Type I and Type II Diabetes, including diabetic nephropathy, diabetic neuropathy, diabetic retinopathy and other observed effects of clinically manifest long term Diabetes; conditions and diseases which result from chronic fatty and fibrotic degeneration of organs due to enforced lipid and specifically triglyceride accumulation and subsequent activation of profibrotic pathways, such as Non-Alcoholic Fatty Liver Disease (NAFLD), or Non-Alcoholic Steatohepatitis (NASH); obesity or metabolic syndrome (combined conditions of dyslipidemia, diabetes or abnormally high body-mass index); and/or cute myocardial infarction, acute stroke or thrombosis which occurs as an endpoint of chronic obstructive atherosclerosis.

In yet another preferred embodiment in combination with any of the above or below embodiments, the disease is selected from non-malignant hyperproliferative disorders and malignant hyperproliferative disorders, specifically of hepatocellular carcinoma, colon adenoma and polyposis, colon adenocarcinoma, breast cancer, pancreas adenocarcinoma, Barrett's esophagus or other forms of neoplastic diseases of the gastrointestinal tract and the liver.

The compounds of the present invention share a common chemical structure according to Formula (1) in claim 1.

In a preferred embodiment in combination with any of the above or below embodiments, R in Formula (1) is selected from the group consisting of $CO_2H$, $SO_3H$, $CONR^7R^9$, tetrazolyl, 1,2,4-oxadiazol-5(4H)-one-3-yl and $SO_2NHCOR^7$.

In a further preferred embodiment in combination with any of the above or below embodiments, $R^7$ in Formula (1) is independently selected from the group consisting of hydrogen, $C_1$-6 alkyl, halo-$C_1$-6 alkyl, $C_1$-6 alkylene-$R^9$ and $SO_2$—$C_1$-6 alkyl, wherein $R^9$ is selected from the group consisting of COOH, OH and $SO_3H$.

In a preferred embodiment in combination with any of the above or below embodiments, $R^8$ in Formula (1) is selected from the group consisting of hydrogen, $C_1$-6 alkyl and halo-$C_1$-6 alkyl.

In an equally preferred embodiment in combination with any of the above or below embodiments, A is selected from the group consisting of phenyl, pyridyl, pyrimidyl, pyrazolyl, indolyl, thienyl, benzothienyl, indazolyl, benzisoxazolyl, benzisothiazolyl, triazolopyridinyl, benzofuranyl, benzotriazolyl, furanyl, benzothiazolyl, thiazolyl, oxadiazolyl, oxazolyl, naphthyl, quinolyl, isoquinolyl and benzimidazolyl, wherein A may be unsubstituted or substituted as defined above.

In a more preferred embodiment in combination with any of the above or below embodiments, A is selected from the group consisting of phenyl, pyridyl, indolyl, indazolyl, benzisothiazolyl, triazolopyridinyl, benzothiazolyl, thiazolyl, oxazolyl, quinolyl, wherein A may be unsubstituted or substituted as defined above.

In another preferred embodiment, A is selected from the group consisting of phenyl, pyridyl, indolyl, indazolyl, benzisothiazolyl, triazolopyridinyl, benzothiazolyl, thiazolyl, oxazolyl, quinolyl, each unsubstituted or substituted with one or two groups independently selected from the group consisting of OH, halogen, CN, O—$C_{1-6}$-alkyl, O-halo-$C_{1-6}$-alkyl, $C_{1-6}$-alkyl, halo-$C_{1-6}$-alkyl, $C_{3-6}$-cycloalkyl and halo-$C_{3-6}$-cycloalkyl.

In a preferred embodiment in combination with any of the above or below embodiments, R-A is selected from
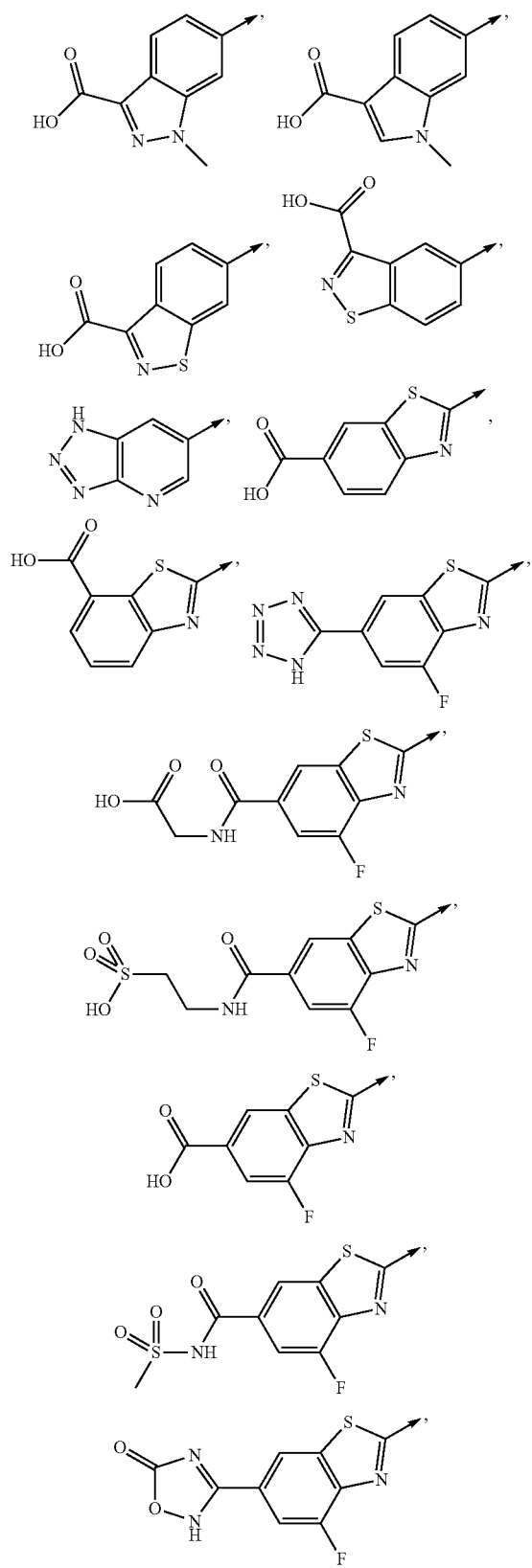
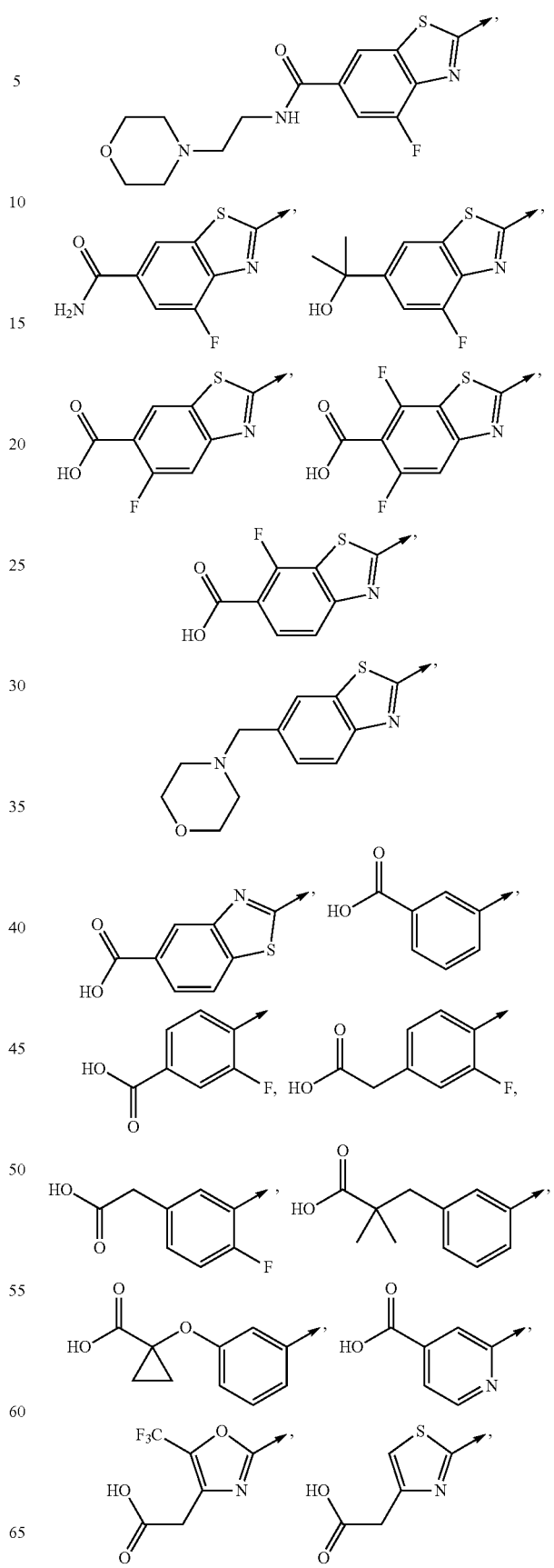

-continued

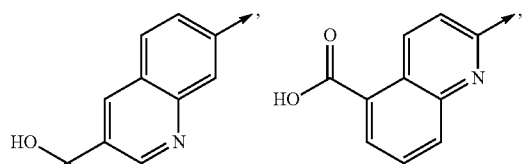

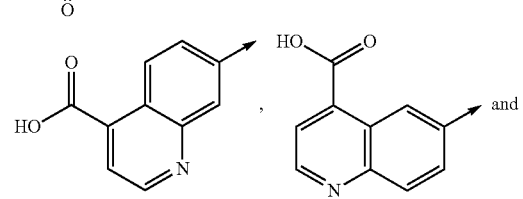

In a more preferred embodiment in combination with any of the above or below embodiments, R-A is selected from

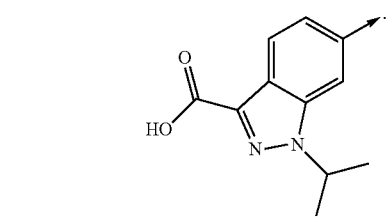

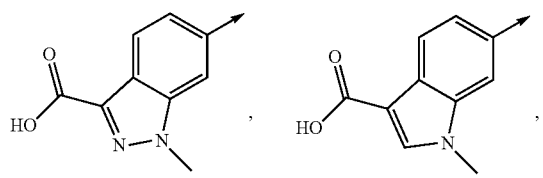

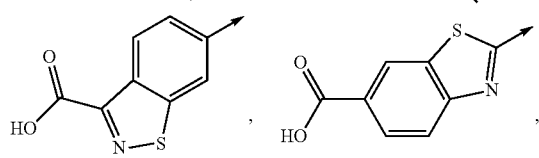

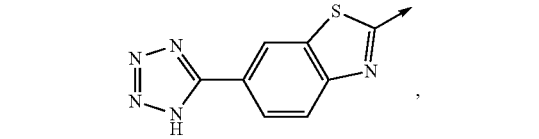

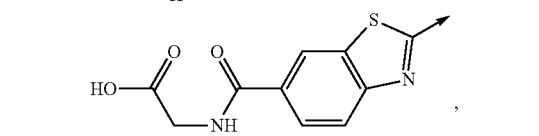

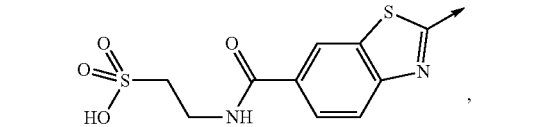

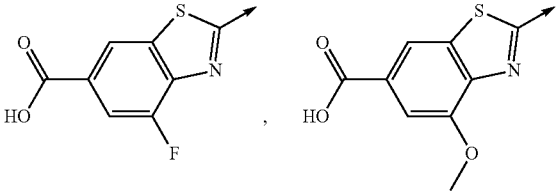

-continued

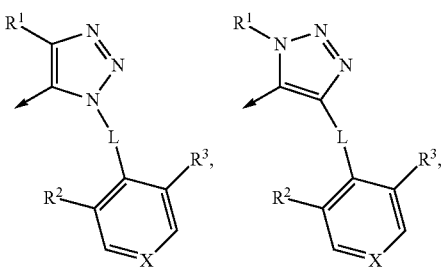

In a further preferred embodiment in combination with any of the above or below embodiments, Z is selected from

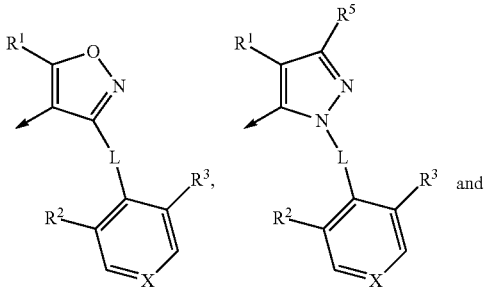

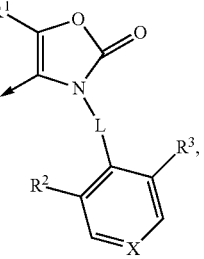

wherein

L is selected from the group consisting of a bond, $C_{1-3}$-alkylene and $C_{1-3}$-alkylene-O—;

X is selected from the group consisting of CH, CF, N and NO;

$R^1$ is selected from the group consisting of $C_{1-4}$-alkyl and $C_{3-6}$-cycloalkyl, wherein $C_{1-4}$-alkyl is unsubstituted or substituted with 1 to 3 substituents independently selected from the group consisting of fluoro, hydroxy, $C_{1-3}$-alkoxy and fluoro-$C_{1-3}$-alkoxy, and $C_m$-cycloalkyl is unsubstituted or substituted with 1 to 3 substituents independently selected from the group consisting of fluoro, hydroxy, $C_{1-3}$-alkyl, fluoro-$C_{1-3}$-alkyl, $C_{1-3}$-alkoxy and fluoro-$C_{1-3}$-alkoxy;

$R^2$ and $R^3$ are independently selected from the group consisting of hydrogen, halogen, $C_{1-3}$-alkyl, halo-$C_{1-3}$-alkyl, $C_{1-3}$-alkoxy, halo-$C_{1-3}$-alkoxy, cyclopropyl and fluoro-cyclopropyl; and $R^5$ is selected from the group consisting of hydrogen, fluoro, $CH_3$, $CHF_2$ and $CF_3$.

In a more preferred embodiment in combination with any of the above or below embodiment, Z is selected from

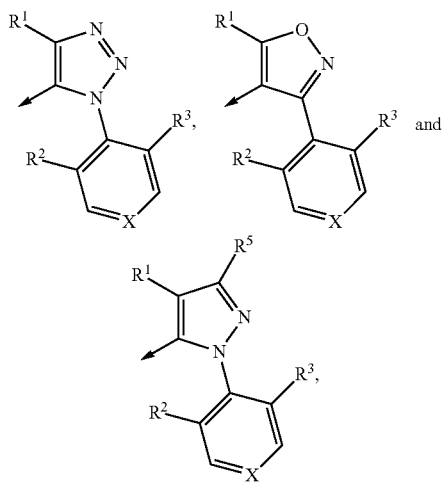

wherein X, $R^1$, $R^2$, $R^3$ and $R^5$ are defined as above.

In a more preferred embodiment in combination with any of the above or below embodiment, X is selected from the group consisting of CH, CF, N and NO; even more preferred X is selected from the group consisting of CH, N and NO.

In a more preferred embodiment in combination with any of the above or below embodiment, $R^1$ is selected from the group consisting of methyl, $CF_3$, $CHF_2$, isopropyl and cyclopropyl, wherein isopropyl and cyclopropyl are unsubstituted or substituted with one or two fluoro or one hydroxy; even more preferred, $R^1$ is selected from the group consisting of isopropyl and cyclopropyl, wherein isopropyl and cyclopropyl are unsubstituted or substituted with one or two fluoro or one hydroxy.

In a more preferred embodiment in combination with any of the above or below embodiment, $R^2$ is selected from the group consisting of fluoro, chloro, $CH_3$, $CHF_2$, $CF_3$, $OCHF_2$ and $OCF_3$.

In a further more preferred embodiment in combination with any of the above or below embodiment, $R^3$ is selected from the group consisting of hydrogen, fluoro, chloro, $CH_3$, $CHF_2$, $CF_3$, $OCHF_2$ and $OCF_3$:

In a preferred embodiment in combination with any of the above or below embodiment, $R^5$ is selected from the group consisting of hydrogen, fluoro, $CH_3$, $CHF_2$ and $CF_3$; more preferably, $R^5$ is hydrogen.

In a preferred embodiment in combination with any of the above or below embodiment,

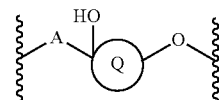

in Formula (1) is selected from

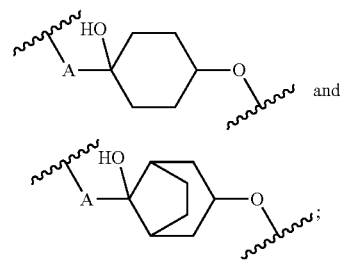

In a more preferred embodiment in combination with any of the above or below embodiment,

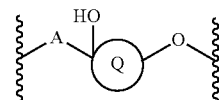

in Formula (1) is selected from

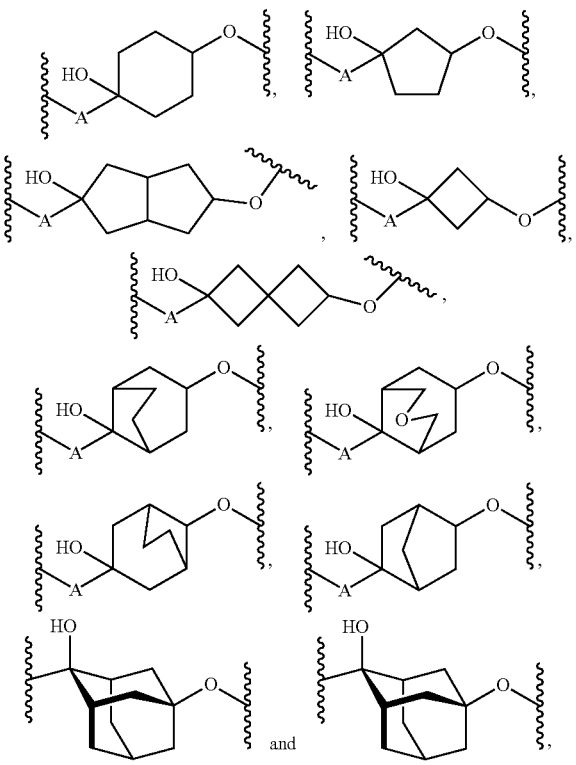

each optionally substituted with $R^4$;
even more preferred

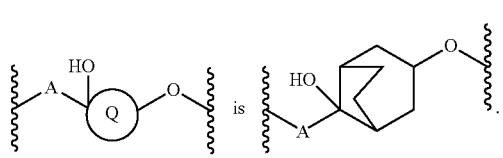

In a further preferred embodiment, the compound of the present invention is according to Formula (2)

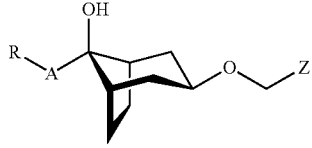
(2)

wherein

A is selected from the group consisting of phenyl, pyridyl, pyrimidyl, pyrazolyl, indolyl, thienyl, benzothienyl, indazolyl, benzisoxazolyl, benzisothiazolyl, triazolopyridinyl, benzofuranyl, benzotriazolyl, furanyl, benzothiazolyl, thiazolyl, oxadiazolyl, oxazolyl, naphthyl, quinolyl, isoquinolyl, benzimidazolyl, each unsubstituted or substituted with one or two groups independently selected from the group consisting of OH, halogen, CN, O—$C_{1-6}$-alkyl, O-halo-$C_{1-6}$-alkyl, $C_{1-6}$-alkyl, halo-$C_{1-6}$-alkyl, $C_{3-6}$-cycloalkyl and halo-$C_{3-6}$-cycloalkyl;

R is selected from the group consisting of $CO_2H$, $SO_3H$, $CONR^7R^9$, tetrazolyl, 1,2,4-oxadiazol-5(4H)-one-3-yl and $SO_2NHCOR^7$, wherein
- $R^7$ selected from the group consisting of H, $C_{1-6}$-alkyl, halo-$C_{1-6}$-alkyl, $C_{1-6}$-alkylene-$R^9$ and $SO_2$—$C_{1-6}$-alkyl;
- $R^8$ selected from the group consisting of H, $C_{1-6}$-alkyl, halo-$C_{1-6}$-alkyl; and
- $R^9$ is selected from the group consisting of COOH, OH and $SO_3H$;

Z is selected from

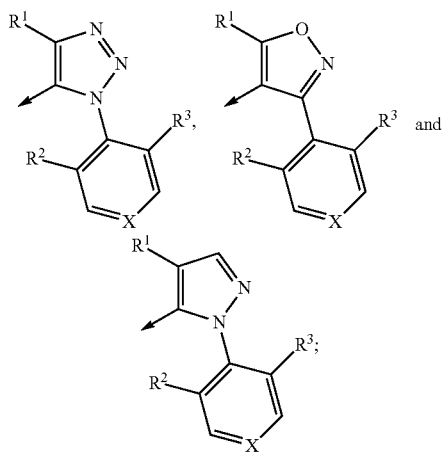

X is selected from the group consisting of CH, N and NO;

$R^1$ is selected from the group consisting of methyl, isopropyl and cyclopropyl, wherein isopropyl and cyclopropyl are unsubstituted or substituted with one or two fluoro or one hydroxy;

$R^2$ is selected from the group consisting of fluoro, chloro, $CH_3$, $CHF_2$, $CF_3$, $OCHF_2$ and $OCF_3$; and $R^3$ is selected from the group consisting of hydrogen, fluoro, chloro, $CH_3$, $CHF_2$, $CF_3$, $OCHF_2$ and $OCF_3$.

In a preferred embodiment in combination with any of the above or below embodiments, the compound is selected from the group consisting of

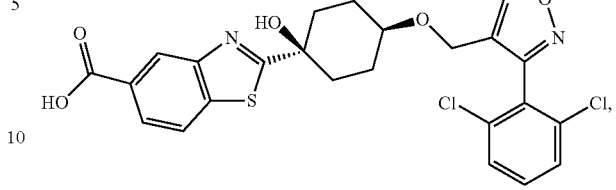

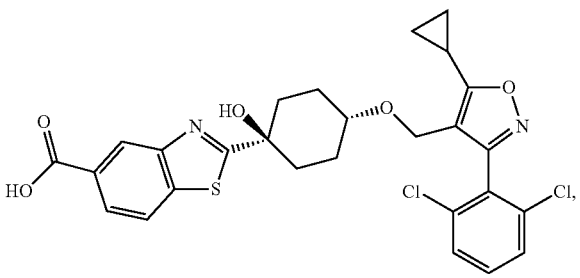

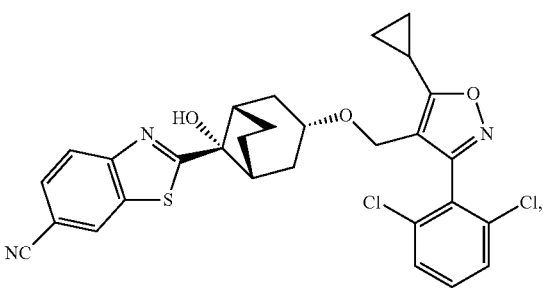

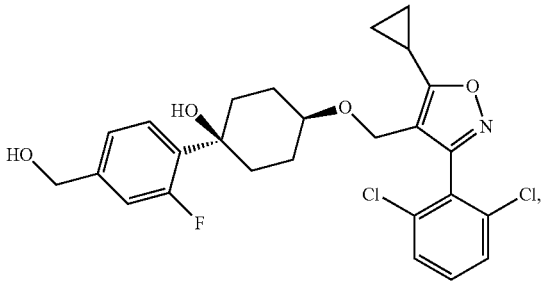

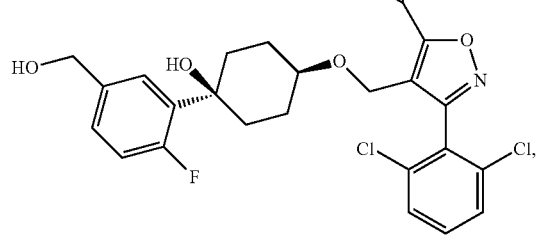

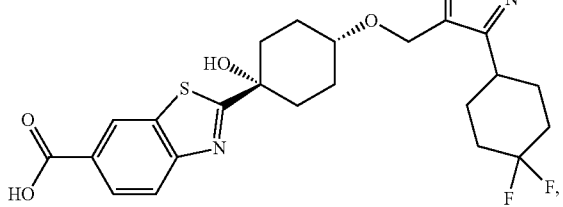

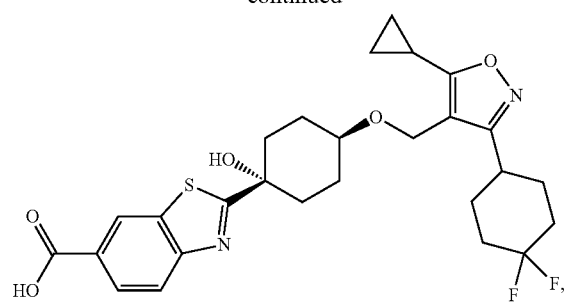
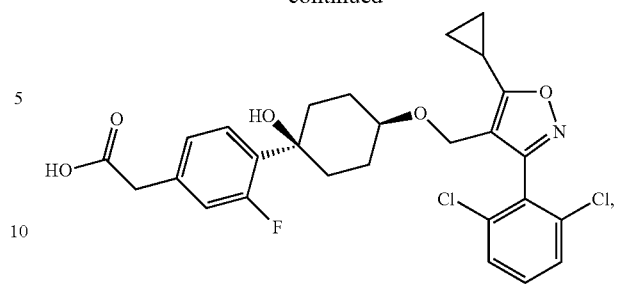
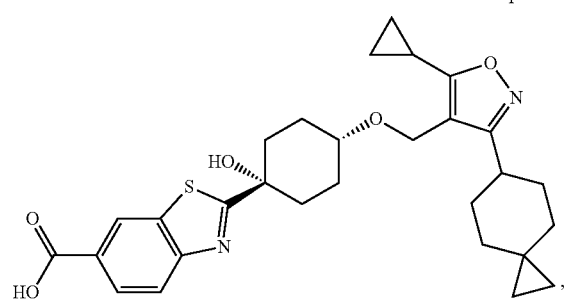
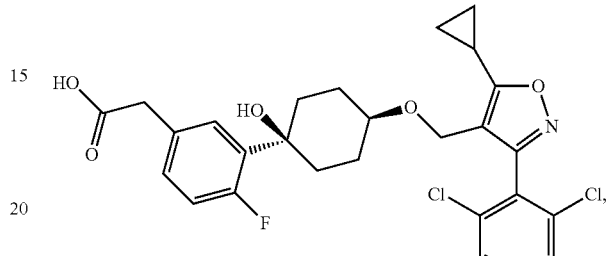
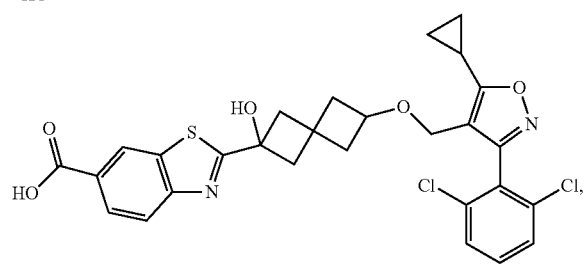
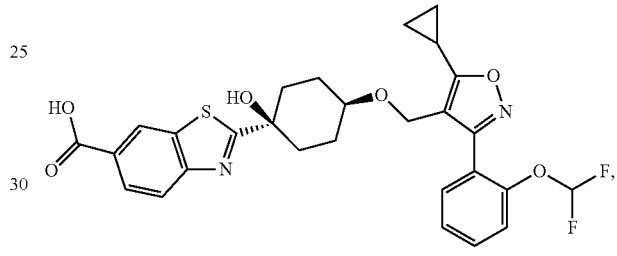
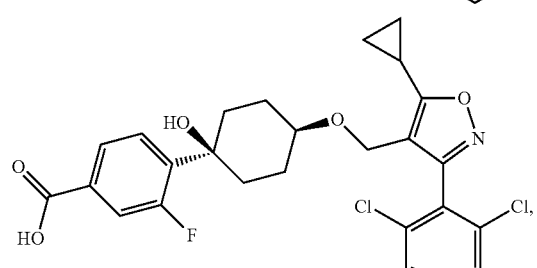
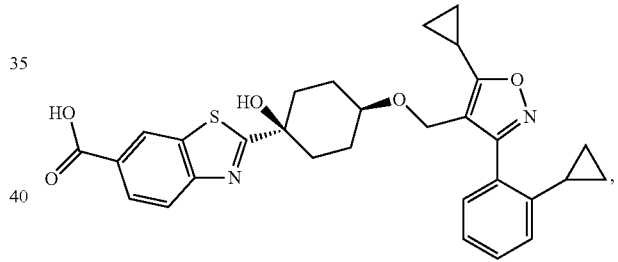
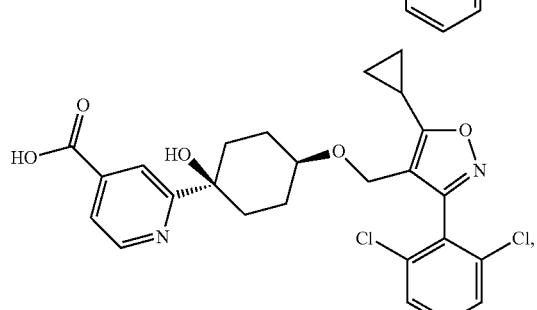
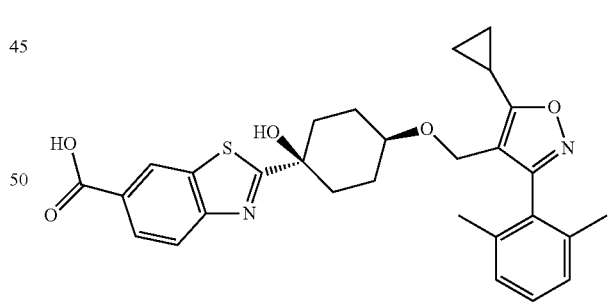
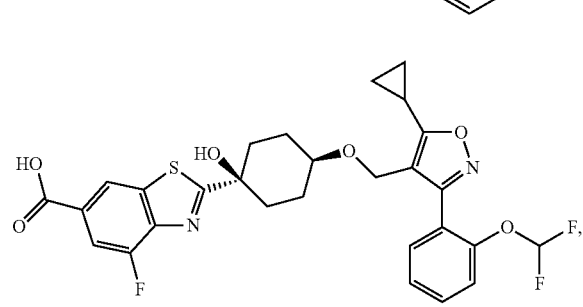
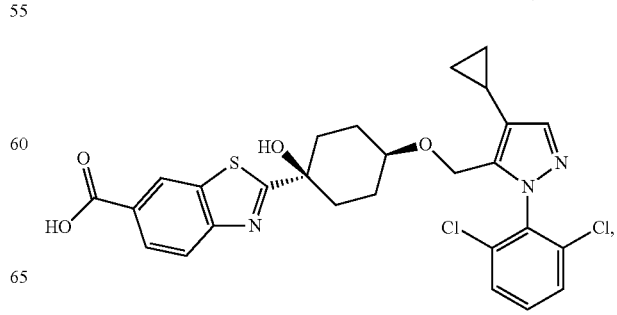

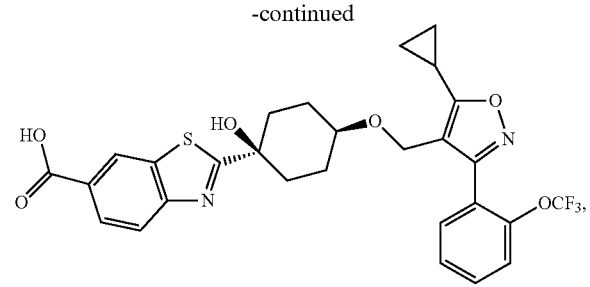
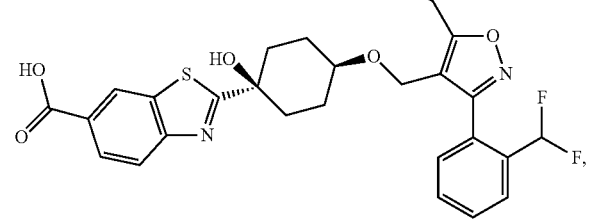
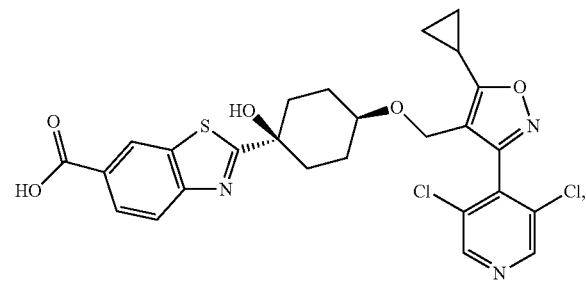
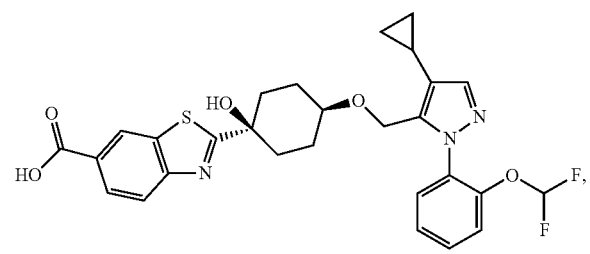
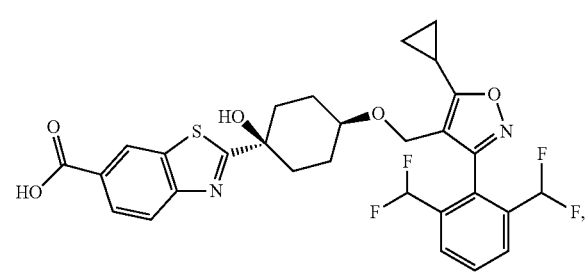
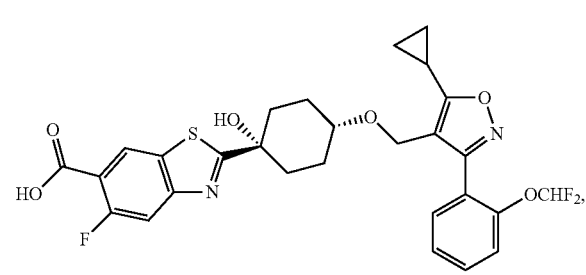
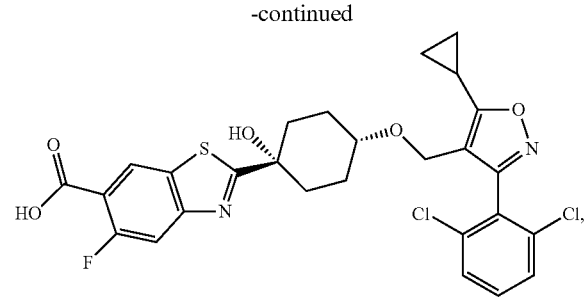
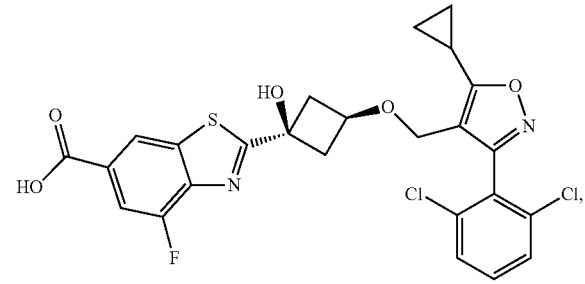
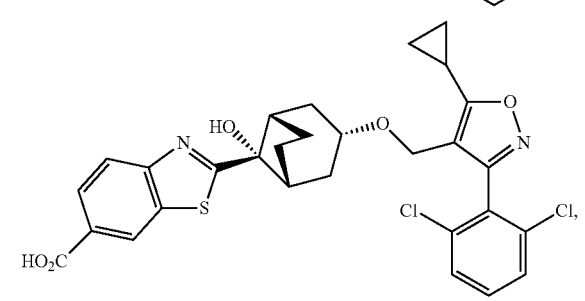
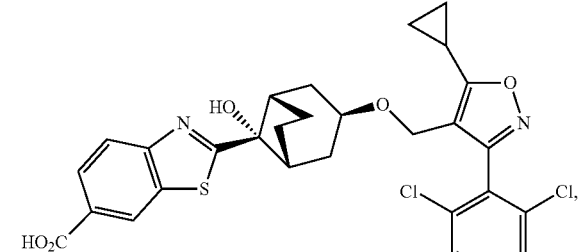
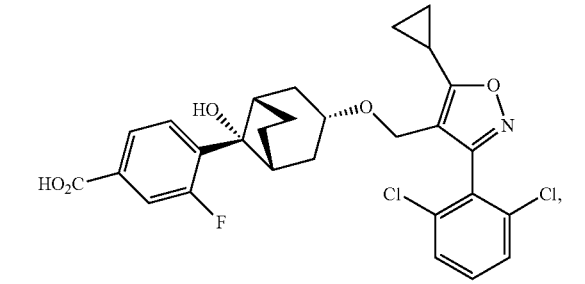
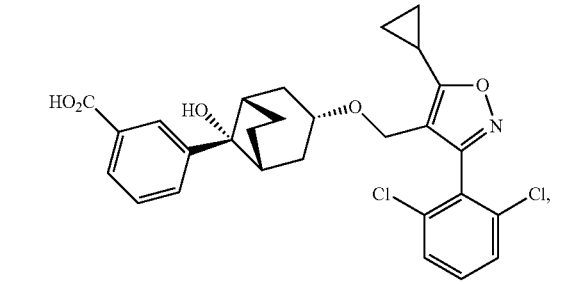

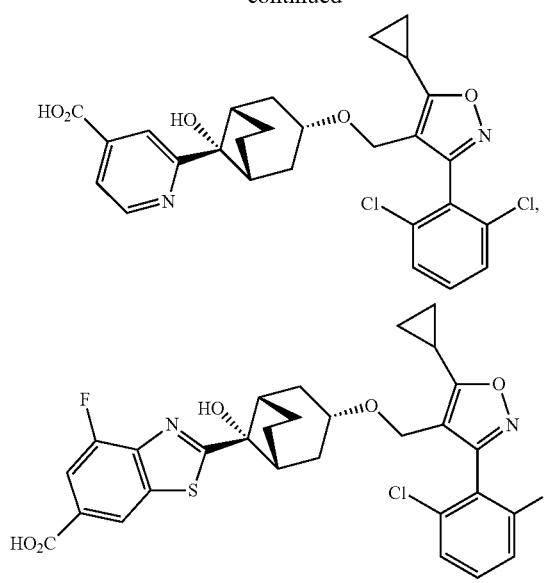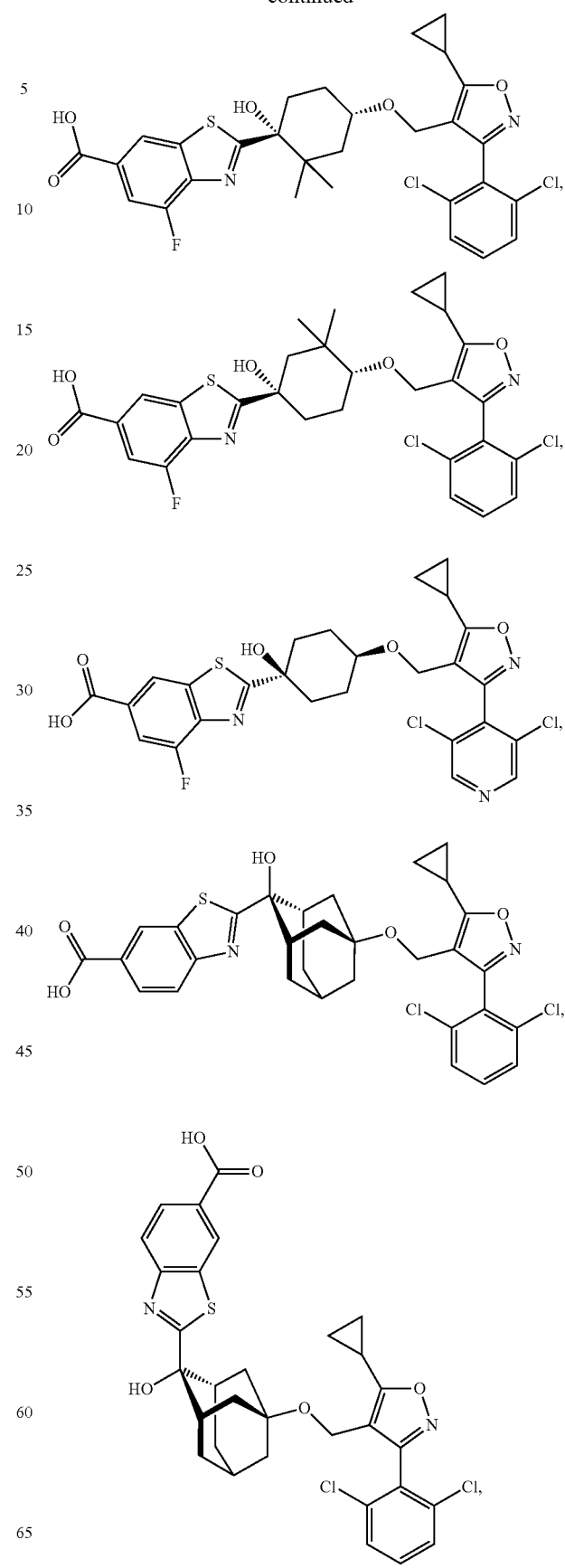

21
-continued
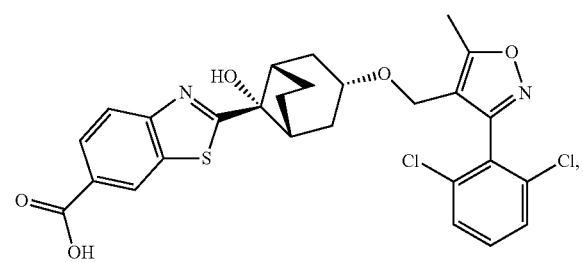
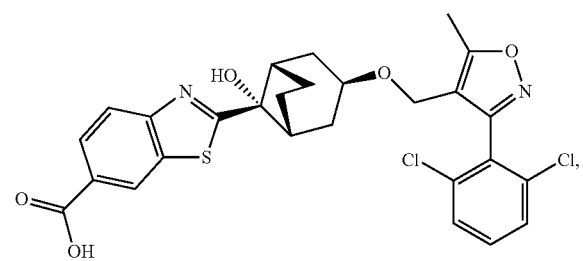
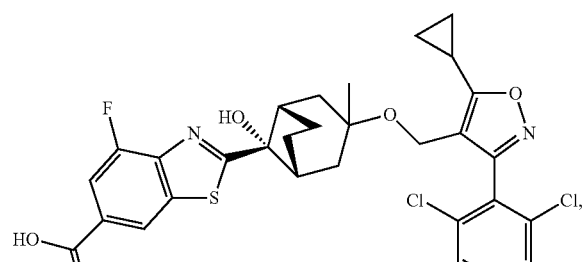
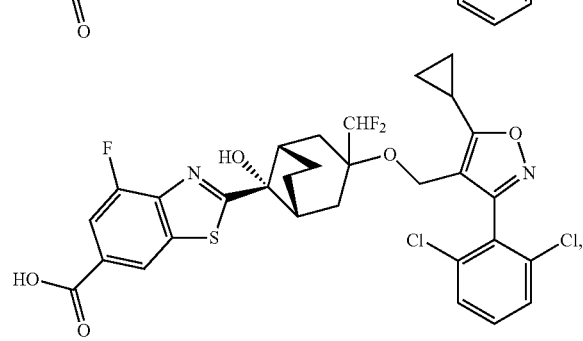
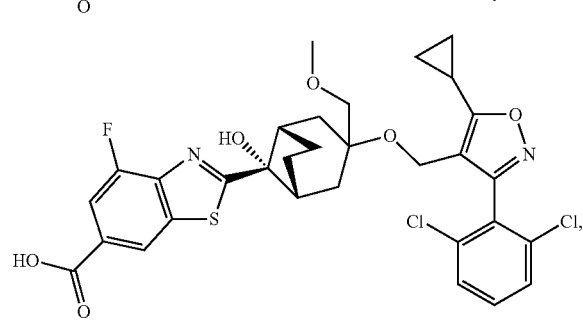
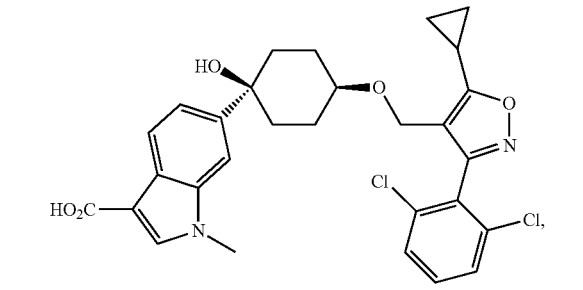
22
-continued
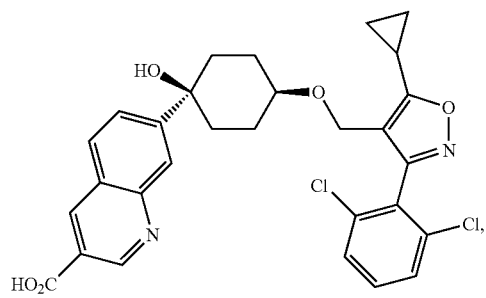
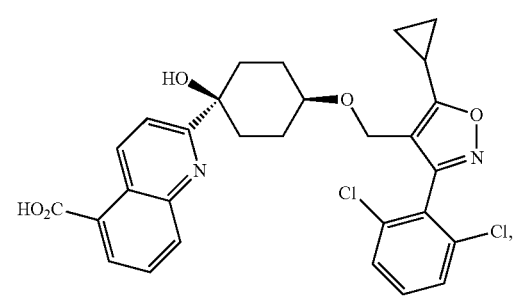
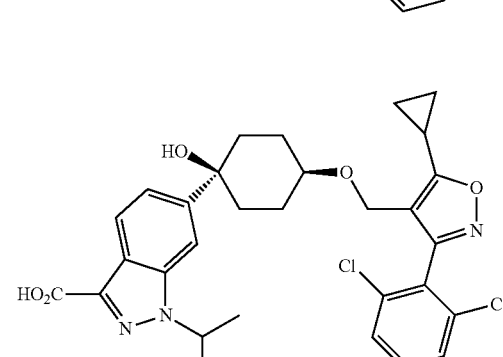
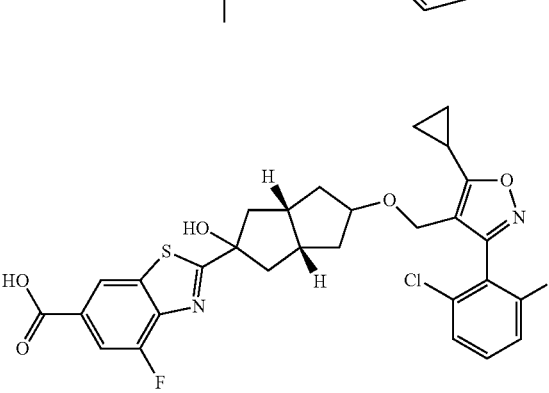
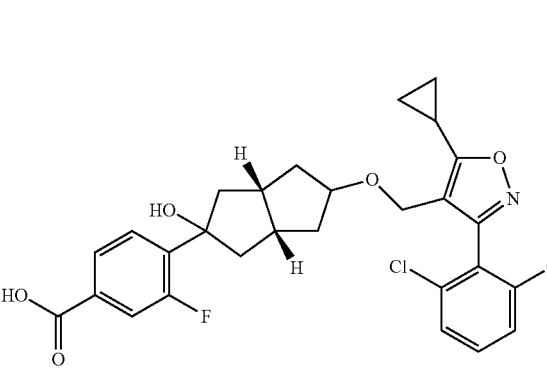

23
-continued
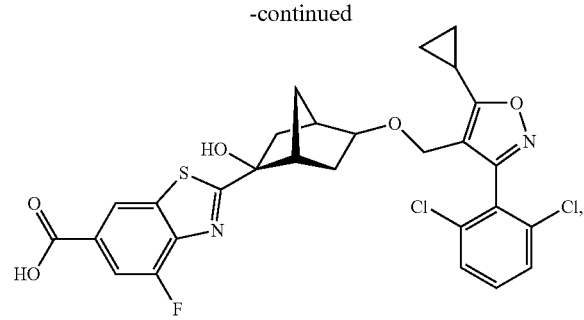
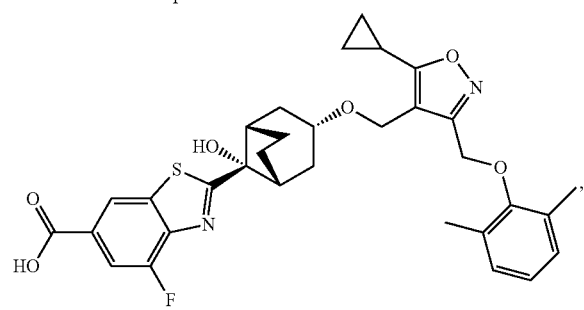
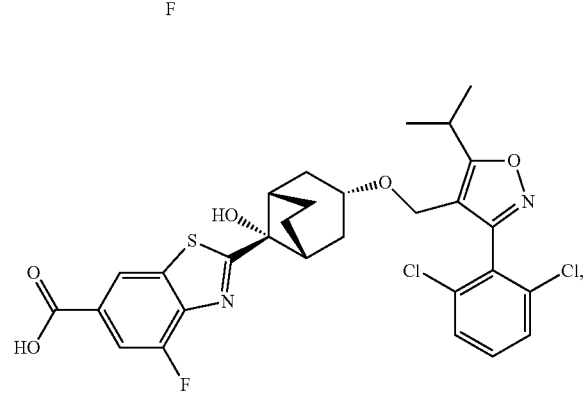
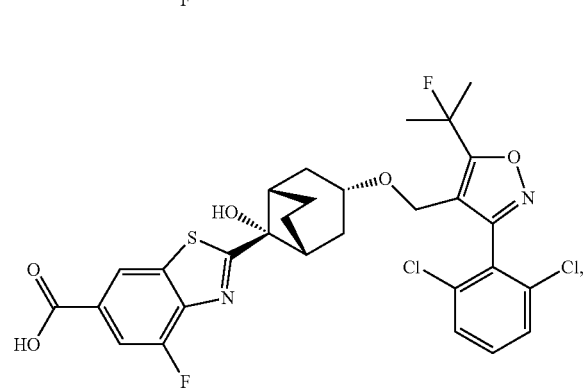
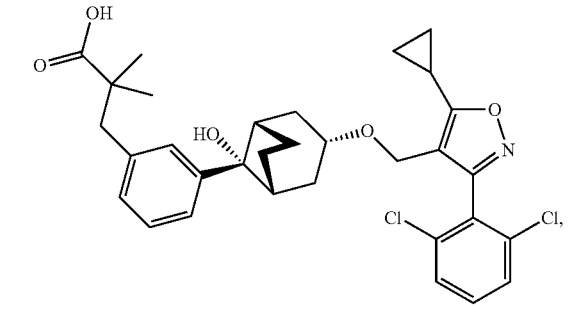
24
-continued
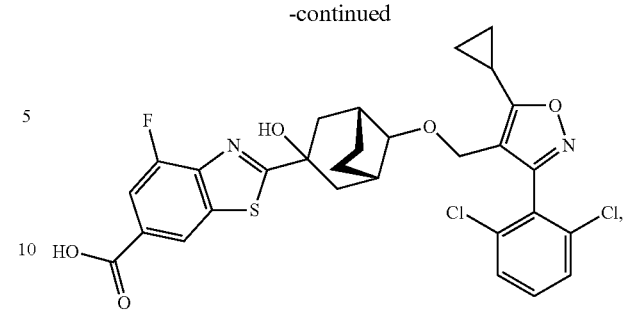
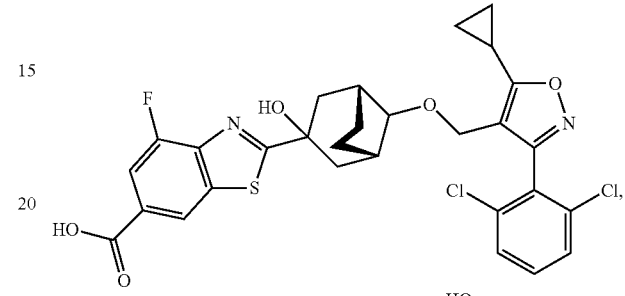
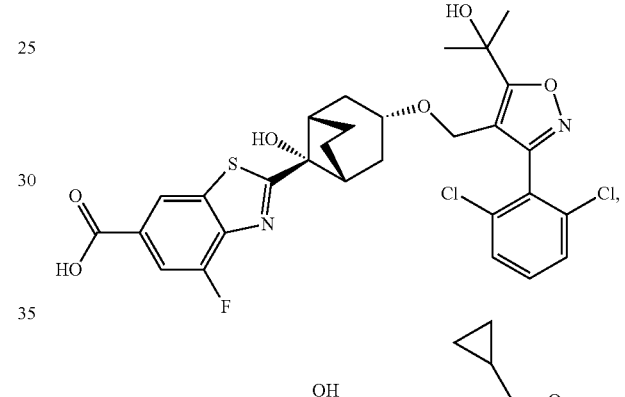

-continued
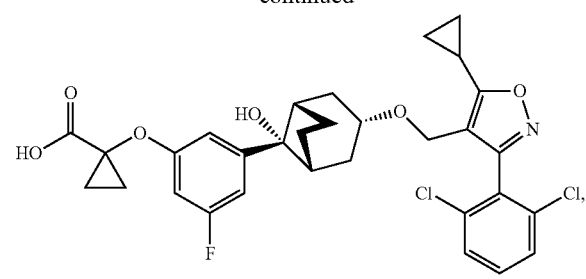
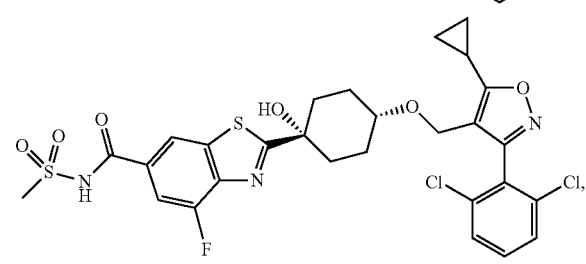
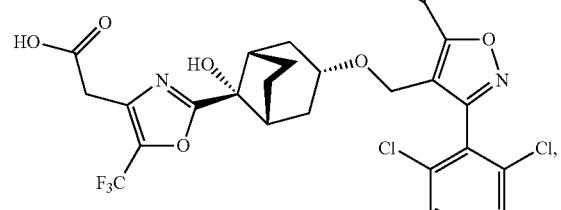
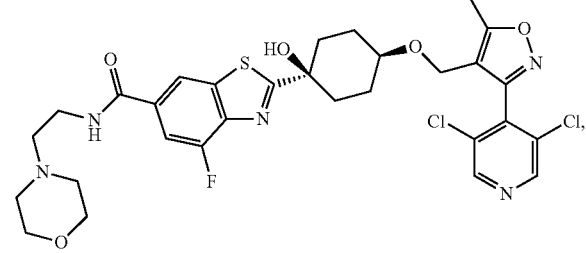
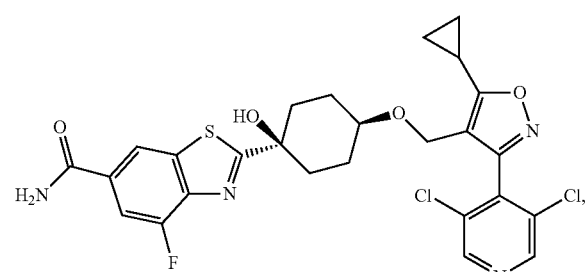
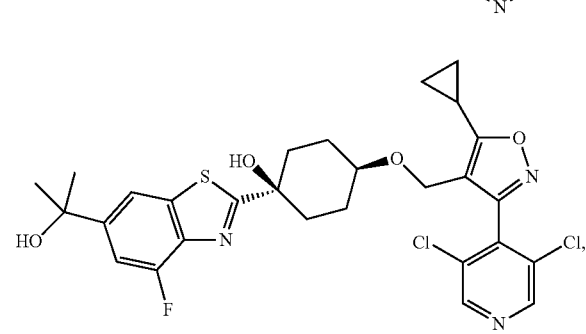
-continued
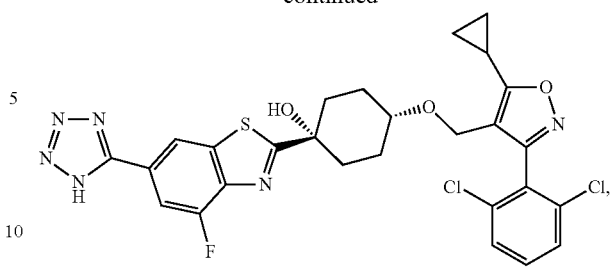
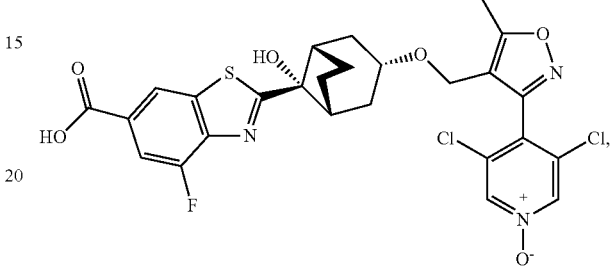
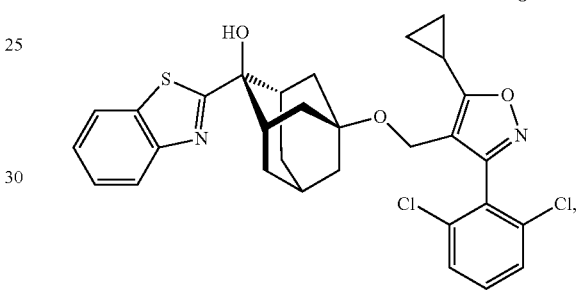
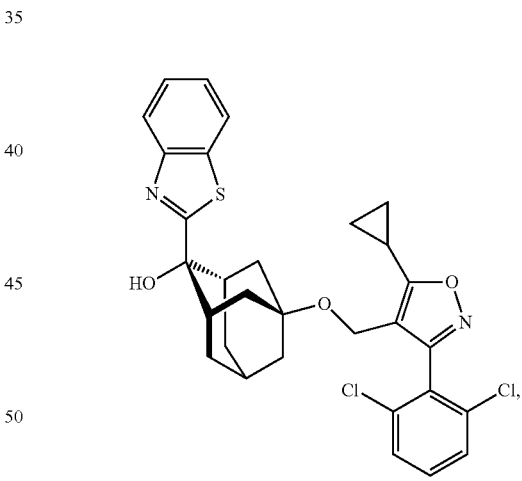
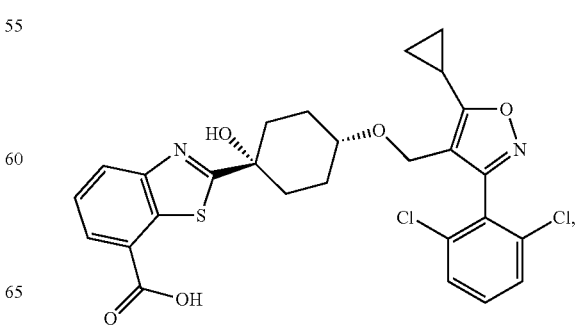

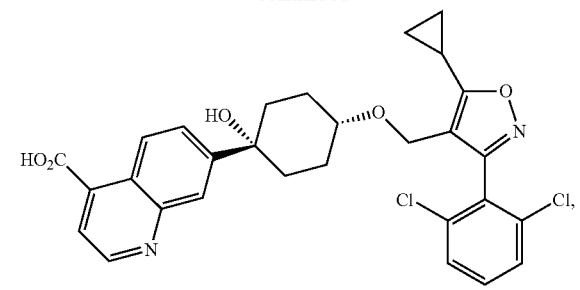
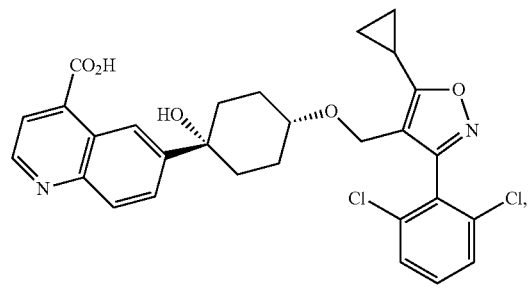
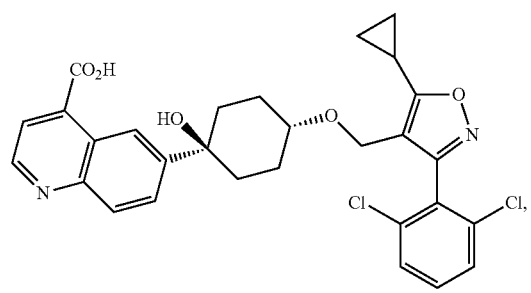
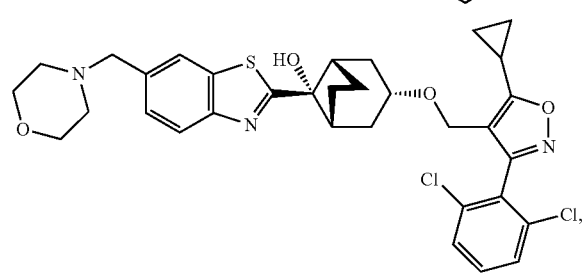
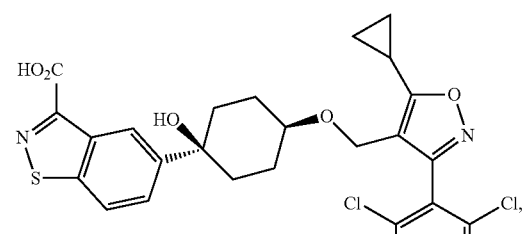
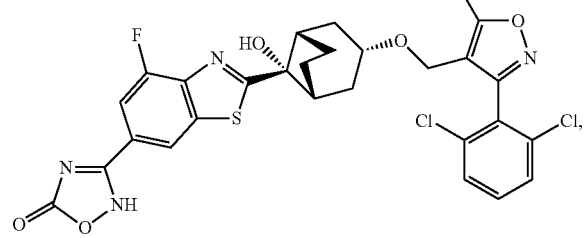
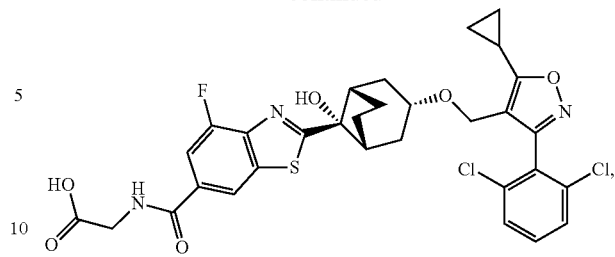
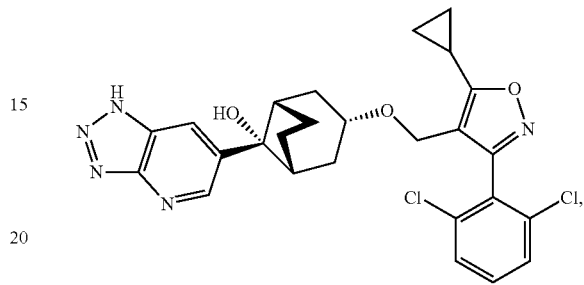
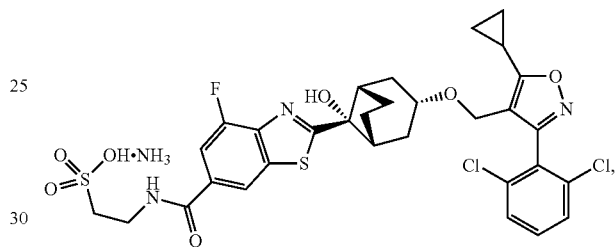
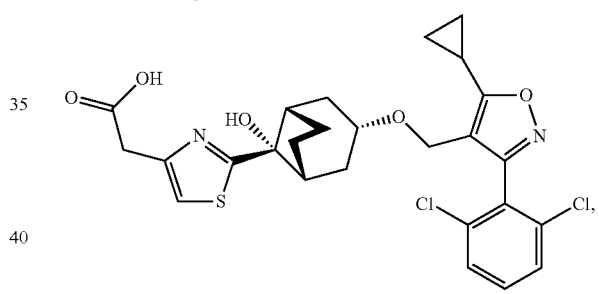
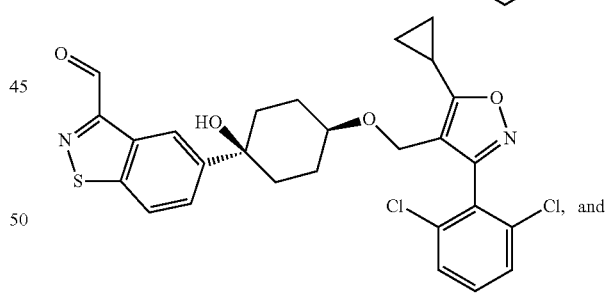
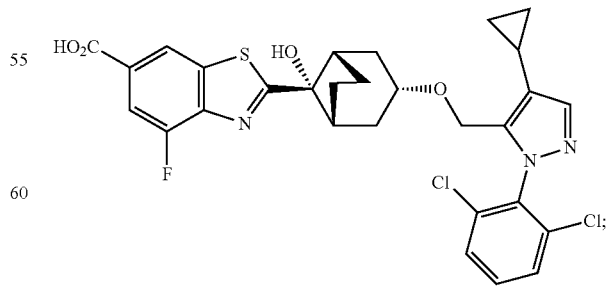
or an enantiomer, diastereomer, tautomer, solvate, prodrug or pharmaceutical acceptable salt thereof.

In the context of the present invention "$C_{1-6}$-alkyl" means a saturated alkyl chain having 1 to 6 carbon atoms which may be straight chained or branched. Examples thereof include methyl, ethyl, propyl, isopropyl, n-butyl, isobutyl, tert-butyl, n-pentyl, isopentyl, neopentyl and hexyl.

The term "halo-$C_{1-6}$-alkyl" means that one or more hydrogen atoms in the alkyl chain are replaced by a halogen. A preferred example thereof is $CF_3$.

"$C_{2-6}$-alkenyl" means an alkyl chain having 1 to 6 carbon atoms which may be straight chained or branched, containing at least one carbon to carbon double bond. Examples thereof include ethenyl, propenyl, butenyl, pentenyl, hexenyl or (1E,3Z)-2-methylpenta-1,3-dien-1-yl. Preferred examples are ethenyl, propenyl or (1E,3Z)-2-methylpenta-1,3-dien-1-yl.

"$C_{2-6}$-alkynyl" means an alkyl chain having 1 to 6 carbon atoms which may be straight chained or branched, containing at least one carbon to carbon triple bond. Examples thereof include ethynyl, propynyl, 1-butynyl, 2-butynyl, 1-pentynyl, 2-pentynyl, 1-hexynyl, 2-hexynyl or 3-hexynyl. Preferred examples thereof include ethynyl and propynyl.

A "$C_{0-6}$-alkylene" means that the respective group is divalent and connects the attached residue with the remaining part of the molecule. Moreover, in the context of the present invention, "$C_0$-alkylene" is meant to represent a bond.

A $C_{4-10}$-cycloalkyl group means a saturated or partially unsaturated mono-, bi- or spirocyclic ring system comprising 4 to 10 carbon atoms. Bridged carbocyclic ring systems comprise two or more ring systems which share non-adjacent bridgehead ring atoms. Examples include cyclopentyl, cyclohexyl, cyclohexenyl, bicyclo[2.2.2]octyl, bicyclo[3.2.1]octanyl, spiro[3.3]heptyl, bicyclo[2.2.1]heptyl, adamantyl and pentacyclo[4.2.0.0$^{2,5}$.0$^{3,8}$.0$^{4,7}$]octyl.

A $C_{3-10}$-heterocycloalkyl group means a saturated or partially unsaturated 3 to 10 membered carbon mono-, bi- or spirocyclic ring wherein 1, 2 or 3 carbon atoms are replaced by 1, 2 or 3 heteroatoms, respectively, wherein the heteroatoms are independently selected from N, O, S, SO and $SO_2$. Examples thereof include epoxidyl, oxetanyl, pyrrolidinyl, tetrahydrofuranyl, piperidinyl, piperazinyl tetrahydropyranyl, 1,4-dioxanyl, morpholinyl, 4-quinuclidinyl, 1,4-dihydropyridinyl and 3,6-dihydro-2H-thiopyranyl. The $C_{3-10}$-heterocycloalkyl group can be connected with the remaining part of the molecule via a carbon or nitrogen atom.

A 5-10-membered mono- or bicyclic heteroaromatic ring system (within the application also referred to as heteroaryl) containing up to 4 heteroatoms means a monocyclic heteroaromatic ring such as pyrrolyl, imidazolyl, furanyl, thiophenyl, pyridinyl, pyrimidinyl, pyrazinyl, pyrazolyl, oxazolyl, isoxazolyl, triazolyl, oxadiazolyl and thiadiazolyl. It further means a bicyclic ring system wherein the heteroatom(s) may be present in one or both rings including the bridgehead atoms. Examples thereof include quinolinyl, isoquinolinyl, quinoxalinyl, benzimidazolyl, benzisoxazolyl, benzofuranyl, benzoxazolyl, indolyl, indolizinyl and pyrazolo[1,5-a]pyrimidinyl. The nitrogen or sulphur atom of the heteroaryl system may also be optionally oxidized to the corresponding N-oxide, S-oxide or S,S-dioxide. If not stated otherwise, the heteroaryl system can be connected via a carbon or nitrogen atom. Examples for N-linked heterocycles are

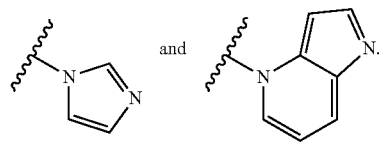 [SMILES: *n1ccnc1 ; *n1cccc2nccc1-2]

A 6-10-membered mono- or bicyclic aromatic ring system (within the application also referred to as aryl) means an aromatic carbon cycle such as phenyl or naphthalenyl.

The term "N-oxide" denotes compounds, where the nitrogen in the heteroaromatic system (preferably pyridinyl) is oxidized. Such compounds can be obtained in a known manner by reacting a compound of the present invention (such as in a pyridinyl group) with $H_2O_2$ or a peracid in an inert solvent.

Halogen is selected from fluorine, chlorine, bromine and iodine, more preferably fluorine or chlorine and most preferably fluorine.

Furthermore, the compounds of the present invention are partly subject to tautomerism. For example, if a heteroaromatic group containing a nitrogen atom in the ring is substituted with a hydroxy group on the carbon atom adjacent to the nitrogen atom, the following tautomerism can appear:

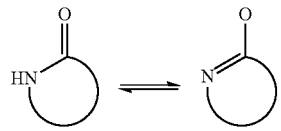

$C_{3-10}$-cycloalkyl group means a saturated or partially unsaturated mono-, bi-, spiro- or multicyclic ring system comprising 5 to 10 carbon atoms. A $C_{3-10}$-heterocycloalkyl group can be connected straight or spirocyclic, e.g. when cyclohexane is substituted with the heterocycloalkyl group oxetane, the following structures are possible:

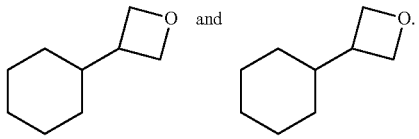 [SMILES: C1CCC(C2COC2)CC1 ; C1CCC(C2COC2)CC1]

It will be appreciated by the skilled person that when lists of alternative substituents include members which, because of their valency requirements or other reasons, cannot be used to substitute a particular group, the list is intended to be read with the knowledge of the skilled person to include only those members of the list which are suitable for substituting the particular group.

The compounds of the present invention can be in the form of a prodrug compound. "Prodrug compound" means a derivative that is converted into a compound according to the present invention by a reaction with an enzyme, gastric acid or the like under a physiological condition in the living body, e.g. by oxidation, reduction, hydrolysis or the like, each of which is carried out enzymatically. Examples of the prodrug are compounds, wherein the amino group in a compound of the present invention is acylated, alkylated or phosphorylated to form, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated. These compounds can be produced from compounds of the present invention according to well-known methods. Other examples of the prodrug are compounds, wherein the carbon/late in a compound of the present invention is, for example, converted into an alkyl-, aryl-, choline-, amino, acyloxymethylester, linolenoylester.

In the human liver, UDP-glucuronosyltransferases act on certain compounds having amino, carbamyl, thio(sulfhydryl) or hydroxyl groups to conjugate uridine diphosphate-α-D-glucuronic acid through glycoside bonds, or to esterify compounds with carboxy or hydroxyl groups in the process of phase II metabolism. Compounds of the present invention may be glucuronidated, that is to say, conjugated to glucuronic acid, to form glucuronides, particularly (β-D)glucuronides.

Metabolites of compounds of the present invention are also within the scope of the present invention.

One step in the formation of bile is the conjugation of the individual bile acids with an amino acid, particularly glycine or taurine. Compounds of the present invention may be conjugated with glycine or taurine at a substitutable position.

Where tautomerism, like e.g. keto-enol tautomerism, of compounds of the present invention or their prodrugs may occur, the individual forms, like e.g. the keto and enol form, are each within the scope of the invention as well as their mixtures in any ratio. Same applies for stereoisomers, like e.g. enantiomers, cis/trans isomers, conformers and the like.

If desired, isomers can be separated by methods well known in the art, e.g. by liquid chromatography. Same applies for enantiomers by using e.g. chiral stationary phases. Additionally, enantiomers may be isolated by converting them into diastereomers, i.e. coupling with an enantiomerically pure auxiliary compound, subsequent separation of the resulting diastereomers and cleavage of the auxiliary residue. Alternatively, any enantiomer of a compound of the present invention may be obtained from stereoselective synthesis using optically pure starting materials. Another way to obtain pure enantiomers from racemic mixtures would use enantioselective crystallization with chiral counterions.

The compounds of the present invention can be in the form of a pharmaceutically acceptable salt or a solvate. The term "pharmaceutically acceptable salts" refers to salts prepared from pharmaceutically acceptable non-toxic bases or acids, including inorganic bases or acids and organic bases or acids. In case the compounds of the present invention contain one or more acidic or basic groups, the invention also comprises their corresponding pharmaceutically or toxicologically acceptable salts, in particular their pharmaceutically utilizable salts. Thus, the compounds of the present invention which contain acidic groups can be present on these groups and can be used according to the invention, for example, as alkali metal salts, alkaline earth metal salts or ammonium salts. More precise examples of such salts include sodium salts, potassium salts, calcium salts, magnesium salts or salts with ammonia or organic amines such as, for example, ethylamine, ethanolamine, triethanolamine or amino acids. The compounds of the present invention which contain one or more basic groups, i.e. groups which can be protonated, can be present and can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to the person skilled in the art like, for example, by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

Further the compounds of the present invention may be present in the form of solvates, such as those which include as solvate water, or pharmaceutically acceptable solvates, such as alcohols, in particular ethanol.

Furthermore, the present invention provides pharmaceutical compositions comprising at least one compound of the present invention, or a prodrug compound thereof, or a pharmaceutically acceptable salt or solvate thereof as active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing at least one compound of the present invention and a pharmaceutically acceptable carrier.

The pharmaceutical composition of the present invention may additionally comprise one or more other compounds as active ingredients like a prodrug compound or other nuclear receptor modulators.

The compositions are suitable for oral, rectal, topical, parenteral (including subcutaneous, intramuscular, and intravenous), ocular (ophthalmic), pulmonary (nasal or buccal inhalation) or nasal administration, although the most suitable route in any given case will depend on the nature and severity of the conditions being treated and on the nature of the active ingredient. They may be conveniently presented in unit dosage form and prepared by any of the methods well-known in the art of pharmacy.

As a result, the present invention relates to compounds according to the general Formula (1) which bind to FXR and act as agonists or modulators of FXR.

The invention further relates to the use of said compounds for the treatment and/or prophylaxis of diseases and/or conditions through binding of said nuclear receptor by said compounds. Further, the present invention relates to the use of said compounds for the preparation of a medicament for the treatment and/or prophylaxis of diseases and/or conditions through binding of said nuclear receptor by said compounds. Specifically, the present invention relates to the use of compounds according to Formula (1) in the preparation of a medicament for the prophylaxis and/or treatment of chronic intrahepatic or some forms of extrahepatic cholestatic conditions, of liver fibrosis, of acute intraheptic cholestatic conditions, of obstructive or chronic inflammatory disorders that arise out of improper bile composition, of gastrointestinal conditions with a reduced uptake of dietary fat and fat-soluble dietary vitamins, of inflammatory bowel diseases, of lipid and lipoprotein disorders, of Type II Diabetes and clinical complications of Type I and Type II Diabetes, of conditions and diseases which result from chronic fatty and fibrotic degeneration of organs due to enforced lipid and specifically triglyceride accumulation and subsequent activation of profibrotic pathways, of obesity and metabolic syndrome (combined conditions of dyslipidemia, diabetes and abnormally high body-mass index), of acute myocardial infarction, of acute stroke, of thrombosis which occurs as an endpoint of chronic obstructive atherosclerosis, of persistant infections by intracellular bacteria or parasitic protozoae, of non-malignant hyperproliferative disorders, of malignant hyperproliferative disorders, of colon adenocarcinoma and hepatocellular carcinoma in particular, of liver steatosis and associated syndromes, of liver failure or liver malfunction as an outcome of chronic liver diseases or of surgical liver resection, of Hepatitis B infection, of Hepatitis C infection and/or of cholestatic and fibrotic effects that are associated with alcohol-induced cirrhosis or with viral-borne forms of hepatitis.

Medicaments as referred to herein may be prepared by conventional processes, including the combination of a compound according to the present invention and a pharmaceutically acceptable carrier.

FXR is proposed to be a nuclear bile acid sensor. As a result, it modulates both, the synthetic output of bile acids in the liver and their recycling in the intestine (by regulating bile acid binding proteins). But beyond bile acid physiology, FXR seems to be involved in the regulation of many diverse physiological processes which are relevant in the etiology and for the treatment of diseases as diverse as cholesterol gallstones, metabolic disorders such as Type II Diabetes, dyslipidemias or obesity, chronic inflammatory diseases such as Inflammatory Bowel Diseases or chronic intrahepatic forms of cholestasis and many others diseases (T. Claude) et al., Arterioscler. Thromb. Vasc. Biol. 2005, 25, 2020; Y. D. Wang et al., Cell Res. 2008, 18, 1087.

FXR regulates a complex pattern of response genes in the liver and in the gastrointestinal tract. The gene products have impact on diverse physiological processes. In the course of functional analysis of FXR, the first regulatory network that was analyzed was the regulation of bile acid synthesis. While the LXRs induce the key enzyme of the conversion of cholesterol into bile acids, Cyp7A1, via the induction of the regulatory nuclear receptor LRH-1, FXR represses the induction of Cyp7A1 via the upregulation of mRNA encoding SHP, a further nuclear receptor that is dominant repressive over LRH-1. Since FXR binds the end products of this pathway, primary bile acids such as cholic acid (CA) or CDCA, this can be regarded as an example of feedback inhibition on the gene expression level (B. Goodwin et al., Mol. Cell 2000, 6, 517; T. T. Lu et al., Mol. Cell 2000, 6, 507). Parallel to the repression of bile acid synthesis via SHP, FXR induces a range of so-called ABC (for ATP-binding cassette) transporters that are responsible for the export of toxic bile acids from the hepatocyte cytosol into the canaliculi, the small bile duct ramifications where the bile originates. This hepatoprotective function of FXR became first apparent with the analysis of FXR knockout mice (C. J. Sinai et al., Cell 2000, 102, 731), where under- or overexpression of several ABC-transporters in the liver was shown. Further detailed analysis revealed that the major bile salt excretory pump BSEP or ABCB11 (M. Ananthanarayanan et al., J. Biol. Chem. 2001, 276, 28857; J. R. Plass et al., Hepatology 2002, 35, 589) as well as the key enzyme which mediates lipid transfer from lipoproteins to phospholipids, PLTP (N. L. Urizar et al., J. Biol. Chem. 2000, 275, 39313), and the two key canalicular membrane transporters for phospholipids, MRP-2 (ABCC4) (H. R. Kast et al., J. Biol. Chem. 2002, 277, 2908) and MDR-3 (ABCB4); L. Huang et al., J. Biol. Chem. 2003, 278, 51085) are direct targets for ligand-directed transcriptional activation by FXR (summarized in: M. Miyata, J. Pharmacol. Exp. Ther. 2005, 312, 759; G. Rizzo et al., Curr. Drug Targets Immune Endocr. Metabol. Disord. 2005, 5, 289).

The fact that FXR seems to be the major metabolite sensor and regulator for the synthesis, export and re-circulation of bile acids suggested the use of FXR ligands to induce bile flow and change bile acid composition towards more hydrophilic composition. With the development of the first synthetic FXR ligand GW4064 (P. R. Maloney et al., J. Med. Chem. 2000, 43, 2971; T. M. Willson et al., Med. Res. Rev. 2001, 21, 513) as a tool compound and of the semi-synthetic artificial bile acid ligand 6-alpha-ethyl-CDCA, the effects of superstimulation of FXR by potent agonists could be analyzed. It was shown that both ligands induce bile flow in bile duct ligated animals. Moreover, in addition to choleretic effects, also hepatoprotective effects could be demonstrated (R. Pellicciari et al., J. Med. Chem. 2002, 45, 3569; Y. Liu et al., J. Clin. Invest. 2003, 112, 1678). This hepatoprotective effect was further narrowed down to an anti-fibrotic effect that results from the repression of Tissue Inhibitors of Matrix-Metalloproteinases, TIMP-1 and 2, the induction of collagen-deposit resolving Matrix-Metalloproteinase 2 in hepatic stellate cells and the subsequent reduction of alpha-collagen mRNA and Transforming growth factor beta (TGF-beta) mRNA which are both pro-fibrotic factors by FXR agonists (S. Fiorucci et al., Gastroenterology 2004, 127, 1497; S. Fiorucci et al., J. Pharmacol. Exp. Ther. 2005, 314, 584). Furthermore, anti-cholestatic activity was demonstrated in bile-duct ligated animal models as well as in animal models of estrogen-induced cholestasis (S. Fiorucci et al., J. Pharmacol. Exp. Ther. 2005, 313, 604).

Genetic studies demonstrate that in hereditary forms of cholestasis (Progressive Familiar Intrahepatic Cholestasis=PFIC, Type I-IV) either nuclear localization of FXR itself is reduced as a consequence of a mutation in the FIC1 gene (in PFIC Type I, also called Byler's Disease) (F. Chen et al., Gastroenterology 2004, 126, 756; L. Alvarez et al., Hum. Mol. Genet. 2004, 13, 2451) or levels of the FXR target gene encoding MDR-3 phospholipid export pump are reduced (in PFIC Type III). Taken together there is a growing body of evidence that FXR binding compounds will demonstrate substantial clinical utility in the therapeutic regimen of chronic cholestatic conditions such as Primary Biliary Cirrhosis (PBC) or Primary Sclerosing Cholangitis (PSC) (reviewed in: G. Rizzo et al., Curr. Drug Targets Immune Endocr. Metabol. Disord. 2005, 5, 289; G. Zollner et al., Mol. Pharm. 2006, 3, 231; S. Y. Cai et al., Expert Opin. Ther. Targets 2006, 10, 409).

The deep impact that FXR activation has on bile acid metabolism and excretion is not only relevant for cholestatic syndromes but even more directly for a therapy against gallstone formation. Cholesterol gallstones form due to low solubility of cholesterol that is actively pumped out of the liver cell into the lumen of the canaliculi. It is the relative percentage of content of the three major components, bile acids, phospholipids and free cholesterol that determines the formation of mixed micelles and hence apparent solubility of free cholesterol in the bile. FXR polymorphisms map as quantitative trait loci as one factor contributing to gallstone disease (H. Wittenburg, Gastroenterology 2003, 125, 868). Using the synthetic FXR tool compound GW4064 it could be demonstrated that activation of FXR leads to an improvement of the Cholesterol Saturation Index (CSI) and directly to an abolishment of gallstone formation in C57L gallstone susceptible mice whereas drug treatment in FXR knockout mice shows no effect on gallstone formation (A. Moschetta et al., Nature Medicine 2004, 10, 1352).

These results qualify FXR as a good target for the development of small molecule agonists that can be used to prevent cholesterol gallstone formation or to prevent re-formation of gallstones after surgical removal or shockwave lithotripsy (discussed in: S. A. Doggrell, Curr. Opin. Investig. Drugs 2006, 7, 344).

Thus, in one embodiment of the invention, the compound according to Formula (1) and pharmaceutical compositions comprising said compound is used for the prophylaxis and/or treatment of obstructive or chronic inflammatory disorders that arise out of improper bile composition such as cholelithiasis also known as cholesterol gallstones.

Beyond its strong hepatoprotective and choleretic as well as anti-fibrotic effects that FXR shows upon small molecule stimulated activation in the liver, FXR seems to have a role in protecting the intestine from neoplastic transformation and from the development of polyps and their transition into adenocarcinoma in the gut (S. Modica et al., Cancer Res. 2008, 68, 9589 and R. R. Maran et al., J. Pharmacol. Exp. Ther. 2009, 328, 469). Similar to the situation in the intestine absence of FXR leads to a high increase in the formation of Hepatocellular Cacrcinoma (HCC), the most prominent form of liver cancer (I. Kim et al., Carcinogenesis 2007, 28, 940 and F. Yang et al., Cancer Res. 2007, 67, 863). Whereas a functional FXR prevents the formation of colon adenocarcinoma and hepatocellular carcinoma, FXR activation induces liver regeneration after hepatectomy (W. Huang et al., Science 2006, 312, 233).

The combined hepatoprotective, anti-neoplastic and liver regenerative effects associated with FXR activation can be therapeutically exploited for the use of FXR agonists in the treatment of sever liver diseases. In one embodiment, the compounds according to the invention and pharmaceutical compositions comprising said compounds are used in the treatment of liver diseases such as HCC, stimulation of liver regrowth and amelioration of side effects associated with major liver resection, liver cirrhosis independent of the etiology and prevention or treatment of liver ischemia in the course of liver transplantation or major liver surgery.

Since the discovery of the first synthetic FXR agonist and its administration to rodents it became evident that FXR is a key regulator of serum triglycerides (P. Maloney et al., J. Med. Chem. 2000, 43, 2971; T. Willson et al., Med. Res. Rev. 2001, 21, 513). Over the past six years accumulating evidence has been published that activation of FXR by synthetic agonists leads to significant reduction of serum triglycerides, mainly in the form of reduced VLDL, but also to reduced total serum cholesterol (H. R. Kast et al., Mol. Endocrinol. 2001, 15, 1720; N. L. Urizar et al., Science 2002, 296, 1703; G. Lambert et al., J. Biol. Chem. 2003, 278, 2563; M. Watanabe et al., J. Clin. Invest. 2004, 113, 1408; A. Figge et al., J. Biol. Chem. 2004, 279, 2790; S. Bilz et al., Am. J. Physiol. Endocrinol. Metab. 2006, 290, E716).

But the lowering of serum triglycerides is not a stand alone effect. Treatment of db/db or ob/ob mice with synthetic FXR agonist GW4064 resulted in marked and combined reduction of serum triglycerides, total cholesterol, free fatty acids, ketone bodies such as 3-OH Butyrate. Moreover, FXR activation engages with the intracellular insulin signaling pathway in hepatocytes, resulting in reduced output of glucose from liver gluconeogenesis but concomitant increase in liver glycogen. Insulin sensitivity as well as glucose tolerance were positively impacted by FXR treatment (K. R. Stayrook et al., Endocrinology 2005, 146, 984; Y. Zhang et al., PNAS 2006, 103, 1006; B. Cariou et al., J. Biol. Chem. 2006, 281, 11039; K. Ma et al., J. Clin. Invest. 2006, 116, 1102; D. Duran-Sandoval et al., Biochimie 2005, 87, 93). An effect on reduction of body weight was also recently observed in mice overfed with a high lipid diet (C. Lihong et al., American Diabetes Association (ADA) 66th annual scientific sessions, June 2006, Abstract Number 856-P). This weight loss effect might results from FXR's induction of FGF-19, a fibroblast growth factor that is known to lead to weight loss and athletic phenotype (J. Holt et al., Genes Dev. 2003, 17, 1581; E. Tomlinson et al., Endocrinology 2002, 143, 1741). In recent patent applications, the effect of FXR agonist on reduction of body weight was demonstrated (WO 2004/087076; WO 2003/080803).

Taken together, these pharmacological effects of FXR agonists can be exploited in different therapeutic ways: FXR binding compounds are thought to be good candidates for the treatment of Type II Diabetes because of their insulin sensitization, glycogenogenic, and lipid lowering effects.

In one embodiment, the compounds according to the invention and pharmaceutical compositions comprising said compounds are used in the prophylaxis and/or treatment of Type II Diabetes which can be overcome by FXR-mediated upregulation of systemic insulin sensitivity and intracellular insulin signalling in liver, increased peripheral glucose uptake and metabolisation, increased glycogen storage in liver, decreased output of glucose into serum from liver-borne gluconeogenesis.

In a further embodiment, said compounds and pharmaceutical compositions are used for the prophylaxis and/or treatment of chronic intrahepatic, such as PBC, PSC, progressive familiar cholestasis (PFIC), alcohol-induced cirrhosis and associated cholestasis, and some forms of extrahepatic cholestatic conditions, or liver fibrosis.

The invention also relates to a compound of Formula (1) or to a pharmaceutical composition comprising said compound for the prophylaxis and/or treatment of gastrointestinal conditions with a reduced uptake of dietary fat and fat-soluble dietary vitamins which can be overcome by increased intestinal levels of bile acids and phospholipids.

In a further embodiment, said compound or pharmaceutical composition is used for preventing and/or treating a disease selected from the group consisting of lipid and lipoprotein disorders such as hypercholesterolemia, hypertriglyceridemia, and atherosclerosis as a clinically manifest condition which can be ameliorated by FXR's beneficial effect on lowering total plasma cholesterol, lowering serum triglycerides, increasing conversion of liver cholesterol into bile acids and increased clearance and metabolic conversion of VLDL and other lipoproteins in the liver.

In one further embodiment, said compound and pharmaceutical composition are used for the prophylaxis and/or treatment of diseases where the combined lipid lowering, anti-cholestatic and anti-fibrotic effects of FXR-targeted medicaments can be exploited for the treatment of liver steatosis and associated syndromes such as NASH, or for the treatment of cholestatic and fibrotic effects that are associated with alcohol-induced cirrhosis, or with viral-borne forms of hepatitis.

In conjunction with the hypolipidemic effects it was also shown that loss of functional FXR leads to increased atherosclerosis in ApoE knockout mice (E. A. Hanniman et al., J. Lipid Res. 2005, 46, 2595). Therefore, FXR agonists might have clinical utility as anti-atherosclerotic and cardioprotective drugs. The downregulation of Endothelin-1 in Vascular Smooth Muscle Cells might also contribute to such beneficial therapeutic effects (F. He et al., Circ. Res. 2006, 98, 192).

The invention also relates to a compound according to Formula (1) or a pharmaceutical composition comprising said compound for preventive and posttraumatic treatment of cardiovascular disorders such as acute myocardial infarction, acute stroke, or thrombosis which occur as an endpoint of chronic obstructive atherosclerosis.

Beyond controlling intestinal and colonic polyp formation, FXR seems to be expressed in breast cancer tissue and cell lines but not in healthy breast tissue and seems to interact with the Estrogen Receptor in ER positive breast cancer cells (K. E. Swales et al., Cancer Res. 2006, 66, 10120 and F. Journe et al., Breast Cancer Res. Treat. 2009, 115, 523).

This would allow to regard FXR also as a potential target for the treatment of proliferative diseases, especially metastasizing cancer forms that express a small molecule responsive form of FXR.

In a further embodiment, said compounds and pharmaceutical compositions are used for the prophylaxis and/or treatment of malignant hyperproliferative disorders such as different forms of cancer, specifically certain forms of breast, liver or colon cancer where interference with an FXR ligand will have a beneficial impact.

Finally, FXR seems also to be involved in the control of antibacterial defense in the intestine (T. Inagaki et al., PNAS. 2006, 103, 3920) although an exact mechanism is not provided. From these published data, however, one can conclude that treatment with FXR agonists might have a beneficial impact in the therapy of Inflammatory Bowel Disorders (IBD), in particular those forms where the upper (ileal) part of the intestine is affected (e.g. ileal Crohn's disease) because this seems to be the site of action of FXR's control on bacterial growth. In IBD the desensitization of the adaptive immune response is somehow impaired in the intestinal immune system. Bacterial overgrowth might then be the causative trigger towards establishment of a chronic inflammatory response. Hence, dampening of bacterial growth by FXR-borne mechanisms might be a key mechanism to prevent acute inflammatory episodes.

Thus, the invention also relates to a compound according to Formula (1) or a pharmaceutical composition comprising said compound for preventing and/or treating a disease related to Inflammatory Bowel Diseases such as Crohn's disease or Colitis ulcerosa. FXR-mediated restoration of intestinal barrier function and reduction in non-commensal bacterial load is believed to be helpful in reducing the exposure of bacterial antigens to the intestinal immune system and can therefore reduce inflammatory responses.

The invention further relates to a compound or pharmaceutical composition for the prophylaxis and/or treatment of obesity and associated disorders such as metabolic syndrome (combined conditions of dyslipidemias, diabetes and abnormally high body-mass index) which can be overcome by FXR-mediated lowering of serum triglycerides, blood glucose and increased insulin sensitivity and FXR-mediated weight loss.

In a further embodiment, the compounds or pharmaceutical composition of the present invention are useful in preventing and/or treating clinical complications of Type I and Type II Diabetes. Examples of such complications include Diabetic Nephropathy, Diabetic Retinopathy, Diabetic Neuropathies, or Peripheral Arterial Occlusive Disease (PAOD). Other clinical complications of Diabetes are also encompassed by the present invention.

Furthermore, conditions and diseases which result from chronic fatty and fibrotic degeneration of organs due to enforced lipid and specifically triglyceride accumulation and subsequent activation of profibrotic pathways may also be prevented and/or treated by applying the compounds or pharmaceutical composition of the present invention. Such conditions and diseases encompass NASH and chronic cholestatic conditions in the liver, Glomerulosclerosis and Diabetic Nephropathy in the kidney, Macula Degeneration and Diabetic Retinopathy in the eye and Neurodegenerative diseases such as Alzheimer's Disease in the brain, or Diabetic Neuropathies in the peripheral nervous system.

In practical use, the compounds of the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Since the compounds of the present invention mostly represent carboxylic acids or similar anionic isosters thereof, and since it is well known that salt forms of ionic drug compounds can substantially affect the bioavailability of drug compounds, the compounds of the present invention may also be used as salts with various countercations to yield an orally available formulation.

Such pharmaceutically acceptable cations may be amongst others mono- or bivalent ions such as ammonium, the alkaline metals sodium or potassium or the alkaline earth metals magnesium or calcium, certain pharmaceutically acceptable amines such as tris(hydroxymethyl)amino-methane, ethylendiamine, diethylamine, piperazine or others, or certain cationic amino acids such as lysine or arginine.

The compounds of the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing FXR mediated conditions for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligram to about 50 milligrams. In the case of a 70 kg adult human, the total daily dose will generally be from about 7 milligrams to about 350 milligrams. This dosage regimen may be adjusted to provide the optimal therapeutic response.

The compounds of the present invention can be prepared according to the procedures of the following Schemes and Examples, using appropriate materials and are further exemplified by the following specific examples. Moreover, by utilizing the procedures described herein, in conjunction with ordinary skills in the art, additional compounds of the present invention claimed herein can be readily prepared. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described above.

The amine-free bases corresponding to the isolated salts can be generated by neutralization with a suitable base, such as aqueous sodium hydrogen carbonate, sodium carbonate, sodium hydroxide and potassium hydroxide, and extraction of the liberated amine-free base into an organic solvent, followed by evaporation. The amine-free base, isolated in this manner, can be further converted into another pharmaceutically acceptable salt by dissolution in an organic solvent, followed by addition of the appropriate acid and subsequent evaporation, precipitation or crystallization. The carboxylic free acids corresponding to the isolated salts can be generated by neutralization with a suitable acid, such as aqueous hydrochloric acid, sodium hydrogen sulfate, sodium dihydrogen phosphate, and extraction of the liberated carboxylic-free acid into an organic solvent, followed by evaporation. The carboxylic acid, isolated in this manner, can be further converted into another pharmaceutically acceptable salt by dissolution in an organic solvent, followed by addition of the appropriate base and subsequent evaporation, precipitation or crystallization.

An illustration of the preparation of compounds of the present invention is shown below. Unless otherwise indicated in the schemes, the variables have the same meaning as described above. The examples presented below are intended to illustrate particular embodiments of the invention. Suitable starting materials, building blocks and reagents employed in the synthesis as described below are commercially available from Sigma-Aldrich or Acros Organics, for example, or can be routinely prepared by procedures described in the literature, for example in "March's Advanced Organic Chemistry: Reactions, Mechanisms, and Structure", 5$^{th}$ Edition; John Wiley & Sons or T. Eicher, S. Hauptmann "The Chemistry of Heterocycles; Structures, Reactions, Synthesis and Application", 2$^{nd}$ edition, Wiley-VCH 2003; Fieser et al. "Fiesers' Reagents for organic Synthesis" John Wiley & Sons 2000.

General Schemes

The compounds of the present invention can be prepared according to Schemes 1 to 3. An alicyclic ring Q which bears a ketal functionality and a hydroxyl group (1-1) can be alkylated with chloro- or bromomethyl heteroaromatics XCH$_2$Z in the presence of a strong base in appropriate solvents at appropriate temperatures to give intermediates 1-2. The ketal functionality of 1-2 can be deprotected under acidic conditions to form a ketone 1-3. Intermediates 1-3 can add metallated aromatics or heteroaromatics to form hydroxyl-bearing intermediates 1-4, which can be further transformed at the substituent R' to the compounds of the present invention.

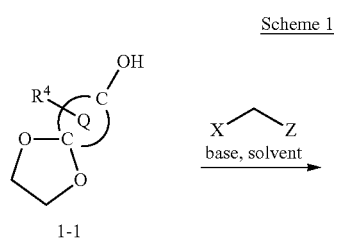

Scheme 1

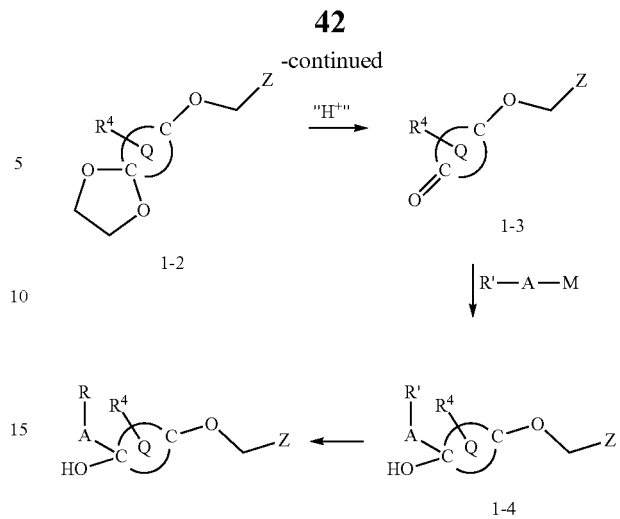

More precisely, as depicted in Scheme 2, 1,4-dioxaspiro[4.5]decan-8-ol (2-1) can be alkylated with chloro- or bromomethyl heteroaromatics XCH$_2$Z in the presence of a strong base in appropriate solvents at appropriate temperatures to give intermediates 2-2. After deprotection under acidic conditions cyclohexanone derivatives 2-3 are formed. Intermediates 2-3 can add metallated aromatics or heteroaromatics to form hydroxyl-bearing cyclohexylderivatives 2-4, which can be separated into the two single isomers 2-4' and 2-4" with the two oxygen substituents at the cyclohexyl ring cis or trans to each other. Intermediates 2-4' and 2-4" can each be further transformed at the substituent R' to the compounds of the present invention.

Scheme 2

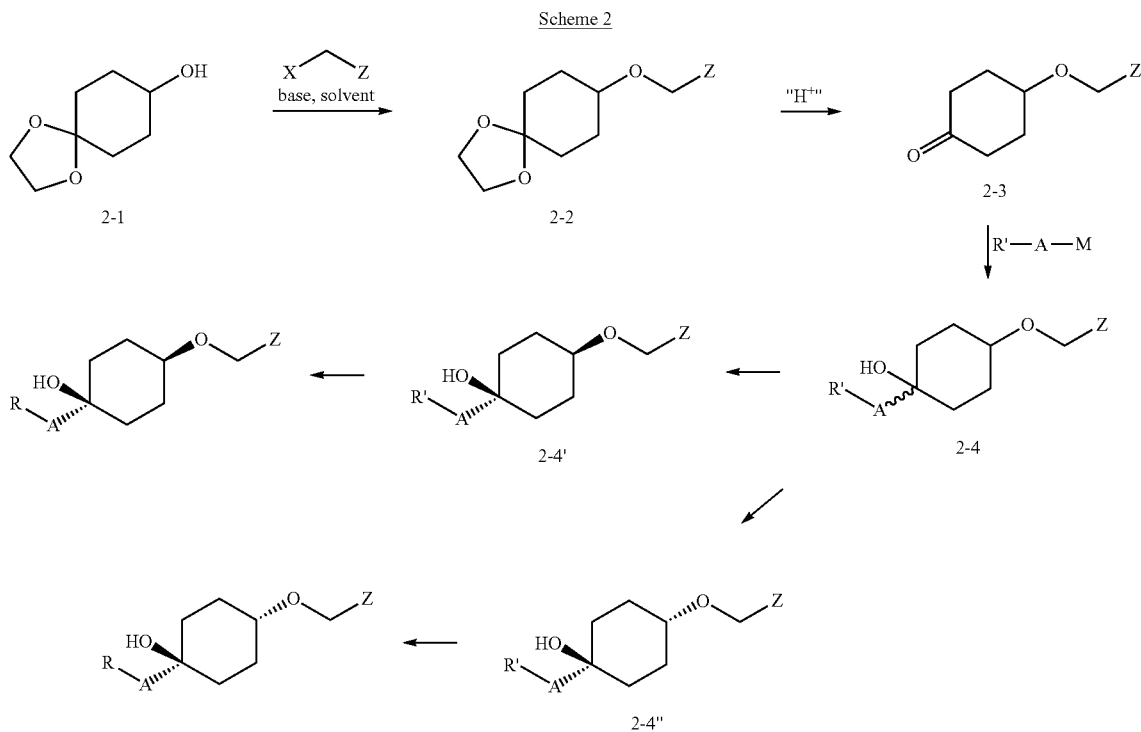

In Scheme 3 is depicted the general synthesis scheme for a bicyclic linker element Q. The bicyclic alcohol Int-5-2, which is a mixture of exo and endo isomers can be alkylated with chloro- or bromomethyl heteroaromatics XCH$_2$Z in the presence of a strong base in appropriate solvents at appropriate temperatures to give intermediates 3-2 and 3-T which can be separated by standard procedures like e.g. flash chromatography on silica gel with appropriate eluents. The cyclic ketals 3-2 can be deprotected under acidic conditions to afford bicyclic ketones 3-3 which undergo addition of metallated aromatics or heteroaromatics to form hydroxyl-bearing intermediates 3-4. These can be further transformed at the substituent R' to the compounds of the present invention by standard reactions known to persons skills in the art. The endo isomers 3-T give rise to the corresponding endo isomeric final compounds of the present invention, following the same transformations as depicted for the exo isomer 3-2 in Scheme 3.

ACN acetonitrile

TMS trimethylsilyl

TEMPO 2,2,6,6-tetramethylpiperidinyloxyl, free radical

PCC pyridinium perchromate

HMPA hexamethylphosphonamide

Dba dibenzylidineacetone

Xantphos 4,5-bis(diphenylphosphino)-9,9-dimethylxanthene

EDCl 1-(3-dimethylaminopropyl)-3-ethylcarbodiimide hydrochloride

DMAP 4-dimethylaminopyridine

Scheme 3

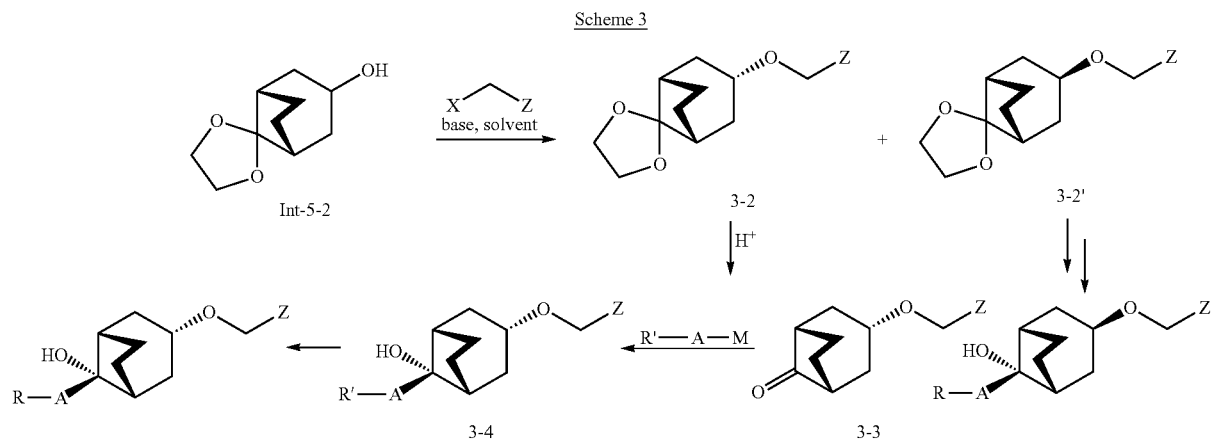

LIST OF ABBREVIATIONS

DMF dimethylformamide

NCS N-chlorosuccinimide

DCM dichloromethane

THF tetrahydrofurane

PE petroleum ether

DMSO dimethylsulfoxide

IBX o-iodoxybenzoic acid

DBU 1,8-diazabicyclo[5.4.0]undec-7-ene p-TsOH p-toluenesulfonic acid

TEA triethylamine

MsCl mesyl chloride

TFA trifruoroacetic acid

DIAD diisopropyl azodicarboxylate

DAST (dimethylamino)sulfur trifluoride

TLC thin layer chromatography

MeCN acetonitrile m-CPBA m-chloroperbenzoic acid

SEM-Cl 2-(trimethylsilyl)ethoxymethyl chloride

TFAA trifluoroacetic anhydride

Intermediate Int-1-1: (5-Cyclopropyl-3-(4,4-difluorocyclohexyl)isoxazol-4-yl)methanol

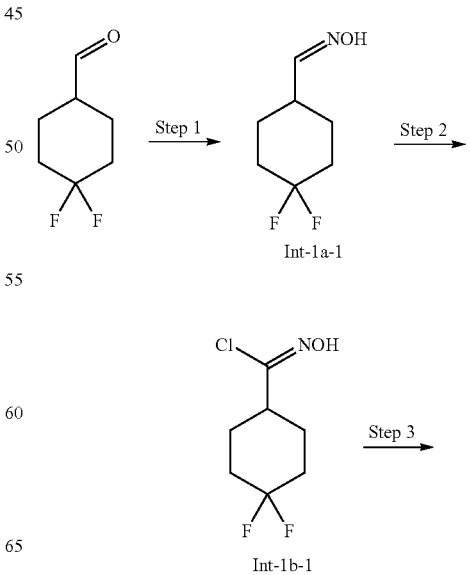

45

-continued

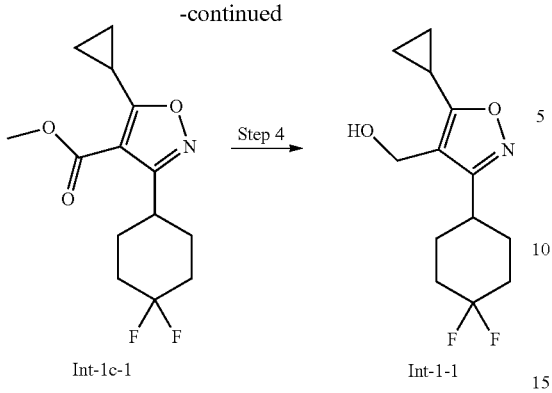

Int-1c-1 → Int-1-1

Step 1:

To a solution of 4,4-difluorocyclohexanecarbaldehyde (7.0 g, 47.3 mmol) in EtOH (70 mL) was added a mixture of $NH_2OH \cdot HCl$ (3.9 g, 56.7 mmol) and $Na_2CO_3$ (6.0 g, 56.7 mmol) in water (18 mL). The mixture was stirred at rt for 2 h, diluted with water (200 mL) and extracted with EtOAc (3×50 mL). The combined the organic layers were wash with brine (50 mL), dried, filtered and concentrated to afford 4,4-difluorocyclohexanecarbaldehyde oxime Int-1a-1.

Step 2:

To a solution of 4,4-difluorocyclohexanecarbaldehyde oxime Int-1a-1 (1.0 g, 6.2 mmol) in DMF (10 mL) was added NCS (1.0 g, 7.4 mmol). The reaction was stirred at rt for 1 h, diluted with water and extracted with DCM (3×500 mL). The combined the organic layers were washed with brine (2×100 mL), dried, filtered and concentrated to give 4,4-difluoro-N-hydroxycyclohexanecarbimidoyl chloride Int-1b-1, which was used without further purification.

Step 3:

To a solution of methyl 3-cyclopropyl-3-oxopropanoate (1.3 g, 9.3 mmol) in THF (60 mL) was added $Et_3N$ (6.3 g 62 mmol) and the reaction was stirred at rt for 30 min, then 4,4-difluoro-N-hydroxycyclohexanecarbimidoyl chloride Int-1b-1 in THF was added dropwise. The resulting mixture was stirred for 2 h at rt, evaporated and the residue was partitioned with water (100 mL) and EtOAc (50 mL). The organic layer was washed with brine, dried, filtered, concentrated and purified by column chromatography (PE/EtOAc=10:1) to afford methyl 5-cyclopropyl-3-(4,4-difluorocyclohexyl)isoxazole-4-carboxylate Int-1c-1.

Step 4:

To a solution of methyl 5-cyclopropyl-3-(4,4-difluorocyclohexyl)isoxazole-4-carboxylate Int-1c-1 (3.9 g, 13.7 mmol) in THF (39 mL) was added $LiAlH_4$ (27.4 mL, 27.4 mmol, 1M in THF) dropwise at 0° C. The reaction was stirred for 30 min, then water (1 mL), 10% NaOH (2 mL) and water (3 mL) was added subsequently. The mixture was filtered, concentrated and purified by column chromatography (PE/EtOAc=2:1) to give (5-cyclopropyl-3-(4,4-difluorocyclohexyl)isoxazol-4-yl)methanol Int-1-1. $^1$H-NMR (500 MHz, $CDCl_3$) δ 4.58 (d, J=5.0 Hz, 2H), 2.86 (t, J=10.8 Hz, 1H), 2.22-2.18 (m, 2H), 2.08-1.79 (m, 7H), 1.58-1.56 (m, 1H), 1.15-1.11 (m, 2H), 1.07-1.03 (m, 2H). LCMS (ESI): m/z 258.2 (M+H)$^+$.

Intermediate Int-1-2: (5-Cyclopropyl-3-(spiro[2.5]octan-6-yl)isoxazol-4-yl)methanol

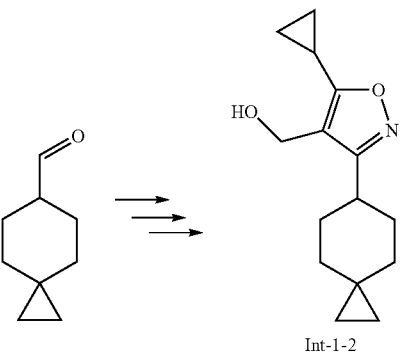 [SMILES: O=CC1CCC2(CC1)CC2 ; OCc1c(C2CCC3(CC2)CC3)noc1C1CC1]

Similar as described for intermediate Int-1-1 (step 1 to step 4) starting from spiro[2.5]octane-6-carbaldehyde the synthesis furnished (5-cyclopropyl-3-(spiro[2.5]octan-6-yl)isoxazol-4-yl)methanol Int-1-2. $^1$H-NMR (500 MHz, $CDCl_3$): δ 4.96 (t, J=5.5 Hz, 1H), 4.35 (d, J=5.0 Hz, 2H), 2.76-2.71 (m, 1H), 2.17-2.14 (m, 1H), 1.89-1.86 (m, 2H), 1.80-1.74 (m, 2H), 1.63-1.55 (m, 2H), 1.03-0.91 (m, 6H), 0.31-0.28 (m, 2H), 0.22-0.20 (m, 2H). LCMS (ESI): m/z 248.3 (M+H)$^+$.

Intermediate Int-1-3: (5-Cyclopropyl-3-(2-(difluoromethoxy)phenyl)isoxazol-4-yl)methanol

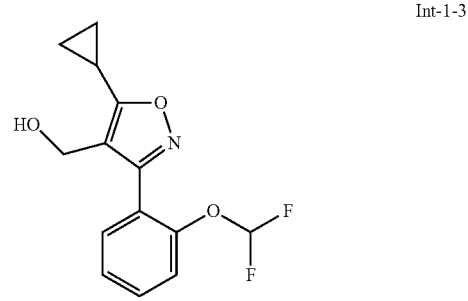 [SMILES: OCc1c(-c2ccccc2OC(F)F)noc1C1CC1]

Intermediate Int-1-3 was synthesized as described in WO2012/087519.

Intermediate Int-1-4: (5-Cyclopropyl-3-(2-cyclopropylphenyl)isoxazol-4-yl)methanol

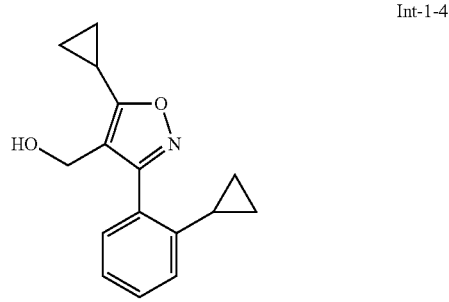 [SMILES: OCc1c(-c2ccccc2C2CC2)noc1C1CC1]

Intermediate Int-1-4 was synthesized as described in WO2012/087519.

Intermediate Int-1-5: (5-Cyclopropyl-3-(2,6-dimethylphenyl)isoxazol-4-yl)methanol

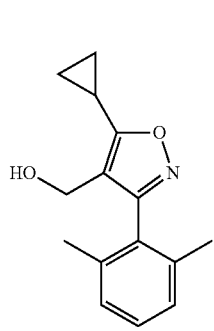

Intermediate Int-1-5 was synthesized as described in WO2012/087519.

Intermediate Int-1-6: (4-Cyclopropyl-1-(2,6-dichlorophenyl)-1H-pyrazol-5-yl)methanol

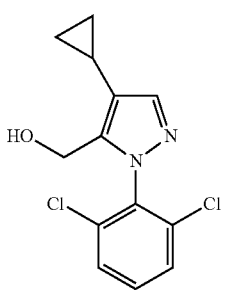

Intermediate Int-1-6 was synthesized as described in WO2009/012125.

Intermediate Int-1-7: (5-Cyclopropyl-3-(2-(trifluoromethoxy)phenyl)isoxazol-4-yl)methanol

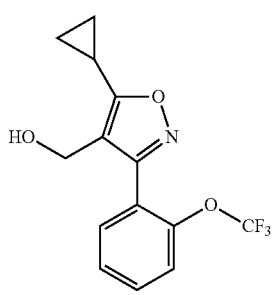

Intermediate Int-1-7 was synthesized as described in WO2012/087519.

Intermediate Int-1-8: (5-Cyclopropyl-3-(2-(difluoromethyl)phenyl)isoxazol-4-yl)methanol

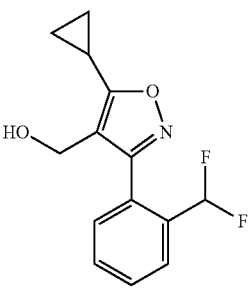

Similar as described for intermediate Int-1-1 (step 1 to step 4) starting from 2-(difluoromethyl)benzaldehyde, the intermediate (5-cyclopropyl-3-(2-(difluoromethyl)phenyl)isoxazol-4-yl)methanol Int-1-8 was synthesized. $^1$H-NMR (500 MHz, DMSO-$d_6$): δ 7.81-7.80 (m, 1H), 7.71-7.66 (m, 3H), 6.95 (t, J=55 Hz, 1H), 5.10 (t, J=5.0 Hz, 1H), 4.27 (d, J=5.0 Hz, 2H), 2.33-2.30 (m, 1H), 1.15-1.07 (m, 4H). LCMS (ESI): m/z 266.2 (M+H)$^+$.

Intermediate Int-1-9: (4-Cyclopropyl-1-(2-(difluoromethoxy)phenyl)-1H-pyrazol-5-yl)methanol

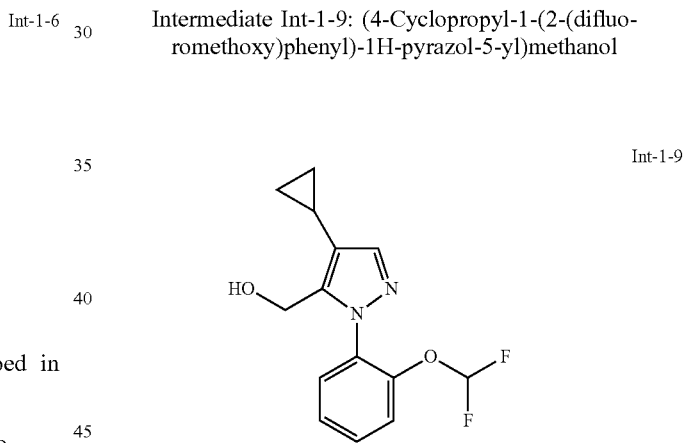

Similar as described in WO2009/012125 for intermediate (4-cyclopropyl-1-(2,6-dichlorophenyl)-1H-pyrazol-5-yl)methanol starting from (2-(difluoromethoxy)phenyl)hydrazine, the intermediate (4-cyclopropyl-1-(2-(difluoromethoxy)phenyl)-1H-pyrazol-5-yl)methanol Int-1-9 was synthesized.

Intermediate Int-1-10: (3-(2,6-Bis(difluoromethyl)phenyl)-5-cyclopropylisoxazol-4-yl)methanol

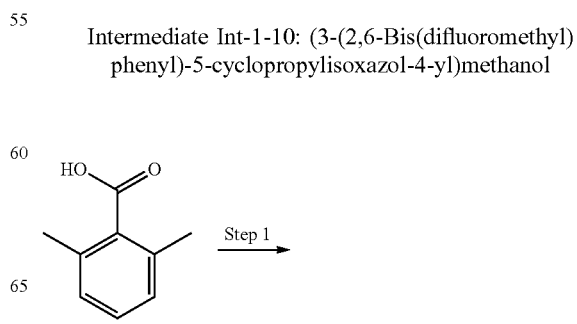

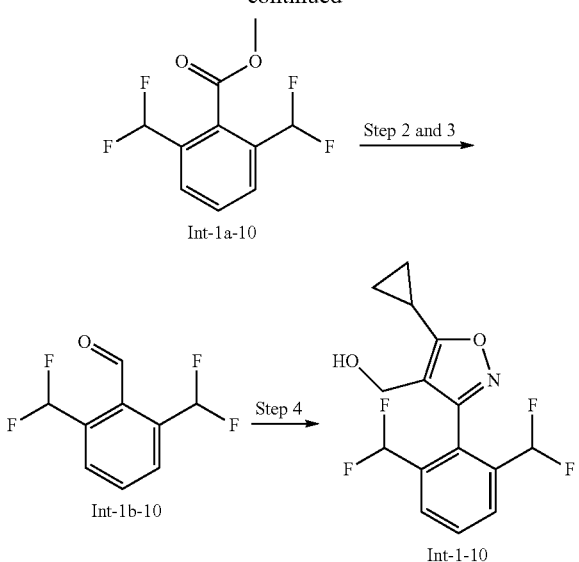

Step 1:

Starting from 2,6-dimethylbenzoic acid the intermediate methyl 2,6-bis(difluoro-methyl)benzoate Int-1a-10 was prepared as described in WO2007/144327.

Step 2:

To a solution of 2,6-bis(difluoromethyl)benzoate Int-1a-10 (51.3 g, 217 mmol) in THF (550 mL) was added LiAlH$_4$ (1N, 430 mL) at 0° C. and stirred at this temperature for 1 h, quenched with water (16 mL), 1N NaOH (32 mL) and then water (48 mL). The mixture was filtered and the crude filtrate concentrated to give (2,6-bis(difluoromethyl)phenyl)methanol, which was used in the next step without purification.

Step 3:

A solution of (2,6-bis(difluoromethyl)phenyl)methanol (46.2 g, crude) and IBX (189 g, 666 mmol) in acetone (450 mL) was stirred at 50° C. overnight and after filtration, the filtrate was evaporated to give 2,6-bis(difluoromethyl)benzaldehyde Int-1b-10 which was used in the next step without purification.

Step 4:

Similar as described for intermediate Int-1-1 (step 1 to step 4) starting from 2,6-bis(difluoromethyl)benzaldehyde Int-1b-10, the intermediate (3-(2,6-bis(difluoromethyl)phenyl)-5-cyclopropylisoxazol-4-yl)methanol Int-1-10 was synthesized. $^1$H-NMR (500 MHz, DMSO-d$_6$): δ 7.97 (d, J=8.0 Hz, 2H), 7.88 (t, J=8.0 Hz, 1H), 6.69 (t, J=54.5 Hz, 2H), 5.02 (t, J=5.0 Hz, 1H), 4.16 (d, J=5.0 Hz, 2H), 2.33-2.30 (m, 1H), 1.17-1.10 (m, 4H). LC/MS (ESI): m/z 316.1 (M+H)$^+$.

Intermediate Int-1-11: 5-Cyclopropyl-3-(2,6-dichlorophenethyl)-4-(hydroxymethyl)oxazol-2(3H)-one

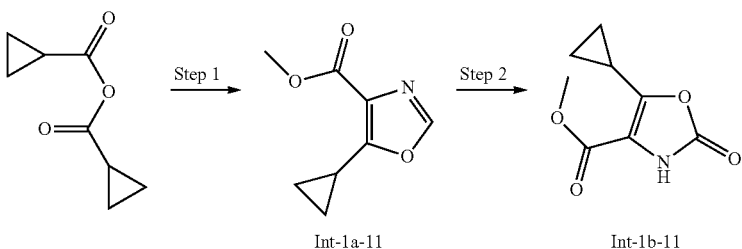

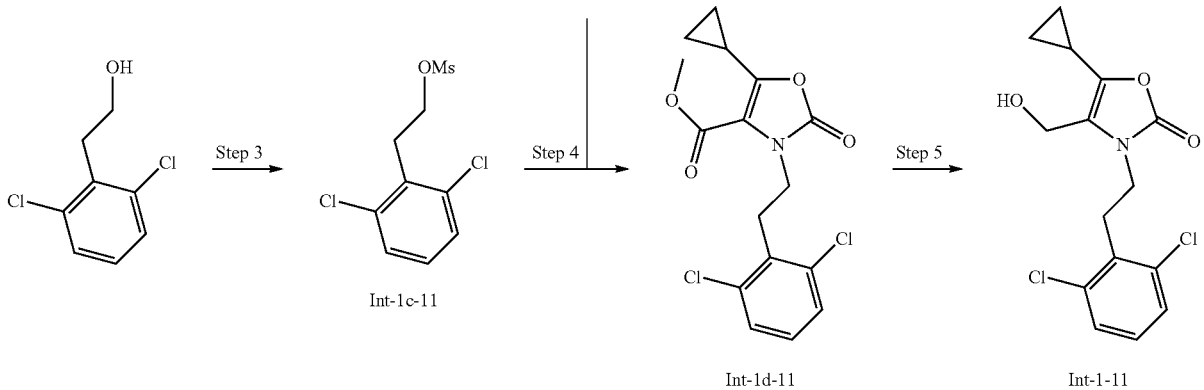

Step 1:

To a solution of methyl 2-isocyanoacetate (72.7 g, 729 mmol) and DBU (111 g, 729 mmol) in THF (1 L) was added a solution of cyclopropanecarboxylic anhydride (112 g, 729 mmol) in THF (100 mL) portionwise at 5° C. The mixture was stirred at rt overnight, concentrated and purified by flash chromatography (PE/EtOAc=5:1) to afford methyl 5-cyclopropyloxazole-4-carboxylate Int-1a-11. $^1$H-NMR (CDCl$_3$, 300 MHz): δ 1.04-1.18 (m, 4H), 2.74-2.79 (m, 1H), 3.91 (s, 3H), 7.60 (s, 1H).

Step 2:

A solution of methyl 5-cyclopropyloxazole-4-carboxylate Int-1a-11 (36.4 g, 218 mmol) and TsOH.H$_2$O (82.9 g, 436 mmol) in MeOH (600 mL) was heated to reflux overnight. The mixture was cooled to rt and concentrated in vacuo. The residue was triturated with Et$_2$O and filtered to afford the crude methyl 2-amino-3-cyclopropyl-3-oxopropanoate (62.8 g, 191 mmol) which was dissolved in THF (1.5 L) and TEA (77.2 g, 764 mmol). Then triphosgene (19.9 g, 67 mmol) was added to the mixture at −50° C. for 1 h. The solution was diluted with Et$_2$O (500 mL) and saturated aqueous NH$_4$Cl (300 mL) was added. The aqueous phase was separated and extracted with Et$_2$O (3×1 L). The combined organic extracts were washed with brine (500 mL), dried over Na$_2$SO$_4$, concentrated and purified by flash chromatography (PE/EtOAc=5:1) to afford methyl 5-cyclopropyl-2-oxo-2,3-dihydrooxazole-4-carboxylate Int-1b-11. $^1$H-NMR (CDCl$_3$, 300 MHz): δ 0.99-1.11 (m, 4H), 2.41-2.50 (m, 1H), 3.84 (s, 3H), 8.57 (s, 1H).

Step 3:

To a solution of 2-(2,6-dichlorophenyl)ethanol (37.3 g, 195 mmol) and TEA (32.7 g, 235 mmol) in DCM (700 mL) was added MsCl (26.9 g, 235 mmol) dropwise at 0° C. After addition, the solution was stirred at rt overnight, diluted with water (200 mL) and extracted with DCM (3×400 mL). The combined organic layer was dried over Na$_2$SO$_4$, filtered, concentrated and purified by flash chromatography (PE/EtOAc=5:1) to afford 2,6-dichlorophenethyl methanesulfonate Int-1c-11. $^1$H-NMR (300 MHz, CDCl$_3$): δ 2.95 (s, 3H), 3.43 (t, J=7.5 Hz, 2H), 4.41 (t, J=7.5 Hz, 2H), 7.12-7.17 (m, 1H), 7.31 (d, J=8.4 Hz, 2H).

Step 4:

To a solution of methyl 5-cyclopropyl-2-oxo-2,3-dihydrooxazole-4-carboxylate Int-1b-11 (23.5 g, 129 mmol) in DMF (800 mL) was added NaH (5.7 g, 142 mmol; 60% in mineral oil) at 0° C. under nitrogen. The mixture was stirred for 15 min, then a solution of 2,6-dichlorophenethyl methanesulfonate Int-1c-11 (41.5 g, 154 mmol) in DMF (400 mL) was added dropwise at 0° C. After addition, the mixture was stirred at 100° C. overnight, cooled, diluted with water (1500 mL) and extracted with EtOAc (3×700 mL). The combined organic layer was washed with water (2×200 mL) and brine (300 mL), dried over Na$_2$SO$_4$, filtered and concentrated in vacuum. The residue was washed with PE/EtOAc (5:1) to afford methyl 5-cyclopropyl-3-(2,6-dichlorophenethyl)-2-oxo-2,3-dihydrooxazole-4-carboxylate Int-1d-11. $^1$H-NMR (300 MHz, CDCl$_3$): δ 0.97-1.08 (m, 4H), 2.44-2.49 (m, 1H), 3.31 (t, J=4.8 Hz, 2H). 3.73 (s, 3H), 4.26 (t, J=4.8 Hz, 2H), 7.08-7.12 (m, 1H), 7.26-7.28 (m, 2H).

Step 5:

To a solution of methyl 5-cyclopropyl-3-(2,6-dichlorophenethyl)-2-oxo-2,3-dihydrooxazole-4-carboxylate Int-1d-11 (13.9 g, 39 mmol) in THF (400 mL) was added a solution of LiAlH$_4$ (16.3 mL, 39 mmol) in THF at 0° C. under nitrogen. After addition, the solution was stirred at 0° C. for 30 min, sequentially diluted with H$_2$O (2 mL), 1M NaOH (2 mL) and H$_2$O (6 mL), filtered and concentrated in vacuum. The residue was washed with PE/EtOAc (2:1) to afford 5-cyclopropyl-3-(2,6-dichlorophenethyl)-4-(hydroxymethyl)oxazol-2(3H)-one Int-1-11. $^1$H-NMR (CD$_3$OD, 300 MHz): δ 0.73-0.77 (m, 2H), 0.83-0.88 (m, 2H), 1.75-1.79 (m, 1H), 3.30-3.38 (m, 2H), 3.95 (t, J=6.6 Hz, 2H). 4.10 (s, 2H), 7.20-7.25 (m, 1H), 7.37 (d, J=8.1 Hz, 2H), hydroxyl proton not resolved. LC/MS (ESI): m/z 328.0 (M+H)$^+$.

Intermediate Int-1-12: (5-Cyclopropyl-3-((2,6-dimethylphenoxy)methyl)isoxazol-4-yl)methanol

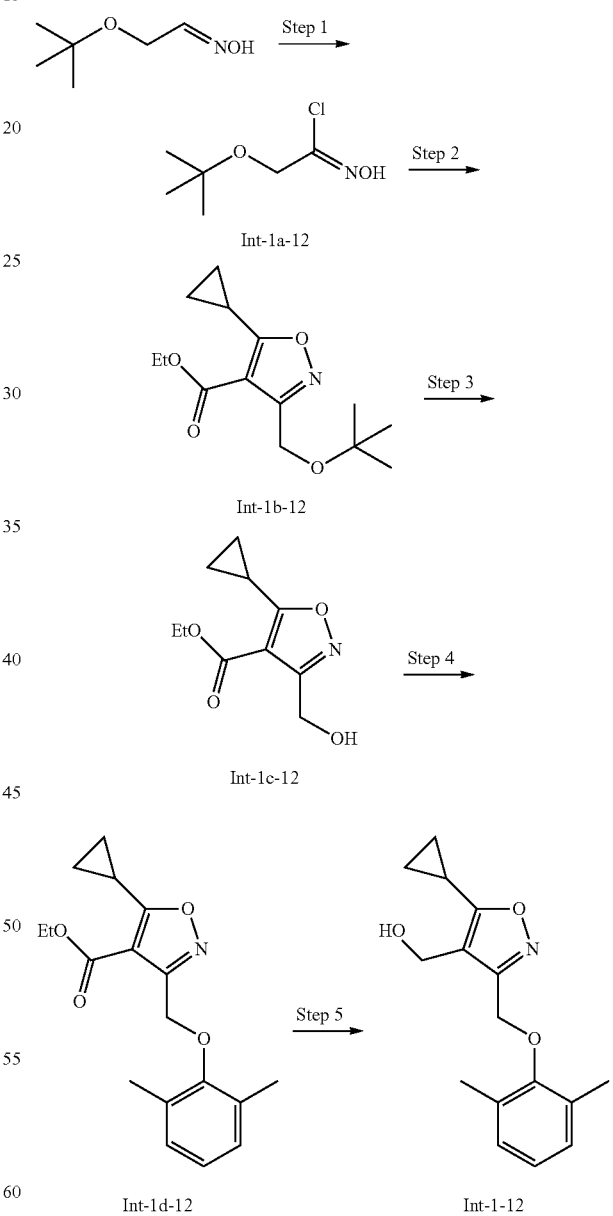

Step 1:

To a solution of 2-(tert-butoxy)acetaldehyde oxime (24.1 g, 184 mmol; prepared as described in WO2009/005998) in DMF (600 mL) was added NCS (23.7 g, 184 mmol) at 0° C.

The mixture was stirred for 1 h, poured into Et₂O (800 mL) and washed with brine (450 mL). The organic layer was dried over MgSO₄ and concentrated to give the crude 2-(tert-butoxy)-N-hydroxyacetimidoyl chloride Int-1a-12, which was used directly in the next step.

Step 2:

To a solution of ethyl 3-cyclopropyl-3-oxopropanoate (31.6 g, 203 mmol) in THF (600 mL) was added a solution of NaOCH₃ (0.5 M, 10.9 g, 203 mmol) in MeOH at 0° C. After stirring for 5 min, a solution of 2-(tert-butoxy)-N-hydroxyacetimidoyl chloride Int-1a-12 (27.9 g, 169 mmol) in THF (200 mL) was added dropwise. The mixture was allowed to warm to rt and stirred overnight, poured into Et₂O (800 mL), washed with brine (450 mL) and concentrated to give the crude ethyl 3-(tert-butoxymethyl)-5-cyclopropylisoxazole-4-carboxylate Int-1b-12, which was used directly in the next step.

Step 3:

To a solution of ethyl 3-(tert-butoxymethyl)-5-cyclopropylisoxazole-4-carboxylate Int-1b-12 (38.4 g, 144 mmol) in DCM (600 mL) was added TFA (100 mL) at rt. The mixture was stirred at rt for 2 h, concentrated and adjust to basic pH with aq. NaHCO₃. The mixture was extracted with EtOAc (3×300 mL). The combined organic layer was washed with brine (400 mL), dried over MgSO₄, concentrated and purified by column chromatography (PE/EtOAc=10:1) to afford ethyl 5-cyclopropyl-3-(hydroxymethyl)isoxazole-4-carboxylate Int-1c-12. ¹H-NMR (300 MHz, DMSO-d₆): δ 4.64 (s, 2H), 4.26 (q, J=7.2 Hz, 2H), 2.79-2.70 (m, 1H), 1.29 (t, J=7.2 Hz, 3H), 1.23-1.13 (m, 4H).

Step 4:

To a solution of ethyl 5-cyclopropyl-3-(hydroxymethyl)isoxazole-4-carboxylate Int-1c-12 (16.1 g, 76.3 mmol), 2,6-dimethylphenol (9.3 g, 76.3 mmol) and PPh₃ (20 g, 76.3 mmol) in toluene (500 mL) was added DIAD (15.4 g, 76.3 mmol) at 0° C. The mixture was stirred at 90° C. for 2 h, cooled, concentrated and purified by column chromatography (PE/EtOAc=15:1) to afford ethyl 5-cyclopropyl-3-((2,6-dimethylphenoxy)methyl)isoxazole-4-carboxylate Int-1d-12. ¹H-NMR (300 MHz, DMSO-d₆): δ 7.03 (d, J=7.8, Hz, 2H), 6.96-6.87 (m, 1H), 5.03 (s, 2H), 4.25 (q, J=7.2 Hz, 2H), 2.82-2.76 (m, 1H), 2.18 (s, 6H), 2.14 (s, 3H), 1.28-1.17 (m, 4H).

Step 5:

To a solution of LiAlH₄ (2.9 g, 77.6 mmol) in THF (250 mL) was added ethyl 5-cyclopropyl-3-((2,6-dimethylphenoxy)methyl)isoxazole-4-carboxylate Int-1d-12 (16.3 g, 51.7 mmol) at 0° C. The mixture was stirred at rt for 1 h, diluted with water (100 mL) and extracted with EtOAc (3×100 mL). The combined organic layer was washed with brine (200 mL), dried over MgSO₄, concentrated and purified by column chromatography (PE/EtOAc=8:1) to afford (5-cyclopropyl-3-((2,6-dimethylphenoxy)methyl)isoxazol-4-yl)methanol Int-1-12. ¹H-NMR (300 MHz, DMSO-d₆): δ 7.04 (d, J=7.5, Hz, 2H), 6.97-6.92 (m, 1H), 5.07 (br s, 1H), 4.85 (s, 2H), 4.46 (s, 2H), 2.30-2.26 (m, 1H), 2.22 (s, 6H), 1.10-0.96 (m, 4H). LC/MS (ESI): m/z 256.1 (M−H₂O+H)⁺.

Intermediate Int-1-13: 2-(3-(2,6-Dichlorophenyl)-4-(hydroxymethyl)isoxazol-5-yl)propan-2-ol

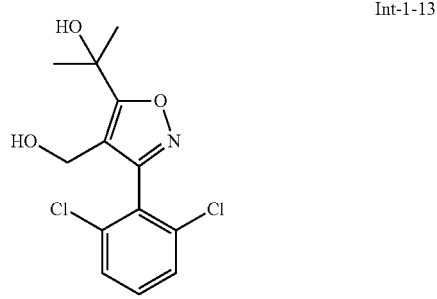 [SMILES: CC(C)(O)c1onc(-c2c(Cl)cccc2Cl)c1CO]

Int-1-13

Intermediate Int-1-13 was synthesized as described in WO2011/020615.

Intermediate Int-2-1: 4-(Chloromethyl)-5-cyclopropyl-3-(4,4-difluorocyclohexyl)isoxazole

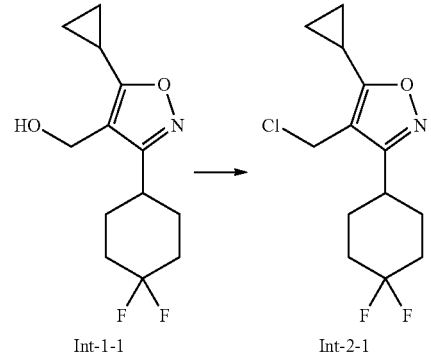 [SMILES: OCc1c(C2CCC(F)(F)CC2)noc1C1CC1 ; FC1(F)CCC(c2noc(C3CC3)c2CCl)CC1]

Int-1-1    Int-2-1

To a solution of (5-cyclopropyl-3-(4,4-difluorocyclohexyl)isoxazol-4-yl)methanol Int-1-1 (500 mg, 1.9 mmol) in DCM (5 mL) was added thionyl chloride (450 mg, 3.8 mmol). The reaction was stirred for 1 h at rt and concentrated to afford 4-(chloromethyl)-5-cyclopropyl-3-(4,4-difluoro-cyclohexyl)isoxazole Int-2-1, which was used without further purification.

Intermediate Int-2-2: 4-(Chloromethyl)-5-cyclopropyl-3-(spiro[2.5]octan-6-yl)isoxazole 4-(chloromethyl)-5-cyclopropyl-3-(spiro[2.5]octan-6-yl)isoxazole

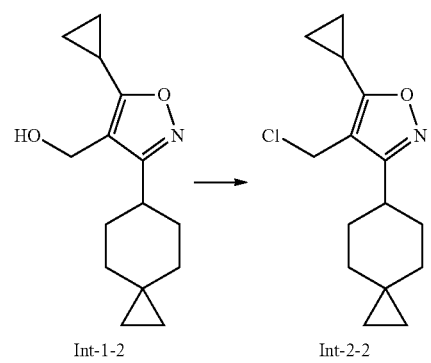 [SMILES: OCc1c(C2CCC3(CC2)CC3)noc1C1CC1 ; ClCc1c(C2CCC3(CC2)CC3)noc1C1CC1]

Int-1-2    Int-2-2

Similar as described for intermediate Int-2-1, starting from (5-cyclopropyl-3-(spiro[2.5]octan-6-yl)isoxazol-4-yl)methanol Int-1-2, the synthesis furnished 4-(chloromethyl)-5-cyclopropyl-3-(spiro[2.5]octan-6-yl)isoxazole Int-2-2.

Intermediate Int-2-3: 4-(Chloromethyl)-5-cyclopropyl-3-(2,6-dichlorophenyl)isoxazole

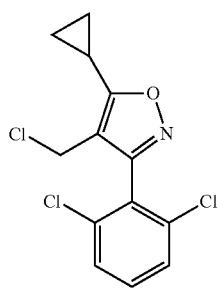

Int-2-3

Intermediate Int-2-3 was synthesized as described in WO2011/020615.

Intermediate Int-2-4: 4-(Chloromethyl)-5-cyclopropyl-3-(2-(difluoromethoxy)phenyl)isoxazole

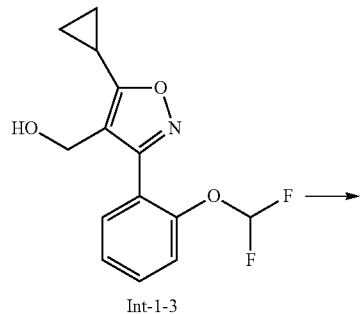

Int-1-3

Int-2-4

Similar as described for intermediate Int-2-1, starting from (5-cyclopropyl-3-(2-(difluoro-methoxy)phenyl)isoxazol-4-yl)methanol Int-1-3, the synthesis furnished 4-(chloromethyl)-5-cyclopropyl-3-(2-(difluoromethoxy)phenyl)isoxazole Int-2-4.

Intermediate Int-2-5: 4-(Chloromethyl)-5-cyclopropyl-3-(2-cyclopropylphenyl)isoxazole

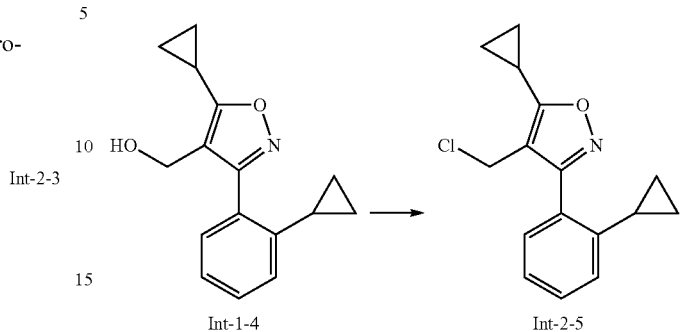

Int-1-4

Int-2-5

Similar as described for intermediate Int-2-1, starting from (5-cyclopropyl-3-(2-cyclopropyl-phenyl)isoxazol-4-yl)methanol Int-1-4, the synthesis furnished 4-(chloromethyl)-5-cyclopropyl-3-(2-cyclopropylphenyl)isoxazole Int-2-5.

Intermediate Int-2-6: 4-(Chloromethyl)-5-cyclopropyl-3-(2,6-dimethylphenyl)isoxazole

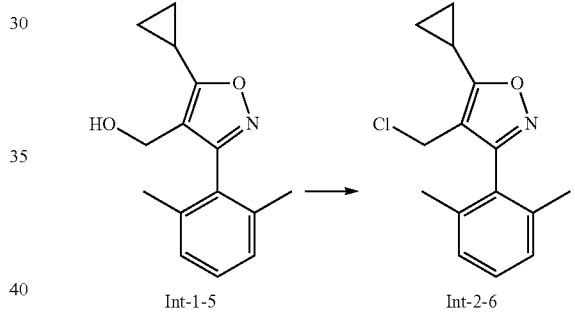

Int-1-5

Int-2-6

Similar as described for intermediate Int-2-1, starting from (5-cyclopropyl-3-(2,6-dimethyl-phenyl)isoxazol-4-yl)methanol Int-1-5, the synthesis furnished 4-(chloromethyl)-5-cyclopropyl-3-(2,6-dimethylphenyl)isoxazole Int-2-6.

Intermediate Int-2-7: 5-(Chloromethyl)-4-cyclopropyl-1-(2,6-dichlorophenyl)-1H-pyrazole

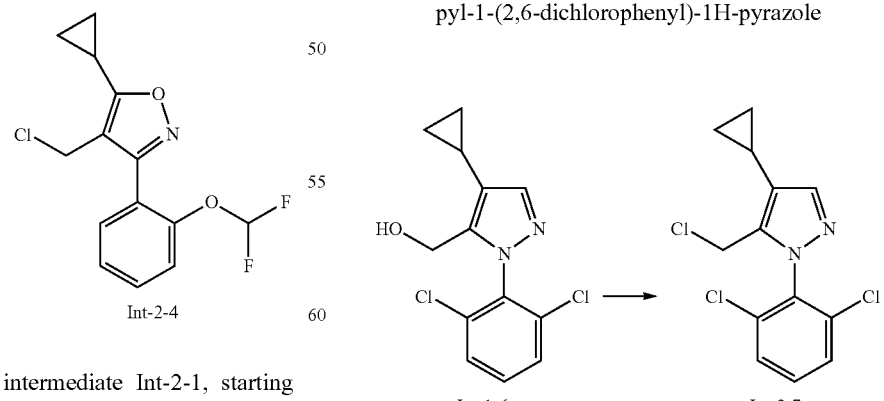

Int-1-6

Int-2-7

Similar as described for intermediate Int-2-1, starting from (4-cyclopropyl-1-(2,6-dichlorophenyl)-1H-pyrazol-5- yl)methanol Int-1-6, the synthesis furnished 5-(chloromethyl)-4-cyclopropyl-1-(2,6-dichlorophenyl)-1H-pyrazole Int-2-7.

Intermediate Int-2-8: 4-(Chloromethyl)-5-cyclopropyl-3-(2-(trifluoromethoxy)phenyl)isoxazole

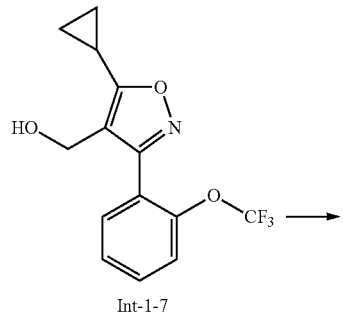

Int-1-7

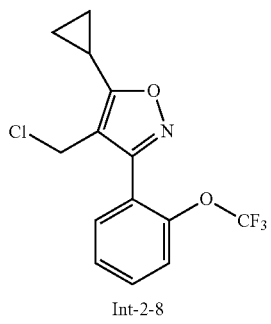

Int-2-8

Similar as described for intermediate Int-2-1, starting from (5-cyclopropyl-3-(2-(trifluoro-methoxy)phenyl)isoxazol-4-yl)methanol Int-1-7, the synthesis furnished 4-(chloromethyl)-5-cyclopropyl-3-(2-(trifluoromethoxy)phenyl) isoxazole Int-2-8.

Intermediate Int-2-9: 4-(Chloromethyl)-5-cyclopropyl-3-(2-(trifluoromethoxy)phenyl)isoxazole

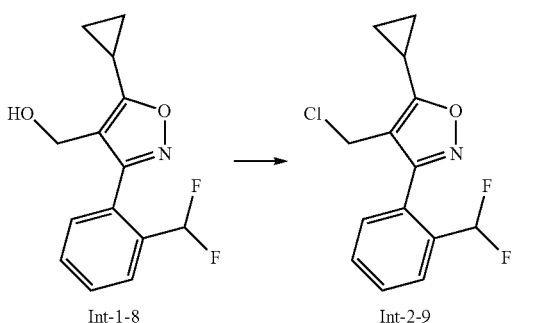 [SMILES: OCc1c(-c2ccccc2C(F)F)noc1C1CC1 ; FC(F)c1ccccc1-c1noc(C2CC2)c1CCl]

Int-1-8      Int-2-9

Similar as described for intermediate Int-2-1, starting from (5-cyclopropyl-3-(2-(difluoro-methyl)phenyl) isoxazol-4-yl)methanol Int-1-8, the synthesis furnished 4-(chloromethyl)-5-cyclopropyl-3-(2-(difluoromethyl)phenyl)isoxazole Int-2-9.

Intermediate Int-2-10: 4-(Chloromethyl)-5-cyclopropyl-3-(3,5-dichloropyridin-4-yl)isoxazole

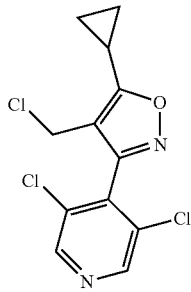

Int-2-10

Intermediate Int-2-10 was synthesized as described in WO2012/087519.

Intermediate Int-2-11: 5-(Chloromethyl)-4-cyclopropyl-1-(2-(difluoromethoxy)phenyl)-1H-pyrazole

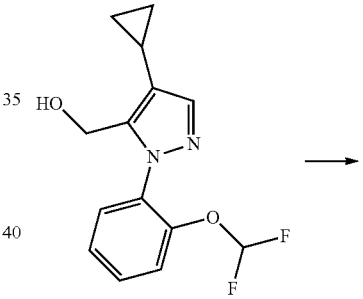

Int-1-9

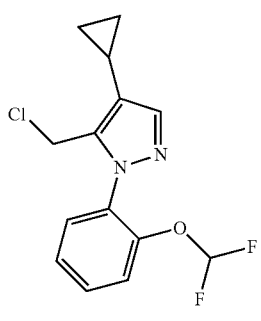

Int-2-11

Similar as described for intermediate Int-2-1, starting from (4-cyclopropyl-1-(2-(difluoromethoxy)phenyl)-1H-pyrazol-5-yl)methanol Int-1-9, the synthesis furnished 5-(chloromethyl)-4-cyclopropyl-1-(2-(difluoromethoxy)phenyl)-1H-pyrazole Int-2-11.

Intermediate Int-2-12: 3-(2,6-Bis(difluoromethyl)phenyl)-4-(chloromethyl)-5-cyclopropylisoxazole

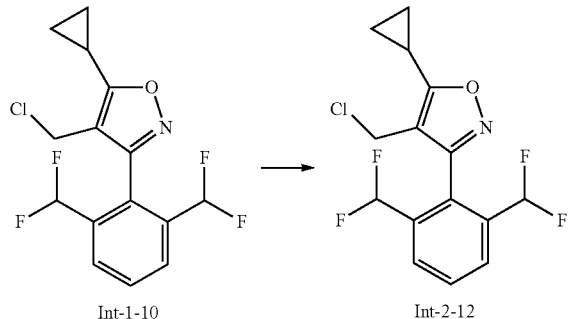 [SMILES: FC(F)c1cccc(C(F)F)c1-c1noc(C2CC2)c1CCl ; FC(F)c1cccc(C(F)F)c1-c1noc(C2CC2)c1CCl]

Similar as described for intermediate Int-2-1, starting from (3-(2,6-bis(difluoromethyl)phenyl)-5-cyclopropylisoxazol-4-yl)methanol Int-1-10, the synthesis furnished 3-(2,6-bis(difluoro-methyl)phenyl)-4-(chloromethyl)-5-cyclopropylisoxazole Int-2-12.

Intermediate Int-2-13: 4-(Bromomethyl)-3-(2,6-dichlorophenyl)-5-methylisoxazole

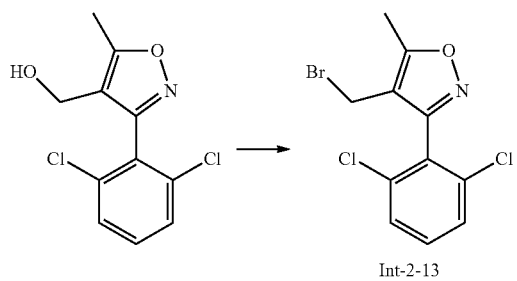 [SMILES: Cc1onc(-c2c(Cl)cccc2Cl)c1CO ; Cc1onc(-c2c(Cl)cccc2Cl)c1CBr]

To a solution of (3-(2,6-dichlorophenyl)-5-methylisoxazol-4-yl)methanol (5.0 g, 17.6 mmol) in CH$_2$Cl$_2$ (100 mL) were added CBr$_4$ (8.7 g, 26.4 mmol) and PPh$_3$ (7.0 g, 26.4 mmol) at rt. The mixture was stirred for 2 h, concentrated and purified by flash chromatography to give 4-(bromomethyl)-3-(2,6-dichlorophenyl)-5-methylisoxazole Int-2-13.

Intermediate Int-2-14: 4-(Bromomethyl)-3-(2,6-dichlorophenyl)-5-isopropylisoxazole

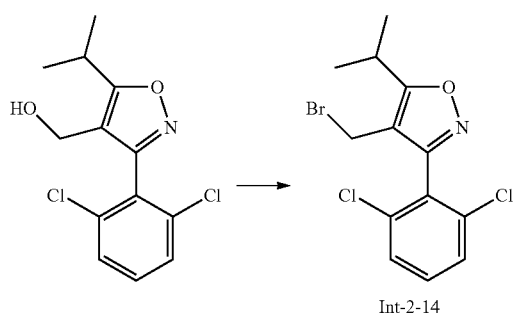 [SMILES: CC(C)c1onc(-c2c(Cl)cccc2Cl)c1CO ; CC(C)c1onc(-c2c(Cl)cccc2Cl)c1CBr]

Similar as described for intermediate Int-2-13, starting from (3-(2,6-dichlorophenyl)-5-isopropylisoxazol-4-yl)methanol, the synthesis furnished 4-(bromomethyl)-3-(2,6-dichlorophenyl)-5-isopropylisoxazole Int-2-14.

Intermediate Int-2-15: 2-(4-(Chloromethyl)-3-(2,6-dichlorophenyl)isoxazol-5-yl)propan-2-ol

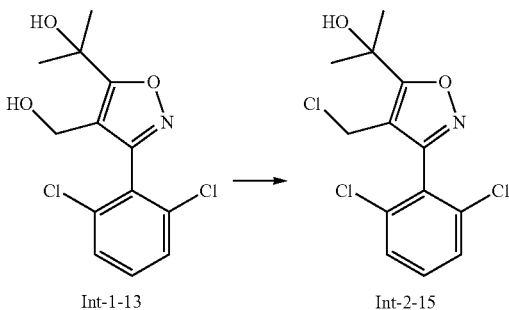 [SMILES: CC(C)(O)c1onc(-c2c(Cl)cccc2Cl)c1CO ; CC(C)(O)c1onc(-c2c(Cl)cccc2Cl)c1CCl]

To a solution of 2-(3-(2,6-dichlorophenyl)-4-(hydroxymethyl)isoxazol-5-yl)propan-2-ol Int-1-13 (6.8 g, 226 mmol) in DCM (120 mL) was added SOCl$_2$ (17.2 mL, 237 mmol) at 0° C. The mixture was stirred at rt for 15 min, quenched with saturated aqueous NaCO$_3$ and extracted with EtOAc (3×150 mL). The combined organic layer was washed with brine, dried over Na$_2$SO$_4$, concentrated and purified by column chromatography (PE/EtOAc=30:1) to afford 2-(4-(chloromethyl)-3-(2,6-dichlorophenyl)isoxazol-5-yl)propan-2-ol Int-2-15. $^1$H-NMR (CDCl$_3$, 300 MHz): δ 7.47-7.37 (m, 3H), 4.51 (s, 2H), 2.43 (s, 1H), 1.75 (s, 6H).

Intermediate Int-2-16: 4-(Chloromethyl)-3-(2,6-dichlorophenyl)-5-(2-fluoropropan-2-yl)isoxazole

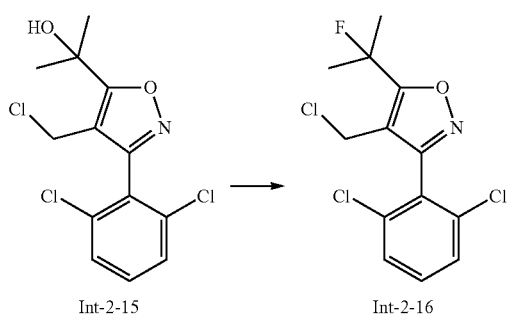 [SMILES: CC(C)(O)c1onc(-c2c(Cl)cccc2Cl)c1CCl ; CC(C)(F)c1onc(-c2c(Cl)cccc2Cl)c1CCl]

To a solution of 2-(4-(chloromethyl)-3-(2,6-dichlorophenyl)isoxazol-5-yl)propan-2-ol Int-2-15 (2.80 g, 9.1 mmol) in DCM (80 mL) was added DAST (1.5 mL, 11.4 mmol). The mixture was stirred at 0° C. for 1.5 h, quenched with saturated aqueous NaHCO$_3$ and extracted with EtOAc (3×100 mL). The combined organic layer was washed with brine, dried over Na$_2$SO$_4$, concentrated and purified by column chromatography (PE/EtOAc=30:1) to afford 4-(chloromethyl)-3-(2,6-dichloro-phenyl)-5-(2-fluoropropan-2-yl)isoxazole Int-2-16. $^1$H-NMR (CDCl$_3$, 300 MHz): δ 7.47-7.37 (m, 3H), 4.43 (s, 2H), 1.87 (d, J=22.2 Hz, 6H). LCMS (ESI): m/z 321.9 (M+1)$^+$.

Intermediate Int-2-17: 4-(Chloromethyl)-5-cyclopropyl-3-((2,6-dimethylphenoxy)methyl)isoxazole

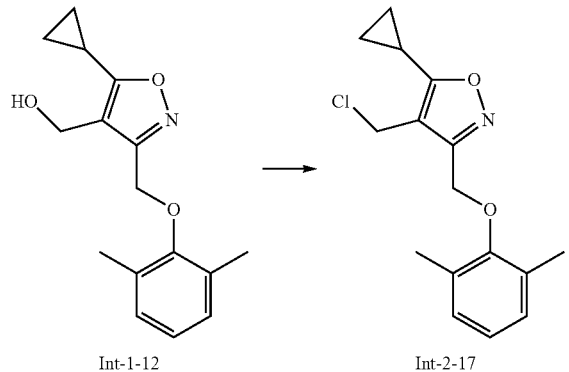 [SMILES: Cc1cccc(C)c1OCc1noc(C2CC2)c1CO ; Cc1cccc(C)c1OCc1noc(C2CC2)c1CCl]

Similar as described for intermediate Int-2-1, starting from (5-cyclopropyl-3-((2,6-dimethyl-phenoxy)methyl)isoxazol-4-yl)methanol Int-1-12, the synthesis furnished 4-(chloromethyl)-5-cyclopropyl-3-((2,6-dimethylphenoxy)methyl)isoxazole Int-2-17.

Intermediate Int-2-18: 5-(Bromomethyl)-4-cyclopropyl-1-(2,6-dichlorophenyl)-1H-pyrazole

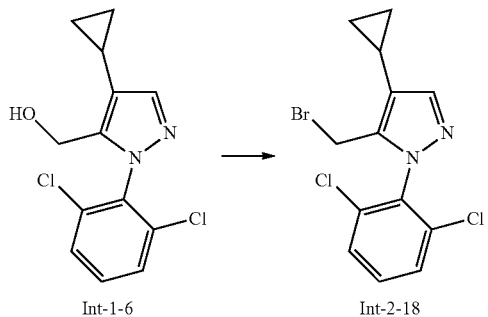 [SMILES: OCc1c(C2CC2)cnn1-c1c(Cl)cccc1Cl ; Clc1cccc(Cl)c1-n1ncc(C2CC2)c1CBr]

To a solution of (4-cyclopropyl-1-(2,6-dichlorophenyl)-1H-pyrazol-5-yl)methanol Int-1-6 (283 mg, 1.0 mmol) in CH$_2$Cl$_2$ (5 mL), CBr$_4$ (497 mg, 1.5 mmol) and PPh$_3$ (393 mg, 1.5 mmol) were added at rt. The mixture was stirred at rt for 2 h, concentrated and purified by flash chromatography on silica gel to give 5-(bromomethyl)-4-cyclopropyl-1-(2,6-dichlorophenyl)-1H-pyrazole Int-2-18.

General Procedure A for the Synthesis of Intermediate Int-3

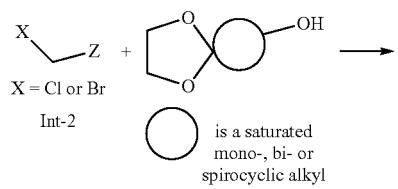

To a 0° C. suspension of NaH (60% in oil; 2.0 eq.) in dry DMF was added the hydroxy-acetal derivative (1.2 eq.). The mixture was stirred at 0° C. for 30 min, then a mixture of halomethyl-Z (1.0 eq.) in DMF (5 mL) was added. The mixture was warmed to rt and stirred for 1 h, carefully diluted with water and extracted with EtOAc. The combined the organic layers were washed with brine, dried, filtered, concentrated and the residue was purified by TLC or flash chromtography to afford selected intermediates Int-3.

Alternative General Procedure A2 for the Synthesis of Intermediate Int-3

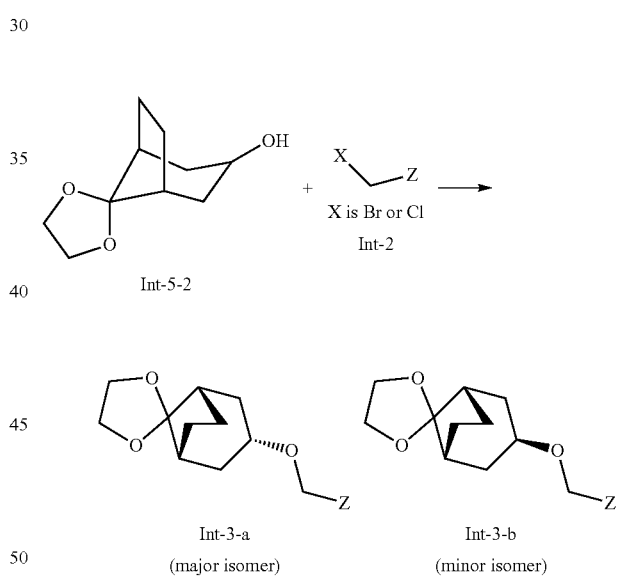

To a suspension of NaH (60% in mineral oil, 1.3 eq.) in dry THF (10 vol.) at 0° C. was added spiro[bicyclo[3.2.1]octane-8,2'-[1,3]dioxolan]-3-ol Int-5-2 (1.0 eq.) in dry THF (3 vol.). The reaction mixture was stirred at 0° C. for 1.5 h, then bromo- or chloromethyl-Z (1.2 eq.) was added at 0° C. The mixture was stirred at reflux overnight, quenched with NH$_4$Cl (sat.) and extracted with EtOAc. The organic layers were combined and washed with brine, dried over Na$_2$SO$_4$ and concentrated. The crude product was purified by silica gel chromatography to give selected intermediates Int-3a (major isomer) and Int-3-b (minor isomer). The minor isomers may not get isolated.

Intermediate Int-3-1: 4-((1,4-Dioxaspiro[4.5]decan-8-yloxy)methyl)-5-cyclopropyl-3-(4,4-difluorocyclohexyl)isoxazole

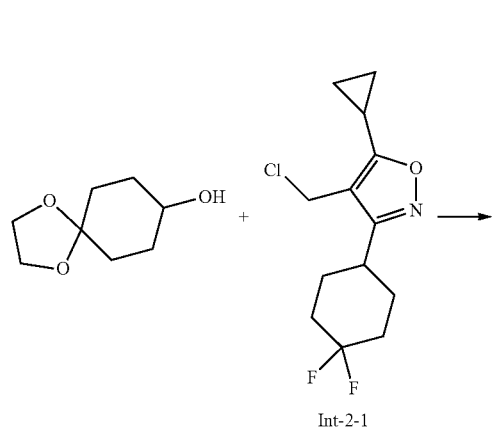

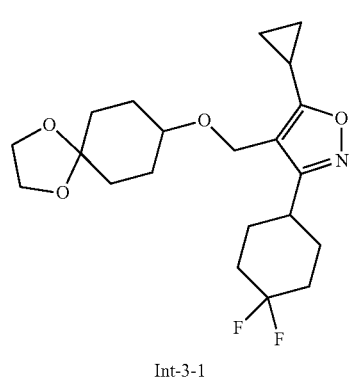

Following general procedure A, beginning with 4-(chloromethyl)-5-cyclopropyl-3-(4,4-difluorocyclohexyl)isoxazole Int-2-1 (520 mg, 1.9 mmol) and 1,4-dioxaspiro[4.5]decan-8-ol, the intermediate 4-((1,4-dioxaspiro[4.5]decan-8-yloxy)methyl)-5-cyclopropyl-3-(4,4-difluorocyclohexyl)isoxazole Int-3-1 was synthesized and purified by TLC (PE/EtOAc=4:1).

Intermediate Int-3-2: 4-((1,4-Dioxaspiro[4.5]decan-8-yloxy)methyl)-5-cyclopropyl-3-(spiro[2.5]octan-6-yl)isoxazole

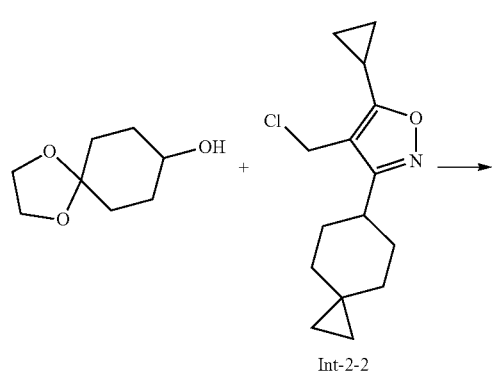

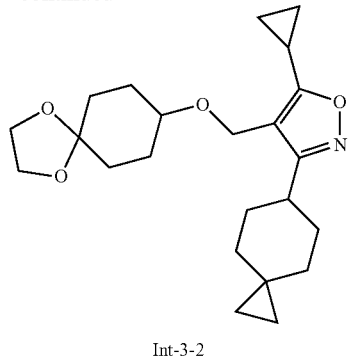

Following general procedure A, beginning with 4-(chloromethyl)-5-cyclopropyl-3-(spiro[2.5]octan-6-yl)isoxazole Int-2-2 (190 mg, 1.2 mmol) and 1,4-dioxaspiro[4.5]decan-8-ol, the intermediate 4-((1,4-dioxaspiro[4.5]decan-8-yloxy)methyl)-5-cyclopropyl-3-(spiro[2.5]octan-6-yl)isoxazole Int-3-2 was synthesized and purified by TLC (PE/EtOAc=4:1).

Intermediate Int-3-3: 4-((1,4-Dioxadispiro[4.1.3.1]undecan-9-yloxy)methyl)-5-cyclopropyl-3-(2,6-dichlorophenyl)isoxazole

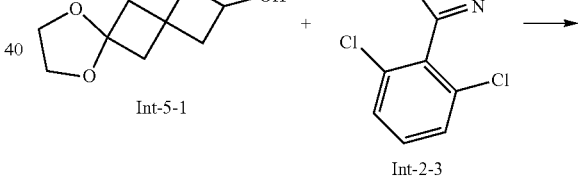

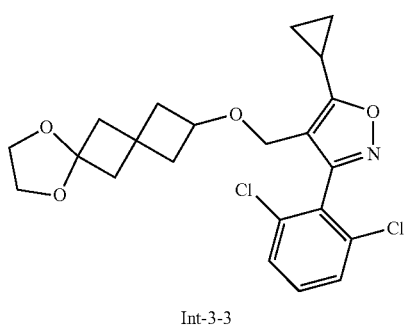

Following general procedure A, beginning with 4-(chloromethyl)-5-cyclopropyl-3-(2,6-dichlorophenyl)isoxazole Int-2-3 and 9-hydroxy-1,4-dioxadispiro[4.1.3.1]undecane Int-5-1, the intermediate 4-((1,4-dioxadispiro[4.1.3.1]undecan-9-yloxy)methyl)-5-cyclopropyl-3-(2,6-dichloro-phenyl)isoxazole Int-3-3 was synthesized.

Intermediate Int-3-4: 4-((1,4-Dioxaspiro[4.5]decan-8-yloxy)methyl)-5-cyclopropyl-3-(2,6-dichlorophenyl)isoxazole

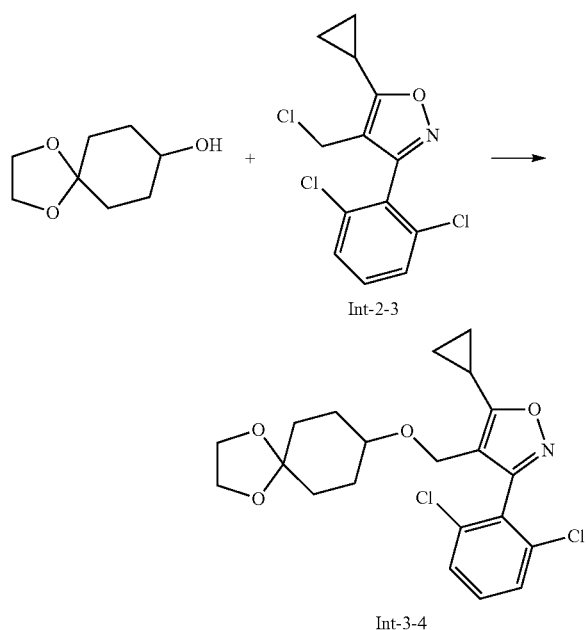

Following general procedure A, beginning with 4-(chloromethyl)-5-cyclopropyl-3-(2,6-dichlorophenyl)isoxazole Int-2-3 and 1,4-dioxaspiro[4.5]decan-8-ol, the intermediate 4-((1,4-dioxaspiro[4.5]decan-8-yloxy)methyl)-5-cyclopropyl-3-(2,6-dichlorophenyl)isoxazole Int-3-4 was synthesized.

Intermediate Int-3-5: 4-((1,4-Dioxaspiro[4.5]decan-8-yloxy)methyl)-5-cyclopropyl-3-(2-(difluoromethoxy)phenyl)isoxazole

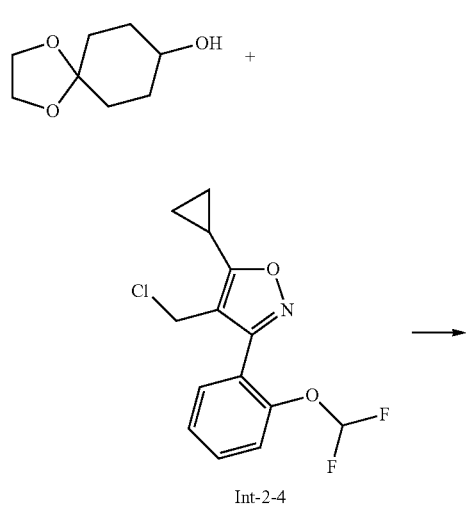

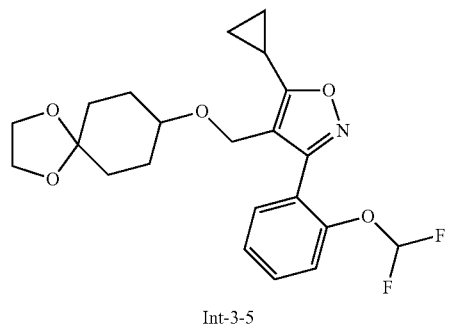

Following general procedure A, beginning with 4-(chloromethyl)-5-cyclopropyl-3-(2-(difluoromethoxy)phenyl)isoxazole Int-2-4 and 1,4-dioxaspiro[4.5]decan-8-ol, the intermediate 4-((1,4-dioxaspiro[4.5]decan-8-yloxy)methyl)-5-cyclopropyl-3-(2-(difluoromethoxy)phenyl)isoxazole Int-3-5 was synthesized.

Intermediate Int-3-6: 4-((1,4-Dioxaspiro[4.5]decan-8-yloxy)methyl)-5-cyclopropyl-3-(2-cyclopropylphenyl)isoxazole

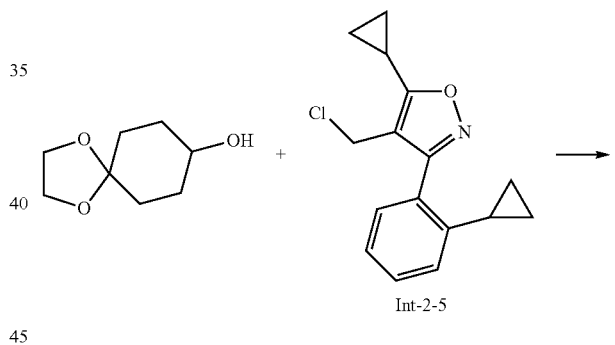

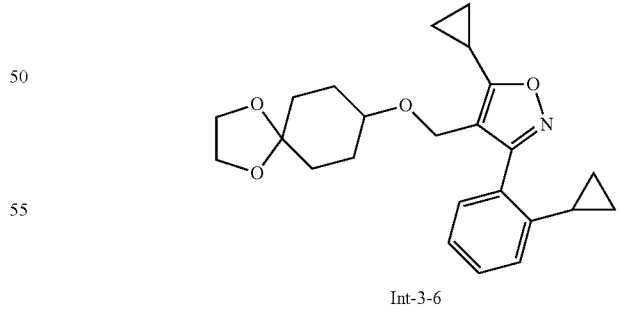

Following general procedure A, beginning with 4-(chloromethyl)-5-cyclopropyl-3-(2-cyclopropylphenyl)isoxazole Int-2-5 and 1,4-dioxaspiro[4.5]decan-8-ol, the intermediate 4-((1,4-dioxaspiro[4.5]decan-8-yloxy)methyl)-5-cyclopropyl-3-(2-cyclopropylphenyl)isoxazole Int-3-6 was synthesized.

Intermediate Int-3-7: 4-((1,4-Dioxaspiro[4.5]decan-8-yloxy)methyl)-5-cyclopropyl-3-(2,6-dimethylphenyl)isoxazole

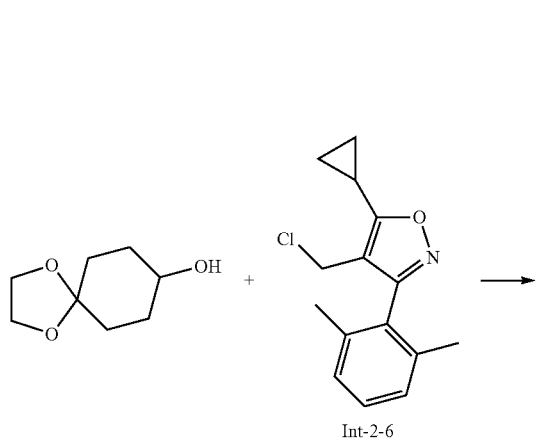

Int-2-6

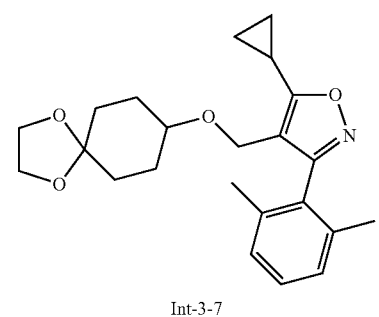

Int-3-7

Following general procedure A, beginning with 4-(chloromethyl)-5-cyclopropyl-3-(2,6-dimethylphenyl)isoxazole Int-2-6 and 1,4-dioxaspiro[4.5]decan-8-ol, the intermediate 4-((1,4-dioxaspiro[4.5]decan-8-yloxy)methyl)-5-cyclopropyl-3-(2,6-dimethylphenyl)isoxazole Int-3-7 was synthesized.

Intermediate Int-3-8: 5-((1,4-dioxaspiro[4.5]decan-8-yloxy)methyl)-4-cyclopropyl-1-(2,6-dichlorophenyl)-1H-pyrazole

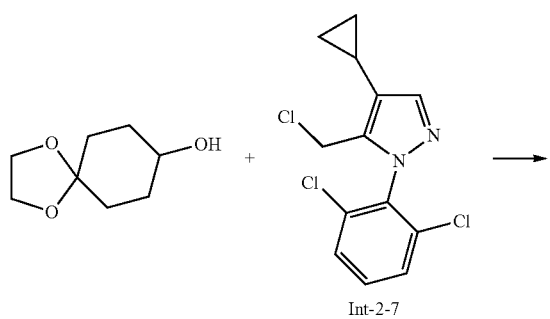

Int-2-7

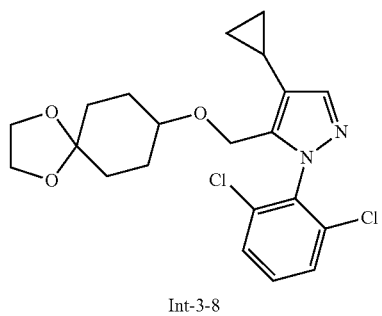

Int-3-8

Following general procedure A, beginning with 5-(chloromethyl)-4-cyclopropyl-1-(2,6-dichlorophenyl)-1H-pyrazole Int-2-7 and 1,4-dioxaspiro[4.5]decan-8-ol, the intermediate 5-((1,4-dioxaspiro[4.5]decan-8-yloxy)methyl)-4-cyclopropyl-1-(2,6-dichlorophenyl)-1H-pyrazole Int-3-8 was synthesized.

Intermediate Int-3-9: 4-((1,4-Dioxaspiro[4.5]decan-8-yloxy)methyl)-5-cyclopropyl-3-(2-(trifluoromethoxy)phenyl)isoxazole

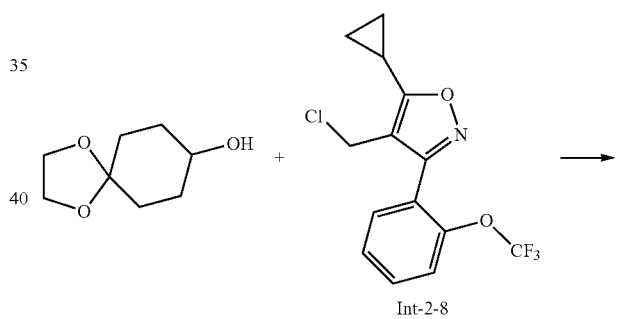

Int-2-8

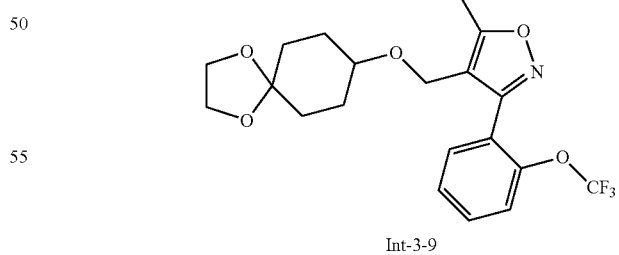

Int-3-9

Following general procedure A, beginning with 4-(chloromethyl)-5-cyclopropyl-3-(2-(trifluoromethoxy)phenyl)isoxazole Int-2-8 and 1,4-dioxaspiro[4.5]decan-8-ol, the intermediate 4-((1,4-dioxaspiro[4.5]decan-8-yloxy)methyl)-5-cyclopropyl-3-(2-(trifluoromethoxy)phenyl)isoxazole Int-3-9 was synthesized.

Intermediate Int-3-10: 4-((1,4-Dioxaspiro[4.5]decan-8-yloxy)methyl)-5-cyclopropyl-3-(2-(difluoromethyl)phenyl)isoxazole

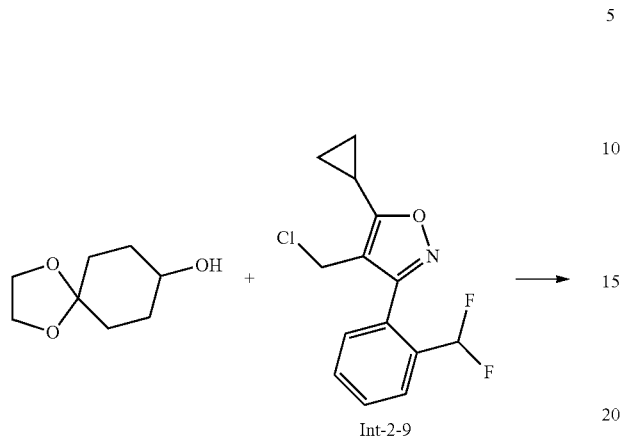

Following general procedure A, beginning with 4-(chloromethyl)-5-cyclopropyl-3-(2-(difluoromethyl)phenyl)isoxazole Int-2-9 and 1,4-dioxaspiro[4.5]decan-8-ol, the intermediate 4-((1,4-dioxaspiro[4.5]decan-8-yloxy)methyl)-5-cyclopropyl-3-(2-(difluoromethyl)phenyl)isoxazole Int-3-10 was synthesized.

Intermediate Int-3-11: 4-((1,4-Dioxaspiro[4.5]decan-8-yloxy)methyl)-5-cyclopropyl-3-(3,5-dichloropyridin-4-yl)isoxazole

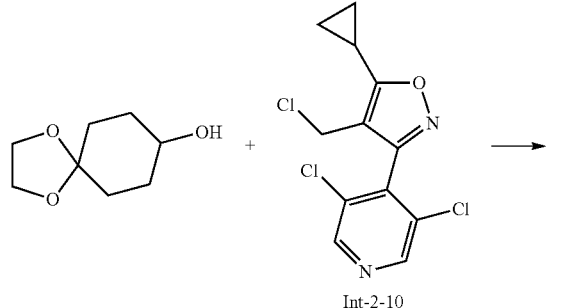

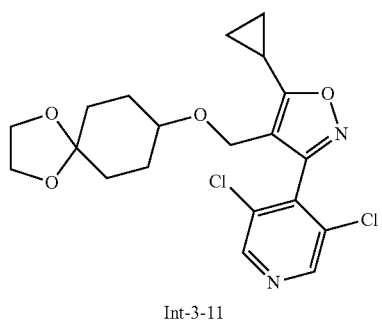

Following general procedure A, beginning with 4-(chloromethyl)-5-cyclopropyl-3-(3,5-dichloropyridin-4-yl)isoxazole Int-2-10 and 1,4-dioxaspiro[4.5]decan-8-ol, the intermediate 4-((1,4-dioxaspiro[4.5]decan-8-yloxy)methyl)-5-cyclopropyl-3-(3,5-dichloropyridin-4-yl)isoxazole Int-3-11 was synthesized.

Intermediate Int-3-12: 5-((1,4-Dioxaspiro[4.5]decan-8-yloxy)methyl)-4-cyclopropyl-1-(2-(difluoromethoxy)phenyl)-1H-pyrazole

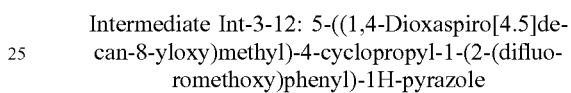

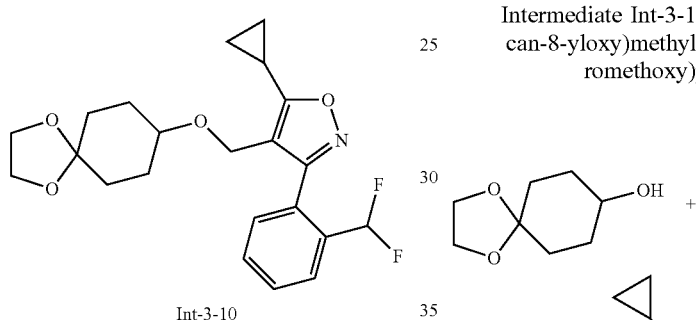

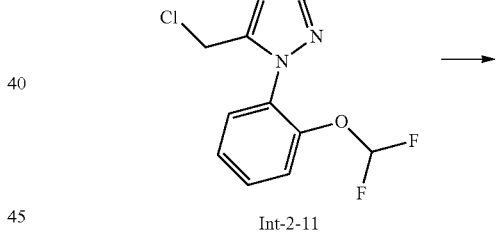

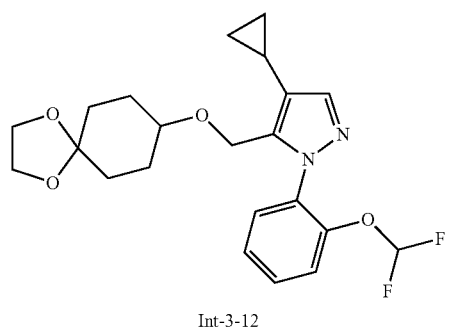

Following general procedure A, beginning with 5-(chloromethyl)-4-cyclopropyl-1-(2-(difluoromethoxy)phenyl)-1H-pyrazole Int-2-11 and 1,4-dioxaspiro[4.5]decan-8-ol, the intermediate 5-((1,4-dioxaspiro[4.5]decan-8-yloxy)methyl)-4-cyclopropyl-1-(2-(difluoro-methoxy)phenyl)-1H-pyrazole Int-3-12 was synthesized.

Intermediate Int-3-13: 4-((1,4-Dioxaspiro[4.5]decan-8-yloxy)methyl)-3-(2,6-bis(difluoro-methyl)phenyl)-5-cyclopropylisoxazole

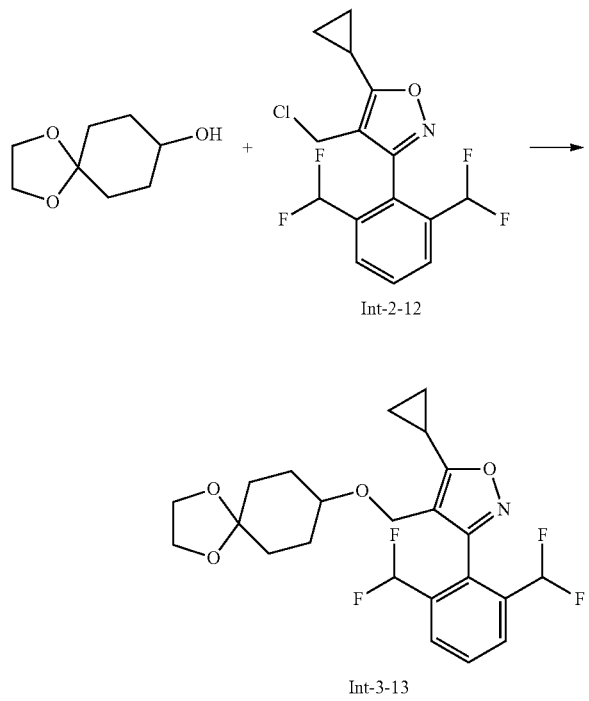

Following general procedure A, beginning with 3-(2,6-bis(difluoromethyl)phenyl)-4-(chloromethyl)-5-cyclopropylisoxazole Int-2-12 and 1,4-dioxaspiro[4.5]decan-8-ol, the intermediate 4-((1,4-dioxaspiro[4.5]decan-8-yloxy)methyl)-3-(2,6-bis(difluoromethyl)phenyl)-5-cyclopropylisoxazole Int-3-13 was synthesized.

Intermediates Int-3-14a and Int-3-14b: 5-Cyclopropyl-3-(2,6-dichlorophenyl)-4-(((((1R,3s,5S)-spiro[bicyclo[3.2.1]octane-8,2'-[1,3]dioxolan]-3-yl)oxy)methyl)isoxazole (Int-3-14a) and 5-cyclopropyl-3-(2,6-dichlorophenyl)-4-(((((1R,3r,5S)-spiro[bicyclo[3.2.1]octane-8,2'-[1,3]dioxolan]-3-yl)oxy)methyl)isoxazole (Int-3-14b)

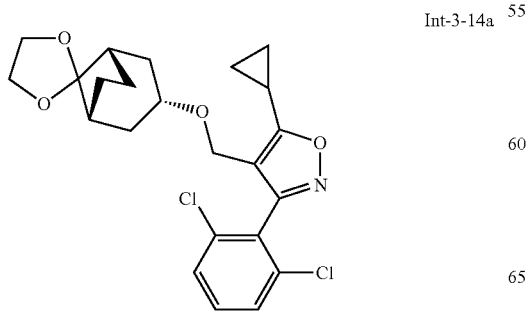

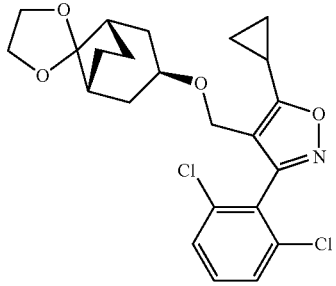

Following general procedure A2, using 4-(bromomethyl)-5-cyclopropyl-3-(2,6-dichloro-phenyl)isoxazole (intermediate 1a from Example 1), the target intermediates were synthesized as a mixture. The crude product was purified by silica gel chromatography to afford separated 5-cyclopropyl-3-(2,6-dichlorophenyl)-4-(((((1R,3s,5S)-spiro[bicyclo[3.2.1]octane-8,2'-[1,3]dioxolan]-3-yl)oxy)methyl)isoxazole Int-3-14a and 5-cyclopropyl-3-(2,6-dichlorophenyl)-4-(((((1R,3r,5S)-spiro[bicyclo[3.2.1]octane-8,2'-[1,3]dioxolan]-3-yl)oxy)methyl)isoxazole Int-3-14b.

Intermediate Int-3-15: 5-Cyclopropyl-3-(2-(difluoromethoxy)phenyl)-4-(((((1R,3s,5S)-spiro[bicyclo[3.2.1]octane-8,2'-[1,3]dioxolan]-3-yl)oxy)methyl)isoxazole

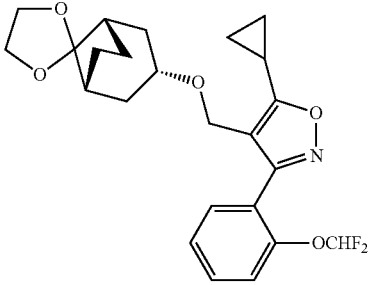

Following general procedure A2, using 4-(chloromethyl)-5-cyclopropyl-3-(2-(difluoro-methoxy)phenyl)isoxazole Int-2-4, the intermediate 5-cyclopropyl-3-(2-(difluoromethoxy)phenyl)-4-(((((1R,3s,5S)-spiro[bicyclo[3.2.1]octane-8,2'-[1,3]dioxolan]-3-yl)oxy)methyl)isoxazole (Int-3-15) was synthesized.

Intermediate Int-3-16: 5-Cyclopropyl-3-(3,5-dichloropyridin-4-yl)-4-(((((1R,3s,5S)-spiro[bicyclo[3.2.1]octane-8,2'-[1,3]dioxolan]-3-yl)oxy)methyl)isoxazole

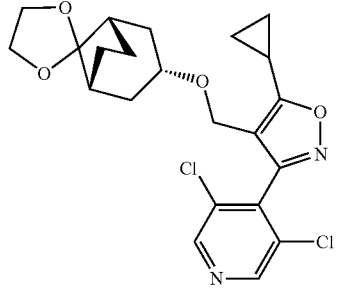

Following general procedure A2, using 4-(chloromethyl)-5-cyclopropyl-3-(3,5-dichloropyridin-4-yl)isoxazole Int-2-10, the intermediate 5-cyclopropyl-3-(3,5-dichloropyridin-4-yl)-4-((((1R,3s,5S)-spiro[bicyclo[3.2.1]octane-8,2'-[1,3]dioxolan]-3-yl)oxy)methyl)isoxazole (Int-3-16) was synthesized.

Intermediates Int-3-17a and Int-3-17b: 3-(2,6-Dichlorophenyl)-5-methyl-4-(((1R,3s,5S)-spiro[bicyclo[3.2.1]octane-8,2'-[1,3]dioxolan]-3-yloxy)methyl)isoxazole (Int-3-17a) and 3-(2,6-dichlorophenyl)-5-methyl-4-(((1R,3r,5S)-spiro[bicyclo[3.2.1]octane-8,2'-[1,3]dioxolan]-3-yloxy)methyl)isoxazole (Int-3-17b)

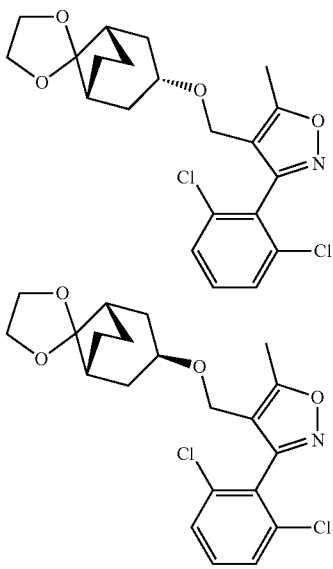

Int-3-17a

Int-3-17b

Following general procedure A2, using 4-(bromomethyl)-3-(2,6-dichlorophenyl)-5-methylisoxazole Int-2-13, the target intermediates were synthesized and purified by silica gel chromatography to give major isomer 3-(2,6-dichlorophenyl)-5-methyl-4-(((1R,3s,5S)-spiro[bicyclo[3.2.1]octane-8,2'-[1,3]dioxolan]-3-yloxy)methyl)isoxazole Int-3-17a and minor isomer 3-(2,6-dichlorophenyl)-5-methyl-4-(((1R,3r,5S)-spiro[bicyclo[3.2.1]octane-8,2'-[1,3]dioxolan]-3-yloxy)methyl)isoxazole Int-3-17b.

Intermediate Int-3-18: 5-Cyclopropyl-3-(2,6-dichlorophenyl)-4-((((1R,5S)-3-methylspiro[bicyclo[3.2.1]octane-8,2'-[1,3]dioxolan]-3-yl)oxy)methyl)isoxazole

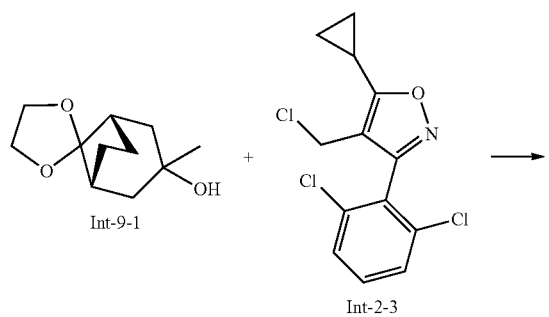

Int-9-1

Int-2-3

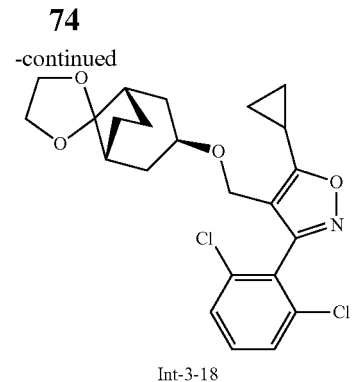

Int-3-18

Following general procedure A2, using (1R,5S)-3-methylspiro[bicyclo[3.2.1]octane-8,2'-[1,3]dioxolan]-3-ol (500 mg, 2.75 mmol) Int-9-1 and 4-(chloromethyl)-5-cyclopropyl-3-(2,6-dichlorophenyl)isoxazole Int-2-3, the target intermediate was synthesized and purified by silica gel chromatography (PE/EtOAc=10:1) to give 5-cyclopropyl-3-(2,6-dichlorophenyl)-4-((((1R,5S)-3-methylspiro[bicyclo[3.2.1]octane-8,2'-[1,3]dioxolan]-3-yl)oxy)methyl)isoxazole Int-3-18.

Intermediate Int-3-19: 5-Cyclopropyl-3-(2,6-dichlorophenyl)-4-((((1R,5S)-3-(difluoro-methyl)spiro[bicyclo[3.2.1]octane-8,2'-[1,3]dioxolan]-3-yl)oxy)methyl)isoxazole

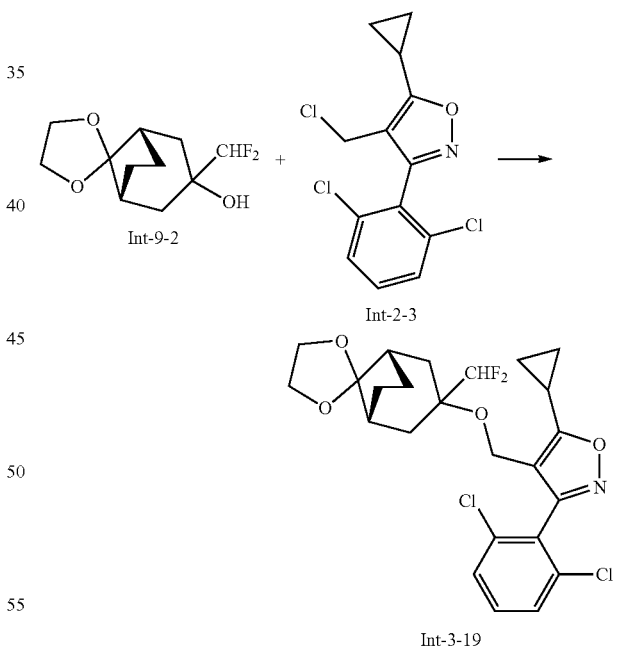

Int-9-2

Int-2-3

Int-3-19

Following general procedure A2, using (1R,5S)-3-(difluoromethyl)spiro[bicyclo[3.2.1]octane-8,2'-[1,3]dioxolan]-3-ol Int-9-2 and 4-(chloromethyl)-5-cyclopropyl-3-(2,6-dichlorophenyl)isoxazole Int-2-3, the target intermediate was synthesized and purified by silica gel chromatography (PE/EtOAc=10:1) to give 5-cyclopropyl-3-(2,6-dichlorophenyl)-4-((((1R,5S)-3-(difluoro-methyl)spiro[bicyclo[3.2.1]octane-8,2'-[1,3]dioxolan]-3-yl)oxy)methyl)isoxazole Int-3-19.

Intermediate Int-3-20: 5-Cyclopropyl-3-(2,6-dichlorophenyl)-4-((((1R,5S)-3-(methoxy-methyl)spiro[bicyclo[3.2.1]octane-8,2'-[1,3]dioxolan]-3-yl)oxy)methyl)isoxazole

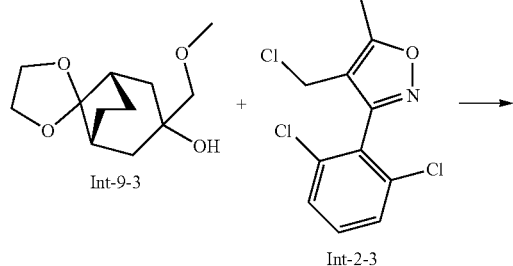

Int-9-3   Int-2-3

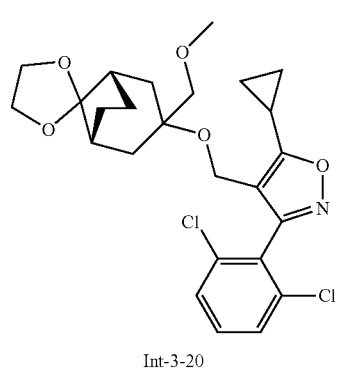

Int-3-20

Following general procedure A2, using (1R,5S)-3-(methoxymethyl)spiro[bicyclo[3.2.1]octane-8,2'-[1,3]dioxolan]-3-ol Int-9-3 and 4-(chloromethyl)-5-cyclopropyl-3-(2,6-dichlorophenyl)isoxazole Int-2-3, the target intermediate was synthesized and purified by silica gel chromatography (PE/EtOAc=10:1) to give 5-cyclopropyl-3-(2,6-dichlorophenyl)-4-((((1R,5S)-3-(methoxy-methyl)spiro[bicyclo[3.2.1]octane-8,2'-[1,3]dioxolan]-3-yl)oxy)methyl)isoxazole Int-3-20.

Intermediate Int-3-21: 5-Cyclopropyl-3-(2,6-dichlorophenyl)-4-((((3a'R,6a'S)-hexahydro-1'H-spiro[[1,3]dioxolane-2,2'-pentalen]-5'-yl)oxy)methyl)isoxazole

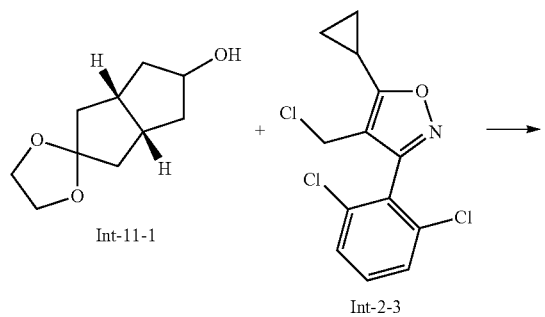

Int-11-1   Int-2-3

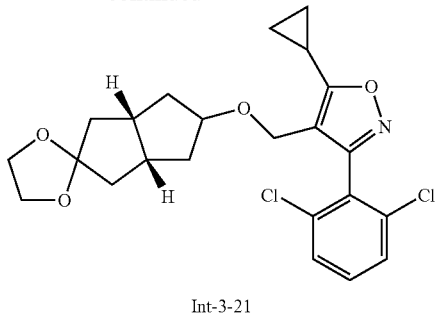

Int-3-21

Following general procedure A2, using (3a'R,6a'S)-hexahydro-1'H-spiro[[1,3]dioxolane-2,2'-pentalen]-5'-ol Int-11-1 and 4-(chloromethyl)-5-cyclopropyl-3-(2,6-dichlorophenyl)isoxazole Int-2-3, the target intermediate was synthesized and purified by silica gel chromatography (PE/EtOAc=5:1) to give single isomer 5-cyclopropyl-3-(2,6-dichlorophenyl)-4-((((3a'R,6a'S)-hexahydro-1'H-spiro[[1,3]dioxolane-2,2'-pentalen]-5'-yl)oxy)methyl)isoxazole Int-3-21.

Intermediate Int-3-22: 5-Cyclopropyl-3-(2,6-dichlorophenyl)-4-((((1R,4R)-spiro[bicyclo[2.2.1]heptane-2,2'-[1,3]dioxolan]-5-yloxy)methyl)isoxazole

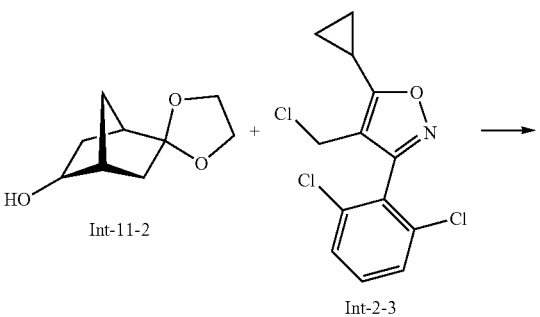

Int-11-2   Int-2-3

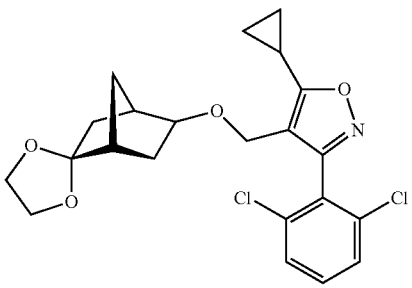

Int-3-22

Following general procedure A2, using (1R,4R)-spiro[bicyclo[2.2.1]heptane-2,2'-[1,3]dioxolan]-5-ol Int-11-2 and 4-(chloromethyl)-5-cyclopropyl-3-(2,6-dichlorophenyl)isoxazole Int-2-3, the target intermediate was synthesized and purified by silica gel chromatography (PE/EtOAc=5:1) to give single isomer 5-cyclopropyl-3-(2,6-dichlorophenyl)-4-(((1R,4R)-spiro[bicyclo[2.2.1]heptane-2,2'-[1,3]dioxolan]-5-yloxy)methyl)isoxazole Int-3-22.

Intermediate Int-3-23: 5-Cyclopropyl-3-((2,6-dimethylphenoxy)methyl)-4-((((1R,3s,5S)-spiro[bicyclo[3.2.1]octane-8,2'-[1,3]dioxolan]-3-yloxy)methyl)isoxazole

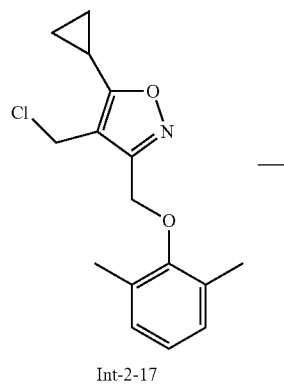

Int-2-17

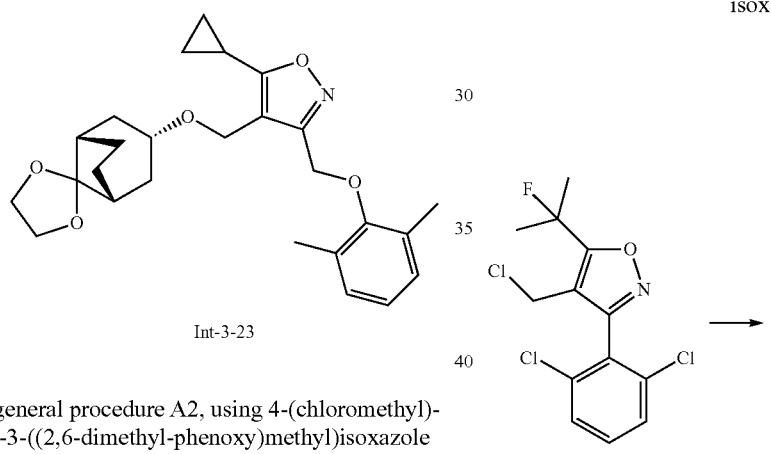

Int-3-23

Following general procedure A2, using 4-(chloromethyl)-5-cyclopropyl-3-((2,6-dimethyl-phenoxy)methyl)isoxazole Int-2-17, the intermediate 5-cyclopropyl-3-((2,6-dimethylphenoxy)methyl)-4-((((1R,3s,5S)-spiro[bicyclo[3.2.1]octane-8,2'-[1,3]dioxolan]-3-yloxy)methyl)isoxazole (Int-3-23) was synthesized.

Intermediate Int-3-24: 3-(2,6-Dichlorophenyl)-5-isopropyl-4-((((1R,3s,5S)-spiro[bicyclo[3.2.1]octane-8,2'-[1,3]dioxolan]-3-yloxy)methyl)isoxazole

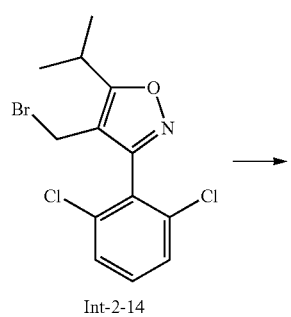

Int-2-14

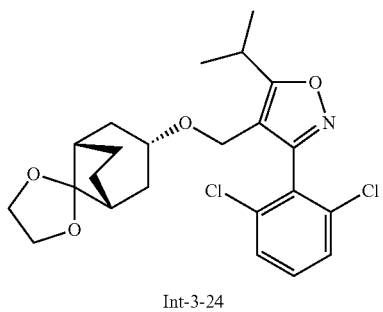

Int-3-24

Following general procedure A2, using 4-(bromomethyl)-3-(2,6-dichlorophenyl)-5-isopropylisoxazole Int-2-14, the intermediate 3-(2,6-dichlorophenyl)-5-isopropyl-4-((((1R,3s,5S)-spiro[bicyclo[3.2.1]octane-8,2'-[1,3]dioxolan]-3-yloxy)methyl)isoxazole (Int-3-24) was synthesized.

Intermediate Int-3-25: 3-(2,6-Dichlorophenyl)-5-(2-fluoropropan-2-yl)-4-((((1R,3s,5S)-spiro[bicyclo[3.2.1]octane-8,2'-[1,3]dioxolan]-3-yloxy)methyl)isoxazole

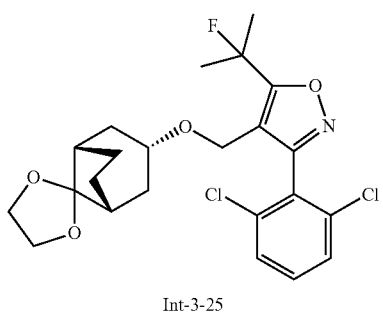

Int-2-16

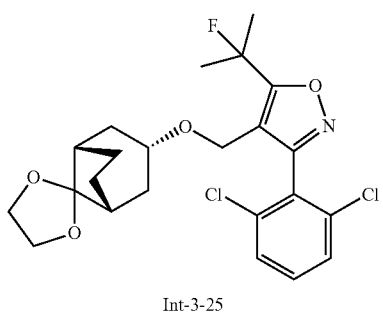

Int-3-25

Following general procedure A2, using 4-(chloromethyl)-3-(2,6-dichlorophenyl)-5-(2-fluoropropan-2-yl)isoxazole Int-2-16, the intermediate 3-(2,6-dichlorophenyl)-5-(2-fluoropropan-2-yl)-4-((((1R,3s,5S)-spiro[bicyclo[3.2.1]octane-8,2'-[1,3]dioxolan]-3-yloxy)methyl)isoxazole (Int-3-25) was synthesized.

Intermediate Int-3-26: 2-(3-(2,6-Dichlorophenyl)-4-(((1R,3s,5S)-spiro[bicyclo[3.2.1]octane-8,2'-[1,3]dioxolan]-3-yloxy)methyl)isoxazol-5-yl)propan-2-ol

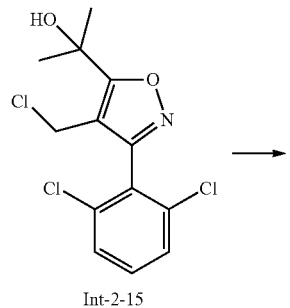

Int-2-15

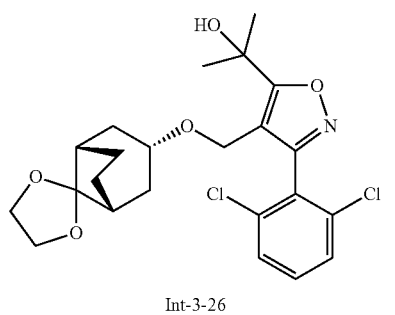

Int-3-26

Following general procedure A2, using 2-(4-(chloromethyl)-3-(2,6-dichlorophenyl)isoxazol-5-yl)propan-2-ol Int-2-15, the intermediate 2-(3-(2,6-dichlorophenyl)-4-(((1R,3s,5S)-spiro[bicyclo[3.2.1]octane-8,2'-[1,3]dioxolan]-3-yloxy)methyl)isoxazol-5-yl)propan-2-ol (Int-3-26) was synthesized.

Intermediate Int-3-27: 4-Cyclopropyl-1-(2,6-dichlorophenyl)-5-((((1R,3s,5S)-spiro[bicyclo[3.2.1]octane-8,2'-[1,3]dioxolan]-3-yl)oxy)methyl)-1H-pyrazole

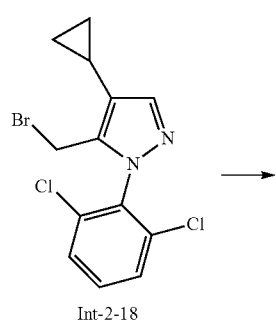

Int-2-18

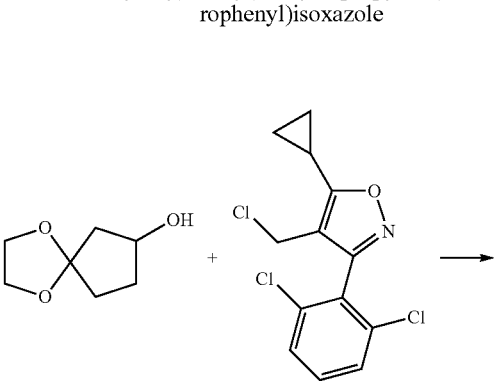

Int-3-27

Following general procedure A2, using 5-(bromomethyl)-4-cyclopropyl-1-(2,6-dichlorophenyl)-1H-pyrazole Int-2-18, the intermediate 4-cyclopropyl-1-(2,6-dichlorophenyl)-5-((((1R,3s,5S)-spiro[bicyclo[3.2.1]octane-8,2'-[1,3]dioxolan]-3-yl)oxy)methyl)-1H-pyrazole (Int-3-27) was synthesized.

Intermediate Int-3-28: 4-((1,4-Dioxaspiro[4.4]nonan-7-yloxy)methyl)-5-cyclopropyl-3-(2,6-dichlorophenyl)isoxazole

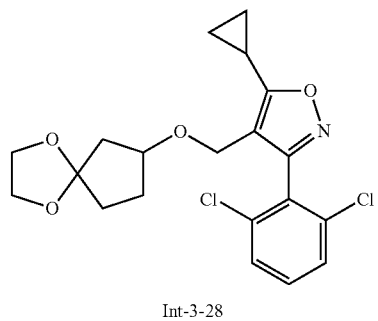

Int-3-28

In a dry flask a solution of 1,4-dioxaspiro[4.4]nonan-7-ol (220 mg, 1.53 mmol) in DMA (10 mL) was treated with sodium hydride (60% disp. in oil; 61 mg, 1.53 mmol) and stirred for 40 min. A solution of 4-(chloromethyl)-5-cyclopropyl-3-(2,6-dichlorophenyl)isoxazole (Int-2-3, 420 mg, 1.39 mmol) in DMA (5 mL) was added and the mixture was stirred at rt for 2 h, quenched with water and stirred for 15 min, then concentrated in vacuo, diluted with EtOAc and water and separated. The organic layer was washed four times with brine, dried over Na$_2$SO$_4$, filtered and concentrated. Purification by chromatography (ISCO 40 g silica, 0-100% EtOAc/hexanes) gave the desired product 4-((1,4-dioxaspiro[4.4]nonan-7-yloxy)methyl)-5-cyclopropyl-3-(2,6-dichloro-phenyl)isoxazole (Int-3-28).

Intermediate Int-3-29: 4-(((1R,5S)-3-Oxaspiro[bicyclo[3.3.1]nonane-9,2'-[1,3]dioxolan]-7-yloxy)methyl)-5-cyclopropyl-3-(2,6-dichlorophenyl)isoxazole

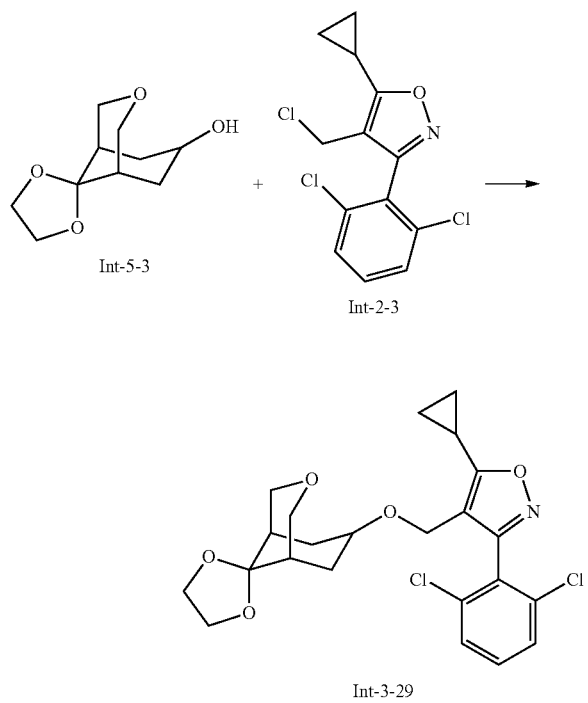

To a suspension of NaH (60% in mineral oil) (580 mg, 14.4 mmol) in THF (30 mL) was added (1R,5S)-3-oxaspiro[bicyclo[3.3.1]nonane-9,2'-[1,3]dioxolan]-7-ol Int-5-3 (570 mg, 2.88 mmol) in THF (10 mL) at 0° C. The reaction mixture was stirred at 0° C. for 1.5 h, then 4-(chloromethyl)-5-cyclopropyl-3-(2,6-dichlorophenyl)isoxazole Int-2-3 (1.2 g, 3.46 mmol) was added at 0° C. and stirred at reflux overnight. The reaction was quenched with NH$_4$Cl (sat.) and extracted with EtOAc (3×20 mL). The organic layers were combined, washed with brine (2×20 mL), dried over Na$_2$SO$_4$, concentrated and purified by chromatography to give 4-(((1R,5S)-3-oxaspiro[bicyclo[3.3.1]nonane-9,2'-[1,3]dioxolan]-7-yloxy)methyl)-5-cyclopropyl-3-(2,6-dichlorophenyl)isoxazole Int-3-29.

General Procedure B for the Synthesis of Intermediate Int-4

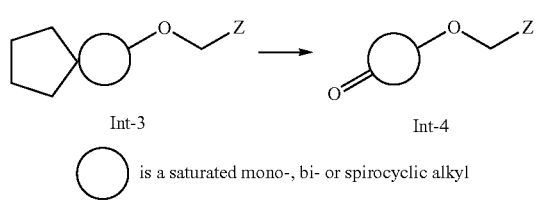

○ is a saturated mono-, bi- or spirocyclic alkyl

To a solution of selected ketal Int-3 (1.0 eq.) in acetone was added aq. HCl (1M) and the mixture was stirred at rt for 2 h, concentrated and the residue was purified by TLC or flash chromtography to afford intermediates Int-4.

Alternative General Procedure B2 for the Synthesis of Intermediate Int-4

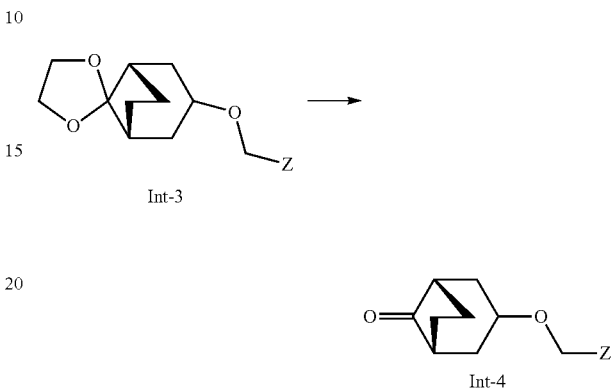

To a stirred solution of selected cyclic ketal Int-3 (1.0 eq.) in acetone/H$_2$O (125 vol., 4:1, v:v) at rt was added p-TsOH (0.45 eq.). The mixture was stirred at reflux for 72 h. The solvent was concentrated under reduced pressure and the pH of the mixture was adjusted to approx. pH=8 with aq. NaHCO$_3$. The mixture was extracted with EtOAc and the combined organic phase was washed with brine, dried over Na$_2$SO$_4$ and concentrated. The crude products were purified by silica gel chromatography.

Intermediate Int-4-1: 4-((5-Cyclopropyl-3-(4,4-difluorocyclohexyl)isoxazol-4-yl)methoxy)cyclohexanone

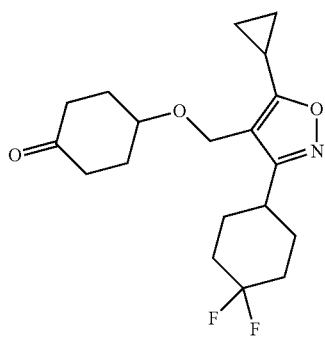

Following general procedure B, beginning with 4-((1,4-dioxaspiro[4.5]decan-8-yloxy)methyl)-5-cyclopropyl-3-(4,4-difluorocyclohexyl)isoxazole Int-3-1 (600 mg, 1.5 mmol) and aq. HCl (3 mL, 1M), the intermediate 4-((5-cyclopropyl-3-(4,4-difluorocyclohexyl)isoxazol-4-yl)methoxy)cyclohexanone Int-4-1 was synthesized and purified by TLC (PE/EtOAc=3:1).

Intermediate Int-4-2: 4-((5-Cyclopropyl-3-(spiro[2.5]octan-6-yl)isoxazol-4-yl)methoxy)cyclohexanone

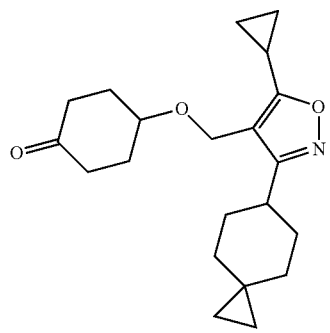

Int-4-2

Following general procedure B, beginning with ((1,4-dioxaspiro[4.5]decan-8-yloxy)methyl)-5-cyclopropyl-3-(spiro[2.5]octan-6-yl)isoxazole Int-3-2 (230 mg, 0.6 mmol) and aq. HCl (3 mL, 1M), the intermediate 4-((5-cyclopropyl-3-(spiro[2.5]octan-6-yl)isoxazol-4-yl)methoxy)cyclohexanone Int-4-2 was synthesized and purified by TLC (PE/EtOAc=3:1).

Intermediate Int-4-3: 6-((5-Cyclopropyl-3-(2,6-dichlorophenyl)isoxazol-4-yl)methoxy)spiro[3.3]heptan-2-one

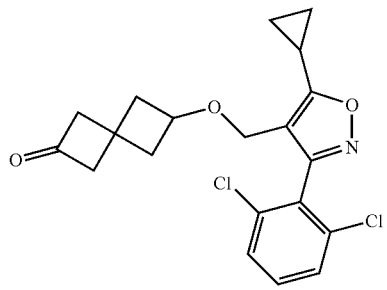

Int-4-3

Following general procedure B, beginning with 4-((1,4-dioxadispiro[4.1.3.1]undecan-9-yloxy)methyl)-5-cyclopropyl-3-(2,6-dichlorophenyl)isoxazole Int-3-3 (500 mg) and p-TsOH (210 mg) in acetone/H$_2$O (1:1, 50 mL) instead of aq. HCl, the intermediate 6-((5-cyclopropyl-3-(2,6-dichlorophenyl)isoxazol-4-yl)methoxy)spiro[3.3]heptan-2-one Int-4-3 was synthesized.

Intermediate Int-4-4: 4-((5-Cyclopropyl-3-(2,6-dichlorophenyl)isoxazol-4-yl)methoxy)cyclohexanone

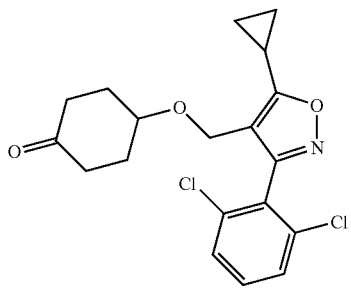

Int-4-4

Following general procedure B, beginning with 4-((1,4-dioxaspiro[4.5]decan-8-yloxy)methyl)-5-cyclopropyl-3-(2,6-dichlorophenyl)isoxazole Int-3-4, the intermediate 4-((5-cyclopropyl-3-(2,6-dichlorophenyl)isoxazol-4-yl)methoxy)cyclohexanone Int-4-4 was synthesized.

Intermediate Int-4-5: 4-((5-Cyclopropyl-3-(2-(difluoromethoxy)phenyl)isoxazol-4-yl)methoxy)cyclohexanone

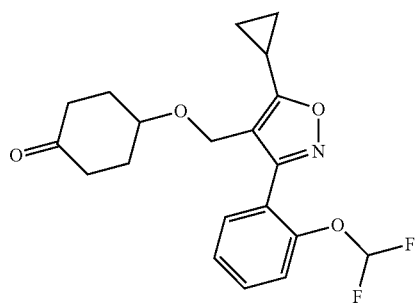

Int-4-5

Following general procedure B, beginning with 4-((1,4-dioxaspiro[4.5]decan-8-yloxy)methyl)-5-cyclopropyl-3-(2-(difluoromethoxy)phenyl)isoxazole Int-3-5, the intermediate 4-((5-cyclopropyl-3-(2-(difluoromethoxy)phenyl)isoxazol-4-yl)methoxy)cyclohexanone Int-4-5 was synthesized.

Intermediate Int-4-6: 4-((5-Cyclopropyl-3-(2-cyclopropylphenyl)isoxazol-4-yl)methoxy)cyclohexanone

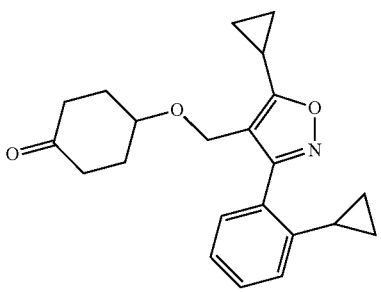

Int-4-6

Following general procedure B, beginning with 4-((1,4-dioxaspiro[4.5]decan-8-yloxy)methyl)-5-cyclopropyl-3-(2-cyclopropylphenyl)isoxazole Int-3-6, the intermediate 4-((5-cyclopropyl-3-(2-cyclopropylphenyl)isoxazol-4-yl)methoxy)cyclohexanone Int-4-6 was synthesized.

Intermediate Int-4-7: 4-((5-Cyclopropyl-3-(2,6-dimethylphenyl)isoxazol-4-yl)methoxy)cyclohexanone

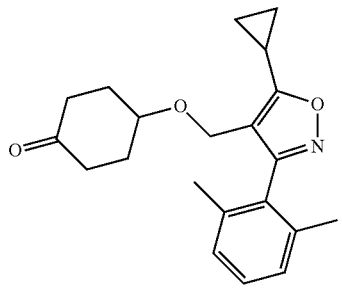

Int-4-7

Following general procedure B, beginning with 4-((1,4-dioxaspiro[4.5]decan-8-yloxy)methyl)-5-cyclopropyl-3-(2,6-dimethylphenyl)isoxazole Int-3-7, the intermediate 4-((5-cyclopropyl-3-(2,6-dimethylphenyl)isoxazol-4-yl)methoxy)cyclohexanone Int-4-7 was synthesized.

Intermediate Int-4-8: 4-((4-Cyclopropyl-1-(2,6-dichlorophenyl)-1H-pyrazol-5-yl)methoxy)cyclohexanone

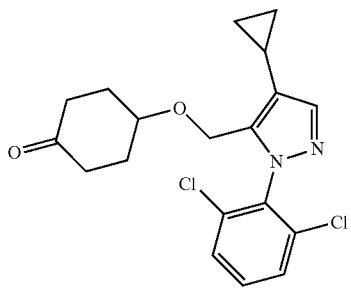

Int-4-8

Following general procedure B, beginning with 5-((1,4-dioxaspiro[4.5]decan-8-yloxy)methyl)-4-cyclopropyl-1-(2,6-dichlorophenyl)-1H-pyrazole Int-3-8, the intermediate 4-((4-cyclopropyl-1-(2,6-dichlorophenyl)-1H-pyrazol-5-yl)methoxy)cyclohexanone Int-4-8 was synthesized.

Intermediate Int-4-9: 4-((5-Cyclopropyl-3-(2-(trifluoromethoxy)phenyl)isoxazol-4-yl)methoxy)cyclohexanone

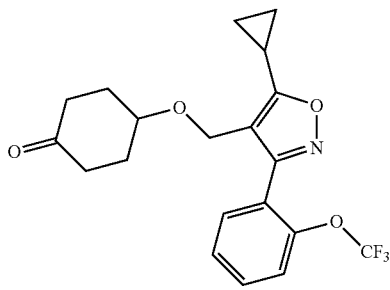

Int-4-9

Following general procedure B, beginning with 4-((1,4-dioxaspiro[4.5]decan-8-yloxy)methyl)-5-cyclopropyl-3-(2-(trifluoromethoxy)phenyl)isoxazole Int-3-9, the intermediate 4-((5-cyclopropyl-3-(2-(trifluoromethoxy)phenyl)isoxazol-4-yl)methoxy)cyclohexanone Int-4-9 was synthesized.

Intermediate Int-4-10: 4-((5-Cyclopropyl-3-(2-(difluoromethyl)phenyl)isoxazol-4-yl)methoxy)cyclohexanone

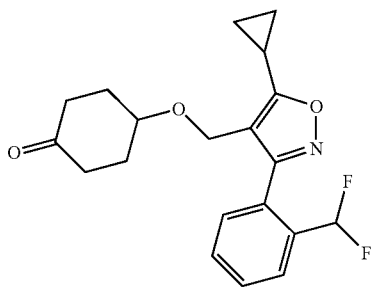

Int-4-10

Following general procedure B, beginning with 4-((1,4-dioxaspiro[4.5]decan-8-yloxy)methyl)-5-cyclopropyl-3-(2-(difluoromethyl)phenyl)isoxazole Int-3-10, the intermediate 4-((5-cyclopropyl-3-(2-(difluoromethyl)phenyl)isoxazol-4-yl)methoxy)cyclohexanone Int-4-10 was synthesized.

Intermediate Int-4-11: 4-((5-Cyclopropyl-3-(3,5-dichloropyridin-4-yl)isoxazol-4-yl)methoxy)cyclohexanone

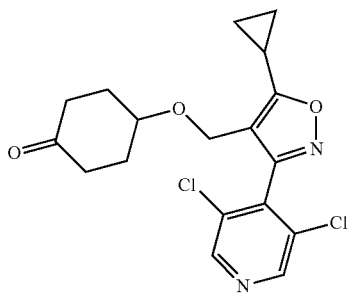

Int-4-11

Following general procedure B, beginning with 4-((1,4-dioxaspiro[4.5]decan-8-yloxy)methyl)-5-cyclopropyl-3-(3,5-dichloropyridin-4-yl)isoxazole Int-3-11, the intermediate 4-((5-cyclopropyl-3-(3,5-dichloropyridin-4-yl)isoxazol-4-yl)methoxy)cyclohexanone Int-4-11 was synthesized.

Intermediate Int-4-12: 4-((4-cyclopropyl-1-(2-(difluoromethoxy)phenyl)-1H-pyrazol-5-yl)methoxy)cyclohexanone

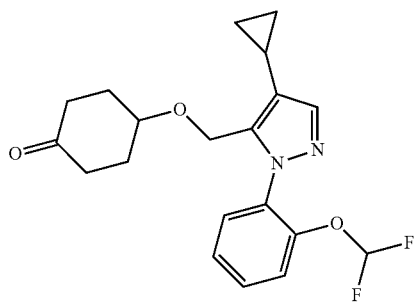

Int-4-12

Following general procedure B, beginning with 5-((1,4-dioxaspiro[4.5]decan-8-yloxy)methyl)-4-cyclopropyl-1-(2-(difluoromethoxy)phenyl)-1H-pyrazole Int-3-12, the intermediate 4-((4-cyclopropyl-1-(2-(difluoromethoxy)phenyl)-1H-pyrazol-5-yl)methoxy)cyclohexanone Int-4-12 was synthesized.

Intermediate Int-4-13: 4-((3-(2,6-Bis(difluoromethyl)phenyl)-5-cyclopropylisoxazol-4-yl)methoxy)cyclohexanone

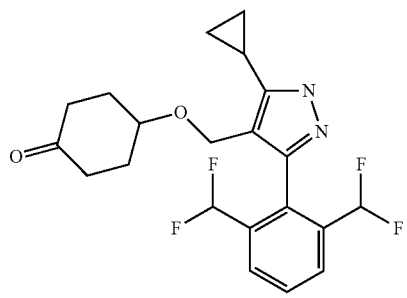

Int-4-13

Following general procedure B, beginning with 4-((1,4-dioxaspiro[4.5]decan-8-yloxy)methyl)-3-(2,6-bis(difluoromethyl)phenyl)-5-cyclopropylisoxazole Int-3-13, the intermediate 4-((3-(2,6-bis(di-fluoromethyl)phenyl)-5-cyclopropylisoxazol-4-yl)methoxy)cyclohexanone Int-4-13 was synthesized.

Intermediate Int-4-14a: (1R,3s,5S)-3-((5-Cyclopropyl-3-(2,6-dichlorophenyl)isoxazol-4-yl)methoxy)bicyclo[3.2.1]octan-8-one

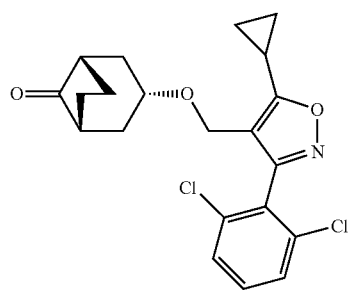

Int-4-14a

Following general procedure B2, beginning with 5-cyclopropyl-3-(2,6-dichlorophenyl)-4-((((1R,3s,5S)-spiro[bicyclo[3.2.1]octane-8,2'-[1,3]dioxolan]-3-yl)oxy)methyl)isoxazole Int-3-14a, the intermediate (1R,3s,5S)-3-((5-cyclopropyl-3-(2,6-dichlorophenyl)isoxazol-4-yl)methoxy)bicyclo-[3.2.1]octan-8-one Int-4-14a was synthesized. $^1$H-NMR (400 MHz, CDCl$_3$) δ 7.44-7.41 (m, 2H), 7.37-7.33 (m, 1H), 4.29 (s, 2H), 3.85-3.78 (m, 1H), 2.16-2.08 (m, 5H), 1.97-1.92 (m, 2H), 1.70-1.65 (m, 4H), 1.29-1.24 (m, 2H), 1.15-1.10 (m, 2H). LCMS (ESI): m/z 405.6 (M+1)$^+$.

Intermediate Int-4-14b: (1R,3r,5S)-3-((5-Cyclopropyl-3-(2,6-dichlorophenyl)isoxazol-4-yl)methoxy)bicyclo[3.2.1]octan-8-one

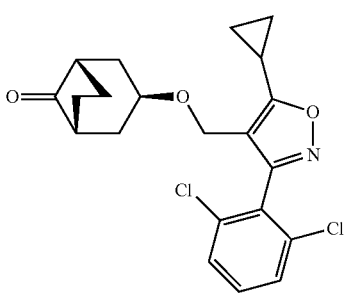

Int-4-14b

Following general procedure B2, beginning with 5-cyclopropyl-3-(2,6-dichlorophenyl)-4-((((1R,3r,5S)-spiro[bicyclo[3.2.1]octane-8,2'-[1,3]dioxolan]-3-yl)oxy)methyl)isoxazole Int-3-14b, the intermediate (1R,3r,5S)-3-((5-cyclopropyl-3-(2,6-dichlorophenyl)isoxazol-4-yl)methoxy)bicyclo[3.2.1]octan-8-one Int-4-14b was synthesized.

Intermediate Int-4-15: (1R,3s,5S)-3-((5-Cyclopropyl-3-(2-(difluoromethoxy)phenyl)isoxazol-4-yl)methoxy)bicyclo[3.2.1]octan-8-one

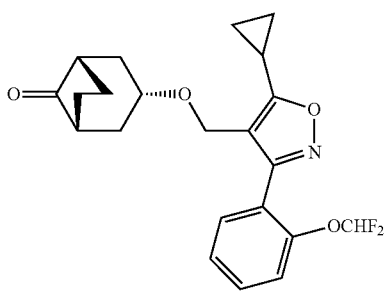

Int-4-15

Following general procedure B2, beginning with 5-cyclopropyl-3-(2-(difluoromethoxy)phenyl)-4-((((1R,3s,5S)-spiro[bicyclo[3.2.1]octane-8,2'-[1,3]dioxolan]-3-yl)oxy)methyl)isoxazole Int-3-15, the intermediate (1R,3s,5S)-3-((5-Cyclopropyl-3-(2-(difluoromethoxy)phenyl)isoxazol-4-yl)methoxy)bicyclo[3.2.1]octan-8-one Int-4-15 was synthesized.

Intermediate Int-4-16: (1R,3s,5S)-3-((5-Cyclopropyl-3-(3,5-dichloropyridin-4-yl)isoxazol-4-yl)methoxy)bicyclo[3.2.1]octan-8-one

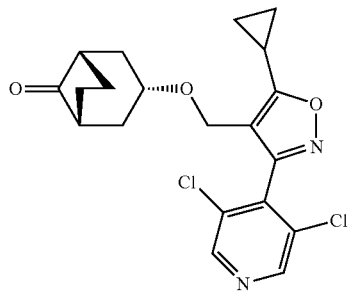

Int-4-16

Following general procedure B2, beginning with 5-cyclopropyl-3-(3,5-dichloropyridin-4-yl)-4-((((1R,3s,5S)-spiro[bicyclo[3.2.1]octane-8,2'-[1,3]dioxolan]-3-yl)oxy)methyl)isoxazole Int-3-16, the intermediate (1R,3s,5S)-3-((5-cyclopropyl-3-(3,5-dichloropyridin-4-yl)isoxazol-4-yl)methoxy)bicyclo[3.2.1]octan-8-one Int-4-16 was synthesized.

Intermediate Int-4-17: (1R,3s,5S)-3-((3-(2,6-Dichlorophenyl)-5-methylisoxazol-4-yl)methoxy)bicyclo[3.2.1]octan-8-one

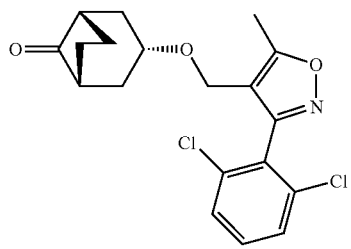

Int-4-17

Following general procedure B2, beginning with 3-(2,6-dichlorophenyl)-5-methyl-4-((((1R,3s,5S)-spiro[bicyclo[3.2.1]octane-8,2'-[1,3]dioxolan]-3-yloxy)methyl)isoxazole Int-3-17a, the intermediate (1R,3s,5S)-3-((3-(2,6-dichlorophenyl)-5-methylisoxazol-4-yl)methoxy)bicyclo[3.2.1]octan-8-one Int-4-17 was synthesized.

Intermediate Int-4-18: (1R,3r,5S)-3-((3-(2,6-Dichlorophenyl)-5-methylisoxazol-4-yl)methoxy)bicyclo[3.2.1]octan-8-one

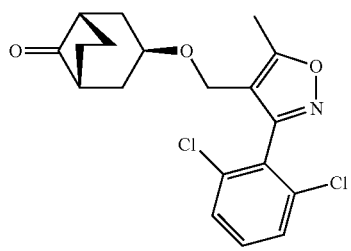

Int-4-18

Following general procedure B2, beginning with 3-(2,6-dichlorophenyl)-5-methyl-4-((((1R,3r,5S)-spiro[bicyclo[3.2.1]octane-8,2'-[1,3]dioxolan]-3-yloxy)methyl)isoxazole Int-3-17b, the intermediate (1R,3r,5S)-3-((3-(2,6-dichlorophenyl)-5-methylisoxazol-4-yl)methoxy)bicyclo[3.2.1]octan-8-one Int-4-18 was synthesized.

Intermediate Int-4-19: (1R,5S)-3-((5-Cyclopropyl-3-(2,6-dichlorophenyl)isoxazol-4-yl)methoxy)-3-methylbicyclo[3.2.1]octan-8-one

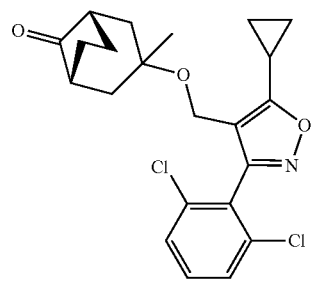

Int-4-19

Following general procedure B, beginning with 5-cyclopropyl-3-(2,6-dichlorophenyl)-4-((((1R,5S)-3-methylspiro[bicyclo[3.2.1]octane-8,2'-[1,3]dioxolan]-3-yl)oxy)methyl)isoxazole Int-3-18, the intermediate (1R,5S)-3-((5-cyclopropyl-3-(2,6-dichlorophenyl) isoxazol-4-yl)methoxy)-3-methylbicyclo[3.2.1]octan-8-one Int-4-19 was synthesized.

Intermediate Int-4-20: (1R,5S)-3-((5-Cyclopropyl-3-(2,6-dichlorophenyl)isoxazol-4-yl)methoxy)-3-(difluoromethyl)bicyclo[3.2.1]octan-8-one

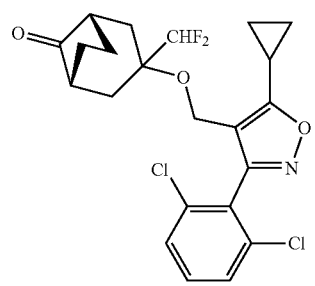

Int-4-20

Following general procedure B, beginning with 5-cyclopropyl-3-(2,6-dichlorophenyl)-4-((((1R,5S)-3-(difluoromethyl)spiro[bicyclo[3.2.1]octane-8,2'-[1,3]dioxolan]-3-yl)oxy)methyl)isoxazole Int-3-19, the intermediate (1R,5S)-3-((5-cyclopropyl-3-(2,6-dichlorophenyl)isoxazol-4-yl)methoxy)-3-(di-fluoromethyl)bicyclo[3.2.1]octan-8-one Int-4-20 was synthesized.

Intermediate Int-4-21: (1R,5S)-3-((5-Cyclopropyl-3-(2,6-dichlorophenyl)isoxazol-4-yl)methoxy)-3-(methoxymethyl)bicyclo[3.2.1]octan-8-one

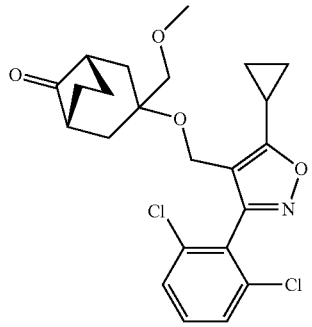

Int-4-21

Following general procedure B, beginning with 5-cyclopropyl-3-(2,6-dichlorophenyl)-4-((((1R,5S)-3-(methoxymethyl)spiro[bicyclo[3.2.1]octane-8,2'-[1,3]dioxolan]-3-yl)oxy)methyl)isoxazole Int-3-20, the intermediate (1R,5S)-3-((5-cyclopropyl-3-(2,6-dichlorophenyl)isoxazol-4-yl)methoxy)-3-(methoxymethyl)bicyclo[3.2.1]octan-8-one Int-4-21 was synthesized.

Intermediate Int-4-22: (3aR,6aS)-5-((5-Cyclopropyl-3-(2,6-dichlorophenyl)isoxazol-4-yl)methoxy)hexahydropentalen-2(1H)-one

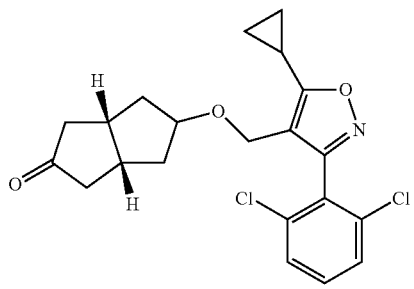

Int-4-22

Following general procedure B, beginning with 5-cyclopropyl-3-(2,6-dichlorophenyl)-4-(((((3a'R,6a'S)-hexahydro-1'H-spiro[[1,3]dioxolane-2,2'-pentalen]-5-yl)oxy)methyl) isoxazole Int-3-21, the intermediate (3aR,6aS)-5-((5-cyclopropyl-3-(2,6-dichlorophenyl)isoxazol-4-yl)methoxy) hexahydropentalen-2(1H)-one Int-4-22 was synthesized and isolated as a single isomer. Chiral HPLC (OZ—H 4.6×250 mm column 5 μm; Eluent: CO$_2$/MeOH 65:35, (0.2% NH$_4$OMe); flow: 1.95 mL/minute; w=214 to 359 nm; T=40.1° C.): retention time 2.94 min (minor isomer (4%) at 3.36 min. $^1$H-NMR (500 MHz, CDCl$_3$) δ ppm: 7.41-7.32 (m, 3H), 4.21 (s, 2H), 3.93-3.89 (m, 1H), 2.65-2.62 (m, 2H), 2.42-2.36 (m, 2H), 2.13-1.99 (m, 5H), 1.40-1.35 (m, 2H), 1.27-1.23 (m, 2H), 1.14-1.10 (m, 2H).

Intermediate Int-4-23: (1R,4R)-5-((5-Cyclopropyl-3-(2,6-dichlorophenyl)isoxazol-4-yl)methoxy)bicyclo[2.2.1]heptan-2-one

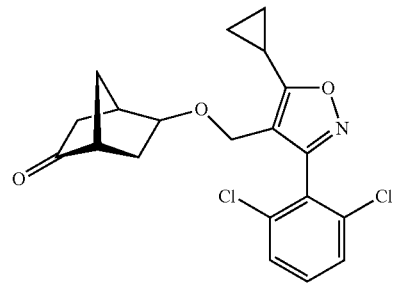

Int-4-23

Following general procedure B, beginning with 5-cyclopropyl-3-(2,6-dichlorophenyl)-4-(((1R,4R)-spiro[bicyclo[2.2.1]heptane-2,2'-[1,3]dioxolan]-5-yloxy)methyl)isoxazole Int-3-22, the intermediate (1R,4R)-5-((5-cyclopropyl-3-(2,6-dichlorophenyl)isoxazol-4-yl)methoxy)bicyclo[2.2.1]heptan-2-one Int-4-23 was synthesized.

Intermediate Int-4-24: (1R,3s,5S)-3-((5-Cyclopropyl-3-((2,6-dimethylphenoxy)methyl)isoxazol-4-yl)methoxy)bicyclo[3.2.1]octan-8-one

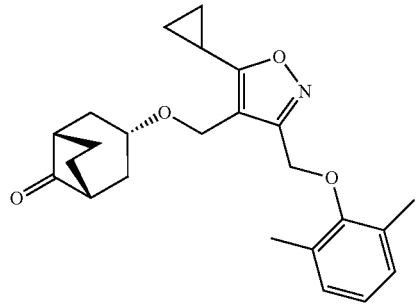

Int-4-24

Following general procedure B, beginning with 5-cyclopropyl-3-((2,6-dimethylphenoxy)methyl)-4-(((1R,3s,5S)-spiro[bicyclo[3.2.1]octane-8,2'-[1,3]dioxolan]-3-yloxy)methyl)isoxazole Int-3-23, the intermediate (1R,3s,5S)-3-((5-cyclopropyl-3-((2,6-dimethylphenoxy)methyl)isoxazol-4-yl)methoxy)bicyclo[3.2.1]octan-8-one Int-4-24 was synthesized.

Intermediate Int-4-25: (1R,3s,5S)-3-((3-(2,6-Dichlorophenyl)-5-isopropylisoxazol-4-yl)methoxy)bicyclo[3.2.1]octan-8-one

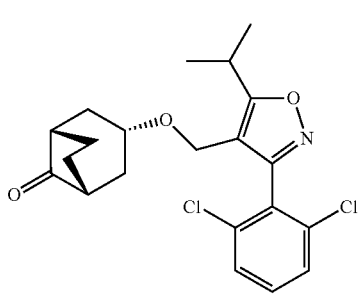

Int-4-25

Following general procedure B, beginning with 3-(2,6-dichlorophenyl)-5-isopropyl-4-(((1R,3s,5S)-spiro[bicyclo[3.2.1]octane-8,2'-[1,3]dioxolan]-3-yloxy)methyl)isoxazole Int-3-24, the intermediate (1R,3s,5S)-3-((3-(2,6-dichlorophenyl)-5-isopropylisoxazol-4-yl)methoxy)bicyclo[3.2.1]octan-8-one Int-4-25 was synthesized.

Intermediate Int-4-26: (1R,3s,5S)-3-((3-(2,6-Dichlorophenyl)-5-(2-fluoropropan-2-yl)isoxazol-4-yl)methoxy)bicyclo[3.2.1]octan-8-one

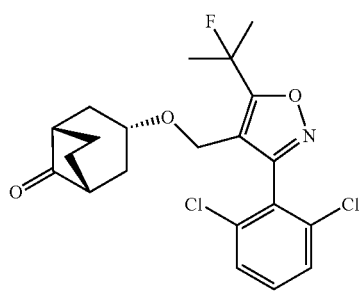

Int-4-26

Following general procedure B, beginning with 3-(2,6-dichlorophenyl)-5-(2-fluoropropan-2-yl)-4-(((1R,3s,5S)-spiro[bicyclo[3.2.1]octane-8,2'-[1,3]dioxolan]-3-yloxy)methyl)isoxazole Int-3-25, the intermediate (1R,3s,5S)-3-((3-(2,6-dichlorophenyl)-5-(2-fluoropropan-2-yl)isoxazol-4-yl)methoxy)bicyclo[3.2.1]octan-8-one Int-4-26 was synthesized.

Intermediate Int-4-27: (1R,3s,5S)-3-((3-(2,6-Dichlorophenyl)-5-(2-hydroxypropan-2-yl)isoxazol-4-yl)methoxy)bicyclo[3.2.1]octan-8-one

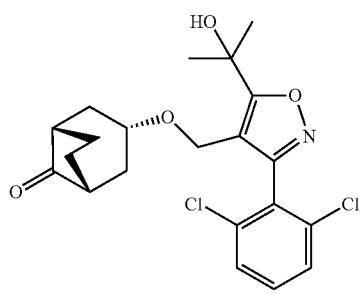

Int-4-27

Following general procedure B, beginning with 2-(3-(2,6-dichlorophenyl)-4-(((1R,3s,5S)-spiro[bicyclo[3.2.1]octane-8,2'-[1,3]dioxolan]-3-yloxy)methyl)isoxazol-5-yl)propan-2-ol Int-3-26, the intermediate (1R,3s,5S)-3-((3-(2,6-dichlorophenyl)-5-(2-hydroxypropan-2-yl)isoxazol-4-yl)methoxy)bicyclo[3.2.1]octan-8-one Int-4-27 was synthesized.

Intermediate Int-4-28: (1R,3s,5S)-3-((4-Cyclopropyl-1-(2,6-dichlorophenyl)-1H-pyrazol-5-yl)methoxy)bicyclo[3.2.1]octan-8-one

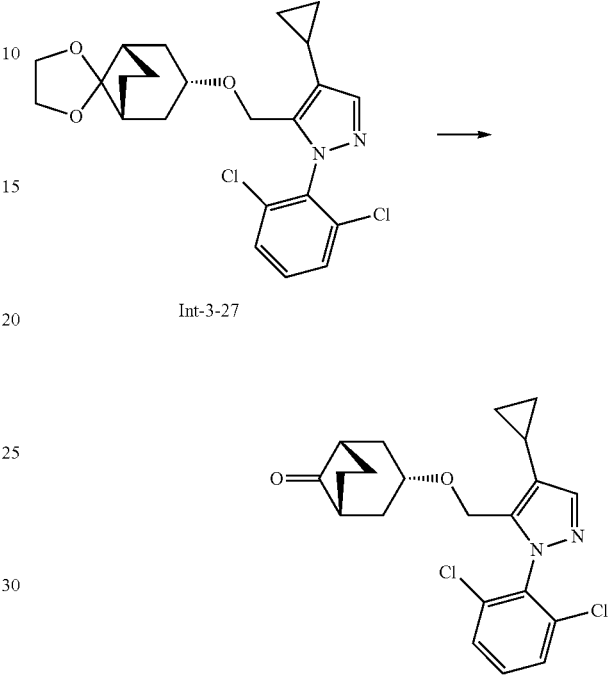

Int-3-27

Int-4-28

Following general procedure B2, beginning with 4-cyclopropyl-1-(2,6-dichlorophenyl)-5-((((1R,3s,5S)-spiro[bicyclo[3.2.1]octane-8,2'-[1,3]dioxolan]-3-yl)oxy)methyl)-1H-pyrazole Int-3-27, the intermediate (1R,3s,5S)-3-((4-cyclopropyl-1-(2,6-dichlorophenyl)-1H-pyrazol-5-yl)methoxy)bicyclo[3.2.1]octan-8-one Int-4-28 was synthesized.

Intermediate Int-4-29: 3-((5-Cyclopropyl-3-(2,6-dichlorophenyl)isoxazol-4-yl)methoxy)cyclopentanone

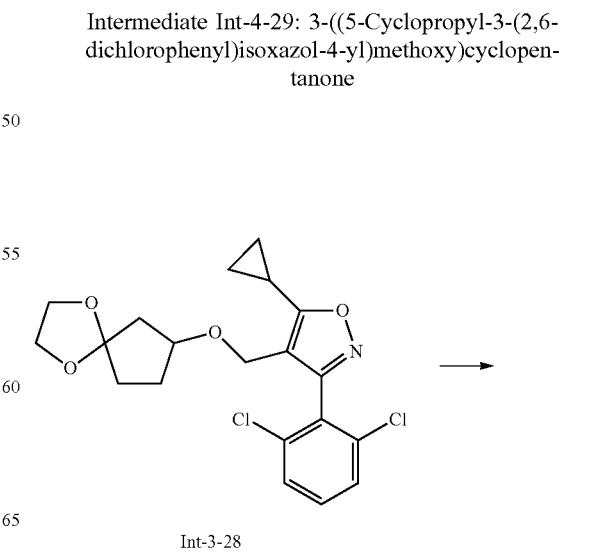

Int-3-28

95

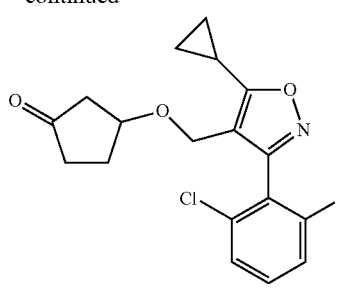

Int-4-29

A solution of 4-((1,4-dioxaspiro[4.4]nonan-7-yloxy)methyl)-5-cyclopropyl-3-(2,6-dichlorophenyl)isoxazole (Int-3-28, 130 mg, 0.32 mmol) in THF (5 mL) was treated with 1N HCl (5 mL) and stirred at rt for 30 min. The mixture was treated with sat. aq. NaHCO₃ and diluted with EtOAc. The phases were separated and the organic layer washed with brine, dried over Na₂SO₄, filtered and concentrated. Purification by chromatography (ISCO 12 g Gold silica, 0-1005 EtOAc/hexanes) gave product 3-((5-cyclopropyl-3-(2,6-dichlorophenyl)isoxazol-4-yl)methoxy)cyclopentanone Int-4-29.

Intermediate Int-4-30: (1R,5S)-7-((5-Cyclopropyl-3-(2,6-dichlorophenyl)isoxazol-4-yl)methoxy)-3-oxabicyclo[3.3.1]nonan-9-one

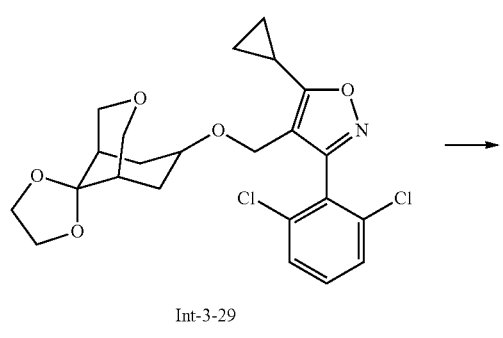

Int-3-29

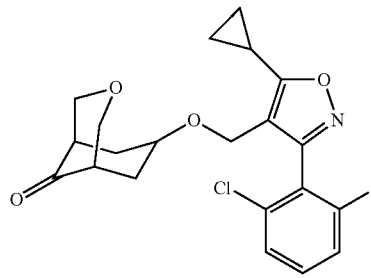

Int-4-30

Following general procedure B2, beginning with 4-(((1R,5S)-3-oxaspiro[bicyclo[3.3.1]nonane-9,2'-[1,3]dioxolan]-7-yloxy)methyl)-5-cyclopropyl-3-(2,6-dichlorophenyl)isoxazole Int-3-29, the intermediate (1R,5S)-7-((5-cyclopropyl-3-(2,6-dichlorophenyl)isoxazol-4-yl)methoxy)-3-oxabicyclo[3.3.1]nonan-9-one Int-4-30 was synthesized.

96

Intermediate Int-5-1: 9-Hydroxy-1,4-dioxadispiro[4.1.3.1]undecane

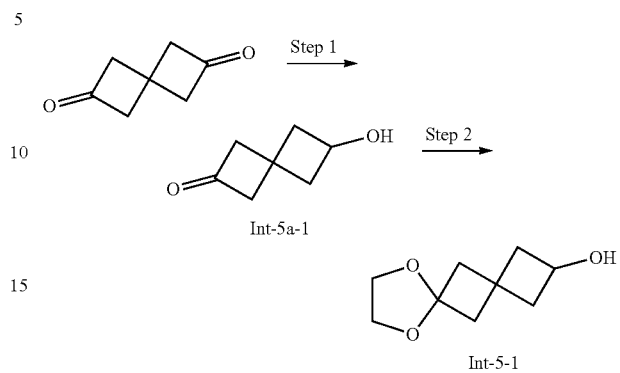

Step 1:

To a solution of spiro[3.3]heptane-2,6-dione (synthesized according R. A. Weatherhead et al. J. Org. Chem. 2009, 74, 8773) (1.0 g, 8.0 mmol) in MeOH (50 mL) was added NaBH₄ (76 mg, 2 mmol) at 0° C. The mixture was stirred for 1 h, quenched with aq. NH₄Cl (10 mL) and extracted with EtOAc (3×100 mL). The organic layer was dried over Na₂SO₄, filtered and concentrated to afford 6-hydroxyspiro[3.3]heptan-2-one Int-5a-1.

Step 2:

To a solution of 6-hydroxyspiro[3.3]heptan-2-one Int-5a-1 (500 mg, 4.0 mmol) in toluene (50 mL) was added ethylene glycol (0.5 g, 8.0 mmol) and p-TsOH (70 mg, 0.4 mmol) at rt. The mixture was refluxed for 1 h, cooled, quenched with aq. NaHCO₃ (10 mL) and extracted with EtOAc (3×100 mL). The organic layer was dried over Na₂SO₄, filtered and concentrated to yield 9-hydroxy-1,4-dioxadispiro[4.1.3.1]undecane Int-5-1.

Intermediate Int-5-2: Spiro[bicyclo[3.2.1]octane-8,2'-[1,3]dioxolan]-3-ol

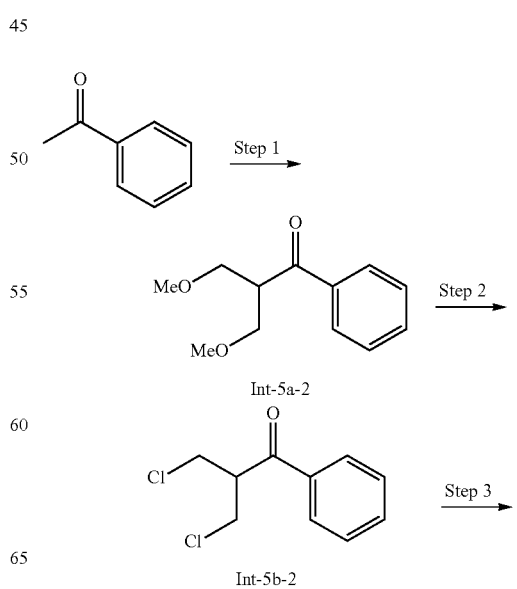

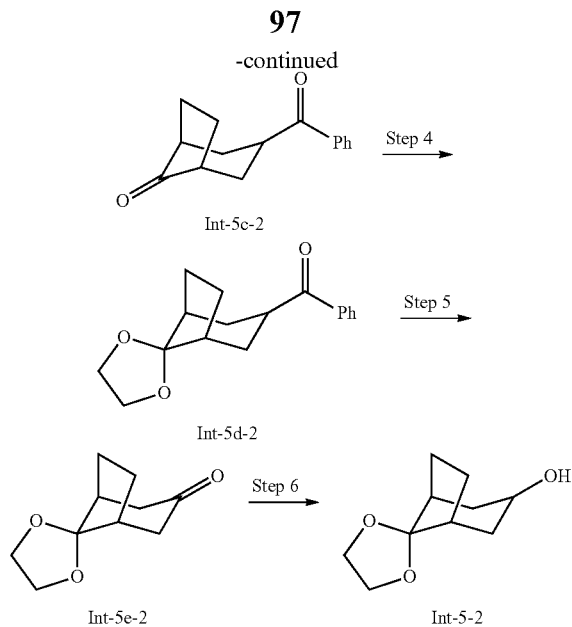

Step 1:

A solution of paraformaldehyde (15 g, 0.5 mol), acetophenone (60 g, 0.5 mol) and $K_2CO_3$ (700 mg) in MeOH (100 mL) was stirred for 7 days at rt and then poured into water (1 L). The mixture was acidified with HCl (conc.) and extracted with EtOAc (4×500 mL). The organic layers were combined, washed with water (2×200 mL) and dried over anhydrous $MgSO_4$. The solvent was removed under reduced pressure. The residue crude product 3-methoxy-2-(methoxymethyl)-1-phenylpropan-1-one Int-5a-2 was used in next step without further purification.

Step 2:

Crude 3-methoxy-2-(methoxymethyl)-1-phenylpropan-1-one Int-5a-2 was dissolved in conc. HCl (50 mL) at rt and the resulting solution was stirred at rt for 24 h. The mixture was extracted with EtOAc (3×200 mL), the organic layers were combined, washed with water (2×100 mL) and dried over $Na_2SO_4$. The solvent was removed under reduced pressure and the residue was purified by column chromatography to afford 3-chloro-2-(chloromethyl)-1-phenylpropan-1-one Int-5b-2.

Step 3:

A solution of 3-chloro-2-(chloromethyl)-1-phenylpropan-1-one Int-5b-2 (1.08 g, 5.0 mmol), 1-(cyclopent-1-en-1-yl)pyrrolidine (680 mg, 5.0 mmol) and TEA (610 mg, 6.0 mmol) in MeCN (15 mL) was heated to reflux for 1 h. The mixture was cooled to rt, diluted with water (15 mL), stirred at rt overnight and extracted with EtOAc (3×10 mL). The organic layers were combined and dried over $Na_2SO_4$, concentrated and purified by column chromatography to afford (1R,5S)-3-benzoylbicyclo[3.2.1]octan-8-one Int-5c-2.

Step 4:

A solution of (1R,5S)-3-benzoylbicyclo[3.2.1]octan-8-one Int-5c-2 (700 mg, 3.0 mmol), ethane-1,2-diol (200 mg, 3.0 mmol) and p-TsOH (30 mg) in toluene (10 mL) was heated to reflux overnight, poured into $NaHCO_3$ (sat. aq. sol.) and extracted with EtOAc (3×10 mL). The organic layers were combined and dried over $Na_2SO_4$, concentrated and purified by column chromatography to give phenyl((1R, 5S)-spiro[bicyclo[3.2.1]octane-8,2'-[1,3]dioxolan]-3-yl)methanone Int-5d-2.

Step 5:

To a mixture of phenyl((1R,5S)-spiro[bicyclo[3.2.1]octane-8,2'-[1,3]dioxolan]-3-yl)methanone Int-5d-2 (2.07 g, 7.61 mmol), potassium tert-butoxide (1.23 g, 10.4 mmol) and tert-butyl alcohol (25 mL) was added hexamethylphosphoric triamide (25 mL). The resulting mixture was saturated with $O_2$ while stirring at 55° C. After the reaction was complete, water was added and the mixture was extracted with EtOAc (3×20 mL). The combined organic layers were washed with water (2×20 mL), dried over $Na_2SO_4$, concentrated and purified by column chromatography to give (1R,5S)-spiro[bicyclo[3.2.1]octane-8,2'-[1,3]dioxolan]-3-one Int-5e-2.

Step 6:

To a mixture of (1R,5S)-spiro[bicyclo[3.2.1]octane-8,2'-[1,3]dioxolan]-3-one Int-5e-2 (5.0 g, 18 mmol) in MeOH/DCM (10 mL/40 mL) was added under stirring $NaBH_4$ (1.36 g, 36 mmol) in several portions. The mixture was stirred at rt overnight, poured into sat. aq. $NaHCO_3$ solution and extracted with EtOAc (3×20 mL). The combined organic layers were dried over $Na_2SO_4$ and concentrated to give crude (1R,5S)-spiro[bicyclo[3.2.1]octane-8,2'-[1,3]dioxolan]-3-ol Int-5-2, which used without further purification.

Intermediate Int-5-3: (1R,5S)-3-Oxaspiro[bicyclo[3.3.1]nonane-9,2'-[1,3]dioxolan]-7-ol

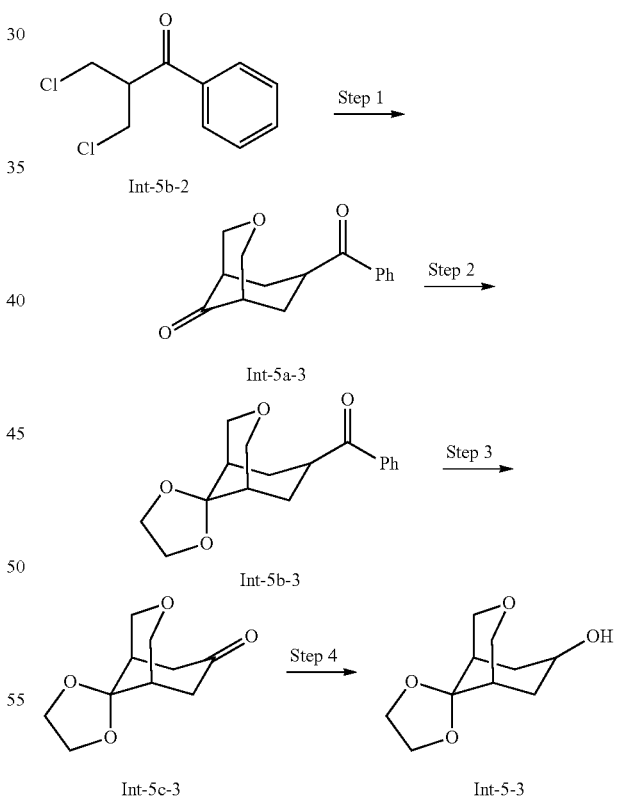

Step 1:

A solution of 3-chloro-2-(chloromethyl)-1-phenylpropan-1-one Int-5b-2 (10 g, 45.8 mmol), 1-(3,6-dihydro-2H-pyran-4-yl)pyrrolidine (7.0 g, 45.8 mmol) and TEA (5.0 g, 50.0 mmol) in $CH_3CN$ (150 mL) was heated to reflux for 1 h, cooled to rt, diluted with water (150 mL) and stirred at rt overnight. The mixture was extracted with EtOAc (3×100 mL). The organic layers were combined, dried over Na$_2$SO$_4$, concentrated and purified column chromatography to give (1R,5S)-7-benzoyl-3-oxabicyclo[3.3.1]nonan-9-one Int-5a-3.

Step 2:
A solution of (1R,5S)-7-benzoyl-3-oxabicyclo[3.3.1]nonan-9-one Int-5a-3 (7.8 g, 32.0 mmol), ethane-1,2-diol (2.4 g, 38.4 mmol) and p-TsOH (500 mg) in toluene (100 mL) was heated to reflux overnight, poured into NaHCO$_3$ (aq.) and extracted with EtOAc (3×100 mL). The organic layers were combined, dried over Na$_2$SO$_4$, concentrated and purified by column chromatography to give phenyl((1R,5S)-3-oxaspiro[bicyclo[3.3.1]nonane-9,2'-[1,3]dioxolan]-7-yl)methanone Int-5b-3.

Step 3:
To a mixture of phenyl((1R,5S)-3-oxaspiro[bicyclo[3.3.1]nonane-9,2'-[1,3]dioxolan]-7-yl)methanone Int-5b-3 (7.5 g, 26.0 mmol), potassium tert-butoxide (3.4 g, 30.0 mmol) and tert-butyl alcohol (100 mL) was added hexamethylphosphoric triamide (100 mL). The mixture was saturated with O$_2$ while stirring at 55° C. After the reaction was complete (determined by TLC), water (1 L) was added and the mixture was extracted with EtOAc (3×100 mL). The organic layers were combined, washed with water (2×100 mL), dried over Na$_2$SO$_4$, concentrated and purified by column chromatography to give (1R,5S)-3-oxaspiro[bicyclo[3.3.1]nonane-9,2'-[1,3]dioxolan]-7-one Int-5c-3.

Step 4:
To the mixture of (1R,5S)-3-oxaspiro[bicyclo[3.3.1]nonane-9,2'-[1,3]dioxolan]-7-one Int-5c-3 (1.0 g, 5.0 mmol) in MeOH/DCM (10 mL/40 mL) was added NaBH$_4$ (760 mg, 20.0 mmol) in several portions at 0° C. The mixture was stirred at rt overnight, poured into a NH$_4$Cl solution and extracted with EtOAc (3×50 mL). The organic layers were combined, dried over Na$_2$SO$_4$ and concentrated to give (1R,5S)-3-oxaspiro[bicyclo[3.3.1]nonane-9,2'-[1,3]dioxolan]-7-ol Int-5-3, which was used in the next step without further purification.

Intermediate Int-6-1:
2-Bromo-4-fluorobenzo[d]thiazole-6-carbonitrile

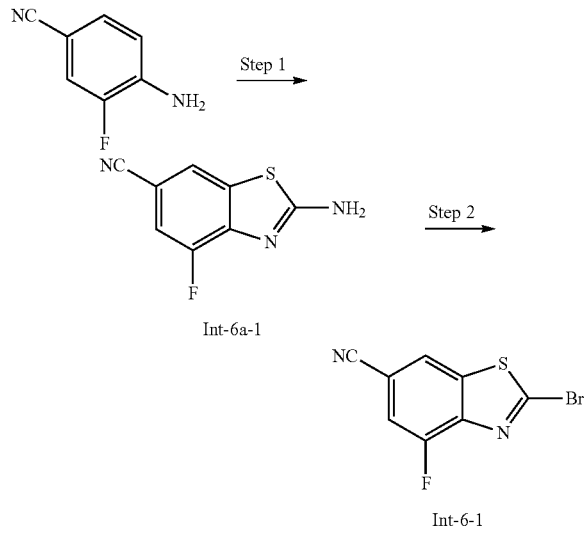

Step 1:
To a stirred solution of 4-amino-3-fluorobenzonitrile (2.0 g, 14.7 mmol) and potassium thiocyanide (5.7 g, 59 mmol) in AcOH (50 mL) was added a solution of bromine (2.3 g, 14.7 mmol) in AcOH (5 mL) over 20 min. The mixture was stirred at rt for 20 h, poured into ice-water (100 mL). Ammonium hydroxide solution (28%) was added to pH 8, stirred for 2 h, filtered, washed with water and dried to afford 4-amino-3-fluorobenzonitrile Int-6a-1.

Step 2:
A solution of 4-amino-3-fluorobenzonitrile Int-6a-1 (2.0 g, 10 mmol), tert-BuONO (1.5 g, 15 mmol) and CuBr$_2$ (3.3 g, 15 mmol) in MeCN (100 mL) was stirred at rt overnight, quenched with water (100 mL) and extracted with EtOAc (3×100 mL). The combined organic layer was dried over Na$_2$SO$_4$, filtered and concentrated to afford 2-bromo-4-fluorobenzo[d]thiazole-6-carbonitrile Int-6-1.

Intermediate Int-6-2:
2,6-Dibromo-7-fluorobenzo[d]thiazole

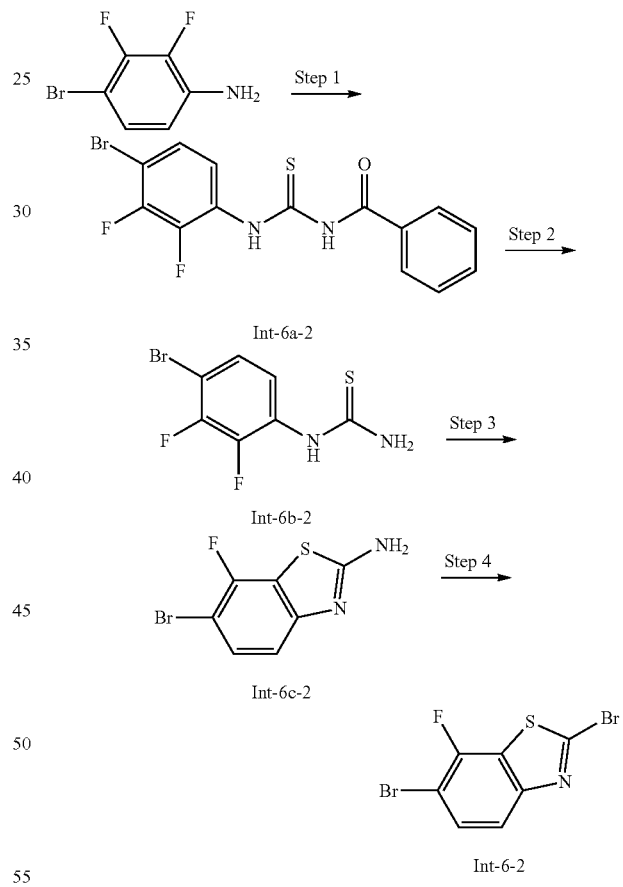

Step 1:
To a solution of 4-bromo-2,3-difluoroaniline (7.66 g, 36.8 mmol) in acetone (60 mL) was dropped under ice-cooling benzoyl isothiocyanate (9.02 g, 55.2 mmol). The mixture was stirred at rt for 18 h. The precipitate was collected by filtration and washed with hexane. The obtained product was dried under reduced pressure to give N-((4-bromo-2,3-difluorophenyl)carbamothioyl)benzamide Int-6a-2.

Step 2:
To a suspension of N-((4-bromo-2,3-difluorophenyl)carbamothioyl)benzamide Int-6a-2 (10.9 g, 29.5 mmol) in methanol (20 mL) was added 2N NaOH (148 mL, 295 mmol) and the mixture was heated under reflux for 1 h, cooled to rt and extracted with EtOAc (3×300 mL), washed with brine (2×50 mL), dried over Na$_2$SO$_4$ and concentrated to give 1-(4-bromo-2,3-difluorophenyl)thiourea Int-6b-2.

Step 3:

To a solution of sodium hydride (60%; 4.01 g, 100 mmol) in dry DMF (50 mL) was added 1-(4-bromo-2,3-difluorophenyl)thiourea Int-6b-2 (6.69 g, 25.1 mmol) under ice-cooling for 15 min. The mixture was stirred for 20 min at rt and stirred for 3 h at 80° C., cooled, diluted with saturated NH$_4$Cl solution and water, extracted with EtOAc (3×200 mL), washed with brine (2×50 mL), dried over Na$_2$SO$_4$, concentrated and purified by flash chromatography (EtOAc/PE=1:1) to give 6-bromo-7-fluorobenzo[d]thiazol-2-amine Int-6c-2.

Step 4:

To a solution of 6-bromo-7-fluorobenzo[d]thiazol-2-amine Int-6c-2 (3.71 g, 15.0 mmol) in MeCN (50 mL) was added isopentyl nitrite (2.64 g, 22.6 mmol) and the solution was stirred at rt for 30 min, then CuBr (4.31 g, 30.1 mmol) was added and the was mixture stirred at rt overnight. EtOAc (300 mL) was added and the solution washed with water (2×50 mL), brine (2×50 mL), dried over Na$_2$SO$_4$, concentrated and purified by flash chromatography (PE/EtOAc=20:1) to give 2,6-dibromo-7-fluorobenzo[d]thiazole Int-6-2.

Intermediate Int-6-3:
2,6-Dibromo-5,7-difluorobenzo[d]thiazole

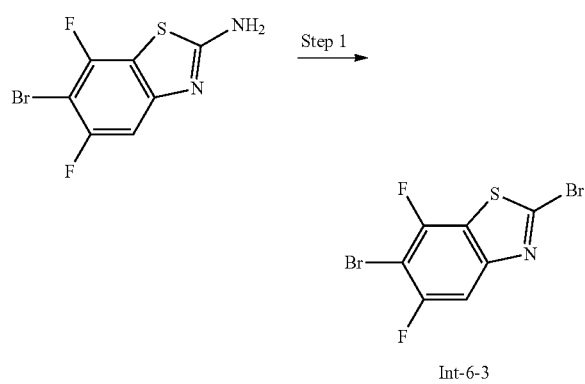

Int-6-3

Similar as described for intermediate Int-6-2 (step 4) starting from 6-bromo-5,7-difluorobenzo[d]thiazol-2-amine, the synthesis furnished 2,6-dibromo-5,7-difluorobenzo[d]thiazole Int-6-3.

Intermediate Int-6-4:
2,6-Dibromo-5-fluorobenzo[d]thiazole

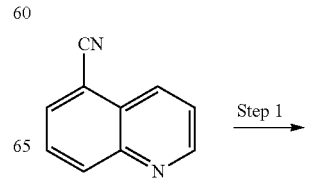

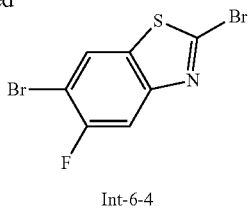

Int-6-4

Similar as described for intermediate Int-6-2 (step 4) starting from 6-bromo-5-fluorobenzo[d]thiazol-2-amine, the synthesis furnished 2,6-dibromo-5-fluorobenzo[d]thiazole Int-6-4.

Intermediate Int-6-5:
6-Bromo-4-fluorobenzo[d]thiazol-2-amine

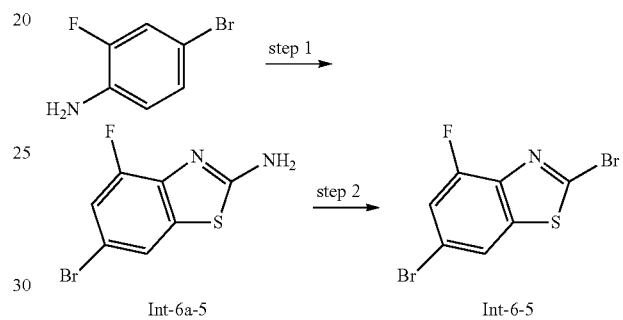

Int-6a-5     Int-6-5

Step 1:

To a solution of 4-bromo-2-fluoroaniline (2.00 g, 10.5 mmol) in AcOH (25 mL) was added KSCN (4.0 g, 42.0 mmol) at rt in one portion and the resulting mixture was stirred at rt until it became a clear solution. Then bromine (1.85 g, 10.5 mmol) in AcOH (10 mL) was added at rt over 15 min and the reaction mixture was stirred at rt for 2 h. The precipitate that formed during the reaction was removed by filtration. The filtrate was poured into water (100 mL) and basified with concentrated NH$_4$OH to pH 8-9. The resulting precipitate was collected by suction filtration to give a crude product. This crude product was purified by chromatography to give 6-bromo-4-fluorobenzo[d]thiazol-2-amine Int-6a-5.

Step 2:

To a mixture of copper (II) bromide (770 mg, 3.5 mmol) in MeCN (10 mL) was added tert-butyl nitrite (1.0 mL, 7.5 mmol) at 0° C. followed by the addition of 6-bromo-4-fluorobenzo[d]thiazol-2-amine Int-6a-5 (800 mg, 3.2 mmol) in one portion. The resulting mixture was stirred at rt for 20 h and extracted with EtOAc. The organic phase was washed with brine, dried over Na$_2$SO$_4$, concentrated and purified by chromatography to give 2,6-dibromo-4-fluorobenzo[d]thiazole Int-6-5.

Intermediate Int-6-6:
2-Bromoquinoline-5-carbonitrile

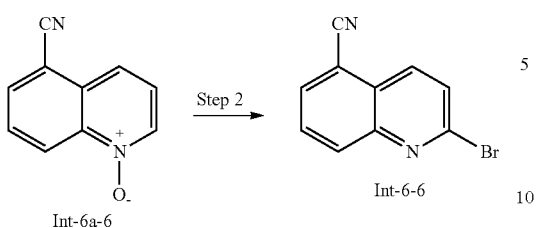

Step 1:

To a solution of quinoline-5-carbonitrile (1.06 g, 9.60 mmol) in DCM (30 mL) was added m-CPBA (2.48 g, 14.40 mmol) at rt and the mixture was stirred overnight, diluted with water and extracted with DCM three times. The combined organic layer was washed with brine, dried over anhydrous $Na_2SO_4$, filtered, concentrated and purified by flash chromatography (PE/EtOAc=2:1) to afford 5-cyanoquinoline 1-oxide Int-6a-6.

Step 2:

A mixture of 5-cyanoquinoline 1-oxide Int-6a-6 (1.13 g, 6.66 mmol) and $POBr_3$ (5.65 g, 20.0 mmol) was heated to 55° C. for 1 h, then ice-water was added and the mixture was extracted with DCM three times. The combined organic layer was washed with brine, dried over anhydrous $Na_2SO_4$, filtered, concentrated and purified by flash chromatography (PE/EtOAc=10:1) to give 2-bromoquinoline-5-carbonitrile Int-6-6.

Intermediate Int-6-7:
6-Bromo-1-isopropyl-1H-indazole-3-carbonitrile

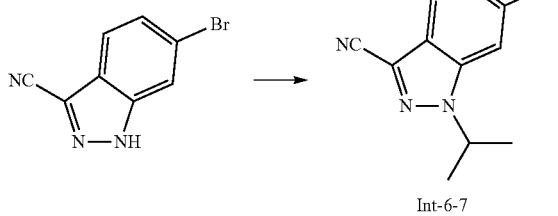

To a solution of 6-bromo-1H-indazole-3-carbonitrile (220 mg, 1.0 mmol) in dry DMF (5 mL) was added NaH (48 mg, 1.2 mmol, 60% suspended in mineral oil) portionwise and the mixture was stirred at rt for 0.5 h. Then isopropyl iodide (200 mg, 1.2 mmol) was added and stirring was continued for 1 h. The mixture was poured into water (20 mL) and the precipitate was collected to give the title compound 6-bromo-1-isopropyl-1H-indazole-3-carbonitrile Int-6-7, which used in the next step without further purification.

Intermediate Int-6-8:
7-(1,3-Dioxolan-2-yl)benzo[d]thiazole

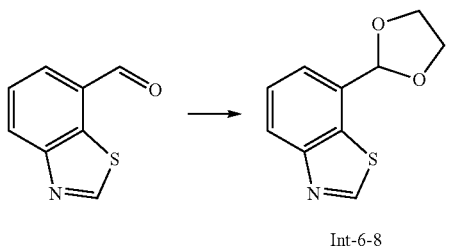 [SMILES: O=Cc1cccc2ncsc12 ; c1cc(C2OCCO2)c2scnc2c1]

A mixture of benzo[d]thiazole-7-carbaldehyde (4.2 g, 25.6 mmol), p-TsOH (100 mg) and ethane-1,2-diol (3.0 mL) in toluene (50 mL) was refluxed overnight, cooled to rt and diluted with EtOAc (100 mL). The solution was washed with sat. $NaHCO_3$ and brine. Then the solution was dried, concentrated and purified by chromatography to give compound 7-(1,3-dioxolan-2-yl)benzo[d]thiazole Int-6-8.

Intermediate Int-6-9: 6-Iodoquinoline-4-carbonitrile

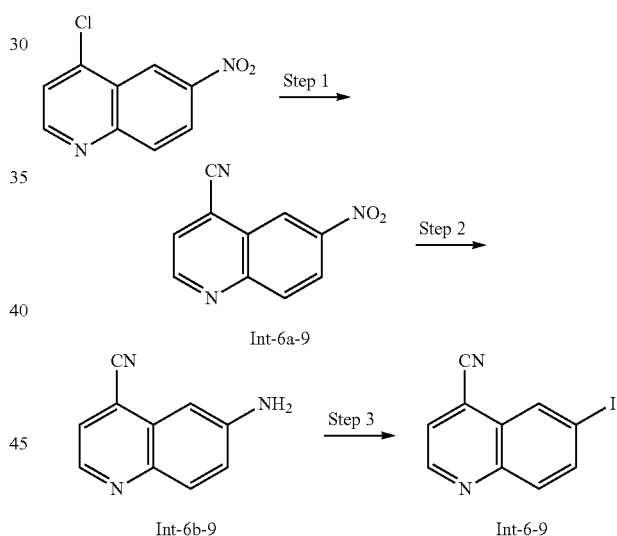

Step 1:

A mixture of 4-chloro-6-nitroquinoline (5.0 g, 24.0 mmol), $Zn(CN)_2$ (5.6 g, 48.0 mmol) and $Pd(PPh_3)_4$ (1.16 g, 1.0 mmol) in DMF (50 mL) was degassed with $N_2$. The mixture was stirred at 125° C. overnight, cooled to rt and diluted with EtOAc. Then the mixture was washed with brine and dried over $Na_2SO_4$, concentrated and purified by chromatography to afford 6-nitroquinoline-4-carbonitrile Int-6a-9.

Step 2:

To a solution of 6-nitroquinoline-4-carbonitrile Int-6a-9 (2.2 g, 11.1 mmol) in MeOH (20 mL) at rt was added $Pd(OH)_2$ (200 mg). The reaction was stirred under $H_2$ atmosphere at rt overnight and filtered. The filtrate was concentrated to dryness to give 6-aminoquinoline-4-carbonitrile Int-6b-9.

Step 3:

To a mixture of 6-aminoquinoline-4-carbonitrile Int-6b-9 (1.83 g, 10.8 mmol) in water (10 mL) was added con. HCl (3 mL) at 0° C. and the solid was dissolved. Then a solution of NaNO₂ (1.4 g, 20.3 mmol) in water (5 mL) was added slowly. After the solution was stirred at 0° C. for 20 min, a solution of KI (5.0 g, 30.1 mmol) in water (5 mL) was added. The reaction was stirred at rt for 1 h and poured into sat. NaHCO₃. The mixture was extracted with EtOAc and the organic phase was washed with brine, dried over Na₂SO₄, concentrated and purified by chromatography to afford 6-iodoquinoline-4-carbonitrile Int-6-9.

Intermediate Int-6-10:
(5-Bromobenzo[d]isothiazol-3-yl)methanol

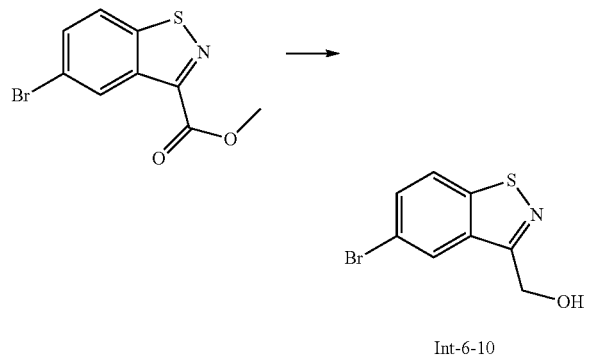

Int-6-10

To a solution of methyl 5-bromobenzo[d]isothiazole-3-carboxylate (2.8 g, 10.3 mmol) in MeOH (30 mL) at rt was slowly added NaBH₄ (760 mg, 20.0 mmol) and the mixture was stirred at 50° C. for 2 h, concentrated, diluted with EtOAc and washed with 0.1N HCl and brine. The organic solution was dried (Na₂SO₄) and concentrated to afford (5-bromobenzo[d]isothiazol-3-yl)methanol Int-6-10.

Intermediate Int-6-11: Mixture of 6-bromo-1-((2-(trimethylsilyl)ethoxy)methyl)-1H-[1,2,3]triazolo[4,5-b]pyridine and 6-bromo-3-((2-(trimethylsilyl)ethoxy)methyl)-3H-[1,2,3]triazolo[4,5-b]pyridine

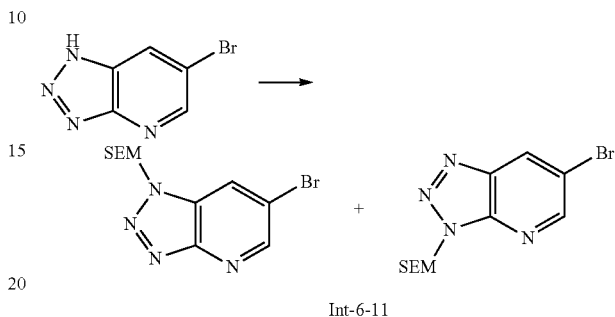

Int-6-11

To a suspension of NaH (60% in mineral oil, 120 mg, 3.0 mmol) in THF (3 mL) at 0° C. was added 6-bromo-1H-[1,2,3]triazolo[4,5-b]pyridine (400 mg, 2.0 mmol) in THF (8 mL). The mixture was stirred at 0° C. for 30 min, then SEM-Cl (500 mg, 3.0 mmol) was added at 0° C. dropwise and stirring was continued for 1 h. The reaction was quenched with NH₄Cl (sat.) and extracted with EtOAc (3×20 mL). The organic layers were combined and washed with brine (2×20 mL), dried over Na₂SO₄, concentrated and purified by chromatography to give Int-6-11 as a mixture of 6-bromo-1-((2-(trimethylsilyl)ethoxy)methyl)-1H-[1,2,3]triazolo[4,5-b]pyridine and 6-bromo-3-((2-(trimethylsilyl)ethoxy)methyl)-3H-[1,2,3]triazolo[4,5-b]pyridine.

Intermediate Int-6-12: Ethyl 2-(5-(trifluoromethyl)oxazol-4-yl)acetate

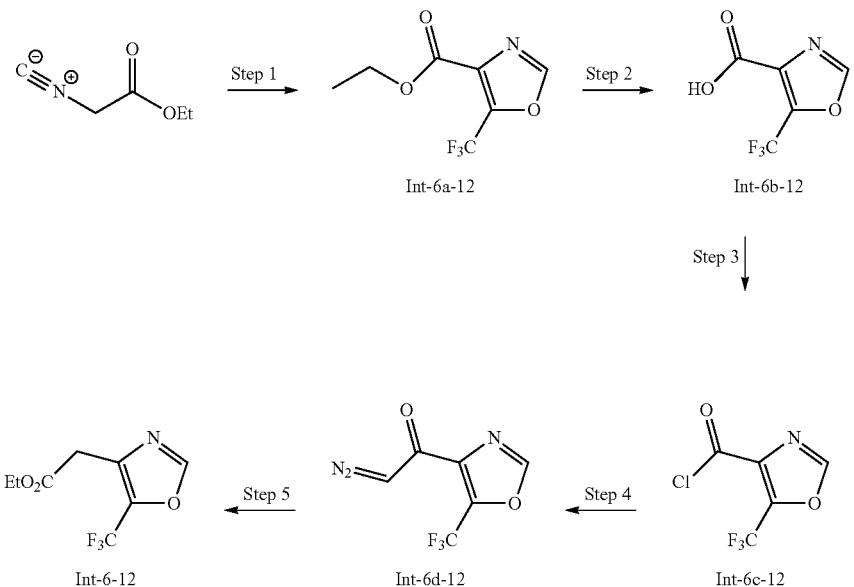

Step 1:

To a mixture of ethyl 2-isocyanoacetate (10.0 g, 88.4 mmol) and DBU (13.2 g, 88.4 mmol) in dry THF (40 mL) at 0° C. was added TFAA (18.7 g, 89 mmol) in dry THF (50 mL) dropwise. The reaction mixture was allowed to warm to rt and stirred for additional 10 h. The solvent was removed under reduced pressure and H₂O (100 mL) was added. The mixture was extracted with EtOAc (3×50 mL). The organic layers were combined, dried over Na₂SO₄, filtered, and concentrated under reduced pressure. The residue was purified by flash column chromatography on silica gel to give ethyl 5-(trifluoromethyl)oxazole-4-carboxylate Int-6a-12.

Step 2:

A mixture of 5-(trifluoromethyl)oxazole-4-carboxylate Int-6a-12 (4.8 g, 23.0 mmol), 1N NaOH (30 mL) and MeOH (50 mL) was stirred at rt for 4 h. The solvent was removed under reduce pressure and the pH adjusted to pH=2 with 1N HCl. The residue was extracted with EtOAc (3×20 mL), the organic layers was combined and dried over Na₂SO₄, then concentrated under reduced pressure, to give 5-(trifluoromethyl)oxazole-4-carboxylic acid Int-6b-12, without further purification, used in next step directly.

Step 3:

A solution of 5-(trifluoromethyl)oxazole-4-carboxylic acid Int-6b-12 (1.6 g, 8.84 mmol) in DCM (10 mL) was cooled to 0° C. in an ice-bath, then (COCl)₂ (2.18 g, 22.1 mmol) was added dropwise. After addition a catalytic amount of DMF (40 µL) was added carefully, the resulting mixture was stirred at rt for additional 1 h. The reaction mixture was concentrated under reduced pressure and the crude 5-(trifluoromethyl)oxazole-4-carbonyl chloride Int-6c-12 was used in next step without further purification.

Step 4:

A solution of crude 5-(trifluoromethyl)oxazole-4-carbonyl chloride Int-6c-12 (2.2 g, 8.84 mmol, th.) in dry ACN/THF (15/15 mL) was cooled to 0° C., TMSCHN₂ (2.0 M in Hexane, 9.0 mL, 18 mmol) was added dropwise over 5 min under Ar atmosphere. The resulting solution was stirred at rt for 1 h, the reaction was quenched with dilute AcOH (0.5 N). The mixture was extracted with EtOAc (3×10 mL) and the organic layers were combined and washed with brine (2×10 mL), dried over Na₂SO₄, and concentrated under reduced pressure. The residue was purified by flash column chromatography on silica gel to give 2-diazo-1-(5-(trifluoromethyl)oxazol-4-yl)ethan-1-one Int-6d-12.

Step 5:

To a solution of 2-diazo-1-(5-(trifluoromethyl)oxazol-4-yl)ethan-1-one Int-6d-12 (1.0 g, 0.49 mmol) in EtOH (5 mL), was added Ag₂O (556 mg, 0.245 mmol) in several portions over 5 min under Ar atmosphere. The resulting solution was protected from light, heated to 50° C., and stirring was continued overnight. The reaction mixture was filtered over a short pad of Celite® and the filtrate was concentrated under reduced pressure. The residue was purified by flash column chromatography on silica gel to give ethyl 2-(5-(trifluoromethyl)oxazol-4-yl)acetate Int-6-12.

Intermediate Int-7-1: 3-((5-Cyclopropyl-3-(2,6-dichlorophenyl)isoxazol-4-yl)methoxy)cyclobutanone

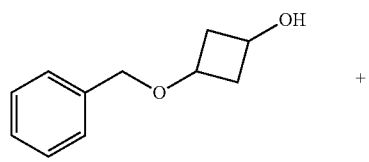

+

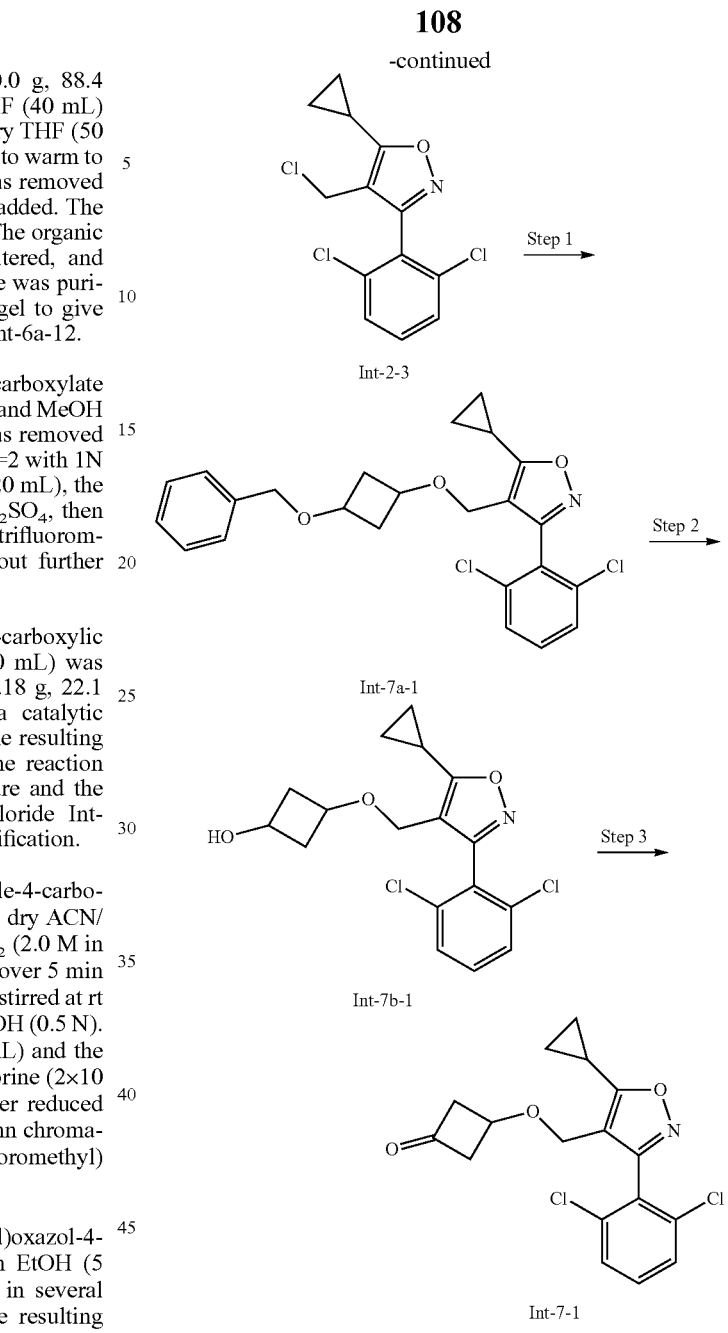

Step 1:

To a solution of 3-(benzyloxy)cyclobutanol (356 mg, 2.00 mmol) in dry DMF (10 mL) was added NaH (60%, 160 mg, 4.00 mmol) at 0° C. and the mixture was stirred for 1 h. Then 4-(chloromethyl)-5-cyclopropyl-3-(2,6-dichlorophenyl) isoxazole Int-2-3 (602 mg, 2.00 mmol) was added and the mixture stirred at rt for 4 h, quenched with aq. NH₄Cl and extracted with EtOAc three times. The organic portion was washed with brine, dried over Na₂SO₄, filtered, concentrated and purified by flash chromatography (PE/EtOAc=8:1) to give 4-((3-(benzyloxy)cyclo-butoxy)methyl)-5-cyclopropyl-3-(2,6-dichlorophenyl)isoxazole Int-7a-1.

Step 2:

To a solution of 4-((3-(benzyloxy)cyclobutoxy)methyl)-5-cyclopropyl-3-(2,6-dichloro-phenyl)isoxazole Int-7a-1 (614 mg, 1.38 mmol) in MeOH (20 mL) was added Pd/C (150 mg) under Ar and then stirred overnight under H₂. The mixture was filtered and concentrated to afford 3((5-cyclopropyl-3-(2,6-dichlorophenyl)isoxazol-4-yl)methoxy)cyclobutanol Int-7b-1.

Step 3:

To a solution of 3-((5-cyclopropyl-3-(2,6-dichlorophenyl)isoxazol-4-yl)methoxy)cyclobutanol Int-7b-1 (294 mg, 0.83 mmol) in MeCN (10 mL) and H₂O (3 mL) was added iodobenzene diacetate (869 mg, 2.70 mmol) and TEMPO (240 mg, 1.35 mmol) and the solution was stirred at rt for 2 h, quenched with aq. Na₂CO₃ and diluted with EtOAc. The organic portion was washed with brine, dried over Na₂SO₄, filtered, concentrated and purified by chromatography (PE/EtOAc=4:1) to afford 3-((5-cyclopropyl-3-(2,6-dichlorophenyl)isoxazol-4-yl)methoxy)cyclobutanone Int-7-1.

Intermediate Int-8-1: 4-((5-Cyclopropyl-3-(2,6-dichlorophenyl)isoxazol-4-yl)methoxy)-2,2-dimethylcyclohexanone

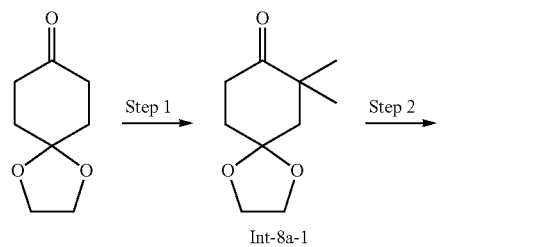

Int-8a-1

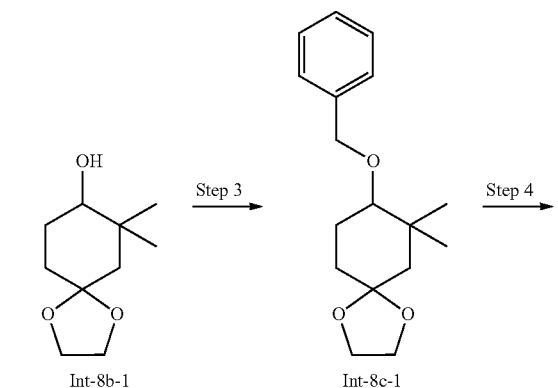

Int-8b-1        Int-8c-1

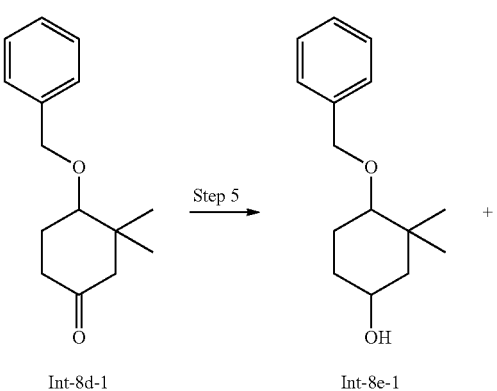

Int-8d-1        Int-8e-1

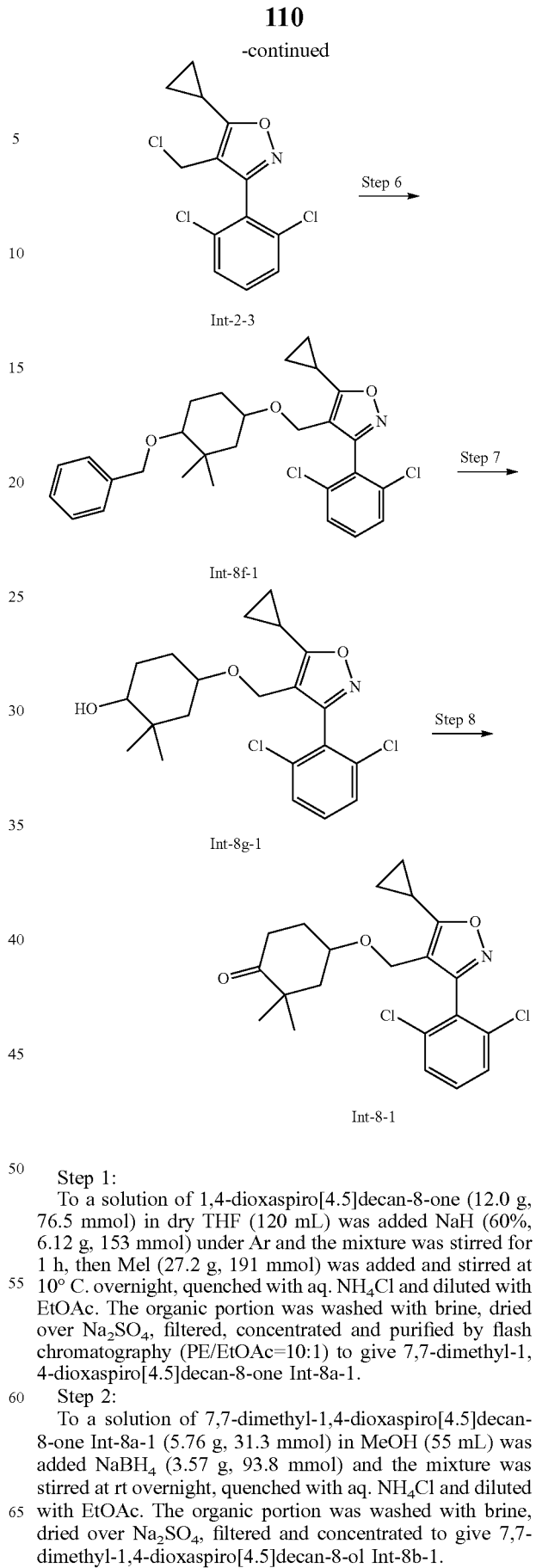

Step 1:

To a solution of 1,4-dioxaspiro[4.5]decan-8-one (12.0 g, 76.5 mmol) in dry THF (120 mL) was added NaH (60%, 6.12 g, 153 mmol) under Ar and the mixture was stirred for 1 h, then MeI (27.2 g, 191 mmol) was added and stirred at 10° C. overnight, quenched with aq. NH₄Cl and diluted with EtOAc. The organic portion was washed with brine, dried over Na₂SO₄, filtered, concentrated and purified by flash chromatography (PE/EtOAc=10:1) to give 7,7-dimethyl-1,4-dioxaspiro[4.5]decan-8-one Int-8a-1.

Step 2:

To a solution of 7,7-dimethyl-1,4-dioxaspiro[4.5]decan-8-one Int-8a-1 (5.76 g, 31.3 mmol) in MeOH (55 mL) was added NaBH₄ (3.57 g, 93.8 mmol) and the mixture was stirred at rt overnight, quenched with aq. NH₄Cl and diluted with EtOAc. The organic portion was washed with brine, dried over Na₂SO₄, filtered and concentrated to give 7,7-dimethyl-1,4-dioxaspiro[4.5]decan-8-ol Int-8b-1.

Step 3:

To a solution of 7,7-dimethyl-1,4-dioxaspiro[4.5]decan-8-ol Int-8b-1 (500 mg, 2.69 mmol) in dry DMF (8 mL) was added NaH (60%, 215 mg, 5.38 mmol) at 0° C. and the mixture was stirred for 1 h, then benzyl bromide (549 mg, 3.23 mmol) was added and stirred at rt overnight, quenched with aq. NH₄Cl and extracted with EtOAc three times. The combined organic portion was washed with brine, dried over Na₂SO₄, filtered, concentrated and purified by flash chromatography (PE/EtOAc=10:1) to give 8-(benzyloxy)-7,7-dimethyl-1,4-dioxaspiro[4.5]decane Int-8c-1.

Step 4:

To a solution of 8-(benzyloxy)-7,7-dimethyl-1,4-dioxaspiro[4.5]decane Int-8c-1 (404 mg, 1.46 mmol) in acetone (10 mL) was added HCl (2N, 1 mL) at rt and the mixture was stirred for 1 h. Then solvent was removed and the residue was diluted with water and extracted with EtOAc three times. The combined organic portion was washed with brine, dried over Na₂SO₄, filtered and concentrated to give 4-(benzyloxy)-3,3-dimethylcyclohexanone Int-8d-1.

Step 5:

To a solution of 4-(benzyloxy)-3,3-dimethylcyclohexanone Int-8d-1 (265 mg, 1.14 mmol) in MeOH (8 mL) was added NaBH₄ (181 mg, 4.77 mmol) and the mixture was stirred at rt overnight, quenched with aq. NH₄Cl and diluted with EtOAc. The organic portion was washed with brine, dried over Na₂SO₄, filtered and concentrated to give 4-(benzyloxy)-3,3-dimethylcyclohexanol Int-8e-1.

Step 6:

To a solution of 4-(benzyloxy)-3,3-dimethylcyclohexanol Int-8e-1 (229 mg, 0.98 mmol) in dry DMSO (10 mL) was added NaH (60%, 78 mg, 1.96 mmol) at 0° C. and the mixture was stirred for 1 h, then 4-(chloromethyl)-5-cyclopropyl-3-(2,6-dichlorophenyl)isoxazole Int-2-3 (602 mg, 2.00 mmol) was added and the mixture was stirred at rt overnight, quenched with aq. NH₄Cl and extracted with EtOAc three times. The combined organic portion was washed with brine, dried over Na₂SO₄, filtered, concentrated and purified by flash chromatography (PE/EtOAc=6:1) to give 4-(((4-(benzyloxy)-3,3-dimethylcyclohexyl)oxy)methyl)-5-cyclopropyl-3-(2,6-dichloro-phenyl)isoxazole Int-8f-1.

Step 7:

To a solution of 4-(((4-(benzyloxy)-3,3-dimethylcyclohexyl)oxy)methyl)-5-cyclopropyl-3-(2,6-dichlorophenyl)isoxazole Int-8f-1 (218 mg, 0.44 mmol) in MeOH (8 mL) was added Pd black (50 mg) under N₂, followed by formic acid (0.5 mL). The mixture was stirred overnight and filtered, then the filtrate was washed with aq. NaHCO₃ extracted with EtOAc three times. The combined organic portion was washed with brine, dried over Na₂SO₄, filtered and concentrated to give 4-((5-cyclopropyl-3-(2,6-dichloro-phenyl)isoxazol-4-yl)methoxy)-2,2-dimethylcyclohexanol Int-8g-1.

Step 8:

To a solution of PCC (148 mg, 0.69 mmol) in DCM (10 mL) was added 4-((5-cyclopropyl-3-(2,6-dichlorophenyl)isoxazol-4-yl)methoxy)-2,2-dimethylcyclohexanol Int-8g-1 (186 mg, 0.46 mmol) and the solution was stirred at rt for 1 h, filtered, concentrated and purified by chromatography (PE/EtOAc=4:1) to give racemic 4-((5-cyclopropyl-3-(2,6-dichloro-phenyl)isoxazol-4-yl)methoxy)-2,2-dimethylcyclohexanone Int-8-1.

Intermediate Int-8-2: 4-((5-Cyclopropyl-3-(2,6-dichlorophenyl)isoxazol-4-yl)methoxy)-3,3-dimethylcyclohexanone

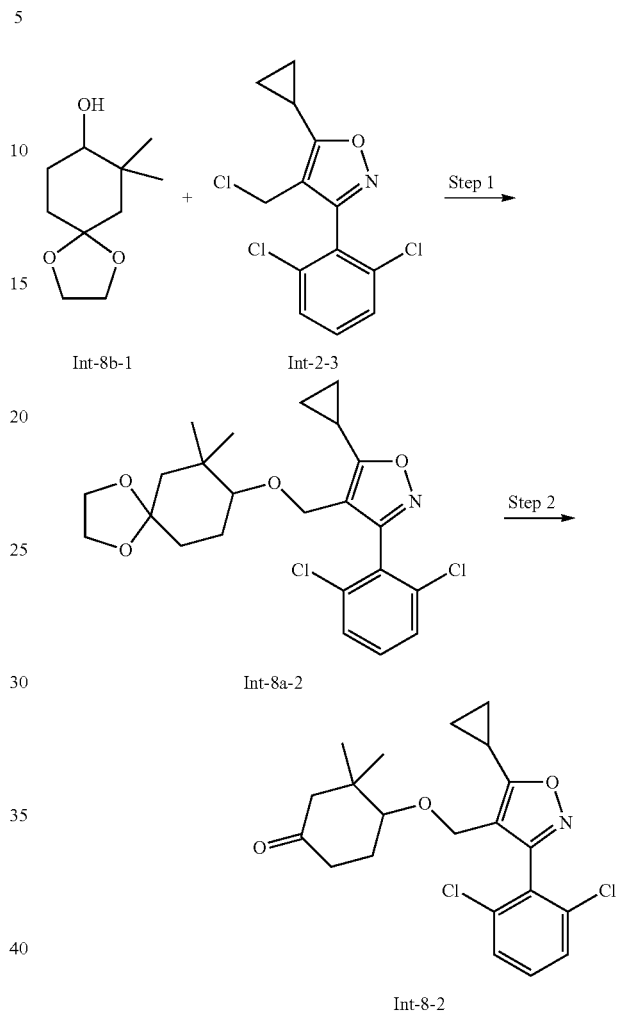

Step 1:

To a solution of 7,7-dimethyl-1,4-dioxaspiro[4.5]decan-8-ol Int-8b-1 (372 mg, 2.00 mmol) in dry DMSO (5 mL) was added NaH (60%, 160 mg, 4.00 mmol) at 0° C. and the mixture was stirred for 1 h. Then 4-(chloromethyl)-5-cyclopropyl-3-(2,6-dichlorophenyl)isoxazole Int-2-3 (602 mg, 2.00 mmol) was added and stirred at rt overnight, quenched with aq. NH₄Cl and extracted with EtOAc three times. The combined organic portion was washed with brine, dried over Na₂SO₄, filtered, concentrated and purified by flash chromatography (PE/EtOAc=8:1) to give 5-cyclopropyl-3-(2,6-dichlorophenyl)-4-(((7,7-dimethyl-1,4-dioxaspiro[4.5]decan-8-yl)oxy)methyl)isoxazole Int-8a-2.

Step 2:

To a solution of 5-cyclopropyl-3-(2,6-dichlorophenyl)-4-(((7,7-dimethyl-1,4-dioxaspiro[4.5]decan-8-yl)oxy)methyl)isoxazole Int-8a-2 (375 mg, 0.83 mmol) in acetone (5 mL) was added HCl (2N, 1 mL) at rt and the mixture was stirred for 1 h. Then the solvent was removed and the residue was diluted with water and extracted with EtOAc three times. The combined organic portion was washed with brine, dried over Na₂SO₄, filtered and concentrated to give racemic 4-((5-cyclopropyl-3-(2,6-dichlorophenyl)isoxazol-4-yl)methoxy)-3,3-dimethylcyclohexanone Int-8-2.

Intermediate Int-8-3: (1R,3S,5s,7s)-5-((5-Cyclopropyl-3-(2,6-dichlorophenyl)isoxazol-4-yl)methoxy)adamantan-2-one

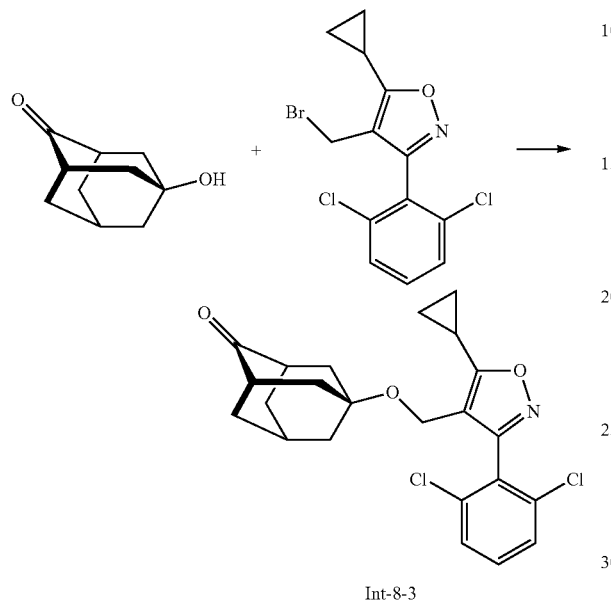

Int-8-3

To a suspension of NaH (120 mg, 3.0 mmol; 60% in mineral oil) in THF (10 mL) at 0° C. was added 5-hydroxy-adamantan-2-one (500 mg, 3.0 mmol) in dry THF (3 mL). The mixture was stirred at 0° C. for 1.5 h, then and 4-(bromomethyl)-5-cyclopropyl-3-(2,6-dichlorophenyl)isoxazole (Example 1, step 1) (1.15 g, 3.3 mmol) in dry THF (5 mL) was added at 0° C. and the mixture was stirred at reflux overnight, cooled, quenched with saturated NH$_4$Cl and extracted with EtOAc (3×20 mL). The organic layers were combined, washed with brine (2×20 mL), dried over Na$_2$SO$_4$, concentrated and purified by silica gel chromatography to give (1R,3S,5s,7s)-5-((5-cyclopropyl-3-(2,6-dichlorophenyl)isoxazol-4-yl)methoxy)adamantan-2-one Int-8-3.

Intermediate Int-9-1: (1R,5S)-3-Methylspiro[bicyclo[3.2.1]octane-8,2'-[1,3]dioxolan]-3-ol

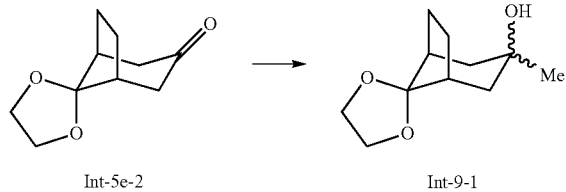

To a solution of (1R,5S)-spiro[bicyclo[3.2.1]octane-8,2'-[1,3]dioxolan]-3-one (500 mg, 2.75 mmol) Int-5e-2 in THF (10 mL) was added methylmagnesium bromide (4 mL, 1M in THF) at 0° C. The mixture was warmed to rt and stirred overnight, diluted with sat. NH$_4$Cl (30 mL) and extracted with EtOAc (3×20 mL). The combined the organic layers and washed with brine (20 mL), dried over anhydrous Na$_2$SO$_4$, filtered, concentrated and purified by silica-gel column (PE/EtOAc=5:1) to give one isomer of (1R,5S)-3-methylspiro[bicyclo[3.2.1]octane-8,2'-[1,3]dioxolan]-3-ol Int-9-1.

Intermediate Int-9-2: (1R,5S)-3-(Difluoromethyl)spiro[bicyclo[3.2.1]octane-8,2'-[1,3]dioxolan]-3-ol

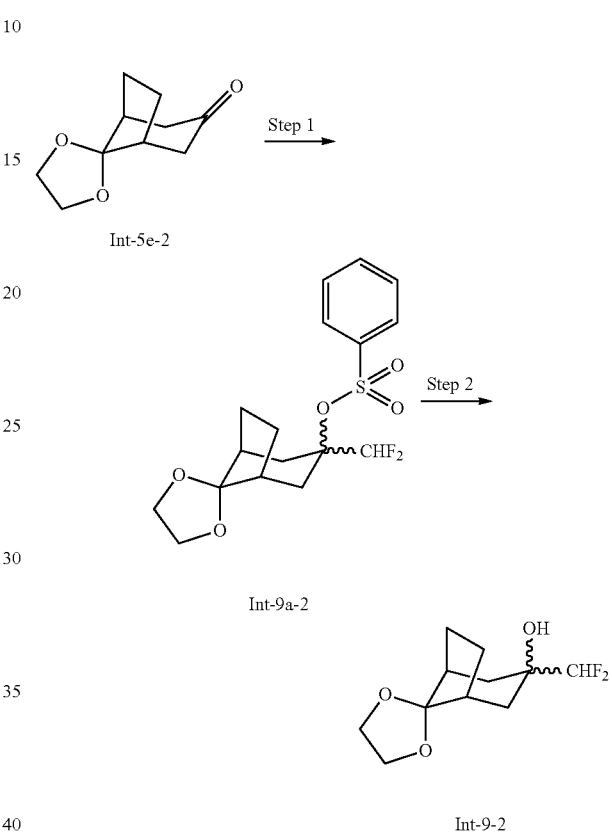

Step 1:
To a solution of (1R,5S)-spiro[bicyclo[3.2.1]octane-8,2'-[1,3]dioxolan]-3-one (500 mg, 2.75 mmol) Int-5e-2 (1.0 g, 5.5 mmol) and PhSO$_2$CF$_2$H (1.1 g, 5.5 mmol) in THF (20 mL)/HMPA (2.0 mL) was added LiHMDS (5.5 mL, 1M in THF) dropwise at −78° C. under N$_2$. The mixture was stirred vigorously at −78° C. for 2 h, diluted with saturated aq. NH$_4$Cl solution (30 mL) at −78° C. and then extracted with Et$_2$O (3×20 mL). The combined organic phase was dried with MgSO$_4$, concentrated and purified by column chromatography (PE/EtOAc=6:1) to give (1R,5S)-3-(difluoromethyl)spiro[bicyclo[3.2.1]octane-8,2'-[1,3]dioxolan]-3-yl benzenesulfonate Int-9a-2.

Step 2:
To a solution of (1R,5S)-3-(difluoromethyl)spiro[bicyclo[3.2.1]octane-8,2'-[1,3]dioxolan]-3-yl benzenesulfonate Int-9a-2 (1.7 g, 4.5 mmol) and Na$_2$HPO$_4$ (1.9 g, 13.5 mmol) in dry MeOH (50 mL) was added Na/Hg amalgam (10 wt.-% Na in Hg, net sodium content 13.5 mmol) at −20° C. under N$_2$. The mixture was stirred at −20° C. to 0° C. for 1 h. The liquid phase was decanted and the solid residue was washed with Et$_2$O. The solids were then treated with elemental sulfur powder to destroy the mercury residue. The solvent of combined organic phase was removed under vacuum, diluted with brine (50 mL) and extracted with Et₂O three times. The combined ether phase was dried with MgSO₄, concentrated and purified by chromatography (PE/EtOAc=5:1) to give one isomer of (1R,5S)-3-(difluoromethyl)spiro[bicyclo[3.2.1]octane-8,2'-[1,3]dioxolan]-3-01 Int-9-2. ¹H-NMR (500 MHz, DMSO-d₆) δ 5.48 (t, J=56.5 Hz, 1H), 4.87 (s, 1H), 3.85 (s, 4H), 1.95-1.89 (m, 4H), 1.84-1.81 (m, 2H), 1.67-1.64 (m, 2H), 1.58-1.55 (m, 2H).

Intermediate Int-9-3: (1R,5S)-3-(Methoxymethyl)spiro[bicyclo[3.2.1]octane-8,2'-[1,3]dioxolan]-3-ol

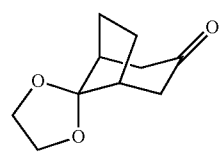

Int-5e-2

Step 1 →

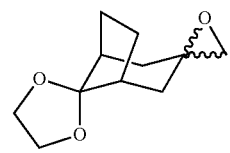

Int-9a-3

Step 2 →

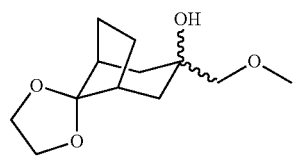

Int-9-3

Step 1:

To a solution of trimethyl-oxo-sulfonium iodide (500 mg, 2.2 mmol) in DMSO (10 mL) was added NaH (60% in mineral oil) (182 mg, 4.5 mmol) at 0° C. under N₂. The mixture was stirred at rt for 30 min, then (1R,5S)-spiro[bicyclo[3.2.1]octane-8,2'-[1,3]dioxolan]-3-one (500 mg, 2.75 mmol) Int-5e-2 (376 mg, 2.0 mmol) in DMSO (4.0 mL) was added and the mixture was stirred at rt overnight, quenched with H₂O (30 mL) and extracted with EtOAc. The organic phase was washed with brine (100 mL), dried over Na₂SO₄, filtered, concentrated and purified by flash chromatography (PE/EtOAc=5:1) to give oxiran Int-9a-3.

Step 2:

To a solution of oxiran Int-9a-3 (324 mg, 1.6 mmol) in CH₃OH (15 mL) was added CH₃ONa (268 mg, 4.9 mmol). The mixture was stirred at reflux overnight, concentrated and purified by flash chromatography (PE/EtOAc=3:1) to give one isomer of (1R,5S)-3-(methoxy-methyl)spiro[bicyclo[3.2.1]octane-8,2'-[1,3]dioxolan]-3-ol Int-9-3. ¹H-NMR (500 MHz, CDCl₃) δ 3.95-3.90 (m, 4H), 3.37 (s, 3H), 3.11 (s, 2H), 2.21 (s, 1H), 1.98-1.95 (m, 4H), 1.92-1.68 (m, 6H).

Intermediate Int-9-4: (1R,5S)-8-((5-Cyclopropyl-3-(2,6-dichlorophenyl)isoxazol-4-yl)methoxy)bicyclo[3.2.1]octan-3-one

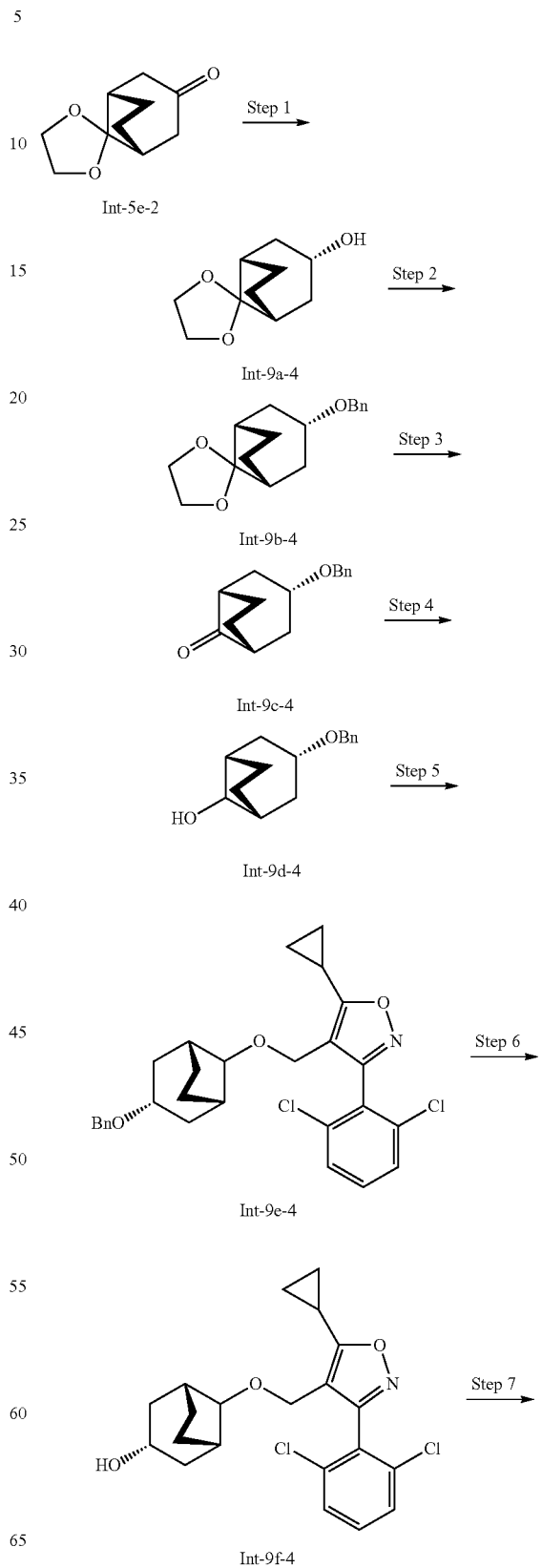

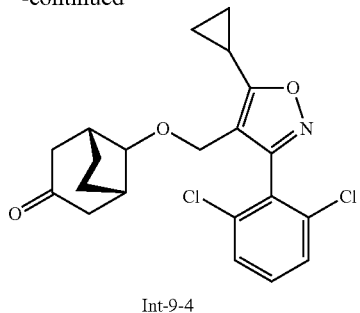

Int-9-4

Step 1:

To a mixture of (1R,5S)-spiro[bicyclo[3.2.1]octane-8,2'-[1,3]dioxolan]-3-one Int-5e-2 (7.0 g, 38.5 mmol) in MeOH/DCM (10 mL/40 mL) was added NaBH₄ (1.46 g, 38.5 mmol) in several portions at 0° C. The mixture was stirred at rt overnight, poured into NH₄Cl solution and extracted with EtOAc (3×50 mL). The organic layers were combined, dried over Na₂SO₄, concentrated and purified by column chromatography (EtOAc/PE=1:3) to afford pure exo isomer (1R,3s,5S)-spiro[bicyclo[3.2.1]octane-8,2'-[1,3]dioxolan]-3-ol Int-9a-4.

Step 2:

To compound (1R,3s,5S)-spiro[bicyclo[3.2.1]octane-8,2'-[1,3]dioxolan]-3-ol Int-9a-4 (1.2 g, 6.5 mmol) in dry DMF (20 mL) was added NaH (60% in oil; 782 mg, 19.5 mmol) slowly at 0° C., then the mixture was stirred at rt for 40 min and BnBr (1.67 g, 9.77 mmol) was added. The mixture was stirred at rt for 3 h, slowly diluted with a saturated solution of NH₄Cl (40 mL) and extracted with EtOAc (3×50 mL). The organic layers were combined, washed with brine (2×20 mL), dried over Na₂SO₄, concentrated and purified by column chromatography (EtOAc/PE=1:8) to give (1R,3s,5S)-3-(benzyloxy)spiro[bicyclo[3.2.1]octane-8,2'-[1,3]dioxolane] Int-9b-4. Chiral HPLC (OJ-H 4.6×250 mm column 5 μm; Eluent: CO₂/MeOH 4:1, (0.2% NH₄OMe); flow: 2.4 mL/minute; w=214 to 359 nm; T=39.8° C.): retention time 3.40 min.

Step 3:

To compound (1R,3s,5S)-3-(benzyloxy)spiro[bicyclo[3.2.1]octane-8,2'-[1,3]dioxolane] Int-9b-4 (1.52 g, 5.54 mmol) in acetone (30 mL) was added 2N HCl (8 mL) and the mixture was stirred at 60° C. for 2 h, concentrated and purified by column chromatography (EtOAc/PE=1:6) to give (1R,3s,5S)-3-(benzyloxy)bicyclo[3.2.1]octan-8-one Int-9c-4.

Step 4:

To compound (1R,3s,5S)-3-(benzyloxy)bicyclo[3.2.1]octan-8-one Int-9c-4 (892 mg, 3.87 mmol) in MeOH (20 mL) was added NaBH₄ (366 mg, 9.68 mmol) at 0° C. and the mixture was stirred at rt for 2 h, concentrated and purified by column chromatography (EtOAc/PE=1:3) to give (1R,3s,5S)-3-(benzyloxy)bicyclo[3.2.1]octan-8-ol Int-9d-4 as a single isomer. Chiral HPLC (AD-H 4.6×250 mm column 5 μm; Eluent: CO₂/MeOH 7:3, (0.2% NH₄OMe); flow: 2.1 mL/minute; w=214 to 359 nm; T=39.9° C.): retention time 4.37 min.

Step 5:

To a suspension of NaH (60% in mineral oil; 395 mg, 9.88 mmol) in dry DMSO (25 mL) at 0° C. was added (1R,3s,5S)-3-(benzyloxy)bicyclo[3.2.1]octan-8-ol Int-9d-4 in dry DMSO (6 mL). The mixture was stirred at rt for 1 h, then 4-(chloromethyl)-5-cyclopropyl-3-(2,6-dichlorophenyl)isoxazole (1.50 g, 4.94 mmol) was added at 0° C. and the mixture was stirred at rt for 4 h, quenched with NH₄Cl (sat.) and extracted with EtOAc (3×50 mL). The organic layers were combined and washed with brine (2×20 mL), dried over Na₂SO₄, concentrated and purified by chromatography (EtOAc/PE=1:5) to give 4-((((1R,3s,5S)-3-(benzyloxy)bicyclo[3.2.1]octan-8-yl)oxy)methyl)-5-cyclopropyl-3-(2,6-dichlorophenyl)isoxazole Int-9e-4.

Step 6:

To compound 4-((((1R,3s,5S)-3-(benzyloxy)bicyclo[3.2.1]octan-8-yl)oxy)methyl)-5-cyclopropyl-3-(2,6-dichlorophenyl)isoxazole Int-9e-4 (830 mg, 1.67 mmol) in MeOH (30 mL) was added HCOOH (2.0 mL) and Pd (400 mg) and the mixture was stirred at rt for 8 h under N₂. The mixture was filtered, the solvent removed and purified by column chromatography (EtOAc/DCM=1:10) to give (1R,3s,5S)-8-((5-cyclopropyl-3-(2,6-dichlorophenyl)isoxazol-4-yl)methoxy)bicyclo[3.2.1]octan-3-ol Int-9f-4.

Step 7:

To compound (1R,3s,5S)-8-((5-cyclopropyl-3-(2,6-dichlorophenyl)isoxazol-4-yl)methoxy)bicyclo[3.2.1]octan-3-ol Int-9f-4 (543 mg, 1.33 mmol) in acetone (30 mL) was added IBX (745 mg, 2.66 mmol) and the mixture was stirred at reflux for 2 h, filtered and the solvent removed to give the single isomer (1R,5S)-8-((5-cyclopropyl-3-(2,6-dichlorophenyl)isoxazol-4-yl)methoxy)bicyclo[3.2.1]octan-3-one Int-9-4.

Intermediates Int-10a/b: (1R,3s,5S,8r)-3-((5-Cyclopropyl-3-(2,6-dichlorophenyl)isoxazol-4-yl)methoxy)-8-(1-((2-(trimethylsilyl)ethoxy)methyl)-1H-[1,2,3]triazolo[4,5-b]pyridin-6-yl)bicyclo[3.2.1]octan-8-ol and (1R,3s,5S,8r)-3-((5-cyclopropyl-3-(2,6-dichlorophenyl)isoxazol-4-yl)methoxy)-8-(3-((2-(trimethylsilyl)ethoxy)methyl)-3H-[1,2,3]triazolo[4,5-b]pyridin-6-yl)bicyclo[3.2.1]octan-8-ol

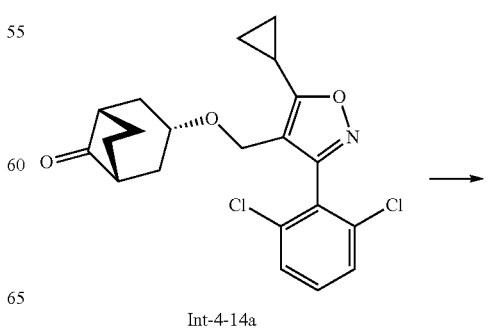

Int-4-14a

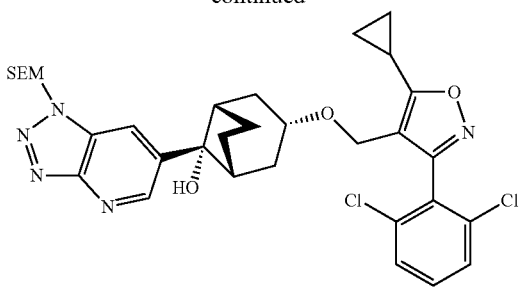

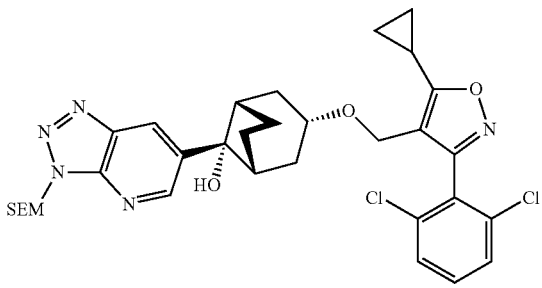

Int-10a/b

Following general procedure 1G, starting from (1R,3s,5S)-3-((5-cyclopropyl-3-(2,6-dichlorophenyl)isoxazol-4-yl)methoxy)bicyclo[3.2.1]octan-8-one (Int-4-14a) and mixture of 6-bromo-1-((2-(trimethylsilyl)ethoxy)methyl)-1H-[1,2,3]triazolo[4,5-b]pyridine and 6-bromo-3-((2-(trimethylsilyl)ethoxy)methyl)-3H-[1,2,3]triazolo[4,5-b]pyridine Int-6-11, the synthesis furnished ((1R,3s,5S,8r)-3-((5-cyclopropyl-3-(2,6-dichlorophenyl)isoxazol-4-yl)methoxy)-8-(1-((2-(trimethyl-silyl)ethoxy)methyl)-1H-[1,2,3]triazolo[4,5-b]pyridin-6-yl)bicyclo[3.2.1]octan-8-ol and (1R,3s,5S,8r)-3-((5-cyclopropyl-3-(2,6-dichlorophenyl) isoxazol-4-yl)methoxy)-8-(3-((2-(trimethylsilyl)ethoxy)methyl)-3H-[1,2,3]triazolo[4,5-b]pyridin-6-yl)bicyclo[3.2.1]octan-8-ol Int-10a/b, separated isomers (SEM regioisomers not assigned).

Intermediate Int-11-1: (3a'R,6a'S)-Hexahydro-1'H-spiro[[1,3]dioxolane-2,2'-pentalen]-5-ol

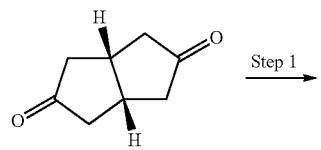

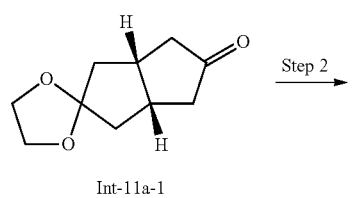

Int-11a-1

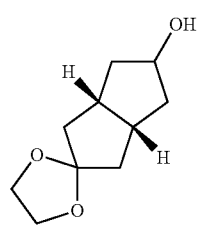

Int-11-1

Step 1:

To a solution of (3as,6as)-tetrahydropentalene-2,5(1H,3H)-dione (500 mg, 3.62 mmol) in toluene (60 mL) was added ethylene glycol (226 mg, 3.65 mmol) and TsOH (20 mg) and the mixture was stirred at 130° C. for 3 h, diluted with water and extracted with EtOAc. The organic portion was washed with brine, dried over $Na_2SO_4$, filtered and concentrated to give (3a'R,6a'S)-tetrahydro-1'H-spiro[[1,3]dioxolane-2,2'-pentalen]-5'(3'H)-one Int-11a-1.

Step 2:

To a solution of (3a'R,6a'S)-tetrahydro-1'H-spiro[[1,3]dioxolane-2,2'-pentalen]-5'(3'H)-one Int-11a-1 (495 mg, 2.72 mmol) in MeOH (8 mL) was added $NaBH_4$ (259 mg, 6.80 mmol) and the mixture was stirred at rt overnight, quenched with aq. $NH_4Cl$ and diluted with EtOAc. The organic portion was washed with brine, dried over $Na_2SO_4$, filtered, concentrated and purified by flash chromatography (PE/EtOAc=9:1) to give (3a'R,6a'S)-hexahydro-1'H-spiro[[1,3]dioxolane-2,2'-pentalen]-5'-ol Int-11-1.

Intermediate Int-11-2: (1R,4R)-Spiro[bicyclo[2.2.1]heptane-2,2'-[1,3]dioxolan]-5-ol

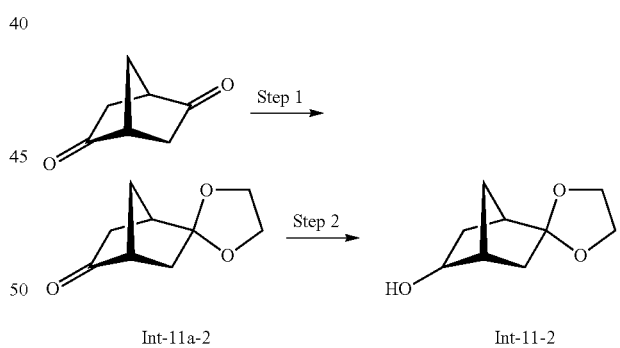

Step 1:

Similar as described for intermediate Int-11a-1 using (1R,4R)-bicyclo[2.2.1]heptane-2,5-dione as starting material, the intermediate (1R,4R)-spiro[bicyclo[2.2.1]heptane-2,2'-[1,3]dioxolan]-5-one Int-11a-2 was synthesized.

Step 2:

Similar as described for intermediate Int-11-1 using (1R,4R)-spiro[bicyclo[2.2.1]heptane-2,2'-[1,3]dioxolan]-5-one Int-11a-2 as starting material, the intermediate (1R,4R)-spiro[bicyclo[2.2.1]heptane-2,2'-[1,3]dioxolan]-5-ol Int-11-2 was synthesized.

Intermediate Int-12-1: Methyl 1-(3-bromo-5-fluorophenoxy)cyclopropanecarboxylate

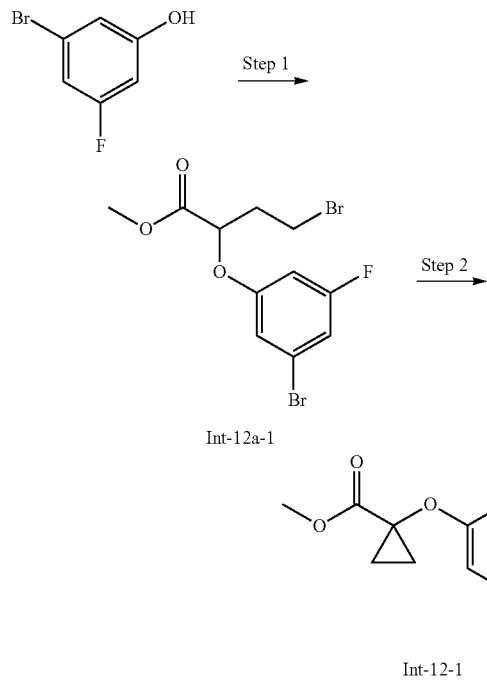

Step 1:

To a solution of 3-bromo-5-fluorophenol (1.0 g, 5.26 mmol) in DMF (20 mL) was added potassium carbonate (0.73 g, 5.26 mmol) and methyl 2,4-dibromobutanoate (1.36 g, 5.26 mmol) and the mixture was heated at 60° C. for 3 h, cooled to rt and extracted with EtOAc (3×100 mL). The organic portion was washed with brine, dried over $Na_2SO_4$, concentrated and purified by column chromatography (PE/EA=10:1) to yield methyl 4-bromo-2-(3-bromo-5-fluorophenoxy)butanoate Int-12a-1.

Step 2:

To a solution of methyl 4-bromo-2-(3-bromo-5-fluorophenoxy)butanoate Int-12a-1 (500 mg, 1.36 mmol) in THF (15 mL) was cooled to −15° C. and potassium tert-butoxide (183 mg, 1.63 mmol) was added. The cooling bath was removed and the mixture was stirred for 5 h at rt, poured in EtOAc (50 mL) and 50 mL water and extracted with EtOAc (3×50 mL). The combined organic layer was washed with brine, dried over $Na_2SO_4$, concentrated and purified by column chromatography (PE/EA=10:1) to yield methyl 1-(3-bromo-5-fluorophenoxy)cyclopropanecarboxylate Int-12-1.

Intermediate Int-13-1: 2-(2-Bromothiazol-4-yl)ethanol

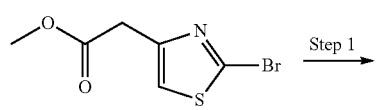

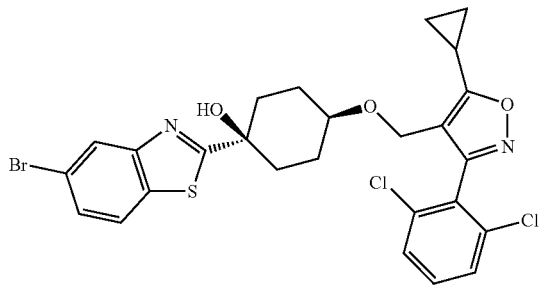 [SMILES: O[C@]1(c2nc3cc(Br)ccc3s2)CC[C@H](OCc2c(-c3c(Cl)cccc3Cl)noc2C2CC2)CC1]

To a solution of methyl 2-(2-bromothiazol-4-yl)acetate (100 mg, 0.43 mmol) in MeOH (50 mL) was added $NaBH_4$ (82 mg, 2.15 mmol) and the mixture was stirred at rt overnight, quenched with aq. $NH_4Cl$ (30 mL) and extracted with EtOAc (3×100 mL). The combined organic layer was washed with brine (100 mL) and condensed under vacuum to give 2-(2-bromothiazol-4-yl)ethanol Int-13-1.

EXAMPLES

Compounds of the present invention can be prepared by methods known to those who are skilled in the art. The following examples are only meant to represent examples of the invention and are in no way meant to be a limit of the invention.

Example 1: (1s,4s)-1-(5-Bromobenzo[d]thiazol-2-yl)-4-((5-cyclopropyl-3-(2,6-dichlorophenyl)isoxazol-4-yl)methoxy)cyclohexanol (1)

Step 1: 4-(Bromomethyl)-5-cyclopropyl-3-(2,6-dichlorophenyl)isoxazole (1a)

A solution of phosphorus tribromide (10.48 g, 38.7 mmol, 3.64 mL) in DCM (5 mL) was added dropwise to a stirred solution of (5-cyclopropyl-3-(2,6-dichlorophenyl)isoxazol-4-yl)methanol (5.0 g, 17.60, mmol) in DCM (145 mL) at 0° C. under argon atmosphere. After addition, the mixture was stirred for another 20 min. at 0° C., followed by 20 min. at rt. The mixture was quenched by adding it slowly to a stirred saturated aqueous $NaHCO_3$ solution (250 mL) at 0° C. and stirring was continued for an additional 10 min. at 0° C. to allow gas evolution to subside. The layers were separated and the aqueous was extracted with DCM (100 mL). The combined organics were washed with brine (75 mL), dried on $Na_2SO_4$ and the solvent was removed under reduced pressure to give the title compound 1a (3.01 g, 49%).

Step 2: 4-((1,4-Dioxaspiro[4.5]decan-8-yloxy)methyl)-5-cyclopropyl-3-(2,6-dichlorophenyl)isoxazole (1b)

Sodium hydride (0.629 g, 15.73 mmol, 60%) was added to a stirred solution of 1,4-dioxaspiro[4.5]decan-8-ol (2.370 g, 14.98 mmol) in ACN (anhydrous) (40 mL) at rt and then stirred at rt for 15 min. Next, intermediate 1a (2.60 g, 7.49 mmol) was added neat and the mixture was stirred at 40° C. for 2.5 h. The mixture was cooled to rt and quenched with sat. aq. NaHCO$_3$ (20 mL). The ACN was removed under reduced pressure. The remaining aqueous phase was extracted with EtOAc (2×25 mL). The combined organics were washed with brine (20 mL), dried on Na$_2$SO$_4$, filtered and the solvent was removed under reduced pressure. The oily residue was purified by flash column chromatography on silica using gradient elution with 5% to 50% EtOAc in heptane. Product containing fractions were combined and solvents removed under reduced pressure to give the title compound 1b (2.20 g, 75% purity by LC/MS, 45.7%).

Step 3: 4-((5-Cyclopropyl-3-(2,6-dichlorophenyl)isoxazol-4-yl)methoxy)cyclohexanone (1c)

An aqueous solution of hydrogen chloride (1.0 M, 20 mmol, 20.0 mL) was added to a stirred solution of intermediate 1b (2.20 g, 3.89 mmol) in acetone (40.0 mL) at rt. The mixture was then stirred and heated at 40° C. for 30 min. The mixture was cooled to rt and basified by addition of sat. aq. NaHCO$_3$ (30 mL) to pH-8. Acetone was removed under reduced pressure and the residual aqueous phase was extracted with EtOAc (2×50 mL). The combined organic layers were dried over Na$_2$SO$_4$, filtered and the solvent was removed under reduced pressure. The oily residue was purified by flash column chromatography on silica using gradient elution with 5% to 65% EtOAc in heptane. Product containing fractions were combined and solvents removed under reduced pressure to give the title compound 1c (1.60 g, 99%).

Step 4: (1s,4s)-1-(5-Bromobenzo[d]thiazol-2-yl)-4-((5-cyclopropyl-3-(2,6-dichlorophenyl)isoxazol-4-yl)methoxy)cyclohexanol (1)

A solution of n-butyllithium, (4.37 mmol, 1.75 mL, 2.5M in hexanes) was added dropwise over 5 min. to a stirred solution of 2,5-dibromobenzo[d]thiazole (1.281 g, 4.37 mmol) in anhydrous THF (35 mL) at −78° C. under nitrogen atmosphere. The mixture was stirred at −78° C. for 20 min. and a solution of intermediate 1c (1.33 g, 3.50 mmol) in anhydrous THF (5.0 mL) was added dropwise over 5 min. to the mixture at −78° C. under nitrogen atmosphere. The mixture was then stirred for 1 h at −78° C. and quenched by addition of water (2.0 mL). Cooling was removed and the quenched reaction mixture was allowed to warm to rt and stirred at rt overnight. The mixture was concentrated in order to remove most of the THF. The aqueous phase was partitioned between sat. aq. NaHCO$_3$ (25 mL) and EtOAc (25 mL). The aqueous layer was extracted with EtOAc (2×15 mL) and the combined organic layers were washed with brine (20 mL), dried on Na$_2$SO$_4$, filtered and the solvent was removed under reduced pressure. The oily residue was purified by flash column chromatography on silica using gradient elution with 10% to 100% EtOAc in Heptane. Two product fractions were pooled and concentrated to dryness and each product was purified again by flash column chromatography on silica using gradient elution with 0% to 2.0% MeOH in DCM. The pooled major product fractions were concentrated to dryness, giving the title compound (1: major isomer, 1.14 g, 55%). $^1$H-NMR (400 MHz, DMSO-d$_6$) δ ppm: 8.12 (s, 1H), 8.03 (d, 1H, J=8.5 Hz), 7.67-7.49 (m, 4H), 6.18 (s, 1H), 4.31 (s, 2H), 3.26-3.18 (m, 1H), 2.39-2.31 (m, 1H), 1.86-1.75 (m, 4H), 1.72-1.61 (m, 2H), 1.49-1.32 (m, 2H), 1.18-1.05 (m, 4H). MS: m/z [M+H]$^+$ 593/595/597.

2D NMR experiments indicate that the two oxygen substituents at the cyclohexyl ring are oriented cis to each other.

Example 2: (1r,4r)-1-(5-Bromobenzo[d]thiazol-2-yl)-4-((5-cyclopropyl-3-(2,6-dichlorophenyl)isoxazol-4-yl)methoxy)cyclohexanol (2)

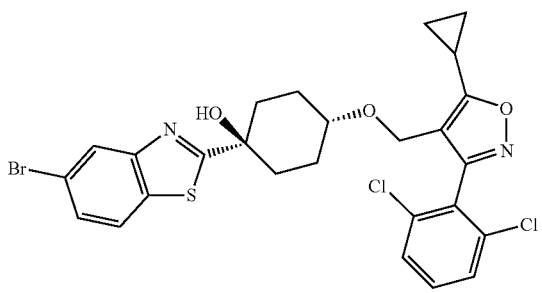 [SMILES: O[C@]1(c2nc3cc(Br)ccc3s2)CC[C@@H](OCc2c(-c3c(Cl)cccc3Cl)noc2C2CC2)CC1]

The title compound was isolated as the minor product from Step 4 of Example 1 (2: 75 mg, 3.6%). $^1$H-NMR (400 MHz, DMSO-d$_6$) δ ppm: 8.165 (s, 1H), 8.03 (d, 1H, J=8.5 Hz), 7.65-7.51 (m, 3H), 7.49-7.43 (m, 1H), 6.11 (s, br, 1H), 4.28 (s, 2H), 3.44-3.32 (m, 1H), 2.46-2.34 (m, 1H), 2.08-1.80 (m, 2H), 1.76-1.453 (m, 6H), 1.30-1.03 (m, 4H). MS: m/z [M+H]$^+$ 593/595/597.

Example 3: 2-((1s,4s)-4-((5-Cyclopropyl-3-(2,6-dichlorophenyl)isoxazol-4-yl)methoxy)-1-hydroxycyclohexyl)benzo[d]thiazole-5-carbonitrile (3)

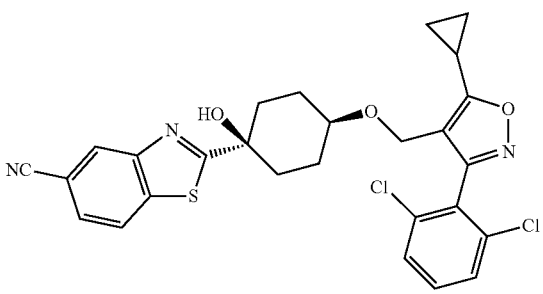 [SMILES: N#Cc1ccc2sc([C@]3(O)CC[C@@H](OCc4c(-c5c(Cl)cccc5Cl)noc4C4CC4)CC3)nc2c1]

A suspension of the compound of Example 1 (250 mg, 0.421 mmol) and zinc cyanide (49.4 mg, 0.421 mmol) in anhydrous DMF (5.0 mL) in a microwave vial at rt was flushed thoroughly for 10 min. with nitrogen-gas. Next, Pd$_2$(dba)$_3$ (38.5 mg, 0.042 mmol) and XantPhos (24.34 mg, 0.042 mmol) were added neat and the mixture was flushed again thoroughly with nitrogen gas for 5 min. The vial was capped and heated in a microwave at 110° C. for 1 h. The mixture was partitioned between sat. aq. NaHCO$_3$ (25 mL) and EtOAc (25 mL). The aqueous layer was extracted again with EtOAc (1x 25 mL). The combined organic phases were washed with brine (3×10 mL), dried on Na$_2$SO$_4$ and solvent was removed under reduced pressure. The residue was purified by flash column chromatography on silica using gradient elution with 20% to 70% EtOAc in heptane. Product containing fractions were combined and solvents removed under reduced pressure to give the title compound Example 3 (138 mg, 51%). $^1$H-NMR (400 MHz, DMSO-d$_6$)

δ ppm: 8.45 (s, 1H), 8.29 (d, 1H, J=8.3 Hz), 7.80-7.75 (m, 1H), 7.68-7.54 (m, 3H), 6.29 (s, 1H), 4.31 (s, 2H), 3.36-3.20 (m, 1H), 2.39-2.32 (m, 1H), 1.82-1.76 (m, 4H), 1.73-1.62 (m, 2H), 1.49-1.33 (m, 2H), 1.19-1.07 (m, 4H). MS: m/z [M+H]+ 540/542.

Example 4: 2-((1s,4s)-4-((5-Cyclopropyl-3-(2,6-dichlorophenyl)isoxazol-4-yl)methoxy)-1-hydroxy-cyclohexyl)benzo[d]thiazole-5-carboxylic acid (4)

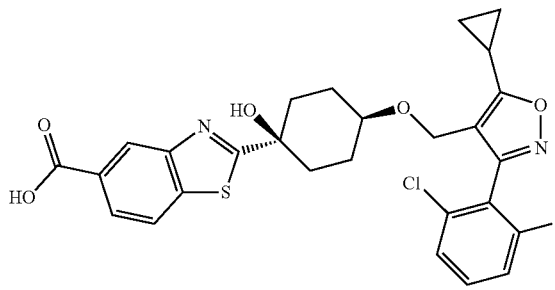

A solution of NaOH, 40% aqueous (900 mg, 9.00 mmol, 0.90 mL) was added to a stirred solution of Example 3 (360 mg, 0.666 mmol) in EtOH (5.0 mL) in a 8-mL screw cap vial at rt. The vial was closed and heated at 85° C. for 1 h. The mixture was cooled to rt and concentrated under reduced pressure. The residue was partitioned between 1M aq. HCl (20 mL) and EtOAc (15 mL). The aqueous layer was extracted again with EtOAc (1x 15 mL) and the combined organic layers were washed with brine, dried on Na₂SO₄, filtered and the solvent was removed under reduced pressure to give the crude title compound with was purified by preparative HPLC. Product containing fractions were combined and ACN was removed under reduced pressure. The remaining aqueous solution was carefully acidified by dropwise addition of 1M aq. HCl to pH-4. A precipitation is formed during the addition. The solids are filtered off, rinsed with water (2×5 mL), collected and dried in high-vacuum at rt overnight to give the title compound 4e (122 mg, 24%). %). ¹H-NMR (400 MHz, DMSO-d₆) δ ppm: 13.2 (s, br, 1H), 8.39 (s, 1H), 8.16 (d, J=8.4 Hz, 1H), 7.93 (d, J=8.3 Hz, 1H), 7.68-7.54 (m, 2H), 6.20 (s, 1H), 4.32 (s, 2H), 3.30-3.18 (m, 1H), 2.40-2.31 (m, 1H), 1.91-1.76 (m, 4H), 1.73-1.63 (m, 2H), 1.51-1.36 (m, 2H), 1.18-1.07 (m, 4H). MS: m/z [M-H]⁻ 557/559.

Example 5: 2-((1r,4r)-4-((5-Cyclopropyl-3-(2,6-dichlorophenyl)isoxazol-4-yl)methoxy)-1-hydroxy-cyclohexyl)benzo[d]thiazole-5-carboxylic acid (5)

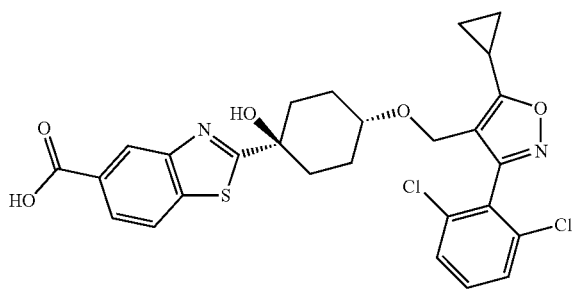 [SMILES: O=C(O)c1ccc2sc([C@]3(O)CC[C@H](OCc4c(-c5c(Cl)cccc5Cl)noc4C4CC4)CC3)nc2c1]

Example 5 was prepared from Example 2 following a similar procedure as described for Example 4. ¹H-NMR (400 MHz, DMSO-d₆) δ ppm: 13.2 (s, br, 1H), 8.44 (s, 1H), 8.17 (d, J=8.4 Hz, 1H), 7.95 (d, J=8.3 Hz, 1H), 7.63-7.57 (m, 2H), 7.50-7.43 (m, 1H), 6.13 (s, 1H), 4.29 (s, 2H), 3.46 (s, 1H), 2.45-2.35 (m, 1H), 2.06-1.95 (m, 2H), 1.75-1.64 (m, 2H), 1.63-1.47 (m, 4H), 1.21-1.10 (m, 4H). MS: m/z [M-H]⁻ 557/559.

General Procedure 1A for the Synthesis of Example 6/7

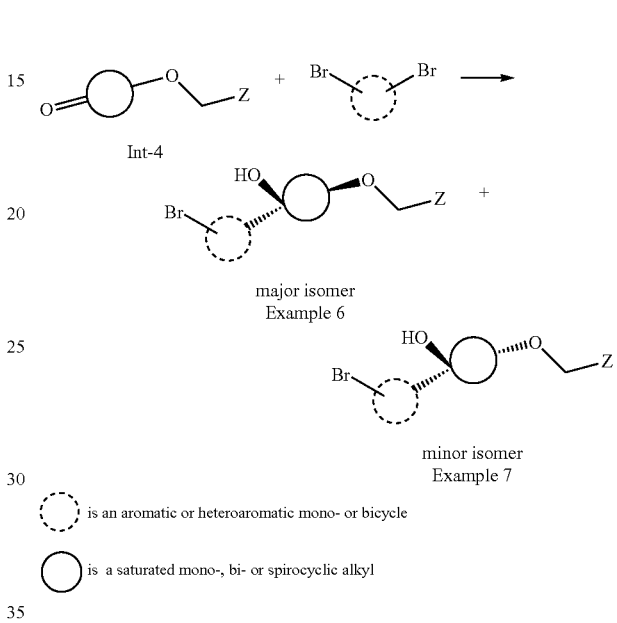

is an aromatic or heteroaromatic mono- or bicycle is a saturated mono-, bi- or spirocyclic alkyl A solution of ketone (1.0 equiv) and bromide (1.2 eq.) in dry THF was cooled to −78° C., then n-BuLi (1.33 eq.) was added dropwise and the mixture was stirred at −78° C. for 2 h, quenched with sat. NH₄Cl and extracted three times with EtOAc. The combined organic layers were washed with brine, dried, filtered, concentrated and the residue was purified with prep-TLC or flash chromatography to give major isomer 6 and minor isomer 7. (The minor isomer may not get isolated.)

Example 6-1 and Example 7-1: (1s,4s)-1-(6-Bromobenzo[d]thiazol-2-yl)-4-((5-cyclopropyl-3-(4,4-difluorocyclohexyl)isoxazol-4-yl)methoxy)cyclohexanol (6-1) and (1r,4r)-1-(6-bromobenzo[d]thiazol-2-yl)-4-((5-cyclopropyl-3-(4,4-difluorocyclohexyl)isoxazol-4-yl)methoxy)cyclohexanol (7-1)

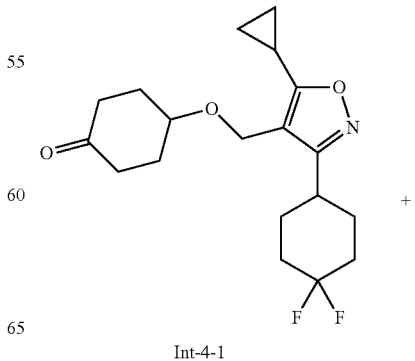

Int-4-1

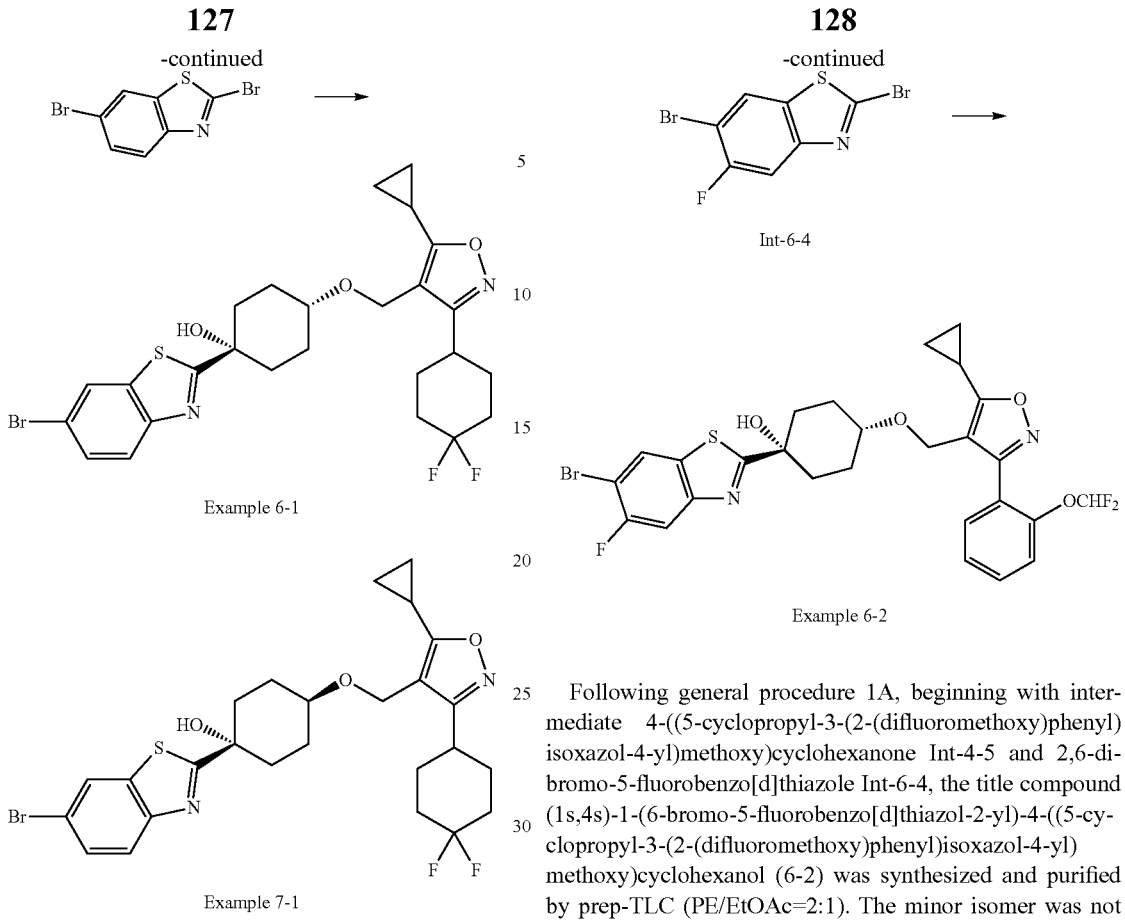

Example 6-1

Example 7-1

Following general procedure 1A, beginning with intermediate 4-((5-cyclopropyl-3-(4,4-difluorocyclohexyl)isoxazol-4-yl)methoxy)cyclohexanone Int-4-1 (420 mg, 1.2 mmol) and 2,6-dibromobenzo[d]thiazole, the title compound (1s,4s)-1-(6-bromobenzo[d]thiazol-2-yl)-4-((5-cyclopropyl-3-(4,4-difluorocyclohexyl)isoxazol-4-yl)methoxy)cyclohexanol (6-1) and (1r,4r)-1-(6-bromobenzo[d]thiazol-2-yl)-4-((5-cyclopropyl-3-(4,4-difluorocyclohexyl)isoxazol-4-yl)methoxy)cyclohexanol (7-1) were synthesized and purified by prep-TLC (CH$_2$Cl$_2$/MeOH=20:1).

Example 6-2: (1s,4s)-1-(6-Bromo-5-fluorobenzo[d]thiazol-2-yl)-4-((5-cyclopropyl-3-(2-(difluoromethoxy)phenyl)isoxazol-4-yl)methoxy)cyclohexanol

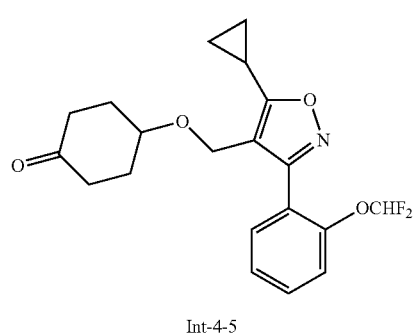

Int-4-5

Example 6-2

Following general procedure 1A, beginning with intermediate 4-((5-cyclopropyl-3-(2-(difluoromethoxy)phenyl)isoxazol-4-yl)methoxy)cyclohexanone Int-4-5 and 2,6-dibromo-5-fluorobenzo[d]thiazole Int-6-4, the title compound (1s,4s)-1-(6-bromo-5-fluorobenzo[d]thiazol-2-yl)-4-((5-cyclopropyl-3-(2-(difluoromethoxy)phenyl)isoxazol-4-yl)methoxy)cyclohexanol (6-2) was synthesized and purified by prep-TLC (PE/EtOAc=2:1). The minor isomer was not isolated.

Example 6-3: (1s,4s)-1-(6-Bromo-5-fluorobenzo[d]thiazol-2-yl)-4-((5-cyclopropyl-3-(2,6-dichlorophenyl)isoxazol-4-yl)methoxy)cyclohexanol

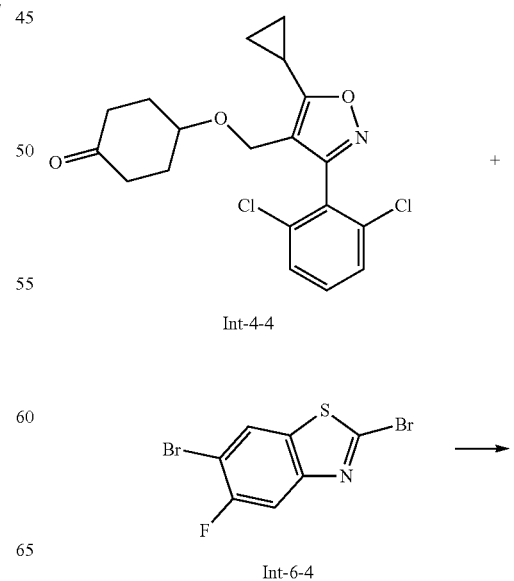

Int-4-4

Int-6-4

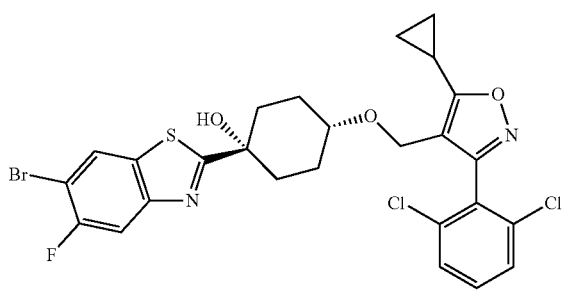

Example 6-3

Following general procedure 1A, beginning with intermediate 4-((5-cyclopropyl-3-(2,6-dichloro-phenyl)isoxazol-4-yl)methoxy)cyclohexanone Int-4-4 and 2,6-dibromo-5-fluorobenzo[d]thiazole Int-6-4, the title compound (1s,4s)-1-(6-bromo-5-fluorobenzo[d]thiazol-2-yl)-4-((5-cyclopropyl-3-(2,6-dichlorophenyl)isoxazol-4-yl)methoxy)cyclohexanol (6-3) was synthesized and purified by prep-TLC (PE/EtOAc=2:1). The minor isomer was not isolated.

Example 6-4: (1s,4s)-1-(6-Bromo-5,7-difluorobenzo[d]thiazol-2-yl)-4-((5-cyclopropyl-3-(2,6-dichlorophenyl)isoxazol-4-yl)methoxy)cyclohexanol

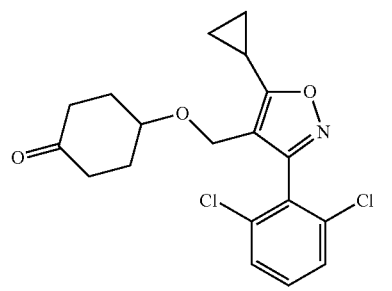

Int-4-4

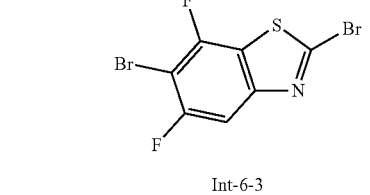

Int-6-3

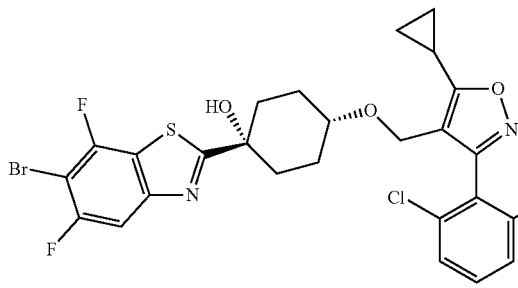

Exampe 6-4

Following general procedure 1A, beginning with intermediate 4-((5-cyclopropyl-3-(2,6-dichloro-phenyl)isoxazol-4-yl)methoxy)cyclohexanone Int-4-4 and 2,6-dibromo-5,7-difluorobenzo[d]thiazole Int-6-3, the title compound (1s,4s)-1-(6-bromo-5,7-difluorobenzo[d]thiazol-2-yl)-4-((5-cyclopropyl-3-(2,6-dichlorophenyl)isoxazol-4-yl)methoxy)cyclohexanol (6-4) was synthesized and purified by prep-TLC (PE/EtOAc=2:1). The minor isomer was not isolated.

Example 6-5: (1s,4s)-1-(6-Bromo-7-fluorobenzo[d]thiazol-2-yl)-4-((5-cyclopropyl-3-(2,6-dichlorophenyl)isoxazol-4-yl)methoxy)cyclohexanol

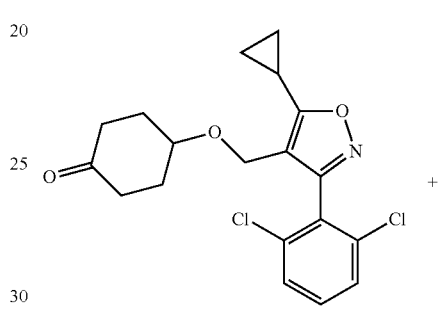

Int-4-4

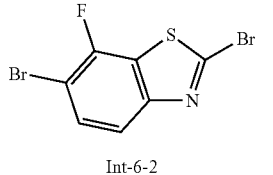

Int-6-2

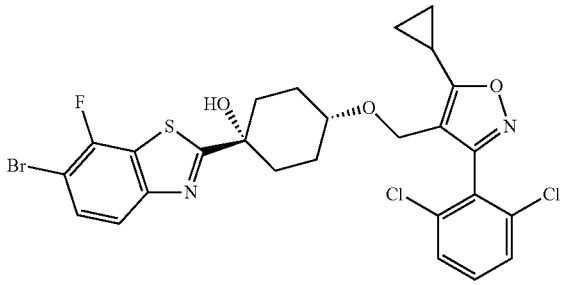

Exampe 6-5

Following general procedure 1A, beginning with intermediate 4-((5-cyclopropyl-3-(2,6-dichloro-phenyl)isoxazol-4-yl)methoxy)cyclohexanone Int-4-4 and 2,6-dibromo-7-fluorobenzo[d]thiazole Int-6-2, the title compound (1s,4s)-1-(6-bromo-7-fluorobenzo[d]thiazol-2-yl)-4-((5-cyclopropyl-3-(2,6-dichlorophenyl)isoxazol-4-yl)methoxy)cyclohexanol (6-5) was synthesized and purified by prep-TLC (PE/EtOAc=2:1). The minor isomer was not isolated.

Example 6-6: 1-(6-Bromobenzo[d]thiazol-2-yl)-3-((5-cyclopropyl-3-(2,6-dichlorophenyl)isoxazol-4-yl)methoxy)cyclopentanol

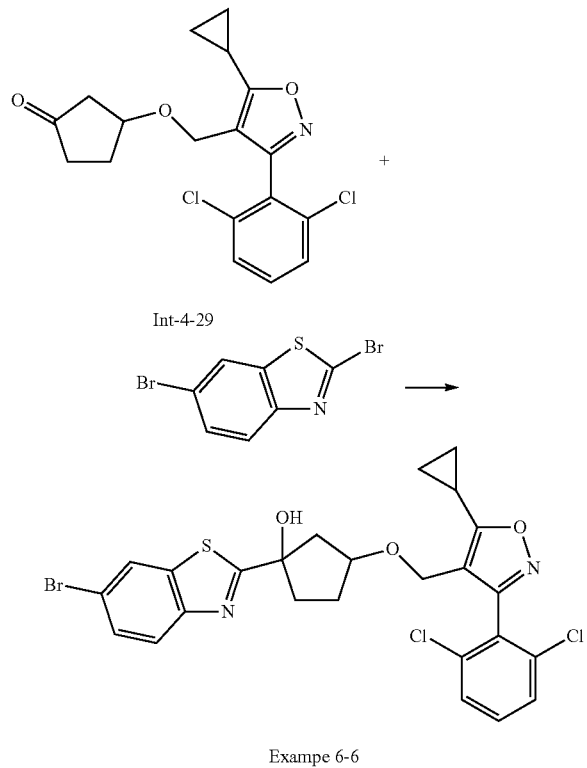

Exampe 6-6

In a dry vial under nitrogen a solution of 2,6-dibromobenzo[d]thiazole (105 mg, 0.36 mmol) in THF (2.2 mL) was cooled in a dry ice/acetone bath to −78° C. 1.6M n-Butyllithium solution in hexanes (0.22 mL, 0.36 mmol) was then added dropwise and the solution stirred for 20 min at −78° C. 3-((5-Cyclopropyl-3-(2,6-dichlorophenyl)isoxazol-4-yl)methoxy)cyclopentanone (Int-4-29, 105 mg, 0.29 mmol) dissolved in THF (0.5 mL) was then added dropwise and the reaction stirred for 1 h at −78° C. The reaction was quenched with water and allowed to warm to rt, then treated with EtOAc. The phases were separated and the organic layer was washed with brine, dried over Na$_2$SO$_4$, filtered and concentrated. Purification by column chromatography (ISCO, 12 g GOLD silica, 0-100% EtOAc/hexanes) gave the target compound 1-(6-bromobenzo[d]thiazol-2-yl)-3-((5-cyclopropyl-3-(2,6-dichlorophenyl)isoxazol-4-yl)methoxy)cyclopentanol (6-6).

General Procedure 1B for the Synthesis of Example 8

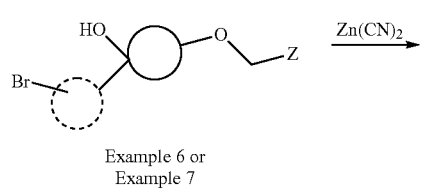

Example 6 or Example 7

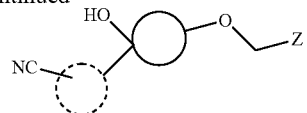

Example 8

◌ is a aromatic or heteroaromatic mono- or bicycle

◯ is a saturated mono-, bi-, or spirocyclic alkyl

A solution of bromide (1.0 eq.), ZnCN$_2$ (1.0 to 1.5 eq.), Pd$_2$(dba)$_3$ (0.1 eq.), Xantphos (0.1 eq.) in DMF was stirred at 110° C. overnight under Ar. The mixture was partitioned between sat. aq. NaHCO$_3$ and EtOAc. The aqueous layer was extracted again with EtOAc. The combined organic phases were washed three times with brine, dried over Na$_2$SO$_4$, evaporated and purified by prep-TLC or flash chromatography to afford example 8-1.

Alternative General Procedure 1B2 for the Synthesis of Example 8

A suspension of bromide (1 eq.) and zinc cyanide (2 eq.) in DMF (ca. 40 vol.) in a microwave vial at rt was flushed thoroughly for 10 min with Ar. Then Pd$_2$(dba)$_3$ (20 mol %) and Xantphos (20 mol %) was added under Ar. The resulting mixture was heated in a microwave oven at 110° C. for 1-2 h, then quenched with NH$_4$Cl (sat.) and extracted with EtOAc. The organic phase was washed with brine, dried over Na$_2$SO$_4$ and concentrated. The crude product was purified by silica gel chromatography to afford the cyanide products.

Example 8-1: 2-((1s,4s)-4-((5-Cyclopropyl-3-(4,4-difluorocyclohexyl)isoxazol-4-yl)methoxy)-1-hydroxycyclohexyl)benzo[d]thiazole-6-carbonitrile

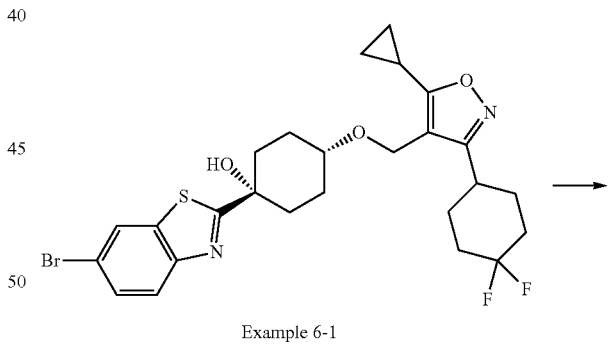

Example 6-1

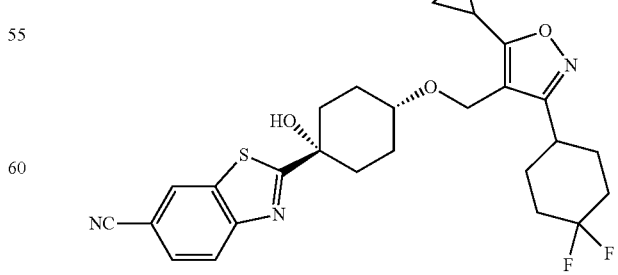

Example 8-1

Following general procedure 1B, beginning with example (1s,4s)-1-(6-bromobenzo[d]thiazol-2-yl)-4-((5-cyclopropyl-3-(4,4-difluorocyclohexyl)isoxazol-4-yl)methoxy)cyclohexanol (6-1), the title compound 2-((1s,4s)-4-((5-cyclopropyl-3-(4,4-difluorocyclohexyl)isoxazol-4-yl)methoxy)-1-hydroxycyclohexyl)benzo[d]thiazole-6-carbonitrile (8-1) was synthesized.

Example 8-2: 2-((1r,4r)-4-((5-Cyclopropyl-3-(4,4-difluorocyclohexyl)isoxazol-4-yl)methoxy)-1-hydroxycyclohexyl)benzo[d]thiazole-6-carbonitrile

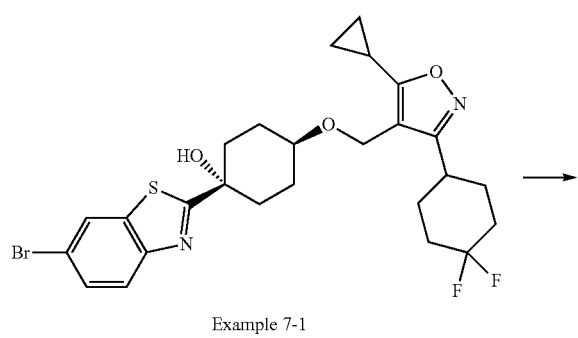

Example 7-1

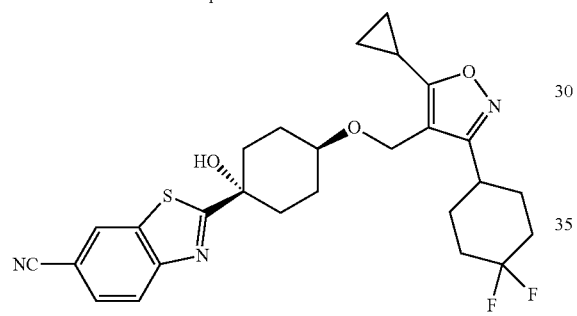

Example 8-2

Following general procedure 1B, beginning with example (1r,4r)-1-(6-bromobenzo[d]thiazol-2-yl)-4-((5-cyclopropyl-3-(4,4-difluorocyclohexyl)isoxazol-4-yl)methoxy)cyclohexanol (7-1), the title compound 2-((1r,4r)-4-((5-cyclopropyl-3-(4,4-difluorocyclohexyl)isoxazol-4-yl)methoxy)-1-hydroxycyclohexyl)benzo[d]thiazole-6-carbonitrile (8-2) was synthesized.

Example 8-3: 2-((1s,4s)-4-((5-Cyclopropyl-3-(2-(difluoromethoxy)phenyl)isoxazol-4-yl)methoxy)-1-hydroxycyclohexyl)-5-fluorobenzo[d]thiazole-6-carbonitrile

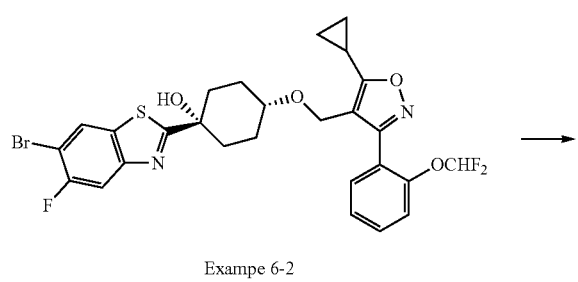

Exampe 6-2

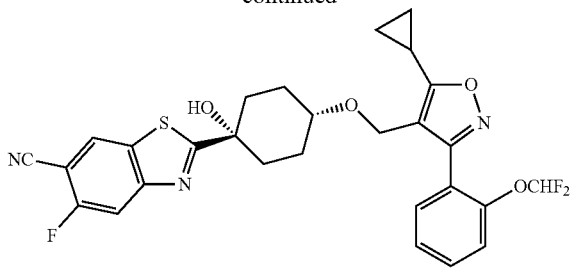

Exampe 8-3

Following general procedure 1B, beginning with example (1s,4s)-1-(6-bromo-5-fluorobenzo[d]thiazol-2-yl)-4-((5-cyclopropyl-3-(2-(difluoromethoxy)phenyl)isoxazol-4-yl)methoxy)cyclohexanol (6-2), the title compound 2-((1s,4s)-4-((5-cyclopropyl-3-(2-(difluoro-methoxy)phenyl)isoxazol-4-yl)methoxy)-1-hydroxycyclohexyl)-5-fluorobenzo[d]thiazole-6-carbonitrile (8-3) was synthesized. $^1$H-NMR (500 MHz, CDCl$_3$): δ 7.82 (d, J=8.5 Hz, 1H), 7.68-7.65 (m, 1H), 7.57-7.55 (m, 1H), 7.51-7.47 (m, 1H), 7.35-7.30 (m, 2H), 6.48 (t, J=74.3 Hz, 1H), 4.44 (s, 2H), 3.42-3.38 (m, 1H), 2.17-1.89 (m, 7H), 1.70-1.64 (m, 2H), 1.24-1.13 (m, 4H), hydroxyl proton not resolved.

Example 8-4: 2-((1s,4s)-4-((5-Cyclopropyl-3-(2,6-dichlorophenyl)isoxazol-4-yl)methoxy)-1-hydroxycyclohexyl)-5-fluorobenzo[d]thiazole-6-carbonitrile

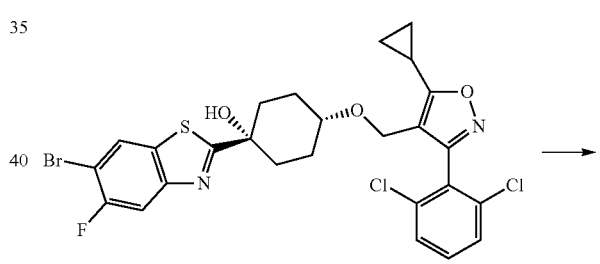

Exampe 6-3

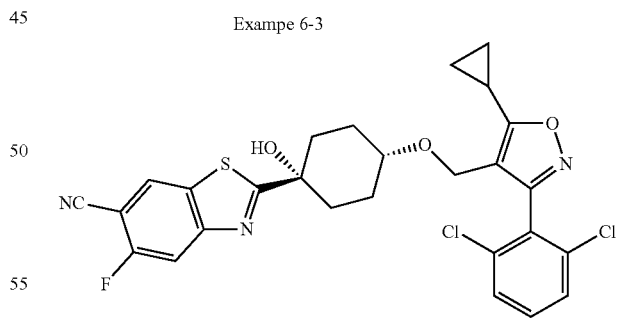

Exampe 8-4

Following general procedure 1B, beginning with example (1s,4s)-1-(6-bromo-5-fluorobenzo[d]thiazol-2-yl)-4-((5-cyclopropyl-3-(2,6-dichlorophenyl)isoxazol-4-yl)methoxy)cyclohexanol (6-3), the title compound 2-((1s,4s)-4-((5-cyclopropyl-3-(2,6-dichlorophenyl)isoxazol-4-yl)methoxy)-1-hydroxycyclohexyl)-5-fluorobenzo[d]thiazole-6-carbonitrile (8-4) was synthesized.

Example 8-5: 2-((1R,3s,5S,8r)-3-((5-Cyclopropyl-3-(2,6-dichlorophenyl)isoxazol-4-yl)methoxy)-8-hydroxybicyclo[3.2.1]octan-8-yl)benzo[d]thiazole-6-carbonitrile

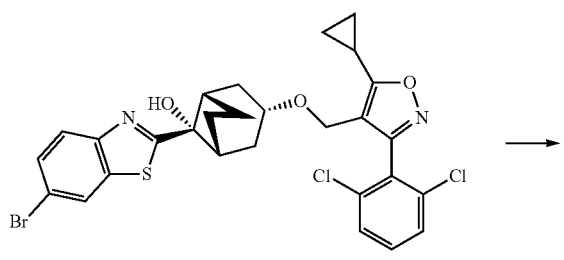

Exampe 15-1

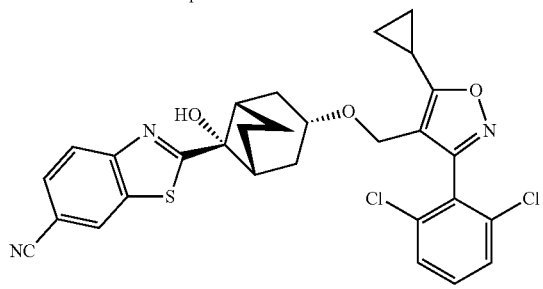

Exampe 8-5

Following general procedure 1B2, beginning with example (1R,3s,5S,8r)-8-(6-bromobenzo[d]thiazol-2-yl)-3-((5-cyclopropyl-3-(2,6-dichlorophenyl)isoxazol-4-yl)methoxy) bicyclo[3.2.1]octan-8-ol (15-1), the title compound 2-((1R,3s,5S,8r)-3-((5-cyclopropyl-3-(2,6-dichlorophenyl)isoxazol-4-yl)methoxy)-8-hydroxybicyclo[3.2.1]octan-8-yl)benzo[d]thiazole-6-carbonitrile (8-5) was synthesized. $^1$H-NMR (400 MHz, DMSO-$d_6$): δ 8.70 (d, J=0.8 Hz, 1H), 8.10 (d, J=8.8 Hz, 1H), 7.88 (dd, J=8.4 Hz, J=1.6 Hz, 1H), 7.67-7.56 (m, 3H), 6.52 (br s, 1H), 4.28 (s, 2H), 3.54-3.48 (m, 1H), 2.40-2.34 (m, 3H), 1.85-1.77 (m, 4H), 1.63-1.60 (m, 2H), 1.43-1.41 (m, 2H), 1.19-1.09 (m, 4H). MS (ESI): m/z 566.1 (M+1)$^+$.

Example 8-6: 2-((1R,3r,5S,8r)-3-((5-Cyclopropyl-3-(2,6-dichlorophenyl)isoxazol-4-yl)methoxy)-8-hydroxybicyclo[3.2.1]octan-8-yl)benzo[d]thiazole-6-carbonitrile

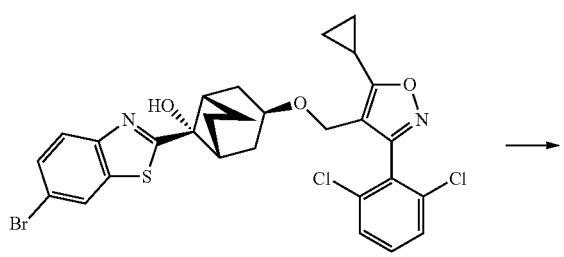

Exampe 15-2

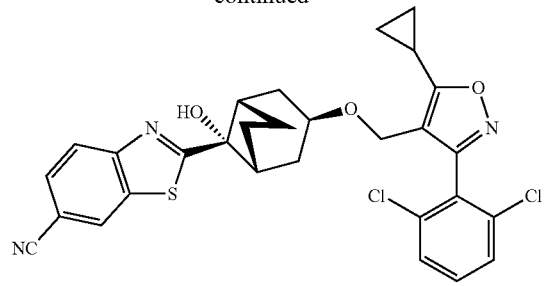

Exampe 8-6

Following general procedure 1B2, beginning with example (1R,3r,5S,8r)-8-(6-bromobenzo[d]thiazol-2-yl)-3-((5-cyclopropyl-3-(2,6-dichlorophenyl)isoxazol-4-yl)methoxy)bicyclo[3.2.1]octan-8-ol (15-2), the title compound 2-((1R,3r,5S,8r)-3-((5-cyclopropyl-3-(2,6-dichlorophenyl)isoxazol-4-yl)methoxy)-8-hydroxybicyclo[3.2.1]octan-8-yl)benzo[d]thiazole-6-carbonitrile (8-6) was synthesized.

Example 8-7: 4-((1R,3s,5S,8r)-3-((5-Cyclopropyl-3-(2,6-dichlorophenyl)isoxazol-4-yl)methoxy)-8-hydroxybicyclo[3.2.1]octan-8-yl)-3-fluorobenzonitrile

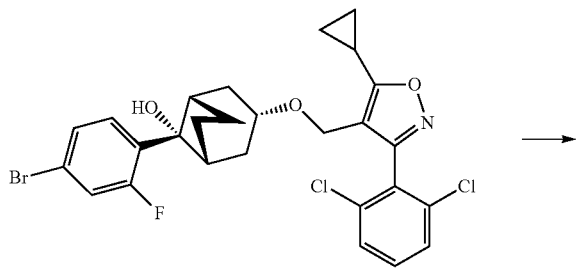

Exampe 15-3

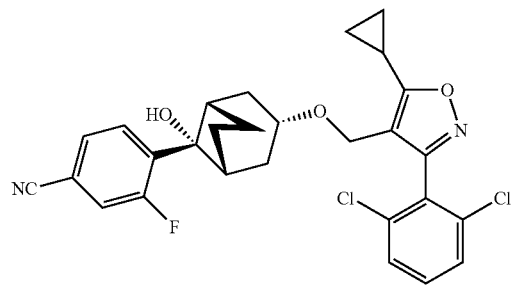

Exampe 8-7

Following general procedure 1B2, beginning with example (1R,3s,5S,8r)-8-(4-bromo-2-fluorophenyl)-3-((5-cyclopropyl-3-(2,6-dichlorophenyl)isoxazol-4-yl)methoxy) bicyclo[3.2.1]octan-8-ol (15-3), the title compound 4-(1R,3s,5S,8r)-3-((5-cyclopropyl-3-(2,6-dichlorophenyl) isoxazol-4-yl)methoxy)-8-hydroxybicyclo[3.2.1]octan-8-yl)-3-fluorobenzonitrile (8-7) was synthesized.

Example 8-8: 3-((1R,3s,5S,8r)-3-((5-Cyclopropyl-3-(2,6-dichlorophenyl)isoxazol-4-yl)methoxy)-8-hydroxybicyclo[3.2.1]octan-8-yl)benzonitrile

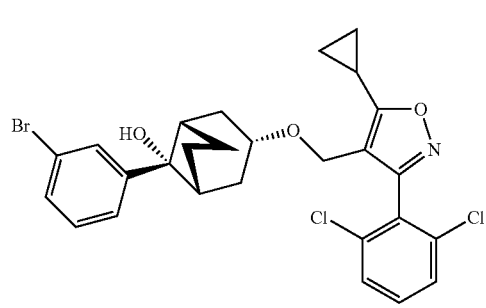

Exampe 15-4

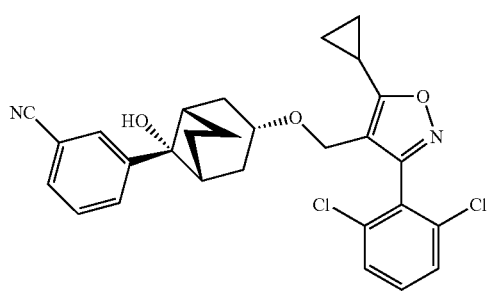

Exampe 8-8

Following general procedure 1B2, beginning with example (1R,3s,5S,8r)-8-(3-bromophenyl)-3-((5-cyclopropyl-3-(2,6-dichlorophenyl)isoxazol-4-yl)methoxy)bicyclo[3.2.1]octan-8-ol (15-4), the title compound 3-((1R,3s,5S,8r)-3-((5-cyclopropyl-3-(2,6-dichlorophenyl)isoxazol-4-yl)methoxy)-8-hydroxybicyclo[3.2.1]octan-8-yl)benzonitrile (8-8) was synthesized.

Example 8-9: 2-((1R,3s,5S,8r)-3-((5-Cyclopropyl-3-(2,6-dichlorophenyl)isoxazol-4-yl)methoxy)-8-hydroxybicyclo[3.2.1]octan-8-yl)-4-fluorobenzo[d]thiazole-6-carbonitrile

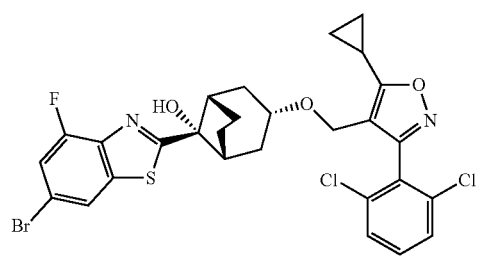

Exampe 15-6

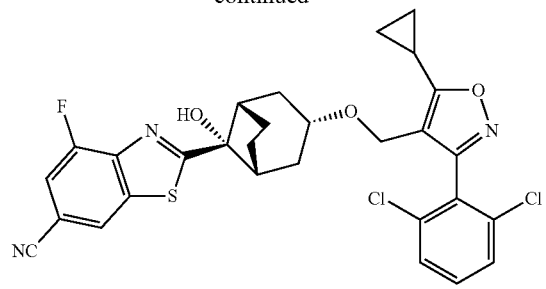

Exampe 8-9

Following general procedure 1B2, beginning with example (1R,3s,5S,8r)-8-(6-bromo-4-fluorobenzo[d]thiazol-2-yl)-3-((5-cyclopropyl-3-(2,6-dichlorophenyl)isoxazol-4-yl)methoxy)bicyclo[3.2.1]octan-8-ol (15-6), the title compound 2-((1R,3s,5S,8r)-3-((5-cyclopropyl-3-(2,6-dichlorophenyl)isoxazol-4-yl)methoxy)-8-hydroxybicyclo[3.2.1]octan-8-yl)-4-fluorobenzo[d]thiazole-6-carbonitrile (8-9) was synthesized. $^1$H NMR (500 MHz, DMSO-d$_6$): δ 8.57 (d, J=1.0 Hz, 1H), 7.95 (dd, J=1.0 Hz, J=10.5 Hz, 1H), 7.64-7.62 (m, 2H), 7.57-7.53 (m, 1H), 6.54 (s, 1H), 4.27 (s, 2H), 3.50-3.48 (m, 1H), 2.38-2.32 (m, 1H), 2.24-2.17 (m, 4H), 1.62-1.55 (m, 6H), 1.17-1.09 (m, 4H).

Example 8-10: 2-((1R,3s,5S,8r)-3-((5-Cyclopropyl-3-(2-(difluoromethoxy)phenyl)isoxazol-4-yl)methoxy)-8-hydroxybicyclo[3.2.1]octan-8-yl)-4-fluorobenzo[d]thiazole-6-carbonitrile

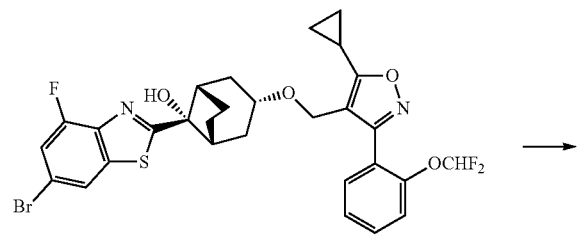

Exampe 15-7

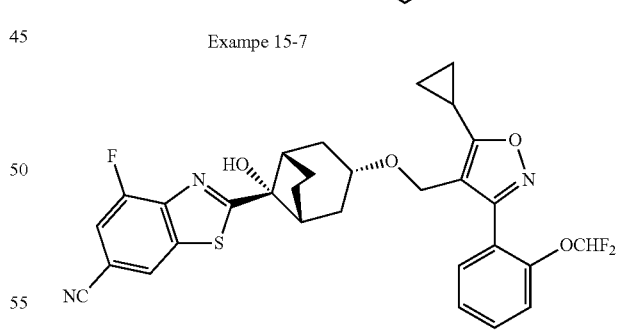

Exampe 8-10

Following general procedure 1B2, beginning with example (1R,3s,5S,8r)-8-(6-bromo-4-fluorobenzo[d]thiazol-2-yl)-3-((5-cyclopropyl-3-(2-(difluoromethoxy)phenyl)isoxazol-4-yl)methoxy)bicyclo[3.2.1]octan-8-ol (15-7), the title compound 2-((1R,3s,5S,8r)-3-((5-cyclopropyl-3-(2-(difluoromethoxy)phenyl)isoxazol-4-yl)methoxy)-8-hydroxybicyclo[3.2.1]octan-8-yl)-4-fluorobenzo[d]thiazole-6-carbonitrile (8-10) was synthesized.

Example 8-11: 2-((1R,3s,5S,8r)-3-((5-Cyclopropyl-3-(3,5-dichloropyridin-4-yl)isoxazol-4-yl)methoxy)-8-hydroxybicyclo[3.2.1]octan-8-yl)-4-fluorobenzo[d]thiazole-6-carbonitrile

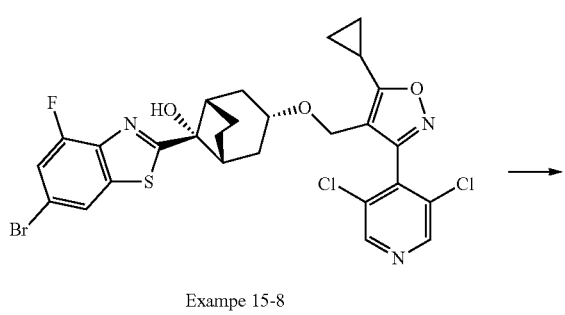

Exampe 15-8

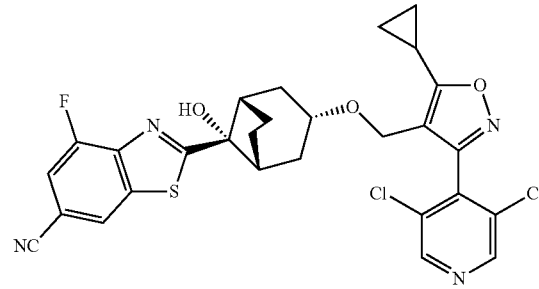

Exampe 8-11

Following general procedure 1B2, beginning with example (1R,3s,5S,8r)-8-(6-bromo-4-fluorobenzo[d]thiazol-2-yl)-3-((5-cyclopropyl-3-(3,5-dichloropyridin-4-yl)isoxazol-4-yl)methoxy)bicyclo[3.2.1]octan-8-ol (15-8), the title compound 2-((1R,3s,5S,8r)-3-((5-cyclopropyl-3-(3,5-dichloropyridin-4-yl)isoxazol-4-yl)methoxy)-8-hydroxybicyclo[3.2.1]octan-8-yl)-4-fluorobenzo[d]thiazole-6-carbonitrile (8-11) was synthesized.

Example 8-12: 2-((1s,4s)-4-((5-Cyclopropyl-3-(2,6-dichlorophenyl)isoxazol-4-yl)methoxy)-1-hydroxy-cyclohexyl)benzo[d]thiazole-6-carbonitrile

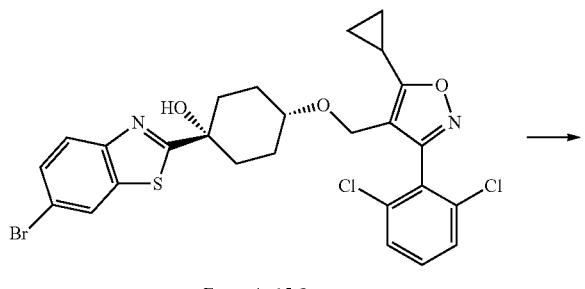

Example 15-9

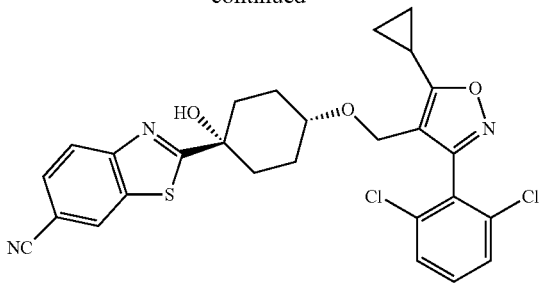

Example 8-12

Following general procedure 1B2, beginning with example (1s,4s)-1-(6-bromobenzo[d]thiazol-2-yl)-4-((5-cyclopropyl-3-(2,6-dichlorophenyl)isoxazol-4-yl)methoxy)cyclohexanol (15-9), the title compound 2-((1s,4s)-4-((5-cyclopropyl-3-(2,6-dichlorophenyl)isoxazol-4-yl)methoxy)-1-hydroxy-cyclohexyl)benzo[d]thiazole-6-carbonitrile (8-12) was synthesized.

Example 8-13: 2-((1s,4s)-4-((5-Cyclopropyl-3-(2,6-dichlorophenyl)isoxazol-4-yl)methoxy)-1-hydroxycyclohexyl)-4-fluorobenzo[d]thiazole-6-carbonitrile

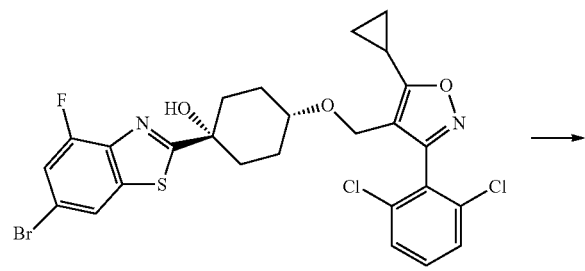

Example 15-10

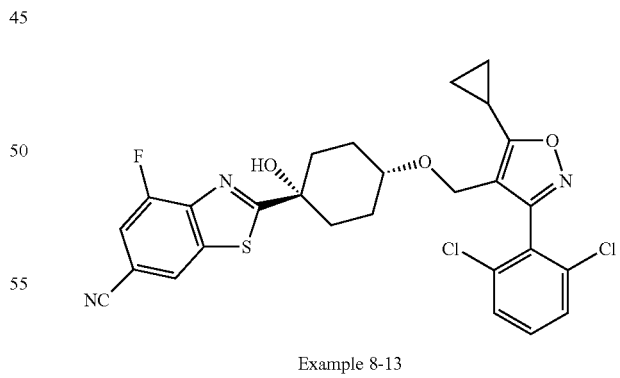

Example 8-13

Following general procedure 1B2, beginning with example (1s,4s)-1-(6-bromo-4-fluorobenzo[d]thiazol-2-yl)-4-((5-cyclopropyl-3-(2,6-dichlorophenyl)isoxazol-4-yl)methoxy)cyclohexanol (15-10), the title compound 2-((1s,4s)-4-((5-cyclopropyl-3-(2,6-dichlorophenyl)isoxazol-4-yl)methoxy)-1-hydroxycyclohexyl)-4-fluorobenzo[d]thiazole-6-carbonitrile (8-13) was synthesized.

Example 8-14: 2-((1R,2r,3S,5s,7s)-5-((5-Cyclopropyl-3-(2,6-dichlorophenyl)isoxazol-4-yl)methoxy)-2-hydroxyadamantan-2-yl)benzo[d]thiazole-6-carbonitrile

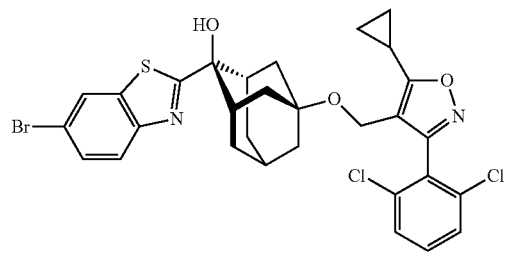

Example 23a

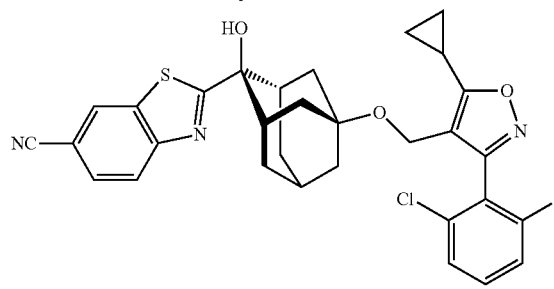

Example 8-14

Following general procedure 1B2, beginning with example (1R,2r,3S,5s,7s)-2-(6-bromobenzo[d]thiazol-2-yl)-5-((5-cyclopropyl-3-(2,6-dichlorophenyl)isoxazol-4-yl)methoxy)adamantan-2-ol (23a), the title compound 2-((1R,2r,3S,5s,7s)-5-((5-cyclopropyl-3-(2,6-dichlorophenyl)isoxazol-4-yl)methoxy)-2-hydroxyadamantan-2-yl)benzo[d]thiazole-6-carbonitrile (8-14) was synthesized.

Example 8-15: 2-((1R,2s,3S,5s,7s)-5-((5-Cyclopropyl-3-(2,6-dichlorophenyl)isoxazol-4-yl)methoxy)-2-hydroxyadamantan-2-yl)benzo[d]thiazole-6-carbonitrile

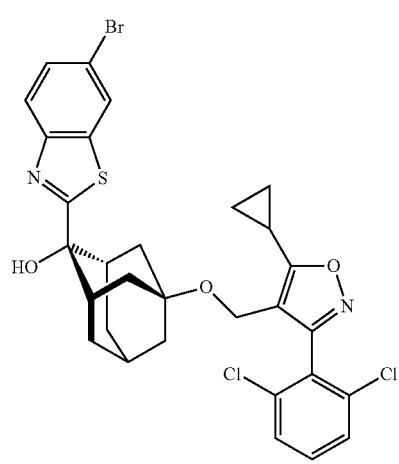

Example 23b

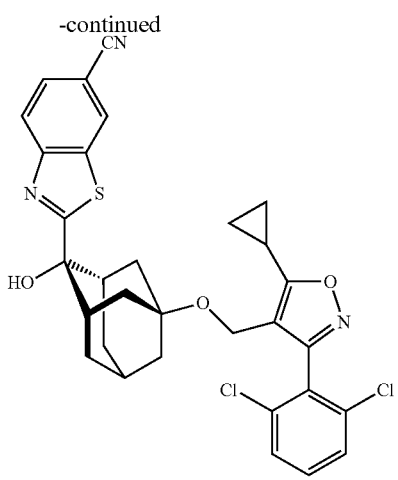

Example 8-15

Following general procedure 1B2, beginning with example (1R,2s,3S,5s,7s)-2-(6-bromobenzo[d]thiazol-2-yl)-5-((5-cyclopropyl-3-(2,6-dichlorophenyl)isoxazol-4-yl)methoxy)adamantan-2-ol (23b), the title compound 2-((1R,2s,3S,5s,7s)-5-((5-cyclopropyl-3-(2,6-dichlorophenyl)isoxazol-4-yl)methoxy)-2-hydroxyadamantan-2-yl)benzo[d]thiazole-6-carbonitrile (8-15) was synthesized.

Example 8-16: 2-((1R,3s,5S,8r)-3-((4-Cyclopropyl-1-(2,6-dichlorophenyl)-1H-pyrazol-5-yl)methoxy)-8-hydroxybicyclo[3.2.1]octan-8-yl)-4-fluorobenzo[d]thiazole-6-carbonitrile

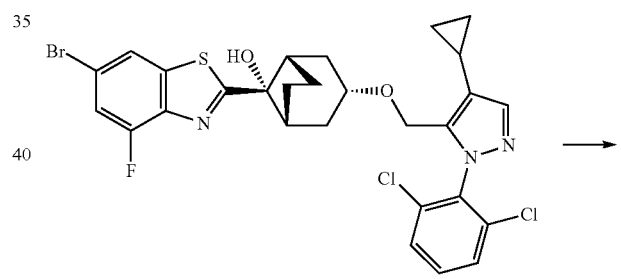

Example 15-24

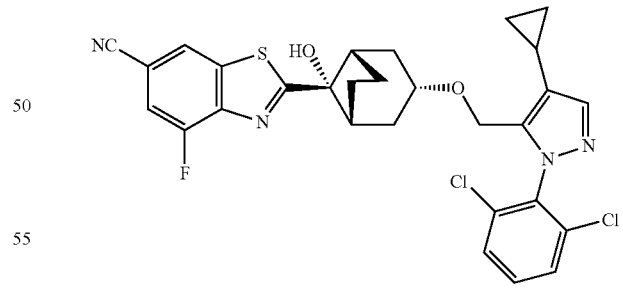

Example 8-16

Following general procedure 1B2, beginning with example (1R,3s,5S,8r)-8-(6-bromo-4-fluorobenzo[d]thiazol-2-yl)-3-((4-cyclopropyl-1-(2,6-dichlorophenyl)-1H-pyrazol-5-yl)methoxy)-bicyclo[3.2.1]octan-8-ol (15-24), the title compound 2-((1R,3s,5S,8r)-3-((4-cyclopropyl-1-(2,6-dichlorophenyl)-1H-pyrazol-5-yl)methoxy)-8-hydroxybicyclo[3.2.1]octan-8-yl)-4-fluorobenzo[d]thiazole-6-carbonitrile (8-16) was synthesized.

Example 8-17: 2-(3-((5-Cyclopropyl-3-(2,6-dichlorophenyl)isoxazol-4-yl)methoxy)-1-hydroxycyclopentyl)benzo[d]thiazole-6-carbonitrile

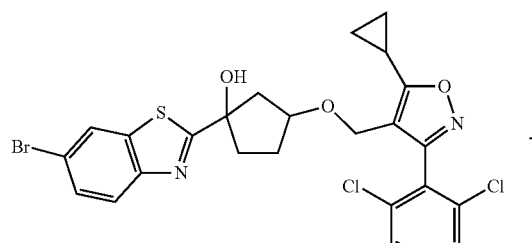

Example 6-6

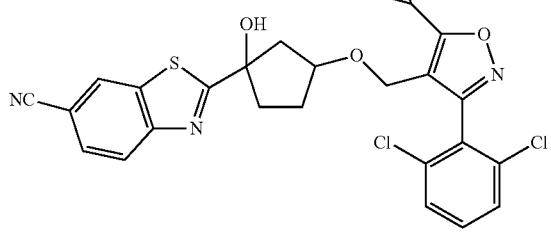

Example 8-17

In a microwave vial was placed 1-(6-bromobenzo[d]thiazol-2-yl)-3-((5-cyclopropyl-3-(2,6-dichlorophenyl)isoxazol-4-yl)methoxy)cyclopentanol (6-6, 92 mg, 0.16 mmol), zinc cyanide (26 mg, 0.22 mmol), Pd$_2$(dba)$_3$ (15 mg, 0.02 mmol), and Xantphos (9 mg, 0.02 mmol). The vial was sealed, evacuated and filled with nitrogen three times. DMF (4 mL) was added and the mixture was irradiated in a microwave reactor for 30 min @100° C. After cooling to rt, the mixture was concentrated under reduced pressure to remove the majority of DMF, then diluted with EtOAc and water and filtered through celite. The phases were separated and the organic layer was washed three times with brine, dried over Na$_2$SO$_4$, filtered and concentrated. Purification by column chromatography (ISCO 12 g GOLD silica, 0-70% EtOAc/hexanes) gave the product 2-(3-((5-cyclopropyl-3-(2,6-dichlorophenyl)isoxazol-4-yl)methoxy)-1-hydroxycyclopentyl)benzo[d]thiazole-6-carbonitrile (8-17).

General Procedure 1C for the Synthesis of Example 9 and Example 10

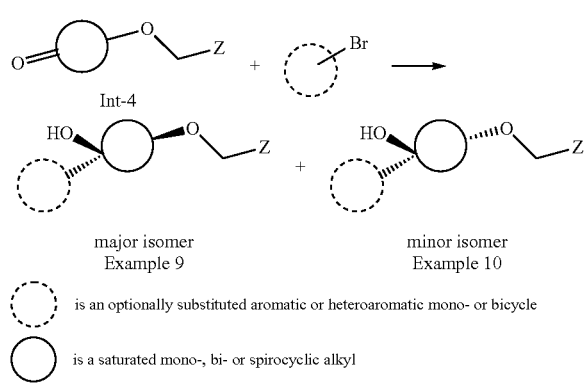

A solution of ketone (1.0 eq.) and bromide (1.0 to 1.2 eq.) in dry THF was cooled to −78° C., then n-BuLi (1.0 to 1.2 eq.) was added dropwise and the mixture was stirred at −78° C. for 2 h, quenched with sat. NH$_4$Cl and extracted three times with EtOAc. The combined organic layers were washed with brine, dried, filtered, concentrated and the residue was purified with prep-TLC or flash chromatography to give major isomer 9 and minor isomer 10. (The minor isomer may not get isolated.)

Example 9-1: 2-((1s,4s)-4-((5-Cyclopropyl-3-(spiro[2.5]octan-6-yl)isoxazol-4-yl)methoxy)-1-hydroxycyclohexyl)benzo[d]thiazole-6-carbonitrile

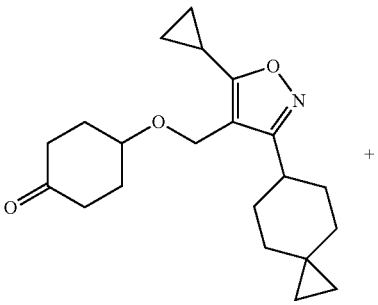

Int-4-2

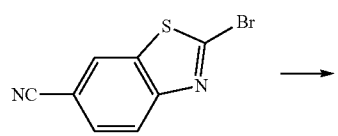

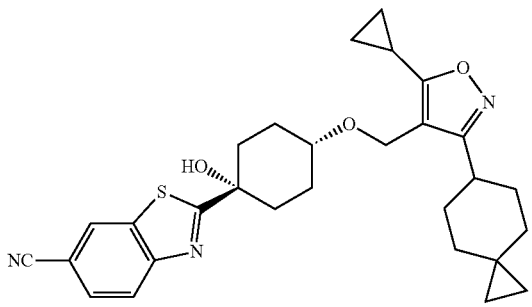

Example 9-1

Following general procedure 1C, beginning with intermediate 4-((5-cyclopropyl-3-(spiro[2.5]octan-6-yl)isoxazol-4-yl)methoxy)cyclohexanone (Int-4-2) and 2-bromobenzo[d]thiazole-6-carbonitrile, the title compound 2-((1s,4s)-4-((5-cyclopropyl-3-(spiro[2.5]octan-6-yl)isoxazol-4-yl)methoxy)-1-hydroxycyclohexyl)benzo[d]thiazole-6-carbonitrile (9-1) was synthesized (the minor isomer was not isolated).

Example 9-2a and Example 9-2b: 2-(6-(5-Cyclopropyl-3-(2,6-dichlorophenyl)isoxazol-4-yl)methoxy)-2-hydroxyspiro[3.3]heptan-2-yl)benzo[d]thiazole-6-carbonitrile (9-2a, first eluting enantiomer) and 2-(6-((5-Cyclopropyl-3-(2,6-dichlorophenyl)isoxazol-4-yl)methoxy)-2-hydroxyspiro[3.3]heptan-2-yl)benzo[d]thiazole-6-carbonitrile (9-2b, second eluting enantiomer)

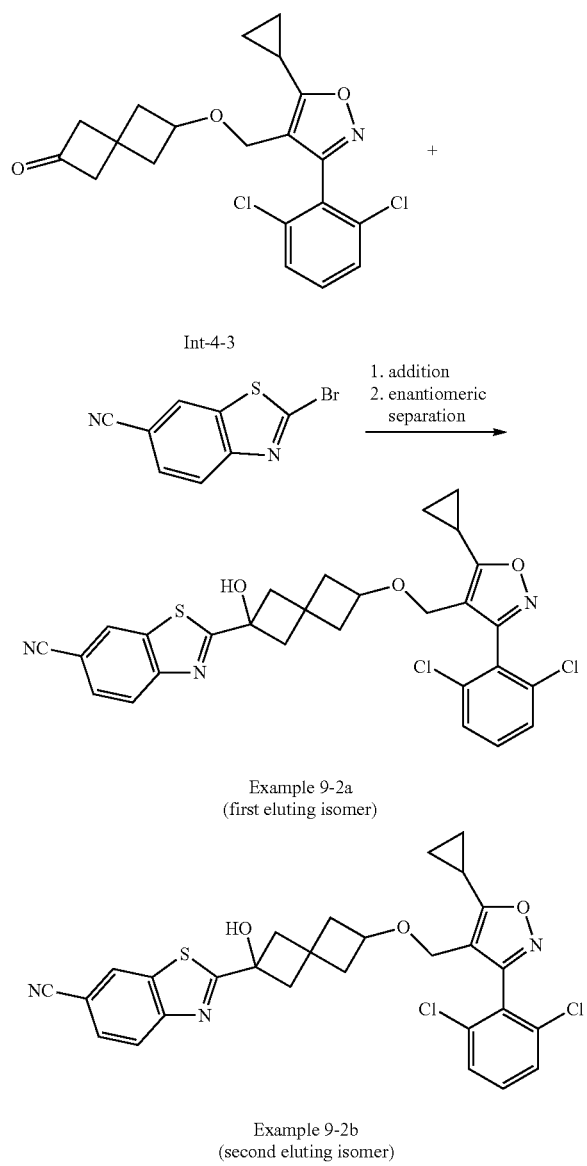

Example 9-2a
(first eluting isomer)

Example 9-2b
(second eluting isomer)

Following general procedure 1C, beginning with intermediate 6-((5-cyclopropyl-3-(2,6-dichloro-phenyl)isoxazol-4-yl)methoxy)spiro[3.3]heptan-2-one Int-4-3 (300 mg) and 2-bromobenzo[d]thiazole-6-carbonitrile (184 mg), the racemate was obtained which was purified by prep-TLC (CH₂Cl₂/MeOH=20:1). Enantiomeric separation by chiral-HPLC funished 2-(6-(5-cyclopropyl-3-(2,6-dichlorophenyl)isoxazol-4-yl)methoxy)-2-hydroxyspiro[3.3]heptan-2-yl)benzo[d]thiazole-6-carbonitrile (9-2a, first eluting) and the enantiomer 2-(6-((5-cyclopropyl-3-(2,6-dichlorophenyl)isoxazol-4-yl)methoxy)-2-hydroxyspiro[3.3]heptan-2-yl)benzo[d]thiazole-6-carbonitrile (9-2b, second eluting).

Example 9-3: 4-((1s,4s)-4-((5-Cyclopropyl-3-(2,6-dichlorophenyl)isoxazol-4-yl)methoxy)-1-hydroxycyclohexyl)-3-fluorobenzonitrile

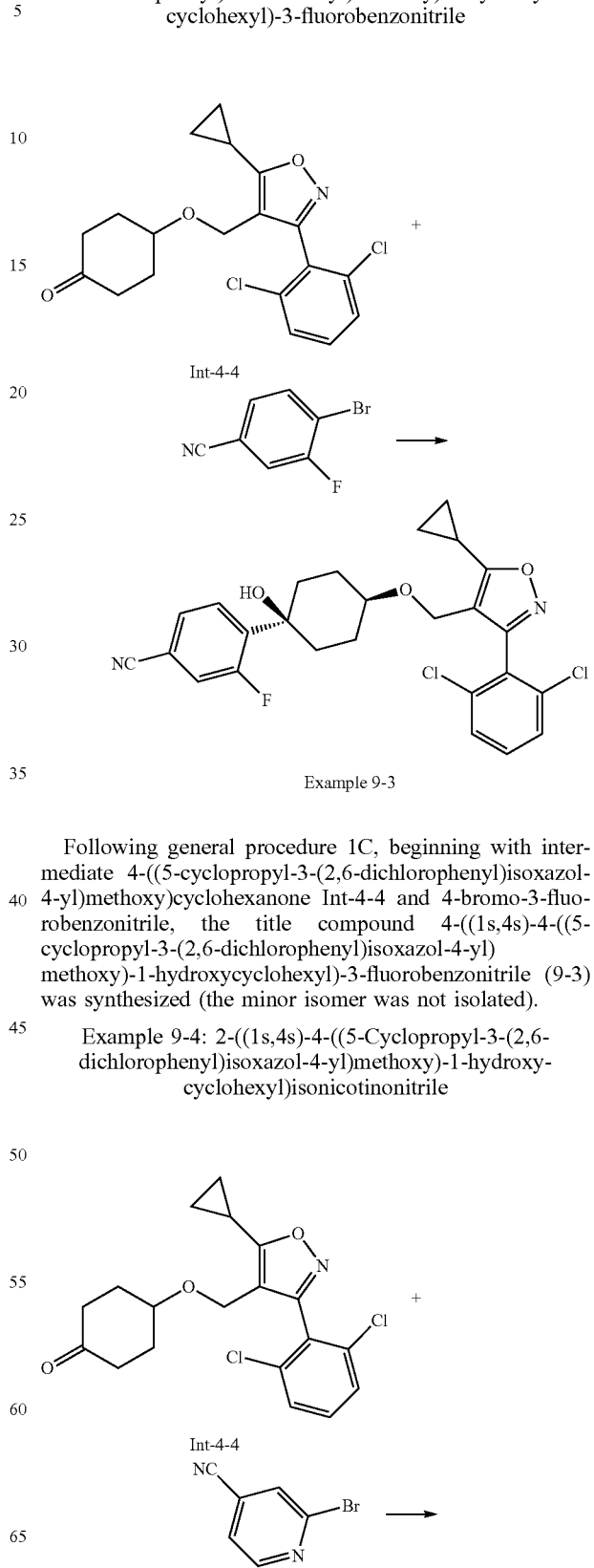

Example 9-3

Following general procedure 1C, beginning with intermediate 4-((5-cyclopropyl-3-(2,6-dichlorophenyl)isoxazol-4-yl)methoxy)cyclohexanone Int-4-4 and 4-bromo-3-fluorobenzonitrile, the title compound 4-((1s,4s)-4-((5-cyclopropyl-3-(2,6-dichlorophenyl)isoxazol-4-yl)methoxy)-1-hydroxycyclohexyl)-3-fluorobenzonitrile (9-3) was synthesized (the minor isomer was not isolated).

Example 9-4: 2-((1s,4s)-4-((5-Cyclopropyl-3-(2,6-dichlorophenyl)isoxazol-4-yl)methoxy)-1-hydroxycyclohexyl)isonicotinonitrile

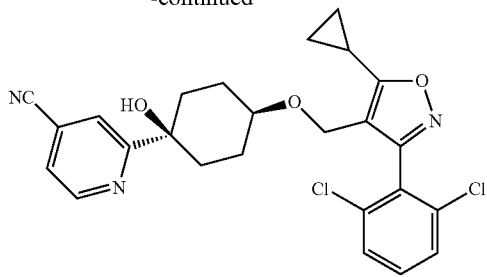

Example 9-4

Following general procedure 1C, beginning with intermediate 4-((5-cyclopropyl-3-(2,6-dichlorophenyl)isoxazol-4-yl)methoxy)cyclohexanone Int-4-4 and 2-bromoisonicotinonitrile, the title compound 2-((1s,4s)-4-((5-cyclopropyl-3-(2,6-dichlorophenyl)isoxazol-4-yl)methoxy)-1-hydroxycyclohexyl)isonicotinonitrile (9-4) was synthesized (the minor isomer was not isolated).

Example 9-5: 2-((1s,4s)-4-((5-Cyclopropyl-3-(2-(difluoromethoxy)phenyl)isoxazol-4-yl)methoxy)-1-hydroxycyclohexyl)-4-fluorobenzo[d]thiazole-6-carbonitrile

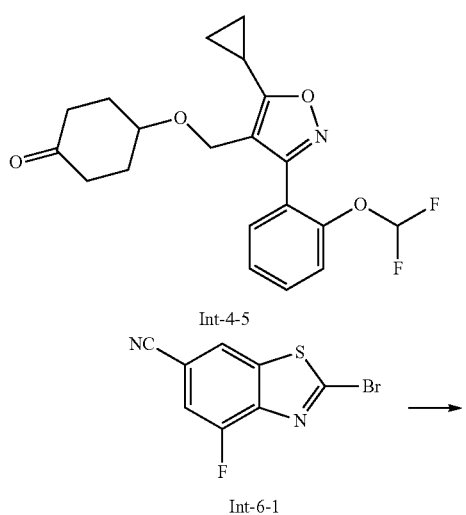

Following general procedure 1C, beginning with intermediate 4-((5-cyclopropyl-3-(2-(difluoro-methoxy)phenyl)isoxazol-4-yl)methoxy)cyclohexanone Int-4-5 and 2-bromo-4-fluorobenzo[d]thiazole-6-carbonitrile Int-6-1, the title compound 2-((1s,4s)-4-((5-cyclopropyl-3-(2-(difluoromethoxy)phenyl)isoxazol-4-yl)methoxy)-1-hydroxy-cyclohexyl)-4-fluorobenzo[d]thiazole-6-carbonitrile (9-5) was synthesized (the minor isomer was not isolated).

Example 9-6: (1s,4s)-4-((5-Cyclopropyl-3-(2,6-dichlorophenyl)isoxazol-4-yl)methoxy)-1-(2-fluoro-4-(hydroxymethyl)phenyl)cyclohexanol

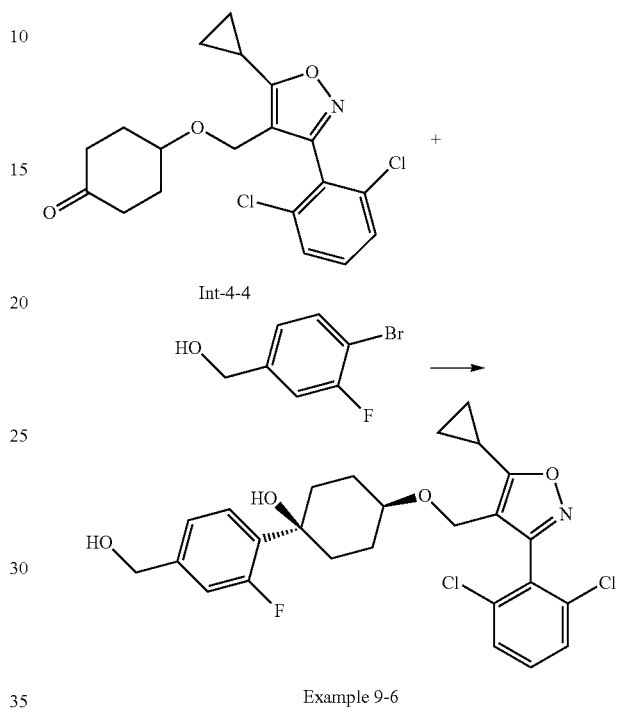

Example 9-6

Following general procedure 1C, beginning with intermediate 4-((5-cyclopropyl-3-(2,6-dichlorophenyl)isoxazol-4-yl)methoxy)cyclohexanone Int-4-4 and (4-bromo-3-fluoro-phenyl)methanol, the title compound (1s,4s)-4-((5-cyclopropyl-3-(2,6-dichlorophenyl)isoxazol-4-yl)methoxy)-1-(2-fluoro-4-(hydroxymethyl)phenyl)cyclohexanol (9-6) was synthesized (the minor isomer was not isolated). $^{1}$H-NMR (500 MHz, DMSO-d$_{6}$): δ 7.66-7.65 (m, 2H), 7.60-7.52 (m, 2H), 7.07 (d, J=7.5 Hz, 1H), 6.99 (d, J=13.0 Hz, 1H), 5.25-5.23 (m, 1H), 4.96 (s, 1H), 4.45 (d, J=5.5 Hz, 2H), 4.31 (s, 2H), 3.18-3.13 (m, 1H), 2.37-2.34 (m, 1H), 1.89-1.84 (m, 2H), 1.54-1.47 (m, 6H), 1.16-1.10 (m, 4H). LCMS (ESI): m/z 506.1 (M+1)$^{+}$.

Example 9-7: (1s,4s)-4-((5-Cyclopropyl-3-(2,6-dichlorophenyl)isoxazol-4-yl)methoxy)-1-(2-fluoro-5-(hydroxymethyl)phenyl)cyclohexanol

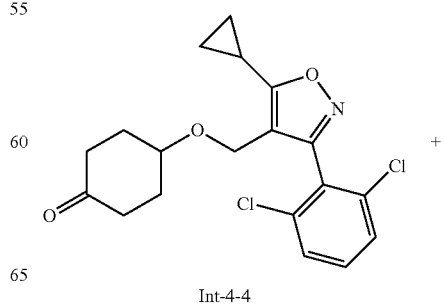

Int-4-4

-continued

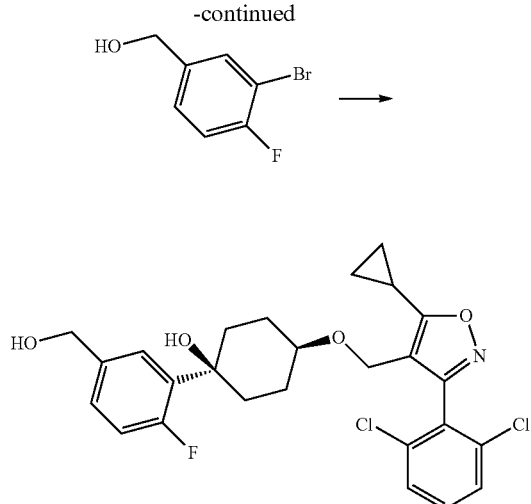

Example 9-7

Following general procedure 1C, beginning with intermediate 4-((5-cyclopropyl-3-(2,6-dichlorophenyl)isoxazol-4-yl)methoxy)cyclohexanone Int-4-4 and (3-bromo-4-fluoro-phenyl)methanol, the title compound (1s,4s)-4-((5-cyclopropyl-3-(2,6-dichlorophenyl)isoxazol-4-yl)methoxy)-1-(2-fluoro-5-(hydroxymethyl)phenyl)cyclohexanol (9-7) was synthesized (the minor isomer was not isolated). $^{1}$H-NMR (500 MHz, DMSO-d$_{6}$): δ 7.55 (dd, J=7.8 Hz, J=1.8 Hz, 1H), 7.44-7.42 (m, 2H), 7.36-7.33 (m, 1H), 7.25-7.23 (m 1H), 7.02-6.98 (m, 1H), 4.65 (s, 2H), 4.37 (s, 2H), 3.29-3.25 (m, 1H), 2.21-2.18 (m, 1H), 2.05-1.98 (m, 2H), 1.78-1.73 (m, 4H), 1.67-1.62 (m, 2H), 1.30-1.27 (m, 2H), 1.15-1.11 (m, 2H), hydroxyl protons not resolved. LCMS (ESI): m/z 506.0 (M+1)$^{+}$.

Example 9-8: 2-((1s,4s)-4-((5-Cyclopropyl-3-(2-(difluoromethoxy)phenyl)isoxazol-4-yl)methoxy)-1-hydroxycyclohexyl)benzo[d]thiazole-6-carbonitrile

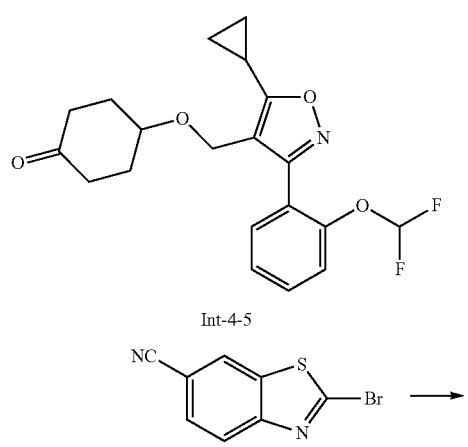

Int-4-5

-continued

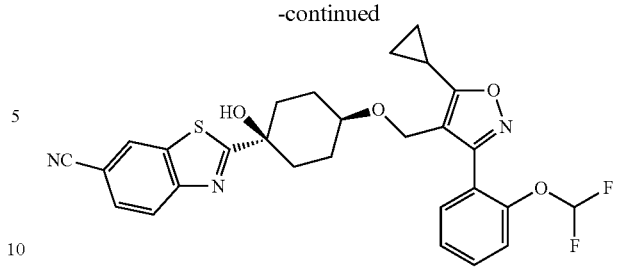

Example 9-8

Following general procedure 1C, beginning with intermediate 4-((5-cyclopropyl-3-(2-(difluoromethoxy)phenyl)isoxazol-4-yl)methoxy)cyclohexanone Int-4-5 and 2-bromobenzo[d]thiazole-6-carbonitrile, the title compound 2-((1s,4s)-4-((5-cyclopropyl-3-(2-(difluoromethoxy)phenyl)isoxazol-4-yl)methoxy)-1-hydroxycyclohexyl)benzo[d]thiazole-6-carbonitrile (9-8) was synthesized (the minor isomer was not isolated).

Example 9-9: 2-((1s,4s)-4-((5-Cyclopropyl-3-(2-cyclopropylphenyl)isoxazol-4-yl)methoxy)-1-hydroxycyclohexyl)benzo[d]thiazole-6-carbonitrile

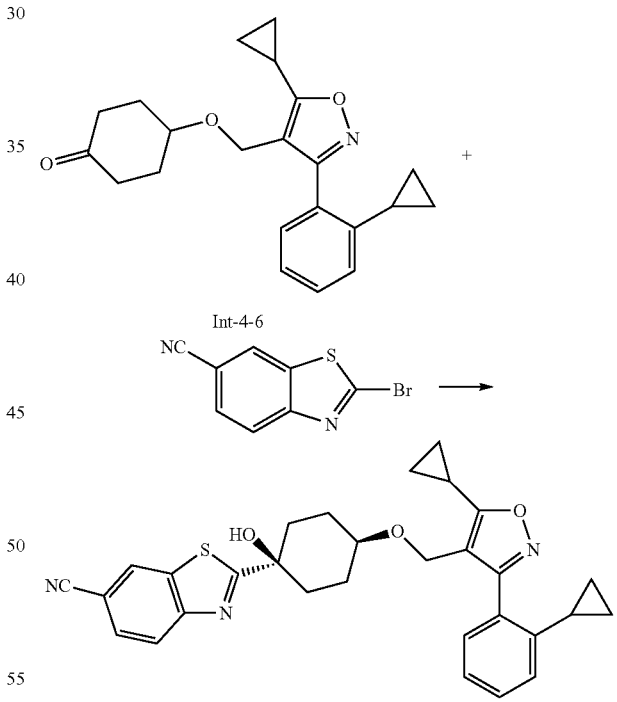

Example 9-9

Following general procedure 1C, beginning with intermediate 4-((5-cyclopropyl-3-(2-cyclo-propylphenyl)isoxazol-4-yl)methoxy)cyclohexanone Int-4-6 and 2-bromobenzo[d]thiazole-6-carbonitrile, the title compound 2-((1s,4s)-4-((5-cyclopropyl-3-(2-cyclopropylphenyl)isoxazol-4-yl)methoxy)-1-hydroxycyclohexyl)benzo[d]thiazole-6-carbonitrile (9-9) was synthesized (the minor isomer was not isolated).

Example 9-10: 2-((1s,4s)-4-((5-Cyclopropyl-3-(2,6-dimethylphenyl)isoxazol-4-yl)methoxy)-1-hydroxy-cyclohexyl)benzo[d]thiazole-6-carbonitrile

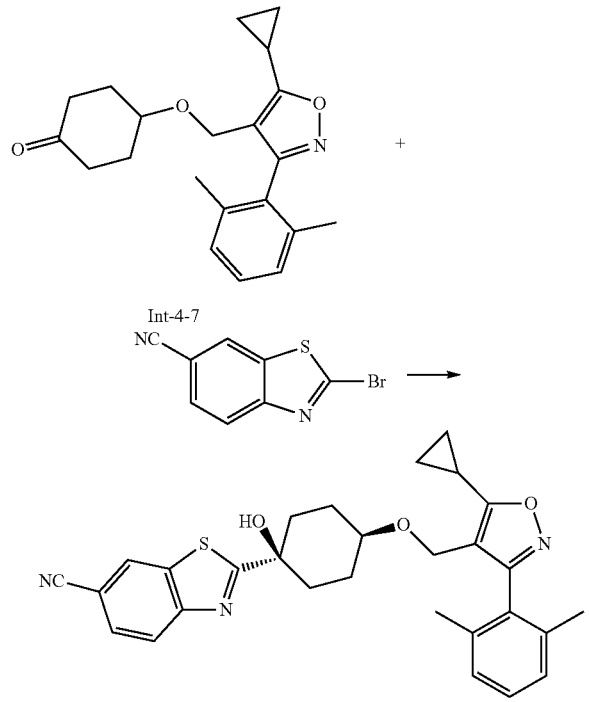

Int-4-7

Example 9-10

Following general procedure 1C, beginning with intermediate 4-((5-cyclopropyl-3-(2,6-dimethyl-phenyl)isoxazol-4-yl)methoxy)cyclohexanone Int-4-7 and 2-bromobenzo[d]thiazole-6-carbonitrile, the title compound 2-((1s,4s)-4-((5-cyclopropyl-3-(2,6-dimethylphenyl)isoxazol-4-yl)methoxy)-1-hydroxycyclohexyl)benzo[d]thiazole-6-carbonitrile (9-10) was synthesized (the minor isomer was not isolated).

Example 9-11: 2-((1s,4s)-4-((4-Cyclopropyl-1-(2,6-dichlorophenyl)-1H-pyrazol-5-yl)methoxy)-1-hydroxycyclohexyl)benzo[d]thiazole-6-carbonitrile

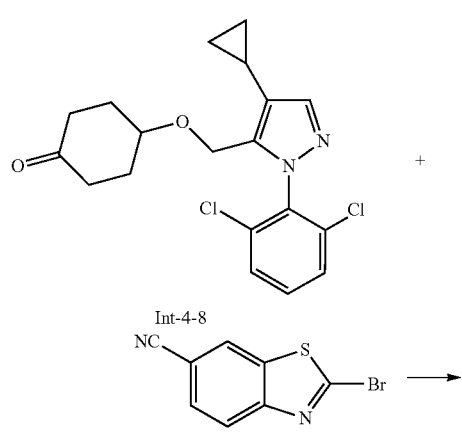

Int-4-8

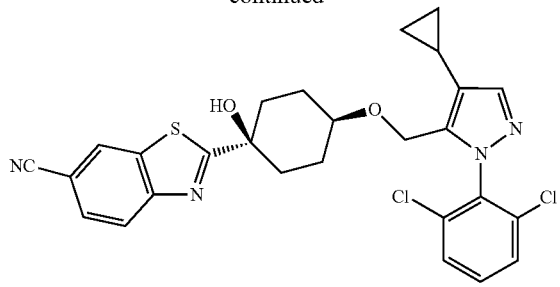

Example 9-11

Following general procedure 1C, beginning with intermediate 4-((4-cyclopropyl-1-(2,6-dichlorophenyl)-1H-pyrazol-5-yl)methoxy)cyclohexanone Int-4-8 and 2-bromobenzo[d]thiazole-6-carbonitrile, the title compound 2-((1s,4s)-4-((4-cyclopropyl-1-(2,6-dichlorophenyl)-1H-pyrazol-5-yl)methoxy)-1-hydroxycyclohexyl)benzo[d]thiazole-6-carbonitrile (9-11) was synthesized (the minor isomer was not isolated).

Example 9-12: 2-((1s,4s)-4-((5-Cyclopropyl-3-(2-(trifluoromethoxy)phenyl)isoxazol-4-yl)methoxy)-1-hydroxycyclohexyl)benzo[d]thiazole-6-carbonitrile

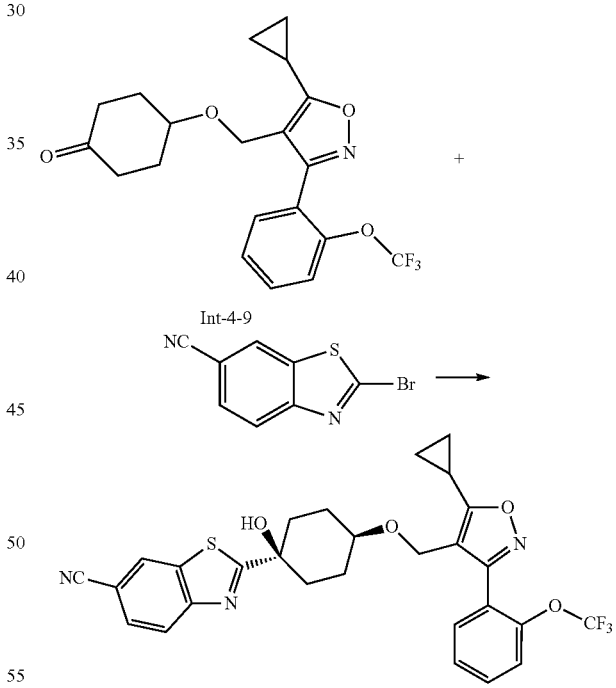

Example 9-12

Following general procedure 1C, beginning with intermediate 4-((5-cyclopropyl-3-(2-(trifluoro-methoxy)phenyl)isoxazol-4-yl)methoxy)cyclohexanone Int-4-9 and 2-bromobenzo[d]thiazole-6-carbonitrile, the title compound 2-((1s,4s)-4-((5-cyclopropyl-3-(2-(trifluoromethoxy)phenyl)isoxazol-4-yl)methoxy)-1-hydroxycyclohexyl)benzo[d]thiazole-6-carbonitrile (9-12) was synthesized (the minor isomer was not isolated).

Example 9-13: 2-((1s,4s)-4-((5-Cyclopropyl-3-(2-(difluoromethyl)phenyl)isoxazol-4-yl)methoxy)-1-hydroxycyclohexyl)benzo[d]thiazole-6-carbonitrile

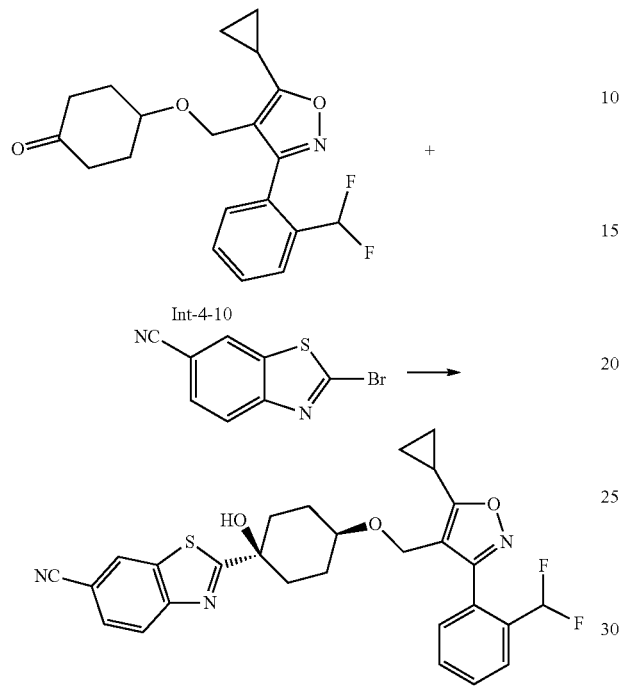

Example 9-13

Following general procedure 1C, beginning with intermediate 4-((5-cyclopropyl-3-(2-(difluoromethyl)phenyl)isoxazol-4-yl)methoxy)cyclohexanone Int-4-10 and 2-bromobenzo[d]thiazole-6-carbonitrile, the title compound 2-((1s,4s)-4-((5-cyclopropyl-3-(2-(difluoro-methyl)phenyl)isoxazol-4-yl)methoxy)-1-hydroxycyclohexyl)benzo[d]thiazole-6-carbonitrile (9-13) was synthesized (the minor isomer was not isolated).

Example 9-14: 2-((1s,4s)-4-((5-Cyclopropyl-3-(3,5-dichloropyridin-4-yl)isoxazol-4-yl)methoxy)-1-hydroxycyclohexyl)benzo[d]thiazole-6-carbonitrile

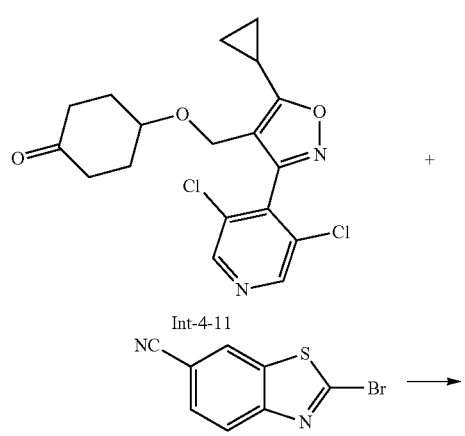

Int-4-11

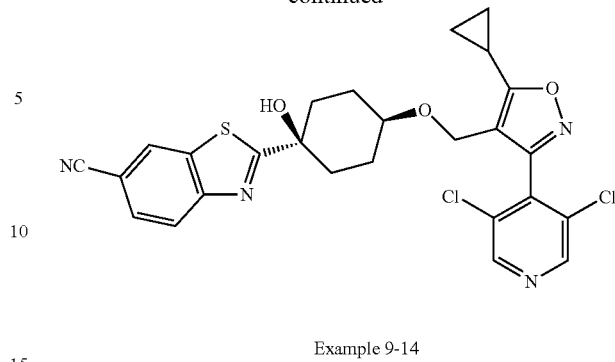

Example 9-14

Following general procedure 1C, beginning with intermediate 4-((5-cyclopropyl-3-(3,5-dichloropyridin-4-yl)isoxazol-4-yl)methoxy)cyclohexanone Int-4-11 and 2-bromobenzo[d]thiazole-6-carbonitrile, the title compound 2-((1s,4s)-4-((5-cyclopropyl-3-(3,5-dichloropyridin-4-yl)isoxazol-4-yl)methoxy)-1-hydroxycyclohexyl)benzo[d]thiazole-6-carbonitrile (9-14) was synthesized (the minor isomer was not isolated).

Example 9-15: 2-((1s,4s)-4-((4-Cyclopropyl-1-(2-(difluoromethoxy)phenyl)-1H-pyrazol-5-yl)methoxy)-1-hydroxycyclohexyl)benzo[d]thiazole-6-carbonitrile

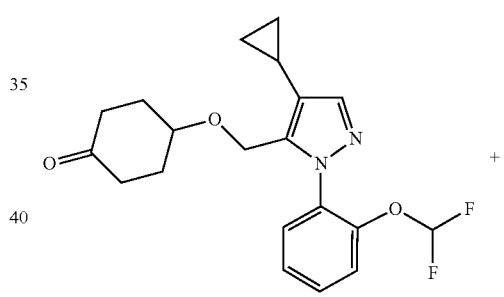

Int-4-12

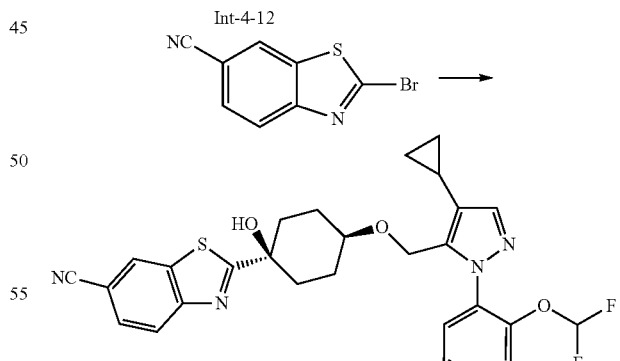

Example 9-15

Following general procedure 1C, beginning with intermediate 4-((4-cyclopropyl-1-(2-(difluoromethoxy)phenyl)-1H-pyrazol-5-yl)methoxy)cyclohexanone Int-4-12 and 2-bromobenzo[d]thiazole-6-carbonitrile, the title compound 2-((1s,4s)-4-((4-cyclopropyl-1-(2-(difluoro-methoxy)phenyl)-1H-pyrazol-5-yl)methoxy)-1-hydroxycyclohexyl)benzo[d]thiazole-6-carbonitrile (9-15) was synthesized (the minor isomer was not isolated).

Example 9-16: 2-((1s,4s)-4-((3-(2,6-Bis(difluoromethyl)phenyl)-5-cyclopropylisoxazol-4-yl)methoxy)-1-hydroxycyclohexyl)benzo[d]thiazole-6-carbonitrile

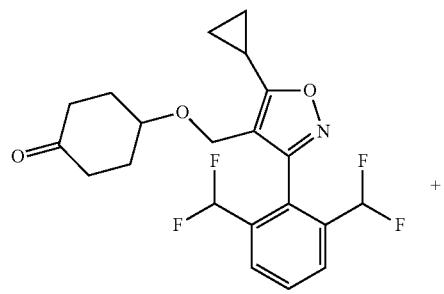

Int-4-13

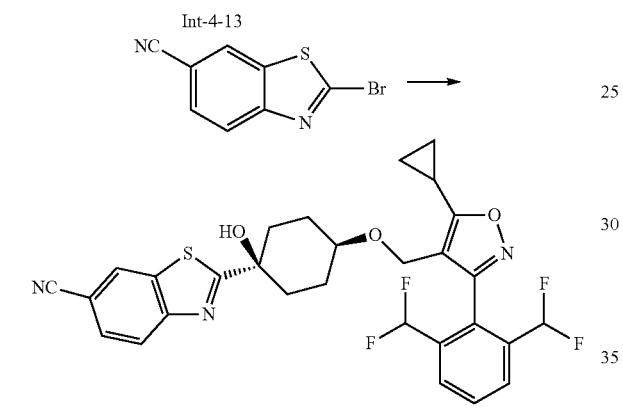

Example 9-16

Following general procedure 1C, beginning with intermediate 4-((3-(2,6-bis(difluoromethyl)phenyl)-5-cyclopropylisoxazol-4-yl)methoxy)cyclohexanone Int-4-13 and 2-bromobenzo[d]thiazole-6-carbonitrile, the title compound 2-((1s,4s)-4-((3-(2,6-bis(difluoro-methyl)phenyl)-5-cyclopropylisoxazol-4-yl)methoxy)-1-hydroxycyclohexyl)benzo[d]thiazole-6-carbonitrile (9-16) was synthesized (the minor isomer was not isolated).

Example 9-17: 2-((1s,3s)-3-((5-Cyclopropyl-3-(2,6-dichlorophenyl)isoxazol-4-yl)methoxy)-1-hydroxycyclobutyl)-4-fluorobenzo[d]thiazole-6-carbonitrile

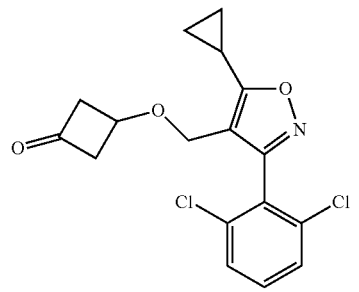

Int-7-1

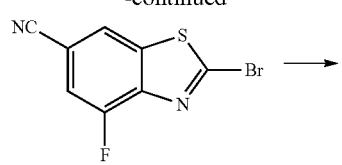

Int-6-1

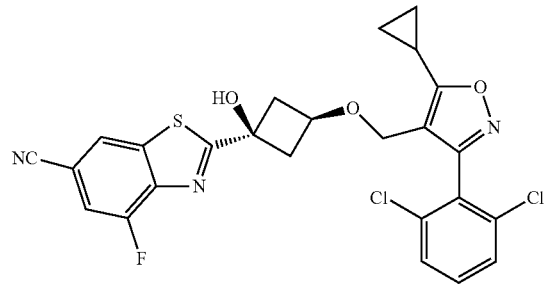

Example 9-17

Following general procedure 1C, beginning with intermediate 3-((5-cyclopropyl-3-(2,6-dichlorophenyl)isoxazol-4-yl)methoxy)cyclobutanone Int-7-1 and 2-bromo-4-fluorobenzo[d]thiazole-6-carbonitrile (Int-6-1), the title compound 2-((1s,3s)-3-((5-cyclopropyl-3-(2,6-dichlorophenyl)isoxazol-4-yl)methoxy)-1-hydroxycyclobutyl)-4-fluorobenzo[d]thiazole-6-carbonitrile (9-17) was synthesized (the minor isomer was not isolated).

Example 9-18: 2-((1S,4R)-4-((5-Cyclopropyl-3-(2,6-dichlorophenyl)isoxazol-4-yl)methoxy)-1-hydroxy-2,2-dimethylcyclohexyl)-4-fluorobenzo[d]thiazole-6-carbonitrile

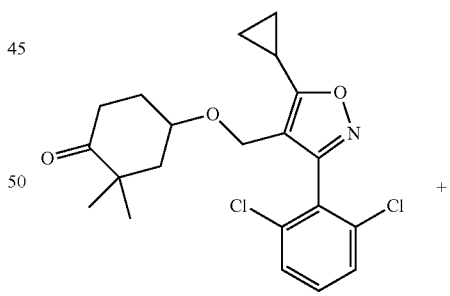

Int-8-1

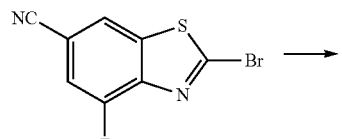

Int-6-1

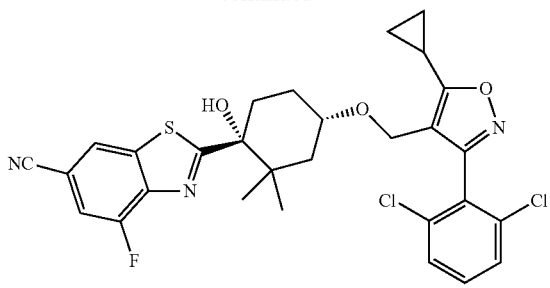

Example 9-18
(cis racemate)

Following general procedure 1C, beginning with intermediate 4-((5-cyclopropyl-3-(2,6-dichlorophenyl)isoxazol-4-yl)methoxy)-2,2-dimethylcyclohexanone Int-8-1 and 2-bromo-4-fluorobenzo[d]thiazole-6-carbonitrile (Int-6-1), the racemic title compound 2-((1S,4R)-4-((5-cyclopropyl-3-(2,6-dichlorophenyl)isoxazol-4-yl)methoxy)-1-hydroxy-2,2-dimethylcyclohexyl)-4-fluorobenzo[d]thiazole-6-carbonitrile (9-18) was synthesized (the minor isomer was not isolated).

Example 9-19: 2-((1S,4R)-4-((5-Cyclopropyl-3-(2,6-dichlorophenyl)isoxazol-4-yl)methoxy)-1-hydroxy-3,3-dimethylcyclohexyl)-4-fluorobenzo[d]thiazole-6-carbonitrile

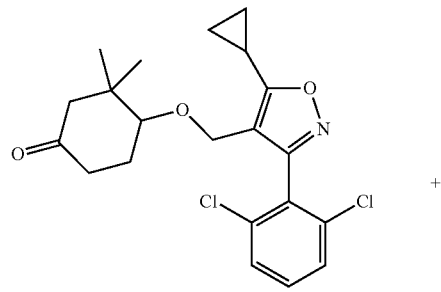

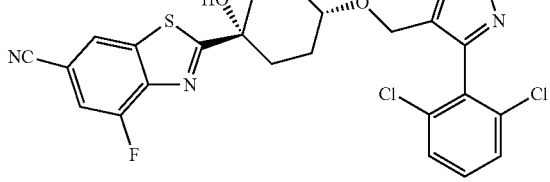

Example 9-19
(cis racemate)

Following general procedure 1C, beginning with intermediate 4-((5-cyclopropyl-3-(2,6-dichlorophenyl)isoxazol-4-yl)methoxy)-3,3-dimethylcyclohexanone Int-8-2 and 2-bromo-4-fluorobenzo[d]thiazole-6-carbonitrile (Int-6-1), the racemic title compound 2-((1S,4R)-4-((5-cyclopropyl-3-(2,6-dichlorophenyl)isoxazol-4-yl)methoxy)-1-hydroxy-3,3-dimethylcyclohexyl)-4-fluorobenzo[d]thiazole-6-carbonitrile (9-19) was synthesized (the minor isomer was not isolated).

Example 9-20: 2-((1s,4s)-4-((5-Cyclopropyl-3-(3,5-dichloropyridin-4-yl)isoxazol-4-yl)methoxy)-1-hydroxycyclohexyl)-4-fluorobenzo[d]thiazole-6-carbonitrile

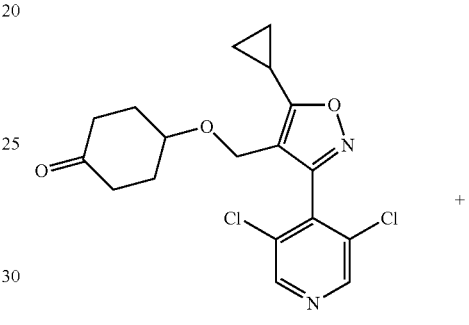

Int-4-11

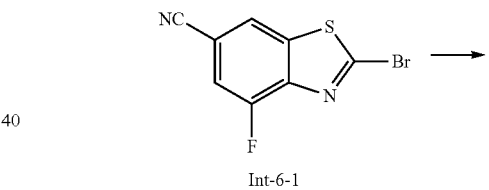

Int-6-1

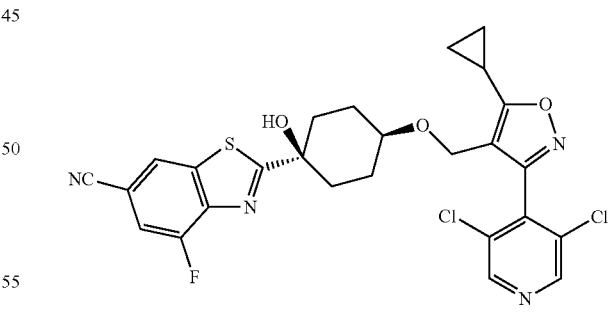

Example 9-20

Following general procedure 1C, beginning with intermediate 4-((5-cyclopropyl-3-(3,5-dichloropyridin-4-yl)isoxazol-4-yl)methoxy)cyclohexanone Int-4-11 and 2-bromo-4-fluorobenzo[d]thiazole-6-carbonitrile (Int-6-1), the title compound 2-((1s,4s)-4-((5-cyclopropyl-3-(3,5-dichloropyridin-4-yl)isoxazol-4-yl)methoxy)-1-hydroxycyclohexyl)-4-fluorobenzo[d]thiazole-6-carbonitrile (9-20) was synthesized (the minor isomer was not isolated).

Example 9-21: 6-((1s,4s)-4-((5-Cyclopropyl-3-(2,6-dichlorophenyl)isoxazol-4-yl)methoxy)-1-hydroxy-cyclohexyl)-1-methyl-1H-indole-3-carbonitrile

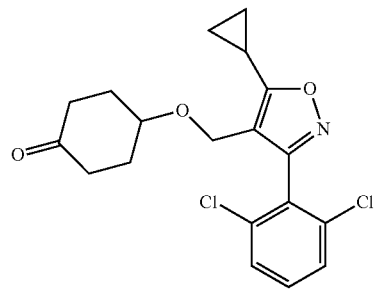

Int-4-4

+

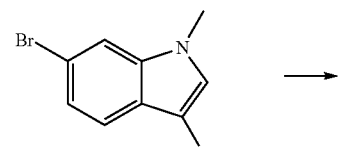

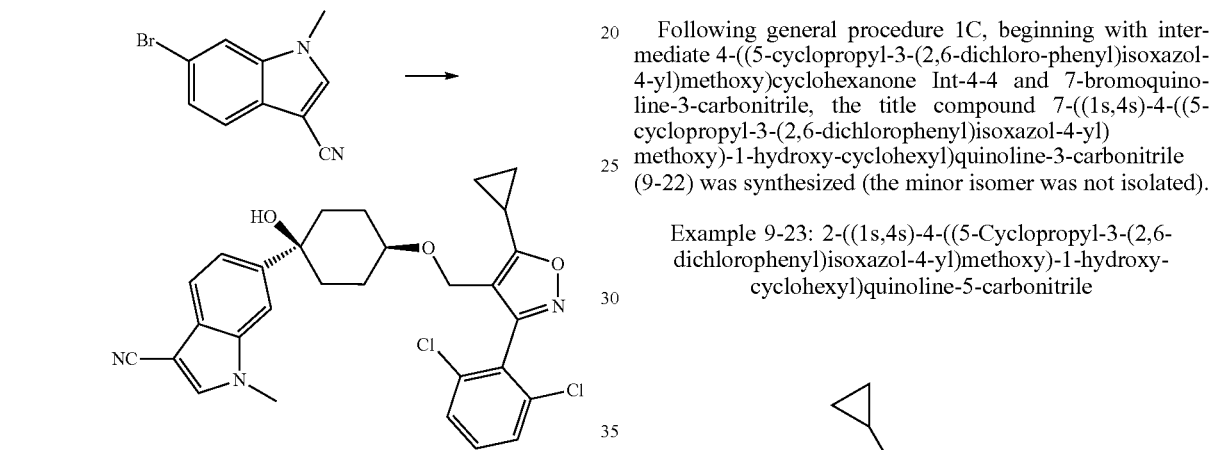

Example 9-21

Following general procedure 1C, beginning with intermediate 4-((5-cyclopropyl-3-(2,6-dichloro-phenyl)isoxazol-4-yl)methoxy)cyclohexanone Int-4-4 and 6-bromo-1-methyl-1H-indole-3-carbonitrile, the title compound 6-((1s,4s)-4-((5-cyclopropyl-3-(2,6-dichlorophenyl)isoxazol-4-yl)methoxy)-1-hydroxycyclohexyl)-1-methyl-1H-indole-3-carbonitrile (9-21) was synthesized (the minor isomer was not isolated).

Example 9-22: 7-((1s,4s)-4-((5-Cyclopropyl-3-(2,6-dichlorophenyl)isoxazol-4-yl)methoxy)-1-hydroxy-cyclohexyl)quinoline-3-carbonitrile

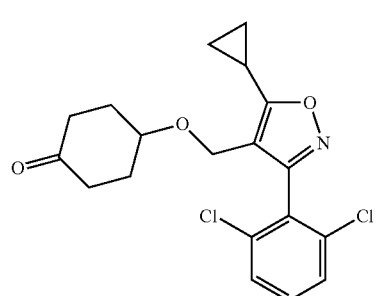

Int-4-4

+

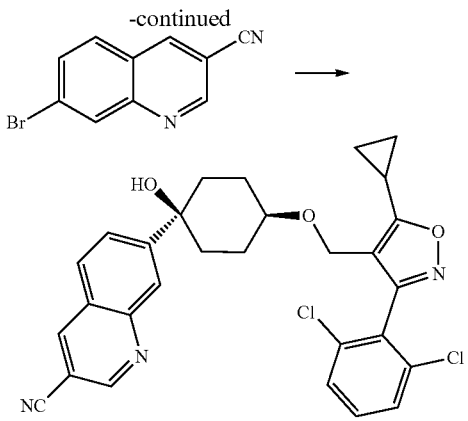

Example 9-22

Following general procedure 1C, beginning with intermediate 4-((5-cyclopropyl-3-(2,6-dichloro-phenyl)isoxazol-4-yl)methoxy)cyclohexanone Int-4-4 and 7-bromoquinoline-3-carbonitrile, the title compound 7-((1s,4s)-4-((5-cyclopropyl-3-(2,6-dichlorophenyl)isoxazol-4-yl)methoxy)-1-hydroxy-cyclohexyl)quinoline-3-carbonitrile (9-22) was synthesized (the minor isomer was not isolated).

Example 9-23: 2-((1s,4s)-4-((5-Cyclopropyl-3-(2,6-dichlorophenyl)isoxazol-4-yl)methoxy)-1-hydroxy-cyclohexyl)quinoline-5-carbonitrile

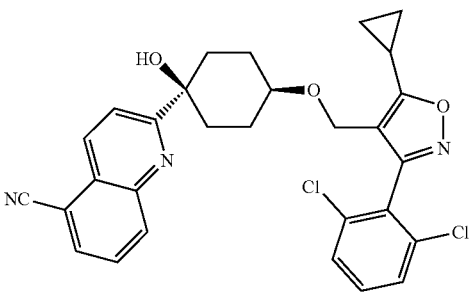

Int-4-4

Int-6-6

+

Example 9-23

Following general procedure 1C, beginning with intermediate 4-((5-cyclopropyl-3-(2,6-dichloro-phenyl)isoxazol-4-yl)methoxy)cyclohexanone Int-4-4 and 2-bromoquinoline-5-carbonitrile Int-6-6, the title compound 2-((1s,4s)-4-((5-cyclopropyl-3-(2,6-dichlorophenyl)isoxazol-4-yl)methoxy)-1-hydroxycyclohexyl)quinoline-5-carbonitrile (9-23) was synthesized (the minor isomer was not isolated).

Example 9-24: 6-((1s,4s)-4-((5-Cyclopropyl-3-(2,6-dichlorophenyl)isoxazol-4-yl)methoxy)-1-hydroxycyclohexyl)-1-isopropyl-1H-indazole-3-carbonitrile

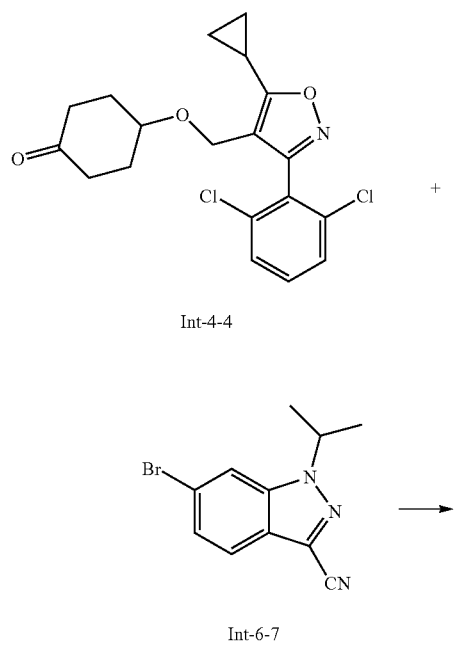

Int-4-4

Int-6-7

Example 9-24

Following general procedure 1C, beginning with intermediate 4-((5-cyclopropyl-3-(2,6-dichlorophenyl)isoxazol-4-yl)methoxy)cyclohexanone Int-4-4 and 6-bromo-1-isopropyl-1H-indazole-3-carbonitrile Int-6-7, the title compound 6-((1s,4s)-4-((5-cyclopropyl-3-(2,6-dichlorophenyl)isoxazol-4-yl)methoxy)-1-hydroxycyclohexyl)-1-isopropyl-1H-indazole-3-carbonitrile (9-24) was synthesized (the minor isomer was not isolated).

Example 9-25: 2-((3aR,6aS)-5-((5-Cyclopropyl-3-(2,6-dichlorophenyl)isoxazol-4-yl)methoxy)-2-hydroxyoctahydropentalen-2-yl)-4-fluorobenzo[d]thiazole-6-carbonitrile

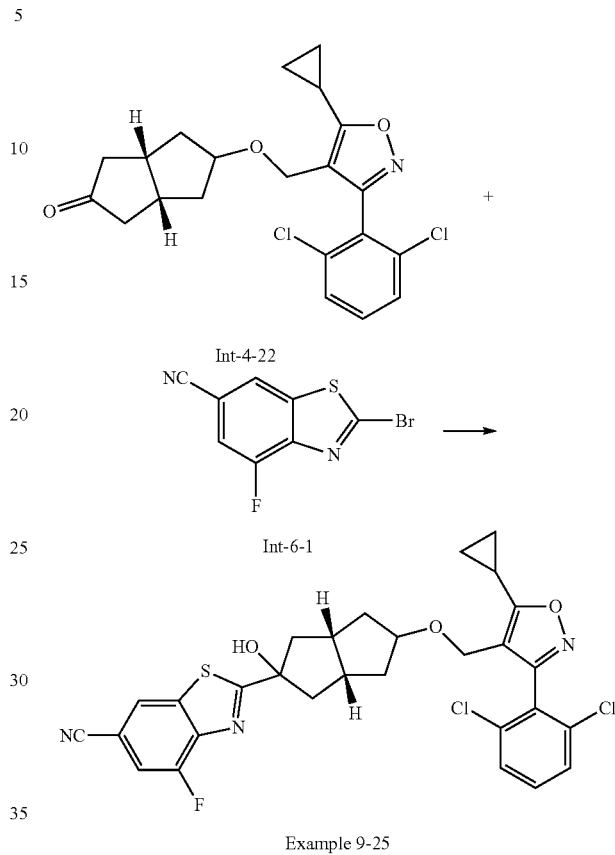

Int-4-22

Int-6-1

Example 9-25

Following general procedure 1C, beginning with intermediate (3aR,6aS)-5-((5-cyclopropyl-3-(2,6-dichlorophenyl)isoxazol-4-yl)methoxy)hexahydropentalen-2(1H)-one Int-4-22 and 2-bromo-4-fluorobenzo[d]thiazole-6-carbonitrile Int-6-1, the title compound 2-((3aR,6aS)-5-((5-cyclopropyl-3-(2,6-dichlorophenyl) isoxazol-4-yl) methoxy)-2-hydroxyoctahydropentalen-2-yl)-4-fluorobenzo[d]thiazole-6-carbonitrile (9-25) was synthesized (the minor isomer was not isolated).

Example 9-26: 4-((3aR,6aS)-5-((5-Cyclopropyl-3-(2,6-dichlorophenyl)isoxazol-4-yl)methoxy)-2-hydroxyoctahydropentalen-2-yl)-3-fluorobenzonitrile

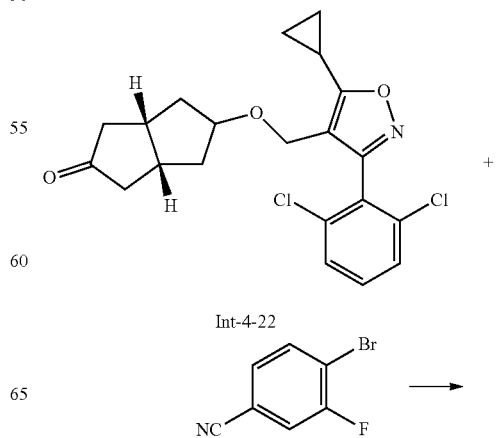

Int-4-22

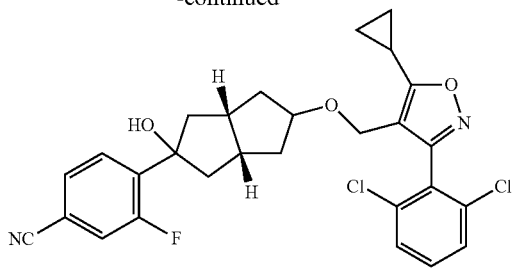

Example 9-26

Following general procedure 1C, beginning with intermediate (3aR,6aS)-5-((5-cyclopropyl-3-(2,6-dichlorophenyl)isoxazol-4-yl)methoxy)hexahydropentalen-2(1H)-one Int-4-22 and 4-bromo-3-fluorobenzonitrile, the title compound 4-((3aR,6aS)-5-((5-cyclopropyl-3-(2,6-dichlorophenyl)isoxazol-4-yl)methoxy)-2-hydroxyoctahydropentalen-2-yl)-3-fluorobenzonitrile (9-26) was synthesized (the minor isomer was not isolated).

Example 9-27 and Example 10-27: 2-((1R,2S,4R)-5-((5-Cyclopropyl-3-(2,6-dichloro-phenyl)isoxazol-4-yl)methoxy)-2-hydroxybicyclo[2.2.1]heptan-2-yl)-4-fluorobenzo[d]thiazole-6-carbonitrile Following general procedure 1C, beginning with (1R,4R)-5-((5-cyclopropyl-3-(2,6-dichloro-phenyl)isoxazol-4-yl)methoxy)bicyclo[2.2.1]heptan-2-one Int-4-23 and 4-bromo-3-fluorobenzonitrile, the title compounds 2-((1R,2S,4R)-5-((5-cyclopropyl-3-(2,6-dichlorophenyl)isoxazol-4-yl)methoxy)-2-hydroxybicyclo[2.2.1]heptan-2-yl)-4-fluorobenzo[d]thiazole-6-carbonitrile as major isomer 9-27 and minor isomer 10-27 were synthesized. The isomers were separated by prep-TLC (DCM/MeOH=20:1) in a ratio of approx. 10:1.

Example 9-28: Methyl 1-(3-((1R,3s,5S,8r)-3-((5-cyclopropyl-3-(2,6-dichlorophenyl)isoxazol-4-yl)methoxy)-8-hydroxybicyclo[3.2.1]octan-8-yl)-5-fluorophenoxy)cyclopropanecarboxylate

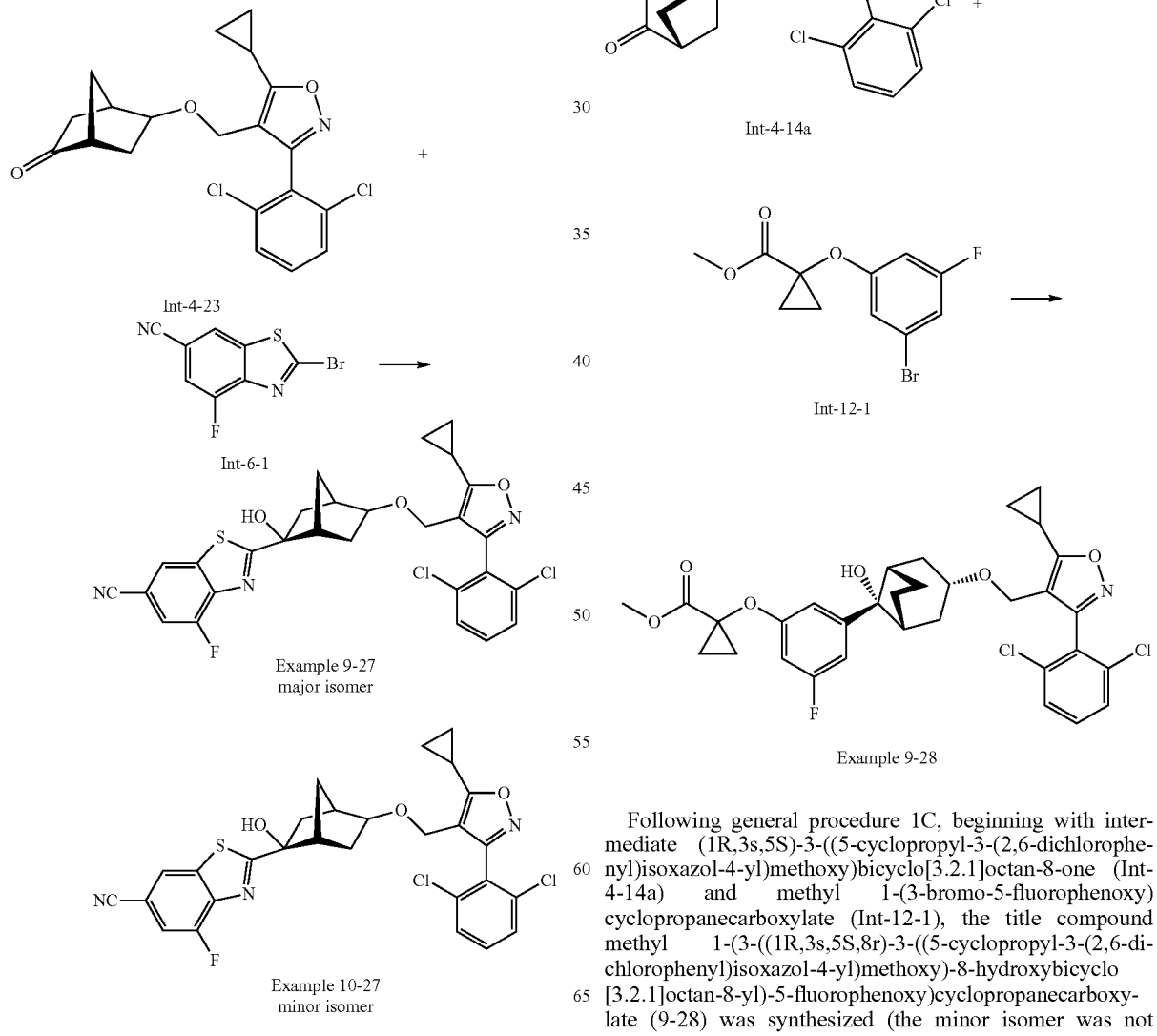

Example 9-27 major isomer

Example 10-27 minor isomer

Int-4-14a

Int-12-1

Example 9-28

Following general procedure 1C, beginning with intermediate (1R,3s,5S)-3-((5-cyclopropyl-3-(2,6-dichlorophenyl)isoxazol-4-yl)methoxy)bicyclo[3.2.1]octan-8-one (Int-4-14a) and methyl 1-(3-bromo-5-fluorophenoxy)cyclopropanecarboxylate (Int-12-1), the title compound methyl 1-(3-((1R,3s,5S,8r)-3-((5-cyclopropyl-3-(2,6-dichlorophenyl)isoxazol-4-yl)methoxy)-8-hydroxybicyclo[3.2.1]octan-8-yl)-5-fluorophenoxy)cyclopropanecarboxylate (9-28) was synthesized (the minor isomer was not isolated).

Example 9-29: 3-(3-((1R,3s,5S,8r)-3-((5-Cyclopropyl-3-(2,6-dichlorophenyl)isoxazol-4-yl)methoxy)-8-hydroxybicyclo[3.2.1]octan-8-yl)phenyl)-2,2-dimethylpropanenitrile

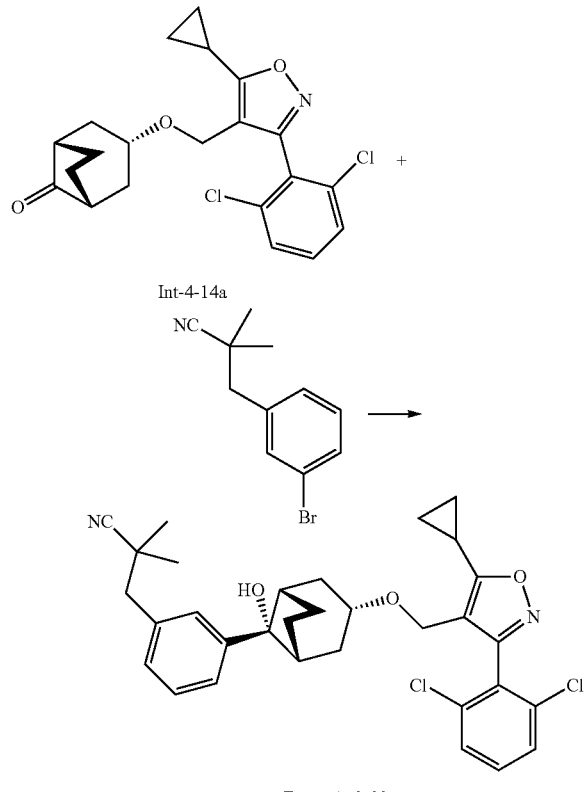

Example 9-29

Following general procedure 1C, beginning with intermediate (1R,3s,5S)-3-((5-cyclopropyl-3-(2,6-dichlorophenyl)isoxazol-4-yl)methoxy)bicyclo[3.2.1]octan-8-one (Int-4-14a) and 3-(3-bromophenyl)-2,2-dimethylpropanenitrile, the title compound 3-(3-((1R,3s,5S,8r)-3-((5-cyclopropyl-3-(2,6-dichlorophenyl)isoxazol-4-yl)methoxy)-8-hydroxybicyclo[3.2.1]octan-8-yl)phenyl)-2,2-dimethylpropanenitrile (9-29) was synthesized (the minor isomer was not isolated). LCMS (ESI): m/z 564.8 (M+1)$^+$.

Example 9-30: (1R,3s,5S,8r)-3-((5-Cyclopropyl-3-(2,6-dichlorophenyl)isoxazol-4-yl)methoxy)-8-(4-(2-hydroxyethyl)thiazol-2-yl)bicyclo[3.2.1]octan-8-ol

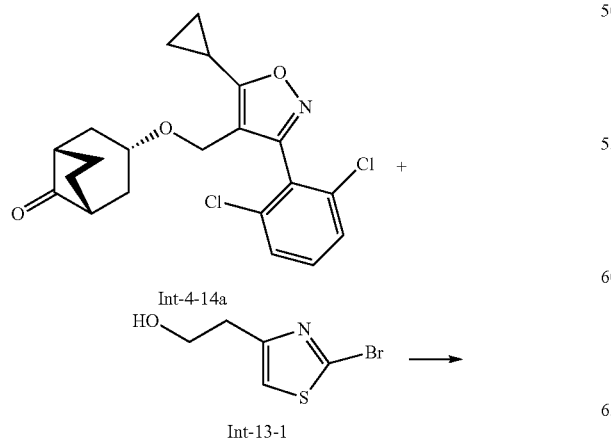

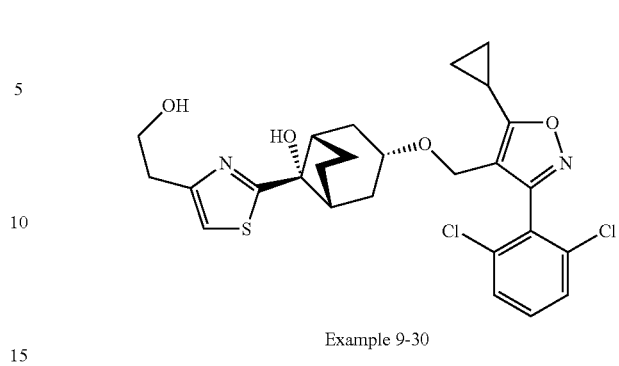

Example 9-30

Following general procedure 1C, beginning with intermediate (1R,3s,5S)-3-((5-cyclopropyl-3-(2,6-dichlorophenyl)isoxazol-4-yl)methoxy)bicyclo[3.2.1]octan-8-one (Int-4-14a) and 2-(2-bromothiazol-4-yl)ethanol (Int-13-1), the title compound (1R,3s,5S,8r)-3-((5-cyclopropyl-3-(2,6-dichloro-phenyl)isoxazol-4-yl)methoxy)-8-(4-(2-hydroxyethyl)thiazol-2-yl)bicyclo[3.2.1]octan-8-ol (9-30) was synthesized (the minor isomer was not isolated). $^1$H-NMR (500 MHz, DMSO-d$_6$): δ 7.65 (d, J=8.0 Hz, 2H), 7.59-7.56 (m, 1H), 7.20 (s, 1H), 5.89 (s, 1H), 4.61 (t, J=5.3 Hz, 1H), 4.26 (s, 2H), 3.68-3.64 (m, 2H), 3.48-3.42 (m, 1H), 2.79 (t, J=7.0 Hz, 2H), 2.37-2.33 (m, 1H), 2.24 (s, 2H), 1.80-1.76 (m, 2H), 1.63-1.52 (m, 4H), 1.34-1.29 (m, 2H), 1.17-1.09 (m, 4H). LCMS (ESI): m/z 635.1 (M+H)$^+$.

Example 9-31: 2-((1R,5S,9s)-7-((5-Cyclopropyl-3-(2,6-dichlorophenyl)isoxazol-4-yl)methoxy)-9-hydroxy-3-oxabicyclo[3.3.1]nonan-9-yl)-4-fluorobenzo[d]thiazole-6-carbonitrile

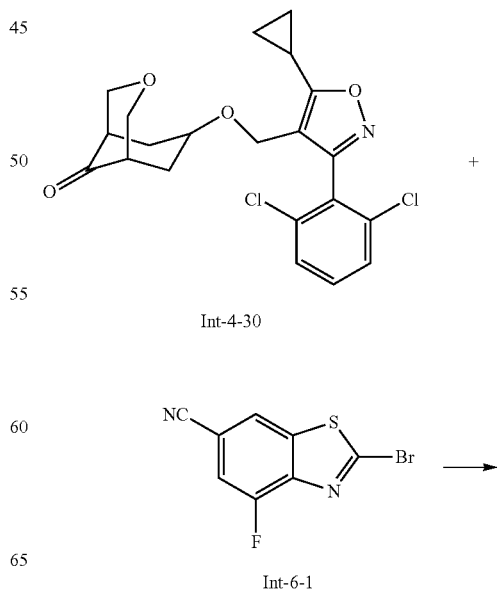

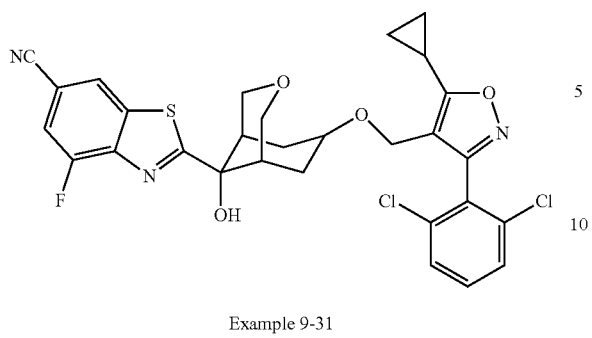

Example 9-31

Following general procedure 1C, beginning with (1R,5S)-7-((5-cyclopropyl-3-(2,6-dichloro-phenyl)isoxazol-4-yl)methoxy)-3-oxabicyclo[3.3.1]nonan-9-one Int-4-30 and 4-bromo-3-fluorobenzonitrile Int-6-1, the title compound 2-((1R,5S,9s)-7-((5-cyclopropyl-3-(2,6-dichlorophenyl)isoxazol-4-yl)methoxy)-9-hydroxy-3-oxabicyclo[3.3.1]nonan-9-yl)-4-fluorobenzo[d]thiazole-6-carbonitrile (9-31) was synthesized.

General Procedure 1D for the Synthesis of Example 11

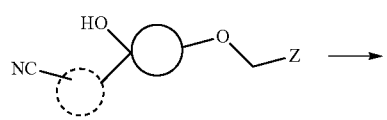

selected compounds from
Example 8 or
Example 9 or
Example 10

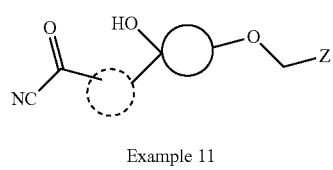

Example 11

◌ is a aromatic or heteroaromatic mono- or bicycle

◯ is a saturated mono-, bi- or spirocyclic alkyl

To a solution of the nitrile (1.0 eq.) in EtOH was added 40% aq. NaOH and the mixture was stirred at 85° C. for 2 h. The mixture was acidified by 4M HCl and extracted twice with EtOAc. The combined organic phases were washed with brine, dried over $Na_2SO_4$, evaporated and the residue was purified by prep-TLC or prep-HPLC to afford example 11.

Example 11-1: 2-((1s,4s)-4-((5-Cyclopropyl-3-(4,4-difluorocyclohexyl)isoxazol-4-yl)methoxy)-1-hydroxycyclohexyl)benzo[d]thiazole-6-carboxylic acid

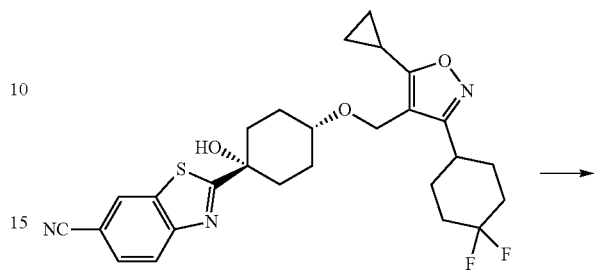

Example 8-1

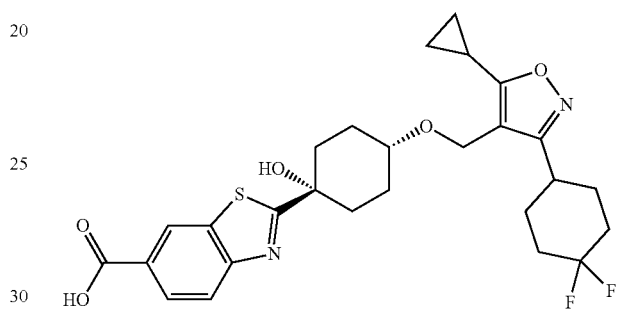

Example 11-1

Following general procedure 1D, beginning with example 2-((1s,4s)-4-((5-cyclopropyl-3-(4,4-di-fluorocyclohexyl)isoxazol-4-yl)methoxy)-1-hydroxycyclohexyl)benzo[d]thiazole-6-carbonitrile (8-1), the title compound 2-((1s,4s)-4-((5-cyclopropyl-3-(4,4-difluorocyclohexyl)isoxazol-4-yl)methoxy)-1-hydroxycyclohexyl)benzo[d]thiazole-6-carboxylic acid 11-1 was synthesized. $^1$H-NMR (500 MHz, DMSO-$d_6$): δ 13.10 (br s, 1H), 8.70 (d, J=1.5 Hz, 1H), 8.04-7.98 (m, 2H), 6.26 (br s, 1H), 4.50 (s, 2H), 3.54-3.50 (m, 1H), 2.93 (t, J=11.0 Hz, 1H), 2.23-2.19 (m, 1H), 2.12-1.94 (m, 12H), 1.73-1.66 (m, 4H), 1.07-0.96 (m, 4H). LCMS (ESI): m/z 533.2 (M+1)$^+$.

Example 11-2: 2-((1r,4r)-4-((5-Cyclopropyl-3-(4,4-difluorocyclohexyl)isoxazol-4-yl)methoxy)-1-hydroxycyclohexyl)benzo[d]thiazole-6-carboxylic acid

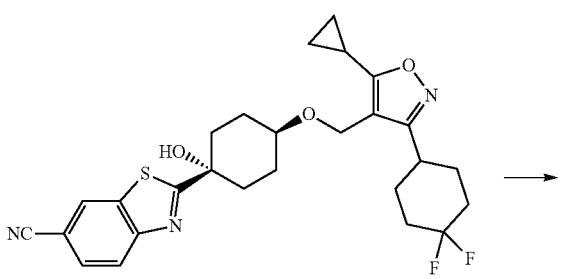

Example 8-2

-continued

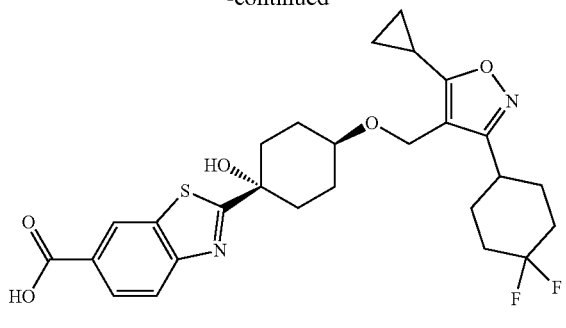

Example 11-2

Following general procedure 1D, beginning with example 2-((1r,4r)-4-((5-cyclopropyl-3-(4,4-di-fluorocyclohexyl)isoxazol-4-yl)methoxy)-1-hydroxycyclohexyl)benzo[d]thiazole-6-carbonitrile (8-2), the title compound 2-((1r,4r)-4-((5-cyclopropyl-3-(4,4-difluorocyclohexyl)isoxazol-4-yl)methoxy)-1-hydroxycyclohexyl)benzo[d]thiazole-6-carboxylic acid 11-2 was synthesized. $^1$H-NMR (500 MHz, DMSO-$d_6$): δ 13.10 (br s, 1H), 8.70 (d, J=1.5 Hz, 1H), 8.03-8.01 (m, 1H), 7.95 (d, J=9.0 Hz, 1H), 6.26 (br s, 1H), 4.41 (s, 2H), 3.74 (s, 1H), 2.98 (t, J=10.8 Hz, 1H), 2.22-2.13 (m, 3H), 2.11-1.88 (m, 10H), 1.78-1.65 (m, 4H), 1.08-0.97 (m, 4H). LCMS (ESI): m/z 533.2 (M+1)$^+$.

Example 11-3: 2-((1s,4s)-4-((5-Cyclopropyl-3-(spiro[2.5]octan-6-yl)isoxazol-4-yl)methoxy)-1-hydroxycyclohexyl)benzo[d]thiazole-6-carboxylic acid

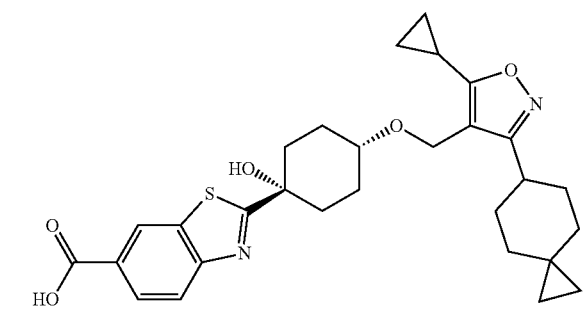

Example 11-3

Following general procedure 1D, beginning with example 2-((1s,4s)-4-((5-cyclopropyl-3-(spiro[2.5]octan-6-yl)isoxazol-4-yl)methoxy)-1-hydroxycyclohexyl)benzo[d]thiazole-6-carbonitrile (9-1), the title compound 2-((1s,4s)-4-((5-cyclopropyl-3-(spiro[2.5]octan-6-yl)isoxazol-4-yl)methoxy)-1-hydroxycyclohexyl)benzo[d]thiazole-6-carboxylic acid 11-3 was synthesized. $^1$H-NMR (500 MHz, DMSO-$d_6$): δ 13.06 (br s, 1H), 8.70 (d, J=1.0 Hz, 1H), 8.04-7.98 (m, 2H), 6.27 (br s, 1H), 4.44 (s, 2H), 3.53-3.49 (m, 1H), 2.76-2.72 (m, 1H), 2.20-2.19 (m, 1H), 2.02-1.88 (m, 8H), 1.79-1.62 (m, 6H), 1.06-0.97 (m, 6H), 0.31-0.22 (m, 4H). LCMS (ESI): m/z 523.2 (M+1)$^+$.

Example 11-4a: 2-(6-((5-Cyclopropyl-3-(2,6-dichlorophenyl)isoxazol-4-yl)methoxy)-2-hydroxyspiro[3.3]heptan-2-yl)benzo[d]thiazole-6-carboxylic acid

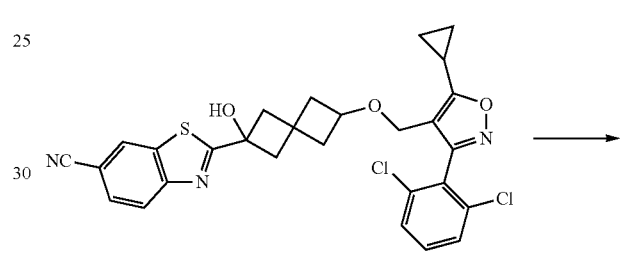

Example 9-2a
(first eluting isomer)

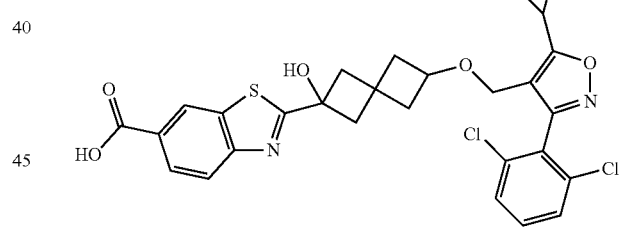

Example 11-4a

Following general procedure 1D, beginning with the first eluting isomer example 2-(6-((5-cyclopropyl-3-(2,6-dichlorophenyl)isoxazol-4-yl)methoxy)-2-hydroxyspiro[3.3]heptan-2-yl)benzo[d]thiazole-6-carbonitrile (9-2a), the title compound 2-(6-((5-cyclopropyl-3-(2,6-dichlorophenyl)isoxazol-4-yl)methoxy)-2-hydroxyspiro[3.3]heptan-2-yl)benzo[d]thiazole-6-carboxylic acid 11-4a was synthesized. $^1$H-NMR (500 MHz, DMSO-$d_6$): δ 13.10 (br s, 1H), 8.67 (s, 1H), 8.04-8.00 (m, 2H), 7.66-7.63 (m, 2H), 7.55 (t, J=8.0 Hz, 1H), 6.66 (s, 1H), 4.13-4.08 (m, 2H), 3.78-3.75 (m, 1H), 2.69-2.57 (m, 2H), 2.36-2.23 (m, 5H), 1.73-1.62 (m, 2H), 1.17-1.09 (m, 4H). LCMS (ESI): m/z 571.1 (M+H)$^+$. Chiral HPLC (OZ—H 4.6×250 mm column 5 μm; Eluent: CO$_2$/MeOH 65:35, (0.5% NH$_4$OH); flow: 1.95 mL/minute; w=214 to 359 nm; T=39.9° C.): retention time 11.02 min.

Example 11-4b: 2-(6-((5-Cyclopropyl-3-(2,6-dichlorophenyl)isoxazol-4-yl)methoxy)-2-hydroxyspiro[3.3]heptan-2-yl)benzo[d]thiazole-6-carboxylic acid

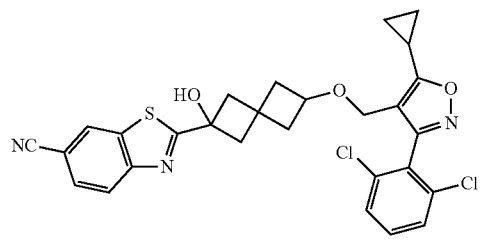

Example 9-2b
(second eluting isomer)

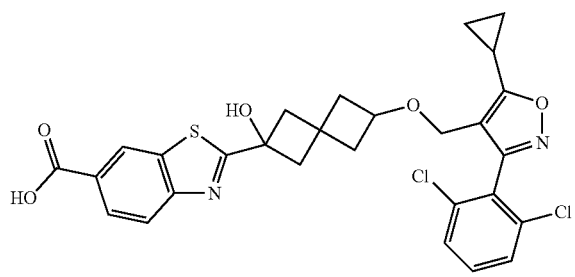

Example 11-4b

Following general procedure 1D, beginning with the second eluting isomer example 2-(6-((5-cyclopropyl-3-(2,6-dichlorophenyl)isoxazol-4-yl)methoxy)-2-hydroxyspiro[3.3]heptan-2-yl)benzo[d]thiazole-6-carbonitrile (9-2b), the title compound 2-(6-((5-cyclopropyl-3-(2,6-dichlorophenyl)isoxazol-4-yl)methoxy)-2-hydroxyspiro[3.3]heptan-2-yl)benzo[d]thiazole-6-carboxylic acid 11-4b was synthesized. $^1$H-NMR (500 MHz, DMSO-$d_6$): δ 13.10 (br s, 1H), 8.67 (s, 1H), 8.04-8.00 (m, 2H), 7.66-7.63 (m, 2H), 7.55 (t, J=8.0 Hz, 1H), 6.66 (s, 1H), 4.13-4.08 (m, 2H), 3.78-3.75 (m, 1H), 2.69-2.57 (m, 2H), 2.36-2.23 (m, 5H), 1.73-1.62 (m, 2H), 1.17-1.09 (m, 4H). LCMS (ESI): m/z 571.1 (M+H)$^+$. Chiral HPLC (OZ—H 4.6×250 mm column 5 μm; Eluent: CO$_2$/MeOH 65:35, (0.5% NH$_4$OH); flow: 1.95 mL/minute; w=214 to 359 nm; T=39.9° C.): retention time 9.56 min.

Example 11-5: 4-((1s,4s)-4-((5-Cyclopropyl-3-(2,6-dichlorophenyl)isoxazol-4-yl)methoxy)-1-hydroxycyclohexyl)-3-fluorobenzoic acid

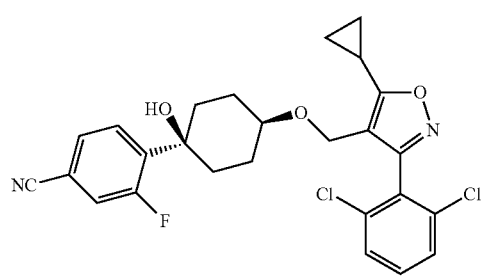

Example 9-3

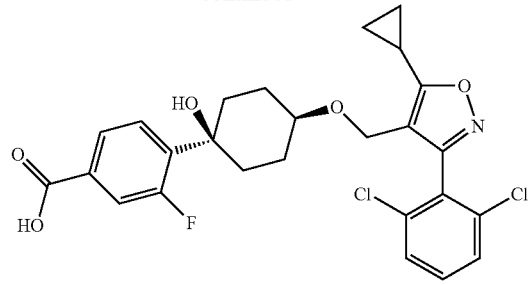

Example 11-5

Following general procedure 1D, beginning with example 4-((1s,4s)-4-((5-cyclopropyl-3-(2,6-dichlorophenyl)isoxazol-4-yl)methoxy)-1-hydroxycyclohexyl)-3-fluorobenzonitrile (9-3), the title compound 4-((1s,4s)-4-((5-cyclopropyl-3-(2,6-dichlorophenyl)isoxazol-4-yl)methoxy)-1-hydroxy-cyclohexyl)-3-fluorobenzoic acid 11-5 was synthesized. $^1$H-NMR (500 MHz, DMSO-$d_6$): δ 13.16 (br s, 1H), 7.74-7.53 (m, 6H), 5.27 (br s, 1H), 4.31 (s, 2H), 3.19-3.15 (m, 1H), 2.38-2.33 (m, 1H), 1.92-1.86 (m, 2H), 1.57-1.45 (m, 6H), 1.18-1.10 (m, 4H). LCMS (ESI): m/z 520.1 (M+H)$^+$ Example 11-6: 2-((1s,4s)-4-((5-Cyclopropyl-3-(2,6-dichlorophenyl)isoxazol-4-yl)methoxy)-1-hydroxycyclohexyl)isonicotinic acid

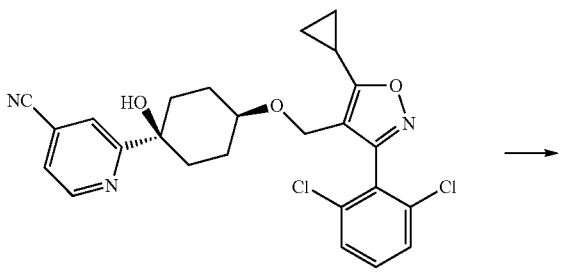

Example 9-4

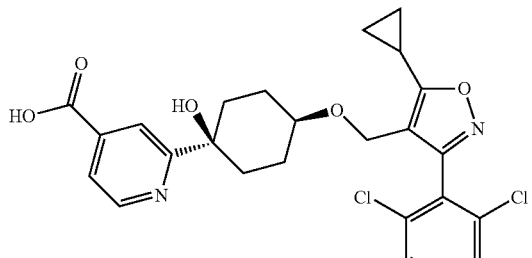

Example 11-6

Following general procedure 1D, beginning with example 2-((1s,4s)-4-((5-cyclopropyl-3-(2,6-dichlorophenyl)isoxazol-4-yl)methoxy)-1-hydroxycyclohexyl)isonicotinonitrile (9-4), the title compound 2-((1s,4s)-4-((5-cyclopropyl-3-(2,6-dichlorophenyl)isoxazol-4-yl)methoxy)-1-hydroxy-cyclohexyl)isonicotinic acid 11-6 was synthesized. $^1$H-NMR (500 MHz, DMSO-$d_6$): δ 13.60 (br s, 1H), 8.55 (dd, J=5.0, J=0.5 Hz, 1H), 8.11 (s, 1H), 7.66-7.57 (m, 4H), 5.15 (br s, 1H), 4.31 (s, 2H), 3.19-3.15 (m, 1H), 2.35-2.33 (m, 1H), 1.89-1.83 (m, 2H), 1.62-1.40 (m, 6H), 1.16-1.11 (m, 4H). LCMS (ESI): m/z 503.0 (M+H)+.

Example 11-7: 2-((1s,4s)-4-((5-Cyclopropyl-3-(2-(difluoromethoxy)phenyl)isoxazol-4-yl)methoxy)-1-hydroxycyclohexyl)-4-fluorobenzo[d]thiazole-6-carboxylic acid

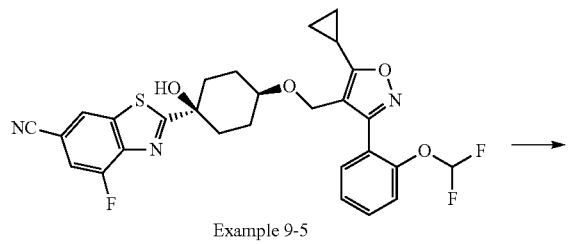

Example 9-5

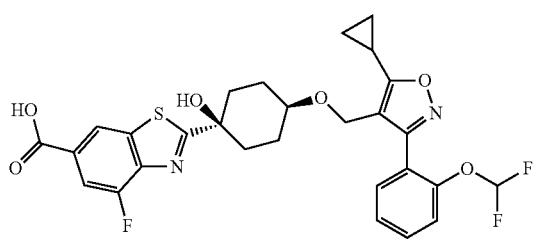

Example 11-7

Following general procedure 1D, beginning with example 2-((1s,4s)-4-((5-cyclopropyl-3-(2-(difluoromethoxy)phenyl)isoxazol-4-yl)methoxy)-1-hydroxycyclohexyl)-4-fluorobenzo[d]thiazole-6-carbonitrile (9-5), the title compound 2-((1s,4s)-4-((5-cyclopropyl-3-(2-(difluoro-methoxy)phenyl)isoxazol-4-yl)methoxy)-1-hydroxycyclohexyl)-4-fluorobenzo[d]thiazole-6-carboxylic acid 11-7 was synthesized. $^1$H-NMR (500 MHz, DMSO-$d_6$): δ 13.36 (br s, 1H), 8.55 (d, J=1.0 Hz, 1H), 7.77-7.74 (m, 1H), 7.62-7.54 (m 2H), 7.40-7.09 (m, 3H), 6.33 (br s, 1H), 4.37 (s, 2H), 3.35-3.30 (m, 1H), 2.35-2.30 (m, 1H), 1.94-1.71 (m, 6H), 1.54-1.47 (m, 2H), 1.14-1.09 (m, 4H). LCMS (ESI): m/z 575.1 (M+H)+.

Example 11-8: 2-(4-((1s,4s)-4-((5-Cyclopropyl-3-(2,6-dichlorophenyl)isoxazol-4-yl)methoxy)-1-hydroxycyclohexyl)-3-fluorophenyl)acetic acid

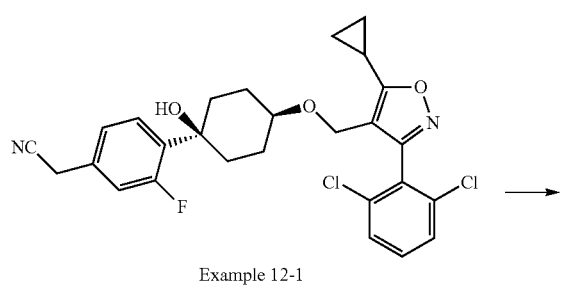

Example 12-1

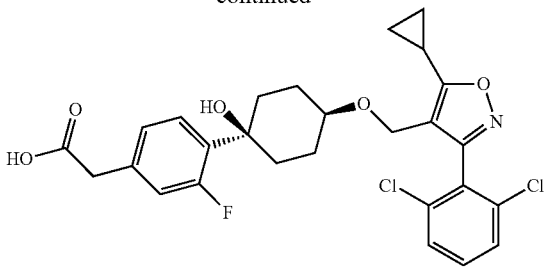

Example 11-8

Following general procedure 1D, beginning with example 2-(4-((1s,4s)-4-((5-cyclopropyl-3-(2,6-dichlorophenyl)isoxazol-4-yl)methoxy)-1-hydroxycyclohexyl)-3-fluorophenyl)acetonitrile 12-1, the title compound 2-(4-((1s,4s)-4-((5-cyclopropyl-3-(2,6-dichlorophenyl)isoxazol-4-yl)methoxy)-1-hydroxycyclohexyl)-3-fluorophenyl)acetic acid 11-8 was synthesized. $^1$H-NMR (500 MHz, DMSO-$d_6$): δ 7.65-7.45 (m, 4H), 6.99-6.93 (m, 2H), 4.93 (br s, 1H), 4.30 (s, 2H), 3.43 (s, 2H), 3.17-3.13 (m, 1H), 2.36-2.33 (m, 1H), 1.88-1.83 (m, 2H), 1.54-1.45 (m, 6H), 1.17-1.09 (m, 4H), CO$_2$H proton not resolved. LC/MS (ESI): m/z 533.7 (M+H)+.

Example 11-9: 2-(3-((1s,4s)-4-((5-Cyclopropyl-3-(2,6-dichlorophenyl)isoxazol-4-yl)methoxy)-1-hydroxycyclohexyl)-4-fluorophenyl)acetic acid

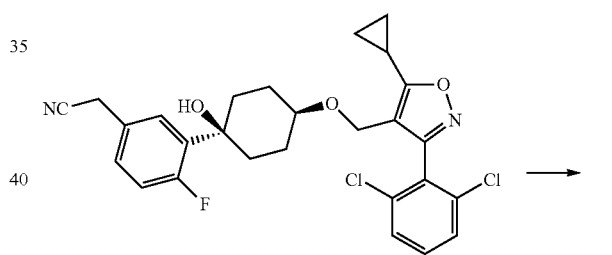

Example 12-2

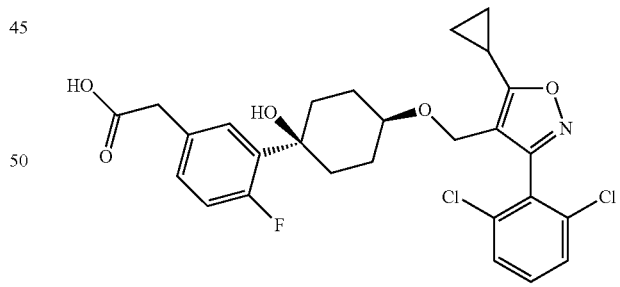

Example 11-9

Following general procedure 1D, beginning with example 2-(3-((1s,4s)-4-((5-cyclopropyl-3-(2,6-dichlorophenyl)isoxazol-4-yl)methoxy)-1-hydroxycyclohexyl)-4-fluorophenyl)acetonitrile 12-2, the title compound 2-(3-((1s,4s)-4-((5-cyclopropyl-3-(2,6-dichlorophenyl)isoxazol-4-yl)methoxy)-1-hydroxycyclohexyl)-4-fluorophenyl)acetic acid 11-9 was synthesized. $^1$H-NMR (500 MHz, DMSO-$d_6$): δ 7.44-7.41 (m, 3H), 7.34-7.31 (m, 1H), 7.10-7.09 (m, 1H), 6.96-6.92 (m, 1H), 4.35 (s, 2H), 3.55 (s, 2H), 3.28-3.24 (m, 1H), 2.23-2.16 (m, 1H), 2.02-1.97 (m, 2H), 1.71-1.69 (m, 4H), 1.63-1.59 (m, 2H), 1.29-1.26 (m, 2H), 1.14-1.10 (m, 2H), CO₂H and hydroxyl proton not resolved. LC/MS (ESI): m/z 534.0 (M+H)⁺.

Example 11-10: 2-((1s,4s)-4-((5-Cyclopropyl-3-(2-(difluoromethoxy)phenyl)isoxazol-4-yl)methoxy)-1-hydroxycyclohexyl)benzo[d]thiazole-6-carboxylic acid

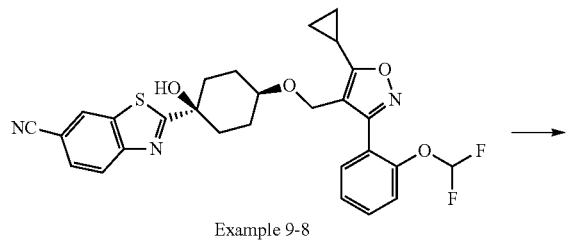

Example 9-8

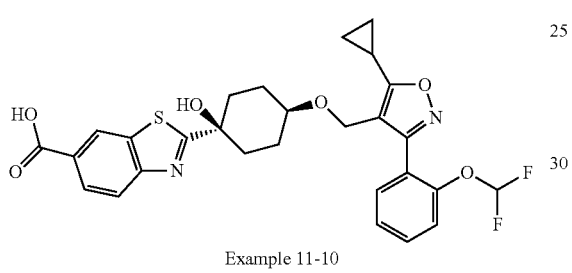

Example 11-10

Following general procedure 1D, beginning with example 2-((1s,4s)-4-((5-cyclopropyl-3-(2-(difluoromethoxy)phenyl)isoxazol-4-yl)methoxy)-1-hydroxycyclohexyl)benzo[d]thiazole-6-carbonitrile (9-8), the title compound 2-((1s,4s)-4-((5-cyclopropyl-3-(2-(difluoromethoxy)phenyl)isoxazol-4-yl)methoxy)-1-hydroxycyclohexyl)benzo[d]thiazole-6-carboxylic acid 11-10 was synthesized. ¹H-NMR (500 MHz, DMSO-d₆): δ 13.04 (br s, 1H), 8.68 (d, J=1.5 Hz, 1H), 8.03-7.97 (m, 2H), 7.63-7.54 (m, 2H), 7.41-7.09 (m, 3H), 6.25 (br s, 1H), 4.38 (s, 2H), 3.33-3.28 (m, 1H), 2.35-2.31 (m, 1H), 1.94-1.48 (m, 8H), 1.15-1.09 (m, 4H). LCMS (ESI): m/z 557.0 (M+H)⁺.

Example 11-11: 2-((1s,4s)-4-((5-Cyclopropyl-3-(2-cyclopropylphenyl)isoxazol-4-yl)methoxy)-1-hydroxycyclohexyl)benzo[d]thiazole-6-carboxylic acid

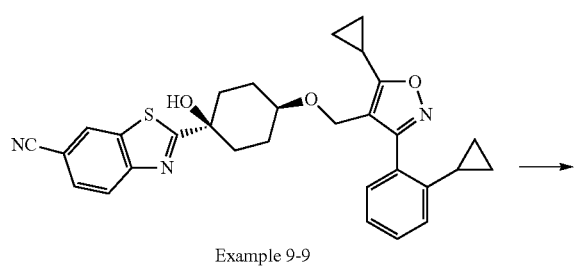

Example 9-9

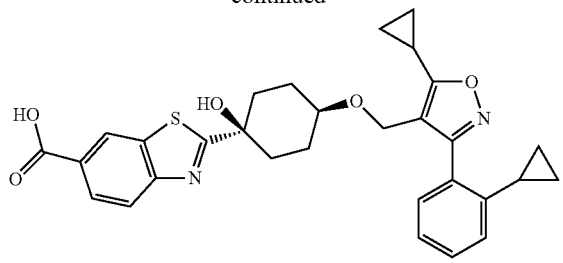

Example 11-11

Following general procedure 1D, beginning with example 2-((1s,4s)-4-((5-cyclopropyl-3-(2-cyclopropylphenyl)isoxazol-4-yl)methoxy)-1-hydroxycyclohexyl)benzo[d]thiazole-6-carbonitrile (9-9), the title compound 2-((1s,4s)-4-((5-cyclopropyl-3-(2-cyclopropylphenyl)isoxazol-4-yl)methoxy)-1-hydroxycyclohexyl)benzo[d]thiazole-6-carboxylic acid 11-11 was synthesized. ¹H-NMR (500 MHz, DMSO-d₆): δ 13.10 (br s, 1H), 8.68 (d, J=1.0 Hz, 1H), 8.03-7.97 (m, 2H), 7.41-7.38 (m, 1H), 7.30-7.24 (m, 2H), 6.98 (d, J=8.0 Hz, 1H), 6.21 (br s, 1H), 4.32 (s, 2H), 3.32-3.26 (m, 1H), 2.35-2.30 (m, 1H), 1.90-1.69 (m, 7H), 1.58-1.50 (m, 2H), 1.15-1.09 (m, 4H), 0.88-0.87 (m, 2H), 0.71-0.69 (m, 2H). LCMS (ESI): m/z 531.1 (M+H)⁺.

Example 11-12: 2-((1s,4s)-4-((5-Cyclopropyl-3-(2,6-dimethylphenyl)isoxazol-4-yl)methoxy)-1-hydroxycyclohexyl)benzo[d]thiazole-6-carboxylic acid

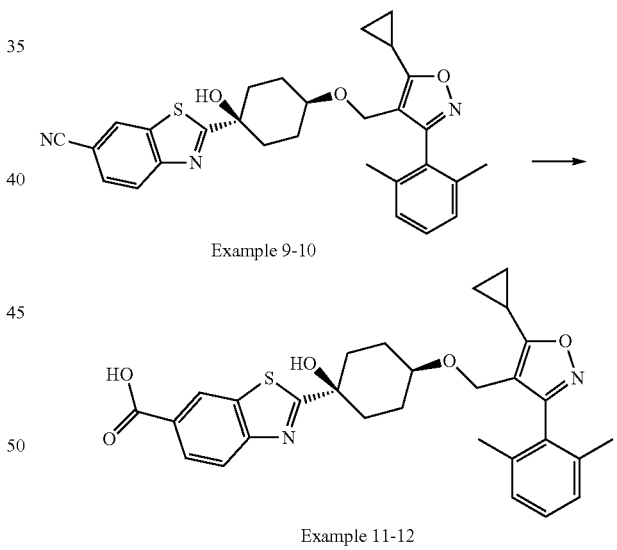

Example 9-10

Example 11-12

Following general procedure 1D, beginning with example 2-((1s,4s)-4-((5-cyclopropyl-3-(2,6-dimethylphenyl)isoxazol-4-yl)methoxy)-1-hydroxycyclohexyl)benzo[d]thiazole-6-carbonitrile (9-10), the title compound 2-((1s,4s)-4-((5-cyclopropyl-3-(2,6-dimethylphenyl)isoxazol-4-yl)methoxy)-1-hydroxycyclohexyl)benzo[d]thiazole-6-carboxylic acid 11-12 was synthesized. ¹H-NMR (500 MHz, DMSO-d₆): δ 13.12 (br s, 1H), 8.69 (s, 1H), 8.03-7.97 (m, 2H), 7.29 (t, J=7.5 Hz, 1H), 7.17-7.16 (m, 2H), 6.15 (br s, 1H), 4.15 (s, 2H), 3.27-3.19 (m, 1H), 2.35-2.32 (m, 1H), 2.05 (s, 6H), 1.94-1.69 (m, 6H), 1.54-1.48 (m, 2H), 1.18-1.08 (m, 4H). LCMS (ESI): m/z 519.1 (M+H)⁺.

Example 11-13: 2-((1s,4s)-4-((4-Cyclopropyl-1-(2,6-dichlorophenyl)-1H-pyrazol-5-yl)methoxy)-1-hydroxycyclohexyl)benzo[d]thiazole-6-carboxylic acid

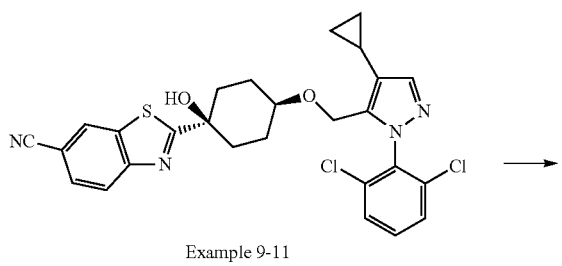

Example 9-11

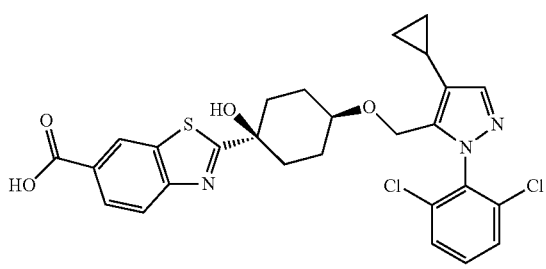

Example 11-13

Following general procedure 1D, beginning with example 2-((1s,4s)-4-((4-cyclopropyl-1-(2,6-dichlorophenyl)-1H-pyrazol-5-yl)methoxy)-1-hydroxycyclohexyl)benzo[d]thiazole-6-carbonitrile (9-11), the title compound 2-((1s,4s)-4-((4-cyclopropyl-1-(2,6-dichlorophenyl)-1H-pyrazol-5-yl)methoxy)-1-hydroxycyclohexyl)benzo[d]thiazole-6-carboxylic acid 11-13 was synthesized. $^1$H-NMR (500 MHz, DMSO-$d_6$): δ 13.09 (s, 1H), 8.68 (d, J=1.5 Hz, 1H), 8.02-7.96 (m, 2H), 7.70 (d, J=8.0 Hz, 2H), 7.62-7.58 (m, 1H), 7.44 (s, 1H), 6.21 (s, 1H), 4.43 (s, 2H), 3.23-3.21 (m, 1H), 1.89-1.79 (m, 5H), 1.71-1.69 (m, 2H), 1.46-1.41 (m, 2H), 0.93-0.89 (m, 2H), 0.65-0.62 (m, 2H). LCMS (ESI): m/z 558.0 (M+1)$^+$.

Example 11-14: 2-((1s,4s)-4-((5-Cyclopropyl-3-(2-(trifluoromethoxy)phenyl)isoxazol-4-yl)methoxy)-1-hydroxycyclohexyl)benzo[d]thiazole-6-carboxylic acid

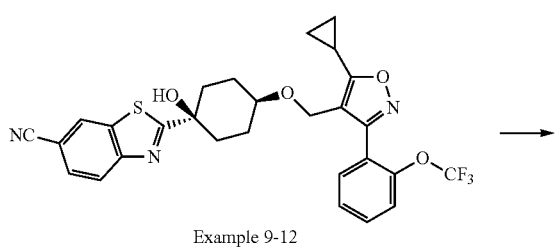

Example 9-12

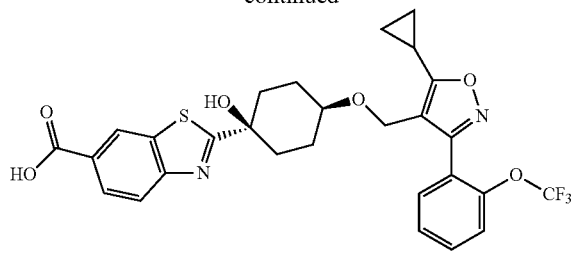

Example 11-14

Following general procedure 1D, beginning with example 2-((1s,4s)-4-((5-cyclopropyl-3-(2-(trifluoromethoxy)phenyl)isoxazol-4-yl)methoxy)-1-hydroxycyclohexyl)benzo[d]thiazole-6-carbonitrile (9-12), the title compound 2-((1s,4s)-4-((5-cyclopropyl-3-(2-(trifluoromethoxy)phenyl)isoxazol-4-yl)methoxy)-1-hydroxycyclohexyl)benzo[d]thiazole-6-carboxylic acid 11-14 was synthesized. $^1$H-NMR (500 MHz, DMSO-$d_6$): δ 13.07 (br s, 1H), 8.68 (d, J=1.0 Hz, 1H), 8.03-7.97 (m, 2H), 7.70-7.66 (m, 2H), 7.58-7.55 (m, 2H), 6.20 (br s, 1H), 4.37 (s, 2H), 3.35-3.31 (m, 1H), 2.36-2.33 (m, 1H), 1.95-1.73 (m, 6H), 1.57-1.49 (m, 2H), 1.16-1.09 (m, 4H). LCMS (ESI): m/z 575.0 (M+1)$^+$.

Example 11-15: 2-((1s,4s)-4-((5-Cyclopropyl-3-(2-(difluoromethyl)phenyl)isoxazol-4-yl)methoxy)-1-hydroxycyclohexyl)benzo[d]thiazole-6-carboxylic acid

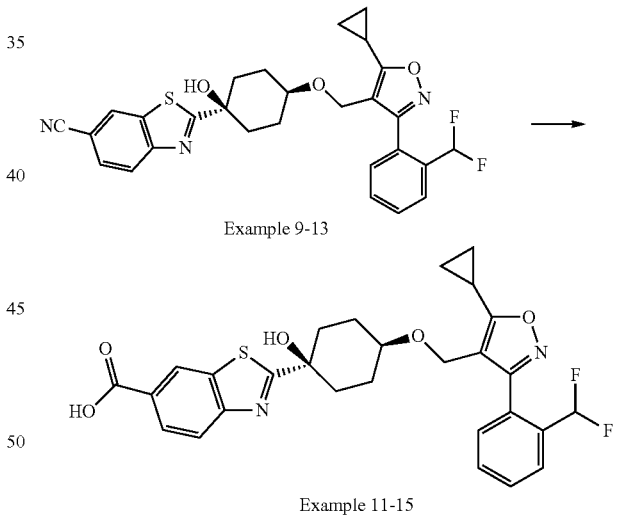

Example 9-13

Example 11-15

Following general procedure 1D, beginning with example 2-((1s,4s)-4-((5-cyclopropyl-3-(2-(difluoromethyl)phenyl)isoxazol-4-yl)methoxy)-1-hydroxycyclohexyl)benzo[d]thiazole-6-carbonitrile (9-13), the title compound 2-((1s,4s)-4-((5-cyclopropyl-3-(2-(difluoromethyl)phenyl)isoxazol-4-yl)methoxy)-1-hydroxycyclohexyl)benzo[d]thiazole-6-carboxylic acid 11-15 was synthesized. $^1$H-NMR (500 MHz, DMSO-$d_6$): δ 8.69 (d, J=1.5 Hz, 1H), 8.03-7.97 (m, 2H), 7.84-7.82 (m, 1H), 7.74-7.65 (m, 3H), 6.97 (t, J=54.8 Hz, 1H), 4.33 (s, 2H), 3.40-3.37 (m, 1H), 2.36-2.35 (m, 1H), 1.98-1.79 (m, 6H), 1.62-1.55 (m, 2H), 1.17-1.12 (m, 4H), $CO_2H$ and hydroxyl proton not resolved. LCMS (ESI): m/z 541.0 (M+1)$^+$.

Example 11-16: 2-((1s,4s)-4-((5-Cyclopropyl-3-(3,5-dichloropyridin-4-yl)isoxazol-4-yl)methoxy)-1-hydroxycyclohexyl)benzo[d]thiazole-6-carboxylic acid

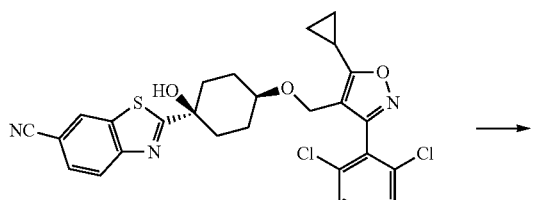

Example 9-14

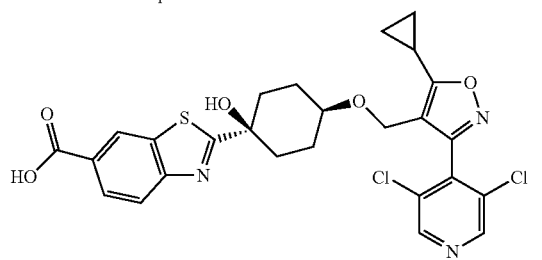

Example 11-16

Following general procedure 1D, beginning with example 2-((1s,4s)-4-((5-cyclopropyl-3-(3,5-dichloropyridin-4-yl)isoxazol-4-yl)methoxy)-1-hydroxycyclohexyl)benzo[d]thiazole-6-carbonitrile (9-14), the title compound 2-((1s,4s)-4-((5-cyclopropyl-3-(3,5-dichloropyridin-4-yl)isoxazol-4-yl)methoxy)-1-hydroxycyclohexyl)benzo[d]thiazole-6-carboxylic acid 11-16 was synthesized. $^1$H-NMR (500 MHz, DMSO-$d_6$): δ 13.12 (br s, 1H), 8.86 (s, 2H), 8.69 (d, J=1.0 Hz, 1H), 8.03-7.97 (m, 2H), 6.16 (br s, 1H), 4.39 (s, 2H), 3.28-3.26 (m, 1H), 2.40-2.36 (m, 1H), 1.92-1.79 (m, 4H), 1.68-1.66 (m, 2H), 1.45-1.38 (m, 2H), 1.20-1.11 (m, 4H). LCMS (ESI): m/z 560.0 (M+1)$^+$.

Example 11-17: 2-((1s,4s)-4-((4-Cyclopropyl-1-(2-(difluoromethoxy)phenyl)-1H-pyrazol-5-yl)methoxy)-1-hydroxycyclohexyl)benzo[d]thiazole-6-carboxylic acid

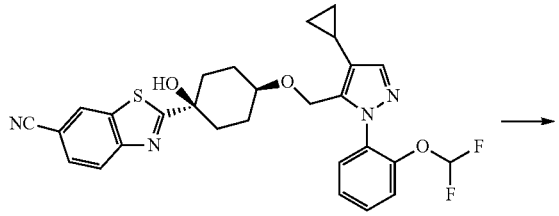

Example 9-15

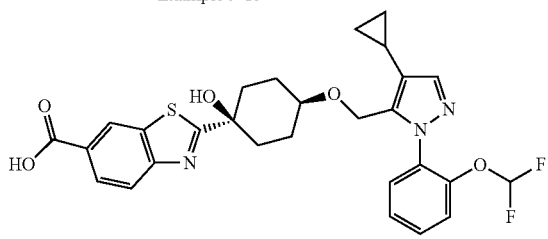

Example 11-17

Following general procedure 1D, beginning with example 2-((1s,4s)-4-((4-cyclopropyl-1-(2-(difluoromethoxy)phenyl)-1H-pyrazol-5-yl)methoxy)-1-hydroxycyclohexyl)benzo[d]thiazole-6-carbonitrile (9-15), the title compound 2-((1s,4s)-4-((4-cyclopropyl-1-(2-(difluoromethoxy)phenyl)-1H-pyrazol-5-yl)methoxy)-1-hydroxycyclohexyl)benzo[d]thiazole-6-carboxylic acid 11-17 was synthesized. $^1$H-NMR (500 MHz, DMSO-$d_6$): δ 13.16 (br s, 1H), 8.68 (d, J=1.0 Hz, 1H), 8.03-7.97 (m, 2H), 7.61-7.57 (m, 1H), 7.53-7.51 (m, 1H), 7.43-7.38 (m, 3H), 7.12 (t, J=73.8 Hz, 1H), 6.22 (br s, 1H), 4.46 (s, 2H), 3.26-3.23 (m, 1H), 1.91-1.78 (m, 5H), 1.70-1.68 (m, 2H), 1.51-1.46 (m, 2H), 0.91-0.89 (m, 2H), 0.63-0.62 (m, 2H). LCMS (ESI): m/z 556.1 (M+1)$^+$.

Example 11-18: 2-((1s,4s)-4-((3-(2,6-Bis(difluoromethyl)phenyl)-5-cyclopropylisoxazol-4-yl)methoxy)-1-hydroxycyclohexyl)benzo[d]thiazole-6-carboxylic acid

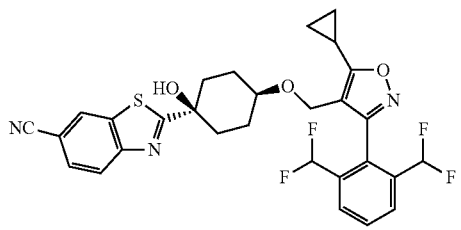

Example 9-16

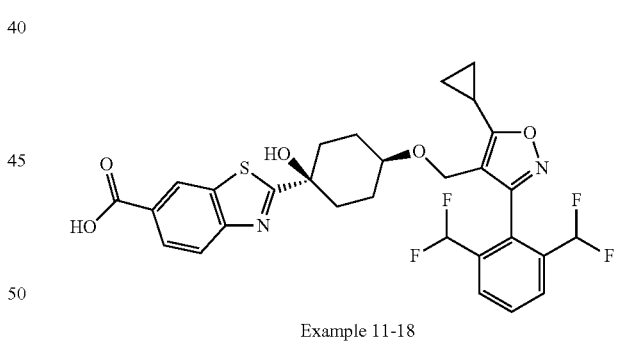

Example 11-18

Following general procedure 1D, beginning with example 2-((1s,4s)-4-((3-(2,6-bis(di-fluoromethyl)phenyl)-5-cyclopropylisoxazol-4-yl)methoxy)-1-hydroxycyclohexyl)benzo[d]thiazole-6-carbonitrile (9-16), the title compound 2-((1s,4s)-4-((3-(2,6-bis(difluoromethyl)phenyl)-5-cyclopropylisoxazol-4-yl)methoxy)-1-hydroxycyclohexyl)benzo[d]thiazole-6-carboxylic acid 11-18 was synthesized. $^1$H-NMR (500 MHz, DMSO-$d_6$): δ 13.11 (br s, 1H), 8.68 (d, J=1.5 Hz, 1H), 8.02-7.89 (m, 5H), 6.70 (t, J=54.0 Hz, 2H), 6.15 (br s, 1H), 4.23 (s, 2H), 3.28-3.24 (m, 1H), 2.37-2.32 (m, 1H), 1.92-1.64 (m, 6H), 1.45-1.37 (m, 2H), 1.20-1.13 (m, 4H). LCMS (ESI): m/z 591.2 (M+1)$^+$.

Example 11-19: 2-((1s,4s)-4-((5-Cyclopropyl-3-(2-(difluoromethoxy)phenyl)isoxazol-4-yl)methoxy)-1-hydroxycyclohexyl)-5-fluorobenzo[d]thiazole-6-carboxylic acid

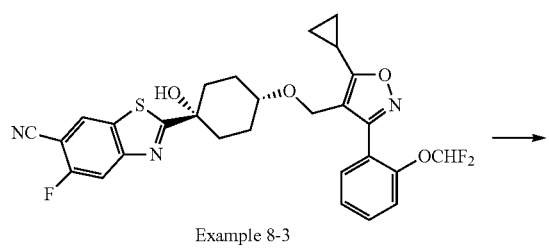

Example 8-3

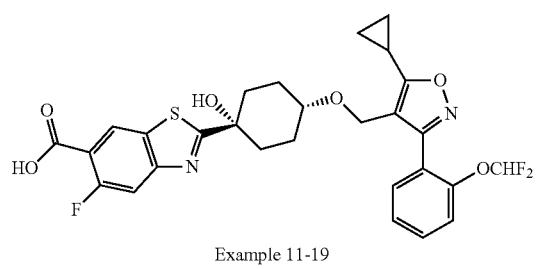

Example 11-19

Following general procedure 1D, beginning with example 2-((1s,4s)-4-((5-cyclopropyl-3-(2-(difluoromethoxy)phenyl)isoxazol-4-yl)methoxy)-1-hydroxycyclohexyl)-5-fluorobenzo[d]thiazole-6-carbonitrile (8-3), the title compound 2-((1s,4s)-4-((5-cyclopropyl-3-(2-(difluoro-methoxy)phenyl)isoxazol-4-yl)methoxy)-1-hydroxycyclohexyl)-5-fluorobenzo[d]thiazole-6-carboxylic acid 11-19 was synthesized. $^1$H-NMR (500 MHz, DMSO-d$_6$): δ 13.36 (br s, 1H), 8.63 (d, J=8.5 Hz, 1H), 7.84 (d, J=14.5 Hz, 1H), 7.63-7.53 (m, 2H), 7.42-7.05 (m, 3H), 6.26 (br s, 1H), 4.37 (s, 2H), 3.30-3.27 (m, 1H), 2.35-2.31 (m, 1H), 1.92-1.70 (m, 6H), 1.54-1.48 (m, 2H), 1.16-1.06 (m, 4H). LC/MS (ESI): m/z 575.2 (M+H)$^+$.

Example 11-20: 2-((1s,4s)-4-((5-Cyclopropyl-3-(2,6-dichlorophenyl)isoxazol-4-yl)methoxy)-1-hydroxycyclohexyl)-5-fluorobenzo[d]thiazole-6-carboxylic acid

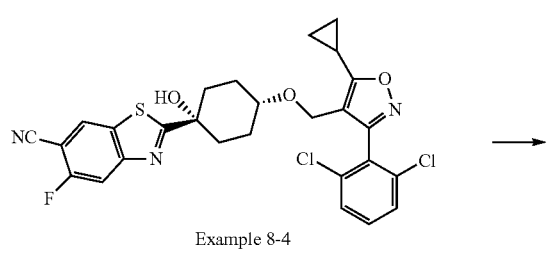

Example 8-4

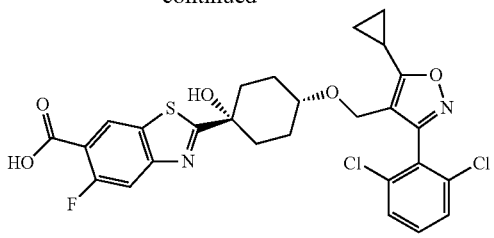

Example 11-20

Following general procedure 1D, beginning with example 2-((1s,4s)-4-((5-cyclopropyl-3-(2,6-dichlorophenyl)isoxazol-4-yl)methoxy)-1-hydroxycyclohexyl)-5-fluorobenzo[d]thiazole-6-carbonitrile (8-4), the title compound 2-((1s,4s)-4-((5-cyclopropyl-3-(2,6-dichlorophenyl)isoxazol-4-yl)methoxy)-1-hydroxycyclohexyl)-5-fluorobenzo[d]thiazole-6-carboxylic acid 11-20 was synthesized. $^1$H-NMR (500 MHz, DMSO-d$_6$): δ 8.32 (d, J=6.5 Hz, 1H), 7.66-7.56 (m, 4H), 6.14 (br s, 1H), 4.31 (s, 2H), 3.25-3.19 (m, 1H), 2.38-2.33 (m, 1H), 1.88-1.77 (m, 4H), 1.68-1.65 (m, 2H), 1.48-1.40 (m, 2H), 1.18-1.10 (m, 4H), CO$_2$H proton not resolved. LC/MS (ESI): m/z 577.1 (M+H)$^+$.

Example 11-21: 2-((1s,3s)-3-((5-Cyclopropyl-3-(2,6-dichlorophenyl)isoxazol-4-yl)methoxy)-1-hydroxycyclobutyl)-4-fluorobenzo[d]thiazole-6-carboxylic acid

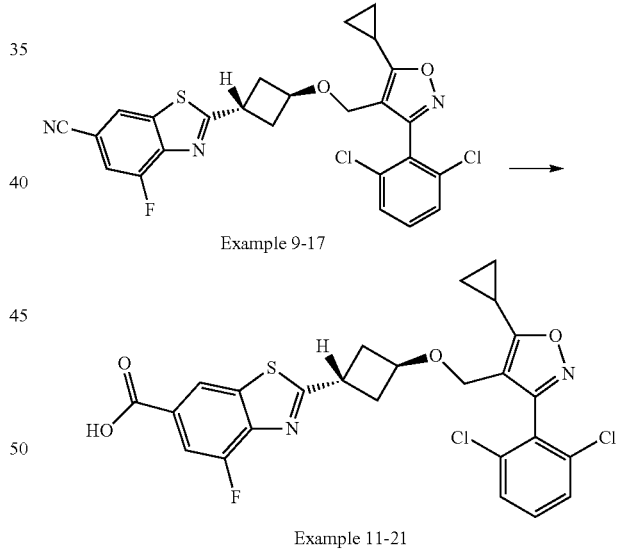

Example 9-17

Example 11-21

Following general procedure 1D, beginning with example 2-((1s,3s)-3-((5-cyclopropyl-3-(2,6-dichlorophenyl)isoxazol-4-yl)methoxy)-1-hydroxycyclobutyl)-4-fluorobenzo[d]thiazole-6-carbonitrile (9-19), the title compound 2-((1s,3s)-3-((5-cyclopropyl-3-(2,6-dichlorophenyl)isoxazol-4-yl)methoxy)-1-hydroxycyclobutyl)-4-fluorobenzo[d]thiazole-6-carboxylic acid 11-21 was synthesized. $^1$H-NMR (500 MHz, DMSO-d$_6$): δ 13.36 (br s, 1H), 8.55 (s, 1H), 7.78 (d, J=11.5 Hz, 1H), 7.64-7.56 (m, 3H), 7.00 (br s, 1H), 4.23 (s, 2H), 4.14-4.09 (m, 1H), 2.79-2.75 (m, 2H), 2.41-2.36 (m, 1H), 2.23-2.19 (m, 2H), 1.19-1.11 (m, 4H). LC/MS (ESI): m/z 548.9 (M+H)$^+$.

Example 11-22: 2-((1R,3s,5S,8r)-3-((5-Cyclopropyl-3-(2,6-dichlorophenyl)isoxazol-4-yl)methoxy)-8-hydroxybicyclo[3.2.1]octan-8-yl)benzo[d]thiazole-6-carboxylic acid

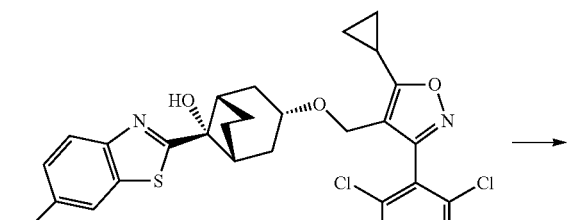

Example 8-5

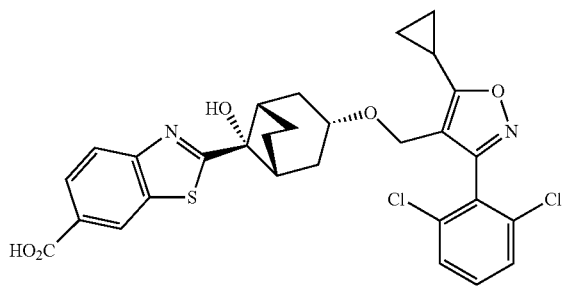

Example 11-22

Following general procedure 1D, beginning with example 2-((1R,3s,5S,8r)-3-((5-cyclopropyl-3-(2,6-dichlorophenyl)isoxazol-4-yl)methoxy)-8-hydroxybicyclo[3.2.1]octan-8-yl)benzo[d]thiazole-6-carbonitrile (8-5), the title compound 2-((1R,3s,5S,8r)-3-((5-cyclopropyl-3-(2,6-dichloro-phenyl)isoxazol-4-yl)methoxy)-8-hydroxybicyclo[3.2.1]octan-8-yl)benzo[d]thiazole-6-carboxylic acid 11-22 was synthesized. $^1$H-NMR (400 MHz, DMSO-$d_6$): δ 13.10 (br s, 1H), 8.69 (s, 1H), 8.10-8.06 (m, 2H), 7.70-7.63 (m, 2H), 7.60-7.54 (m, 1H), 6.41 (s, 1H), 4.29 (s, 2H), 3.53-3.47 (m, 1H), 2.37-2.33 (m, 3H), 1.86-1.74 (m, 4H), 1.65-1.58 (m, 2H), 1.45-1.39 (m, 2H), 1.21-1.10 (m, 4H). LC/MS (ESI): m/z 584.9 (M+H)$^+$.

Example 11-23: 2-((1R,3r,5S,8r)-3-((5-Cyclopropyl-3-(2,6-dichlorophenyl)isoxazol-4-yl)methoxy)-8-hydroxybicyclo[3.2.1]octan-8-yl)benzo[d]thiazole-6-carboxylic acid

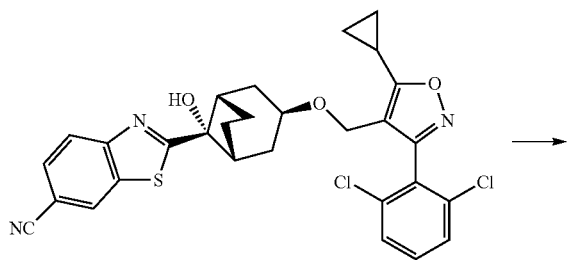

Example 8-6

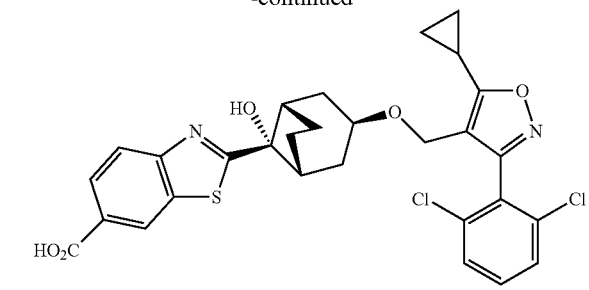

Example 11-23

Following general procedure 1D, beginning with example 2-((1R,3r,5S,8r)-3-((5-cyclopropyl-3-(2,6-dichlorophenyl)isoxazol-4-yl)methoxy)-8-hydroxybicyclo[3.2.1]octan-8-yl)benzo[d]thiazole-6-carbonitrile (8-6), the title compound 2-((1R,3r,5S,8r)-3-((5-cyclopropyl-3-(2,6-dichloro-phenyl)isoxazol-4-yl)methoxy)-8-hydroxybicyclo[3.2.1]octan-8-yl)benzo[d]thiazole-6-carboxylic acid 11-23 was synthesized. $^1$H-NMR (400 MHz, DMSO-$d_6$): δ 13.10 (s, 1H), 8.68 (s, 1H), 8.11-7.99 (m, 2H), 7.65-7.60 (m, 2H), 7.57-7.50 (m, 1H), 6.31 (s, 1H), 4.26 (s, 2H), 3.50-3.46 (m, 1H), 2.38-2.32 (m, 1H), 2.25-2.14 (m, 4H), 1.62-1.57 (m, 2H), 1.55-1.48 (m, 4H), 1.19-1.05 (m, 4H). LC/MS (ESI): m/z 584.9 (M+H)$^+$.

Example 11-24: 4-((1R,3s,5S,8r)-3-((5-Cyclopropyl-3-(2,6-dichlorophenyl)isoxazol-4-yl)methoxy)-8-hydroxybicyclo[3.2.1]octan-8-yl)-3-fluorobenzoic acid

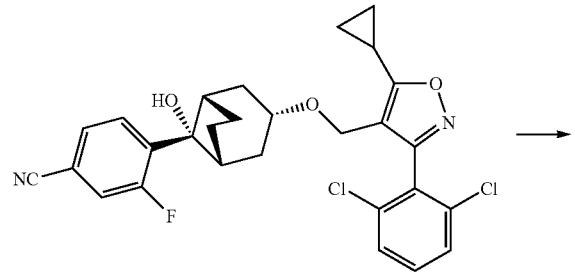

Example 8-7

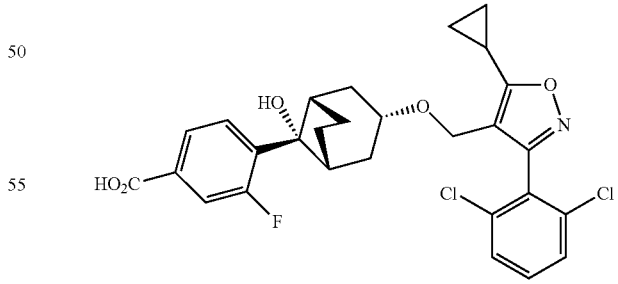

Example 11-24

Following general procedure 1D, beginning with example 4-(1R,3s,5S,8r)-3-((5-cyclopropyl-3-(2,6-dichlorophenyl)isoxazol-4-yl)methoxy)-8-hydroxybicyclo[3.2.1]octan-8-yl)-3-fluorobenzonitrile (8-7), the title compound 4-((1R,3s,5S,8r)-3-((5-cyclopropyl-3-(2,6-dichlorophenyl)isoxazol-4- yl)methoxy)-8-hydroxybicyclo[3.2.1]octan-8-yl)-3-fluorobenzoic acid (11-24) was synthesized. $^1$H-NMR (400 MHz, CDCl$_3$): δ 7.82 (d, J=8.4 Hz, 1H), 7.75 (d, J=12.8 Hz, 1H), 7.45-7.30 (m, 4H), 4.35 (s, 2H), 3.62-3.56 (m, 1H), 2.63 (s, 2H), 2.23-2.18 (m, 1H), 1.97 (t, J=10.8 Hz, 2H), 1.78-1.71 (m, 2H), 1.55-1.44 (m, 4H), 1.32-1.24 (m, 2H), 1.17-1.08 (m, 2H). Carboxylate and hydroxyl proton not resolved. $^{19}$F-NMR (376 MHz, CDCl$_3$): δ −110.02. LC/MS (ESI): m/z 544.0 (M−H)$^−$.

Example 11-25: 3-((1R,3s,5S,8r)-3-((5-Cyclopropyl-3-(2,6-dichlorophenyl)isoxazol-4-yl)methoxy)-8-hydroxybicyclo[3.2.1]octan-8-yl)benzoic acid

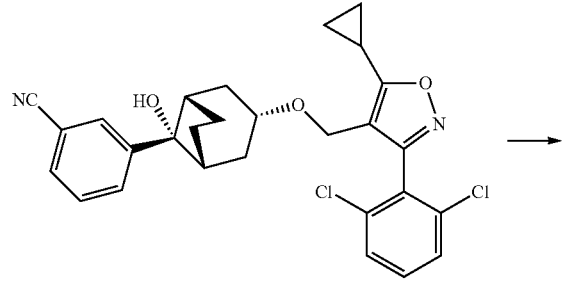

Example 8-8

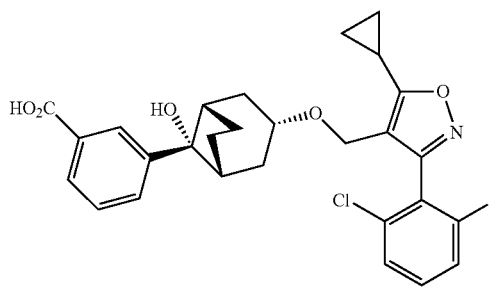

Example 11-25

Following general procedure 1D, beginning with example 3-(1R,3s,5S,8r)-3-((5-cyclopropyl-3-(2,6-dichlorophenyl)isoxazol-4-yl)methoxy)-8-hydroxybicyclo[3.2.1]octan-8-yl)benzonitrile (8-8), the title compound 3-((1R,3s,5S,8r)-3-((5-cyclopropyl-3-(2,6-dichlorophenyl)isoxazol-4-yl)methoxy)-8-hydroxybicyclo[3.2.1]octan-8-yl)benzoic acid (11-25) was synthesized. $^1$H-NMR (400 MHz, DMSO): δ 12.91 (br s, 1H), 8.03 (s, 1H), 7.80 (d, J=7.6 Hz, 1H), 7.70-7.63 (m, 3H), 7.60-7.55 (m, 1H), 7.41 (t, J=7.6 Hz, 1H), 5.12 (s, 1H), 4.28 (s, 2H), 3.50-3.42 (m, 1H), 2.39-2.34 (m, 3H), 1.85 (t, J=10.8 Hz, 2H), 1.61-1.54 (m, 2H), 1.32-1.22 (m, 4H), 1.17-1.09 (m, 4H). LC/MS (ESI): m/z 525.9 (M−H)$^−$.

Example 11-26: 2-((1R,3s,5S,8r)-3-((5-Cyclopropyl-3-(2,6-dichlorophenyl)isoxazol-4-yl)methoxy)-8-hydroxybicyclo[3.2.1]octan-8-isonicotinic acid

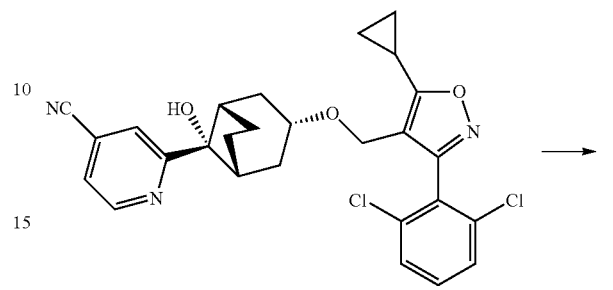

Example 15-5

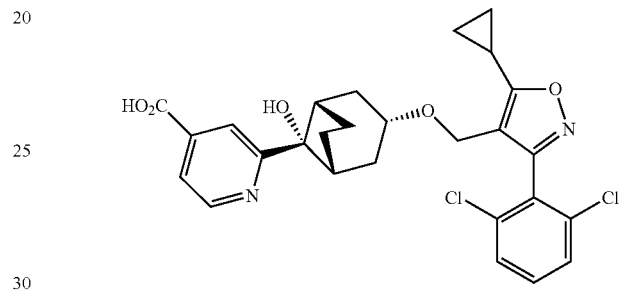

Example 11-26

Following general procedure 1D, beginning with example 2-((1R,3s,5S,8r)-3-((5-cyclopropyl-3-(2,6-dichlorophenyl)isoxazol-4-yl)methoxy)-8-hydroxybicyclo[3.2.1]octan-8-yl)isonicotinonitrile (15-5), the title compound 2-((1R,3s,5S,8r)-3-((5-cyclopropyl-3-(2,6-dichlorophenyl)isoxazol-4-yl)methoxy)-8-hydroxybicyclo[3.2.1]octan-8-yl)isonicotinic acid (11-26) was synthesized. $^1$H-NMR (400 MHz, DMSO): δ 13.75 (br s, 1H), 8.61 (d, J=4.8 Hz, 1H), 7.97 (s, 1H), 7.68-7.63 (m, 3H), 7.57 (dd, J=9.2, 6.8 Hz, 1H), 5.33 (s, 1H), 4.28 (s, 2H), 3.50-3.42 (m, 1H), 2.39-2.34 (m, 1H), 1.84 (t, J=10.8 Hz, 2H), 1.60-1.54 (m, 2H), 1.34-1.23 (m, 5H), 1.17-1.08 (m, 5H). LC/MS (ESI): m/z 529.0 (M+H)$^+$.

Example 11-27: 2-((1R,3s,5S,8r)-3-((5-Cyclopropyl-3-(2,6-dichlorophenyl)isoxazol-4-yl)methoxy)-8-hydroxybicyclo[3.2.1]octan-8-yl)-4-fluorobenzo[d]thiazole-6-carboxylic acid

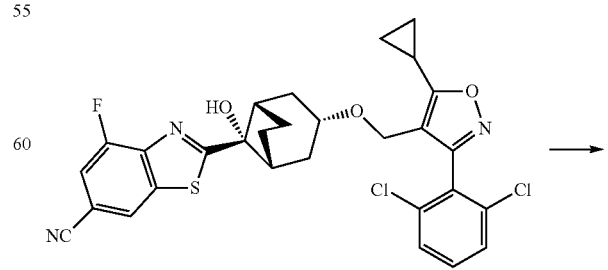

Example 8-9

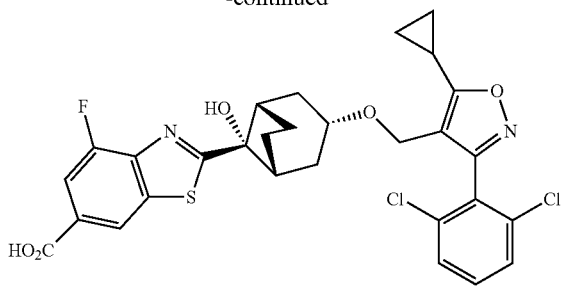

Example 11-27

Following general procedure 1D, beginning with example 2-((1R,3s,5S,8r)-3-((5-cyclopropyl-3-(2,6-dichlorophenyl)isoxazol-4-yl)methoxy)-8-hydroxybicyclo[3.2.1]octan-8-yl)-4-fluorobenzo[d]thiazole-6-carbonitrile (8-9), the title compound 2-((1R,3s,5S,8r)-3-((5-cyclopropyl-3-(2,6-dichlorophenyl)isoxazol-4-yl)methoxy)-8-hydroxybicyclo[3.2.1]octan-8-yl)-4-fluorobenzo[d]thiazole-6-carboxylic acid (11-27) was synthesized. $^1$H-NMR (400 MHz, DMSO-d$_6$): δ 13.36 (br s, 1H), 8.55 (s, 1H), 7.75 (d, J=10.8 Hz, 1H), 7.67-7.60 (m, 2H), 7.59-7.55 (m, 1H), 6.51 (br s, 1H), 4.29 (s, 2H), 3.53-3.34 (m, 1H), 2.39-2.33 (m, 3H), 1.88-1.78 (m, 4H), 1.65-1.59 (m, 2H), 1.48-1.39 (m, 2H), 1.25-1.08 (m, 4H). $^{19}$F-NMR (376 MHz, DMSO-d$_6$): δ −122.37. LC/MS (ESI): m/z 603.2 (M+H)$^+$.

Example 11-28: 2-((1R,3s,5S,8r)-3-((5-Cyclopropyl-3-(2-(difluoromethoxy)phenyl)isoxazol-4-yl)methoxy)-8-hydroxybicyclo[3.2.1]octan-8-yl)-4-fluorobenzo[d]thiazole-6-carboxylic acid

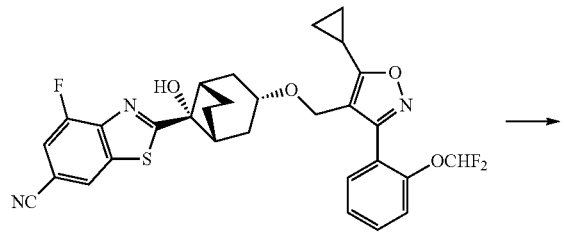

Example 8-10

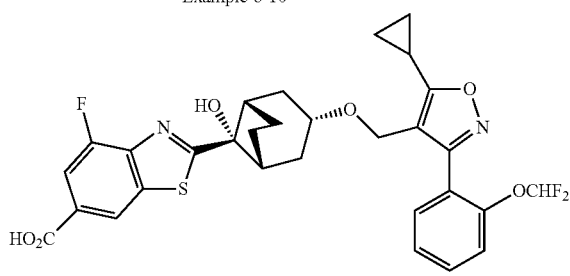

Example 11-28

Following general procedure 1D, beginning with 2-((1R,3s,5S,8r)-3-((5-cyclopropyl-3-(2-(di-fluoromethoxy)phenyl)isoxazol-4-yl)methoxy)-8-hydroxybicyclo[3.2.1]octan-8-yl)-4-fluorobenzo[d]thiazole-6-carbonitrile (8-10), the title compound 2-((1R,3s,5S,8r)-3-((5-cyclopropyl-3-(2-(difluoromethoxy)phenyl)isoxazol-4-yl)methoxy)-8-hydroxybicyclo[3.2.1]octan-8-yl)-4-fluorobenzo[d]thiazole-6-carboxylic acid (11-28) was synthesized. $^1$H-NMR (400 MHz, DMSO-d$_6$): δ 13.35 (br s, 1H), 8.55 (s, 1H), 7.75 (d, J=11.2 Hz, 1H), 7.61 (t, J=8.0 Hz, 1H), 7.55 (d, J=7.2 Hz, 1H), 7.42-7.35 (m, 2H), 7.22 (t, J=73.6 Hz, 1H), 6.52 (br s, 1H), 4.35 (s, 2H), 3.62-3.52 (m, 1H), 2.45-2.25 (m, 3H), 1.93-1.75 (m, 4H), 1.73-1.57 (m, 2H), 1.45-1.38 (m, 2H), 1.19-1.04 (m, 4H). $^{19}$F-NMR (376 MHz, DMSO-d$_6$): δ −122.36, −82.04. LC/MS (ESI): m/z 601.2 (M+H)$^+$.

Example 11-29: 2-((1R,3s,5S,8r)-3-((5-Cyclopropyl-3-(3,5-dichloropyridin-4-yl)isoxazol-4-yl)methoxy)-8-hydroxybicyclo[3.2.1]octan-8-yl)-4-fluorobenzo[d]thiazole-6-carboxylic acid

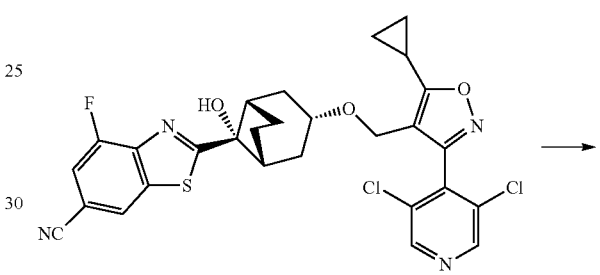

Example 8-11

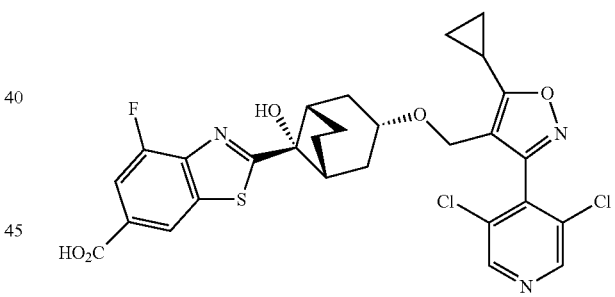

Example 11-29

Following general procedure 1D, beginning with 2-((1R,3s,5S,8r)-3-((5-cyclopropyl-3-(3,5-dichloropyridin-4-yl)isoxazol-4-yl)methoxy)-8-hydroxybicyclo[3.2.1]octan-8-yl)-4-fluorobenzo[d]thiazole-6-carbonitrile (8-11), the title compound 2-((1R,3s,5S,8r)-3-((5-cyclopropyl-3-(3,5-dichloropyridin-4-yl)isoxazol-4-yl)methoxy)-8-hydroxybicyclo[3.2.1]octan-8-yl)-4-fluorobenzo[d]thiazole-6-carboxylic acid (11-29) was synthesized. $^1$H-NMR (400 MHz, DMSO-d$_6$): δ 13.35 (br s, 1H), 8.84 (s, 2H), 8.54 (s, 1H), 7.65 (d, J=10.8 Hz, 1H), 6.49 (s, 1H), 4.35 (s, 2H), 3.55-3.51 (m, 1H), 2.44-2.33 (m, 3H), 1.83-1.72 (m, 4H), 1.63-1.56 (m, 2H), 1.48-1.41 (m, 2H), 1.20-1.08 (m, 4H). $^{19}$F-NMR (376 MHz, DMSO-d$_6$): δ −122.42. LC/MS (ESI): m/z 604.2 (M+H)$^+$.

Example 11-30: 2-((1s,4s)-4-((5-Cyclopropyl-3-(2,6-dichlorophenyl)isoxazol-4-yl)methoxy)-1-hydroxycyclohexyl)benzo[d]thiazole-6-carboxylic acid

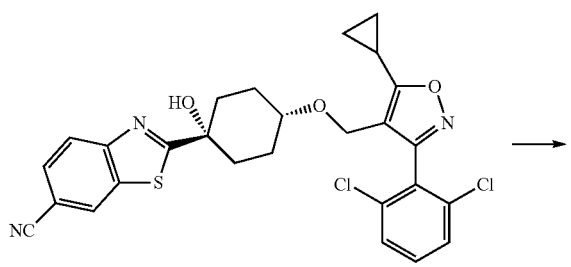

Example 8-12

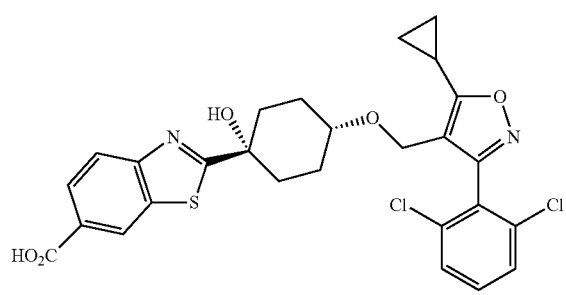

Example 11-30

Following general procedure 1D, beginning with 2-((1s,4s)-4-((5-cyclopropyl-3-(2,6-dichloro-phenyl)isoxazol-4-yl)methoxy)-1-hydroxycyclohexyl)benzo[d]thiazole-6-carbonitrile (8-12), the title compound 2-((1s,4s)-4-((5-cyclopropyl-3-(2,6-dichlorophenyl)isoxazol-4-yl)methoxy)-1-hydroxy-cyclohexyl)benzo[d]thiazole-6-carboxylic acid (11-30) was synthesized. $^1$H-NMR (400 MHz, DMSO-d$_6$): δ 13.07 (br s, 1H), 8.67 (s, 1H), 8.02-7.96 (m, 2H), 7.66-7.56 (m, 3H), 6.19 (s, 1H), 4.31 (s, 2H), 3.25-3.22 (m, 1H), 2.36-2.32 (m, 1H), 1.87-1.81 (m, 4H), 1.68-1.66 (m, 2H), 1.48-1.43 (m, 2H), 1.16-1.11 (m, 4H). LC/MS (ESI): m/z 558.7 (M+H)$^+$.

Example 11-31: 2-((1s,4s)-4-((5-Cyclopropyl-3-(2,6-dichlorophenyl)isoxazol-4-yl)methoxy)-1-hydroxycyclohexyl)-4-fluorobenzo[d]thiazole-6-carboxylic acid

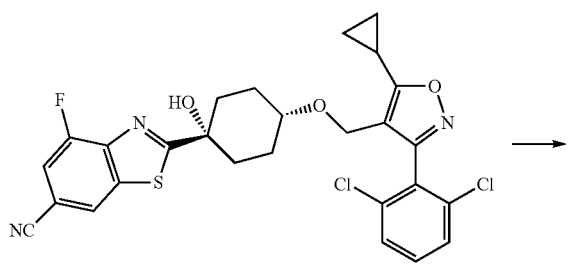

Example 8-13

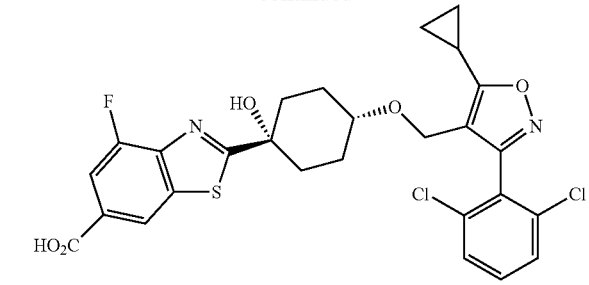

Example 11-31

Following general procedure 1D, beginning with 2-((1s,4s)-4-((5-cyclopropyl-3-(2,6-dichloro-phenyl)isoxazol-4-yl)methoxy)-1-hydroxycyclohexyl)-4-fluorobenzo[d]thiazole-6-carbonitrile (8-13), the title compound 2-((1s,4s)-4-((5-cyclopropyl-3-(2,6-dichlorophenyl)isoxazol-4-yl)methoxy)-1-hydroxycyclohexyl)-4-fluorobenzo[d]thiazole-6-carboxylic acid (11-31) was synthesized. $^1$H-NMR (400 MHz, DMSO): δ 13.34 (br s, 1H), 8.54 (s, 1H), 7.76-7.56 (m, 4H), 6.30 (s, 1H), 4.32 (s, 2H), 3.27-3.25 (m, 1H), 2.37-2.33 (m, 1H), 1.88-1.79 (m, 4H), 1.70-1.67 (m, 2H), 1.45-1.42 (m, 2H), 1.16-1.09 (m, 4H). LC/MS (ESI): m/z 577.4 (M+H)$^+$.

Example 11-32: 2-((1R,4S)-4-((5-Cyclopropyl-3-(2,6-dichlorophenyl)isoxazol-4-yl)methoxy)-1-hydroxy-2,2-dimethylcyclohexyl)-4-fluorobenzo[d]thiazole-6-carboxylic acid

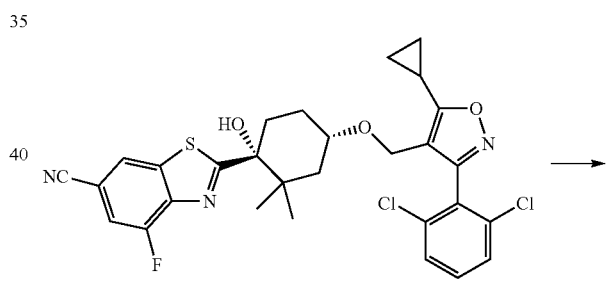

Example 9-18
(cis racemate)

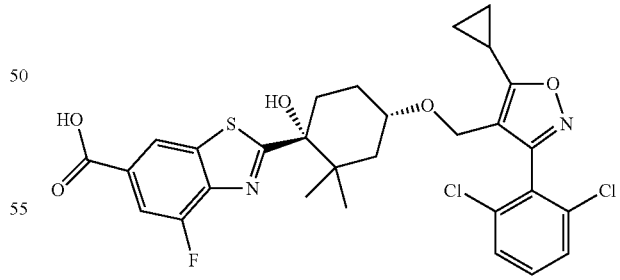

Example 11-32
(cis racemate)

Following general procedure 1D, beginning with example 2-((1R,4S)-4-((5-cyclopropyl-3-(2,6-di-chlorophenyl)isoxazol-4-yl)methoxy)-1-hydroxy-2,2-dimethylcyclohexyl)-4-fluorobenzo[d]thiazole-6-carbonitrile (9-18), the racemic title compound 2-((1R,4S)-4-((5-cyclopropyl-3-(2,6-di-chloro-phenyl)isoxazol-4-yl)methoxy)-1-hydroxy-2,2-dimethylcyclohexyl)-4-fluorobenzo[d]thiazole-6-carboxylic acid 11-32 was synthesized. $^1$H-NMR (500 MHz, DMSO-d$_6$): δ 13.35 (br s, 1H), 8.54 (d, J=1.5 Hz, 1H), 7.74 (dd, J=14.0 Hz, J=2.0 Hz, 1H), 7.67-7.57 (m, 3H), 6.23 (br s, 1H), 4.31 (q, J=16.0 Hz, 2H), 3.47-3.41 (m, 1H), 2.39-2.34 (m, 2H), 1.78-1.70 (m, 2H), 1.55-1.33 (m, 3H), 1.23-1.09 (m, 4H), 0.90 (s, 3H), 0.80 (s, 3H). LC/MS (ESI): m/z 605.2 (M+H)$^+$.

Example 11-33: 2-((1S,4R)-4-((5-Cyclopropyl-3-(2,6-dichlorophenyl)isoxazol-4-yl)methoxy)-1-hydroxy-3,3-dimethylcyclohexyl)-4-fluorobenzo[d]thiazole-6-carboxylic acid

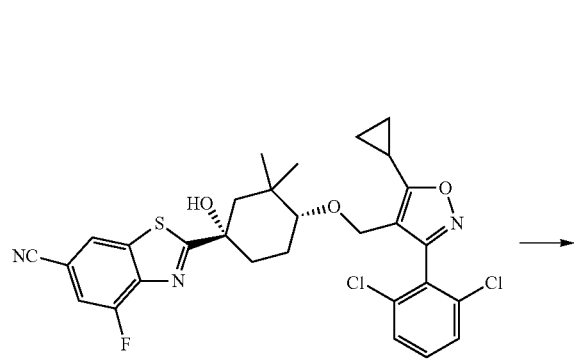

Example 9-19
(cis racemate)

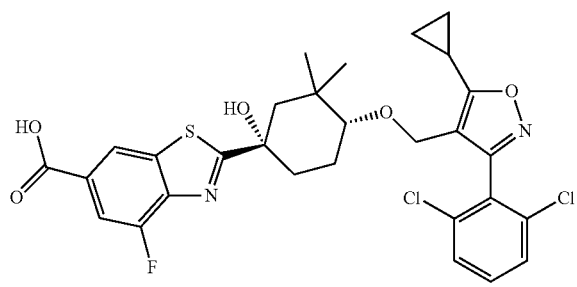

Example 11-33
(cis racemate)

Following general procedure 1D, beginning with example 2-((1S,4R)-4-((5-cyclopropyl-3-(2,6-di-chlorophenyl)isoxazol-4-yl)methoxy)-1-hydroxy-3,3-dimethylcyclohexyl)-4-fluorobenzo[d]thiazole-6-carbonitrile (9-19), the racemic title compound 2-((1S,4R)-4-((5-cyclopropyl-3-(2,6-di-chloro-phenyl)isoxazol-4-yl)methoxy)-1-hydroxy-3,3-dimethylcyclohexyl)-4-fluorobenzo[d]thiazole-6-carboxylic acid 11-33 was synthesized. $^1$H-NMR (500 MHz, DMSO-d$_6$): δ 13.35 (br s, 1H), 8.55 (s, J=1.5 Hz, 1H), 7.75 (dd, J=14.0 Hz, J=1.5 Hz, 1H), 7.66-7.55 (m, 3H), 6.21 (br s, 1H), 4.50 (d, J=14.5 Hz, 1H), 4.15 (d, J=14.5 Hz, 1H), 3.07-3.04 (m, 1H), 2.37-2.33 (m, 1H), 1.93-1.84 (m, 3H), 1.70-1.63 (m, 2H), 1.53-1.49 (m, 1H), 1.18-1.11 (m, 4H), 0.90 (s, 3H), 0.65 (s, 3H). LC/MS (ESI): m/z 605.1 (M+H)$^+$.

Example 11-34: 2-((1s,4s)-4-((5-Cyclopropyl-3-(3,5-dichloropyridin-4-yl)isoxazol-4-yl)methoxy)-1-hydroxycyclohexyl)-4-fluorobenzo[d]thiazole-6-carboxylic acid

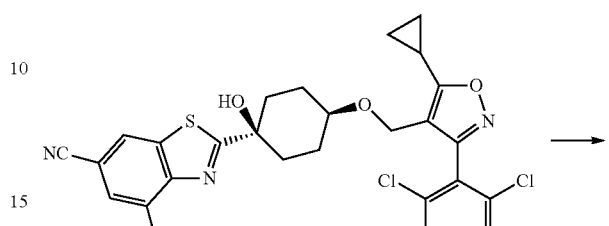

Example 9-20

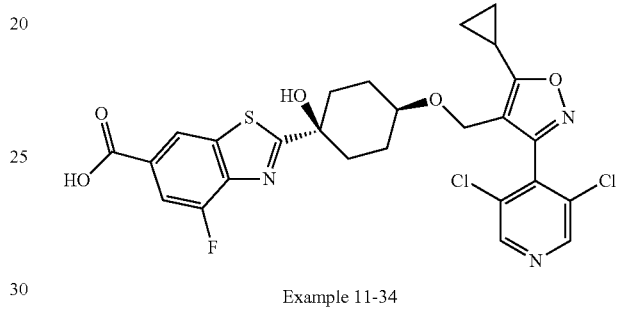

Example 11-34

Following general procedure 1D, beginning with example 2-((1s,4s)-4-((5-cyclopropyl-3-(3,5-dichloropyridin-4-yl)isoxazol-4-yl)methoxy)-1-hydroxycyclohexyl)-4-fluorobenzo[d]thiazole-6-carbonitrile (9-20), the title compound 2-((1s,4s)-4-((5-cyclopropyl-3-(3,5-dichloropyridin-4-yl)isoxazol-4-yl)methoxy)-1-hydroxycyclohexyl)-4-fluorobenzo[d]thiazole-6-carboxylic acid 11-34 was synthesized. $^1$H-NMR (500 MHz, DMSO-d$_6$): δ 13.46 (br s, 1H), 8.89 (s, 2H), 8.59 (s, 1H), 7.80 (d, J=11.5 Hz, 1H), 6.37 (br s, 1H), 4.43 (s, 2H), 3.35-3.31 (m, 1H), 2.44-2.41 (m, 1H), 1.97-1.71 (m, 6H), 1.48-1.40 (m, 2H), 1.24-1.15 (m, 4H). LCMS (ESI): m/z 578.0 (M+H)$^+$.

Example 11-35: 2-((1R,2r,3S,5s,7s)-5-((5-Cyclopropyl-3-(2,6-dichlorophenyl)isoxazol-4-yl)methoxy)-2-hydroxyadamantan-2-yl)benzo[d]thiazole-6-carboxylic acid

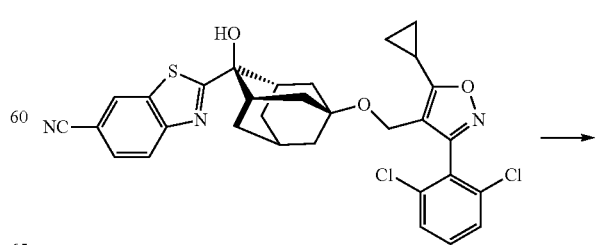

Example 8-14

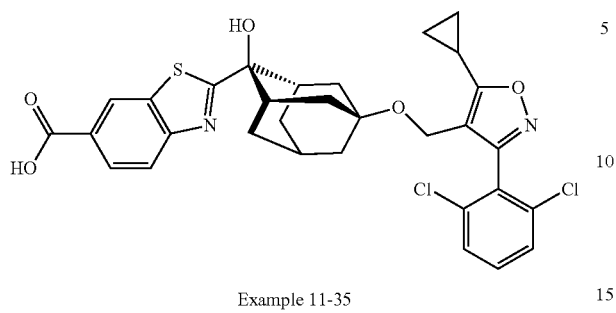

Example 11-35

Following general procedure 1D, beginning with example 2-((1R,2r,3S,5s,7s)-5-((5-cyclopropyl-3-(2,6-dichlorophenyl)isoxazol-4-yl)methoxy)-2-hydroxyadamantan-2-yl)benzo[d]thiazole-6-carbonitrile (8-14), the title compound 2-((1R,2r,3S,5s,7s)-5-((5-cyclopropyl-3-(2,6-dichlorophenyl)isoxazol-4-yl)methoxy)-2-hydroxyadamantan-2-yl)benzo[d]thiazole-6-carboxylic acid 11-35 was synthesized. $^1$H-NMR (400 MHz, DMSO): δ 13.13 (br s, 1H), 8.69 (s, 1H), 8.05-8.00 (m, 2H), 7.64-7.54 (m, 3H), 6.10 (br s, 1H), 4.24 (s, 2H), 2.42-2.28 (m, 3H), 2.18-2.15 (m, 2H), 1.94-1.87 (m, 3H), 1.49-1.08 (m, 10H). MS (ESI): m/z 611.2 (M+1)$^+$.

Example 11-36: 2-((1R,2s,3S,5s,7s)-5-((5-Cyclopropyl-3-(2,6-dichlorophenyl)isoxazol-4-yl)methoxy)-2-hydroxyadamantan-2-yl)benzo[d]thiazole-6-carboxylic acid

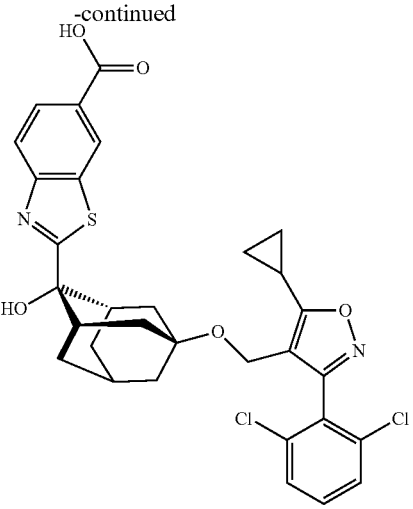

Example 11-36

Following general procedure 1D, beginning with example 2-((1R,2s,3S,5s,7s)-5-((5-cyclopropyl-3-(2,6-dichlorophenyl)isoxazol-4-yl)methoxy)-2-hydroxyadamantan-2-yl)benzo[d]thiazole-6-carbonitrile (8-15), the title compound 2-((1R,2s,3S,5s,7s)-5-((5-cyclopropyl-3-(2,6-dichlorophenyl)isoxazol-4-yl)methoxy)-2-hydroxyadamantan-2-yl)benzo[d]thiazole-6-carboxylic acid 11-36 was synthesized. $^1$H-NMR (400 MHz, DMSO-d$_6$): δ 8.71 (s, 1H), 8.11 (d, J=8.4 Hz, 1H), 8.04 (d, J=8.8 Hz, 1H), 7.17 (d, J=8.4 Hz, 2H), 6.92 (t, J=8.4 Hz, 1H), 5.98 (s, 1H), 4.15 (s, 2H), 2.42-2.36 (m, 2H), 2.23-2.15 (m, 3H), 2.03-1.98 (m, 1H), 1.55-1.40 (m, 6H), 1.38-1.30 (m, 2H), 1.08-0.96 (m, 4H), CO$_2$H proton not resolved. MS (ESI): m/z 611.2 (M+1)$^+$.

Example 11-37: 2-((1R,3s,5S,8r)-3-((3-(2,6-Dichlorophenyl)-5-methylisoxazol-4-yl)methoxy)-8-hydroxybicyclo[3.2.1]octan-8-yl)benzo[d]thiazole-6-carboxylic acid

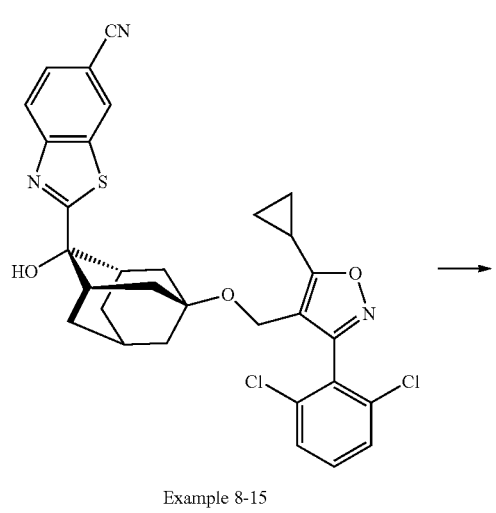

Example 8-15

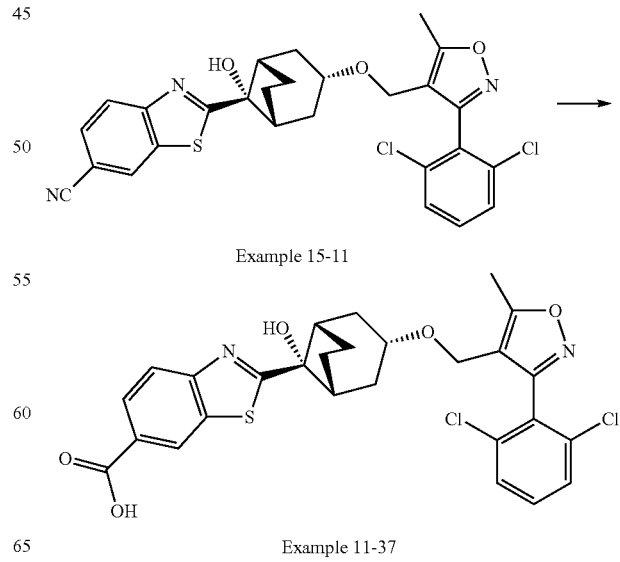

Example 15-11

Example 11-37

Following general procedure 1D, beginning with example 2-((1R,3s,5S,8r)-3-((3-(2,6-dichloro-phenyl)-5-methylisoxazol-4-yl)methoxy)-8-hydroxybicyclo[3.2.1]octan-8-yl)benzo[d]thiazole-6-carbonitrile (15-11), the title compound 2-((1R,3s,5S,8r)-3-((3-(2,6-dichlorophenyl)-5-methylisoxazol-4-yl)methoxy)-8-hydroxybicyclo[3.2.1]octan-8-yl)benzo[d]thiazole-6-carboxylic acid 11-37 was synthesized. $^1$H-NMR (500 MHz, DMSO-$d_6$): δ 13.16 (br s, 1H), 8.69 (s, 1H), 8.03-7.99 (m, 2H), 7.67-7.57 (m, 3H), 6.42 (br s, 1H), 4.23 (s, 2H), 3.51-3.45 (m, 1H), 2.54 (s, 3H), 2.36 (s, 2H), 1.84-1.75 (m, 4H), 1.61-1.57 (m, 2H), 1.44-1.38 (m, 2H). LCMS (ESI): m/z 559.0 (M+H)$^+$.

Example 11-38: 2-((1R,3r,5S,8r)-3-((3-(2,6-Dichlorophenyl)-5-methylisoxazol-4-yl)methoxy)-8-hydroxybicyclo[3.2.1]octan-8-yl)benzo[d]thiazole-6-carboxylic acid

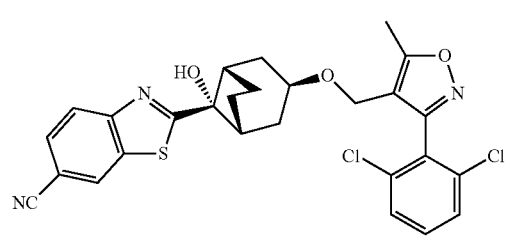

Example 15-12

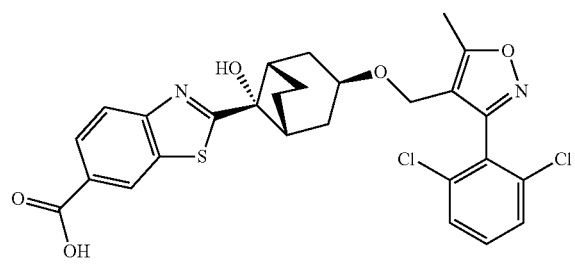

Example 11-38

Following general procedure 1D, beginning with example 2-((1R,3r,5S,8r)-3-((3-(2,6-dichloro-phenyl)-5-methylisoxazol-4-yl)methoxy)-8-hydroxybicyclo[3.2.1]octan-8-yl)benzo[d]thiazole-6-carbonitrile (15-12), the title compound 2-((1R,3r,5S,8r)-3-((3-(2,6-dichlorophenyl)-5-methylisoxazol-4-yl)methoxy)-8-hydroxybicyclo[3.2.1]octan-8-yl)benzo[d]thiazole-6-carboxylic acid 11-38 was synthesized. $^1$H-NMR (500 MHz, DMSO-$d_6$): δ 13.13 (br s, 1H), 8.68 (s, 1H), 8.02 (s, 2H), 7.64-7.53 (m, 3H), 6.31 (br s, 1H), 4.21 (s, 2H), 3.57 (1H, under solvent signal), 2.53-2.51 (m, 3H), 2.25-2.17 (m, 4H), 1.60-1.50 (m, 6H). LCMS (ESI): m/z 559.1 (M+H)$^+$.

Example 11-39: 2-((1R,5S,8r)-3-((5-Cyclopropyl-3-(2,6-dichlorophenyl)isoxazol-4-yl)methoxy)-8-hydroxy-3-methylbicyclo[3.2.1]octan-8-yl)-4-fluorobenzo[d]thiazole-6-carboxylic acid

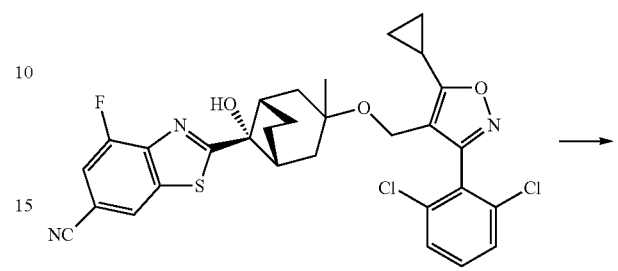

Example 15-13

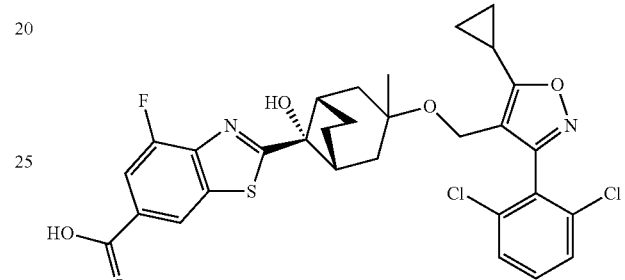

Example 11-39

Following general procedure 1D, beginning with example 2-((1R,5S,8r)-3-((5-cyclopropyl-3-(2,6-dichlorophenyl)isoxazol-4-yl)methoxy)-8-hydroxy-3-methylbicyclo[3.2.1]octan-8-yl)-4-fluorobenzo[d]thiazole-6-carbonitrile 15-13, the title compound 2-((1R,5S,8r)-3-((5-cyclopropyl-3-(2,6-dichlorophenyl)isoxazol-4-yl)methoxy)-8-hydroxy-3-methylbicyclo[3.2.1]octan-8-yl)-4-fluorobenzo[d]thiazole-6-carboxylic acid 11-39 was synthesized as a single isomer. $^1$H-NMR (500 MHz, DMSO-$d_6$): δ 13.40 (br s, 1H), 8.55 (d, J=1.5 Hz, 1H), 7.76 (dd, J=8.0 Hz, J=1.5 Hz, 1H), 7.63-7.52 (m, 3H), 6.44 (br s, 1H), 4.22 (s, 2H), 2.32-2.27 (m, 3H), 2.01-1.98 (m, 2H), 1.70-1.42 (m, 6H), 1.16-1.06 (m, 4H), 0.91 (s, 3H). LCMS (ESI): m/z 617.1 (M+H)$^+$.

Example 11-40: 2-((1R,5S,8r)-3-((5-Cyclopropyl-3-(2,6-dichlorophenyl)isoxazol-4-yl)methoxy)-3-(difluoromethyl)-8-hydroxybicyclo[3.2.1]octan-8-yl)-4-fluorobenzo[d]thiazole-6-carboxylic acid

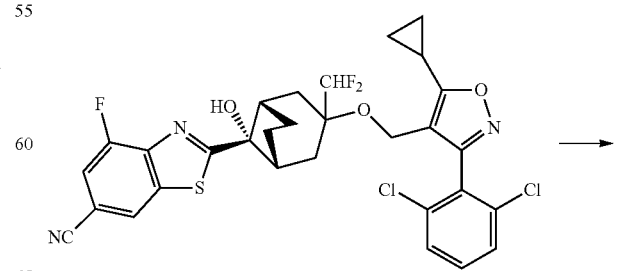

Example 15-14

197
-continued

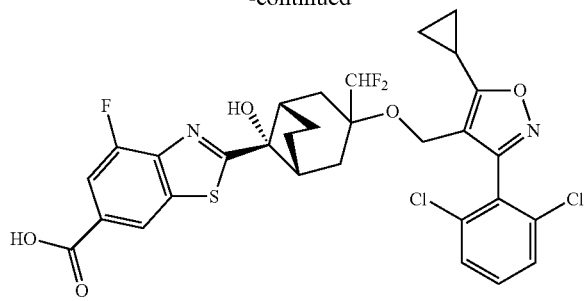

Example 11-40

Following general procedure 1D, beginning with example 2-((1R,5S,8r)-3-((5-cyclopropyl-3-(2,6-dichlorophenyl)isoxazol-4-yl)methoxy)-3-(difluoromethyl)-8-hydroxybicyclo[3.2.1]octan-8-yl)-4-fluorobenzo[d]thiazole-6-carbonitrile 15-14, the title compound 2-((1R,5S,8r)-3-((5-cyclopropyl-3-(2,6-dichlorophenyl) isoxazol-4-yl)methoxy)-3-(difluoromethyl)-8-hydroxybicyclo[3.2.1]octan-8-yl)-4-fluorobenzo[d]thiazole-6-carboxylic acid 11-40 was synthesized as a single isomer. $^1$H-NMR (500 MHz, DMSO-d$_6$): δ 13.39 (br s, 1H), 8.57 (d, J=1.5 Hz, 1H), 7.77 (dd, J=8.0 Hz, J=1.5 Hz, 1H), 7.62-7.51 (m, 3H), 6.55 (br s, 1H), 5.78 (t, J=55.3 Hz, 1H), 4.45 (s, 2H), 2.39-2.31 (m, 3H), 2.19-2.17 (m, 2H), 1.73-1.70 (m, 2H), 1.48 (s, 4H), 1.18-1.06 (m, 4H). LCMS (ESI): m/z 653.1 (M+H)$^+$.

Example 11-41: 2-((1R,5S,8r)-3-((5-Cyclopropyl-3-(2,6-dichlorophenyl)isoxazol-4-yl)methoxy)-8-hydroxy-3-(methoxymethyl)bicyclo[3.2.1]octan-8-yl)-4-fluorobenzo[d]thiazole-6-carboxylic acid

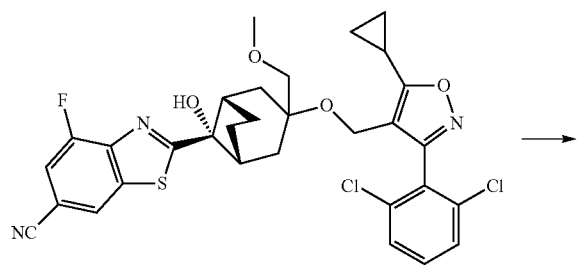

Example 15-15

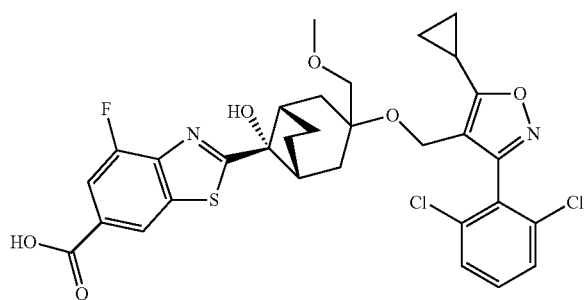

Example 11-41

198

Following general procedure 1D, beginning with example 2-((1R,5S,8r)-3-((5-cyclopropyl-3-(2,6-dichlorophenyl)isoxazol-4-yl)methoxy)-8-hydroxy-3-(methoxymethyl)bicyclo[3.2.1]octan-8-yl)-4-fluorobenzo[d]thiazole-6-carbonitrile 15-15, the title compound 2-((1R,5S,8r)-3-((5-cyclopropyl-3-(2,6-dichlorophenyl) isoxazol-4-yl)methoxy)-8-hydroxy-3-(methoxymethyl) bicyclo[3.2.1]octan-8-yl)-4-fluorobenzo[d]thiazole-6-carboxylic acid 11-41 was synthesized as a single isomer. $^1$H-NMR (500 MHz, DMSO-d$_6$): δ 13.39 (br s, 1H), 8.55 (d, J=1.5 Hz, 1H), 7.76 (d, J=8.0 Hz, J=1.5 Hz, 1H), 7.62-7.52 (m, 3H), 6.40 (br s, 1H), 4.30 (s, 2H), 3.15 (s, 3H), 3.10 (s, 2H), 2.34-2.30 (m, 3H), 2.00-1.97 (m, 2H), 1.69-1.66 (m, 2H), 1.53-1.44 (m, 4H), 1.15-1.09 (m, 4H). LCMS (ESI): m/z 647.1 (M+H)$^+$.

Example 11-42: 6-((1s,4s)-4-((5-Cyclopropyl-3-(2,6-dichlorophenyl)isoxazol-4-yl)methoxy)-1-hydroxycyclohexyl)-1-methyl-1H-indole-3-carboxylic acid

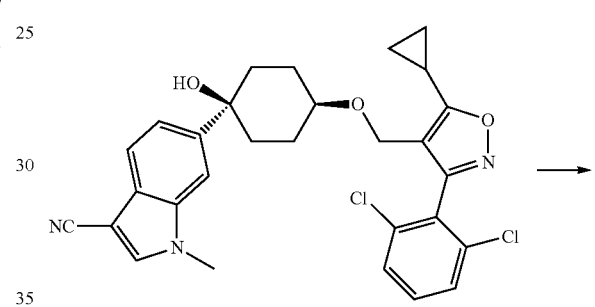

Example 9-21

Example 11-42

Following general procedure 1D, beginning with example 6-((1s,4s)-4-((5-cyclopropyl-3-(2,6-dichlorophenyl)isoxazol-4-yl)methoxy)-1-hydroxycyclohexyl)-1-methyl-1H-indole-3-carbonitrile (9-21), the title compound 6-((1s,4s)-4-((5-cyclopropyl-3-(2,6-dichlorophenyl)isoxazol-4-yl)methoxy)-1-hydroxycyclohexyl)-1-methyl-1H-indole-3-carboxylic acid 11-42 was synthesized. $^1$H-NMR (500 MHz, DMSO-d$_6$): δ 11.89 (br s, 1H), 7.98 (s, 1H), 7.88 (d, J=8.5 Hz, 1H), 7.68-7.65 (m, 2H), 7.60-7.55 (m, 2H), 7.29 (d, J=8.5 Hz, 1H), 4.77 (s, 1H), 4.32 (s, 2H), 3.82 (s, 3H), 3.23-3.19 (m, 1H), 2.38-2.33 (m, 1H), 1.75-1.70 (m, 2H), 1.63-1.48 (m, 6H), 1.18-1.10 (m, 4H). LCMS (ESI): m/z 555.0 (M+H)$^+$.

Example 11-43: 7-((1s,4s)-4-((5-Cyclopropyl-3-(2,6-dichlorophenyl)isoxazol-4-yl)methoxy)-1-hydroxycyclohexyl)quinoline-3-carboxylic acid

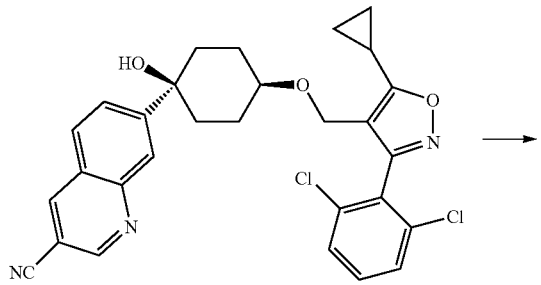

Example 9-22

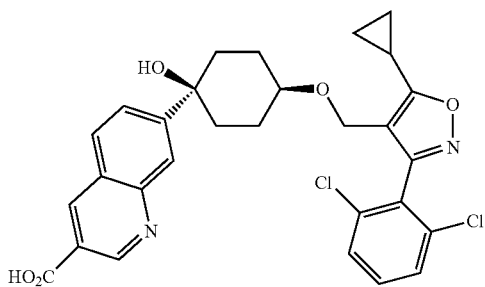

Example 11-43

Following general procedure 1D, beginning with example 7-((1s,4s)-4-((5-cyclopropyl-3-(2,6-di-chlorophenyl)isoxazol-4-yl)methoxy)-1-hydroxycyclohexyl)quinoline-3-carbonitrile (9-22), the title compound 7-((1s,4s)-4-((5-cyclopropyl-3-(2,6-dichlorophenyl)isoxazol-4-yl)methoxy)-1-hydroxy-cyclohexyl)quinoline-3-carboxylic acid 11-43 was synthesized. $^1$H-NMR (500 MHz, DMSO-$d_6$): δ 13.48 (br s, 1H), 9.29 (d, J=2.5 Hz, 1H), 8.93 (d, 1H, J=1.5 Hz), 8.15-8.10 (m, 2H), 7.81-7.78 (m, 1H), 7.67-7.66 (m, 2H), 7.60-7.57 (m, 1H), 4.33 (s, 2H), 3.29-3.25 (m, 1H), 2.38-2.35 (m, 1H), 1.83-1.78 (m, 2H), 1.67-1.50 (m, 6H), 1.19-1.11 (m, 4H). LCMS (ESI): m/z 553.0 (M+H)$^+$.

Example 11-44: 2-((1s,4s)-4-((5-Cyclopropyl-3-(2,6-dichlorophenyl)isoxazol-4-yl)methoxy)-1-hydroxycyclohexyl)quinoline-5-carboxylic acid

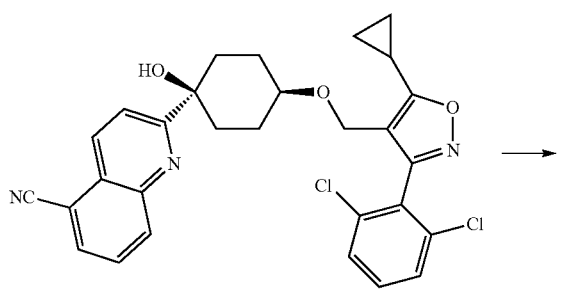

Example 9-23

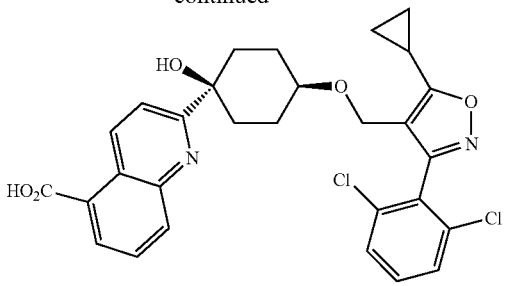

Example 11-44

Following general procedure 1D, beginning with example 2-((1s,4s)-4-((5-cyclopropyl-3-(2,6-dichlorophenyl)isoxazol-4-yl)methoxy)-1-hydroxycyclohexyl)quinoline-5-carbonitrile (9-23), the title compound 2-((1s,4s)-4-((5-cyclopropyl-3-(2,6-dichlorophenyl)isoxazol-4-yl)methoxy)-1-hydroxycyclohexyl)quinoline-5-carboxylic acid 11-44 was synthesized. $^1$H-NMR (500 MHz, CDCl$_3$): δ 9.86 (d, J=9.0 Hz, 1H), 8.85 (d, J=8.5 Hz, 1H), 8.50 (d, J=7.5 Hz, 1H), 8.03-7.98 (m, 1H), 7.75 (d, J=9.0 Hz, 1H), 7.45-7.42 (m, 2H), 7.38-7.33 (m, 1H), 4.41 (s, 2H), 3.39-3.35 (m, 1H), 2.24-2.19 (m, 1H), 2.03-1.98 (m, 2H), 1.90-1.79 (m, 6H), 1.30-1.25 (m, 2H), 1.17-1.10 (m, 2H), hydroxyl and carboxylate protons not resolved. LCMS (ESI): m/z 553.2 (M+H)$^+$.

Example 11-45: 6-((1s,4s)-4-((5-Cyclopropyl-3-(2,6-dichlorophenyl)isoxazol-4-yl)methoxy)-1-hydroxycyclohexyl)-1-isopropyl-1H-indazole-3-carboxylic acid

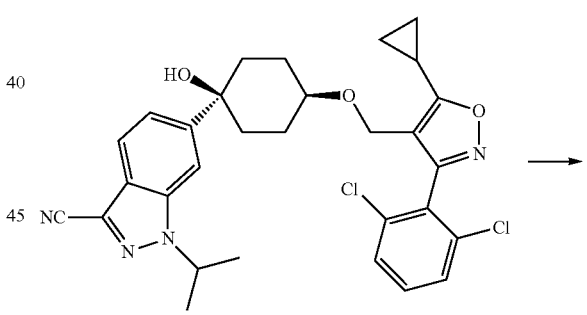

Example 9-24

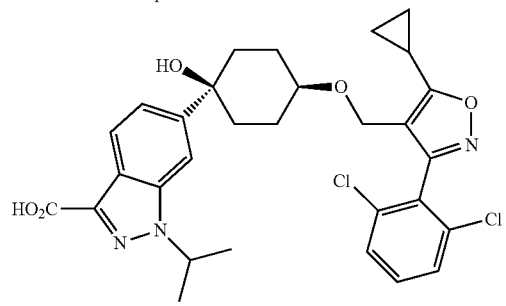

Example 11-45

Following general procedure 1D, beginning with example 6-((1s,4s)-4-((5-cyclopropyl-3-(2,6-di-chlorophenyl)isoxazol-4-yl)methoxy)-1-hydroxycyclohexyl)-1-isopropyl-1H- indazole-3-carbonitrile (9-24), the title compound 6-((1s,4s)-4-((5-cyclopropyl-3-(2,6-dichlorophenyl)isoxazol-4-yl)methoxy)-1-hydroxycyclohexyl)-1-isopropyl-1H-indazole-3-carboxylic acid 11-45 was synthesized. $^1$H-NMR (500 MHz, CDCl$_3$): δ 8.08 (d, J=8.5 Hz, 1H), 7.54 (s, 1H), 7.41-7.39 (m, 2H), 7.34-7.30 (m, 1H), 7.18 (d, J=8.5 Hz, 1H), 4.78-4.75 (m, 1H), 4.37 (s, 2H), 3.27-3.25 (m, 1H), 2.21-2.18 (m, 1H), 1.79-1.62 (m, 8H), 1.48 (d, J=6.5 Hz, 6H), 1.28-1.25 (m, 2H), 1.14-1.10 (m, 2H), hydroxyl and carboxylate protons not resolved. LCMS (ESI): m/z 584.1 (M+H)$^+$.

Example 11-46: 2-((3aR,6aS)-5-((5-Cyclopropyl-3-(2,6-dichlorophenyl)isoxazol-4-yl)methoxy)-2-hydroxyoctahydropentalen-2-yl)-4-fluorobenzo[d]thiazole-6-carboxylic acid

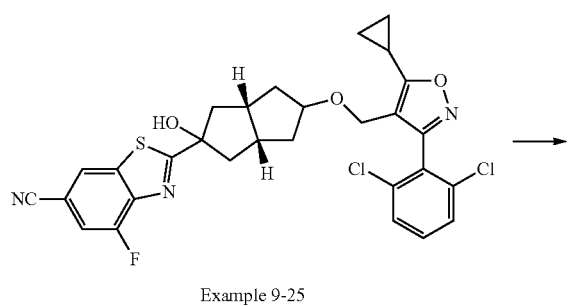

Example 9-25

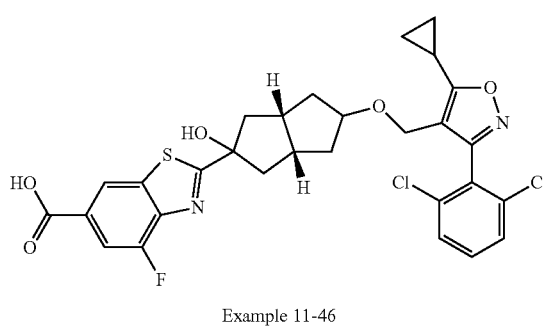

Example 11-46

Following general procedure 1D, beginning with example 2-((3aR,6aS)-5-((5-cyclopropyl-3-(2,6-dichlorophenyl)isoxazol-4-yl)methoxy)-2-hydroxyoctahydropentalen-2-yl)-4-fluorobenzo[d]thiazole-6-carbonitrile (9-25), the title compound 2-((3aR,6aS)-5-((5-cyclopropyl-3-(2,6-dichlorophenyl)isoxazol-4-yl) methoxy)-2-hydroxyoctahydropentalen-2-yl)-4-fluorobenzo[d]thiazole-6-carboxylic acid 11-46 was synthesized. $^1$H-NMR (500 MHz, DMSO-d$_6$): δ 13.33 (br s, 1H), 8.55 (s, 1H), 7.75 (d, 1H, J=11.0 Hz), 7.67-7.65 (m, 2H), 7.60-7.57 (m, 1H), 6.36 (br s, 1H), 4.25 (s, 2H), 3.66-3.62 (m, 1H), 2.58-2.57 (m, 2H), 2.37-2.31 (m, 3H), 1.95-1.89 (m, 4H), 1.54-1.49 (m, 2H), 1.17-1.11 (m, 4H). LC/MS (ESI): m/z 603.0 (M+H)$^+$.

Example 11-47: 4-((3aR,6aS)-5-((5-Cyclopropyl-3-(2,6-dichlorophenyl)isoxazol-4-yl)methoxy)-2-hydroxyoctahydropentalen-2-yl)-3-fluorobenzoic acid

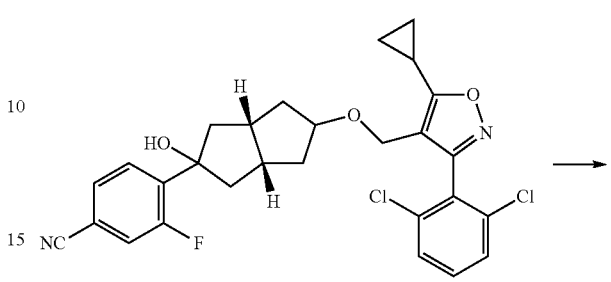

Example 9-26

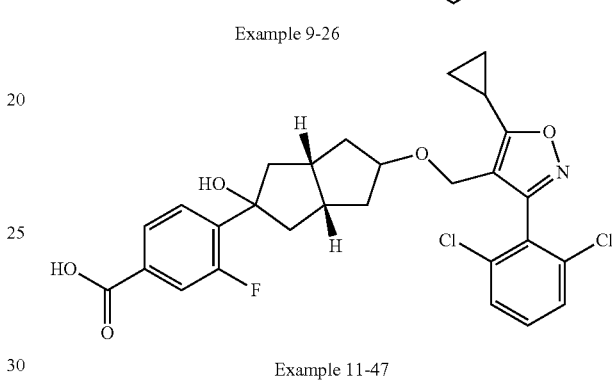

Example 11-47

Following general procedure 1D, beginning with example 4-((3aR,6aS)-5-((5-cyclopropyl-3-(2,6-dichlorophenyl)isoxazol-4-yl)methoxy)-2-hydroxyoctahydropentalen-2-yl)-3-fluorobenzonitrile (9-26), the title compound 4-((3aR,6aS)-5-((5-cyclopropyl-3-(2,6-dichlorophenyl)isoxazol-4-yl)methoxy)-2-hydroxyoctahydropentalen-2-yl)-3-fluorobenzoic acid 11-47 was synthesized. $^1$H-NMR (500 MHz, DMSO-d$_6$): δ 13.15 (br s, 1H), 7.73-7.71 (m, 1H), 7.72-7.53 (m, 5H), 4.23 (s, 2H), 3.61-3.57 (m, 1H), 2.40-2.30 (m, 3H), 2.25-2.20 (m, 2H), 1.91-1.79 (m, 4H), 1.61-1.55 (m, 2H), 1.16-1.10 (m, 4H), hydroxyl proton not resolved. LC/MS (ESI): m/z 546.0 (M+H)$^+$.

Example 11-48: 2-((1R,2S,4R)-5-((5-Cyclopropyl-3-(2,6-dichlorophenyl)isoxazol-4-yl)methoxy)-2-hydroxybicyclo[2.2.1]heptan-2-yl)-4-fluorobenzo[d]thiazole-6-carboxylic acid

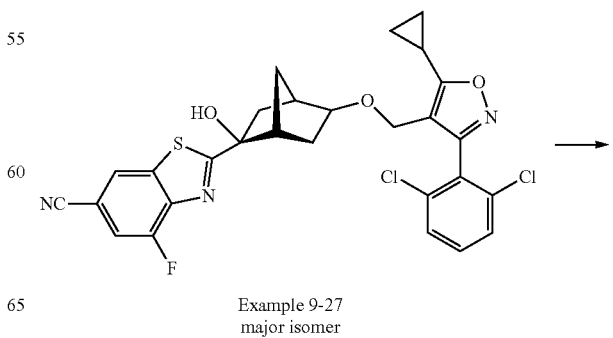

Example 9-27
major isomer

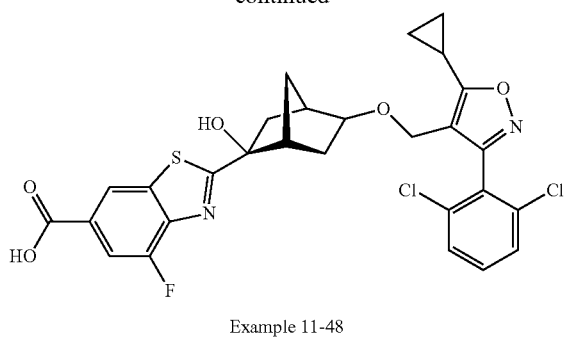

Example 11-48

Following general procedure 1D, beginning with example 2-((1R,2S,4R)-5-((5-cyclopropyl-3-(2,6-dichlorophenyl)isoxazol-4-yl)methoxy)-2-hydroxybicyclo[2.2.1]heptan-2-yl)-4-fluorobenzo[d]thiazole-6-carbonitrile (major isomer 9-27), the title compound 2-((1R,2S,4R)-5-((5-cyclopropyl-3-(2,6-dichlorophenyl)isoxazol-4-yl)methoxy)-2-hydroxybicyclo[2.2.1]heptan-2-yl)-4-fluorobenzo[d]thiazole-6-carboxylic acid 11-48 was synthesized. $^1$H-NMR (500 MHz, DMSO-d$_6$): δ 13.35 (br s, 1H), 8.53 (d, J=1.5 Hz, 1H), 7.75 (dd, J=11.0 Hz, J=1.5 Hz, 1H), 7.67-7.65 (m, 2H), 7.60-7.57 (m, 1H), 6.50 (br s, 1H), 4.27-4.20 (m, 2H), 3.76-3.74 (m, 1H), 2.40-2.38 (m, 1H), 2.25-2.09 (m, 4H), 1.89-1.80 (m, 2H), 1.58-1.56 (m, 1H), 1.25-1.23 (m, 1H), 1.18-1.11 (m, 4H). LC/MS (ESI): m/z 589.1 (M+H)$^+$.

Example 11-49: 2-((1R,2S,4R)-5-((5-Cyclopropyl-3-(2,6-dichlorophenyl)isoxazol-4-yl)methoxy)-2-hydroxybicyclo[2.2.1]heptan-2-yl)-4-fluorobenzo[d]thiazole-6-carboxylic acid

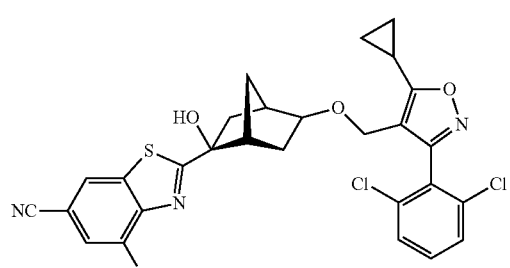

Example 10-27
major isomer

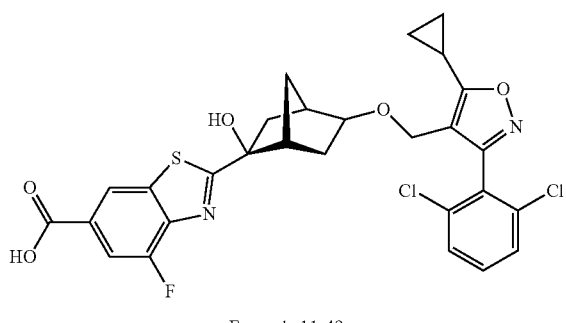

Example 11-49

Following general procedure 1D, beginning with example 2-((1R,2S,4R)-5-((5-cyclopropyl-3-(2,6-dichlorophenyl)isoxazol-4-yl)methoxy)-2-hydroxybicyclo[2.2.1]heptan-2-yl)-4-fluorobenzo[d]thiazole-6-carbonitrile (minor isomer 10-27), the title compound 2-((1R,2S,4R)-5-((5-cyclopropyl-3-(2,6-dichlorophenyl)isoxazol-4-yl)methoxy)-2-hydroxybicyclo[2.2.1]heptan-2-yl)-4-fluorobenzo[d]thiazole-6-carboxylic acid 11-49 was synthesized. $^1$H NMR (500 MHz, DMSO-d$_6$): δ 13.38 (br s, 1H), 8.53 (d, J=1.0 Hz, 1H), 7.75 (dd, J=11.5 Hz, J=1.0 Hz, 1H), 7.65-7.64 (m, 2H), 7.58-7.55 (m, 1H), 6.53 (br s, 1H), 4.30-4.23 (m, 2H), 3.46-3.45 (m, 1H), 2.43-2.30 (m, 3H), 2.16 (br s, 2H), 1.90-1.88 (m, 1H), 1.23-1.09 (m, 6H), 0.90-0.88 (m, 1H). LC/MS (ESI): m/z 589.1 (M+H)$^+$.

Example 11-50: 2-((1R,3s,5S,8r)-3-((5-Cyclopropyl-3-((2,6-dimethylphenoxy)methyl)isoxazol-4-yl)methoxy)-8-hydroxybicyclo[3.2.1]octan-8-yl)-4-fluorobenzo[d]thiazole-6-carboxylic acid

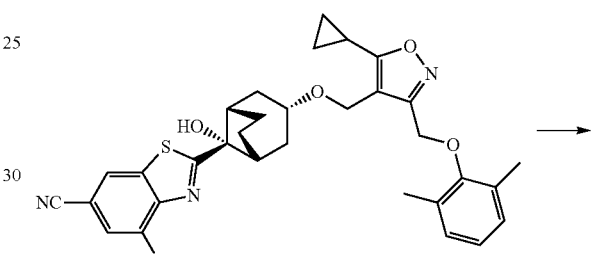

Example 15-23

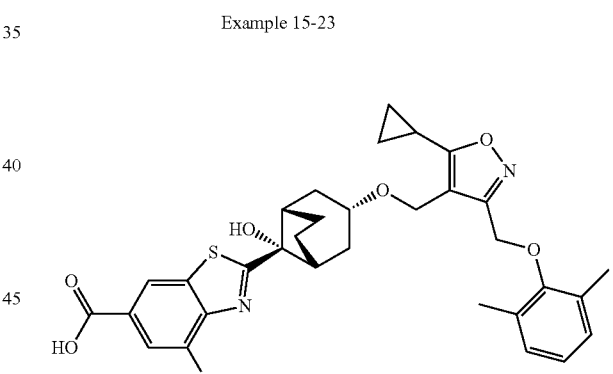

Example 11-50

Following general procedure 1D, beginning with example 2-((1R,3s,5S,8r)-3-((5-cyclopropyl-3-((2,6-dimethylphenoxy)methyl)isoxazol-4-yl)methoxy)-8-hydroxybicyclo[3.2.1]octan-8-yl)-4-fluorobenzo[d]thiazole-6-carbonitrile (15-23), the title compound 2-((1R,3s,5S,8r)-3-((5-Cyclopropyl-3-((2,6-dimethylphenoxy)methyl)isoxazol-4-yl)methoxy)-8-hydroxybicyclo[3.2.1]octan-8-yl)-4-fluorobenzo[d]thiazole-6-carboxylic acid 11-50 was synthesized. $^1$H-NMR (500 MHz, DMSO-d$_6$): δ 13.41 (br s, 1H), 8.57 (d, J=1.5 Hz, 1H), 7.78 (dd, J=11.0 Hz, J=1.5 Hz, 1H), 7.07-6.95 (m, 3H), 6.61 (br s, 1H), 4.85 (s, 2H), 4.48 (s, 2H), 3.81-3.76 (m, 1H), 2.45 (s, 2H), 2.31-2.27 (m, 1H), 2.24 (s, 6H), 2.02 (t, J=11.0 Hz, 2H), 1.87-1.84 (m, 4H), 1.57-1.54 (m, 2H), 1.14-1.02 (s, 4H). LCMS (ESI): m/z 593.2 (M+H)$^+$.

Example 11-51: 2-((1R,3s,5S,8r)-3-((3-(2,6-Dichlorophenyl)-5-isopropylisoxazol-4-yl)methoxy)-8-hydroxybicyclo[3.2.1]octan-8-yl)-4-fluorobenzo[d]thiazole-6-carboxylic acid

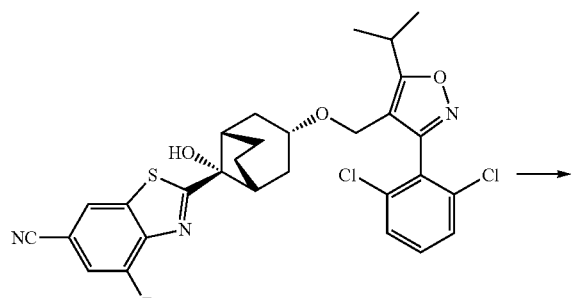

Example 15-20

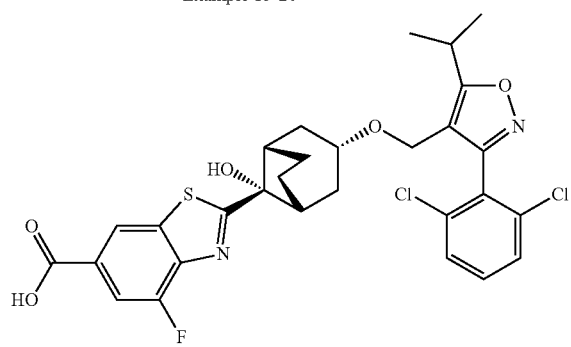

Example 11-51

Following general procedure 1D, beginning with example 2-((1R,3s,5S,8r)-3-((3-(2,6-dichloro-phenyl)-5-isopropylisoxazol-4-yl)methoxy)-8-hydroxybicyclo[3.2.1]octan-8-yl)-4-fluorobenzo[d]thiazole-6-carbonitrile (15-20), the title compound 2-((1R,3s,5S,8r)-3-((3-(2,6-dichlorophenyl)-5-isopropylisoxazol-4-yl)methoxy)-8-hydroxybicyclo[3.2.1]octan-8-yl)-4-fluorobenzo[d]thiazole-6-carboxylic acid 11-51 was synthesized. $^1$H-NMR (500 MHz, DMSO-$d_6$): δ 13.39 (br s, 1H), 8.56 (d, J=1.5 Hz, 1H), 7.77-7.57 (m, 4H), 6.52 (br s, 1H), 4.24 (s, 2H), 3.50-3.45 (m, 1H), 3.42-3.37 (m, 1H), 2.35 (s, 2H), 1.83-1.76 (m, 4H), 1.61-1.56 (m, 2H), 1.43-1.40 (m, 2H), 1.35 (d, J=6.5 Hz, 6H). LCMS (ESI): m/z 605.2 (M+H)$^+$.

Example 11-52: 2-((1R,3s,5S,8r)-3-((3-(2,6-Dichlorophenyl)-5-(2-fluoropropan-2-yl)isoxazol-4-yl)methoxy)-8-hydroxybicyclo[3.2.1]octan-8-yl)-4-fluorobenzo[d]thiazole-6-carboxylic acid

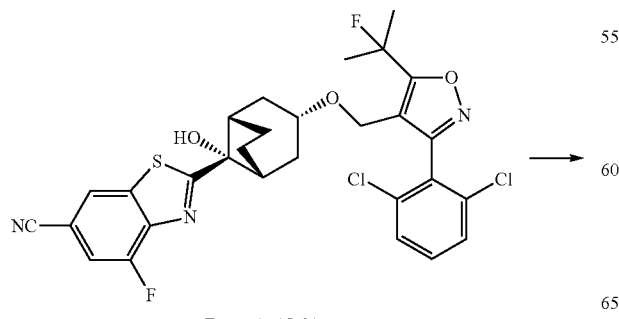

Example 15-21

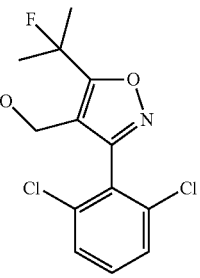

Example 11-52

Following general procedure 1D, beginning with example 2-((1R,3s,5S,8r)-3-((3-(2,6-dichloro-phenyl)-5-(2-fluoropropan-2-yl)isoxazol-4-yl)methoxy)-8-hydroxybicyclo[3.2.1]octan-8-yl)-4-fluorobenzo[d]thiazole-6-carbonitrile (15-21), the title compound 2-((1R,3s,5S,8r)-3-((3-(2,6-dichloro-phenyl)-5-(2-fluoropropan-2-yl)isoxazol-4-yl)methoxy)-8-hydroxybicyclo[3.2.1]octan-8-yl)-4-fluorobenzo[d]thiazole-6-carboxylic acid 11-52 was synthesized. $^1$H-NMR (500 MHz, DMSO-$d_6$): δ 13.67 (br s, 1H), 8.56 (d, J=1.0 Hz, 1H), 7.77-7.59 (dd, J=11.0 Hz, J=1.0 Hz, 1H), 7.69-7.59 (m, 3H), 6.46 (br s, 1H), 4.34 (s, 2H), 3.50-3.44 (m, 1H), 2.34 (s, 2H), 1.87 (s, 3H), 1.83 (s, 3H), 1.80-1.72 (m, 4H), 1.57-1.52 (m, 2H), 1.45-1.38 (m, 2H). LCMS (ESI): m/z 623.0 (M+H)$^+$.

Example 11-53: 3-(3-((1R,3s,5S,8r)-3-((5-Cyclopropyl-3-(2,6-dichlorophenyl)isoxazol-4-yl)methoxy)-8-hydroxybicyclo[3.2.1]octan-8-yl)phenyl)-2,2-dimethylpropanoic acid

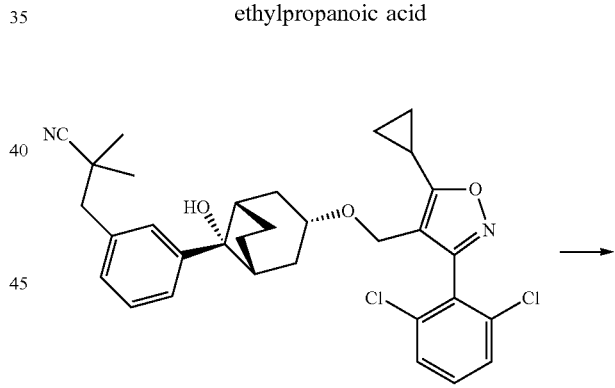

Example 9-29

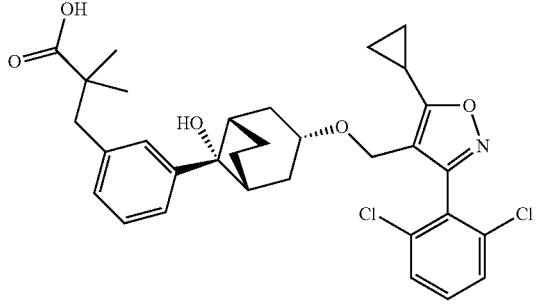

Example 11-53

Following general procedure 1D, beginning with example 2-(3-(1R,3s,5S,8r)-3-((5-cyclopropyl-3-(2,6-dichlorophenyl) isoxazol-4-yl) methoxy)-8-hydroxybicyclo[3.2.1]octan-8-yl)phenyl)-2-methyl-propanenitrile (9-29), the title compound 3-(3-((1R,3s,5S,8r)-3-((5-cyclopropyl-3-(2,6-dichloro-phenyl)isoxazol-4-yl)methoxy)-8-hydroxybicyclo[3.2.1]octan-8-yl)phenyl)-2,2-dimethylpropanoic acid 11-53 was synthesized. ¹H-NMR (500 MHz, DMSO-d₆): δ 12.20 (br s, 1H), 7.67-7.57 (m, 3H), 7.29 (d, J=8.0 Hz, 1H), 7.22-7.18 (m, 2H), 6.99 (d, J=7.0 Hz, 1H), 4.28 (s, 2H), 3.47-3.43 (m, 1H), 2.78 (s, 2H), 2.38-2.34 (m, 3H), 1.87-1.83 (m, 2H), 1.57-1.52 (m, 2H), 1.29-1.10 (m, 8H), 1.05 (s, 6H), hydroxyl proton not resolved. LCMS (ESI): m/z 605.3 (M+Na)⁺.

Example 11-54: 2-((1R,5S)-8-((5-Cyclopropyl-3-(2,6-dichlorophenyl)isoxazol-4-yl)methoxy)-3-hydroxybicyclo[3.2.1]octan-3-yl)-4-fluorobenzo[d]thiazole-6-carboxylic acid

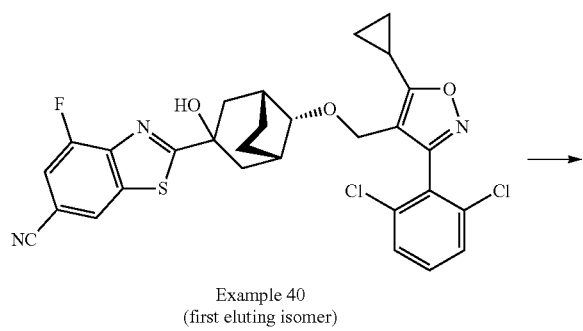

Example 40
(first eluting isomer)

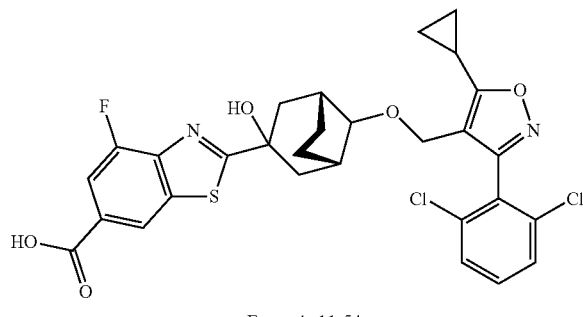

Example 11-54

Following general procedure 1D, beginning with example 2-((1R,5S)-8-((5-cyclopropyl-3-(2,6-dichlorophenyl)isoxazol-4-yl)methoxy)-3-hydroxybicyclo[3.2.1]octan-3-yl)-4-fluorobenzo[d]thiazole-6-carbonitrile 40, the title compound 2-((1R,5S)-8-((5-cyclopropyl-3-(2,6-dichlorophenyl)isoxazol-4-yl)methoxy)-3-hydroxybicyclo[3.2.1]octan-3-yl)-4-fluorobenzo[d]thiazole-6-carboxylic acid 11-54 was synthesized as a single isomer. ¹H-NMR (500 MHz, DMSO-d₆): δ 13.37 (br s, 1H), 8.54 (d, J=1.5 Hz, 1H), 7.76 (dd, J=1.5 Hz, J=11.5 Hz, 1H), 7.60-7.50 (m, 3H), 6.16 (br s, 1H), 4.34 (s, 2H), 3.43 (t, J=4.5 Hz, 1H), 2.46-2.40 (m, 3H), 2.08-2.01 (m, 4H), 1.67-1.65 (m, 2H), 1.52-1.49 (m, 2H), 1.14-1.11 (m, 4H). LCMS (ESI): m/z 603.0 (M+H)⁺.

Example 11-55: 2-((1R,5S)-8-((5-Cyclopropyl-3-(2,6-dichlorophenyl)isoxazol-4-yl)methoxy)-3-hydroxybicyclo[3.2.1]octan-3-yl)-4-fluorobenzo[d]thiazole-6-carboxylic acid

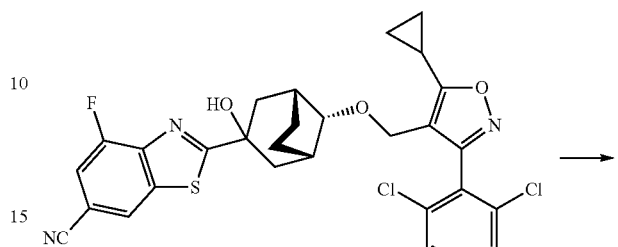

Example 41
(second eluting isomer)

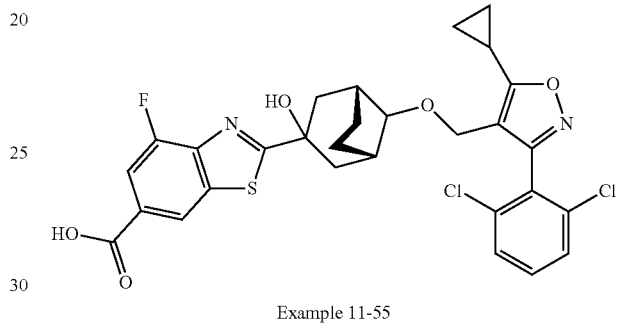

Example 11-55

Following general procedure 1D, beginning with example 2-((1R,5S)-8-((5-cyclopropyl-3-(2,6-dichlorophenyl)isoxazol-4-yl)methoxy)-3-hydroxybicyclo[3.2.1]octan-3-yl)-4-fluorobenzo[d]thiazole-6-carbonitrile 41, the title compound 2-((1R,5S)-8-((5-cyclopropyl-3-(2,6-dichlorophenyl)isoxazol-4-yl)methoxy)-3-hydroxybicyclo[3.2.1]octan-3-yl)-4-fluorobenzo[d]thiazole-6-carboxylic acid 11-55 was synthesized as a single isomer. ¹HNMR (500 MHz, DMSO-d₆): δ 13.42 (br s, 1H), 8.57 (d, J=1.0 Hz, 1H), 7.78 (dd, J=1.5 Hz, J=11.0 Hz, 1H), 7.66-7.56 (m, 3H), 5.90 (br s, 1H), 4.37 (s, 2H), 3.32 (t, J=5.3 Hz, 1H), 2.45-2.39 (m, 3H), 2.15-2.01 (m, 4H), 1.27-1.14 (m, 8H). LC/MS (ESI): m/z 603.1 (M+H)⁺.

Example 11-56: 2-((1R,3s,5S,8r)-3-((3-(2,6-Dichlorophenyl)-5-(2-hydroxypropan-2-yl)isoxazol-4-yl)methoxy)-8-hydroxybicyclo[3.2.1]octan-8-yl)-4-fluorobenzo[d]thiazole-6-carboxylic acid

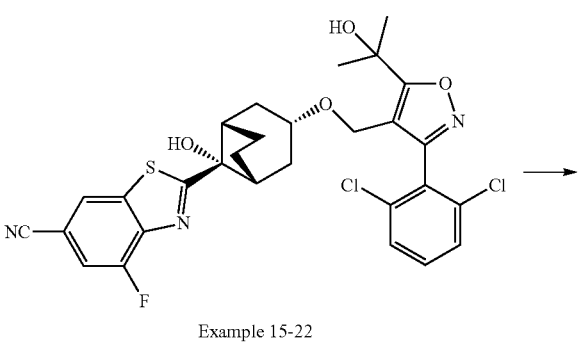

Example 15-22

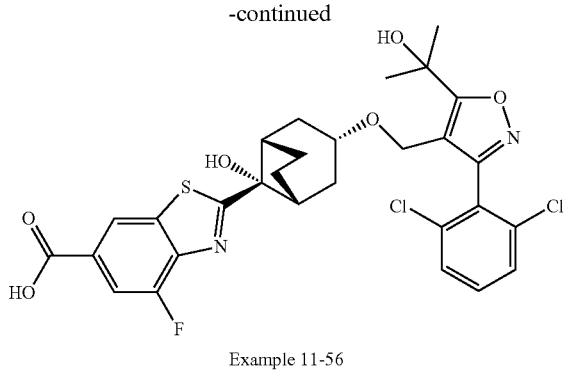

Example 11-56

Following general procedure 1D, beginning with example 2-((1R,3s,5S,8r)-3-((3-(2,6-dichloro-phenyl)-5-(2-hydroxypropan-2-yl)isoxazol-4-yl)methoxy)-8-hydroxybicyclo[3.2.1]octan-8-yl)-4-fluorobenzo[d]thiazole-6-carbonitrile (15-22), the title compound 2-((1R,3s,5S,8r)-3-((3-(2,6-dichlorophenyl)-5-(2-hydroxypropan-2-yl)isoxazol-4-yl)methoxy)-8-hydroxybicyclo[3.2.1]octan-8-yl)-4-fluorobenzo[d]thiazole-6-carboxylic acid 11-56 was synthesized. $^1$H-NMR (500 MHz, DMSO-$d_6$): δ 13.43 (br s, 1H), 8.53 (s, 1H), 7.75 (dd, J=11.0 Hz, J=0.7 Hz, 1H), 7.66-7.55 (m, 3H), 6.48 (s, 1H), 5.81 (s, 1H), 4.46 (s, 2H), 3.50-3.44 (m, 1H), 2.33 (s, 2H), 1.77-1.71 (s, 4H), 1.58-1.53 (m, 8H), 1.42-1.39 (m, 2H). LCMS (ESI): m/z 603.1 (M−H$_2$O+H)$^+$, 621.1 (M+H)$^+$.

Example 11-57: 2-(3-((5-Cyclopropyl-3-(2,6-dichlorophenyl)isoxazol-4-yl)methoxy)-1-hydroxy-cyclopentyl)benzo[d]thiazole-6-carboxylic acid

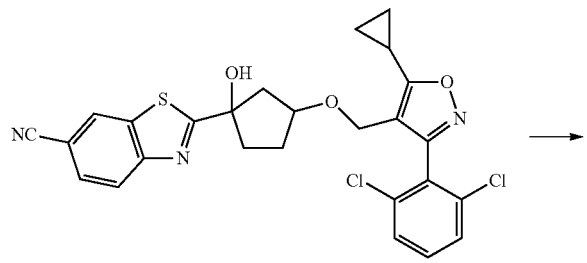

Example 8-17

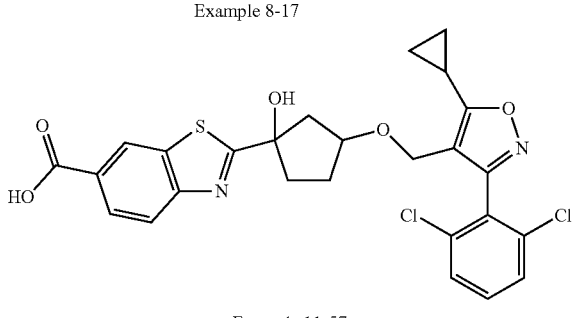

Example 11-57

A solution of 2-(3-((5-cyclopropyl-3-(2,6-dichlorophenyl)isoxazol-4-yl)methoxy)-1-hydroxycyclopentyl)benzo[d]thiazole-6-carbonitrile (8-17, 35 mg, 0.07 mmol) and ethanol (1.5 mL) was treated with 4M NaOH (0.66 mL, 2.7 mmol) and the mixture was stirred at 85° C. overnight. The mixture was cooled to rt and concentrated under vacuum, then cooled in ice bath and treated with water (2 mL) and the pH was adjusted ~4 with 1M HCl. The mixture was extracted twice with EtOAc (30 mL) and the combined organic layer was washed with brine, dried over Na$_2$SO$_4$, filtered and concentrated. Purification by chromatography (ISCO 4 g GOLD silica, 0-100% EtOAc) gave the title compound 2-(3-((5-cyclopropyl-3-(2,6-dichlorophenyl)isoxazol-4-yl)methoxy)-1-hydroxycyclopentyl)benzo[d]thiazole-6-carboxylic acid. $^1$H-NMR (300 MHz, DMSO-$d_6$) δ 13.04 (s, 1H), 8.70-8.61 (m, 1H), 8.04-7.88 (m, 2H), 7.68-7.46 (m, 3H), 6.28 (s, 1H), 4.32-4.12 (m, 2H), 4.10-3.89 (m, 1H), 2.48-2.27 (m, 2H), 2.06-1.91 (m, 3H), 1.86 (dd, J=14.2, 4.4 Hz, 1H), 1.78-1.59 (m, 1H), 1.24-1.01 (m, 4H). MS (M+H): 544.9.

Example 12-1: 2-(4-((1s,4s)-4-((5-Cyclopropyl-3-(2,6-dichlorophenyl)isoxazol-4-yl)methoxy)-1-hydroxycyclohexyl)-3-fluorophenyl)acetonitrile

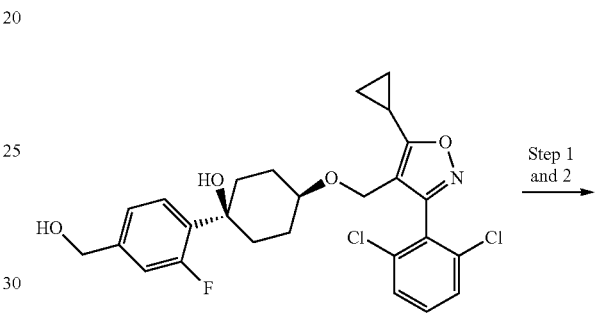

Example 9-6

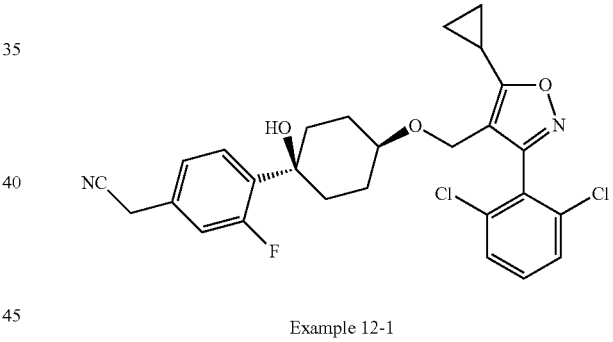

Example 12-1

Step 1:

To a solution of (1s,4s)-4-((5-cyclopropyl-3-(2,6-dichlorophenyl)isoxazol-4-yl)methoxy)-1-(2-fluoro-4-(hydroxymethyl)phenyl)cyclohexanol (9-6) (250 mg, 0.50 mmol) in DCM (10 mL) was added MsCl (91 mg, 0.80 mmol) at 0° C. and the mixture was stirred for 1 h at rt, quenched with water and extracted with DCM three times. The combined organic layers were washed with brine, dried over Na$_2$SO$_4$, filtered and concentrated to yield 4-((1s,4s)-4-((5-cyclopropyl-3-(2,6-dichloro-phenyl)isoxazol-4-yl)methoxy)-1-hydroxycyclohexyl)-3-fluorobenzyl methanesulfonate.

Step 2:

To a solution of 4-((1s,4s)-4-((5-cyclopropyl-3-(2,6-dichlorophenyl)isoxazol-4-yl)methoxy)-1-hydroxycyclohexyl)-3-fluorobenzyl methanesulfonate (238 mg, 0.41 mmol) in MeCN (8 mL) was added K$_2$CO$_3$ (113 mg, 0.82 mmol) and TMSCN (81 mg, 0.82 mmol). The mixture was stirred at 80° C. overnight, quenched with water and extracted with EtOAc. The organic layer was washed with brine, dried over Na$_2$SO$_4$, filtered, concentrated and purified by prep-TLC (PE/EtOAc=4:1) to give 2-(4-((1s,4s)-4-((5-cyclopropyl-3-(2,6-dichlorophenyl)isoxazol-4-yl)methoxy)-1-hydroxycyclohexyl)-3-fluorophenyl)acetonitrile 12-1.

Example 12-2: 2-(3-((1s,4s)-4-((5-Cyclopropyl-3-(2,6-dichlorophenyl)isoxazol-4-yl)methoxy)-1-hydroxycyclohexyl)-4-fluorophenyl)acetonitrile

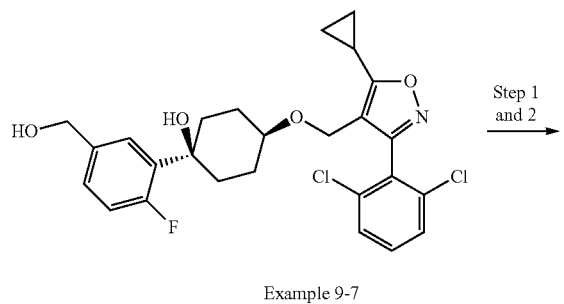

Example 9-7

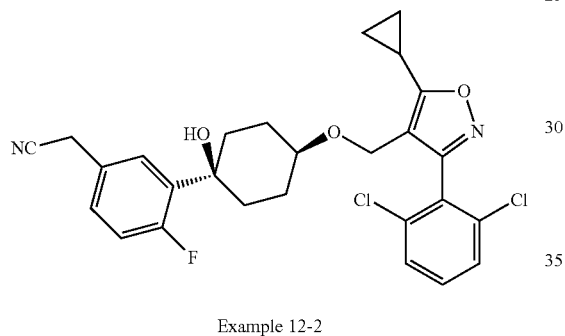

Example 12-2

Similar as described for example 12-1 starting from (1s,4s)-4-((5-cyclopropyl-3-(2,6-dichloro-phenyl)isoxazol-4-yl)methoxy)-1-(2-fluoro-5-(hydroxymethyl)phenyl)cyclohexanol (9-7), the synthesis furnished 2-(3-((1s,4s)-4-((5-cyclopropyl-3-(2,6-dichlorophenyl)isoxazol-4-yl)methoxy)-1-hydroxycyclohexyl)-4-fluorophenyl)acetonitrile 12-2.

General Procedure 1E for the Synthesis of Example 13

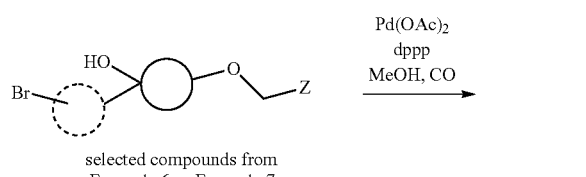

selected compounds from Example 6 or Example 7

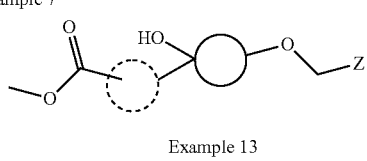

Example 13

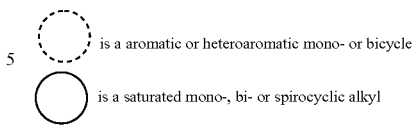

To a solution of the bromide (1.0 eq.), dppp (0.2 eq.), Pd(OAc)$_2$ (0.2 eq.), NEt$_3$ (20 eq.) in MeOH was stirred at 60° C. under a CO atmosphere overnight, cooled, diluted with water and extracted twice with EtOAc. The combined organic phases were washed with brine, dried over Na$_2$SO$_4$, evaporated and the residue was purified by prep-TLC or flash chromatography to afford examples 13.

Example 13-1: Methyl 2-((1s,4s)-4-((5-cyclopropyl-3-(2,6-dichlorophenyl)isoxazol-4-yl)methoxy)-1-hydroxycyclohexyl)-7-fluorobenzo[d]thiazole-6-carboxylate

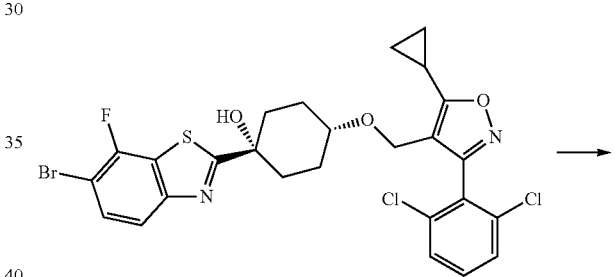

Example 6-5

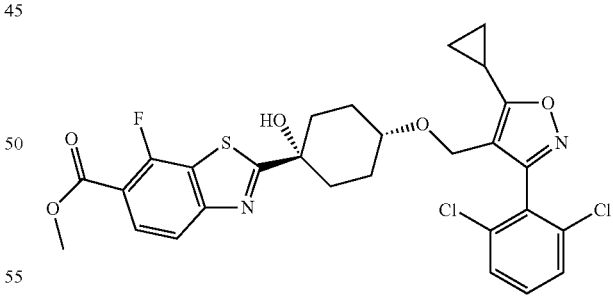

Example 13-1

Following general procedure 1E, starting from (1s,4s)-1-(6-bromo-7-fluorobenzo[d]thiazol-2-yl)-4-((5-cyclopropyl-3-(2,6-dichlorophenyl)isoxazol-4-yl)methoxy)cyclohexanol (6-5), the synthesis furnished methyl 2-((1s,4s)-4-((5-cyclopropyl-3-(2,6-dichlorophenyl)isoxazol-4-yl)methoxy)-1-hydroxycyclohexyl)-7-fluorobenzo[d]thiazole-6-carboxylate 13-1.

Example 13-2: Methyl 2-((1s,4s)-4-((5-cyclopropyl-3-(2,6-dichlorophenyl)isoxazol-4-yl)methoxy)-1-hydroxycyclohexyl)-5,7-difluorobenzo[d]thiazole-6-carboxylate

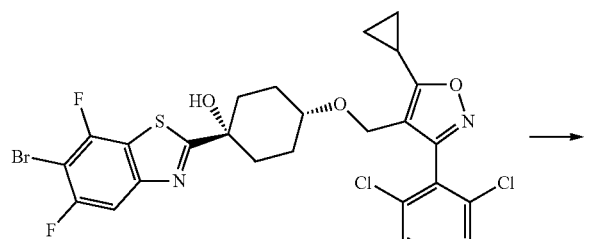

Example 6-4

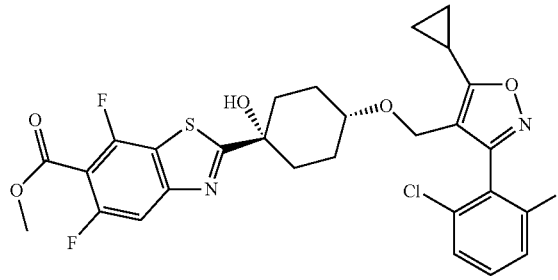

Example 13-2

Following general procedure 1E, starting from (1s,4s)-1-(6-bromo-5,7-difluorobenzo[d]thiazol-2-yl)-4-((5-cyclopropyl-3-(2,6-dichlorophenyl)isoxazol-4-yl)methoxy)cyclohexanol (6-4), the synthesis furnished methyl 2-((1s,4s)-4-((5-cyclopropyl-3-(2,6-dichlorophenyl)isoxazol-4-yl)methoxy)-1-hydroxycyclohexyl)-5,7-difluorobenzo[d]thiazole-6-carboxylate 13-2.

General Procedure 1F for the Synthesis of Example 14

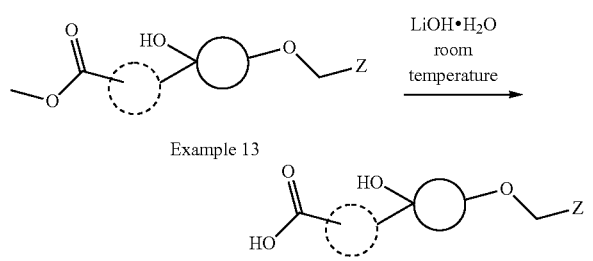

is a aromatic or heteroaromatic mono- or bicycle is a saturated mono-, bi- or spirocyclic alkyl To a solution of the ester (1.0 eq.) in MeOH was added LiOH.H₂O (10 eq.) and the mixture was stirred at rt overnight, concentrated, diluted with water, acidified to pH ~4 and extracted twice with EtOAc. The combined organic phases were washed with brine, dried over Na₂SO₄, evaporated and the residue was purified by prep-HPLC to afford examples 14-1.

Example 14-1: 2-((1s,4s)-4-((5-Cyclopropyl-3-(2,6-dichlorophenyl)isoxazol-4-yl)methoxy)-1-hydroxycyclohexyl)-7-fluorobenzo[d]thiazole-6-carboxylic acid

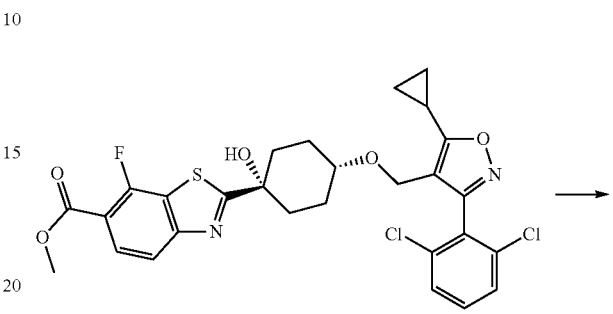

Example 13-1

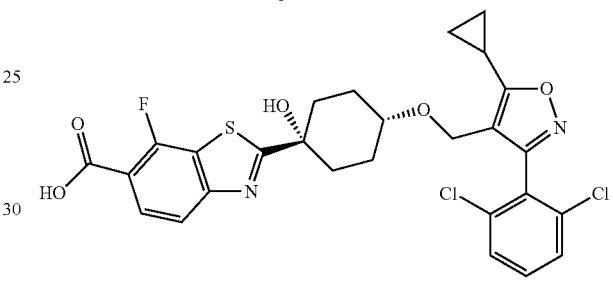

Example 14-1

Following general procedure 1F, starting from methyl 2-((1s,4s)-4-((5-cyclopropyl-3-(2,6-dichloro-phenyl)isoxazol-4-yl)methoxy)-1-hydroxycyclohexyl)-7-fluorobenzo[d]thiazole-6-carboxylate 13-1, the synthesis furnished 2-((1s,4s)-4-((5-cyclopropyl-3-(2,6-dichlorophenyl)isoxazol-4-yl)methoxy)-1-hydroxycyclohexyl)-7-fluorobenzo[d]thiazole-6-carboxylic acid 14-1. $^1$H-NMR (500 MHz, DMSO-d₆): δ 13.40 (br s, 1H), 7.97-7.94 (m, 1H), 7.84 (d, J=8.5 Hz, 1H), 7.66-7.56 (m, 3H), 6.40 (br s, 1H), 4.32 (s, 2H), 3.27-3.23 (m, 1H), 2.38-2.34 (m, 1H), 1.89-1.80 (m, 4H), 1.71-1.68 (m, 2H), 1.49-1.41 (m, 2H), 1.17-1.11 (m, 4H). LC/MS (ESI): m/z 577.0 (M+H)$^+$.

Example 14-2: 2-((1s,4s)-4-((5-Cyclopropyl-3-(2,6-dichlorophenyl)isoxazol-4-yl)methoxy)-1-hydroxycyclohexyl)-5,7-difluorobenzo[d]thiazole-6-carboxylic acid

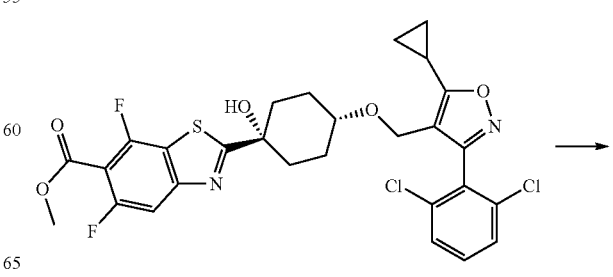

Example 13-2

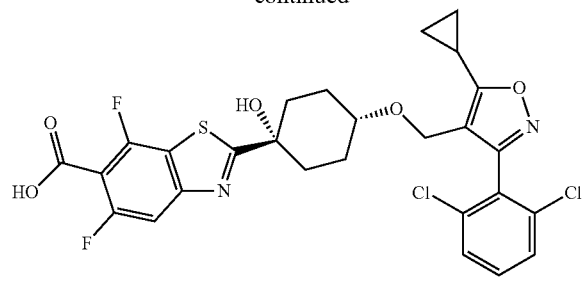

Example 14-2

Following general procedure 1F, starting from methyl 2-((1s,4s)-4-((5-cyclopropyl-3-(2,6-dichloro-phenyl)isoxazol-4-yl)methoxy)-1-hydroxycyclohexyl)-5,7-difluorobenzo[d]thiazole-6-carboxylate 13-2, the synthesis furnished 2-((1s,4s)-4-((5-cyclopropyl-3-(2,6-dichlorophenyl)isoxazol-4-yl)methoxy)-1-hydroxycyclohexyl)-5,7-difluorobenzo[d]thiazole-6-carboxylic acid 14-2. $^1$H-NMR (500 MHz, DMSO-$d_6$): δ 14.05 (br s, 1H), 7.84 (d, J=10.0 Hz, 1H), 7.66-7.60 (m, 2H), 7.58-7.56 (m, 1H), 6.43 (br s, 1H), 4.31 (s, 2H), 3.25-3.23 (m, 1H), 2.37-2.34 (m, 1H), 1.85-1.79 (m, 4H), 1.70-1.67 (m, 2H), 1.46-1.41 (m, 2H), 1.18-1.09 (m, 4H). LC/MS (ESI): m/z 595.0 (M+H)$^+$.

Example 14-3: 1-(3-(((1R,3s,5S,8r)-3-((5-Cyclopropyl-3-(2,6-dichlorophenyl)isoxazol-4-yl)methoxy)-8-hydroxybicyclo[3.2.1]octan-8-yl)-5-fluorophenoxy)cyclopropanecarboxylic acid

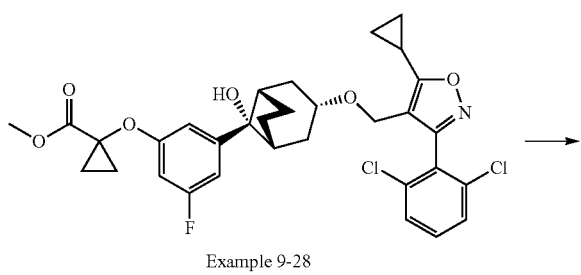

Example 9-28

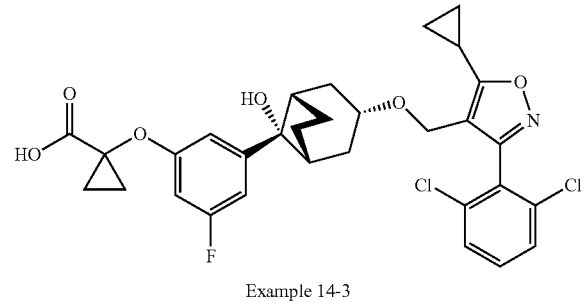

Example 14-3

Following general procedure 1F, starting from methyl 1-(3-(((1R,3s,5S,8r)-3-((5-cyclopropyl-3-(2,6-dichlorophenyl)isoxazol-4-yl)methoxy)-8-hydroxybicyclo[3.2.1]octan-8-yl)-5-fluorophenoxy)cyclopropanecarboxylate (9-28), the synthesis furnished 1-(3-(((1R,3s,5S,8r)-3-((5-cyclopropyl-3-(2,6-dichlorophenyl)isoxazol-4-yl)methoxy)-8-hydroxy-bicyclo[3.2.1]octan-8-yl)-5-fluorophenoxy)cyclopropanecarboxylic acid 14-3. $^1$H-NMR (500 MHz, DMSO-$d_6$): δ 13.02 (br s, 1H), 7.66-7.56 (m, 3H), 6.84 (d, J=10.5 Hz, 1H), 6.79 (s, 1H), 6.60-6.57 (m, 1H), 4.26 (s, 2H), 3.46-3.41 (m, 1H), 2.37-2.34 (m, 1H), 2.26 (s, 2H), 1.80 (t, J=11.0 Hz, 2H), 1.57-1.51 (m, 4H), 1.28-1.09 (m, 10H), hydroxyl proton not resolved. LCMS (ESI): m/z 602.2 (M+H)$^+$.

General Procedure 1G for the Synthesis of Example 15

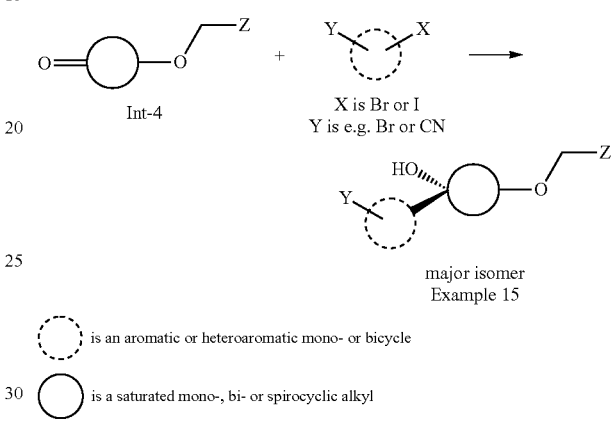

major isomer
Example 15

⟨⋯⟩ is an aromatic or heteroaromatic mono- or bicycle

◯ is a saturated mono-, bi- or spirocyclic alkyl

A solution of n-BuLi, (1.6M in hexane) (2 eq.) was added dropwise over 20 min to a solution of bromo/iodo-deriative (2 eq.) in THF (10 vol.) at −78° C. under an Ar atmosphere. The resulting solution was stirred at −78° C. for 20 min and then a solution of ketone Int-4 (1 eq.) in THF (10 vol.) was added dropwise over 20 min. The solution was stirred at −78° C. for additional 2 h and then quenched with NH$_4$Cl (sat.). The reaction mixture was extracted with EtOAc and the organic layers were combined and washed with brine, dried over Na$_2$SO$_4$ and concentrated. The crude product was purified by silica gel chromatography.

Example 15-1: (1R,3s,5S,8r)-8-(6-Bromobenzo[d]thiazol-2-yl)-3-((5-cyclopropyl-3-(2,6-dichlorophenyl)isoxazol-4-yl)methoxy)bicyclo[3.2.1]octan-8-ol

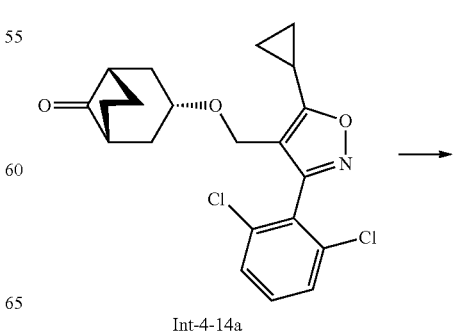

Int-4-14a

217

-continued

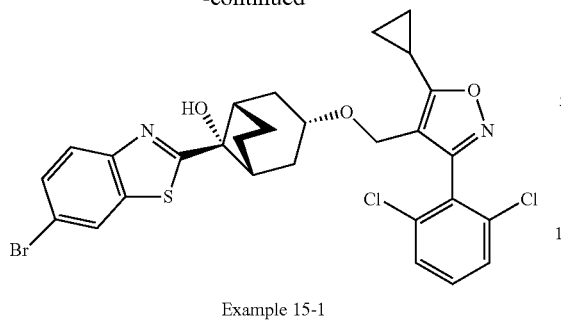

Example 15-1

Following general procedure 1G, starting from (1R,3s, 5S)-3-((5-cyclopropyl-3-(2,6-dichlorophenyl)isoxazol-4-yl)methoxy)bicyclo[3.2.1]octan-8-one (Int-4-14a) and 2,6-dibromobenzo[d]thiazole, the synthesis furnished (1R,3s,5S, 8r)-8-(6-bromobenzo[d]thiazol-2-yl)-3-((5-cyclopropyl-3-(2,6-dichlorophenyl)isoxazol-4-yl)methoxy)bicyclo[3.2.1] octan-8-ol 15-1. $^1$H-NMR (400 MHz, CDCl$_3$): δ 8.02 (d, J=2.0 Hz, 1H), 7.83 (d, J=8.8 Hz, 1H), 7.58 (dd, J=8.8 Hz, J=2.0 Hz, 1H), 7.44-7.33 (m, 3H), 4.35 (s, 2H), 3.65-3.59 (m, 1H), 2.22-2.16 (m, 1H), 2.04-1.73 (m, 8H), 1.53-1.48 (m, 2H), 1.30-1.24 (m, 2H), 1.16-1.10 (m, 2H), hydroxyl proton not resolved. MS (ESI): m/z 620.5 (M+1)$^+$.

Example 15-2: (1R,3r,5S,8r)-8-(6-Bromobenzo[d] thiazol-2-yl)-3-((5-cyclopropyl-3-(2,6-dichlorophenyl)isoxazol-4-yl)methoxy)bicyclo[3.2.1]octan-8-ol

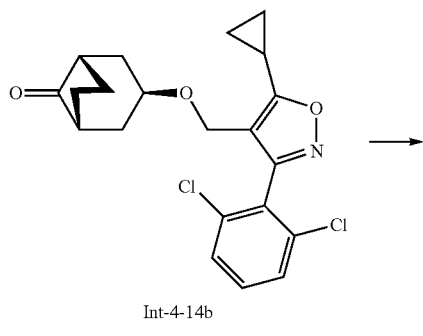

Example 15-2

Following general procedure 1G, starting from (1R,3s, 5S)-3-((5-cyclopropyl-3-(2,6-dichloro-phenyl)isoxazol-4-yl)methoxy)bicyclo[3.2.1]octan-8-one (Int-4-14b) and 2,6-dibromobenzo[d]thiazole, the synthesis furnished (1R,3r,5S, 8r)-8-(6-bromobenzo[d]thiazol-2-yl)-3-((5-cyclopropyl-3-(2,6-dichlorophenyl)isoxazol-4-yl)methoxy)bicyclo[3.2.1] octan-8-ol 15-2.

218

Example 15-3: (1R,3s,5S,8r)-8-(4-Bromo-2-fluorophenyl)-3-((5-cyclopropyl-3-(2,6-dichlorophenyl)isoxazol-4-yl)methoxy)bicyclo[3.2.1]octan-8-ol

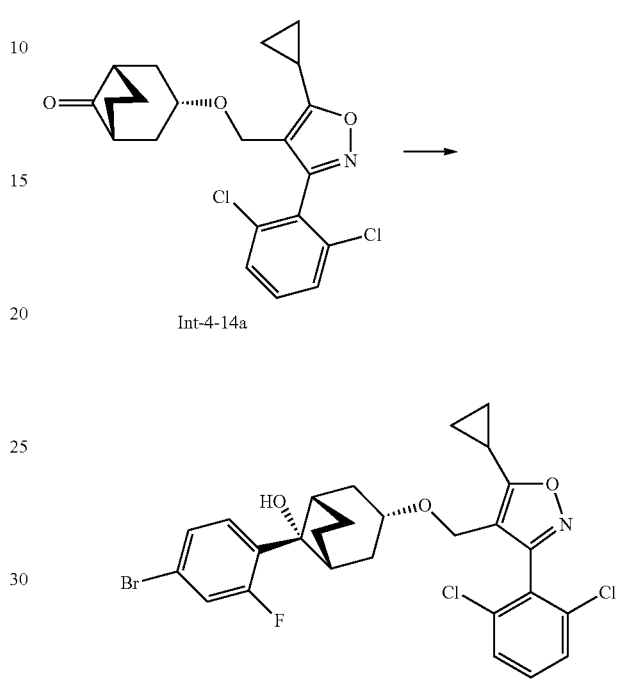

Example 15-3

Following general procedure 1G, starting from (1R,3s, 5S)-3-((5-cyclopropyl-3-(2,6-dichloro-phenyl)isoxazol-4-yl)methoxy)bicyclo[3.2.1]octan-8-one (Int-4-14a) and 4-bromo-2-fluoro-1-iodobenzene, the synthesis furnished (1R,3s,5S,8r)-8-(4-bromo-2-fluorophenyl)-3-((5-cyclopropyl-3-(2,6-dichlorophenyl)isoxazol-4-yl)methoxy)bicyclo [3.2.1]octan-8-ol 15-3.

Example 15-4: (1R,3s,5S,8r)-8-(3-Bromophenyl)-3-((5-cyclopropyl-3-(2,6-dichlorophenyl)isoxazol-4-yl)methoxy)bicyclo[3.2.1]octan-8-ol

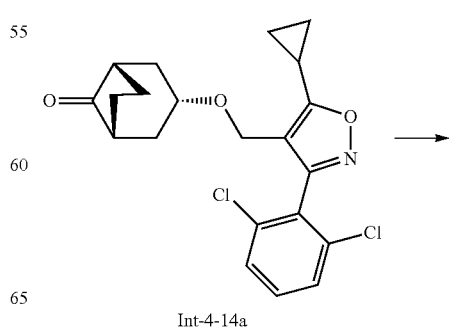

Int-4-14a

-continued

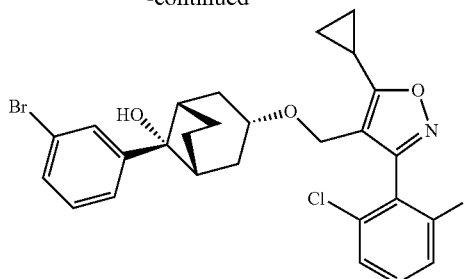

Example 15-4

Following general procedure 1G, starting from (1R,3s,5S)-3-((5-cyclopropyl-3-(2,6-dichloro-phenyl)isoxazol-4-yl)methoxy)bicyclo[3.2.1]octan-8-one (Int-4-14a) and 1,3-dibromobenzene, the synthesis furnished (1R,3s,5S,8r)-8-(3-bromophenyl)-3-((5-cyclopropyl-3-(2,6-dichlorophenyl)isoxazol-4-yl)methoxy)bicyclo[3.2.1]octan-8-ol 15-4.

Example 15-5: 2-((1R,3s,5S,8r)-3-((5-Cyclopropyl-3-(2,6-dichlorophenyl)isoxazol-4-yl)methoxy)-8-hydroxybicyclo[3.2.1]octan-8-yl)isonicotinonitrile

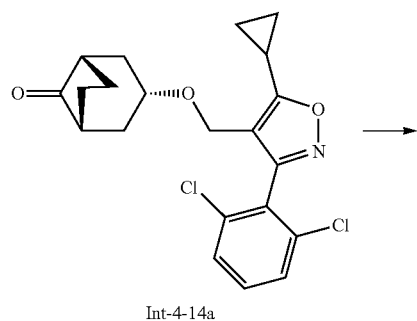

Int-4-14a

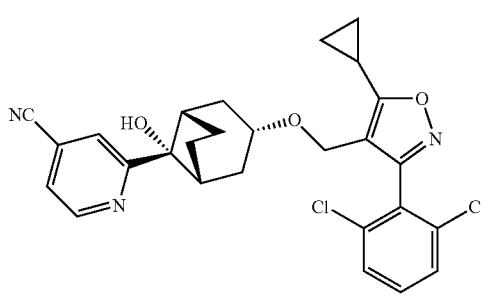

Example 15-5

Following general procedure 1G, starting from (1R,3s,5S)-3-((5-cyclopropyl-3-(2,6-dichloro-phenyl)isoxazol-4-yl)methoxy)bicyclo[3.2.1]octan-8-one (Int-4-14a) and 2-bromoisonicotinonitrile, the synthesis furnished 2-((1R,3s,5S,8r)-3-((5-cyclopropyl-3-(2,6-dichlorophenyl)isoxazol-4-yl)methoxy)-8-hydroxybicyclo[3.2.1]octan-8-yl)isonicotinonitrile 15-5.

Example 15-6: (1R,3s,5S,8r)-8-(6-Bromo-4-fluorobenzo[d]thiazol-2-yl)-3-((5-cyclopropyl-3-(2,6-dichlorophenyl)isoxazol-4-yl)methoxy)bicyclo[3.2.1]octan-8-ol

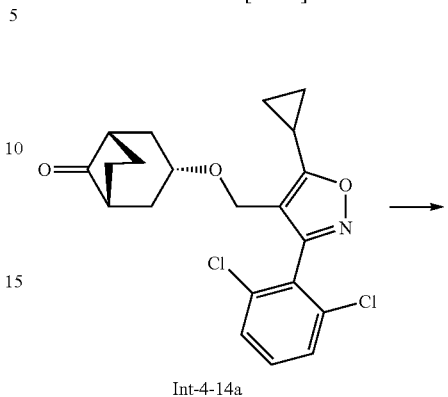

Int-4-14a

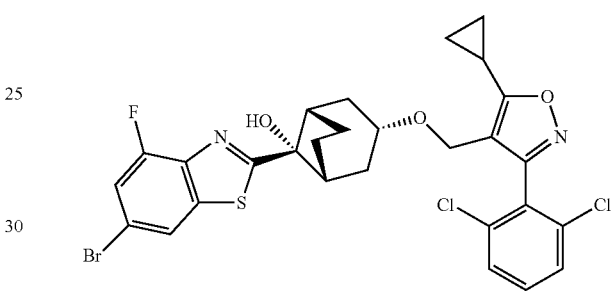

Example 15-6

Following general procedure 1G, starting from (1R,3s,5S)-3-((5-cyclopropyl-3-(2,6-dichloro-phenyl)isoxazol-4-yl)methoxy)bicyclo[3.2.1]octan-8-one (Int-4-14a) and 6-bromo-4-fluorobenzo[d]thiazol-2-amine (Int-6-5), the synthesis furnished (1R,3s,5S,8r)-8-(6-bromo-4-fluorobenzo[d]thiazol-2-yl)-3-((5-cyclopropyl-3-(2,6-dichlorophenyl)isoxazol-4-yl)methoxy)bicyclo[3.2.1]octan-8-ol 15-6.

Example 15-7: (1R,3s,5S,8r)-8-(6-Bromo-4-fluorobenzo[d]thiazol-2-yl)-3-((5-cyclopropyl-3-(2-(difluoromethoxy)phenyl)isoxazol-4-yl)methoxy)bicyclo[3.2.1]octan-8-ol

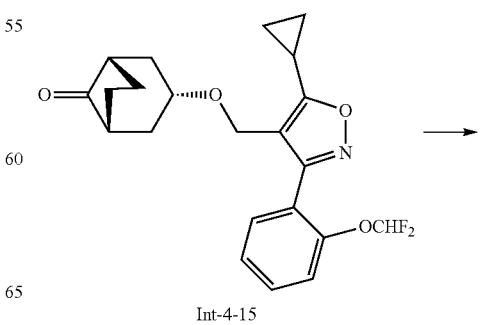

Int-4-15

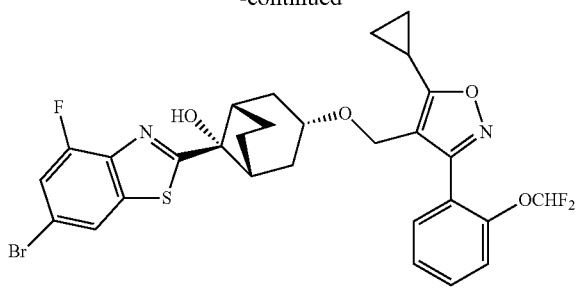

Example 15-7

Following general procedure 1G, starting from (1R,3s, 5S)-3-((5-cyclopropyl-3-(2-(difluoro-methoxy)phenyl)isoxazol-4-yl)methoxy)bicyclo[3.2.1]octan-8-one (Int-4-15) and 6-bromo-4-fluorobenzo[d]thiazol-2-amine (Int-6-5), the synthesis furnished (1R,3s,5S,8r)-8-(6-bromo-4-fluorobenzo[d]thiazol-2-yl)-3-((5-cyclopropyl-3-(2-(difluoromethoxy)phenyl)isoxazol-4-yl)methoxy)bicyclo[3.2.1]octan-8-ol 15-7.

Example 15-8: (1R,3s,5S,8r)-8-(6-Bromo-4-fluorobenzo[d]thiazol-2-yl)-3-((5-cyclopropyl-3-(3,5-dichloropyridin-4-yl)isoxazol-4-yl)methoxy)bicyclo[3.2.1]octan-8-ol

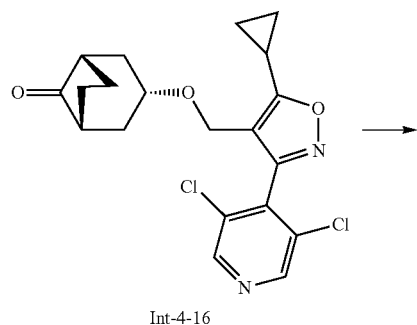

Int-4-16

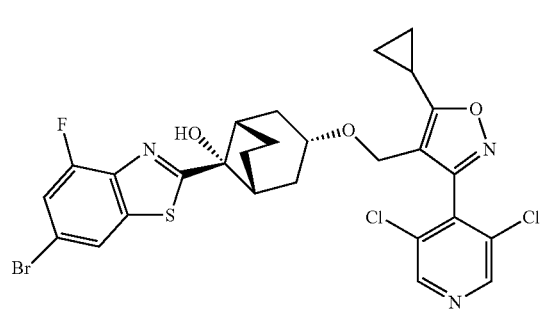

Example 15-8

Following general procedure 1G, starting from (1R,3s, 5S)-3-((5-cyclopropyl-3-(3,5-dichloropyridin-4-yl)isoxazol-4-yl)methoxy)bicyclo[3.2.1]octan-8-one (Int-4-16) and 6-bromo-4-fluorobenzo[d]thiazol-2-amine (Int-6-5), the synthesis furnished (1R,3s,5S,8r)-8-(6-bromo-4-fluorobenzo[d]thiazol-2-yl)-3-((5-cyclopropyl-3-(3,5-dichloropyridin-4-yl)isoxazol-4-yl)methoxy)bicyclo[3.2.1]octan-8-ol 15-8.

Example 15-9: (1s,4s)-1-(6-Bromobenzo[d]thiazol-2-yl)-4-((5-cyclopropyl-3-(2,6-dichlorophenyl)isoxazol-4-yl)methoxy)cyclohexan-1-ol

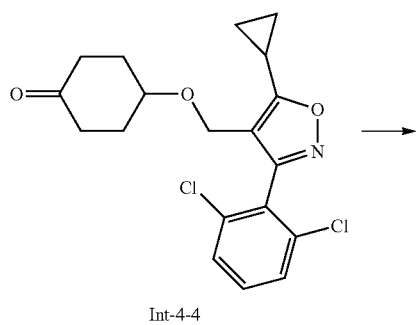

Int-4-4

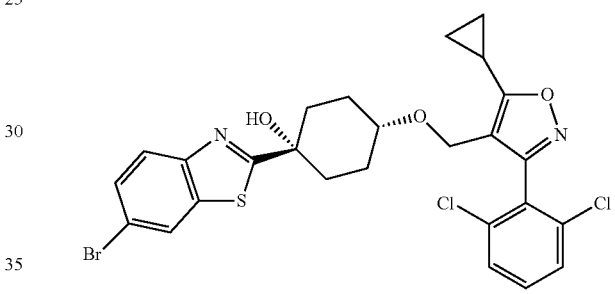

Example 15-9

Following general procedure 1G, starting from 4-((5-cyclopropyl-3-(2,6-dichlorophenyl)isoxazol-4-yl)methoxy)cyclohexanone (Int-4-4) and 2,6-dibromobenzo[d]thiazole, the synthesis furnished (1s,4s)-1-(6-bromobenzo[d]thiazol-2-yl)-4-((5-cyclopropyl-3-(2,6-dichlorophenyl)isoxazol-4-yl)methoxy)cyclohexan-1-ol 15-9.

Example 15-10: (1s,4s)-1-(6-Bromo-4-fluorobenzo[d]thiazol-2-yl)-4-((5-cyclopropyl-3-(2,6-dichlorophenyl)isoxazol-4-yl)methoxy)cyclohexan-1-ol

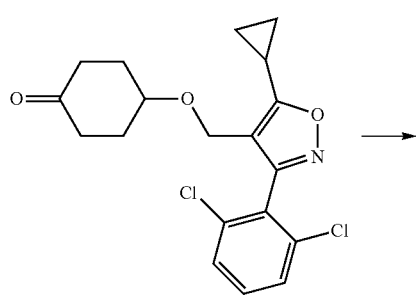

Int-4-4

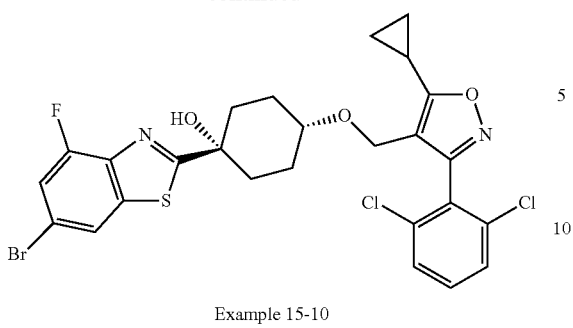

Example 15-10

Following general procedure 1G, starting from 4-((5-cyclopropyl-3-(2,6-dichlorophenyl)isoxazol-4-yl)methoxy)cyclohexanone (Int-4-4) and 6-bromo-4-fluorobenzo[d]thiazol-2-amine (Int-6-5), the synthesis furnished (1s,4s)-1-(6-bromo-4-fluorobenzo[d]thiazol-2-yl)-4-((5-cyclopropyl-3-(2,6-dichlorophenyl)isoxazol-4-yl)methoxy)cyclohexan-1-ol 15-10.

Example 15-11: 2-((1R,3s,5S,8r)-3-((3-(2,6-Dichlorophenyl)-5-methylisoxazol-4-yl)methoxy)-8-hydroxybicyclo[3.2.1]octan-8-yl)benzo[d]thiazole-6-carbonitrile

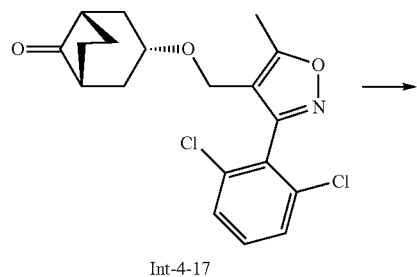

Int-4-17

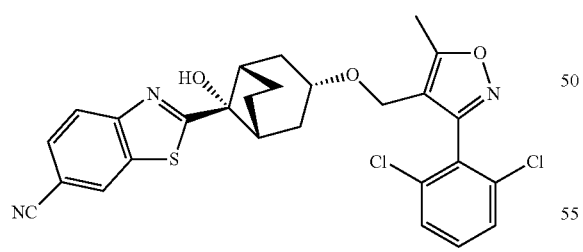

Example 15-11

Following general procedure 1G, starting from (1R,3s,5S)-3-((3-(2,6-dichlorophenyl)-5-methylisoxazol-4-yl)methoxy)bicyclo[3.2.1]octan-8-one (Int-4-17) and 2-bromobenzo[d]thiazole-6-carbonitrile, the synthesis furnished 2-((1R,3s,5S,8r)-3-((3-(2,6-dichlorophenyl)-5-methylisoxazol-4-yl)methoxy)-8-hydroxybicyclo[3.2.1]octan-8-yl)benzo[d]thiazole-6-carbonitrile 15-11.

Example 15-12: 2-((1R,3r,5S,8r)-3-((3-(2,6-Dichlorophenyl)-5-methylisoxazol-4-yl)methoxy)-8-hydroxybicyclo[3.2.1]octan-8-yl)benzo[d]thiazole-6-carbonitrile

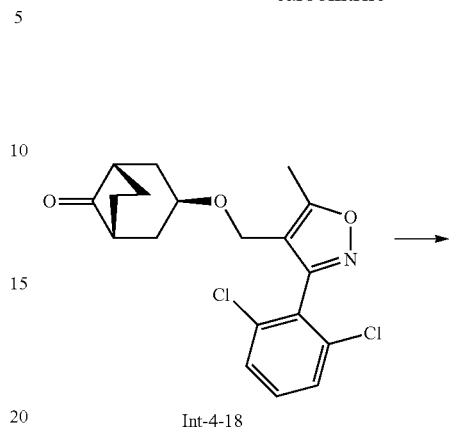

Int-4-18

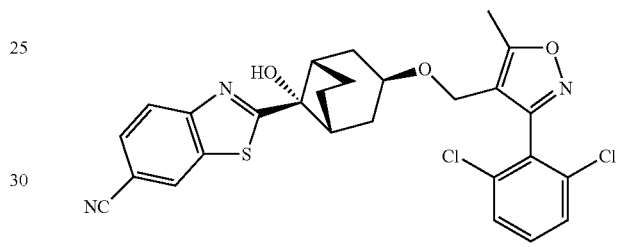

Example 15-12

Following general procedure 1G, starting from (1R,3r,5S)-3-((3-(2,6-dichlorophenyl)-5-methylisoxazol-4-yl)methoxy)bicyclo[3.2.1]octan-8-one (Int-4-18) and 2-bromobenzo[d]thiazole-6-carbonitrile, the synthesis furnished 2-((1R,3r,5S,8r)-3-((3-(2,6-dichlorophenyl)-5-methylisoxazol-4-yl)methoxy)-8-hydroxybicyclo[3.2.1]octan-8-yl)benzo[d]thiazole-6-carbonitrile 15-12.

Example 15-13: 2-((1R,5S,8r)-3-((5-Cyclopropyl-3-(2,6-dichlorophenyl)isoxazol-4-yl)methoxy)-8-hydroxy-3-methylbicyclo[3.2.1]octan-8-yl)-4-fluorobenzo[d]thiazole-6-carbonitrile

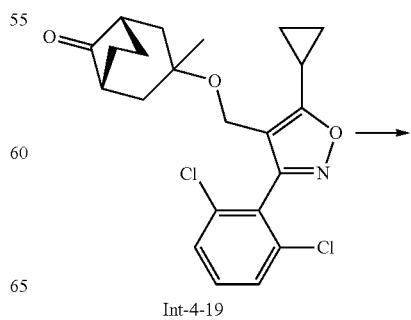

Int-4-19

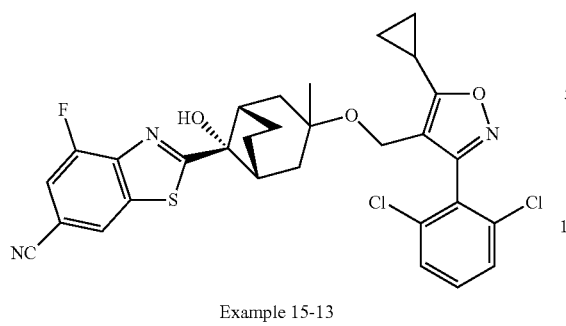

Example 15-13

Following general procedure 1G, starting from (1R,5S)-3-((5-cyclopropyl-3-(2,6-dichlorophenyl)isoxazol-4-yl)methoxy)-3-methylbicyclo[3.2.1]octan-8-one (Int-4-19) and 6-bromo-4-fluorobenzo[d]thiazol-2-amine (Int-6-5), the synthesis furnished 2-((1R,5S,8r)-3-((5-cyclopropyl-3-(2,6-dichlorophenyl)isoxazol-4-yl)methoxy)-8-hydroxy-3-methylbicyclo[3.2.1]octan-8-yl)-4-fluorobenzo[d]thiazole-6-carbonitrile 15-13 as a single isomer.

Example 15-14: 2-((1R,5S,8r)-3-((5-Cyclopropyl-3-(2,6-dichlorophenyl)isoxazol-4-yl)methoxy)-3-(difluoromethyl)-8-hydroxybicyclo[3.2.1]octan-8-yl)-4-fluorobenzo[d]thiazole-6-carbonitrile

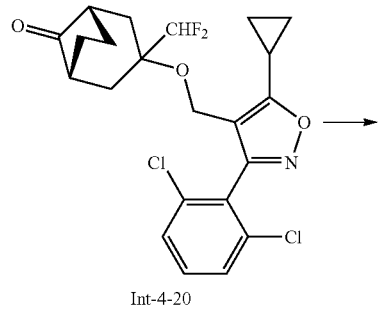

Int-4-20

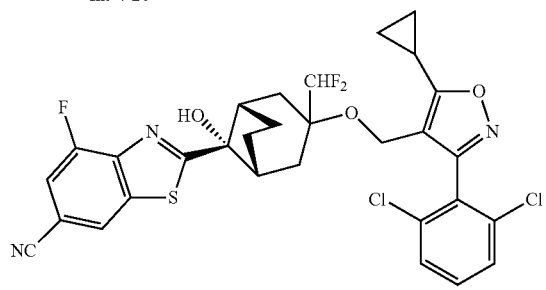

Example 15-14

Following general procedure 1G, starting from (1R,5S)-3-((5-cyclopropyl-3-(2,6-dichlorophenyl)isoxazol-4-yl)methoxy)-3-(difluoromethyl)bicyclo[3.2.1]octan-8-one (Int-4-20) and 6-bromo-4-fluorobenzo[d]thiazol-2-amine (Int-6-5), the synthesis furnished 2-((1R,5S,8r)-3-((5-cyclopropyl-3-(2,6-dichlorophenyl)isoxazol-4-yl)methoxy)-3-(difluoromethyl)-8-hydroxybicyclo[3.2.1]octan-8-yl)-4-fluorobenzo[d]thiazole-6-carbonitrile 15-14 as a single isomer.

Example 15-15: 2-((1R,5S,8r)-3-((5-Cyclopropyl-3-(2,6-dichlorophenyl)isoxazol-4-yl)methoxy)-8-hydroxy-3-(methoxymethyl)bicyclo[3.2.1]octan-8-yl)-4-fluorobenzo[d]thiazole-6-carbonitrile

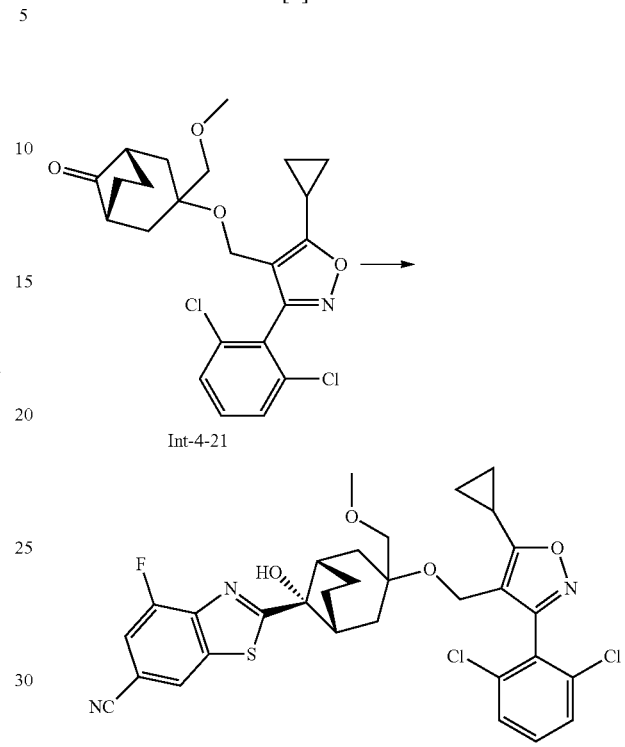

Int-4-21

Example 15-15

Following general procedure 1G, starting from 5-cyclopropyl-3-(2,6-dichlorophenyl)-4-((((1R,5S)-3-(methoxymethyl)spiro[bicyclo[3.2.1]octane-8,2'-[1,3]dioxolan]-3-yl)oxy)methyl)isoxazole (Int-4-21) and 6-bromo-4-fluorobenzo[d]thiazol-2-amine (Int-6-5), the synthesis furnished 2-((1R,5S,8r)-3-((5-cyclopropyl-3-(2,6-dichlorophenyl) isoxazol-4-yl) methoxy)-8-hydroxy-3-(methoxymethyl)bicyclo[3.2.1]octan-8-yl)-4-fluorobenzo[d]thiazole-6-carbonitrile 15-15 as a single isomer.

Example 15-16: (1s,4s)-1-(7-(1,3-Dioxolan-2-yl)benzo[d]thiazol-2-yl)-4-((5-cyclopropyl-3-(2,6-dichlorophenyl)isoxazol-4-yl)methoxy)cyclohexan-1-ol

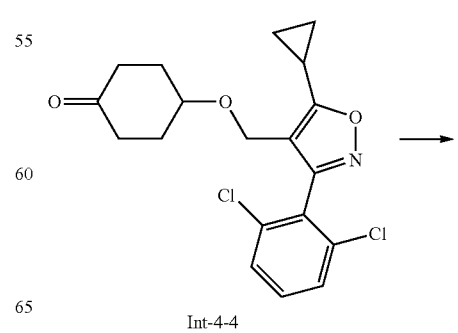

Int-4-4

-continued

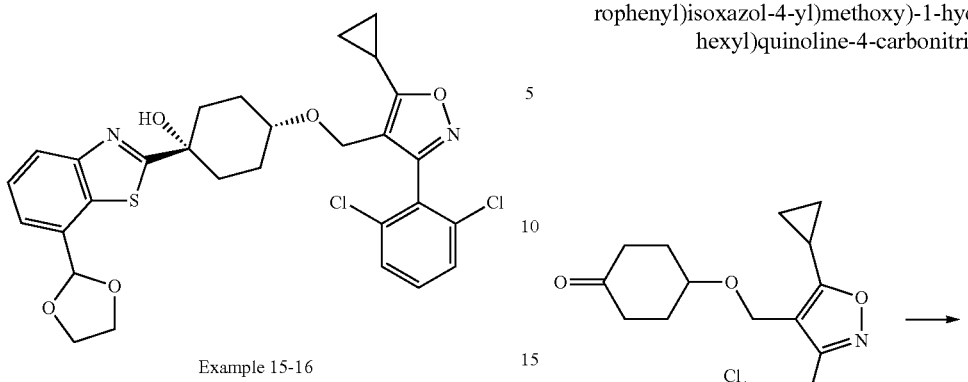

Example 15-16

Following general procedure 1G, starting from 4-((5-cyclopropyl-3-(2,6-dichlorophenyl)isoxazol-4-yl)methoxy)cyclohexanone (Int-4-4) and 7-(1,3-dioxolan-2-yl)benzo[d]thiazole Int-6-8, the synthesis furnished (1s,4s)-1-(7-(1,3-dioxolan-2-yl)benzo[c]thiazol-2-yl)-4-((5-cyclopropyl-3-(2,6-dichlorophenyl)isoxazol-4-yl)methoxy)cyclohexan-1-ol 15-16.

Example 15-17: (1s,4s)-1-(4-Chloroquinolin-7-yl)-4-((5-cyclopropyl-3-(2,6-dichlorophenyl)isoxazol-4-yl)methoxy)cyclohexan-1-ol

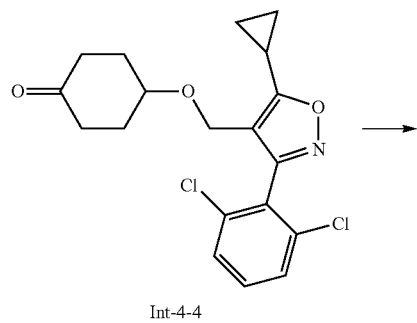

Example 15-17

Following general procedure 1G, starting from 4-((5-cyclopropyl-3-(2,6-dichlorophenyl)isoxazol-4-yl)methoxy)cyclohexanone (Int-4-4) and 7-bromo-4-chloroquinoline, the synthesis furnished (1s,4s)-1-(4-chloroquinolin-7-yl)-4-((5-cyclopropyl-3-(2,6-dichlorophenyl)isoxazol-4-yl)methoxy)cyclohexan-1-ol 15-17.

Example 15-18: 6-(4-((5-Cyclopropyl-3-(2,6-dichlorophenyl)isoxazol-4-yl)methoxy)-1-hydroxy-cyclohexyl)quinoline-4-carbonitrile

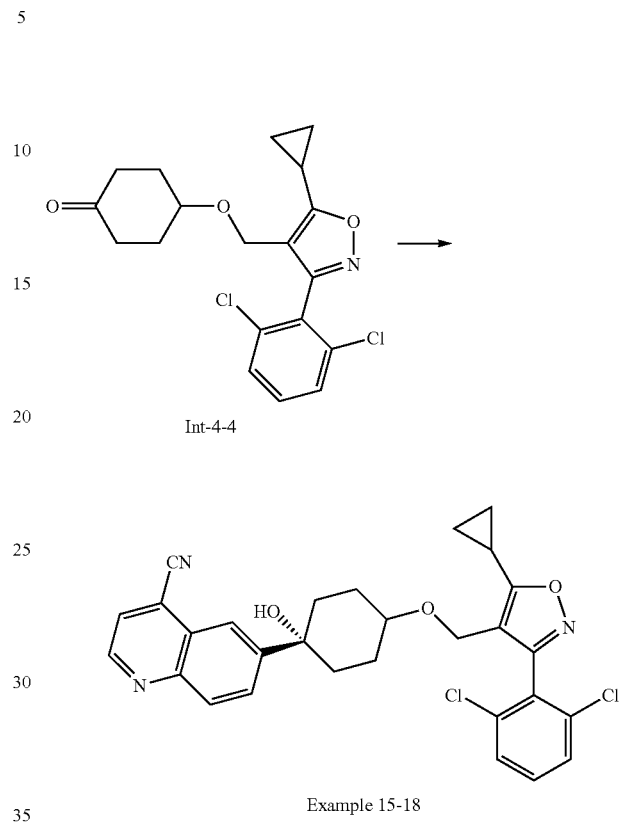

Example 15-18

Following general procedure 1G, starting from 4-((5-cyclopropyl-3-(2,6-dichlorophenyl)isoxazol-4-yl)methoxy)cyclohexanone (Int-4-4) and 6-iodoquinoline-4-carbonitrile Int-6-9, the synthesis furnished 6-(4-((5-cyclopropyl-3-(2,6-dichlorophenyl)isoxazol-4-yl)methoxy)-1-hydroxycyclohexyl)quinoline-4-carbonitrile 15-18.

Example 15-19: (1s,4s)-4-((5-Cyclopropyl-3-(2,6-dichlorophenyl)isoxazol-4-yl)methoxy)-1-(3-(hydroxymethyl)benzo[d]isothiazol-5-yl)cyclohexan-1-ol

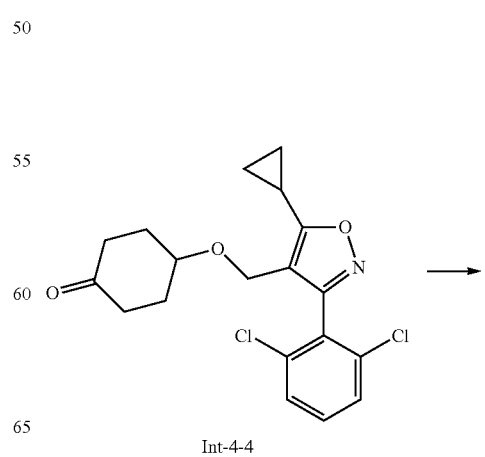

Int-4-4

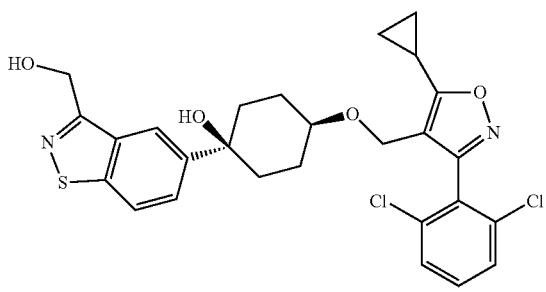

Example 15-19

Following general procedure 1G, starting from 4-((5-cyclopropyl-3-(2,6-dichlorophenyl)isoxazol-4-yl)methoxy)cyclohexanone (Int-4-4) and (5-bromobenzo[d]isothiazol-3-yl)methanol Int-6-10, the synthesis furnished (1s,4s)-4-((5-cyclopropyl-3-(2,6-dichlorophenyl)isoxazol-4-yl)methoxy)-1-(3-(hydroxymethyl)benzo[d]isothiazol-5-yl)cyclohexan-1-ol 15-19.

Example 15-20: 2-((1R,3s,5S,8r)-3-((3-(2,6-Dichlorophenyl)-5-isopropylisoxazol-4-yl)methoxy)-8-hydroxybicyclo[3.2.1]octan-8-yl)-4-fluorobenzo[d]thiazole-6-carbonitrile

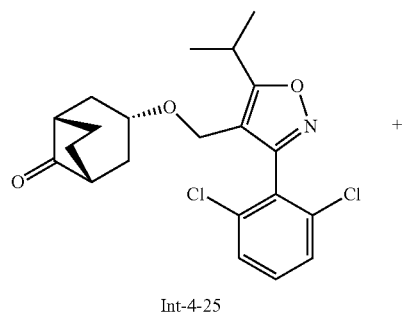

Int-4-25

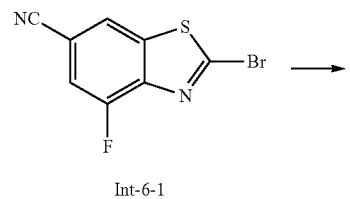

Int-6-1

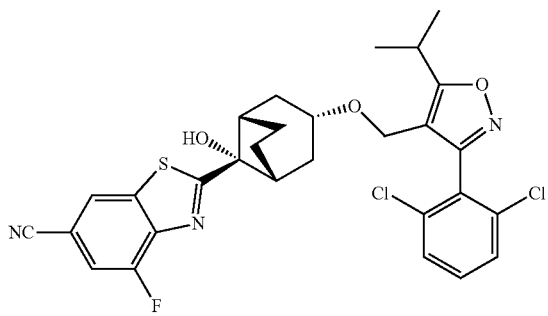

Example 15-20

Following general procedure 1G, beginning with intermediate (1R,3s,5S)-3-((3-(2,6-dichloro-phenyl)-5-isopropylisoxazol-4-yl)methoxy)bicyclo[3.2.1]octan-8-one Int-4-25 and 2-bromo-4-fluorobenzo[d]thiazole-6-carbonitrile Int-6-1, the title compound 2-((1R,3s,5S,8r)-3-((3-(2,6-dichlorophenyl)-5-isopropylisoxazol-4-yl)methoxy)-8-hydroxybicyclo[3.2.1]octan-8-yl)-4-fluorobenzo[d]thiazole-6-carbonitrile (15-20) was synthesized (the minor isomer was not isolated).

Example 15-21: 2-((1R,3s,5S,8r)-3-((3-(2,6-Dichlorophenyl)-5-(2-fluoropropan-2-yl)isoxazol-4-yl)methoxy)-8-hydroxybicyclo[3.2.1]octan-8-yl)-4-fluorobenzo[d]thiazole-6-carbonitrile

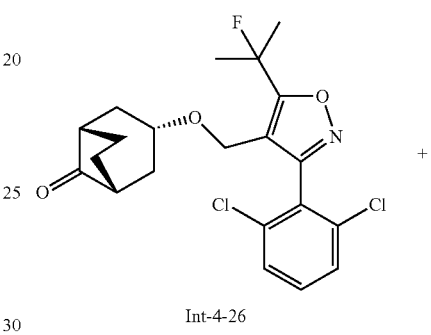

Int-4-26

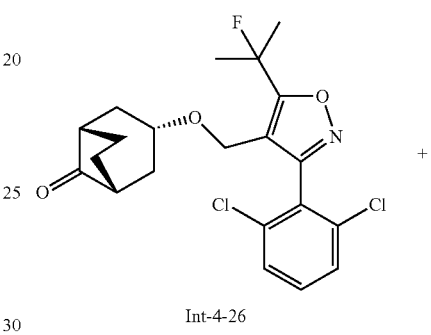

Example 15-21

Following general procedure 1G, beginning with intermediate (1R,3s,5S)-3-((3-(2,6-dichloro-phenyl)-5-(2-fluoropropan-2-yl)isoxazol-4-yl)methoxy)bicyclo[3.2.1]octan-8-one Int-4-26 and 2-bromo-4-fluorobenzo[d]thiazole-6-carbonitrile Int-6-1, the title compound 2-((1R,3s,5S,8r)-3-((3-(2,6-dichlorophenyl)-5-(2-fluoropropan-2-yl) isoxazol-4-yl)methoxy)-8-hydroxybicyclo[3.2.1]octan-8-yl)-4-fluorobenzo[d]thiazole-6-carbonitrile (15-21) was synthesized (the minor isomer was not isolated).

Example 15-22: 2-((1R,3s,5S,8r)-3-((3-(2,6-Dichlorophenyl)-5-(2-hydroxypropan-2-yl)isoxazol-4-yl)methoxy)-8-hydroxybicyclo[3.2.1]octan-8-yl)-4-fluorobenzo[d]thiazole-6-carbonitrile

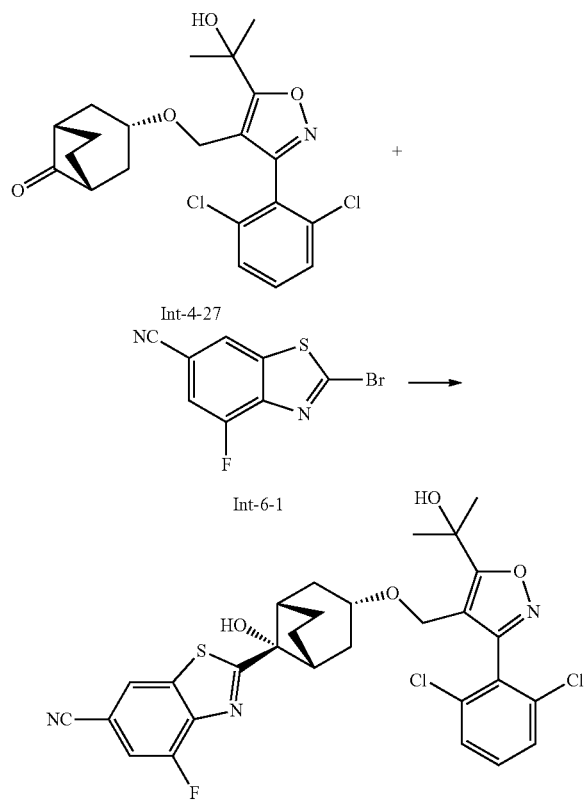

Example 15-22

Following general procedure 1G, beginning with intermediate (1R,3s,5S)-3-((3-(2,6-dichlorophenyl)-5-(2-hydroxypropan-2-yl)isoxazol-4-yl)methoxy)bicyclo[3.2.1]octan-8-one Int-4-27 and 2-bromo-4-fluorobenzo[d]thiazole-6-carbonitrile Int-6-1, the title compound 2-((1R,3s,5S,8r)-3-((3-(2,6-Dichlorophenyl)-5-(2-hydroxypropan-2-yl)isoxazol-4-yl)methoxy)-8-hydroxybicyclo[3.2.1]octan-8-yl)-4-fluorobenzo[d]thiazole-6-carbonitrile (15-22) was synthesized (the minor isomer was not isolated).

Example 15-23: 2-((1R,3s,5S,8r)-3-((5-Cyclopropyl-3-((2,6-dimethylphenoxy)methyl)isoxazol-4-yl)methoxy)-8-hydroxybicyclo[3.2.1]octan-8-yl)-4-fluorobenzo[d]thiazole-6-carbonitrile

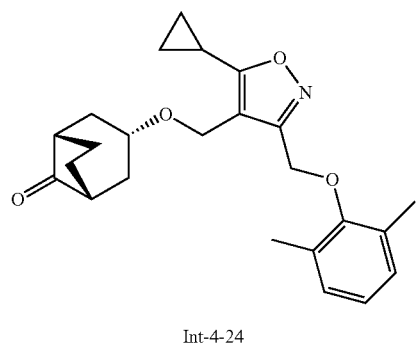

Int-4-24

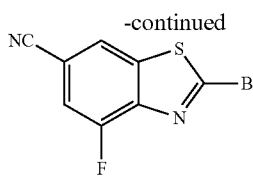

Int-6-1

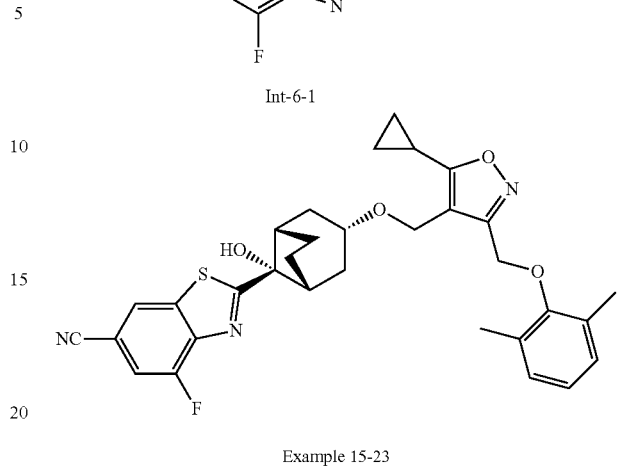

Example 15-23

Following general procedure 1G, beginning with intermediate (1R,3s,5S)-3-((5-cyclopropyl-3-((2,6-dimethylphenoxy)methyl)isoxazol-4-yl)methoxy)bicyclo[3.2.1]octan-8-one Int-4-24 and 2-bromo-4-fluorobenzo[d]thiazole-6-carbonitrile Int-6-1, the title compound 2-((1R,3s,5S,8r)-3-((5-cyclopropyl-3-((2,6-dimethylphenoxy)methyl)isoxazol-4-yl)methoxy)-8-hydroxybicyclo[3.2.1]octan-8-yl)-4-fluorobenzo[d]thiazole-6-carbonitrile (15-23) was synthesized (the minor isomer was not isolated).

Example 15-24: (1R,3s,5S,8r)-8-(6-Bromo-4-fluorobenzo[d]thiazol-2-yl)-3-((4-cyclopropyl-1-(2,6-dichlorophenyl)-1H-pyrazol-5-yl)methoxy)bicyclo[3.2.1]octan-8-ol

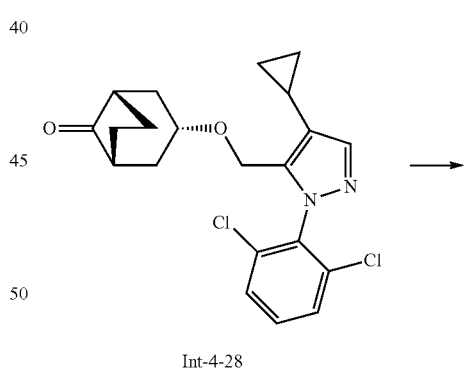

Int-4-28

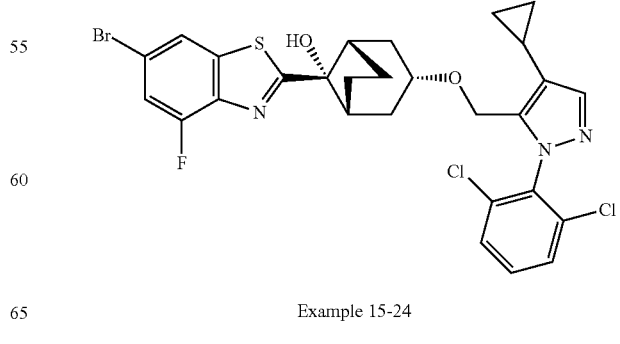

Example 15-24

Following general procedure 1G, starting from (1R,3s,5S)-3-((4-cyclopropyl-1-(2,6-dichloro-phenyl)-1H-pyrazol-5-yl)methoxy)bicyclo[3.2.1]octan-8-one (Int-4-28) and 6-bromo-4-fluorobenzo[d]thiazol-2-amine Int-6-5, the synthesis furnished (1R,3s,5S,8r)-8-(6-bromo-4-fluorobenzo[d]thiazol-2-yl)-3-((4-cyclopropyl-1-(2,6-dichlorophenyl)-1H-pyrazol-5-yl)methoxy)bicyclo[3.2.1]octan-8-ol 15-24.

Example 16: 2-((1s,4s)-4-((5-Cyclopropyl-3-(2,6-dichlorophenyl)isoxazol-4-yl)methoxy)-1-hydroxy-cyclohexyl)-4-fluoro-N-(methylsulfonyl)benzo[d]thiazole-6-carboxamide

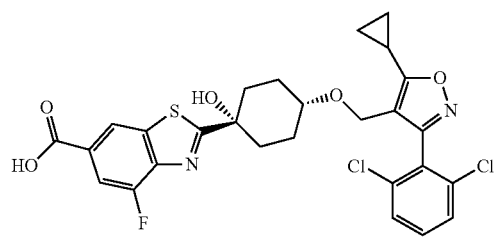

Example 11-31

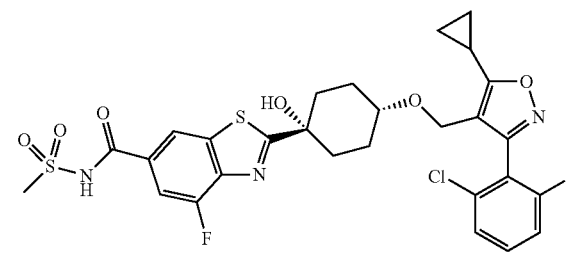

Example 16

To a solution of 2-((1s,4s)-4-((5-cyclopropyl-3-(2,6-dichlorophenyl)isoxazol-4-yl)methoxy)-1-hydroxycyclohexyl)-4-fluorobenzo[d]thiazole-6-carboxylic acid 11-31 (200 mg, 0.35 mmol) in DMF (10 mL) was added EDCl (134 mg, 0.7 mmol), DMAP (85 mg, 0.7 mmol) and methanesulfon-amide (67 mg, 0.7 mmol). The mixture was stirred at rt for 12 h, diluted with water (100 mL) and extracted with EtOAc (3×100 mL). The combined organic layer was washed with brine (50 mL), dried, concentrated and purified by prep-HPLC to give 2-((1s,4s)-4-((5-cyclopropyl-3-(2,6-di-chlorophenyl)isoxazol-4-yl)methoxy)-1-hydroxycyclohexyl)-4-fluoro-N-(methyl-sulfonyl)benzo[d]thiazole-6-carboxamide 16. $^1$H-NMR (500 MHz, DMSO-d$_6$): δ 12.30 (br s, 1H), 8.57 (d, J=2.0 Hz, 1H), 7.86 (dd, J=8.0 Hz, J=1.5 Hz, 1H), 7.67-7.56 (m, 3H), 6.34 (br s, 1H), 4.33 (s, 2H), 3.41 (s, 3H), 3.30-3.25 (m, 1H), 2.40-2.33 (m, 1H), 1.92-1.65 (m, 6H), 1.49-1.38 (m, 2H), 1.20-1.10 (m, 4H). LCMS (ESI): m/z 654.0 (M+H)$^+$.

Example 17: 2-((1s,4s)-4-((5-Cyclopropyl-3-(3,5-dichloropyridin-4-yl)isoxazol-4-yl)methoxy)-1-hydroxycyclohexyl)-4-fluoro-N-(2-morpholinoethyl)benzo[d]thiazole-6-carboxamide

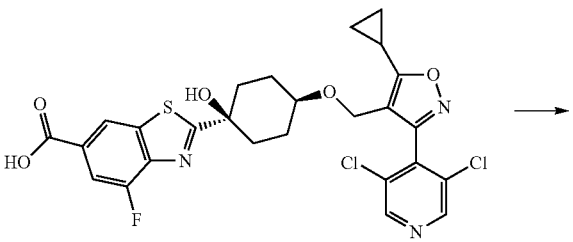

Example 11-24

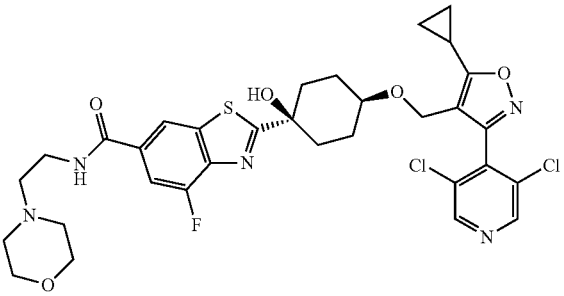

Example 17

Similar as described in Example 16, except using 2-((1s,4s)-4-((5-cyclopropyl-3-(3,5-dichloropyridin-4-yl) isoxazol-4-yl)methoxy)-1-hydroxycyclohexyl)-4-fluorobenzo[d]thiazole-6-carboxylic acid 11-24 and 2-morpholinoethanamine as starting material, the title compound 2-((1s,4s)-4-((5-cyclopropyl-3-(3,5-dichloropyridin-4-yl)isoxazol-4-yl)methoxy)-1-hydroxycyclohexyl)-4-fluoro-N-(2-morpholinoethyl)benzo[d]thiazole-6-carboxamide 17 was prepared. $^1$H-NMR (500 MHz, DMSO-d$_6$): δ 8.85 (s, 2H), 8.58 (t, J=5.5 Hz, 1H), 8.40 (s, 1H), 7.76 (d, J=12.0 Hz, 1H), 6.28 (s, 1H), 4.39 (s, 2H), 3.58 (t, J=4.8 Hz, 4H), 3.42 (q, J=6.5 Hz, 2H), 3.31-3.28 (m, 1H), 2.51-2.38 (m, 7H), 1.93-1.79 (m, 4H), 1.69-1.65 (m, 2H), 1.45-1.37 (m, 2H), 1.21-1.11 (m, 4H). LCMS (ESI): m/z 690.2 (M+H)$^+$.

Example 18: 2-((1s,4s)-4-((5-Cyclopropyl-3-(3,5-dichloropyridin-4-yl)isoxazol-4-yl)methoxy)-1-hydroxycyclohexyl)-4-fluorobenzo[d]thiazole-6-carboxamide

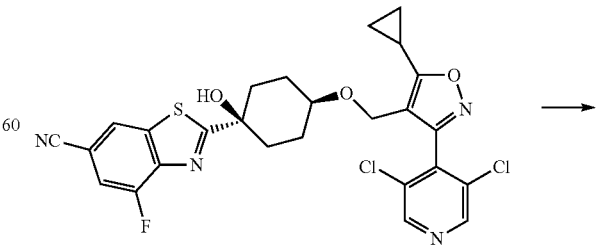

Example 9-20

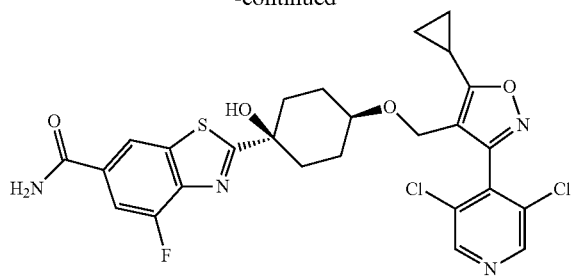

Example 18

To a solution of 2-((1s,4s)-4-((5-cyclopropyl-3-(3,5-dichloropyridin-4-yl)isoxazol-4-yl)methoxy)-1-hydroxycyclohexyl)-4-fluorobenzo[d]thiazole-6-carbonitrile (9-20) (200 mg, 0.36 mmol) in EtOH (5 mL) was added aq. NaOH (1N, 1 mL) and the mixture was stirred at 75° C. for 1 h, cooled, acidified by HCl (4M, 1 mL) and extracted with EtOAc (3×20 mL). The combined organic layer was washed with brine (50 mL), dried, concentrated and purified by prep-HPLC to give 2-((1 s,4s)-4-((5-Cyclopropyl-3-(3,5-dichloropyridin-4-yl)isoxazol-4-yl)methoxy)-1-hydroxycyclohexyl)-4-fluorobenzo[d]thiazole-6-carboxamide 18. $^1$H-NMR (500 MHz, DMSO-d$_6$): δ 8.85 (s, 2H), 8.44 (s, 1H), 8.12 (s, 1H), 7.80 (d, J=11.5 Hz, 1H), 7.59 (s, 1H), 6.28 (br s, 1H), 4.39 (s, 2H), 3.32-3.25 (m, 1H), 2.40-2.35 (m, 1H), 1.92-1.65 (m, 6H), 1.46-1.37 (m, 2H), 1.19-1.10 (m, 4H). LCMS (ESI): m/z 577.0 (M+H)$^+$.

Example 19: Methyl 2-((1s,4s)-4-((5-cyclopropyl-3-(3,5-dichloropyridin-4-yl)isoxazol-4-yl)methoxy)-1-hydroxycyclohexyl)-4-fluorobenzo[d]thiazole-6-carboxylate To a solution of 2-((1s,4s)-4-((5-cyclopropyl-3-(3,5-dichloropyridin-4-yl)isoxazol-4-yl)methoxy)-1-hydroxycyclohexyl)-4-fluorobenzo[d]thiazole-6-carboxylic acid (11-24) (200 mg, 0.35 mmol) in a mixture of THF (8 mL) and MeOH (2 mL) was added TMSCHN$_2$ (2M in hexane, 0.4 mL, 0.8 mmol) at 0° C. The mixture was stirred at rt for 2 h, diluted with water (100 mL) and extracted with EtOAc (3×100 mL). The combined organic layer was washed with brine (50 mL), dried, concentrated and purified by silica-gel column (DCM/EtOAc=10:1) to give methyl 2-((1s,4s)-4-((5-cyclopropyl-3-(3,5-dichloropyridin-4-yl)isoxazol-4-yl)methoxy)-1-hydroxycyclohexyl)-4-fluorobenzo[d]thiazole-6-carboxylate 19.

Example 20: (1s,4s)-4-((5-Cyclopropyl-3-(3,5-dichloropyridin-4-yl)isoxazol-4-yl)methoxy)-1-(4-fluoro-6-(2-hydroxypropan-2-yl)benzo[d]thiazol-2-yl)cyclohexanol

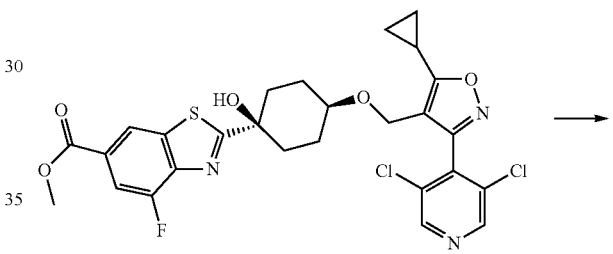

Example 19

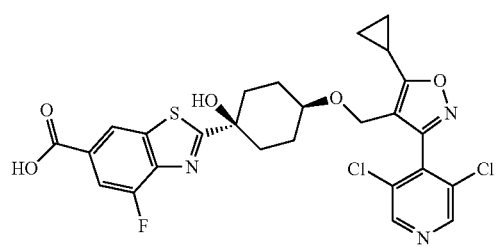

Example 11-24

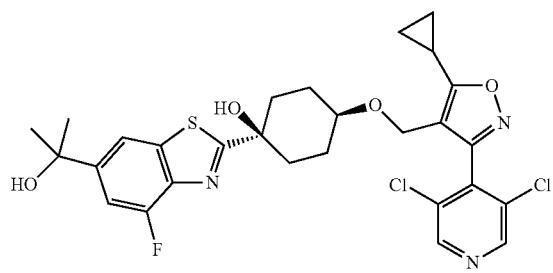

Example 20

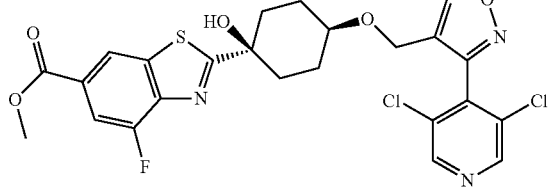

Example 19

To a solution of methyl 2-((1s,4s)-4-((5-cyclopropyl-3-(3,5-dichloropyridin-4-yl)isoxazol-4-yl)methoxy)-1-hydroxycyclohexyl)-4-fluorobenzo[d]thiazole-6-carboxylate (19) (200 mg, 0.34 mmol) in dry THF (10 mL) at −10° C. was added slowly MeMgBr (3M in Et$_2$O, 1.2 mL, 3.6 mmol). The mixture was stirred at rt for 2 h, diluted with aq. NH$_4$Cl (50 mL) and extracted with EtOAc (3×100 mL). The combined organic layer was washed with brine (50 mL), dried, concentrated and purified by prep-HPLC to give (1s,4s)-4-((5-cyclopropyl-3-(3,5-dichloropyridin-4-yl)isoxazol-4-yl)methoxy)-1-(4-fluoro-6-(2-hydroxypropan-2-yl)

benzo[d]thiazol-2-yl)cyclohexanol 20. $^1$H-NMR (500 MHz, DMSO-$d_6$): δ 8.85 (s, 2H), 7.92 (s, 1H), 7.40 (d, J=12.5 Hz, 1H), 6.16 (s, 1H), 5.27 (s, 1H), 4.38 (s, 2H), 3.31-3.24 (m, 1H), 2.41-2.35 (m, 1H), 1.91-1.77 (m, 4H), 1.68-1.64 (m, 2H), 1.47 (s, 6H), 1.44-1.34 (m, 2H), 1.19-1.11 (m, 4H). LCMS (ESI): m/z 592.1 (M+H)$^+$.

Example 21: (1s,4s)-4-((5-Cyclopropyl-3-(2,6-dichlorophenyl)isoxazol-4-yl)methoxy)-1-(4-fluoro-6-(1H-tetrazol-5-yl)benzo[d]thiazol-2-yl)cyclohexanol 1.20-1.09 (m, 4H), tetrazole hydrogen not resolved. LCMS (ESI): m/z 600.7 (M+H)$^+$ Example 22: 4-(4-((((1R,3s,5S,8r)-8-(6-Carboxy-4-fluorobenzo[d]thiazol-2-yl)-8-hydroxybicyclo[3.2.1]octan-3-yl)oxy)methyl)-5-cyclopropylisoxazol-3-yl)-3,5-dichloropyridine 1-oxide

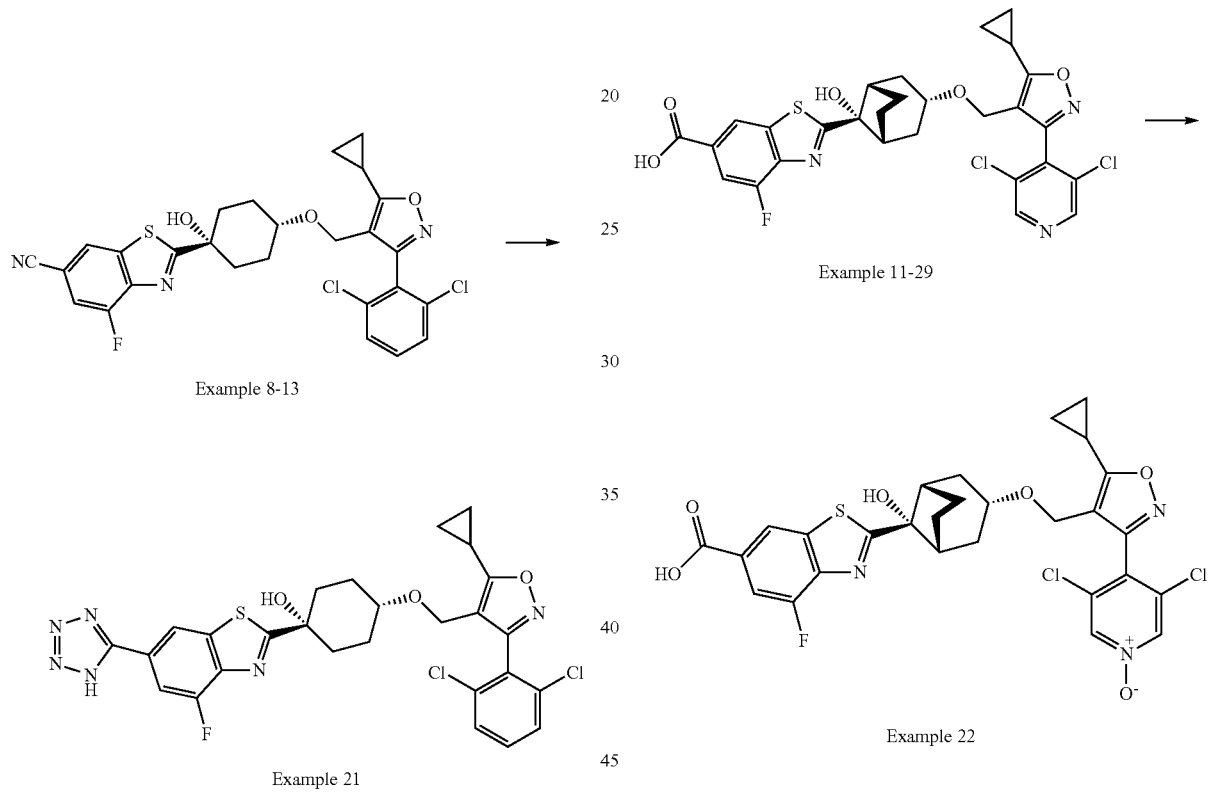

Example 8-13

Example 11-29

Example 21

Example 22

To a solution of 2-((1s,4s)-4-((5-cyclopropyl-3-(2,6-dichlorophenyl)isoxazol-4-yl)methoxy)-1-hydroxycyclohexyl)-4-fluorobenzo[d]thiazole-6-carbonitrile 8-13 (300 mg, 0.54 mmol) in DMF (20 mL) was added NaN$_3$ (350 mg, 5.4 mmol) and NH$_4$Cl (290 mg, 5.4 mmol) and the mixture was stirred at 120° C. for 12 h, cooled, diluted with water (100 mL) and extracted with EtOAc (3×100 mL). The combined organic layer was washed with brine (50 mL), dried, concentrated and purified by prep-HPLC to give (1s,4s)-4-((5-cyclopropyl-3-(2,6-dichlorophenyl)isoxazol-4-yl)methoxy)-1-(4-fluoro-6-(1H-tetrazol-5-yl)benzo[d]thiazol-2-yl)cyclohexanol 21. $^1$H-NMR (500 MHz, DMSO-$d_6$): δ 8.64 (s, 1H), 7.95 (d, J=11.0 Hz, 1H), 7.67-7.57 (m, 3H), 6.33 (br s, 1H), 4.33 (s, 2H), 3.31-3.24 (m, 1H), 2.40-2.34 (m, 1H), 1.95-1.65 (m, 6H), 1.46-1.38 (m, 2H), To a solution of 2-((1R,3s,5S,8r)-3-((5-cyclopropyl-3-(3,5-dichloropyridin-4-yl)isoxazol-4-yl)methoxy)-8-hydroxybicyclo[3.2.1]octan-8-yl)-4-fluorobenzo[d]thiazole-6-carboxylic acid (11-29) (150 mg, 0.25 mmol) in AcOH (5 mL) was added H$_2$O$_2$ (30% aq.; 3.0 mL) and the resulting mixture was heated at 50° C. for additional 12 h, quenched by adding saturated NaHSO$_3$ solution and extracted with EtOAc (3×10 mL). The combined organic layers and washed with brine (10 mL), concentrated and purified by prep-HPLC twice to give 4-(4-((((1R,3s,5S,8r)-8-(6-carboxy-4-fluorobenzo[d]thiazol-2-yl)-8-hydroxybicyclo[3.2.1]octan-3-yl)oxy)methyl)-5-cyclopropylisoxazol-3-yl)-3,5-dichloropyridine 1-oxide 22. $^1$H-NMR (400 MHz, DMSO-$d_6$): δ (ppm) 13.23 (br s, 1H), 8.79 (s, 2H), 8.56 (s, 1H), 7.76 (d, J=11.2 Hz, 1H), 6.57 (s, 1H), 4.36 (s, 2H), 3.67-3.55 (m, 1H), 2.41-2.36 (m, 3H), 1.88-1.82 (m, 4H), 1.77-1.65 (m, 2H), 1.55-1.46 (m, 2H), 1.19-1.05 (m, 4H). MS (ESI): m/z 619.8 (M+1)$^+$.

Example 23a and Example 23b: (1R,2r,3S,5s,7s)-2-(6-Bromobenzo[d]thiazol-2-yl)-5-((5-cyclopropyl-3-(2,6-dichlorophenyl)isoxazol-4-yl)methoxy)adamantan-2-ol 23a and (1R,2s,3S,5s,7s)-2-(6-bromobenzo[d]thiazol-2-yl)-5-((5-cyclopropyl-3-(2,6-dichlorophenyl)isoxazol-4-yl)methoxy)adamantan-2-ol 23b

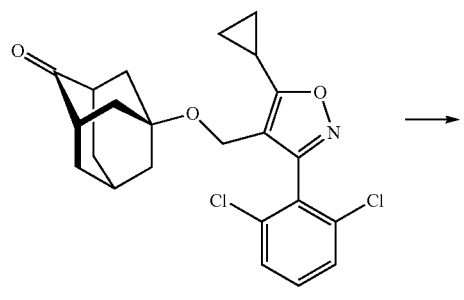

Int-8-3

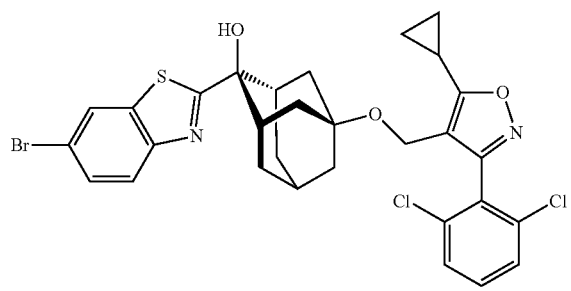

Example 23a

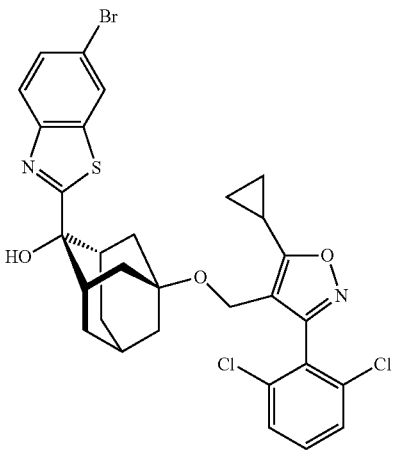

and

Example 23b

A solution of (1R,3S,5s,7s)-5-((5-cyclopropyl-3-(2,6-dichlorophenyl)isoxazol-4-yl)methoxy)adamantan-2-one Int-8-3 (600 mg, 1.39 mmol) and 2,6-dibromobenzo[d]thiazole (815 mg, 2.78 mmol) in THF (10 mL) was cooled down to −78° C. under Ar atmosphere, then n-BuLi (1.6M, 1.56 mL, 2.5 mmol) was added dropwise over 20 min at −78° C. The solution was stirred at −78° C. for additional 2 h, then quenched with NH₄Cl (sat.) and extracted with EtOAc (3×10 mL). The organic layers were combined and washed with brine (2×10 mL), dried over Na₂SO₄, concentrated and purified by chromatography to give minor isomer (1R,2r,3S,5s,7s)-2-(6-bromobenzo[d]thiazol-2-yl)-5-((5-cyclopropyl-3-(2,6-dichlorophenyl)isoxazol-4-yl)methoxy)adamantan-2-ol 23a and major isomer (1R,2s,3S,5s,7s)-2-(6-bromobenzo[d]thiazol-2-yl)-5-((5-cyclopropyl-3-(2,6-dichlorophenyl)isoxazol-4-yl)methoxy)adamantan-2-ol 23b (500 mg).

Example 24a and Example 24b: (1R,2r,3S,5s,7s)-2-(Benzo[d]thiazol-2-yl)-5-((5-cyclopropyl-3-(2,6-dichlorophenyl)isoxazol-4-yl)methoxy)adamantan-2-ol 24a and (1R,2s,3S,5s,7s)-2-(benzo[d]thiazol-2-yl)-5-((5-cyclopropyl-3-(2,6-dichlorophenyl)isoxazol-4-yl)methoxy)adamantan-2-ol 24b

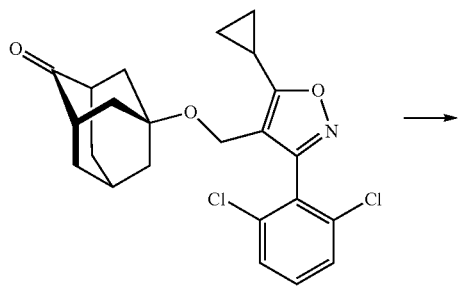

Int-8-3

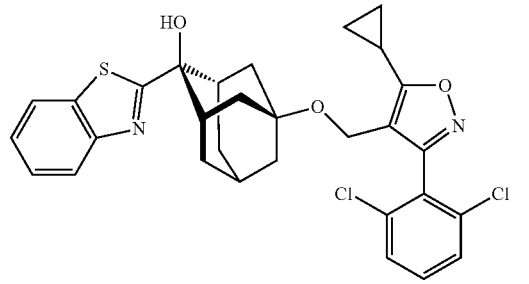

Example 24a

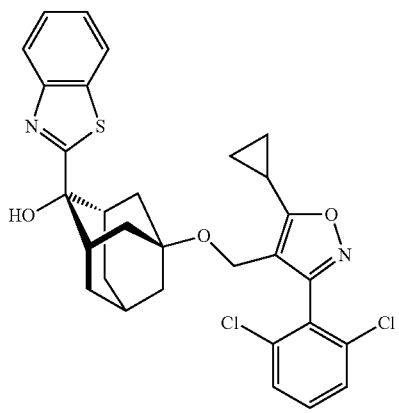

Example 24b

A solution of (1R,3S,5s,7s)-5-((5-cyclopropyl-3-(2,6-dichlorophenyl)isoxazol-4-yl)methoxy)adamantan-2-one Int-8-3 (50 mg, 116 μmol) and 2-bromobenzo[d]thiazole (50 mg, 232 μmol) was treated as described in Example 23 to give minor isomer (1R,2r,3S,5s,7s)-2-(benzo[d]thiazol-2-yl)-5-((5-cyclopropyl-3-(2,6-dichlorophenyl) isoxazol-4-yl)methoxy)adamantan-2-ol 24a and major isomer (1R,2s,3S, 5s,7s)-2-(benzo[d]thiazol-2-yl)-5-((5-cyclopropyl-3-(2,6-dichlorophenyl)isoxazol-4-yl)methoxy)adamantan-2-ol 24b. 24a: $^1$H-NMR (400 MHz, DMSO-$d_6$): δ 8.06 (d, J=8.0 Hz, 1H), 7.96 (d, J=8.0 Hz, 1H), 7.65-7.62 (m, 2H), 7.60-7.53 (m, 1H), 7.48 (t, J=7.2 Hz, 1H), 7.41 (t, J=7.2 Hz, 1H), 5.97 (s, 1H), 4.24 (s, 2H), 2.43-2.38 (m, 2H), 2.35-2.30 (m, 1H), 2.19-2.13 (m, 2H), 1.93-1.84 (m, 3H), 1.49-1.37 (m, 4H), 1.29-1.21 (m, 2H), 1.18-1.06 (m, 4H). MS (ESI): m/z 566.9 (M+1)$^+$. 24b: $^1$H-NMR (400 MHz, DMSO-$d_6$): δ 8.15 (d, J=7.2 Hz, 1H), 8.05 (d, J=8.0 Hz, 1H), 7.58-7.47 (m, 2H), 7.15 (d, J=8.0 Hz, 2H), 6.91 (t, J=8.0 Hz, 1H), 5.92 (s, 1H), 4.15 (s, 2H), 2.52-2.47 (m, 2H), 2.40-2.15 (m, 3H), 2.02-1.98 (m, 1H), 1.53-1.23 (m, 9H), 1.08-0.98 (m, 4H). MS (ESI): m/z 566.9 (M+1)$^+$.

Example 25: 2-((1s,4s)-4-((5-Cyclopropyl-3-(2,6-dichlorophenyl)isoxazol-4-yl)methoxy)-1-hydroxy-cyclohexyl)benzo[d]thiazole-7-carbaldehyde

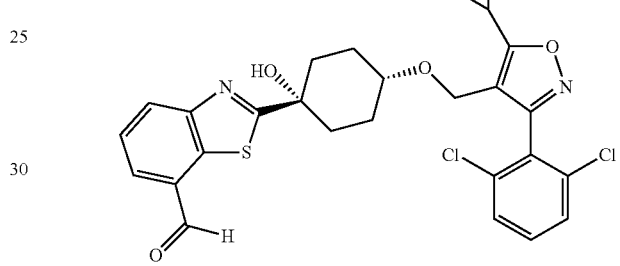

Example 25

To a solution of (1s,4s)-1-(7-(1,3-dioxolan-2-yl)benzo[d]thiazol-2-yl)-4-((5-cyclopropyl-3-(2,6-di-chlorophenyl)isoxazol-4-yl)methoxy)cyclohexan-1-ol 15-16 (1.2 g, 2.0 mmol) in acetone (20 mL) was added $H_2SO_4$ (2.0 mL) at rt and the mixture was stirred at rt overnight, diluted with EtOAc (100 mL) and washed with sat. $NaHCO_3$. The organic phase was dried over $Na_2SO_4$, concentrated and purified by chromatography to give the 2-((1s,4s)-4-((5-cyclopropyl-3-(2,6-di-chlorophenyl)isoxazol-4-yl)methoxy)-1-hydroxycyclohexyl)benzo[d]thiazole-7-carbaldehyde 25.

Example 26: 2-((1s,4s)-4-((5-Cyclopropyl-3-(2,6-dichlorophenyl)isoxazol-4-yl)methoxy)-1-hydroxy-cyclohexyl)benzo[d]thiazole-7-carboxylic acid

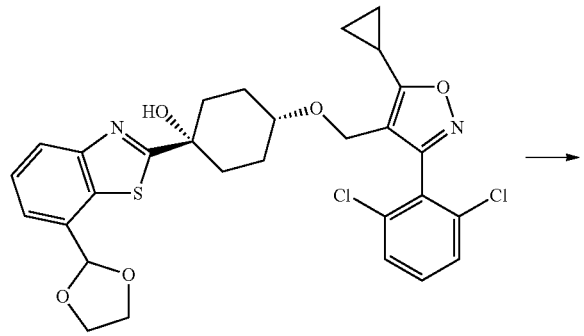

Example 15-16

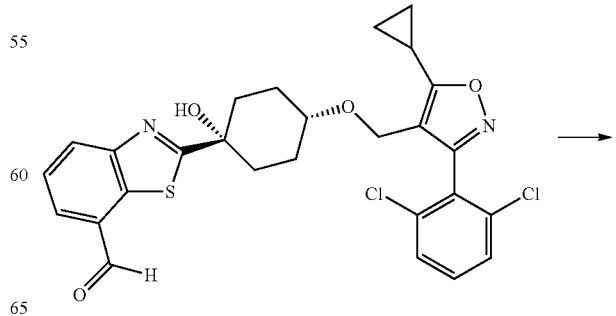

Example 25

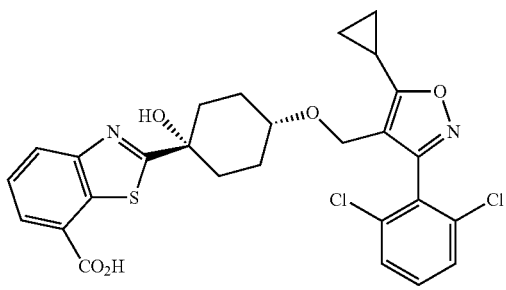

Example 26

To a solution of KMnO₄ (1.0 g) in H₂O (50 mL) was added H₂SO₄ (1.0 mL). Then this solution was slowly added to a stirred solution of 2-((1 s,4s)-4-((5-cyclopropyl-3-(2,6-dichlorophenyl)isoxazol-4-yl)methoxy)-1-hydroxycyclohexyl)benzo[d]thiazole-7-carbaldehyde 25 (400 mg, 0.74 mmol) in acetone (10 mL) and stirring was continued until consumption of the starting material. The mixture was filtered, diluted with EtOAc and washed with brine. The organic phase was dried, concentrated and purified by prep-HPLC to give the title compound 2-((1s,4s)-4-((5-cyclopropyl-3-(2,6-dichlorophenyl)isoxazol-4-yl)methoxy)-1-hydroxycyclohexyl)benzo[d]thiazole-7-carboxylic acid 26. $^1$H-NMR (400 MHz, DMSO-d₆) δ 13.62 (br s, 1H), 8.16 (d, J=8.0 Hz, 1H), 8.03 (d, J=7.2 Hz, 1H), 7.67-7.56 (m, 4H), 6.06 (s, 1H), 4.32 (s, 2H), 3.26-3.21 (m, 1H), 2.40-2.32 (m, 1H), 1.91-1.74 (m, 4H), 1.73-1.67 (m, 2H), 1.50-1.43 (m, 2H), 1.19-1.10 (m, 4H). LC/MS (ESI): m/z 559.5 (M+H)⁺.

Example 27: (1s,4s)-4-((5-Cyclopropyl-3-(2,6-dichlorophenyl)isoxazol-4-yl)methoxy)-1-(4-iodoquinolin-7-yl)cyclohexan-1-ol

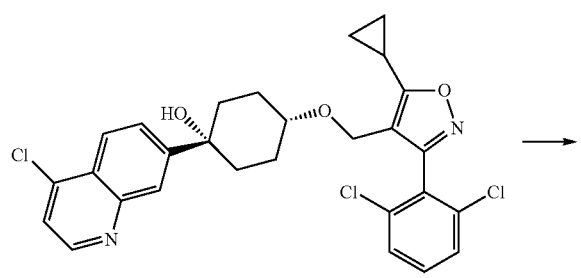

Example 15-17

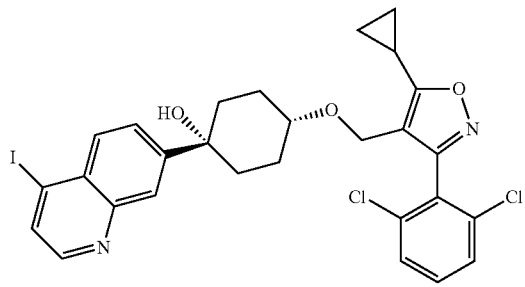

Example 27

A mixture of (1s,4s)-1-(4-chloroquinolin-7-yl)-4-((5-cyclopropyl-3-(2,6-dichlorophenyl)isoxazol-4-yl)methoxy)cyclohexan-1-ol 15-17 (1.05 g, 1.96 mmol) and KI (1.66 g, 10.0 mmol) in acetone (20 mL) was heated to reflux overnight. The mixture was cooled to rt and filtered. The filtrate was concentrated and the residue was diluted with EtOAc, washed with brine, dried over Na₂SO₄ and concentrated to give the product (1 s,4s)-4-((5-cyclopropyl-3-(2,6-dichlorophenyl)isoxazol-4-yl)methoxy)-1-(4-iodoquinolin-7-yl)cyclohexan-1-ol 27 which used in the next step without purification.

Example 28: 7-((1s,4s)-4-((5-Cyclopropyl-3-(2,6-dichlorophenyl)isoxazol-4-yl)methoxy)-1-hydroxycyclohexyl)quinoline-4-carbonitrile

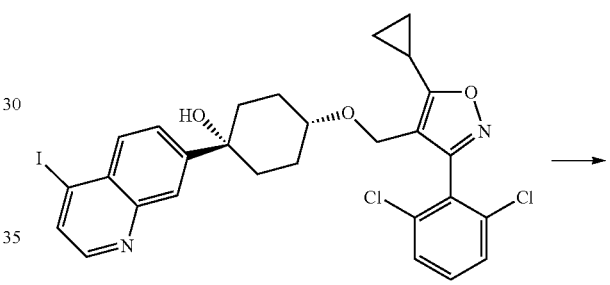

Example 27

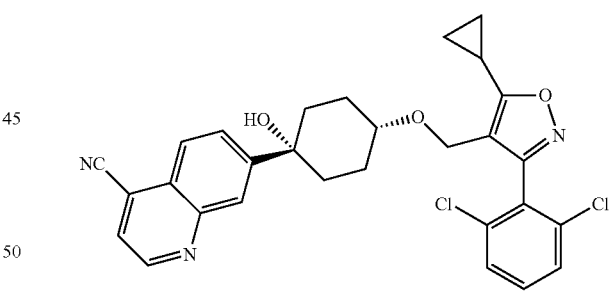

Example 28

A mixture of (1s,4s)-4-((5-cyclopropyl-3-(2,6-dichlorophenyl)isoxazol-4-yl)methoxy)-1-(4-iodoquinolin-7-yl)cyclohexan-1-ol 27 (1.3 g, 1.96 mmol), Zn(CN)₂ (468 mg, 4.0 mmol) and Pd(PPh₃)₄ (230 mg, 0.2 mmol) in DMF (10 mL) was degassed with N₂. The mixture was stirred at 125° C. overnight, cooled to rt, diluted with EtOAc, washed with brine and dried over Na₂SO₄. The solution was concentrated and purified by chromatography to afford 7-((1s,4s)-4-((5-cyclopropyl-3-(2,6-dichlorophenyl)isoxazol-4-yl)methoxy)-1-hydroxycyclohexyl)quinoline-4-carbonitrile 28.

Example 29: 7-((1s,4s)-4-((5-cyclopropyl-3-(2,6-dichlorophenyl)isoxazol-4-yl)methoxy)-1-hydroxy-cyclohexyl)quinoline-4-carboxylic acid

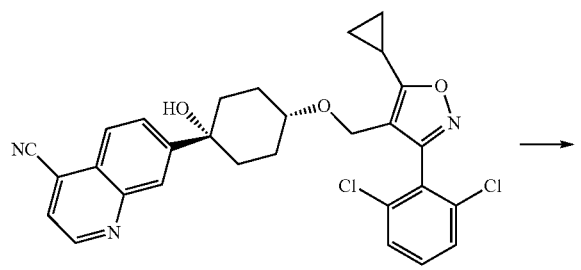

Example 28

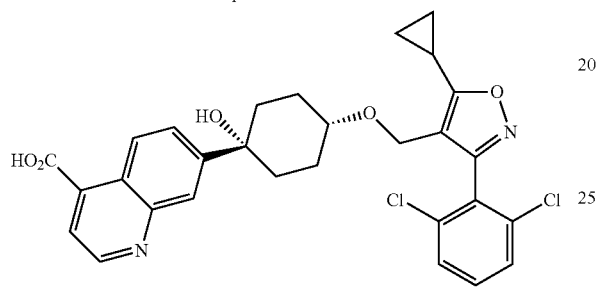

Example 29

To a solution of 7-((1s,4s)-4-((5-cyclopropyl-3-(2,6-dichlorophenyl)isoxazol-4-yl)methoxy)-1-hydroxycyclohexyl)quinoline-4-carbonitrile 28 (460 mg, 0.86 mmol) in EtOH (10 mL) was added aq. NaOH (20%, 10 mL) and the reaction was refluxed overnight, cooled to rt, concentrated, diluted with water and acidified with aq. HCl. Then the mixture was extracted with EtOAc and the organic phase was dried over $Na_2SO_4$, concentrated and purified by prep-HPLC to give 7-((1s,4s)-4-((5-cyclopropyl-3-(2,6-dichlorophenyl)isoxazol-4-yl)methoxy)-1-hydroxycyclohexyl)quinoline-4-carboxylic acid 29. $^1$H-NMR (400 MHz, DMSO-$d_6$) δ 13.83 (br s, 1H), 9.00 (d, J=4.4 Hz, 1H), 8.61 (d, J=8.8 Hz, 1H), 8.13 (s, 1H), 7.86 (d, J=4.0 Hz, 1H), 7.80 (d, J=9.2 Hz, 1H), 7.68-7.65 (m, 2H), 7.59 (d, J=7.6 Hz, 1H), 5.07 (s, 1H), 4.33 (s, 2H), 3.29-3.25 (m, 1H), 2.38-2.33 (m, 1H), 1.83-1.49 (m, 8H), 1.18-1.12 (m, 4H). LC/MS (ESI): m/z 553.5 (M+H)$^+$.

Examples 30 and 31: 6-((1s,4s)-4-((5-Cyclopropyl-3-(2,6-dichlorophenyl)isoxazol-4-yl)methoxy)-1-hydroxycyclohexyl)quinoline-4-carboxylic acid (30) and 6-((1r,4r)-4-((5-cyclopropyl-3-(2,6-dichlorophenyl)isoxazol-4-yl)methoxy)-1-hydroxycyclohexyl)quinoline-4-carboxylic acid (31)

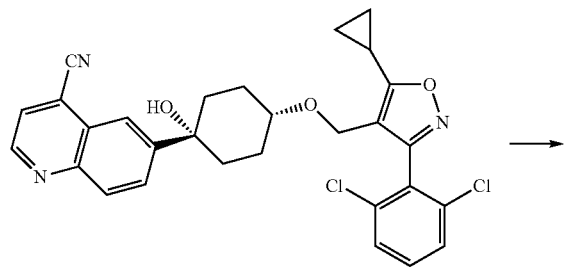

Example 15-18

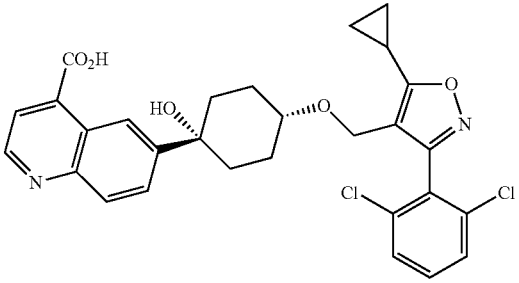

Example 30

+

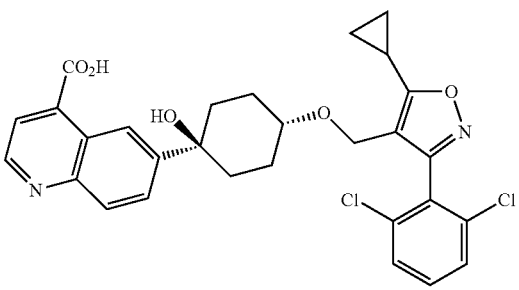

Example 31

To a solution of 6-(4-((5-cyclopropyl-3-(2,6-dichlorophenyl)isoxazol-4-yl)methoxy)-1-hydroxy-cyclohexyl)quinoline-4-carbonitrile 15-18 (460 mg, 0.86 mmol) in EtOH (10 mL) was added aq. NaOH (20%, 10 mL) and the reaction was refluxed overnight, cooled to rt, concentrated, diluted with water and acidified with aq. HCl. Then the mixture was extracted with EtOAc and the organic phase was dried over $Na_2SO_4$, concentrated and purified by prep-HPLC to afford separated 6-((1s,4s)-4-((5-cyclopropyl-3-(2,6-dichlorophenyl)isoxazol-4-yl)methoxy)-1-hydroxycyclohexyl)quinoline-4-carboxylic acid 30 (major isomer) and 6-((1r,4r)-4-((5-cyclopropyl-3-(2,6-dichlorophenyl)isoxazol-4-yl)methoxy)-1-hydroxycyclohexyl)quinoline-4-carboxylic acid 31 (minor isomer). 30: $^1$H-NMR (400 MHz, DMSO-$d_6$) δ 14.0 (br s, 1H), 9.04 (d, J=4.0 Hz, 1H), 8.82 (s, 1H), 8.10 (d, J=8.8 Hz, 1H), 7.99-7.93 (m, 2H), 7.75-7.67 (m, 3H), 4.39 (s, 2H), 3.35-3.30 (m, 1H), 2.47-2.40 (m, 1H), 1.84-1.57 (m, 8H), 1.24-1.18 (m, 5H). LC/MS (ESI): m/z 553.1 (M+H)$^+$. 31: LC/MS (ESI): m/z 553.1 (M+H)$^+$.

Example 32: 5-((1s,4s)-4-((5-Cyclopropyl-3-(2,6-dichlorophenyl)isoxazol-4-yl)methoxy)-1-hydroxy-cyclohexyl)benzo[d]isothiazole-3-carbaldehyde

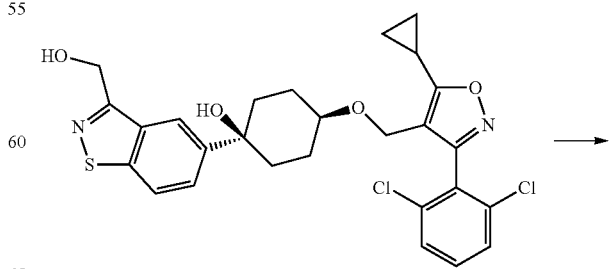

Example 15-19

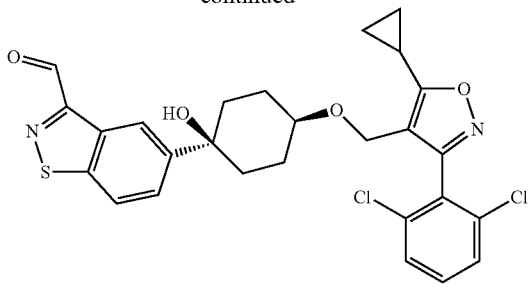

Example 32

To a solution of (1s,4s)-4-((5-cyclopropyl-3-(2,6-dichlorophenyl)isoxazol-4-yl)methoxy)-1-(3-(hydroxymethyl)benzo[d]isothiazol-5-yl)cyclohexan-1-ol 15-19 (500 mg, 0.91 mmol) in DCM (10 mL) at 0° C. was portionwise added Dess-Martin reagent until the starting material was consumed. PE (20 mL) was added to the reaction and the mixture was filtered. The filtrate was washed with sat. NaHCO₃ and brine. The organic phase was dried, concentrated and purified by chromatography to afford 5-((1s,4s)-4-((5-cyclopropyl-3-(2,6-dichlorophenyl)isoxazol-4-yl)methoxy)-1-hydroxycyclohexyl)benzo[d]isothiazole-3-carbaldehyde 32. $^1$H-NMR (400 MHz, CDCl₃) δ 10.28 (s, 1H), 8.84 (s, 1H), 7.96 (d, J=8.4 Hz, 1H), 7.81 (d, J=8.4 Hz, 1H), 7.50-7.35 (m, 3H), 4.39 (s, 2H), 3.33-3.27 (m, 1H), 2.25-2.15 (m, 1H), 1.89-1.65 (m, 8H), 1.32-1.22 (m, 2H), 1.17-1.14 (m, 2H), hydroxyl proton not resolved.

Example 33: 5-((1s,4s)-4-((5-Cyclopropyl-3-(2,6-dichlorophenyl)isoxazol-4-yl)methoxy)-1-hydroxycyclohexyl)benzo[d]isothiazole-3-carboxylic acid

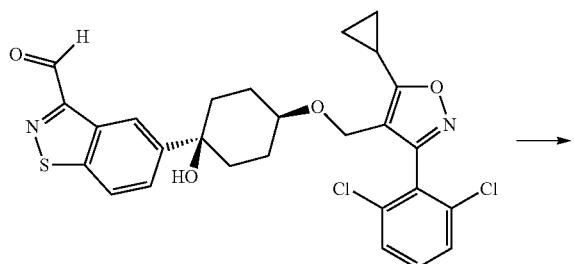

Example 32

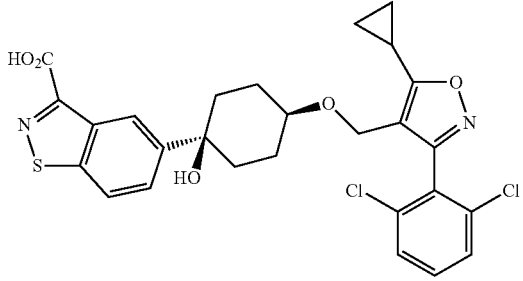

Example 33

To a mixture of 5-((1s,4s)-4-((5-cyclopropyl-3-(2,6-dichlorophenyl)isoxazol-4-yl)methoxy)-1-hydroxycyclohexyl)benzo[d]isothiazole-3-carbaldehyde 32 (240 mg, 0.44 mmol) in H₂O (3 mL) and EtOAc (5 mL) was added Oxone (168 mg, 1.0 mmol). The reaction was stirred at rt for 5 h, diluted with EtOAc and washed with brine. The organic phase was dried (Na₂SO₄), concentrated and purified by prep-HPLC to afford 5-((1s,4s)-4-((5-cyclopropyl-3-(2,6-dichlorophenyl)isoxazol-4-yl)methoxy)-1-hydroxycyclohexyl)benzo[d]isothiazole-3-carboxylic acid 33. $^1$H-NMR (400 MHz, DMSO-d₆) δ 13.62 (br s, 1H), 8.16 (d, J=8.0 Hz, 1H), 8.03 (d, J=7.2 Hz, 1H), 7.67-7.56 (m, 4H), 6.06 (s, 1H), 4.32 (s, 2H), 3.26-3.21 (m, 1H), 2.40-2.32 (m, 1H), 1.91-1.67 (m, 6H), 1.50-1.43 (m, 2H), 1.12-1.09 (m, 4H). LC/MS (ESI): m/z 559.5 (M+H)⁺.

Example 34: (1R,3s,5S,8r)-8-(1H-[1,2,3]Triazolo[4,5-b]pyridin-6-yl)-3-((5-cyclopropyl-3-(2,6-dichlorophenyl)isoxazol-4-yl)methoxy)bicyclo[3.2.1]octan-8-ol

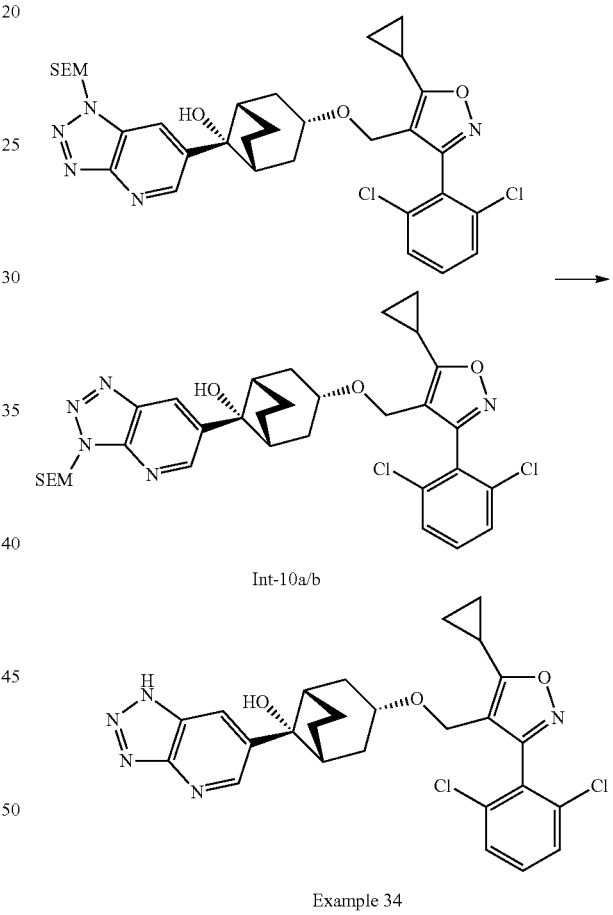

Int-10a/b

Example 34

To a solution of SEM-protected intermediate Int-10a (major isomer, 150 mg, 0.23 mmol) in EtOAc (2 mL) was added HCl/EtOAc (2.0 M, 0.5 mL) at rt. The mixture was stirred at rt for 2 h, concentrated and purified by prep-HPLC to afford (1R,3s,5S,8r)-8-(1H-[1,2,3]triazolo[4,5-b]pyridin-6-yl)-3-((5-cyclopropyl-3-(2,6-dichlorophenyl)isoxazol-4-yl)methoxy)bicyclo[3.2.1]octan-8-ol 34. The same procedure was applied to SEM-protected intermediate Int-10b (minor isomer). The same final compound 34 was obtained. $^1$H-NMR (400 MHz, DMSO-d₆): δ 16.26 and 15.89 (2 br s, 1H), 8.85 (s, 1H), 8.42 and 8.21 (2 br s, 1H), 7.67-7.65 (m, 2H), 7.60-7.56 (m, 1H), 5.35 (s, 1H), 4.30 (s, 2H), 3.52-3.47

(m, 1H), 2.56-2.53 (m, 2H), 2.41-2.34 (m, 1H), 1.92 (t, J=11.2 Hz, 2H), 1.64-1.62 (m, 2H), 1.36-1.31 (m, 4H), 1.19-1.08 (m, 4H). LC/MS (ESI): m/z 526.0 (M+H)+.

Example 35: 2-((1R,3s,5S,8r)-3-((5-Cyclopropyl-3-(2,6-dichlorophenyl)isoxazol-4-yl)methoxy)-8-hydroxybicyclo[3.2.1]octan-8-yl)-4-fluoro-N-hydroxybenzo[d]thiazole-6-carboximidamide

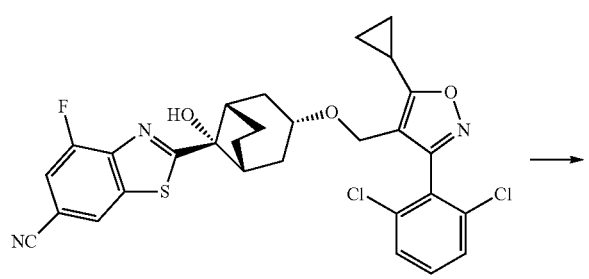

Example 8-9

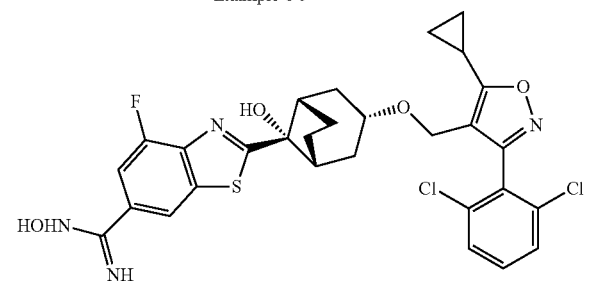

Example 35

To a solution of 2-((1R,3s,5S,8r)-3-((5-cyclopropyl-3-(2,6-dichlorophenyl)isoxazol-4-yl)methoxy)-8-hydroxybicyclo[3.2.1]octan-8-yl)-4-fluorobenzo[d]thiazole-6-carbonitrile 8-9 (150 mg, 0.26 mmol) in EtOH (4 mL) and H$_2$O (1 mL) was added Na$_2$CO$_3$ (55 mg, 0.52 mmol) and hydroxylamine hydrochloride (36 mg, 0.52 mmol). The mixture was stirred at 70° C. overnight, diluted with water and extracted with EtOAc. The organic portion was washed with brine, dried over Na$_2$SO$_4$, filtered and concentrated to give 2-((1R,3s,5S,8r)-3-((5-cyclopropyl-3-(2,6-dichloro-phenyl)isoxazol-4-yl)methoxy)-8-hydroxybicyclo[3.2.1]octan-8-yl)-4-fluoro-N-hydroxybenzo[d]thiazole-6-carboximidamide 35.

Example 36: 3-(2-((1R,3s,5S,8r)-3-((5-Cyclopropyl-3-(2,6-dichlorophenyl)isoxazol-4-yl)methoxy)-8-hydroxybicyclo[3.2.1]octan-8-yl)-4-fluorobenzo[d]thiazol-6-yl)-1,2,4-oxadiazol-5(2H)-one

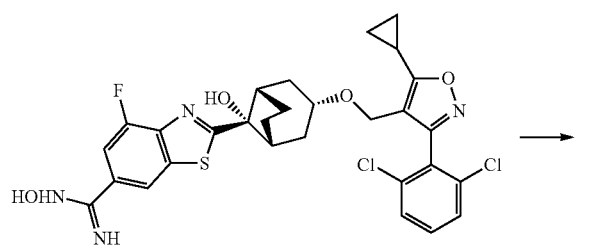

Example 35

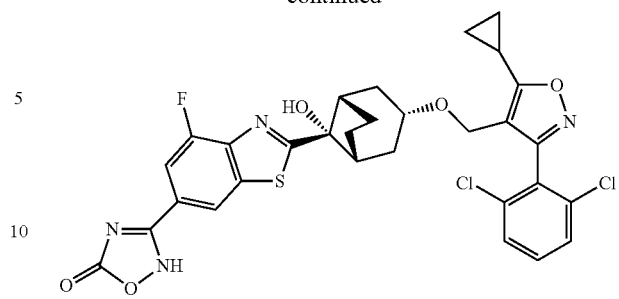

Example 36

To a solution of 2-((1R,3s,5S,8r)-3-((5-cyclopropyl-3-(2,6-dichlorophenyl)isoxazol-4-yl)methoxy)-8-hydroxybicyclo[3.2.1]octan-8-yl)-4-fluoro-N-hydroxybenzo[d]thiazole-6-carboximidamide 35 (118 mg, 0.19 mmol) in THF (5 mL) was added CDI (92 mg, 0.57 mmol) and DBU (87 mg, 0.57 mmol). The mixture was stirred at rt for 30 min, acidified with HCl (1M) and then extracted with EtOAc. The organic portion was washed with brine, dried over Na$_2$SO$_4$, filtered, concentrated and purified by prep-HPLC to give 3-(2-((1R,3s,5S,8r)-3-((5-cyclopropyl-3-(2,6-dichlorophenyl)isoxazol-4-yl)methoxy)-8-hydroxybicyclo[3.2.1]octan-8-yl)-4-fluorobenzo[d]thiazol-6-yl)-1,2,4-oxadiazol-5(2H)-one 36. $^1$H-NMR (500 MHz, DMSO-d$_6$): δ 13.10 (br s, 1H), 8.42 (d, J=1.0 Hz, 1H), 7.74-7.57 (m, 4H), 6.57 (s, 1H), 4.29 (s, 2H), 3.54-3.48 (m, 1H), 2.40-2.35 (m, 3H), 1.85-1.79 (m, 4H), 1.65-1.60 (m, 2H), 1.45-1.41 (m, 2H), 1.19-1.09 (m, 4H). LC/MS (ESI): m/z 643.2 (M+H)+.

Example 37: Ethyl 2-(2-((1R,3s,5S,8r)-3-((5-cyclopropyl-3-(2,6-dichlorophenyl)isoxazol-4-yl)methoxy)-8-hydroxybicyclo[3.2.1]octan-8-yl)-4-fluorobenzo[d]thiazole-6-carboxamido)acetate

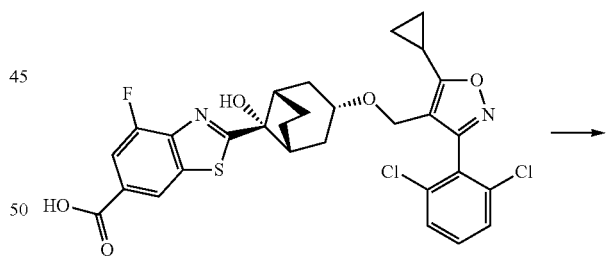

Example 11-27

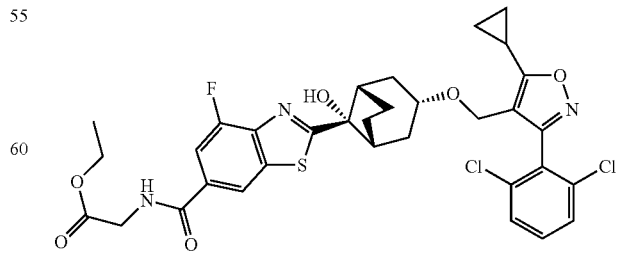

Example 37

To a solution of 2-((1R,3s,5S,8r)-3-((5-cyclopropyl-3-(2,6-dichlorophenyl)isoxazol-4-yl)methoxy)-8-hydroxybicyclo[3.2.1]octan-8-yl)-4-fluorobenzo[d]thiazole-6-carboxylic acid 11-27 (150 mg, 0.25 mmol) in DMF (10 mL) was added EDCl (100 mg, 0.5 mmol), DMAP (60 mg, 0.5 mmol) and glycine ethyl ester hydrochloride (70 mg, 0.5 mmol) and the mixture was stirred at rt for 12 h, diluted with water (100 mL) and extracted with EtOAc (3×100 mL). The combined organic layer was washed with brine (50 mL), dried over Na$_2$SO$_4$, filtered, concentrated and purified by column chromatography (DCM/MeOH=100:1) to give ethyl 2-(2-((1R,3s,5S,8r)-3-((5-cyclopropyl-3-(2,6-dichlorophenyl)isoxazol-4-yl)methoxy)-8-hydroxybicyclo[3.2.1]octan-8-yl)-4-fluorobenzo[d]thiazole-6-carboxamido)acetate 37.

Example 38: 2-(2-((1R,3s,5S,8r)-3-((5-Cyclopropyl-3-(2,6-dichlorophenyl)isoxazol-4-yl)methoxy)-8-hydroxybicyclo[3.2.1]octan-8-yl)-4-fluorobenzo[d]thiazole-6-carboxamido)acetic acid

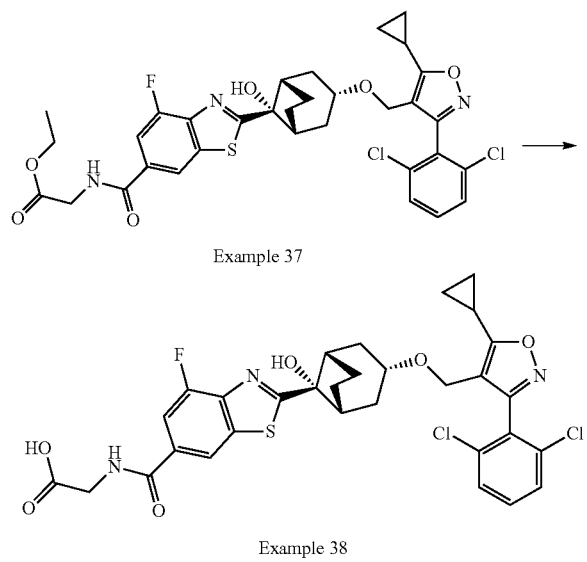

Example 37

Example 38

To a solution of ethyl 2-(2-((1R,3s,5S,8r)-3-((5-cyclopropyl-3-(2,6-dichlorophenyl)isoxazol-4-yl)methoxy)-8-hydroxybicyclo[3.2.1]octan-8-yl)-4-fluorobenzo[d]thiazole-6-carboxamido)acetate 37 (100 mg, 0.15 mmol) in MeOH (50 mL) was added aq. NaOH (1N, 10 mL) and the mixture was stirred at rt for 5 h, acidified by HCl (4M, 10 mL) and extracted with EtOAc (3×50 mL). The combined organic layer was washed with brine (50 mL), dried over Na$_2$SO$_4$, filtered, concentrated and purified by prep-HPLC to give 2-(2-((1R,3s,5S,8r)-3-((5-cyclopropyl-3-(2,6-dichlorophenyl)isoxazol-4-yl)methoxy)-8-hydroxybicyclo[3.2.1]octan-8-yl)-4-fluorobenzo[d]thiazole-6-carboxamido)acetic acid 38. $^1$H-NMR (500 MHz, DMSO-d$_6$): δ 12.66 (br s, 1H), 9.03 (t, J=6.0 Hz, 1H), 8.45 (d, J=1.5 Hz, 1H), 7.81-7.58 (m, 4H), 6.53 (br s, 1H), 4.29 (s, 2H), 3.97 (d, J=5.5 Hz, 2H), 3.55-3.50 (m, 1H), 2.40-2.36 (m, 3H), 1.85-1.79 (m, 4H), 1.65-1.61 (m, 2H), 1.45-1.41 (m, 2H), 1.19-1.12 (m, 4H). LCMS (ESI): m/z 660.1 (M+H)$^+$.

Example 39: 2-(2-((1R,3s,5S,8r)-3-((5-Cyclopropyl-3-(2,6-dichlorophenyl)isoxazol-4-yl) methoxy)-8-hydroxybicyclo[3.2.1]octan-8-yl)-4-fluorobenzo[d]thiazole-6-carboxamido)ethanesulfonic acid, ammonia salt

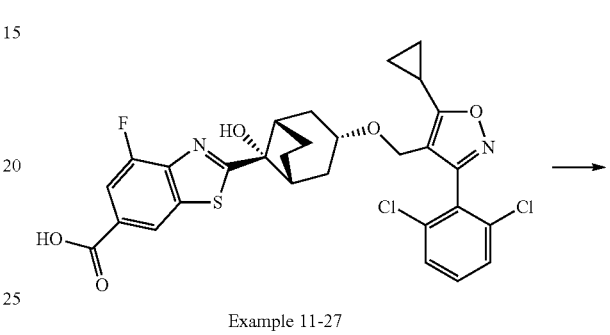

Example 11-27

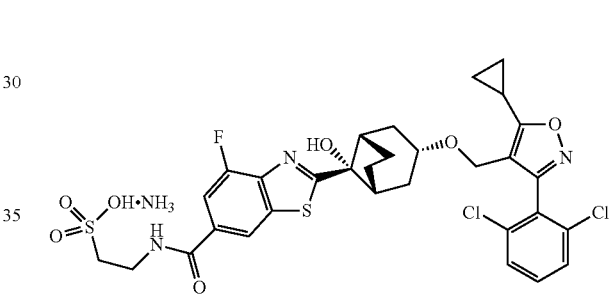

Example 39

To a solution of 2-((1R,3s,5S,8r)-3-((5-cyclopropyl-3-(2,6-dichlorophenyl)isoxazol-4-yl)methoxy)-8-hydroxybicyclo[3.2.1]octan-8-yl)-4-fluorobenzo[d]thiazole-6-carboxylic acid 11-27 (150 mg, 250 μmol) in DMF (10 mL) was added EDCl (100 mg, 500 μmol), DMAP (60 mg, 500 μmol) and taurine (63 mg, 500 μmol) and the mixture was stirred at rt for 12 h, diluted with water (100 mL) and extracted with EtOAc (3×100 mL). The combined organic layer was washed with brine (50 mL) and concentrated. The residue was redissolved in MeOH (5 mL) and 1N NH$_4$OH (0.5 mL) was added, concentrated and then purified by prep-HPLC to give the ammonia salt of 2-(2-((1R,3s,5S,8r)-3-((5-Cyclopropyl-3-(2,6-dichlorophenyl) isoxazol-4-yl)methoxy)-8-hydroxybicyclo[3.2.1]octan-8-yl)-4-fluorobenzo[d]thiazole-6-carboxamido)ethanesulfonic acid 39. $^1$H-NMR (500 MHz, DMSO-d$_6$): δ 8.66 (t, J=5.5 Hz, 1H), 8.35 (d, J=1.0 Hz, 1H), 7.71-7.58 (m, 4H), 7.20-6.98 (m, 3H), 6.51 (s, 1H), 4.29 (s, 2H), 3.57-3.49 (m, 3H), 2.69 (t, J=7.3 Hz, 2H), 2.41-2.36 (m, 3H), 1.85-1.76 (m, 4H), 1.64-1.60 (m, 2H), 1.43-1.40 (m, 2H), 1.20-1.10 (m, 4H). LCMS (ESI): m/z 710.0 (M−NH$_3$)$^+$.

Example 40 and Example 41: 2-((1R,5S)-8-((5-Cyclopropyl-3-(2,6-dichlorophenyl)isoxazol-4-yl)methoxy)-3-hydroxybicyclo[3.2.1]octan-3-yl)-4-fluorobenzo[d]thiazole-6-carbonitrile (40, first eluting isomer) and 2-((1R,5S)-8-((5-cyclopropyl-3-(2,6-dichlorophenyl)isoxazol-4-yl)methoxy)-3-hydroxybicyclo[3.2.1]octan-3-yl)-4-fluorobenzo[d]thiazole-6-carbonitrile (41, second eluting isomer)

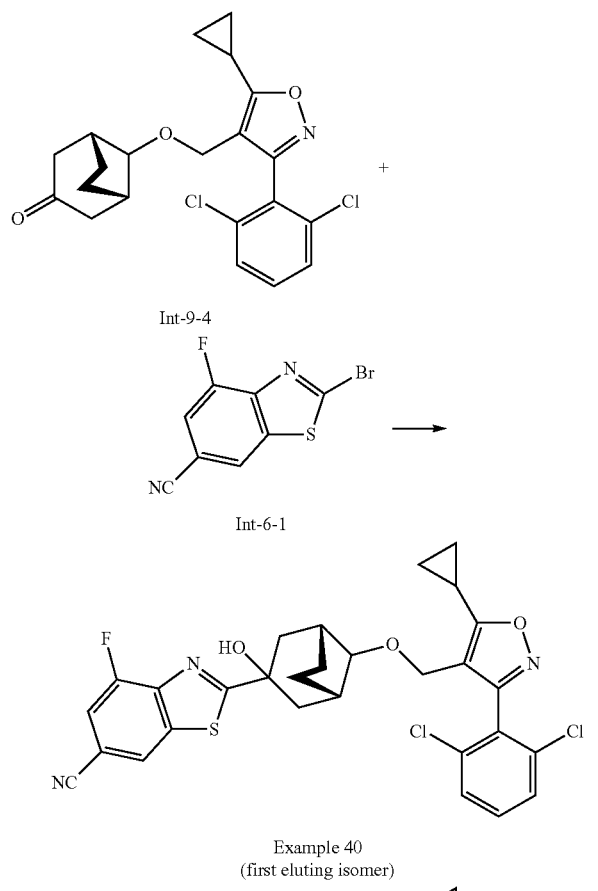

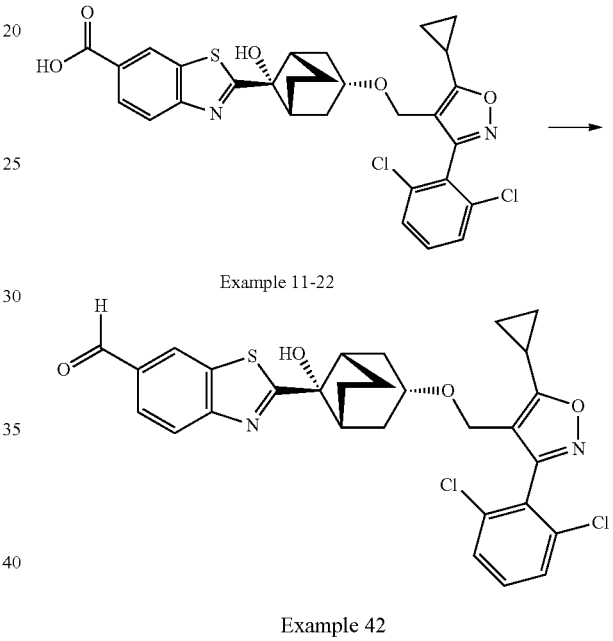

washed with brine (2×20 mL), dried over Na₂SO₄, concentrated and purified by prep-TLC (EtOAc/DCM=1:30) to give first eluting isomer 2-((1R,5S)-8-((5-cyclopropyl-3-(2,6-dichlorophenyl)isoxazol-4-yl)methoxy)-3-hydroxybicyclo[3.2.1]octan-3-yl)-4-fluorobenzo[d]thiazole-6-carbonitrile 40 and second eluting isomer 2-((1R,5S)-8-((5-cyclopropyl-3-(2,6-dichlorophenyl)isoxazol-4-yl)methoxy)-3-hydroxybicyclo[3.2.1]octan-3-yl)-4-fluorobenzo[d]thiazole-6-carbonitrile 41. LCMS (ESI): m/z 584.0 (M+H)⁺, 608.0 (M+Na)⁺.

Example 42: 2-((1R,3s,5S,8r)-3-((5-Cyclopropyl-3-(2,6-dichlorophenyl)isoxazol-4-yl)methoxy)-8-hydroxybicyclo[3.2.1]octan-8-yl)benzo[d]thiazole-6-carbaldehyde To compound (1R,5S)-8-((5-cyclopropyl-3-(2,6-dichlorophenyl)isoxazol-4-yl)methoxy)bicyclo[3.2.1]octan-3-one Int-9-4 (200 mg, 492 μmol) and 2-bromo-4-fluorobenzo[d]thiazole-6-carbonitrile Int-6-1 (190 mg, 738 μmol) in dry THF (20 mL) was added n-BuLi (1.6M in hexane; 0.6 mL, 984 μmol) at −78° C. under N₂. The mixture was stirred at −78° C. for 1 h, quenched with NH₄Cl (sat.) and extracted with EtOAc (3×50 mL). The organic layers were combined, Step 1:
A solution of 2-((1R,3s,5S,8r)-3-((5-cyclopropyl-3-(2,6-dichlorophenyl)isoxazol-4-yl)methoxy)-8-hydroxybicyclo[3.2.1]octan-8-yl)benzo[d]thiazole-6-carboxylic acid 11-22 (200 mg, 0.34 mmol) in THF/MeOH (4/2 mL) was cooled to 0° C., TMSCHN₂ (2.0 M in Hexane, 0.26 mL, 0.51 mmol) was added dropwise over 5 min under Ar atmosphere. The resulting solution was stirred at rt for 2 h, the reaction was quenched with dilute AcOH (0.5 N). The mixture was extracted with EtOAc (3×10 mL) and the organic layers were combined and washed with brine (2×10 mL), dried over Na₂SO₄, and concentrated. The crude methyl 2-((1R,3s,5S,8r)-3-((5-cyclopropyl-3-(2,6-dichlorophenyl)isoxazol-4-yl)methoxy)-8-hydroxybicyclo[3.2.1]octan-8-yl)benzo[d]thiazole-6-carboxylate (200 mg) was used in the next step without further purification.

Step 2:
A solution of crude methyl 2-((1R,3s,5S,8r)-3-((5-cyclopropyl-3-(2,6-dichloro-phenyl)isoxazol-4-yl)methoxy)-8-hydroxybicyclo[3.2.1]octan-8-yl)benzo[d]thiazole-6-carboxylate (200 mg) in MeOH (5 mL) was cooled to 0° C., NaBH₄ (27 mg, 0.7 mmol) was added in several portions over 10 min under Ar atmosphere. The resulting solution was stirred at rt for 2 h, the reaction was quenched with NH$_4$Cl (sat. aq. sol.). The mixture was extracted with EtOAc (3×10 mL) and the organic layers were combined and washed with brine (2×10 mL), dried over Na$_2$SO$_4$, and concentrated. The crude (1R,3s,5S,8r)-3-((5-cyclopropyl-3-(2,6-dichlorophenyl)isoxazol-4-yl)methoxy)-8-(6-(hydroxymethyl)benzo[d]thiazol-2-yl)bicyclo[3.2.1]octan-8-ol (100 mg) was used in next step without further purification.

Step 3:

A solution of crude (1R,3s,5S,8r)-3-((5-cyclopropyl-3-(2,6-dichlorophenyl)isoxazol-4-yl)methoxy)-8-(6-(hydroxymethyl)benzo[d]thiazol-2-yl)bicyclo[3.2.1]octan-8-ol (100 mg) in DCM (3 mL) was added activated MnO$_2$ (76 mg, 0.88 mmol) and the resulting dark-black suspension was stirred at rt for 1 h. The mixture was filtered off on a pad of cellite, and the filtrate was concentrated to dryness and the residue was purified by flash column chromatography on silica gel to give 2-((1R,3s,5S,8r)-3-((5-cyclopropyl-3-(2,6-dichlorophenyl)isoxazol-4-yl)methoxy)-8-hydroxybicyclo[3.2.1]octan-8-yl)benzo[d]thiazole-6-carbaldehyde 42.

Example 43: (1R,3s,5S,8r)-3-((5-Cyclopropyl-3-(2,6-dichlorophenyl)isoxazol-4-yl)methoxy)-8-(6-(morpholinomethyl)benzo[d]thiazol-2-yl)bicyclo[3.2.1]octan-8-ol

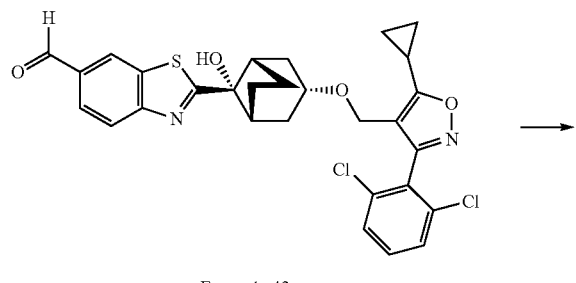

Example 42

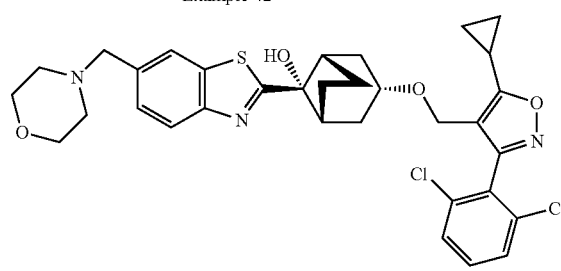

Example 43

To a solution of 2-((1R,3s,5S,8r)-3-((5-cyclopropyl-3-(2,6-dichlorophenyl)isoxazol-4-yl)methoxy)-8-hydroxybicyclo[3.2.1]octan-8-yl)benzo[d]thiazole-6-carbaldehyde 42 (70 mg, 0.12 mmol) in MeOH (2 mL) was added Ti(OiPr)$_4$ (70 mg, 0.24 mmol) and morpholine (21 mg, 0.24 mmol) at rt and the resulting mixture was stirred overnight. NaBH$_4$ (10 mg, 0.24 mmol) was added in several portions at 0° C. under Ar atmosphere. The resulting solution was stirred at rt for additional 2 h, the reaction was quenched with NH$_4$Cl (sat. aq. sol.). The mixture was extracted with EtOAc (3×10 mL) and the organic layers were combined and washed with brine (2×10 mL), dried over Na$_2$SO$_4$, and concentrated. The residue was purified by prep-HPLC to afford (1R,3s,5S,8r)-3-((5-cyclopropyl-3-(2,6-dichlorophenyl)isoxazol-4-yl)methoxy)-8-(6-(morpholinomethyl)benzo-[d]thiazol-2-yl)bicyclo[3.2.1]octan-8-ol 43 $^1$H-NMR (400 MHz, DMSO-d$_6$): δ 7.96 (s, 1H), 7.88 (d, J=8.4 Hz, 1H), 7.67-7.56 (m, 3H), 7.41 (d, J=7.6 Hz, 1H), 6.23 (s, 1H), 4.28 (s, 2H), 3.57 (s, 6H), 3.58-3.47 (m, 1H), 2.39-2.32 (m, 7H), 1.86-1.81 (m, 2H), 1.75-1.70 (m, 2H), 1.65-1.65 (m, 2H), 1.42-1.34 (m, 2H), 1.19-1.07 (m, 4H). LC/MS (ESI): m/z 639.8 (M+H)$^+$.

Example 44: Ethyl 2-(2-((1R,3s,5S,8r)-3-((5-cyclopropyl-3-(2,6-dichlorophenyl)isoxazol-4-yl)methoxy)-8-hydroxybicyclo[3.2.1]octan-8-yl)-5-(trifluoromethyl)oxazol-4-yl)acetate

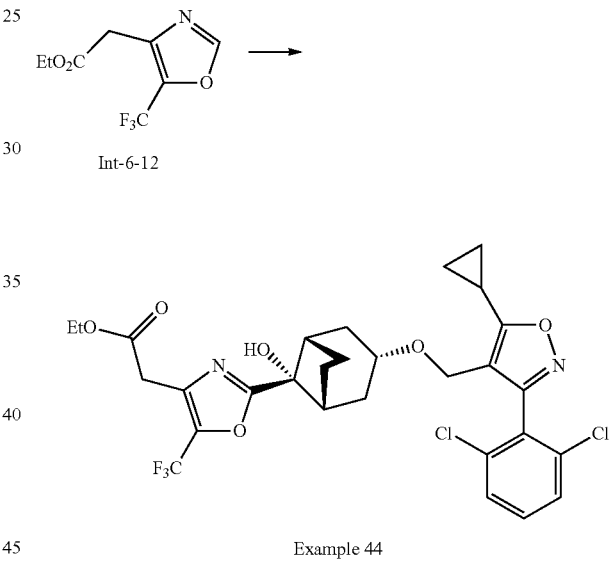

Example 44

A solution of ethyl 2-(5-(trifluoromethyl)oxazol-4-yl)acetate Int-6-12 (200 mg, 0.9 mmol) and (1R,3s,5S)-3-((5-cyclopropyl-3-(2,6-dichlorophenyl) isoxazol-4-yl)methoxy)bicyclo[3.2.1]octan-8-one (Int-4-14a) (243 mg, 0.6 mmol) in dry THF (6 mL) was cooled to −78° C. in a dry-ice/acetone bath, then n-BuLi (1.5 M in THF, 0.6 mL, 0.9 mmol) was added dropwise during 10 min under Ar atmosphere. The resulting solution was stirred at −78° C. for 2 h, the reaction was quenched with NH$_4$Cl (sat. aq.). The reaction mixture was extracted with EtOAc (3×10 mL) and the organic layers were combined and washed with brine (2×10 mL), dried over Na$_2$SO$_4$, and concentrated under reduced pressure. The residue was purified by flash column chromatography on silica gel to give ethyl 2-(2-((1R,3s,5S,8r)-3-((5-cyclopropyl-3-(2,6-dichlorophenyl)isoxazol-4-yl)methoxy)-8-hydroxybicyclo[3.2.1]octan-8-yl)-5-(trifluoromethyl)oxazol-4-yl)acetate 44.

Example 45: 2-(2-((1R,3s,5S,8r)-3-((5-Cyclopropyl-3-(2,6-dichlorophenyl)isoxazol-4-yl)methoxy)-8-hydroxybicyclo[3.2.1]octan-8-yl)-5-(trifluoromethyl)oxazol-4-yl)acetic acid

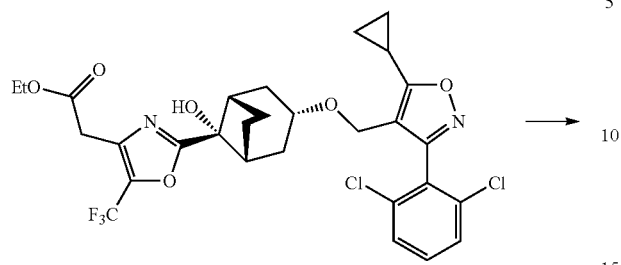

Example 44

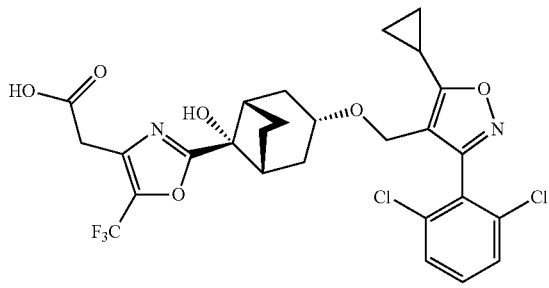

Example 45

To a solution of ethyl 2-(2-((1R,3s,5S,8r)-3-((5-cyclopropyl-3-(2,6-dichlorophenyl)isoxazol-4-yl)methoxy)-8-hydroxybicyclo[3.2.1]octan-8-yl)-5-(trifluoromethyl)oxazol-4-yl)acetate 44 (70 mg, 0.11 mmol) in MeOH (5 mL) was added LiOH (1N, aq., 0.25 mL), the resulting mixture was stirred at rt for additional 4 h. The solvent was removed under reduce pressure and the pH adjusted to pH=4-5 with diluted HCl (0.5N, aq.). The residue was extracted with EtOAc (3×5 mL), the organic layers was combined and dried over Na$_2$SO$_4$, then concentrated under reduced pressure. The residue was purified by prep-TLC to afford give 2-(2-((1R,3s,5S,8r)-3-((5-cyclopropyl-3-(2,6-dichlorophenyl)isoxazol-4-yl)methoxy)-8-hydroxybicyclo[3.2.1]octan-8-yl)-5-(trifluoromethyl)-oxazol-4-yl)acetic acid 45. $^1$H-NMR (400 MHz, DMSO-d$_6$): δ 12.98 (br s, 1H), 7.67-7.54 (m, 3H), 6.18 (s, 1H), 4.26 (s, 2H), 3.62 (s, 2H), 3.48-3.36 (m, 1H), 2.42-2.31 (m, 3H), 1.72 (t, J=11.2 Hz, 2H), 1.58-1.54 (m, 2H), 1.46-1.22 (m, 4H), 1.19-1.09 (m, 4H). $^{19}$F-NMR (376 MHz, DMSO-d$_6$): δ −60.95. LC/MS (ESI): m/z 600.9 (M+H)$^+$.

Example 46: 2-(2-((1R,3s,5S,8r)-3-((5-Cyclopropyl-3-(2,6-dichlorophenyl)isoxazol-4-yl)methoxy)-8-hydroxybicyclo[3.2.1]octan-8-yl)thiazol-4-yl)acetic acid

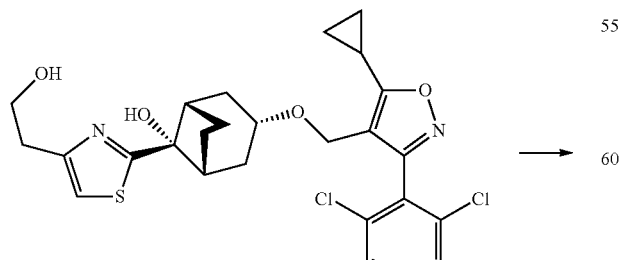

Example 9-30

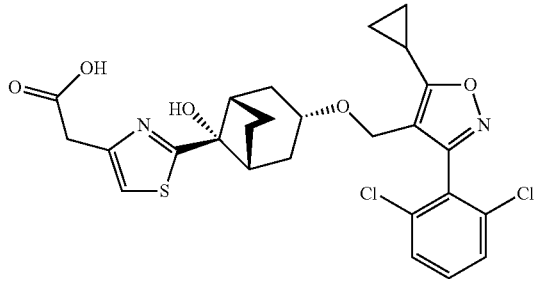

Example 46

To a solution of (1R,3s,5S,8r)-3-((5-cyclopropyl-3-(2,6-dichlorophenyl)isoxazol-4-yl)methoxy)-8-(4-(2-hydroxyethyl)thiazol-2-yl)bicyclo[3.2.1]octan-8-ol (9-30, 85 mg, 0.16 mmol) in MeCN (10 mL) and water (3 mL) was added TEMPO (4 N, 2 mL) and iodobenzene diacetate (100 mg, 0.11 mmol) and the mixture was stirred at rt for 1 h, diluted with water and extracted with EtOAc (3×50 mL). The combined organic layer was washed with brine (50 mL), concentrated and purified by prep-HPLC to give compound 2-(2-((1R,3s,5S,8r)-3-((5-cyclopropyl-3-(2,6-dichlorophenyl)isoxazol-4-yl)methoxy)-8-hydroxybicyclo[3.2.1]octan-8-yl)thiazol-4-yl)acetic acid 46. $^1$H-NMR (500 MHz, DMSO-d$_6$): δ 7.65-7.64 (m, 2H), 7.59-7.55 (m, 1H), 7.25 (s, 1H), 5.90 (s, 1H), 4.26 (s, 2H), 3.47-3.41 (m, 3H), 2.37-2.33 (m, 1H), 2.25 (s, 2H), 1.80-1.76 (m, 2H), 1.62-1.52 (m, 4H), 1.30-1.28 (m, 2H), 1.16-1.08 (m, 4H), CO$_2$H proton not resolved. LCMS (ESI): m/z 549 (M+H)$^+$.

Example 47: 2-((1R,3s,5S,8r)-3-((4-Cyclopropyl-1-(2,6-dichlorophenyl)-1H-pyrazol-5-yl)methoxy)-8-hydroxybicyclo[3.2.1]octan-8-yl)-4-fluorobenzo[d]thiazole-6-carboxylic acid

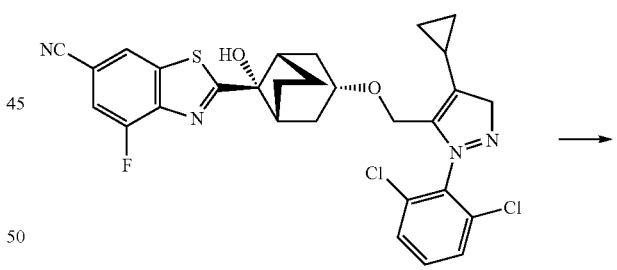

Example 8-16

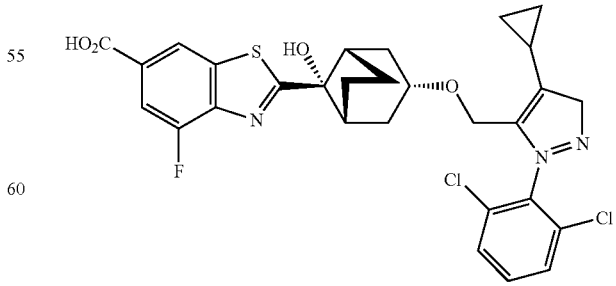

Example 47

NaOH (40% aq., 1.0 mL) was added to 2-((1R,3s,5S,8r)-3-((4-cyclopropyl-1-(2,6-dichlorophenyl)-1H-pyrazol-5-yl)methoxy)-8-hydroxybicyclo[3.2.1]octan-8-yl)-4-fluorobenzo[d]thiazole-6-carbonitrile (8-16, 200 mg, 0.34 mmol) in a sealed tube. The vial was closed and heated at 80° C. overnight, concentrated and purified by prep-TLC to afford 2-((1R,3s,5S,8r)-3-((4-cyclopropyl-1-(2,6-dichlorophenyl)-1H-pyrazol-5-yl)methoxy)-8-hydroxybicyclo[3.2.1]octan-8-yl)-4-fluorobenzo[d]thiazole-6-carboxylic acid 47. $^1$H-NMR (400 MHz, DMSO-$d_6$): δ 13.43 (br s, 1H), 8.53 (s, 1H), 7.77-7.66 (m, 3H), 7.59 (t, J=8.0 Hz, 1H), 7.43 (s, 1H), 6.52 (s, 1H), 4.39 (s, 2H), 3.53-3.45 (m, 1H), 2.36-2.32 (m, 2H), 1.83-1.75 (m, 5H), 1.66-1.60 (m, 2H), 1.44-1.39 (m, 2H), 0.94-0.89 (m, 2H), 0.66-0.62 (m, 2H). $^{19}$F-NMR (376 MHz, DMSO-$d_6$): δ −122.53. LC/MS (ESI): m/z 601.8 (M+H)$^+$.

Example 48: 2-((1R,3s,5S,8r)-3-((5-Cyclopropyl-3-(2,6-dichlorophenyl)isoxazol-4-yl)methoxy)-8-hydroxybicyclo[3.2.1]octan-8-yl)-4-fluorobenzo[d]thiazole-6-carboxamide

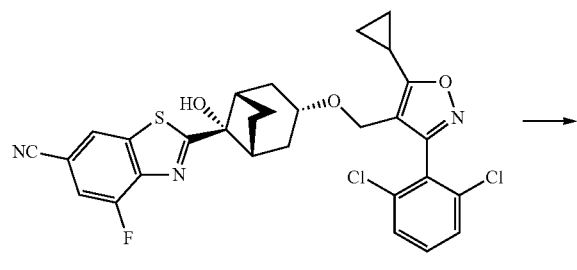

Example 8-9

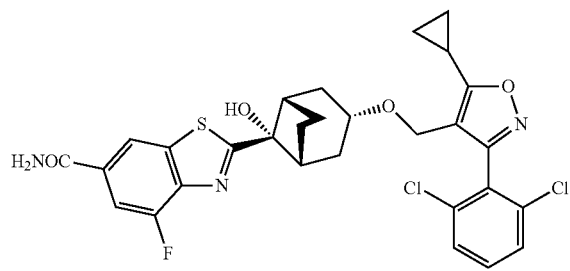

Example 48

To a solution of 2-((1R,3s,5S,8r)-3-((5-cyclopropyl-3-(2,6-dichlorophenyl)isoxazol-4-yl)methoxy)-8-hydroxybicyclo[3.2.1]octan-8-yl)-4-fluorobenzo[d]thiazole-6-carbonitrile (8-9, 200 mg, 0.34 mmol) in DMSO (5 mL) was added H$_2$O$_2$ (1 mL) dropwise. The mixture was stirred at rt for 2 h, poured into water (30 mL) and extracted with EtOAc (3×50 mL): The combined organic layers were washed with brine (100 mL), concentrated and purified by column chromatography (EtOAc/PE=1:3) to give compound 2-((1R,3s,5S,8r)-3-((5-cyclopropyl-3-(2,6-dichlorophenyl)isoxazol-4-yl)methoxy)-8-hydroxybicyclo[3.2.1]octan-8-yl)-4-fluorobenzo[d]thiazole-6-carboxamide 48.

Example 49: (1R,3s,5S,8r)-8-(6-(Aminomethyl)-4-fluorobenzo[d]thiazol-2-yl)-3-((5-cyclopropyl-3-(2,6-dichlorophenyl)isoxazol-4-yl)methoxy)bicyclo[3.2.1]octan-8-ol

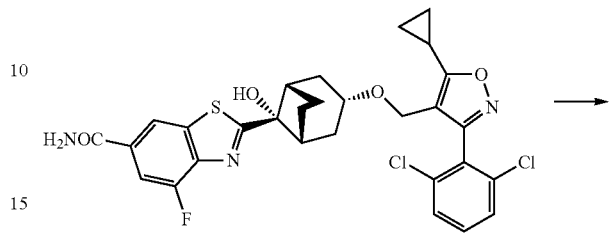

Example 48

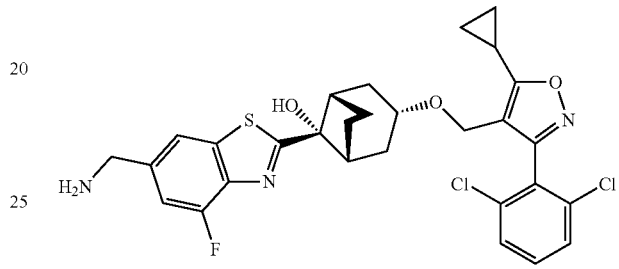

Example 49

To a solution of 2-((1R,3s,5S,8r)-3-((5-cyclopropyl-3-(2,6-dichlorophenyl)isoxazol-4-yl)methoxy)-8-hydroxybicyclo[3.2.1]octan-8-yl)-4-fluorobenzo[d]thiazole-6-carboxamide 48 (150 mg, 0.25 mmol) in THF (20 mL) was added 1N LAH (1 mL) dropwise. The mixture was stirred at rt overnight, poured into water (30 mL) and extracted with EtOAc (3×50 mL): The combined organic layer was washed with brine (100 mL), concentrated and purified by column chromatography (EtOAc/PE=1:1) to give (1R,3s,5S,8r)-8-(6-(aminomethyl)-4-fluorobenzo[d]thiazol-2-yl)-3-((5-cyclopropyl-3-(2,6-dichlorophenyl)isoxazol-4-yl)methoxy)bicyclo[3.2.1]octan-8-ol 49.

Assays

FRET Activity Assay

Determination of a ligand mediated cofactor peptide interaction to quantify ligand binding to the nuclear receptor FXR was performed as follows: Preparation of human FXR alpha ligand binding domain: The human FXRalpha LBD was expressed in *E. coli* strain BL21(DE3) as an N-terminally GST tagged fusion protein. The DNA encoding the FXR ligand binding domain was cloned into vector pDEST15 (Invitrogen). Expression was under control of an IPTG inducible T7 promoter. The amino acid boundaries of the ligand binding domain were amino acids 187-472 of Database entry NM_005123 (RefSeq). Expression and purification of the FXR-LBD: An overnight preculture of a transformed *E. coli* strain was diluted 1:20 in LB-Ampicillin medium and grown at 30° C. to an optical density of OD$_{600}$=0.4-0.6. Gene expression was then induced by addition of 0.5 mM IPTG. Cells were incubated an additional 6 h at 30° C., 180 rpm. Cells were collected by centrifugation (7000×g, 7 min, rt). Per liter of original cell culture, cells were resuspended in 10 mL lysis buffer (50 mM Glucose, 50 mM Tris pH 7.9, 1 mM EDTA and 4 mg/mL lysozyme) and left on ice for 30 min. Cells were then subjected to sonication and cell debris removed via centrifugation (22000×g, 30 min, 4° C.). Per 10 mL of supernatant 0.5 mL prewashed Glutathione 4B sepharose slurry (Qiagen) was added and the suspension kept slowly rotating for 1 h at 4° C. Glutathione 4B sepharose beads were pelleted by centrifugation (2000× g, 15 sec, 4° C.) and washed twice in wash buffer (25 mM Tris, 50 mM KCl, 4 mM $MgCl_2$ and 1M NaCl). The pellet was resuspended in 3 mL elution buffer per liter of original culture (elution buffer: 20 mM Tris, 60 mM KCl, 5 mM $MgCl_2$ and 80 mM glutathione added immediately prior to use as powder). The suspension was left rotating for 15 min at 4° C., the beads pelleted and eluted again with half the volume of elution buffer than the first time. The eluates were pooled and dialysed overnight in 20 mM Hepes buffer (pH 7.5) containing 60 mM KCl, 5 mM $MgCl_2$ as well as 1 mM dithiothreitol and 10% (v/v) glycerol. The protein was analysed by SDS-Page.

The method measures the ability of putative ligands to modulate the interaction between the purified bacterial expressed FXR ligand binding domain (LBD) and a synthetic biotinylated peptide based on residues 676-700 of SRC-1 (LCD2, 676-700). The sequence of the peptide used was B—CPSSHSSLTERHKILHRLLQEGSPS—COOH where the N-terminus was biotinylated (B). The ligand binding domain (LBD) of FXR was expressed as fusion protein with GST in BL-21 cells using the vector pDEST15. Cells were lysed by sonication, and the fusion proteins purified over glutathione sepharose (Pharmacia) according to the manufacturers instructions. For screening of compounds for their influence on the FXR-peptide interaction, the Perkin Elmer LANCE technology was applied. This method relies on the binding dependent energy transfer from a donor to an acceptor fluorophor attached to the binding partner of interest. For ease of handling and reduction of background from compound fluorescence LANCE technology makes use of generic fluorophore labels and time resolved detection Assays were done in a final volume of 25 μL in a 384 well plate, in a Tris-based buffer (20 mM Tris-HCl pH 7.5; 60 mM KCl, 5 mM $MgCl_2$; 35 ng/μL BSA), containing 20-60 ng/well recombinantly expressed FXR-LBD fused to GST, 200-600 nM N-terminally biotinylated peptide, representing SRC1 aminoacids 676-700, 200 ng/well Streptavidin-xlAPC conjugate (Prozyme) and 6-10 ng/well Eu W1024-antiGST (Perkin Elmer). DMSO content of the samples was kept at 1%. After generation of the assay mix and diluting the potentially FXR modulating ligands, the assay was equilibrated for 1 h in the dark at rt in FIA-plates black 384 well (Greiner). The LANCE signal was detected by a Perkin Elmer VICTOR2VTM Multilabel Counter. The results were visualized by plotting the ratio between the emitted light at 665 and 615 nm. A basal level of FXR-peptide formation is observed in the absence of added ligand. Ligands that promote the complex formation induce a concentration-dependent increase in time-resolved fluorescent signal. Compounds which bind equally well to both monomeric FXR and to the FXR-peptide complex would be expected to give no change in signal, whereas ligands which bind preferentially to the monomeric receptor would be expected to induce a concentration-dependent decrease in the observed signal.

To assess the agonistic potential of the compounds, $EC_{50}$-values were determined for example compounds as listed below in Table 1 (F $EC_{50}$).

Mammalian One Hybrid (M1H) Assay

Determination of a ligand mediated Gal4 promoter driven transactivation to quantify ligand binding mediated activation of FXR was performed as follows: The cDNA part encoding the FXR ligand binding domain was cloned into vector pCMV-BD (Stratagene) as a fusion to the yeast GAL4 DNA binding domain under the control of the CMV promoter. The amino acid boundaries of the ligand binding domain were amino acids 187-472 of Database entry NM_005123 (RefSeq). The plasmid pFR-Luc (Stratagene) was used as the reporter plasmid, containing a synthetic promoter with five tandem repeats of the yeast GAL4 binding sites, driving the expression of the *Photinus pyralis* (American firefly) luciferase gene as the reporter gene. In order to improve experimental accuracy the plasmid pRL-CMV (Promega) was cotransfected. pRL-CMV contains the constitutive CMV promoter, controlling the expression of the *Renilla reniformis* luciferase. All Gal4 reporter gene assays were done in HEK293 cells (obtained from DSMZ, Braunschweig, Germany) grown in MEM with L-Glutamine and Earle's BSS supplemented with 10% fetal bovine serum, 0.1 mM nonessential amino acids, 1 mM sodium pyruvate, and 100 units Penicilin/Streptavidin per mL at 37° C. in 5% $CO_2$. Medium and supplements were obtained from Invitrogen. For the assay, $5×10^5$ cells were plated per well in 96 well plates in 100 μL per well MEM without Phenol Red and L-Glutamine and with Earle's BSS supplemented with 10% charcoal/dextran treated FBS (HyClone, South Logan, Utah), 0.1 mM nonessential amino acids, 2 mM glutamine, 1 mM sodium pyruvate, and 100 units Penicilin/Streptavidin per mL, incubated at 37° C. in 5% $CO_2$. The following day the cells were >90% confluence. Medium was removed and cells were transiently transfected using 20 μL per well of a OptiMEM—polyethylene-imine-based transfection-reagent (OptiMEM, Invitrogen; Polyethyleneimine, Aldrich Cat No. 40,827-7) including the three plasmids described above. MEM with the same composition as used for plating cells was added 2-4 h after addition of transfection mixture. Then compound stocks, prediluted in MEM were added (final vehicle concentration not exceeding 0.1%). Cells were incubated for additional 16 h before firefly and *renilla* luciferase activities were measured sequentially in the same cell extract using a Dual-Light-Luciferase-Assay system (Dyer et al., Anal. Biochem. 2000, 282, 158-161). All experiments were done in triplicates.

To assess the FXR agonistic potency of the example compounds, potency was determined in the M1H assay as listed below in Table 1 (M $EC_{50}$).

TABLE 1

| Ex # | F $EC_{50}$ | M $EC_{50}$ | Ex # | F $EC_{50}$ | M $EC_{50}$ | Ex # | F $EC_{50}$ | M $EC_{50}$ |
|---|---|---|---|---|---|---|---|---|
| 4 | 21 | 100 | 5 | 620 | 1900 | 8-5 | 31 | 58 |
| 9-6 | 220 | 320 | 9-7 | 110 | 150 | 11-1 | 2200 | >3000 |
| 11-2 | 8600 | >3000 | 11-3 | 1300 | 2100 | 11-4a | 56 | 300 |
| 11-4b | 120 | 380 | 11-5 | 60 | 94 | 11-6 | 40 | 51 |
| 11-7 | 150 | 1300 | 11-8 | 8000 | >3000 | 11-9 | 47 | 120 |
| 11-10 | 250 | 1200 | 11-11 | 1000 | 1400 | 11-12 | 360 | 430 |
| 11-13 | 110 | 440 | 11-14 | 230 | 270 | 11-15 | 1500 | 2200 |
| 11-16 | 84 | 570 | 11-17 | 980 | 1800 | 11-18 | 350 | 170 |
| 11-19 | 570 | 2500 | 11-20 | 180 | 1500 | 11-21 | 23 | 310 |

TABLE 1-continued

| Ex # | F EC$_{50}$ | M EC$_{50}$ | Ex # | F EC$_{50}$ | M EC$_{50}$ | Ex # | F EC$_{50}$ | M EC$_{50}$ |
|---|---|---|---|---|---|---|---|---|
| 11-22 | 3.7 | 1.6 | 11-23 | 41 | 18 | 11-24 | 7.8 | 14 |
| 11-25 | 79 | 430 | 11-26 | 53 | 1800 | 11-27 | 3.8 | 1.0 |
| 11-28 | 9.7 | 17 | 11-29 | 4.3 | 5.8 | 11-30 | 64 | 67 |
| 11-31 | 50 | 130 | 11-32 | 120 | 23 | 11-33 | 36 | 38 |
| 11-34 | 55 | 380 | 11-35 | 9.6 | 5.2 | 11-36 | 1100 | 930 |
| 11-37 | 8.8 | 43 | 11-38 | 270 | 460 | 11-39 | 390 | 250 |
| 11-40 | 420 | 290 | 11-41 | 190 | 320 | 11-42 | 20 | 36 |
| 11-43 | 16 | 1800 | 11-44 | 49 | 120 | 11-45 | 7.0 | 140 |
| 11-46 | 44 | 180 | 11-47 | 12 | 99 | 11-48 | 46 | 190 |
| 11-49 | 28 | 93 | 11-50 | 82 | 6.4 | 11-51 | 3.7 | 0.62 |
| 11-52 | 4.9 | 1.9 | 11-53 | 235 | 391 | 11-54 | 810 | 390 |
| 11-55 | 77 | 24 | 11-56 | 23 | 290 | 11-57 | 31 | 29 |
| 14-1 | 25 | 550 | 14-2 | 32 | 2700 | 14-3 | 41 | 520 |
| 15-1 | 37 | 77 | | | | | | |
| 16 | 22 | 1900 | 17 | 150 | 670 | 18 | 98 | 440 |
| 20 | 150 | 200 | 21 | 64 | 1700 | 22 | 3.9 | 140 |
| 24a | 49 | 140 | 24b | 240 | 730 | 26 | 17 | 210 |
| 29 | 51 | 2600 | 30 | 190 | >3000 | 31 | 4900 | >3000 |
| 32 | 190 | 400 | 33 | 120 | 2700 | 34 | 4.1 | 5.3 |
| 36 | 4.6 | 37 | 38 | 3.0 | 1270 | 39 | 3.2 | 760 |
| 43 | 15 | 15 | 45 | 6.0 | 7.9 | 46 | 42 | 260 |
| 47 | 1.1 | 7.9 | | | | | | |

The invention claimed is:

1. A compound according to the following Formula (1), an enantiomer, diastereomer, tautomer, solvate, prodrug or pharmaceutical acceptable salt thereof

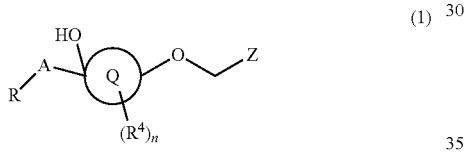

wherein:

R is selected from the group consisting of hydrogen, halogen, $C_{1-6}$-alkyl, $C_{2-6}$-alkenyl, $C_{2-6}$-alkynyl, halo-$C_{1-6}$-alkyl, $C_{0-6}$-alkylene-$R^7$, $C_{0-6}$-alkylene-O—$R^7$, $C_{0-6}$-alkylene-CN, $C_{0-6}$-alkylene-N$R^7R^8$, O—$C_{3-10}$-cycloalkyl, O—$C_{1-6}$-alkylene-O—$R^7$, O—$C_{3-10}$-heterocycloalkyl, $C_{0-6}$-alkylene-CO$_2R^7$, $C_{0-6}$-alkylene-C(O)$R^7$, $C_{0-6}$-alkylene-C(O)N$R^7R^8$, $C_{0-6}$-alkylene-C(O)N$R^7$SO$_2R^7$, $C_{0-6}$-alkylene-N($R^7$)C(O)$R^7$, $C_{0-6}$-alkylene-SO$_x$—$R^7$, $C_{0-6}$-alkylene-SO$_3$H, $C_{0-6}$-alkylene-SO$_2$—N$R^7R^8$, $C_{0-6}$-alkylene-SO$_2$—N$R^8$COR$^7$, $C_{0-6}$-alkylene-N($R^7$)SO$_2$—$R^8$, and $C_{0-6}$-alkylene-SO$_2$—$C_{3-10}$-heterocycloalkyl,
wherein alkylene, cycloalkyl, heterocycloalkyl and the 5- or 6-membered heteroaryl are unsubstituted or substituted by 1 to 4 substituents independently selected from the group consisting of halogen, CN, $C_{1-3}$-alkyl, halo-$C_{1-3}$-alkyl, OH, oxo, CO$_2$H, SO$_3$H, O—$C_{1-3}$-alkyl and O-halo-$C_{1-3}$-alkyl;

$R^7$ is independently selected from the group consisting of hydrogen, $C_{1-6}$-alkyl, halo-$C_{1-6}$-alkyl, $C_{0-6}$-alkylene-$C_{3-8}$-cycloalkyl, $C_{0-6}$-alkylene-$C_{3-8}$-heterocycloalkyl, 5- or 6-membered heteroaryl and phenyl, wherein alkyl, alkylene, cyclolalkyl, heterocycloalkyl, phenyl and heteroaryl are unsubstituted or substituted with 1 to 6 substituents independently selected from the group consisting of halogen, CN, OH, oxo, CO$_2$H, $C_{1-3}$-alkyl, halo-$C_{1-3}$-alkyl, O—$C_{1-3}$-alkyl, O-halo-$C_{1-3}$-alkyl, SO$_3$H and SO$_2$—$C_{1-3}$-alkyl;

$R^8$ is independently selected from the group consisting of hydrogen, $C_{1-6}$-alkyl, halo-$C_{1-6}$-alkyl and $C_{3-6}$-cycloalkyl;

or $R^7$ and $R^8$ when taken together with the nitrogen to which they are attached may complete a 3- to 8-membered ring containing carbon atoms and optionally containing 1 or 2 heteroatoms selected from O, S or N, wherein the ring is unsubstituted or substituted with 1 to 4 substituents independently selected from the group consisting of fluoro, OH, oxo, $C_{1-4}$-alkyl and halo-$C_{1-4}$-alkyl;

A is a 6-10 membered mono- or bicyclic aryl or a 5-10 membered mono- or bicyclic heteroaryl containing 1 to 5 heteroatoms independently selected from the group consisting of N, O and S, wherein aryl and heteroaryl are unsubstituted or substituted with one or two groups independently selected from the group consisting of OH, halogen, CN, O—$C_{1-6}$-alkyl, O-halo-$C_{1-6}$-alkyl, $C_{1-6}$-alkyl, halo-$C_{1-6}$-alkyl, $C_{3-6}$-cycloalkyl, $C_{6-6}$-heterocycloalkyl and halo-$C_{3-6}$-cycloalkyl;

Q is a $C_{3-10}$-cycloalkyl ring, or $C_{6-10}$-bridged cycloalkyl ring wherein the —O—CH$_2$—Z-substituent is not directly adjacent to substituent A, wherein when Q is a bi- or multicyclic ring system, a carbon atom may optionally be replaced by a oxygen, SO$_x$ or N$R^7$;

Z is selected from

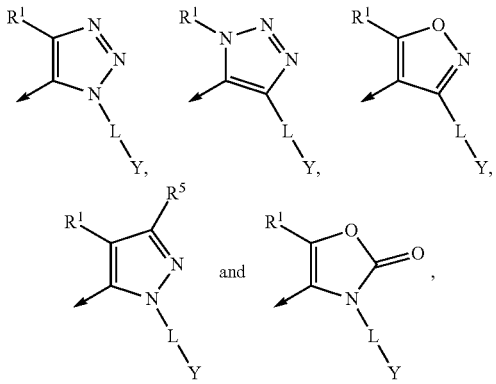

wherein
L is selected from the group consisting of a bond, $C_{1-3}$-alkylene and $C_{1-3}$-alkylene-O—;

Y is selected from the group consisting of phenyl, pyridyl, pyridyl-N-oxide, pyrimidyl, pyridinonyl, pyrimidinonyl, $C_{4-8}$-cycloalkyl and $C_{4-8}$-heterocycloalkyl, wherein phenyl, pyridyl, pyridyl-N-oxide, pyrimidyl, pyridinonyl, pyrimidinonyl, $C_{4-8}$-cycloalkyl and $C_{4-8}$-heterocycloalkyl are substituted with $R^2$ and $R^3$ and optionally substituted one or two times with a group selected from fluoro, chloro, CN, $NH_2$, $NH(C_{1-3}$-alkyl), $N(C_{1-3}$-alkyl$)_2$, $C_{1-3}$-alkyl, fluoro-$C_{1-3}$-alkyl, OH, $C_{1-3}$-alkoxy, fluoro-$C_{1-3}$-alkoxy, $C_{3-6}$-cycloalkyl and fluoro-$C_{3-6}$-cycloalkyl;

$R^1$ is selected from the group consisting of $C_{1-4}$-alkyl and $C_{3-6}$-cycloalkyl, wherein $C_{1-4}$-alkyl is unsubstituted or substituted with 1 to 3 substituents independently selected from the group consisting of fluoro, hydroxy, $C_{1-3}$-alkoxy and fluoro-$C_{1-3}$-alkoxy, and $C_{3-6}$-cycloalkyl is unsubstituted or substituted with 1 to 3 substituents independently selected from the group consisting of fluoro, hydroxy, $C_{1-3}$-alkyl, fluoro-$C_{1-3}$-alkyl, $C_{1-3}$-alkoxy and fluoro-$C_{1-3}$-alkoxy;

$R^2$ and $R^3$ are independently selected from the group consisting of hydrogen, halogen, $C_{1-3}$-alkyl, halo-$C_{1-3}$-alkyl, $C_{1-3}$-alkoxy, halo-$C_{1-3}$-alkoxy, cyclopropyl and fluoro-cyclopropyl;

$R^4$ is independently selected from the group consisting of halogen, $C_{1-3}$-alkyl, halo-$C_{1-3}$-alkyl, $C_{1-3}$-alkoxy, halo-$C_{1-3}$-alkoxy, $C_{3-6}$-cycloalkyl, $C_{1-3}$-alkylene-O—$C_{1-3}$-alkyl and fluoro-$C_{3-6}$-cycloalkyl;

$R^5$ is selected from the group consisting of hydrogen, fluoro, $CH_3$, $CHF_2$ and $CF_3$;

n is selected from 0, 1, 2, 3 and 4;

x is independently selected from 0, 1 and 2.

2. The compound according to claim 1 wherein
R is selected from the group consisting of $CO_2H$, $SO_3H$, $CONR^7R^9$, tetrazolyl, 1,2,4-oxadiazol-5(4H)-one-3-yl and $SO_2NHCOR^7$;

$R^7$ selected from the group consisting of hydrogen, $C_{1-6}$-alkyl, halo-$C_{1-6}$-alkyl, and $C_{1-6}$-alkylene-$R^9$;

$R^8$ selected from the group consisting of hydrogen, $C_{1-6}$-alkyl and halo-$C_{1-6}$-alkyl; and $R^9$ is selected from the group consisting of COOH, OH and $SO_3H$.

3. The compound according to claim 1 wherein
A is selected from the group consisting of phenyl, pyridyl, pyrimidyl, pyrazolyl, indolyl, thienyl, benzothienyl, indazolyl, benzisoxazolyl, benzisothiazolyl, triazolopyridinyl, benzofuranyl, benzotriazolyl, furanyl, benzothiazolyl, thiazolyl, oxadiazolyl, oxazolyl, naphthyl, quinolyl, isoquinolyl and benzimidazolyl, each unsubstituted or substituted with one or two groups independently selected from the group consisting of OH, halogen, CN, O—$C_{1-6}$-alkyl, O-halo-$C_{1-6}$-alkyl, $C_{1-6}$-alkyl, halo-$C_{1-6}$-alkyl, $C_{3-6}$-cycloalkyl and halo-$C_{3-6}$-cycloalkyl.

4. The compound according to claim 3 wherein A is selected from the group consisting of phenyl, pyridyl, indolyl, indazolyl, benzisothiazolyl, triazolopyridinyl, benzothiazolyl, thiazolyl, oxazolyl and quinolyl, each unsubstituted or substituted with one or two groups independently selected from the group consisting of OH, halogen, CN, O—$C_{1-6}$-alkyl, O-halo-$C_{1-6}$-alkyl, $C_{1-6}$-alkyl, halo-$C_{1-6}$-alkyl, $C_{3-6}$-cycloalkyl and halo-$C_{3-6}$-cycloalkyl.

5. The compound according to claim 1 wherein R-A is selected from

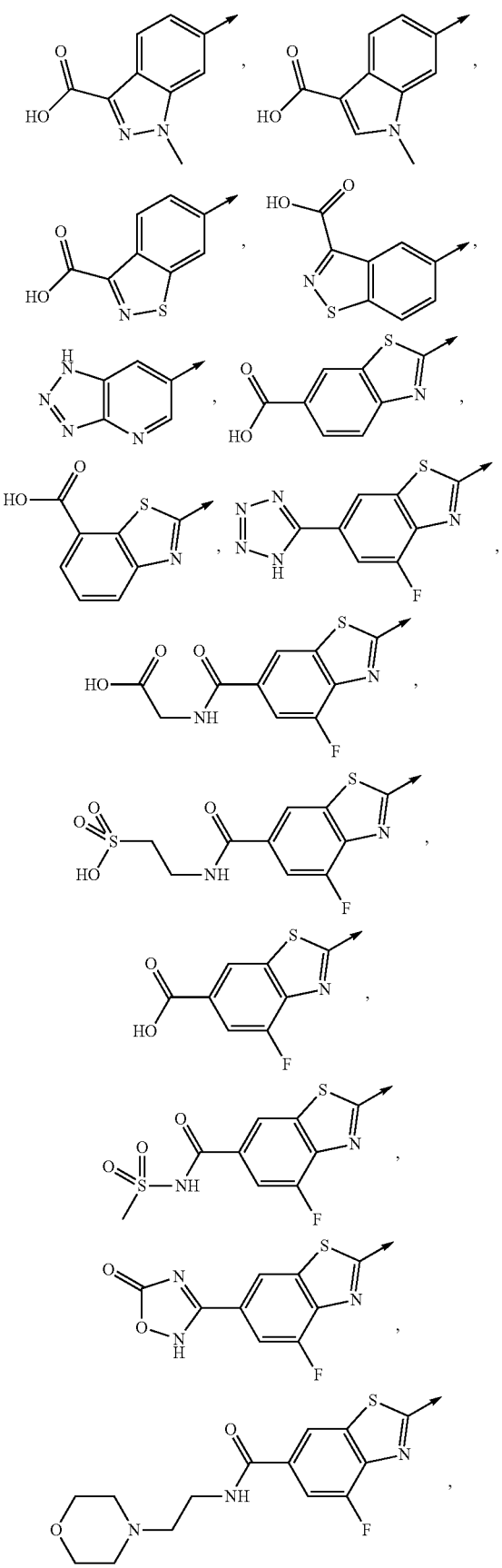

-continued
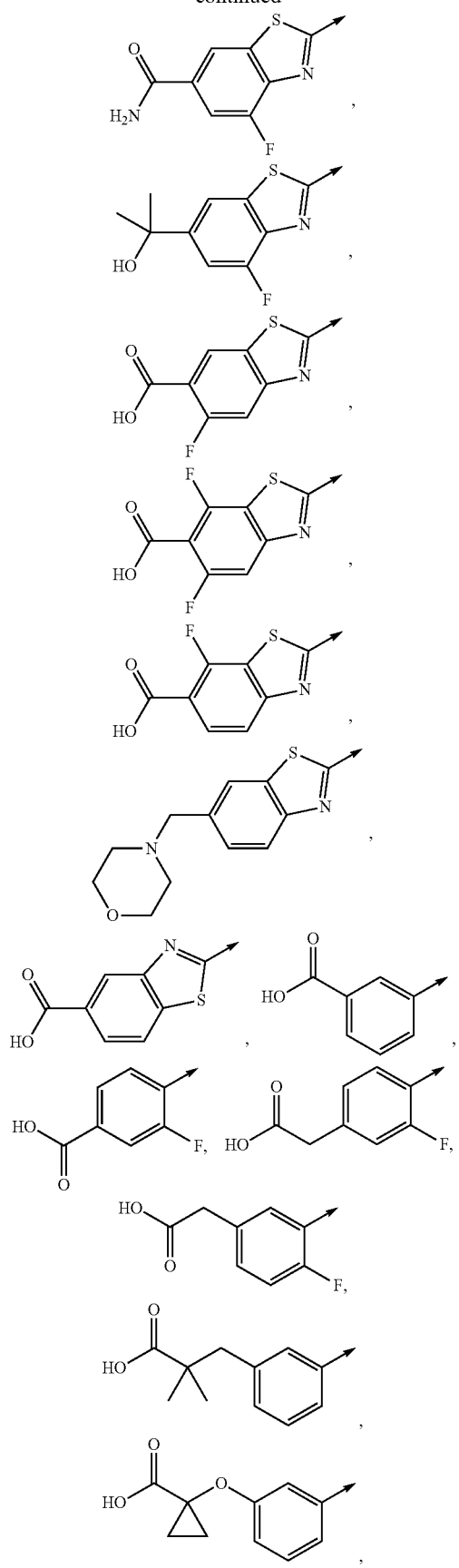
-continued
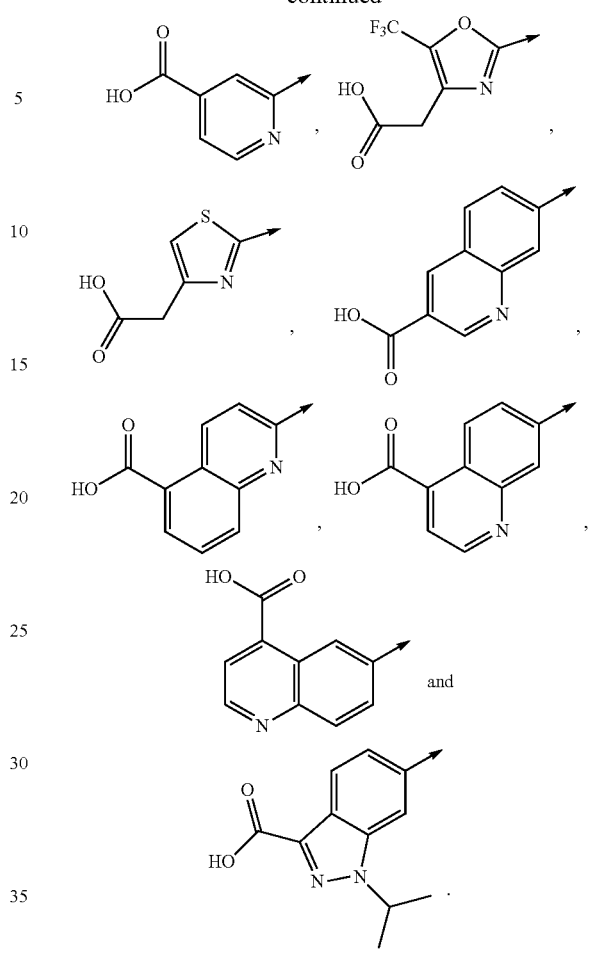
6. The compound according to claim 1 wherein Z is selected from the group consisting of:
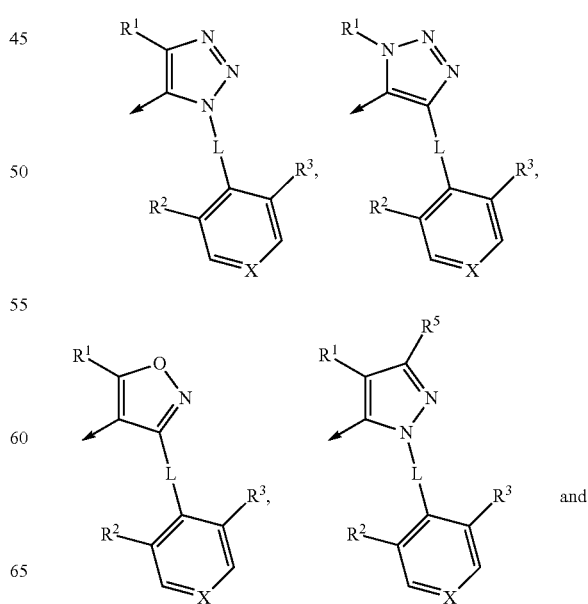
and -continued

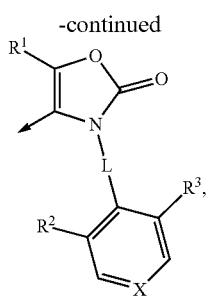

wherein
L is selected from the group consisting of a bond, $C_{1-3}$-alkylene and $C_{1-3}$-alkylene-O—;
X is selected from the group consisting of CH, CF, N and NO;
$R^1$ is selected from the group consisting of $C_{1-4}$-alkyl and $C_{3-6}$-cycloalkyl, wherein $C_{1-4}$-alkyl is unsubstituted or substituted with 1 to 3 substituents independently selected from the group consisting of fluoro, hydroxy, $C_{1-3}$-alkoxy and fluoro-$C_{1-3}$-alkoxy, and $C_{3-6}$-cycloalkyl is unsubstituted or substituted with 1 to 3 substituents independently selected from the group consisting of fluoro, hydroxy, $C_{1-3}$-alkyl, fluoro-$C_{1-3}$-alkyl, $C_{1-3}$-alkoxy and fluoro-$C_{1-3}$-alkoxy;
$R^2$ and $R^3$ are independently selected from the group consisting of hydrogen, halogen, $C_{1-3}$-alkyl, halo-$C_{1-3}$-alkyl, $C_{1-3}$-alkoxy, halo-$C_{1-3}$-alkoxy, cyclopropyl and fluoro-cyclopropyl; and
$R^5$ is selected from the group consisting of hydrogen, fluoro, $CH_3$, $CHF_2$ and $CF_3$.

7. The compound according to claim 1 wherein Z is selected from

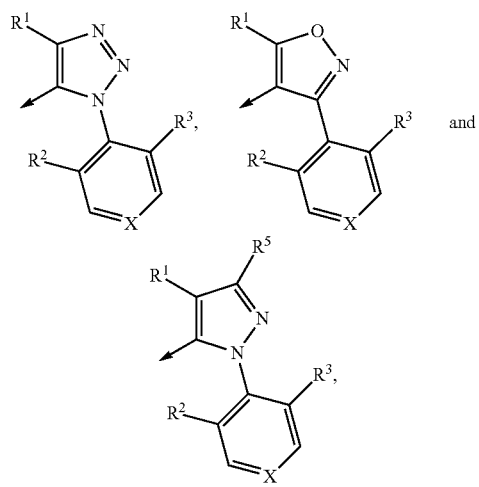

wherein
X is selected from the group consisting of CH, CF, N and NO;
$R^1$ is selected from the group consisting of methyl, $CF_3$, $CHF_2$, isopropyl and cyclopropyl, wherein isopropyl and cyclopropyl are unsubstituted or substituted with one or two fluoro or one hydroxy;
$R^2$ is selected from the group consisting of fluoro, chloro, $CH_3$, $CHF_2$, $CF_3$, $OCHF_2$ and $OCF_3$;
$R^3$ is selected from the group consisting of hydrogen, fluoro, chloro, $CH_3$, $CHF_2$, $CF_3$, $OCHF_2$ and $OCF_3$; and $R^5$ is selected from the group consisting of hydrogen, fluoro, $CH_3$, $CHF_2$ and $CF_3$.

8. The compound according to claim 1 wherein

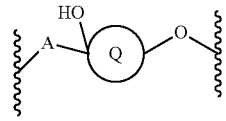

is selected from

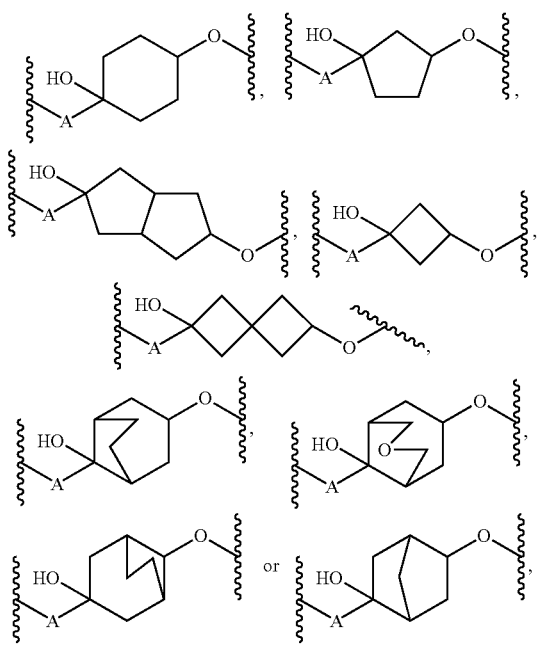

each optionally substituted with $R^4$.

9. The compound according to claim 1, wherein the compound is according to Formula (2)

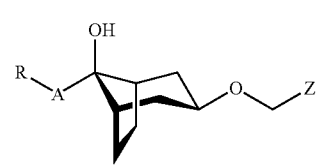

wherein
A is selected from the group consisting of phenyl, pyridyl, pyrimidyl, pyrazolyl, indolyl, thienyl, benzothienyl, indazolyl, benzisoxazolyl, benzisothiazolyl, triazolopyridinyl, benzofuranyl, benzotriazolyl, furanyl, benzothiazolyl, thiazolyl, oxadiazolyl, oxazolyl, naphthyl, quinolyl, isoquinolyl and benzimidazolyl, each unsubstituted or substituted with one or two groups independently selected from the group consisting of OH, halogen, CN, O—$C_{1-6}$-alkyl, O-halo-$C_{1-6}$-alkyl, $C_{1-6}$-alkyl, halo-$C_{1-6}$-alkyl, $C_{3-6}$-cycloalkyl and halo-$C_{3-6}$-cycloalkyl;
R is selected from the group consisting of $CO_2H$, $SO_3H$, $CONR^7R^5$, tetrazolyl, 1,2,4-oxadiazol-5(4H)-one-3-yl and $SO_2NHCOR^7$, wherein R[7] selected from the group consisting of H, $C_{1-6}$-alkyl, halo-$C_{1-6}$-alkyl, and $C_{1-6}$-alkylene-R[9];

R[8] selected from the group consisting of H, $C_{1-6}$-alkyl, halo-$C_{1-6}$-alkyl; and R[9] is selected from the group consisting of COOH, OH and $SO_3H$;

Z is selected from

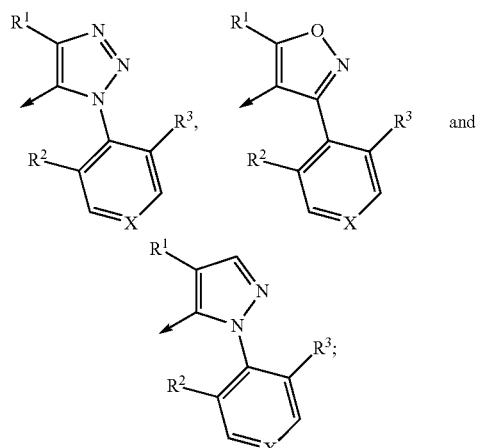

X is selected from the group consisting of CH, N and NO;

R[1] is selected from the group consisting of methyl, isopropyl and cyclopropyl, wherein isopropyl and cyclopropyl are unsubstituted or substituted with one or two fluoro or one hydroxy;

R[2] is selected from the group consisting of fluoro, chloro, $CH_3$, $CHF_2$, $CF_3$, $OCHF_2$ and $OCF_3$; and R[3] is selected from the group consisting of hydrogen, fluoro, chloro, $CH_3$, $CHF_2$, $CF_3$, $OCHF_2$ and $OCF_3$.

10. A compound selected from the group consisting of:

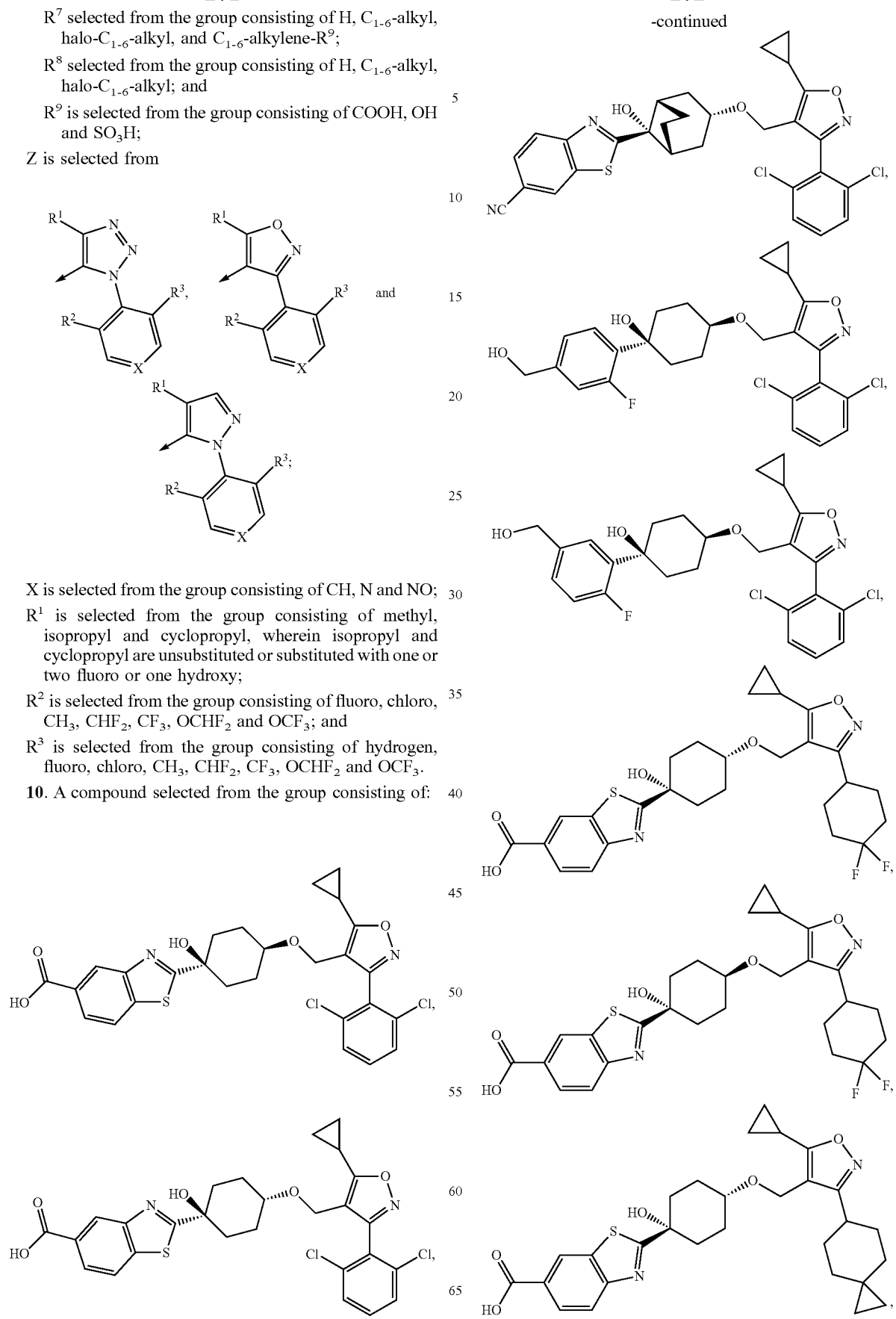

273
-continued
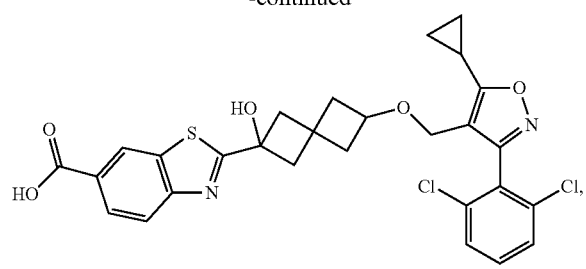
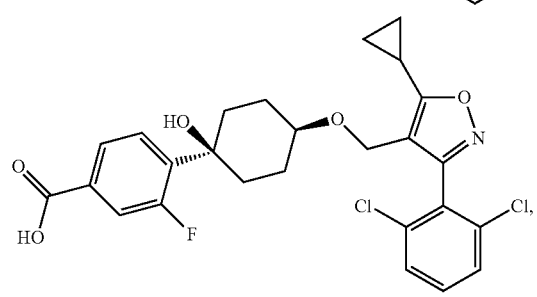
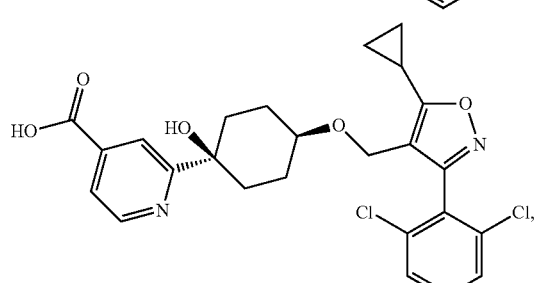
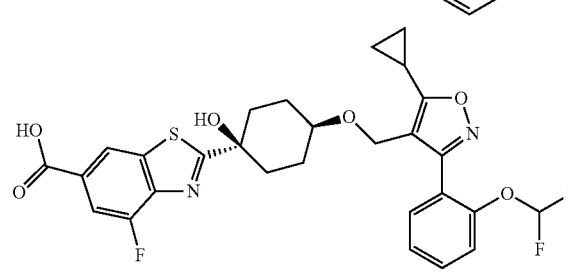
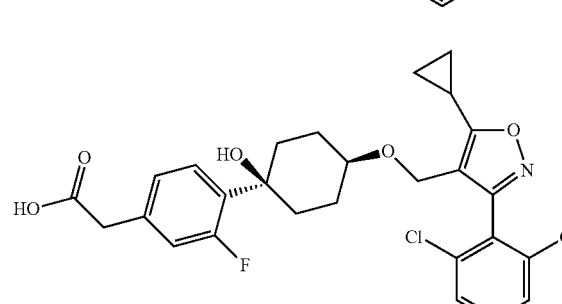
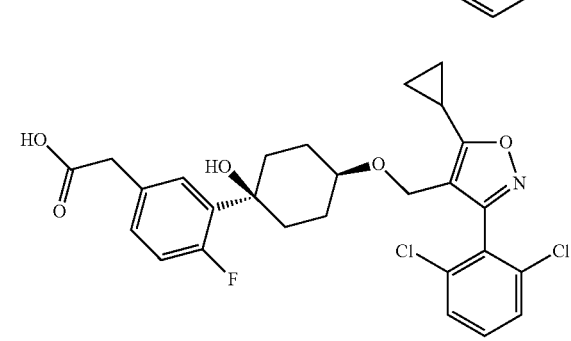
274
-continued
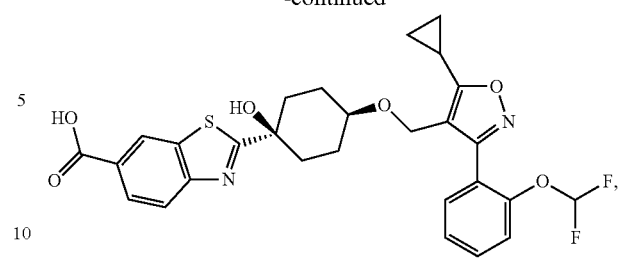
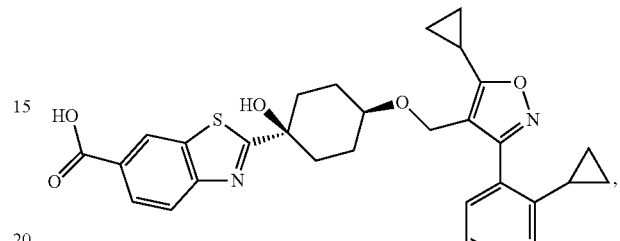
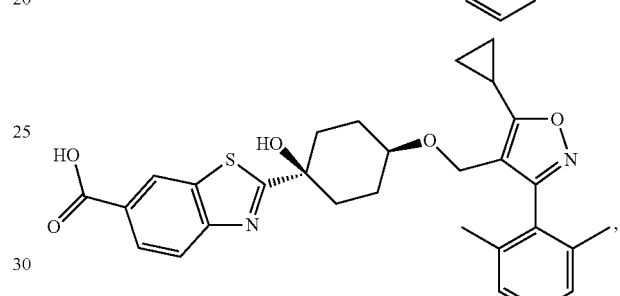
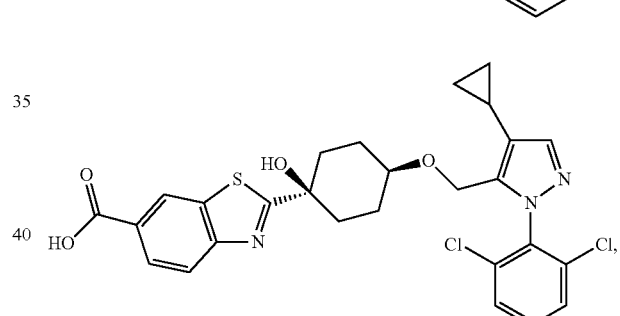
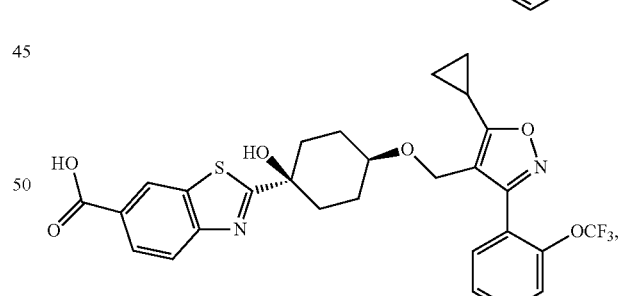
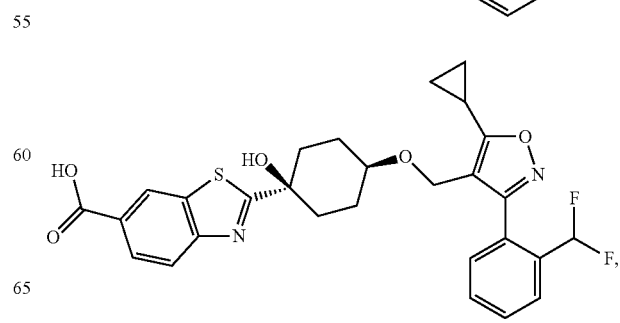

275
-continued
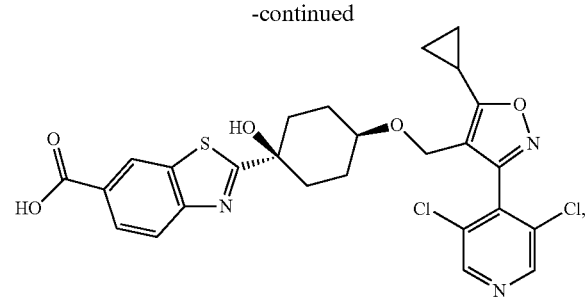
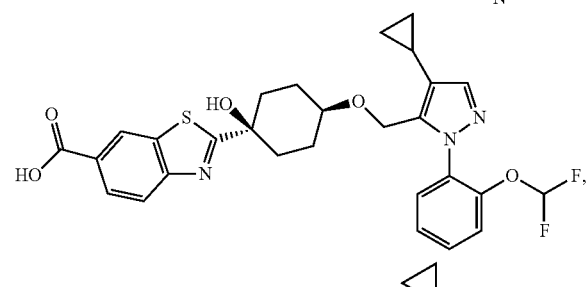
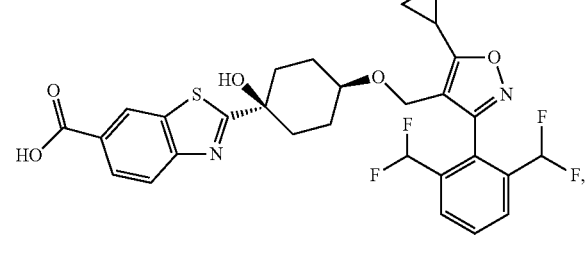
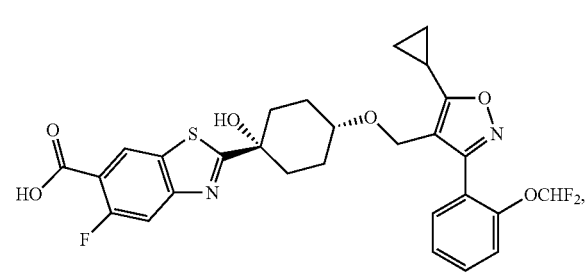
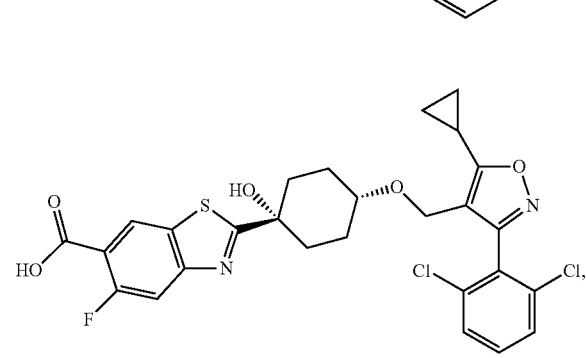
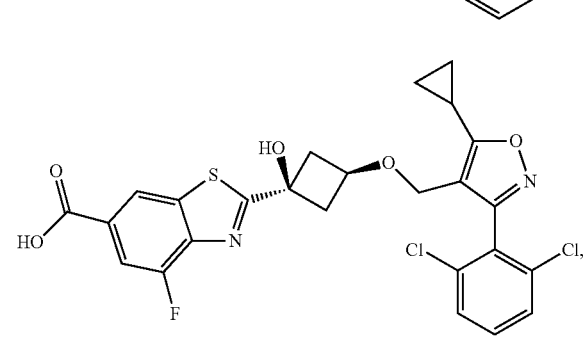
276
-continued
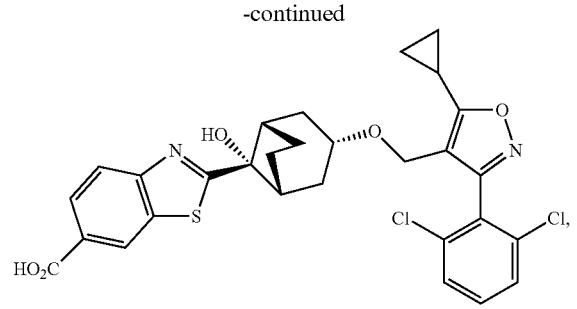
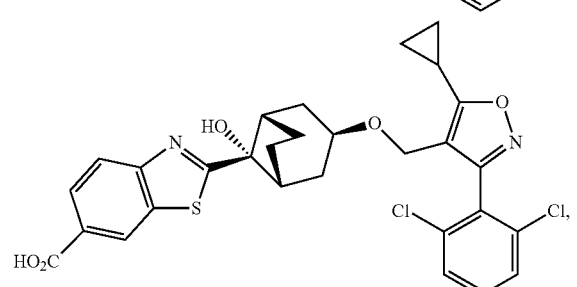
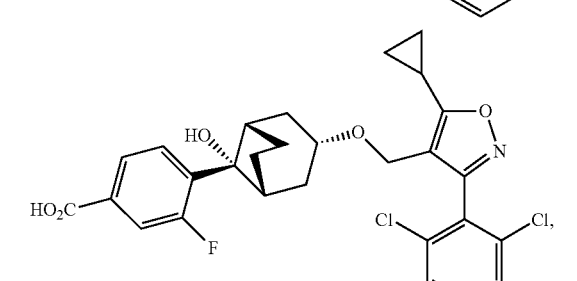
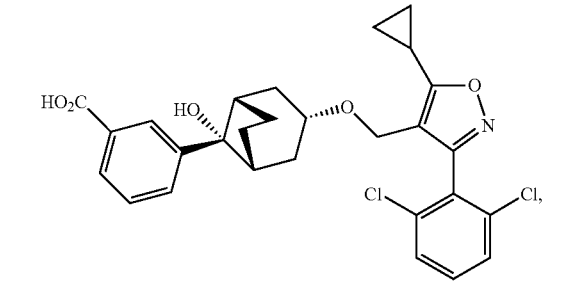
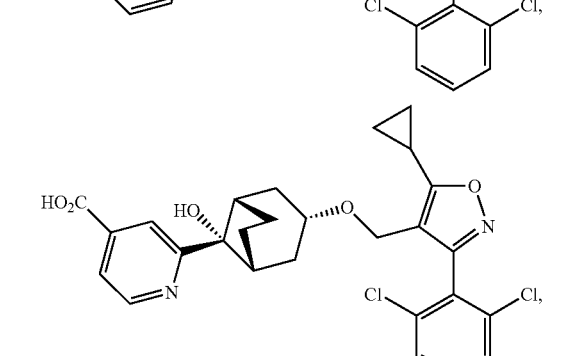
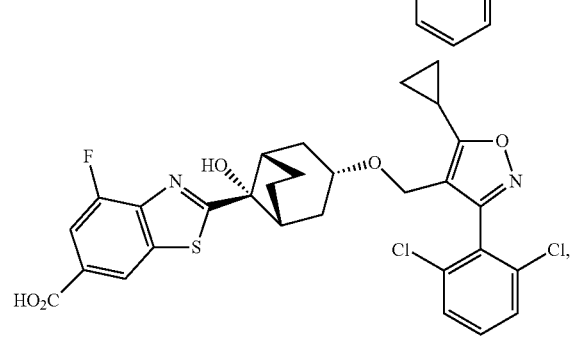

-continued
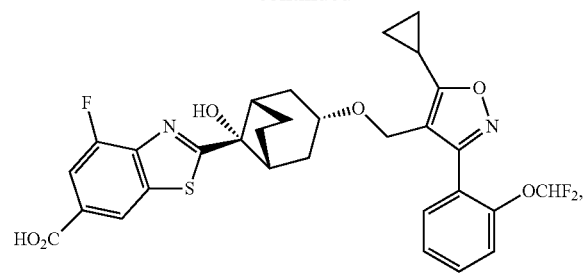
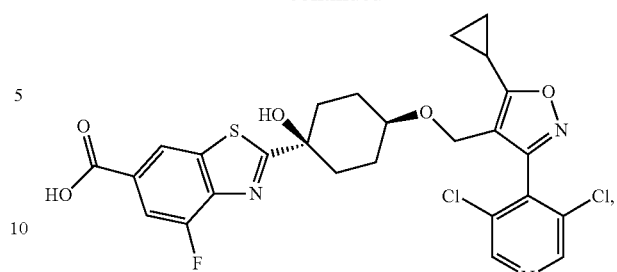
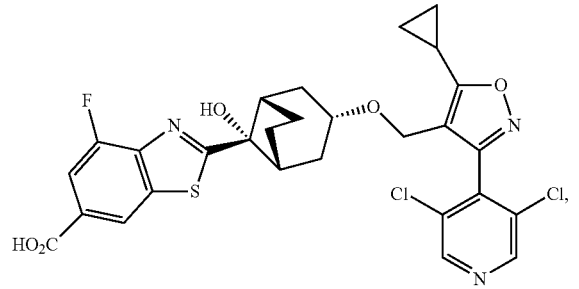
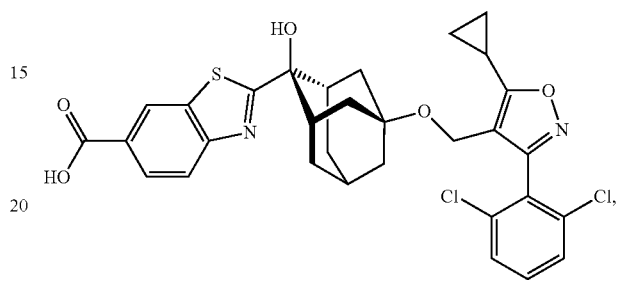
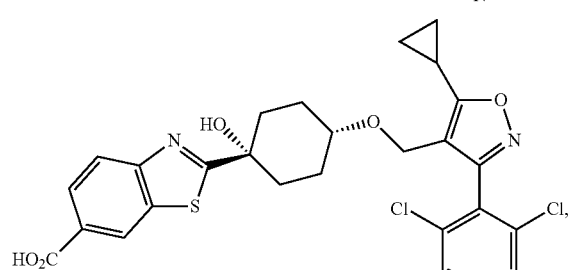
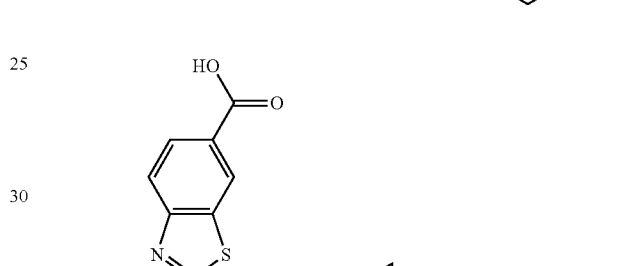
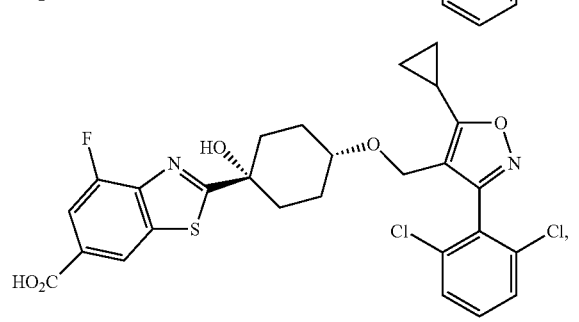
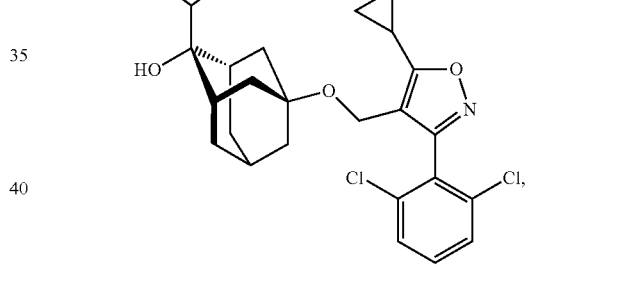
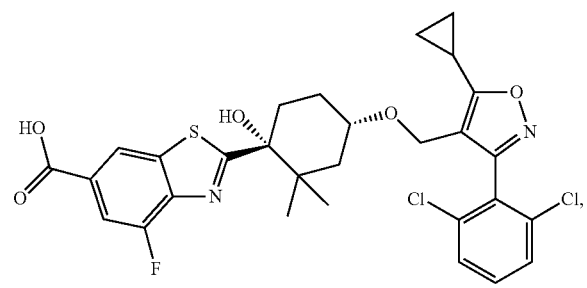
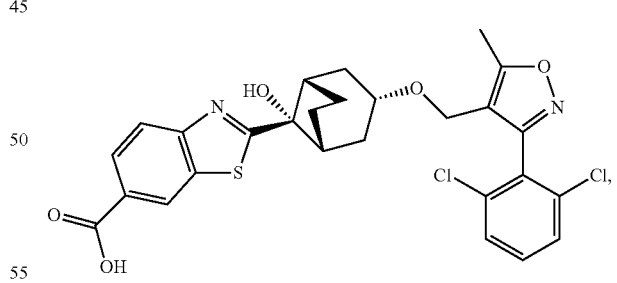
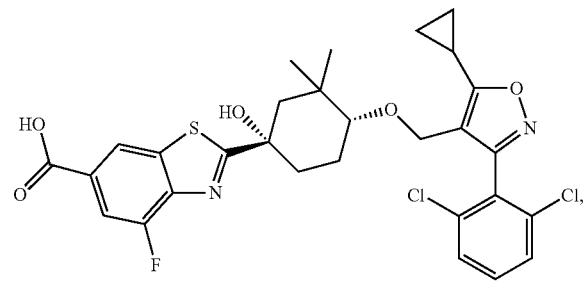
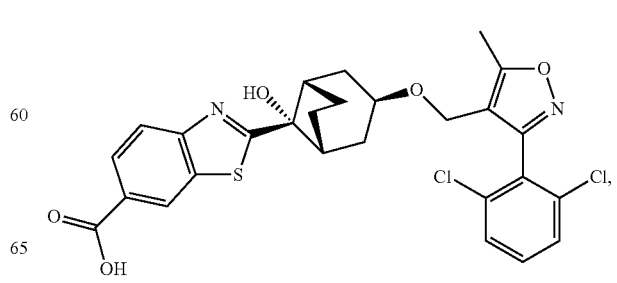

279
-continued
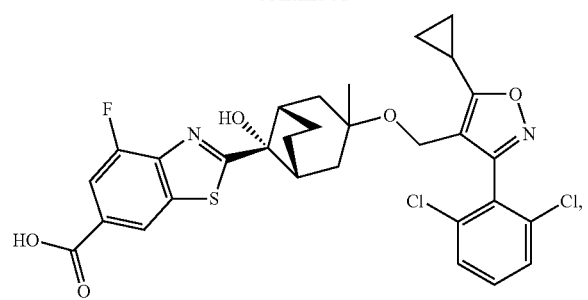
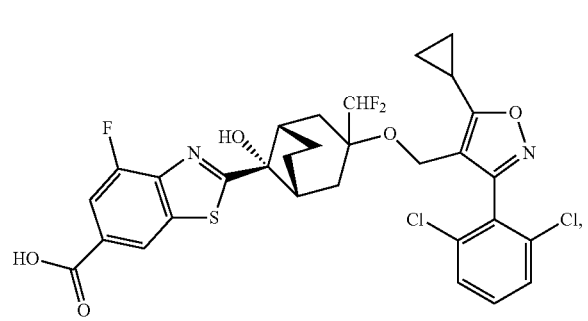
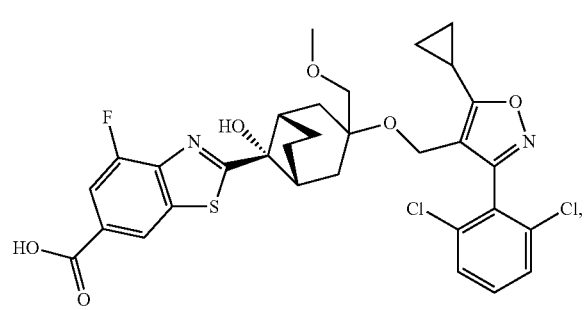
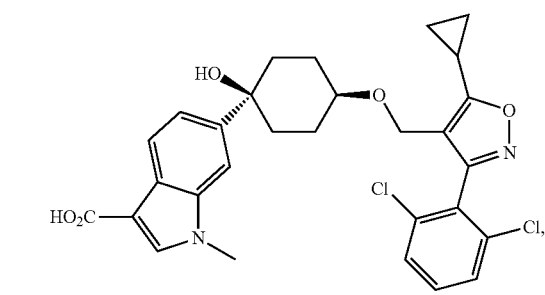
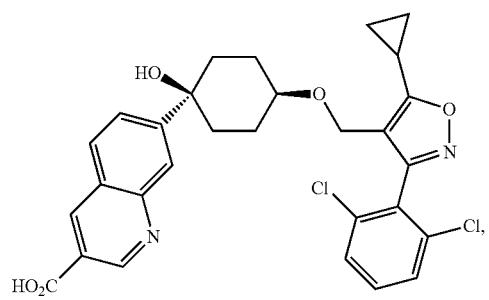
280
-continued
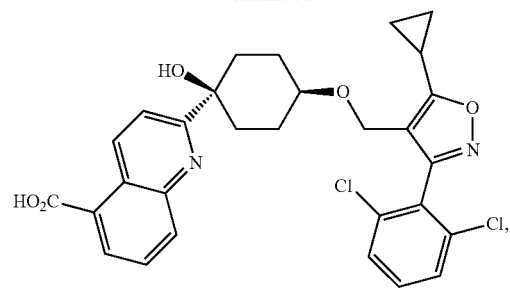
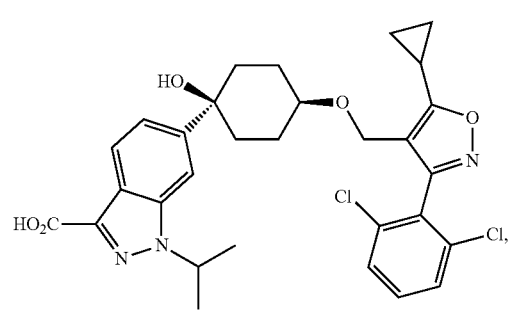
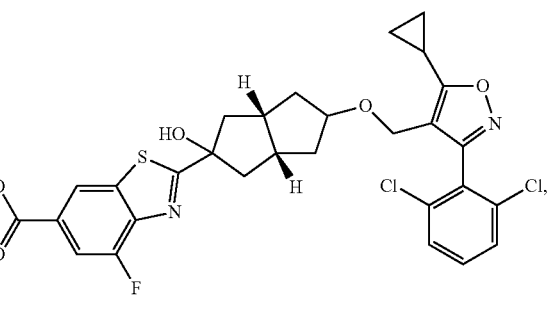
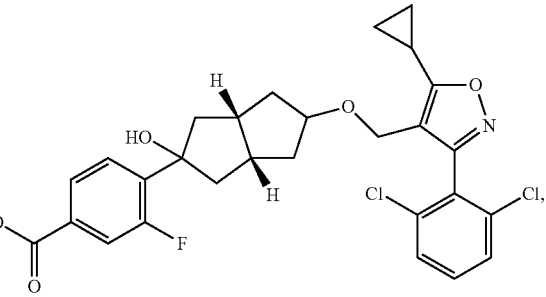
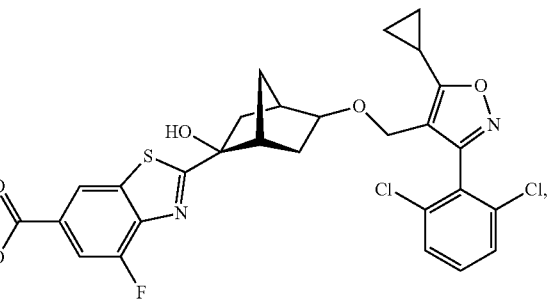

-continued
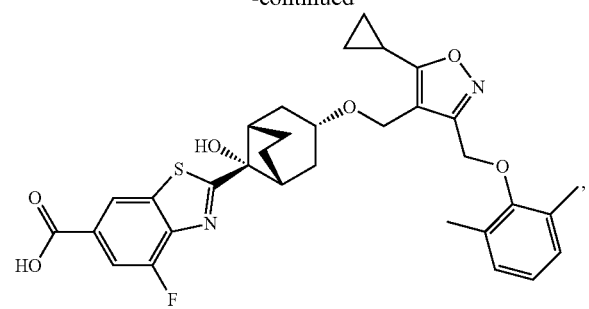
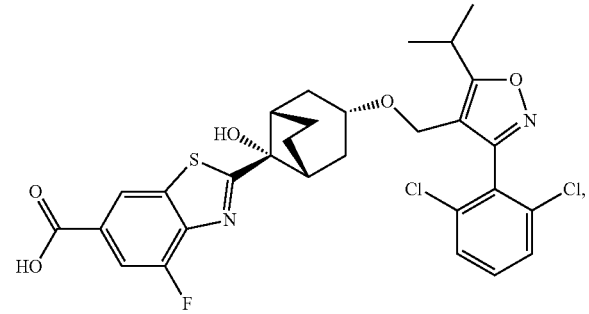
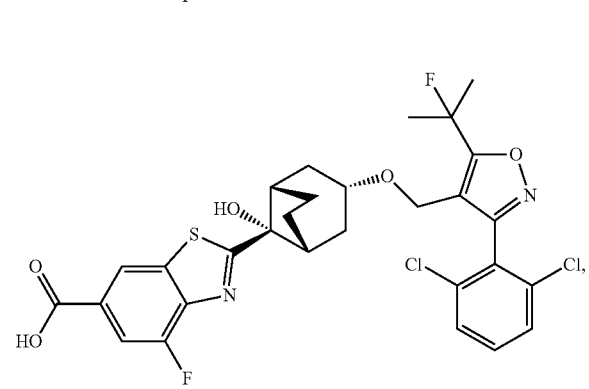
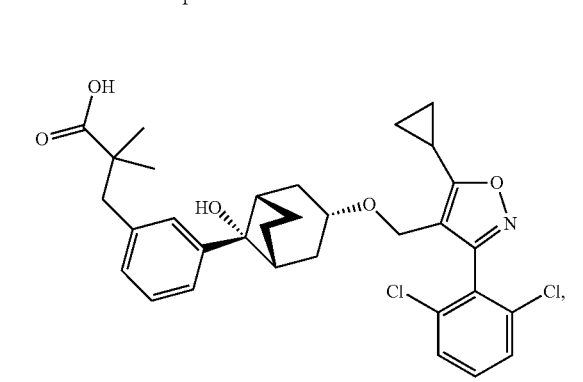
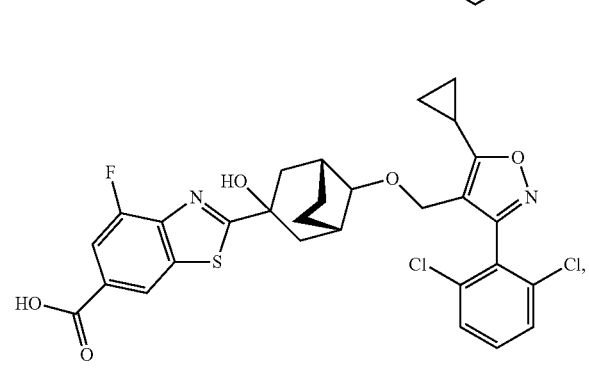
-continued
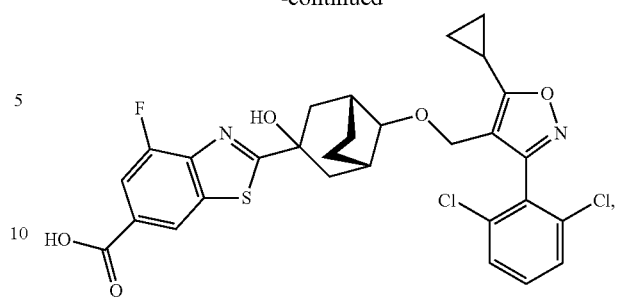
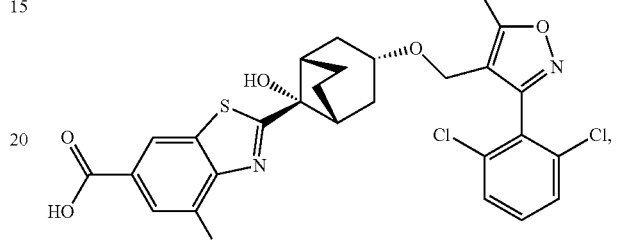
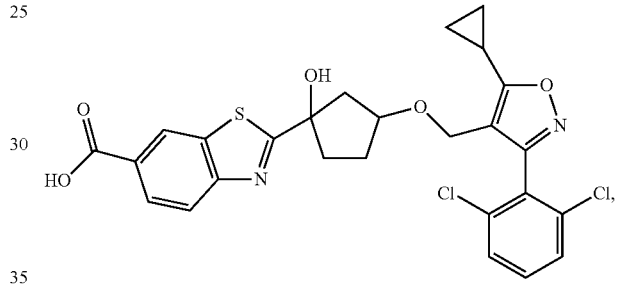
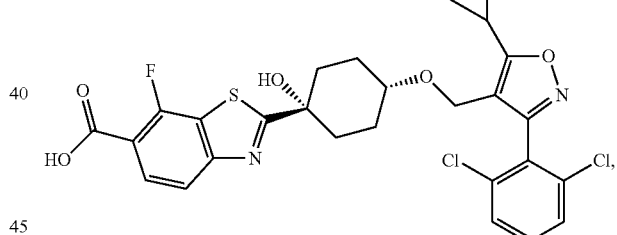
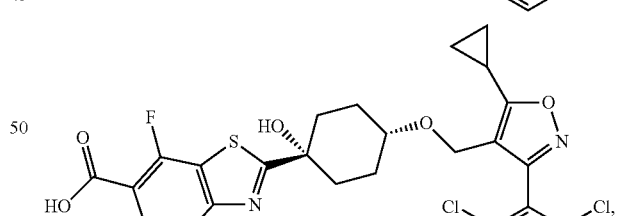
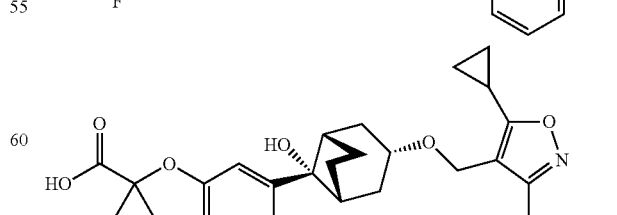

-continued
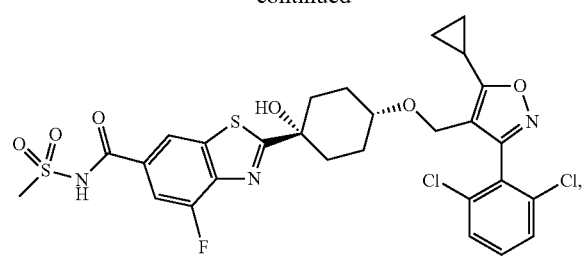
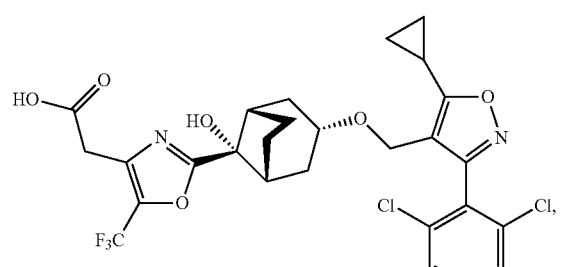
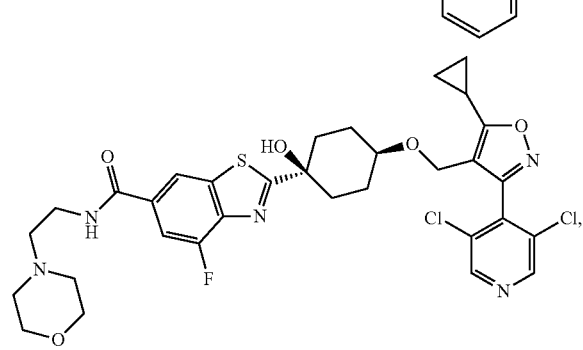
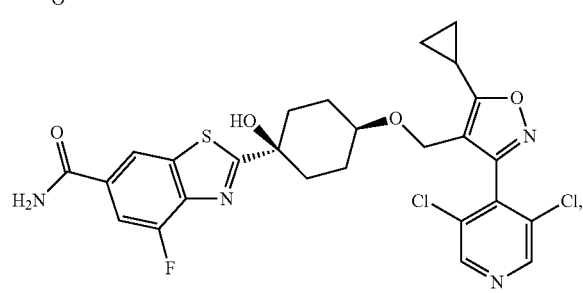
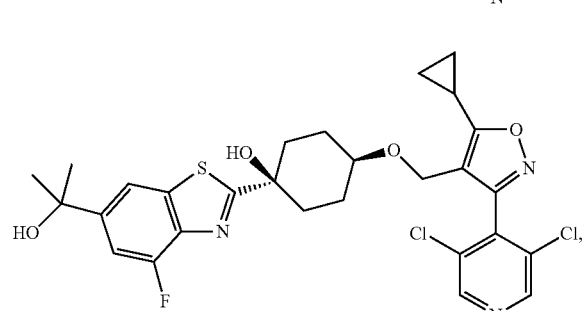
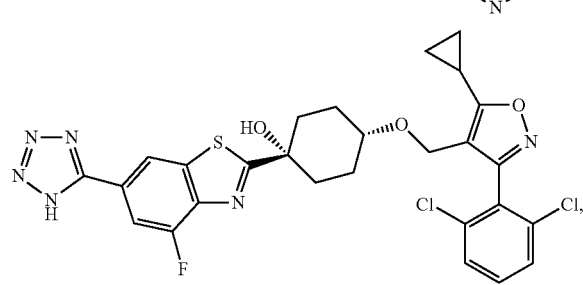
-continued
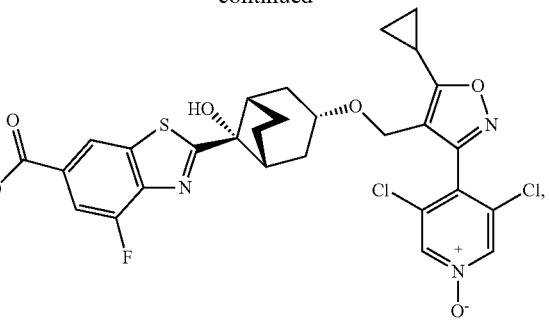
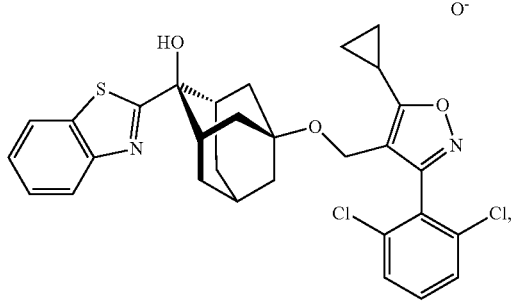
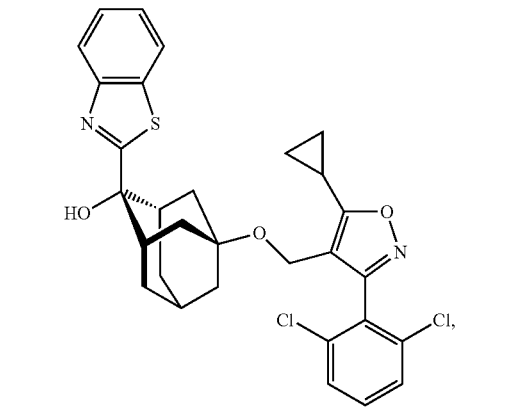
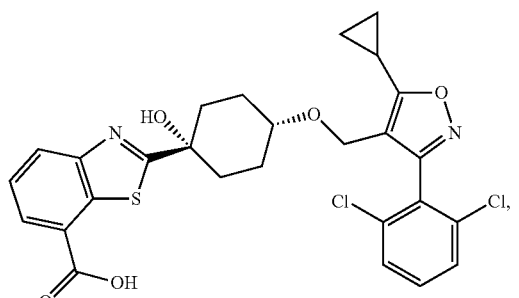
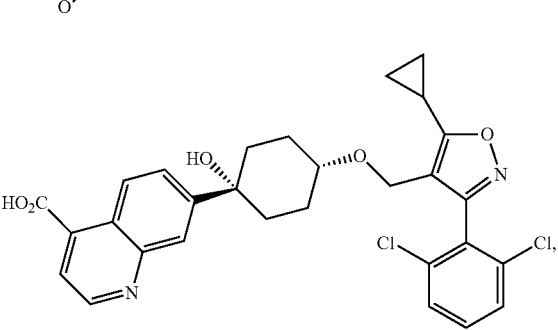

-continued

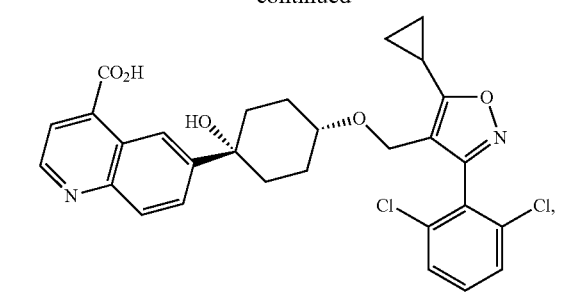

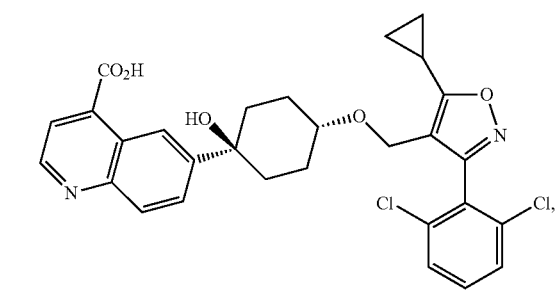

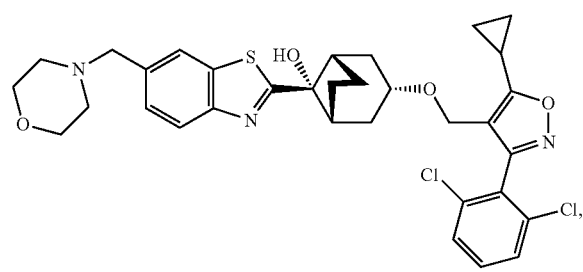

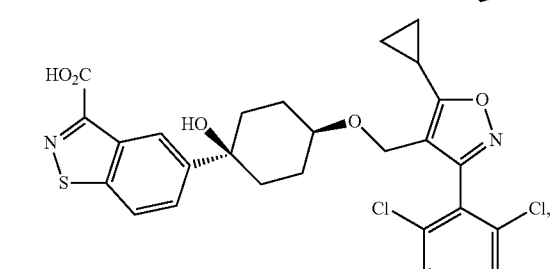

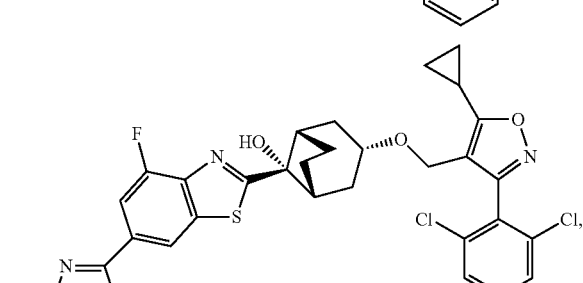

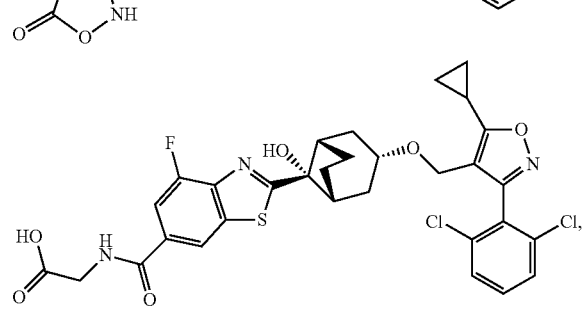

-continued

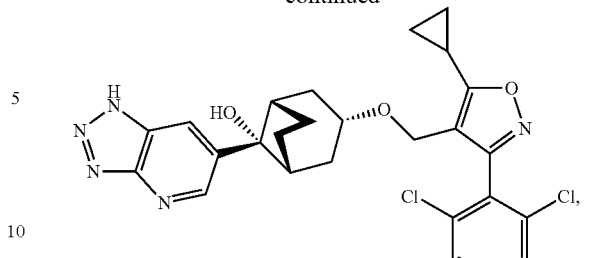

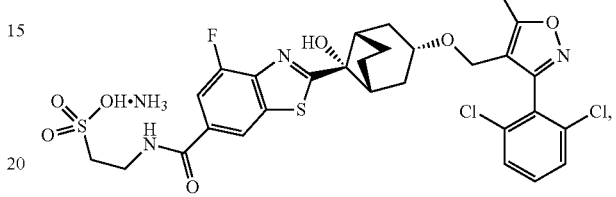

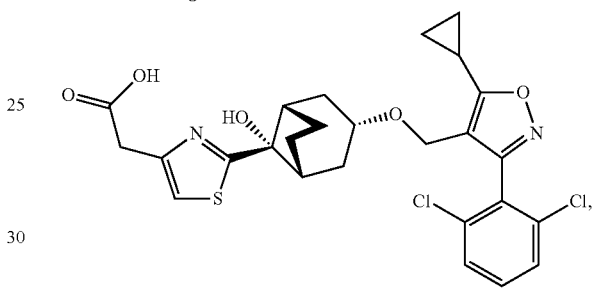

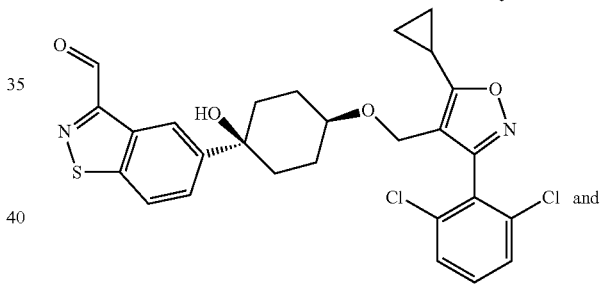

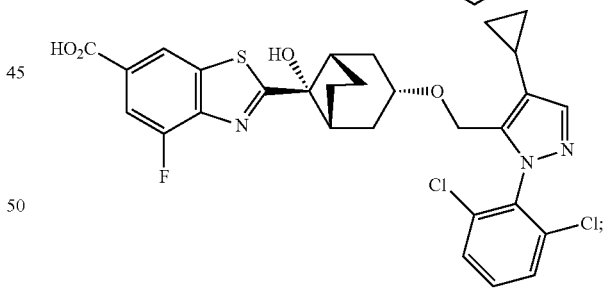

or an enantiomer, diastereomer, tautomer, solvate, prodrug or pharmaceutical acceptable salt thereof.

11. A method of treating a patient having an FXR mediated condition, the method comprising administering a compound of claim 1 to a patient in need thereof, wherein the FXR mediated condition is selected from chronic intrahepatic or some forms of extrahepatic cholestatic conditions;
liver fibrosis;
obstructive or chronic inflammatory disorders of the liver;
liver cirrhosis;
liver steatosis and associated syndromes, cholestatic or fibrotic effects that are associated with alcohol-induced cirrhosis or with viral-borne forms of hepatitis;

liver failure or liver ischemia after major liver resection;
chemotherapy associated steatohepatitis (CASH);
acute liver failure; and
Inflammatory Bowel Diseases.

12. A method of treating a patient having an FXR mediated condition, the method comprising administering a compound of claim 1 to a patient in need thereof, wherein the FXR mediated condition is selected from the group consisting of:

Type II Diabetes and clinical complications of Type I and Type II Diabetes, selected from the group consisting of diabetic nephropathy, diabetic neuropathy, diabetic retinopathy and other observed effects of clinically manifest long term Diabetes;

Non-Alcoholic Fatty Liver Disease (NAFLD), or Non-Alcoholic Steatohepatitis (NASH);

obesity or metabolic syndrome (combined conditions of dyslipidemia, diabetes or abnormally high body-mass index); and acute myocardial infarction, acute stroke or thrombosis which occurs as an endpoint of chronic obstructive atherosclerosis.

\* \* \* \* \*

UNITED STATES PATENT AND TRADEMARK OFFICE
CERTIFICATE OF CORRECTION

PATENT NO. : 9,751,874 B2
APPLICATION NO. : 14/971875
DATED : September 5, 2017
INVENTOR(S) : Christian Gege et al.

It is certified that error appears in the above-identified patent and that said Letters Patent is hereby corrected as shown below:

In the Claims

Claim 1, Column 263, Lines 49-50, replace "cycloalkyl, heterocycloalkyl and the 5- or 6- membered heteroaryl" with -- cycloalkyl and heterocycloalkyl --

Claim 1, Column 263, Line 59, replace "cyclolalkyl" with -- cycloalkyl --

Claim 1, Column 265, Line 31, replace "n is selected from 0, 1, 2, 3 and 4;" with -- n is selected from 0, 1, 2, 3 and 4; and --

Claim 9, Column 271, Lines 3-4, replace "H, $C_{1-6}$-alkyl, halo-$C_{1-6}$-alkyl;" with -- H, $C_{1-6}$-alkyl, and halo-$C_{1-6}$-alkyl --

Signed and Sealed this
Second Day of April, 2019

Andrei Iancu
*Director of the United States Patent and Trademark Office*